US008785151B2

(12) United States Patent
Geierstanger et al.

(10) Patent No.: US 8,785,151 B2
(45) Date of Patent: Jul. 22, 2014

(54) BIOSYNTHETICALLY GENERATED PYRROLINE-CARBOXY-LYSINE AND SITE SPECIFIC PROTEIN MODIFICATIONS VIA CHEMICAL DERIVATIZATION OF PYRROLINE-CARBOXY-LYSINE AND PYRROLYSINE RESIDUES

(76) Inventors: Bernhard Geierstanger, Solana Beach, CA (US); Weijia Ou, San Diego, CA (US); Susan E. Cellitti, San Diego, CA (US); Tetsuo Uno, San Diego, CA (US); Tiffany Crossgrove, San Diego, CA (US); Hsien-Po Chiu, San Diego, CA (US); Jan Grunewald, San Diego, CA (US); Xueshi Hao, San Diego, CA (US)

( * ) Notice: Subject to any disclaimer, the term of this patent is extended or adjusted under 35 U.S.C. 154(b) by 137 days.

(21) Appl. No.: 13/125,547

(22) PCT Filed: Oct. 23, 2009

(86) PCT No.: PCT/US2009/061954
§ 371 (c)(1),
(2), (4) Date: Jul. 11, 2011

(87) PCT Pub. No.: WO2010/048582
PCT Pub. Date: Apr. 29, 2010

(65) Prior Publication Data
US 2011/0262963 A1    Oct. 27, 2011

Related U.S. Application Data

(60) Provisional application No. 61/108,434, filed on Oct. 24, 2008.

(51) Int. Cl.
*C12P 21/02*        (2006.01)
*C07D 207/22*    (2006.01)
*C07K 16/00*      (2006.01)
*C07K 14/50*      (2006.01)

(52) U.S. Cl.
USPC ....... 435/68.1; 548/537; 530/387.1; 530/351; 530/399; 530/350; 435/175

(58) Field of Classification Search
None
See application file for complete search history.

(56) References Cited

U.S. PATENT DOCUMENTS

| 7,083,970 | B2 | 8/2006 | Schultz et al. |
| 7,354,761 | B2 | 4/2008 | Schultz et al. |
| 2006/0166319 | A1 | 7/2006 | Chan et al. |
| 2008/0183888 | A1 | 7/2008 | Brown et al. |

FOREIGN PATENT DOCUMENTS

| EP | 1992698 | 11/2008 |
| WO | WO2005003294 | 1/2005 |

OTHER PUBLICATIONS

Pyrrolysine analogues as substrates for pyrrolysyl-tRNA synthetase Carla R. Polycarpo et al. FEBS Letters 580 (2006) 6695-6700.*
Namy et al (Adding pyrrolysine to the *Escherichia coli* genetic code FEBS Lett. Nov. 13, 2007;581(27):5282-8. Epub Oct. 23, 2007.*
Neumann, et al., "Genetically encoding N-epsilon-acetyllysine in recombinant proteins", Nature Chemical Biology, Apr. 1, 2008, pp. 232-234, vol. 4, No. 4, Nature Publishing Group, New York, NY, US.
Polycarpo, et al., "Pyrrolysine analogues as substrates for pyrrolysyl-tRNA synthetase", FEBS Letters, Dec. 11, 2006, pp. 6695-6700, vol. 580, No. 28-29, Elsevier, Amsterdam, NL.
Mukai et al., "Adding I-lysine derivatives to the genetic code of mammalian cells with engineered pyrrolysyl-tRNA synthetases", Biochemical and Biophysical Research Communications, Jul. 11, 2008, pp. 818-822, vol. 371, No. 4, Academic Press Inc., Orlando, FL, US.
Xie, et al, "Adding amino acids to the genetic repertoire", Current Opinion in Chemical Biology, Dec. 1, 2005, pp. 548-554, vol. 9, No. 6, Current Biology, Ltd., London, GB.
Fekner, et al., "A pyrrolysine analogue for protein click chemistry", Angewandte Chemie (International Edition), Jan. 1, 2009, pp. 1633-1635, vol. 48, No. 9, Wiley-VCH Verlag GMBH & Co., DE.
Kobayashi, et al., "Recognition of Non-alpha-amino substrates by pyrrolysyl-tRNA Synthetase", Journal of Molecular Biology, Feb. 6, 2009, pp. 1352-1360, vol. 385, No. 5, London, GB.
Chen, et al., "A facile system for encoding unnatural amino acids in mammalian cells", Angewandte Chemie (International Edition), Jan. 1, 2009, pp. 4052-4055, vol. 48, No. 22, Wiley-VCH Verlag GMBH & Co., DE.
Nguyen, et al., "Genetic encoding and labeling of aliphatic azides and alkynes in recombinant proteins via a pyrrolysyl-tRNA Synthetase/tRNA(CUA) pair and click chemistry", Journal of the American Chemical Society, Jul. 1, 2009, pp. 8720-8721, vol. 131, No. 25, American Chemical Society, US.
Williams, et al, "Improved Chemical Synthesis and Enzymatic Assay of Delta1-Pyrroline-5-Carboxylic Acid", Analytical Biochemistry, 1975, 64, pp. 85-97.
Wu et al., "A New Method for the Preparation of Delta1-Pyrroline 5 Carboxylic Acid and Proline", Analytical Biochemistry, 1975, 67, pp. 413-421.
Mezl et al., "Properties and Analysis of a Stable Derivative of Pyrroline-5-Carboxylic Acid for Use in Metabolic Studies", Analytical Biochemistry, 1976, 74, pp. 430-440.
Schopf et al., "Zur Frage der Biogenese des Vasicins (Peganins)-Die Synthese des Desoxgvasicins unter physiologischen Bedingungen", Justus Liebegs Annalen der Chemie, 1936, 523, pp. 1-29.

(Continued)

*Primary Examiner* — Kagnew H Gebreyesus
(74) *Attorney, Agent, or Firm* — Daniel E. Raymond; Genomics Institute of the Novartis Research Foundation

(57) ABSTRACT

Disclosed herein is pyrroline-carboxy-lysine (PCL), a pyrrolysine analogue, which is a natural, biosynthetically generated amino acid, and methods for biosynthetically generating PCL. Also disclosed herein are proteins, polypeptides and peptides that have PCL incorporated therein and methods for incorporating PCL into such proteins, polypeptides and peptides. Also disclosed herein is the site-specific derivatization of proteins, polypeptides and peptides having PCL or pyrrolysine incorporated therein. Also disclosed herein is the crosslinking of proteins, polypeptides and peptides having PCL or pyrrolysine incorporated therein.

7 Claims, 59 Drawing Sheets

(56) References Cited

OTHER PUBLICATIONS

Schopf et al., "Zur Frage der Biogehese des Rutaecarpins and Evodiamins-Die Synthese des Rutaecarpins unter zellmoglichen Bedingungen", Justus Liebegs Annalen der Chemie, 1947, 523, pp. 124-136.

Krzycki, J.A., "Function of genetically encoded pyrrolysine in corrinoid-dependent methylamine methyltransferases", Current Opinion in Chemical Biology, 2004, 8, pp. 484-491.

Krzycki, J.A., "The direct genetic encoding of pyrrolysine", Current Opinion in Microbiology, 2005, 8, pp. 706-712.

Namy et al., "Adding pyrrolysine to the *Escherichia coli* genetic code", FEBS Letters, 2007, 581, pp. 5282-5288.

Vogel et al, "Glutamic gamma-Semialdehyde and Delta1-Pyrroline-5-carboxylic Acid, Intermediates in the Biosynthesis of Proline", Journal of the American Chemical Society, 1952, 74, pp. 109-112.

Strecker, H.J., "The Interconversion of Glutamic Acid and Proline-I. The Formation of Delta1-Pyrroline-5-carboxylic Acid from Glutamic Acid in *Escherichia coli*", J. Biol. Chem., 1957, 225, pp. 825-834.

Strecker, H.J., "The Interconversion of Glutamic Acid and Proline", J. Biol. Chem., 1960, 235, pp. 2045-2050.

Soares et al., "The Residue Mass of L-Pyrrolysine in Three Distinct Methylamine Methyltransferases", J. Biol. Chem., 2005, 280, pp. 36962-36969.

Ambrogelly, et al., "Natural expansion of the genetic code", Nature Chemical Biology, 2007, 3, pp. 29-35.

Longstaff et al., "A natural genetic code expansion cassette enables transmissible biosynthesis and genetic encoding of pyrrolysine", PNAS, 2007, 104, pp. 1021-1026.

Hao et al., "A New UAG-Encoded Residue in the Structure of a Methanogen Methyltransferase", Science, 2002, 296, pp. 1462-1466.

Srinivasan et al., "Pyrrolysine Encoded by UAG in Archaea: Charging of a UAG-Decoding Specialized tRNA", Science, 2002, 296, pp. 1459-1462.

Yanagisawa et al., "Multistep Engineering of Pyrrolysyl-tRNA Synthetase to Genetically Encode N3-(o-Azidobenzyloxycarbonyl) lysine for Site-Specific Protein Modification", Chemistry and Biology, 2008, 15, pp. 1187-1197.

Hao et al., "Reactivity and Chemical Synthesis of L-Pyrrolysine-the 22nd Genetically Encoded Amino Acid", Chemistry and Biology, 2004, 11, pp. 11317-11324.

Ibba et al., "Genetic Code: Introducing Pyrrolysine", Current Biology, 2002, 12, pp. R464-R466.

Hanford et al, "The Structure of Vasicine. II. Synthesis of Desoxyvasicine", Journal of the American Chemical Society, 1935, 57, pp. 921-924.

James et al., "The Amber Codon in the Gene Encoding the Monomethylamine Methyltransferase Isolated from *Methanosarcina barkeri* Is Translated as a Sense Codon", J. Biol. Chem., 2001, 276, pp. 34252-34258.

Zhang et al., "Pyrrolysine and Selenocysteine Use Dissimilar Decoding Strategies", J. Biol. Chem., 2005, 280, pp. 20740-20751.

Polycarpo et al., "An aminoacyl-tRNA synthetase that specifically activates pyrrolysine", PNAS, 2004, 101, pp. 12450-12454.

Ambrogelly et al., "Pyrrolysine is not hardwired for cotranslational insertion at UAG codons", PNAS, 2007, 104, pp. 3141-3146.

\* cited by examiner

SEQUENCE LISTING

<160> NUMBER OF SEQ ID NOS: 35

<210> SEQ ID NO 1
<211> LENGTH: 1365
<212> TYPE: DNA
<213> ORGANISM: Methanosarcina mazeii

<400> SEQUENCE: 1
atggataaaa aaccactaaa cactctgata tctgcaaccg ggctctggat gtccaggacc      60
ggaacaattc ataaaataaa acaccacgaa gtctctcgaa gcaaaatcta tattgaaatg     120
gcatgcggag accaccttgt tgtaaacaac tccaggagca gcaggactgc aagagcgctc    180

| | |
|---|---|
| aggcaccaca aatacaggaa gacctgcaaa cgctgcaggg tttcggatga ggatctcaat | 240 |
| aagttcctca caaaggcaaa cgaagaccag acaagcgtaa aagtcaaggt cgtttctgcc | 300 |
| cctaccagaa cgaaaaaggc aatgccaaaa tccgttgcga gagccccgaa acctcttgag | 360 |
| aatacagaag cggcacaggc tcaaccttct ggatctaaat tttcacctgc gataccggtt | 420 |
| tccacccaag agtcagtttc tgtcccggca tctgtttcaa catcaatatc aagcatttct | 480 |
| acaggagcaa ctgcatccgc actggtaaaa gggaatacga accccattac atccatgtct | 540 |
| gccctgttc aggcaagtgc ccccgcactt acgaagagcc agactgacag gcttgaagtc | 600 |
| ctgttaaacc caaagatga gatttccctg aattccggca agcctttcag ggagcttgag | 660 |
| tccgaattgc tctctcgcag aaaaaaagac ctgcagcaga tctacgcgga agaaagggag | 720 |
| aattatctgg ggaaactcga gcgtgaaatt accaggttct tgtggacag gggttttctg | 780 |
| gaaataaaat ccccgatcct gatccctctt gagtatatcg aaaggatggg cattgataat | 840 |
| gataccgaac tttcaaaaca gatcttcagg gttgacaaga acttctgcct gagacccatg | 900 |
| cttgctccaa acctttacaa ctacctgcgc aagcttgaca gggcctgcc tgatccaata | 960 |
| aaaatttttg aaataggccc atgctacaga aaagagtccg acggcaaaga acacctcgaa | 1020 |
| gagtttacca tgctgaactt ctgccagatg ggatcgggat gcacacggga aatcttgaa | 1080 |
| agcataatta cggacttcct gaaccacctg gaattgatt tcaagatcgt aggcgattcc | 1140 |
| tgcatggtct atggggatac ccttgatgta atgcacggag acctggaact ttcctctgca | 1200 |
| gtagtcggac ccataccgct tgaccggaa tgggtattg ataaaccctg gatagggca | 1260 |
| ggtttcgggc tcgaacgcct tctaaaggtt aaacacgact ttaaaaatat caagagagct | 1320 |
| gcaaggtccg agtcttacta taacgggatt tctaccaacc tgtaa | 1365 |

<210> SEQ ID NO 2
<211> LENGTH: 1050
<212> TYPE: DNA
<213> ORGANISM: Methanosarcina mazeii

<400> SEQUENCE: 2

| | |
|---|---|
| atgatccaga aaatggcaac cgaagaactt gacaggttcg gggagaaaat tattgaaggt | 60 |
| tttaaattgt ctgatgatga cctcagggct cttctttctc ttgaattcga agaagagctg | 120 |
| gaaaagcttt actatgtagc tagaaaggtc agaaactatt atttcggcaa cagggtgttt | 180 |
| cttaactgtt ttatttattt ctcaacttat tgtaaaaacc agtgctcttt ttgctactat | 240 |
| aactgtaaaa acgaaattaa ccgctaccgc ctgaccggtg aagaggttaa agagatgtgc | 300 |
| aaagccctga aggtgcagg cttcacatg atcgacctga caatgggaga ggatccctat | 360 |
| tactatgatg accctgaccg cttcgttgaa cttgtcagga cagtaaaaga gaactcggg | 420 |
| cttccaataa tgatttctcc gggagttatg gatgacagca ccctcctgaa agccagggaa | 480 |
| gaaggagcaa atttctttgc cctttatcag gagacttatg accgcgaact ttatggaaag | 540 |
| ctaaggggtag gtcagtcctt cgaaggaagg tttaatgccc gcaggtttgc aaaagaacag | 600 |
| gggtactgta tagaagacgg cattcttacc ggcgtaggaa atgatatcga atcaactctt | 660 |
| atatccctga aggggatgaa agcaaacaat cctgatatgg taagggtaat gacttttctg | 720 |
| cctcaggaag gaactccgct tgaaggtttc agcgatagtt caaagctttc ggagctgaaa | 780 |
| atcatagcga ttctcaggct catgttttcct gaatgcctga taccggcttc tcttgacctt | 840 |
| gaaggcatag acggcatggt gcaccgttta aatgccggag caaatattgt aacctccatc | 900 |

```
ctcccagatt cacgcctgga aggggttgcc aattacgacc gcggcatgga agagagggac    960
agggacgtta caagcgttgt caaaaggctg aaggttatgg aatggaacc tgcgccgcag    1020 gctgagtttg agagagtcct ggggtgctaa                                    1050
```

<210> SEQ ID NO 3
<211> LENGTH: 1116
<212> TYPE: DNA
<213> ORGANISM: Methanosarcina mazeii

<400> SEQUENCE: 3

```
atgagagagt cctggggtgc tagcctgaaa acaatatgcc ttataggcgg gaagctgcag    60
ggcttcgagg ctgcatacct atctaagaaa gccggaatga aagtgcttgt aatagacaaa    120
aacccgcagg cgcttataag gaattatgcg gatgagttcc agtgttttaa cataacggaa    180
gagccggaaa aactcgtcgc gatatcaaaa aatgttgatg ccatactgcc ggtaaatgaa    240
aaccttgaat gtatagaatt tctgaattct ataaaagaaa aattctcctg cccggtactt    300
ttcgattttg aagcttacag gatcagcagg gataagagaa atcaaaagaa atacttcgca    360
tccataggaa ccccgacccc tcaggacaaa ccgtcggaac caccttattt tgtaaagcct    420
ccctgcgaaa gcagcagtgt gggagcgaga ataatccatg acaggaaaga gcttaaagag    480
cttgagcccg ggatgctcat agaagaatac gttgaagggg aagtggtctc acttgaggtc    540
ataggggatg gaaataattt tgctgtggta aggaaacccc ttgtacatat cgatgacacc    600
tatgactgcc atatggtgac ccctctccct ctagaccctt ccttcaggga actatcctac    660
tcccttgcag caaacctgcc cttaaaagga attatggacg tggaagcgat ttccggcccc    720
ctggggttaa aagttattga gatagatgcc cgtttcccga gccagactcc gactgcggtc    780
tattattctt ccgggatcaa cctcatgaa ctcctgttcc gggcttttaa tggaggcata    840
gaagagatca aaactctccc tgaagacagg tactgcattt acgaacatct catgcttgca    900
gaaaatggag tacttatccc tgtgggagaa caggtcctgt ccatgggaaa tgattacggc    960
aattattatg aagaacctgg aatagagatt ttcctgtgca aggagagaa ccctgtattc    1020 accctggttt tctggggcag agacagggaa gaagctgaag ctagaaaaaa caagggctt    1080 tcgattctaa aaagccgttt cggagctgct gcataa                             1116
```

<210> SEQ ID NO 4
<211> LENGTH: 795
<212> TYPE: DNA
<213> ORGANISM: Methanosarcina mazeii

<400> SEQUENCE: 4

```
atggcacttt taaccccaga agacctggaa aatattaaca acagcttca agaagctgat    60 tctactgtcc gcagagttac agggcttgat ataaaaggta tctgtaaaga tttctacggc    120
acaactccat gctgtgaaaa agtaggtatc gtgcctgtga cctcagggaa cgggatcata    180
gggagctttt ccgaatccct gaatgcaatt gccgggtatt cgggtttga cagttttatt    240 actgatatgc ctgacgtcag cggatattat gaggcagtaa agaacggagc ccggatcata    300
cttatggcag atgataatac cttccttgcc cacaacctga aaaatggaaa atcgccaat    360 aaccagccgt gtacaggcat aatttatgct gaaatagctt caagataact gaaagccgat    420
tccaaagaag tgcttgccgt gggtcttggg aaggttggat tccgggagc agcccatctc    480 gtacagaaag gcttcaaggt ttacggatat gatgctgaca gaacccttct agaaaaaagc    540
gtttccagcc tcggaattat accttcaat cccgtcagcc ccgaaggcga caggcaaagg    600
```

```
aagttttcca ttattttcga agcaaccccc tgtgcagaca cgattccgga atccgtaatt    660
tcggaaaact gtgtgatttc taccctgggg atacctgtg caatctcaaa ggagctgcaa     720
aaaaagtgtg gagttgaact tgtaatggaa ccactgggga taggtacagc atcaatgctg    780
tattctgtac tctaa                                                     795
```

<210> SEQ ID NO 5
<211> LENGTH: 72
<212> TYPE: DNA
<213> ORGANISM: Methanosarcina mazeii

<400> SEQUENCE: 5

```
ggaaacctga tcatgtagat cgaatggact ctaaatccgt tcagccgggt tagattcccg     60
gggtttccgc ca                                                        72
```

<210> SEQ ID NO 6
<211> LENGTH: 223
<212> TYPE: PRT
<213> ORGANISM: Homo sapiens

<400> SEQUENCE: 6

```
Met Lys Thr Phe Ile Leu Leu Leu Trp Val Leu Leu Leu Trp Val Ile
1               5                   10                  15

Phe Leu Leu Pro Gly Ala Thr Ala Gln Pro Glu Arg Asp Cys Arg Val
            20                  25                  30

Ser Ser Phe Arg Val Lys Glu Asn Phe Asp Lys Ala Arg Phe Ser Gly
        35                  40                  45

Thr Trp Tyr Ala Met Ala Lys Lys Asp Pro Glu Gly Leu Phe Leu Gln
    50                  55                  60

Asp Asn Ile Val Ala Glu Phe Ser Val Asp Thr Gly Gln Met Ser
65                  70                  75                  80

Ala Thr Ala Lys Gly Arg Val Arg Leu Leu Asn Asn Trp Asp Val Cys
                85                  90                  95

Ala Asp Met Val Gly Thr Phe Thr Asp Thr Glu Asp Pro Ala Lys Phe
            100                 105                 110

Lys Met Lys Tyr Trp Gly Val Ala Ser Phe Leu Gln Lys Gly Asn Asp
        115                 120                 125

Asp His Trp Ile Val Asp Thr Asp Tyr Asp Thr Tyr Ala Val Gln Tyr
    130                 135                 140

Ser Cys Arg Leu Leu Asn Leu Asp Gly Thr Cys Ala Asp Ser Tyr Ser
145                 150                 155                 160

Phe Val Phe Ser Arg Asp Pro Asn Gly Leu Pro Pro Glu Ala Gln Lys
                165                 170                 175

Ile Val Arg Gln Arg Gln Glu Glu Leu Cys Leu Ala Arg Gln Tyr Arg
            180                 185                 190

Leu Ile Val His Asn Gly Tyr Cys Asp Gly Arg Ser Glu Arg Asn Leu
        195                 200                 205

Leu Asp Tyr Lys Asp Asp Asp Lys His His His His His
    210                 215                 220
```

<210> SEQ ID NO 7
<211> LENGTH: 672
<212> TYPE: DNA
<213> ORGANISM: Homo sapiens

<400> SEQUENCE: 7

```
atgaaaacat tcatactcct gctctgggta ctgctgctct gggttatctt cctgcttccc    60
ggtgccactg ctcagcctga gcgcgactgc cgagtgagca gcttccgagt caaggagaac   120
ttcgacaagg ctcgcttctc tgggacctgg tacgccatgg ccaagaagga ccccgagggc   180
ctctttctgc aggacaacat cgtcgcggag ttctccgtgg acgagaccgg ccagatgagc   240
gccacagcca agggccgagt ccgtcttttg aataactggg acgtgtgcgc agacatggtg   300
ggcaccttca cagacaccga ggaccctgcc aagttcaaga tgaagtactg gggcgtagcc   360
tcctttctcc agaaaggaaa tgatgaccac tggatcgtcg acacagacta cgacacgtat   420
gccgtgcagt actcctgccg cctcctgaac ctcgatggca cctgtgctga cagctactcc   480
ttcgtgtttt cccgggaccc caacggcctg cccccagaag cgcagaagat tgtaaggcag   540
cggcaggagg agctgtgcct ggccaggcag tacaggctga tcgtccacaa cggttactgc   600
gatggcagat cagaaagaaa ccttttggac tataaagacg atgacgataa gcatcaccat   660
caccatcact aa                                                       672
```

<210> SEQ ID NO 8
<211> LENGTH: 672
<212> TYPE: DNA
<213> ORGANISM: Homo sapiens

<400> SEQUENCE: 8

```
atgaaaacat tcatactcct gctctgggta ctgctgctct gggttatctt cctgcttccc    60
ggtgccactg ctcagcctga gcgcgactgc cgagtgagca gcttccgagt caaggagaac   120
ttcgacaagg ctcgcttctc tgggacctgg taggccatgg ccaagaagga ccccgagggc   180
ctctttctgc aggacaacat cgtcgcggag ttctccgtgg acgagaccgg ccagatgagc   240
gccacagcca agggccgagt ccgtcttttg aataactggg acgtgtgcgc agacatggtg   300
ggcaccttca cagacaccga ggaccctgcc aagttcaaga tgaagtactg gggcgtagcc   360
tcctttctcc agaaaggaaa tgatgaccac tggatcgtcg acacagacta cgacacgtat   420
gccgtgcagt actcctgccg cctcctgaac ctcgatggca cctgtgctga cagctactcc   480
ttcgtgtttt cccgggaccc caacggcctg cccccagaag cgcagaagat tgtaaggcag   540
cggcaggagg agctgtgcct ggccaggcag tacaggctga tcgtccacaa cggttactgc   600
gatggcagat cagaaagaaa ccttttggac tataaagacg atgacgataa gcatcaccat   660
caccatcact aa                                                       672
```

<210> SEQ ID NO 9
<211> LENGTH: 672
<212> TYPE: DNA
<213> ORGANISM: Homo sapiens

<400> SEQUENCE: 9

```
atgaaaacat tcatactcct gctctgggta ctgctgctct gggttatctt cctgcttccc    60
ggtgccactg ctcagcctga gcgcgactgc cgagtgagca gcttccgagt caaggagaac   120
ttcgacaagg ctcgcttctc tgggacctgg tacgccatgg ccaagaagga ccccgagggc   180
ctctagctgc aggacaacat cgtcgcggag ttctccgtgg acgagaccgg ccagatgagc   240
gccacagcca agggccgagt ccgtcttttg aataactggg acgtgtgcgc agacatggtg   300
ggcaccttca cagacaccga ggaccctgcc aagttcaaga tgaagtactg gggcgtagcc   360
tcctttctcc agaaaggaaa tgatgaccac tggatcgtcg acacagacta cgacacgtat   420
gccgtgcagt actcctgccg cctcctgaac ctcgatggca cctgtgctga cagctactcc   480
```

```
ttcgtgtttt cccgggaccc caacggcctg cccccagaag cgcagaagat tgtaaggcag      540
cggcaggagg agctgtgcct ggccaggcag tacaggctga tcgtccacaa cggttactgc      600
gatggcagat cagaaagaaa ccttttggac tataaagacg atgacgataa gcatcaccat      660
caccatcact aa                                                          672

<210> SEQ ID NO 10
<211> LENGTH: 672
<212> TYPE: DNA
<213> ORGANISM: Homo sapiens

<400> SEQUENCE: 10
atgaaaacat tcatactcct gctctgggta ctgctgctct ggttatctt cctgcttccc       60 ggtgccactg ctcagcctga gcgcgactgc cgagtgagca gcttccgagt caaggagaac      120
ttcgacaagg ctcgcttctc tgggacctgg tacgccatgg ccaagaagga ccccgagggc      180
ctctttctgc aggacaacat cgtcgcggag ttctccgtgg acgagaccgg ccagatgagc      240
gccacagcca agggccgagt ccgtcttttg aataactagg acgtgtgcgc agacatggtg      300
ggcaccttca cagacaccga ggaccctgcc aagttcaaga tgaagtactg gggcgtagcc      360
tcctttctcc agaaaggaaa tgatgaccac tggatcgtcg acacagacta cgacacgtat      420
gccgtgcagt actcctgccg cctcctgaac ctcgatggca cctgtgctga cagctactcc      480
ttcgtgtttt cccgggaccc caacggcctg cccccagaag cgcagaagat tgtaaggcag      540
cggcaggagg agctgtgcct ggccaggcag tacaggctga tcgtccacaa cggttactgc      600
gatggcagat cagaaagaaa ccttttggac tataaagacg atgacgataa gcatcaccat      660
caccatcact aa                                                          672

<210> SEQ ID NO 11
<211> LENGTH: 672
<212> TYPE: DNA
<213> ORGANISM: Homo sapiens

<400> SEQUENCE: 11
atgaaaacat tcatactcct gctctgggta ctgctgctct ggttatctt cctgcttccc       60 ggtgccactg ctcagcctga gcgcgactgc cgagtgagca gcttccgagt caaggagaac      120
ttcgacaagg ctcgcttctc tgggacctgg tacgccatgg ccaagaagga ccccgagggc      180
ctctttctgc aggacaacat cgtcgcggag ttctccgtgg acgagaccgg ccagatgagc      240
gccacagcca agggccgagt ccgtcttttg aataactggg acgtgtgcgc agacatggtg      300
ggcaccttca cagacaccga ggaccctgcc aagttcaaga tgaagtagtg gggcgtagcc      360
tcctttctcc agaaaggaaa tgatgaccac tggatcgtcg acacagacta cgacacgtat      420
gccgtgcagt actcctgccg cctcctgaac ctcgatggca cctgtgctga cagctactcc      480
ttcgtgtttt cccgggaccc caacggcctg cccccagaag cgcagaagat tgtaaggcag      540
cggcaggagg agctgtgcct ggccaggcag tacaggctga tcgtccacaa cggttactgc      600
gatggcagat cagaaagaaa ccttttggac tataaagacg atgacgataa gcatcaccat      660
caccatcact aa                                                          672

<210> SEQ ID NO 12
<211> LENGTH: 672
<212> TYPE: DNA
<213> ORGANISM: Homo sapiens
```

<400> SEQUENCE: 12

```
atgaaaacat tcatactcct gctctgggta ctgctgctct gggttatctt cctgcttccc      60
ggtgccactg ctcagcctga gcgcgactgc cgagtgagca gcttccgagt caaggagaac     120
ttcgacaagg ctcgcttctc tgggacctgg tacgccatgg ccaagaagga ccccgagggc     180
ctctttctgc aggacaacat cgtcgcggag ttctccgtgg acgagaccgg ccagatgagc     240
gccacagcca agggccgagt ccgtcttttg aataactggg acgtgtgcgc agacatggtg     300
ggcaccttca cagacaccga ggaccctgcc aagttcaaga tgaagtacta gggcgtagcc     360
tcctttctcc agaaaggaaa tgatgaccac tggatcgtcg acacagacta cgacacgtat     420
gccgtgcagt actcctgccg cctcctgaac ctcgatggca cctgtgctga cagctactcc     480
ttcgtgtttt cccgggaccc caacggcctg cccccagaag cgcagaagat tgtaaggcag     540
cggcaggagg agctgtgcct ggccaggcag tacaggctga tcgtccacaa cggttactgc     600
gatggcagat cagaaagaaa cctttggac tataaagacg atgacgataa gcatcaccat     660
caccatcact aa                                                         672
```

<210> SEQ ID NO 13
<211> LENGTH: 672
<212> TYPE: DNA
<213> ORGANISM: Homo sapiens

<400> SEQUENCE: 13

```
atgaaaacat tcatactcct gctctgggta ctgctgctct gggttatctt cctgcttccc      60
ggtgccactg ctcagcctga gcgcgactgc cgagtgagca gcttccgagt caaggagaac     120
ttcgacaagg ctcgcttctc tgggacctgg tacgccatgg ccaagaagga ccccgagggc     180
ctctttctgc aggacaacat cgtcgcggag ttctccgtgg acgagaccgg ccagatgagc     240
gccacagcca agggccgagt ccgtcttttg aataactggg acgtgtgcgc agacatggtg     300
ggcaccttca cagacaccga ggaccctgcc aagttcaaga tgaagtactg ggcgtagcc     360
tcctagctcc agaaaggaaa tgatgaccac tggatcgtcg acacagacta cgacacgtat     420
gccgtgcagt actcctgccg cctcctgaac ctcgatggca cctgtgctga cagctactcc     480
ttcgtgtttt cccgggaccc caacggcctg cccccagaag cgcagaagat tgtaaggcag     540
cggcaggagg agctgtgcct ggccaggcag tacaggctga tcgtccacaa cggttactgc     600
gatggcagat cagaaagaaa cctttggac tataaagacg atgacgataa gcatcaccat     660
caccatcact aa                                                         672
```

<210> SEQ ID NO 14
<211> LENGTH: 672
<212> TYPE: DNA
<213> ORGANISM: Homo sapiens

<400> SEQUENCE: 14

```
atgaaaacat tcatactcct gctctgggta ctgctgctct gggttatctt cctgcttccc      60
ggtgccactg ctcagcctga gcgcgactgc cgagtgagca gcttccgagt caaggagaac     120
ttcgacaagg ctcgcttctc tgggacctgg tacgccatgg ccaagaagga ccccgagggc     180
ctctttctgc aggacaacat cgtcgcggag ttctccgtgg acgagaccgg ccagatgagc     240
gccacagcca agggccgagt ccgtcttttg aataactggg acgtgtgcgc agacatggtg     300
ggcaccttca cagacaccga ggaccctgcc aagttcaaga tgaagtactg ggcgtagcc     360
tcctttctcc agaaaggaaa tgatgaccac tggatcgtcg acacagacta cgacacgtag     420
```

```
gccgtgcagt actcctgccg cctcctgaac ctcgatggca cctgtgctga cagctactcc    480
ttcgtgtttt cccgggaccc caacggcctg cccccagaag cgcagaagat tgtaaggcag    540
cggcaggagg agctgtgcct ggccaggcag tacaggctga tcgtccacaa cggttactgc    600
gatggcagat cagaaagaaa cctttttggac tataaagacg atgacgataa gcatcaccat    660
caccatcact aa                                                        672
```

<210> SEQ ID NO 15
<211> LENGTH: 672
<212> TYPE: DNA
<213> ORGANISM: Homo sapiens

<400> SEQUENCE: 15

```
atgaaaacat tcatactcct gctctgggta ctgctgctct gggttatctt cctgcttccc    60
ggtgccactg ctcagcctga gcgcgactgc cgagtgagca gcttccgagt caaggagaac    120
ttcgacaagg ctcgcttctc tgggacctgg tacgccatgg ccaagaagga ccccgagggc    180
ctctttctgc aggacaacat cgtcgcggag ttctccgtgg acgagaccgg ccagatgagc    240
gccacagcca agggccgagt ccgtcttttg aataactggg acgtgtgcgc agacatggtg    300
ggcaccttca cagacaccga ggaccctgcc aagttcaaga tgaagtactg ggcgtagcc     360 tcctttctcc agaaaggaaa tgatgaccac tggatcgtcg acacagacta cgacacgtat    420
gccgtgcagt actcctgccg cctcctgaac ctcgatggca cctgtgctga cagctactcc    480
ttcgtgtttt cccgggaccc caacggcctg cccccagaag cgcagaagat tgtaaggcag    540
cggcaggagg agctgtgcct ggccaggcag tagaggctga tcgtccacaa cggttactgc    600
gatggcagat cagaaagaaa cctttttggac tataaagacg atgacgataa gcatcaccat    660
caccatcact aa                                                        672
```

<210> SEQ ID NO 16
<211> LENGTH: 672
<212> TYPE: DNA
<213> ORGANISM: Homo sapiens

<400> SEQUENCE: 16

```
atgaaaacat tcatactcct gctctgggta ctgctgctct gggttatctt cctgcttccc    60
ggtgccactg ctcagcctga gcgcgactgc cgagtgagca gcttccgagt caaggagaac    120
ttcgacaagg ctcgcttctc tgggacctgg tacgccatgg ccaagaagga ccccgagggc    180
ctctttctgc aggacaacat cgtcgcggag ttctccgtgg acgagaccgg ccagatgagc    240
gccacagcca agggccgagt ccgtcttttg aataactggg acgtgtgcgc agacatggtg    300
ggcaccttca cagacaccga ggaccctgcc aagttcaaga tgaagtactg ggcgtagcc     360 tcctttctcc agaaaggaaa tgatgaccac tggatcgtcg acacagacta cgacacgtat    420
gccgtgcagt actcctgccg cctcctgaac ctcgatggca cctgtgctga cagctactcc    480
ttcgtgtttt cccgggaccc caacggcctg cccccagaag cgcagaagat tgtaaggcag    540
cggcaggagg agctgtgcct ggccaggcag tacaggctga tcgtccacaa cggttagtgc    600
gatggcagat cagaaagaaa cctttttggac tataaagacg atgacgataa gcatcaccat    660
caccatcact aa                                                        672
```

<210> SEQ ID NO 17
<211> LENGTH: 10
<212> TYPE: PRT

```
<213> ORGANISM: Homo sapiens
<220> FEATURE:
<221> NAME/KEY: MOD_RES
<222> LOCATION: (7)..(7)
<223> OTHER INFORMATION: Xaa is a PCL residue

<400> SEQUENCE: 17

Tyr Trp Gly Val Ala Ser Xaa Leu Gln Lys
1               5                   10

<210> SEQ ID NO 18
<211> LENGTH: 29
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Xaa is Cyc residue

<400> SEQUENCE: 18

Lys Asp Pro Glu Gly Leu Xaa Leu Gln Asp Asn Ile Val Ala Glu Phe
1               5                   10                  15

Ser Val Asp Glu Thr Gly Gln Met Ser Ala Thr Ala Lys
            20                  25

<210> SEQ ID NO 19
<211> LENGTH: 166
<212> TYPE: PRT
<213> ORGANISM: Homo sapiens

<400> SEQUENCE: 19

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 20
<211> LENGTH: 166
<212> TYPE: PRT
<213> ORGANISM: mouse

<400> SEQUENCE: 20

Ala Pro Pro Arg Leu Ile Cys Asp Ser Arg Val Leu Glu Arg Tyr Leu
```

```
1               5                   10                  15
Leu Glu Ala Lys Glu Ala Glu Asn Val Thr Met Gly Cys Ala Glu Gly
            20                  25                  30

Pro Arg Leu Ser Glu Asn Ile Thr Val Pro Asp Thr Lys Val Asn Phe
            35                  40                  45

Tyr Ala Trp Lys Arg Met Glu Val Glu Glu Gln Ala Ile Glu Val Trp
            50                  55                  60

Gln Gly Leu Ser Leu Leu Ser Glu Ala Ile Leu Gln Ala Gln Ala Leu
 65                 70                  75                  80

Leu Ala Asn Ser Ser Gln Pro Pro Glu Thr Leu Gln Leu His Ile Asp
                85                  90                  95

Lys Ala Val Ser Gly Leu Arg Ser Leu Thr Ser Leu Leu Arg Val Leu
                100                 105                 110

Gly Ala Gln Lys Glu Leu Met Ser Pro Pro Asp Thr Thr Pro Pro Ala
                115                 120                 125

Pro Leu Arg Thr Leu Thr Val Asp Thr Phe Cys Lys Leu Phe Arg Val
                130                 135                 140

Tyr Ala Asn Phe Leu Arg Gly Lys Leu Lys Leu Tyr Thr Gly Glu Val
145                 150                 155                 160

Cys Arg Arg Gly Asp Arg
                165

<210> SEQ ID NO 21
<211> LENGTH: 19
<212> TYPE: PRT
<213> ORGANISM: Artificial Sequence
<220> FEATURE:
<223> OTHER INFORMATION: synthetic construct

<400> SEQUENCE: 21

Met Gly Asp Ser Lys Ile His His His His His Glu Asn Leu Tyr
 1               5                   10                  15

Phe Gln Gly

<210> SEQ ID NO 22
<211> LENGTH: 301
<212> TYPE: PRT
<213> ORGANISM: Homo sapiens

<400> SEQUENCE: 22

Met Gly Ser Asp Lys Ile His His His His His His Glu Asn Leu Tyr
 1               5                   10                  15

Phe Gln Gly Ser Leu Leu Val Asn Pro Glu Gly Pro Thr Leu Met Arg
            20                  25                  30

Leu Asn Ser Val Gln Ser Ser Glu Arg Pro Leu Phe Leu Val His Pro
            35                  40                  45

Ile Glu Gly Ser Thr Thr Val Phe His Ser Leu Ala Ser Arg Leu Ser
            50                  55                  60

Ile Pro Thr Tyr Gly Leu Gln Cys Thr Arg Ala Ala Pro Leu Asp Ser
 65                 70                  75                  80

Ile His Ser Leu Ala Ala Tyr Tyr Ile Asp Cys Ile Arg Gln Val Gln
                85                  90                  95

Pro Glu Gly Pro Tyr Arg Val Ala Gly Tyr Ser Tyr Gly Ala Cys Val
                100                 105                 110

Ala Phe Glu Met Cys Ser Gln Leu Gln Ala Gln Gln Ser Pro Ala Pro
                115                 120                 125
```

```
Thr His Asn Ser Leu Phe Leu Phe Asp Gly Ser Pro Thr Tyr Val Leu
    130                 135                 140

Ala Tyr Thr Gln Ser Tyr Arg Ala Lys Leu Thr Pro Gly Ser Glu Ala
145                 150                 155                 160

Glu Ala Glu Thr Glu Ala Ile Cys Phe Phe Val Gln Gln Phe Thr Asp
                165                 170                 175

Met Glu His Asn Arg Val Leu Glu Ala Leu Leu Pro Leu Lys Gly Leu
                180                 185                 190

Glu Glu Arg Val Ala Ala Ala Val Asp Leu Ile Ile Lys Ser His Gln
            195                 200                 205

Gly Leu Asp Arg Gln Glu Leu Ser Phe Ala Ala Arg Ser Phe Tyr Tyr
        210                 215                 220

Lys Leu Arg Ala Ala Glu Gln Tyr Thr Pro Lys Ala Lys Tyr His Gly
225                 230                 235                 240

Asn Val Met Leu Leu Arg Ala Lys Thr Gly Gly Ala Tyr Gly Glu Asp
                245                 250                 255

Leu Gly Ala Asp Tyr Asn Leu Ser Gln Val Cys Asp Gly Lys Val Ser
                260                 265                 270

Val His Val Ile Glu Gly Asp His Arg Thr Leu Leu Glu Gly Ser Gly
            275                 280                 285

Leu Glu Ser Ile Ile Ser Ile Ile His Ser Ser Leu Ala
        290                 295                 300

<210> SEQ ID NO 23
<211> LENGTH: 18
<212> TYPE: PRT
<213> ORGANISM: Artificial Sequence
<220> FEATURE:
<223> OTHER INFORMATION: synthetic construct

<400> SEQUENCE: 23

Met Gly Ser Ser His His His His His His Leu Glu Val Leu Phe Gln
1               5                   10                  15

Gly Pro

<210> SEQ ID NO 24
<211> LENGTH: 125
<212> TYPE: PRT
<213> ORGANISM: Homo sapiens

<400> SEQUENCE: 24

Met Gly Ser Ser His His His His His His Leu Glu Val Leu Phe Gln
1               5                   10                  15

Gly Pro Gly Val Gln Val Glu Thr Ile Ser Pro Gly Asp Gly Arg Thr
            20                  25                  30

Phe Pro Lys Arg Gly Gln Thr Cys Val Val His Tyr Thr Gly Met Leu
        35                  40                  45

Glu Asp Gly Lys Lys Phe Asp Ser Ser Arg Asp Arg Asn Lys Pro Phe
    50                  55                  60

Lys Phe Met Leu Gly Lys Gln Glu Val Ile Arg Gly Trp Glu Glu Gly
65                  70                  75                  80

Val Ala Gln Met Ser Val Gly Gln Arg Ala Lys Leu Thr Ile Ser Pro
                85                  90                  95

Asp Tyr Ala Tyr Gly Ala Thr Gly His Pro Gly Ile Ile Pro Pro His
            100                 105                 110

Ala Thr Leu Val Phe Asp Val Glu Leu Leu Lys Leu Glu
        115                 120                 125
```

<210> SEQ ID NO 25
<211> LENGTH: 196
<212> TYPE: PRT
<213> ORGANISM: Homo sapiens

<400> SEQUENCE: 25

Met Gly Ser Ser His His His His His Ser Ser Gly Glu Asn Leu
1               5                   10                  15

Tyr Phe Gln Gly Asp Ser Ser Pro Leu Leu Gln Phe Gly Gly Val Arg
                20                  25                  30

Gln Arg Tyr Leu Tyr Thr Asp Asp Ala Gln Gln Thr Glu Ala His Leu
            35                  40                  45

Glu Ile Arg Glu Asp Gly Thr Val Gly Gly Ala Ala Asp Gln Ser Pro
50                  55                  60

Glu Ser Leu Leu Gln Leu Lys Ala Leu Lys Pro Gly Val Ile Gln Ile
65                  70                  75                  80

Leu Gly Val Lys Thr Ser Arg Phe Leu Cys Gln Arg Pro Asp Gly Ala
                85                  90                  95

Leu Tyr Gly Ser Leu His Phe Asp Pro Glu Ala Cys Ser Phe Arg Glu
            100                 105                 110

Leu Leu Leu Glu Asp Gly Tyr Asn Val Tyr Gln Ser Glu Ala His Gly
        115                 120                 125

Leu Pro Leu His Leu Pro Gly Asn Lys Ser Pro His Arg Asp Pro Ala
    130                 135                 140

Pro Arg Gly Pro Ala Arg Phe Leu Pro Leu Pro Gly Leu Pro Pro Ala
145                 150                 155                 160

Leu Pro Glu Pro Pro Gly Ile Leu Ala Pro Gln Pro Pro Asp Val Gly
                165                 170                 175

Ser Ser Asp Pro Leu Ser Met Val Gly Pro Ser Gln Gly Arg Ser Pro
            180                 185                 190

Ser Tyr Ala Ser
        195

<210> SEQ ID NO 26
<211> LENGTH: 173
<212> TYPE: PRT
<213> ORGANISM: mouse

<400> SEQUENCE: 26

Met Arg Gly Ser His His His His His Gly Ser Gly Ile Glu Gly
1               5                   10                  15

Arg Leu Arg Ser Ser Gln Asn Ser Ser Asp Lys Pro Val Ala His
                20                  25                  30

Val Val Ala Asn His Gln Val Glu Glu Gln Leu Trp Leu Ser Gln Arg
            35                  40                  45

Ala Asn Ala Leu Leu Ala Asn Gly Met Asp Leu Lys Asp Asn Gln Leu
        50                  55                  60

Val Val Pro Ala Asp Gly Leu Tyr Leu Val Tyr Ser Gln Val Leu Phe
65                  70                  75                  80

Lys Gly Gln Gly Cys Pro Asp Tyr Val Leu Leu Thr His Thr Val Ser
                85                  90                  95

Arg Phe Ala Ile Ser Tyr Gln Glu Lys Val Asn Leu Leu Ser Ala Val
            100                 105                 110

Lys Ser Pro Cys Pro Lys Asp Thr Pro Glu Gly Ala Glu Leu Lys Pro
        115                 120                 125

```
Trp Tyr Glu Pro Ile Tyr Leu Gly Gly Val Phe Gln Leu Glu Lys Gly
            130                 135                 140

Asp Gln Leu Ser Ala Glu Val Asn Leu Pro Lys Tyr Leu Asp Phe Ala
145                 150                 155                 160

Glu Ala Ser Gly Gln Val Tyr Phe Gly Val Ile Ala Leu
                165                 170

<210> SEQ ID NO 27
<211> LENGTH: 62
<212> TYPE: PRT
<213> ORGANISM: mouse

<400> SEQUENCE: 27

Met Asn Ser Tyr Pro Gly Cys Pro Ser Ser Tyr Asp Gly Tyr Cys Leu
1               5                   10                  15

Asn Gly Gly Val Cys Met His Ile Glu Ser Leu Asp Ser Tyr Thr Cys
            20                  25                  30

Asn Cys Val Ile Gly Tyr Ser Gly Asp Arg Cys Gln Thr Arg Asp Leu
        35                  40                  45

Arg Trp Trp Glu Leu Arg Leu Glu His His His His His
    50                  55                  60

<210> SEQ ID NO 28
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: D-alanine
<220> FEATURE:
<221> NAME/KEY: MOD_RES
<222> LOCATION: (4)..(4)
<223> OTHER INFORMATION: cyclohexyl-alanine
<220> FEATURE:
<221> NAME/KEY: MOD_RES
<222> LOCATION: (4)..(4)
<223> OTHER INFORMATION: cyclohexyl-alanine
<220> FEATURE:
<221> NAME/KEY: MOD_RES
<222> LOCATION: (13)..(13)
<223> OTHER INFORMATION: D-alanine

<400> SEQUENCE: 28

Gly Xaa Lys Xaa Val Ala Ala Trp Thr Leu Lys Ala Xaa Gly
1               5                   10

<210> SEQ ID NO 29
<211> LENGTH: 19
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (7)..(7)
<223> OTHER INFORMATION: D-alanine
<220> FEATURE:
<221> NAME/KEY: MOD_RES
<222> LOCATION: (9)..(9)
<223> OTHER INFORMATION: cyclohexyl-alanine
<220> FEATURE:
<221> NAME/KEY: MOD_RES
<222> LOCATION: (9)..(9)
<223> OTHER INFORMATION: cyclohexyl-alanine
<220> FEATURE:
```

```
<221> NAME/KEY: MOD_RES
<222> LOCATION: (18)..(18)
<223> OTHER INFORMATION: D-alanine

<400> SEQUENCE: 29

Ala Gly Ser Arg Ser Gly Xaa Lys Xaa Val Ala Ala Trp Thr Leu Lys
1               5                   10                  15

Ala Xaa Gly

<210> SEQ ID NO 30
<211> LENGTH: 20
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(20)
<223> OTHER INFORMATION: phosphothioate backbone

<400> SEQUENCE: 30
tccatgacgt tcctgacgtt                                            20

<210> SEQ ID NO 31
<211> LENGTH: 22
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(22)
<223> OTHER INFORMATION: phosphothioate backbone

<400> SEQUENCE: 31
tcgtcgtttt cggcgcgcgc cg                                         22

<210> SEQ ID NO 32
<211> LENGTH: 22
<212> TYPE: PRT
<213> ORGANISM: mouse
<220> FEATURE:
<221> NAME/KEY: MOD_RES
<222> LOCATION: (11)..(11)
<223> OTHER INFORMATION: PCL

<400> SEQUENCE: 32

Met Asn Ser Tyr Pro Gly Cys Pro Ser Ser Xaa Asp Gly Tyr Cys Leu
1               5                   10                  15

Asn Gly Gly Val Cys Met
            20

<210> SEQ ID NO 33
<211> LENGTH: 22
<212> TYPE: PRT
<213> ORGANISM: mouse
<220> FEATURE:
<221> NAME/KEY: MISC_FEATURE
<222> LOCATION: (11)..(11)
<223> OTHER INFORMATION: pyrrolysine

<400> SEQUENCE: 33

Met Asn Ser Tyr Pro Gly Cys Pro Ser Ser Xaa Asp Gly Tyr Cys Leu
1               5                   10                  15

Asn Gly Gly Val Cys Met
            20
```

```
<210> SEQ ID NO 34
<211> LENGTH: 14
<212> TYPE: PRT
<213> ORGANISM: mouse
<220> FEATURE:
<221> NAME/KEY: MISC_FEATURE
<222> LOCATION: (3)..(3)
<223> OTHER INFORMATION: pyrrolysine

<400> SEQUENCE: 34

Asn His Xaa Val Glu Glu Gln Leu Glu Trp Leu Ser Gln Arg
1               5                   10

<210> SEQ ID NO 35
<211> LENGTH: 14
<212> TYPE: PRT
<213> ORGANISM: mouse
<220> FEATURE:
<221> NAME/KEY: MOD_RES
<222> LOCATION: (3)..(3)
<223> OTHER INFORMATION: PCL

<400> SEQUENCE: 35

Asn His Xaa Val Glu Glu Gln Leu Glu Trp Leu Ser Gln Arg
1               5                   10
```

BIOSYNTHETICALLY GENERATED PYRROLINE-CARBOXY-LYSINE AND SITE SPECIFIC PROTEIN MODIFICATIONS VIA CHEMICAL DERIVATIZATION OF PYRROLINE-CARBOXY-LYSINE AND PYRROLYSINE RESIDUES

CROSS-REFERENCE TO RELATED APPLICATIONS

This application is a 371 U.S. national phase application of international application number PCT/US2009/061954 filed 23 Oct. 2009, which application claims the benefit of priority under 35 U.S.C. §119(e) to U.S. Provisional Patent Application No. 61/108,434, filed Oct. 24, 2008. The disclosures of which are incorporated herein by reference in their entirety and for all purposes.

FIELD OF THE INVENTION

The invention relates to the selective introduction of genetically encoded amino acids into proteins. The invention also relates to the chemical derivatization of such amino acids.

BACKGROUND OF THE INVENTION

Methylamine methyltransferases of methanogenic archaea of the family Methanosarcina naturally contain pyrrolysine (PYL). Pyrrolysine is a lysine analogue co-translationally incorporated at in-frame UAG codons in the respective mRNA, and it is considered the $22^{nd}$ natural amino acid.

DESCRIPTION OF FIGURES

FIG. 11A shows CYC incorporation at different sites in hRBP4 as detected by SDS-PAGE and Western blotting with anti-His-tag and anti-RBP4 antibodies. FIG. 11B shows SDS-PAGE results of purified hRBP4 Phe62CYC (mutant #2). FIG. 11C shows a mass spectrum of hRBP4 Phe62CYC.

FIG. 13A is a Western blot of unpurified samples with anti-His-tag antibody and FIG. 13B is a SDS-PAGE gel of Ni-NTA purified protein.

FIG. 18 shows the SDS-PAGE (A) and the mass spectra (B) for PCL incorporation.

FIG. 19 shows the SDS-PAGE (A) and the mass spectra for PCL incorporation (B) and a crystal of FKBP12-I90PCL (C).

FIG. 21A shows SDS-PAGE analysis of PYL- or PCL-incorporation into mTNF-α with glutamine Gln21 (CAA) mutated to a TAG stop codon in the presence and absence of pylB. FIG. 21B SDS-PAGE evaluating the purity of the protein. FIG. 21C are intact mass spectra of mEGF Tyr10TAG expressed in *Escherichia coli* suggesting a mixture of proteins with PYL and PCL incorporated (FIG. 21C, bottom) and predominantly PCL (FIG. 21C, top).

FIGS. 33C and 33D show derivatization of FAS-TE Tyr2454PCL with 2.4 kDa 2-AAP-PEG (TU3205-048) (FIG. 33C derivatized at room temperature and FIG. 33D at 4° C.

FIG. 44A shows the mass spectrum of crosslinked FGF-21, where the reaction conditions are altered from those used in FIG. 43. FIG. 44B shows the SDS-PAGE for reactions at pH 5 and pH 7.5.

FIG. 47A shows the ESI mass spectrometric analysis of mEGF-Y10PCL conjugated with biotin. FIG. 47B shows the Western blot of mEGF-Y10PCL-ABA-biotin conjugate using a horseradish peroxidase (HRP) conjugated goat anti-biotin antibody. FIG. 47C shows the ESI mass spectrometric analysis of mEGF-Y10PCL conjugated with fluorescein. FIG. 47D shows the ESI mass spectrometric analysis of mEGF-Y10PCL conjugated with a disaccharide.

FIG. 48A shows the ESI mass spectrometric analysis of mTNF-Q21PCL conjugated with a mono-nitrophenyl hapten. FIG. 48B shows the ESI mass spectrometric analysis of mEGF-Y10PCL conjugated with a mono-nitrophenyl hapten. FIG. 48C shows the ESI mass spectrometric analysis of mTNF-Q21PCL conjugated with a di-nitrophenyl hapten. FIG. 48D shows the ESI mass spectrometric analysis of mEGF-Y10PCL conjugated with a di-nitrophenyl hapten.

FIG. 49A shows the ESI mass spectrometric analysis of mEGF-Y10PCL conjugated with a TLR7 agonist, FIG. 49B shows the ESI mass spectrometric analysis of mEGF-Y10PCL conjugated with a phospholipid.

FIG. 50A and FIG. 50B show the MALDI-TOF mass spectrometric analysis of mTNF-Q21PCL conjugation with PX2-PADRE at two different pH values (FIG. 50A: pH 5.0; FIG. 50B: pH 7.5). FIG. 50C shows the ESI mass spectrometric analysis of mTNF-Q21PCL conjugation with BHA-exPADRE.

FIG. 51 is an ESI mass spectrum showing the coupling of BHA-exPADRE to mEGF-Y10PCL.

FIG. 52A is a gel shift assay of the coupling of BHA-BG1 (7.4 kDa) and BHA-BG2 (7.4 kDa) to mTNF-Q21PCL (19.3 kDa). FIG. 52B is a gel shift assay of the coupling of BHA-BG2 (7.4 kDa) to mEGF-Y10PCL (7.2 kDa).

FIG. 53 illustrates an embodiment of such site-specific oriented attachment.

FIG. 54A shows the ESI mass spectrometric analysis of hFGF21-K150PCL coupled to 2-ABA and then reduced with 20 mM NaCNBH$_3$ for 1 hour. FIG. 54B shows the ESI mass spectrometric analysis of the reduced hFGF21-K150PCL 2-ABA conjugate after being dialyzed into 10 mM phosphate buffer (pH 7.5) and incubated at 50° C. for 1 day.

FIG. 55 demonstrates the stability of the PCL linkage for pegylated FGF21 with and without reduction using NaCNBH$_3$. An SDS-PAGE gel of reduced samples and non-reduced samples are shown in FIG. 55A. In addition, FIG. 55B shows an SDS-PAGE gel for non-reduced samples incubated at for 60 hours at 4° C., room temperature, 37° C. and 50° C., and 95° C.

FIG. 57A is a proposed structure of the product resulting from the reaction between PCL-A and 2-ABA. FIG. 57B shows proposed equilibrium structures of the product resulting from the reaction between PCL-A and 2-ABA. FIG. 57C is a proposed structure of the reduced product.

SUMMARY OF THE INVENTION

Figure 1:
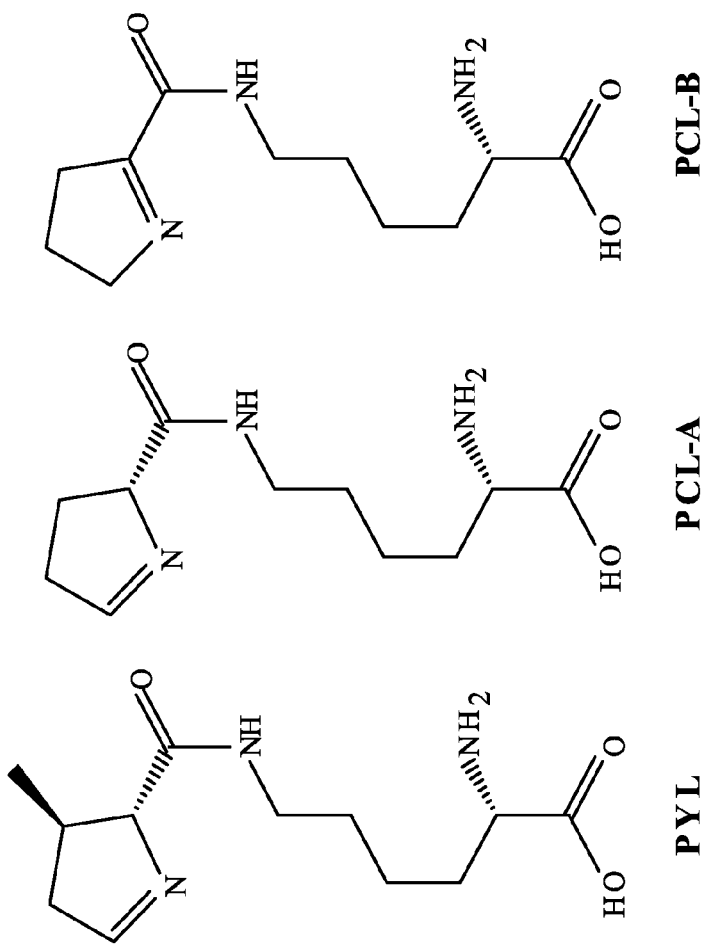
FIG. 1. Structures of pyrrolysine (PYL) and the pyrrolysine analogue pyrroline-carboxy-lysine (PCL: PCL-A or PCL-B).

Provided herein are proteins and/or polypeptides having one or more PCL incorporated therein, wherein the PCL is biosynthetically generated and incorporated into the proteins and/or polypeptides. Also provided herein are proteins and/or polypeptides having one or more pyrrolysine (PYL) incorporated therein, wherein the PYL is biosynthetically generated and incorporated into the proteins and/or polypeptides. Also provided herein are proteins and/or polypeptides having one or more PCL incorporated therein and one or more PYL incorporated therein, wherein the PCL and PYL are biosynthetically generated and incorporated into the proteins and/or polypeptides.

Also provided herein are proteins and/or polypeptides having one or more PCL moieties, wherein the PCL is biosynthetically generated and incorporated into the proteins and/or polypeptides, and the one or more PCL moieties are derivatized thereby coupling to the proteins and/or polypeptides a group selected from a label, a dye, a polymer, a water-soluble polymer, a polyalkylene glycol, a poly(ethylene glycol), a derivative of poly(ethylene glycol), a sugar, a lipid, a photocrosslinker, a cytotoxic compound, a drug, an affinity label, a photoaffinity label, a reactive compound; a resin, a peptide, a second protein or polypeptide or polypeptide analog, an antibody or antibody fragment, a metal chelator, a cofactor, a fatty acid, a carbohydrate, a polynucleotide, a DNA, a RNA, a PCR probe, an antisense polynucleotide, a ribo-oligonucleotide, a deoxyribo-oligonucleotide, phosphorothioate-modified DNA, modified DNA and RNA, a peptide nucleic acid, a saccharide, a disaccharide, an oligosaccharide, a polysaccharide, a water-soluble dendrimer, a cyclodextrin, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a ligand, a photoisomerizable moiety, biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chromophoric group, a chemiluminescent group, a fluorescent moiety, an electron dense group, a magnetic group, an intercalating group, a chelating group, a chromophore, an energy transfer agent, a biologically active agent, a detectable label, a small molecule, an inhibitory ribonucleic acid, an siRNA, a radionucleotide, a neutron-capture agent, a derivative of biotin, quantum dot(s), a nanotransmitter, a radiotransmitter, an abzyme, an enzyme, an activated complex activator, a virus, a toxin, an adjuvant, a TLR2 agonist, a TLR4 agonist, a TLR7 agonist, a TLR9 agonist, a TLR8 agonist, a T-cell epitope, a phospho-lipid, a LPS-like molecule, keyhole limpet hemocyanin (KLH), an immunogenic hapten, an aglycan, an allergen, an angiostatin, an antihormone, an antioxidant, an aptamer, a guide RNA, a saponin, a shuttle vector, a macromolecule, a mimotope, a receptor, a reverse micelle, detergents, immune response potentiators, fluorescence dyes, FRET reagents, radio-imaging probes, other spectroscopy probe, prodrugs, toxins for immunotherapy, a solid support, a —$C_{H2}C_{H2}$—(OCH$_2$CH$_2$O)$_p$—OX$^2$, and a —O—(CH$_2$CH$_2$O)$_p$CH$_2$CH$_2$—X$^2$ (wherein p is 1 to 10,000 and X$^2$ is H, a C$_{1-8}$alkyl, a protecting group or a terminal functional group).

In certain embodiments, such proteins and/or polypeptides having one or more PYL moieties incorporated therein, wherein the PYL is biosynthetically generated and incorporated into the proteins and/or polypeptides, the pyrrolysine is derivatized thereby coupling to the proteins and/or polypeptides one of the aforementioned groups given above for proteins and/or polypeptides having one or more PCL1 moieties incorporated therein.

In certain embodiments, such proteins and/or polypeptides having one or more PCL and one or more PYL moieties incorporated therein, wherein the PCL and PYL are biosynthetically generated and incorporated into the proteins and/or polypeptides, the PCL and pyrrolysine are derivatized thereby coupling to the proteins and/or polypeptides one of the aforementioned groups given above for proteins and/or polypeptides having one or more PCL1 moieties incorporated therein.

In certain embodiments, such aforementioned biosynthesis occurs in eukaryotic cells, mammalian cells, yeast cells or insect cells. In certain embodiments, the cells are *Escherichia coli* cells, while in other embodiments the yeast cells are *Saccharomyces cerevisiae* or *Pichia pastoralis* cells. In certain embodiments, the cells are CHO cells, HeLa cells, HEK293F cells or sf9 cells.

One aspect provide herein are compounds having the structure of Formula (I) or Formula (II):

$$R_1\text{-}(AA)_n\text{-}R_2 \quad (I)$$

$$R_1\text{—}(BB)_n\text{—}R_2 \quad (II)$$

wherein:
R$_1$ is H or an amino terminus modification group;
R$_2$ is OH or a carboxy terminus modification group;
n is an integer from 1 to 5000;
each AA is independently selected from an amino acid residue, a pyrrolysine analogue amino acid residue having the structure of Formula (A-2) and a pyrrolysine analogue amino acid residue having the structure of Formula (B-2);
each BB is independently selected from an amino acid residue, a pyrrolysine analogue amino acid residue having the structure of Formula (A-2), a pyrrolysine analogue amino acid residue having the structure of Formula (B-2), a pyrrolysine analogue amino acid residue having the structure of Formula (C-1), a pyrrolysine analogue amino acid residue having the structure of Formula (D-1), a pyrrolysine analogue amino acid residue having the structure of Formula (E-1), a pyrrolysine analogue amino acid residue having the structure of Formula (F-1), a pyrrolysine analogue amino acid residue having the structure of Formula (G-1), a pyrrolysine analogue amino acid residue having the structure of Formula (H-1), a pyrrolysine analogue amino acid residue having the structure of Formula (I-1), a pyrrolysine analogue amino acid residue having the structure of Formula (J-1), a pyrrolysine analogue amino acid residue having the structure of Formula (K-1) and a pyrrolysine analogue amino acid residue having the structure of Formula (L-1);
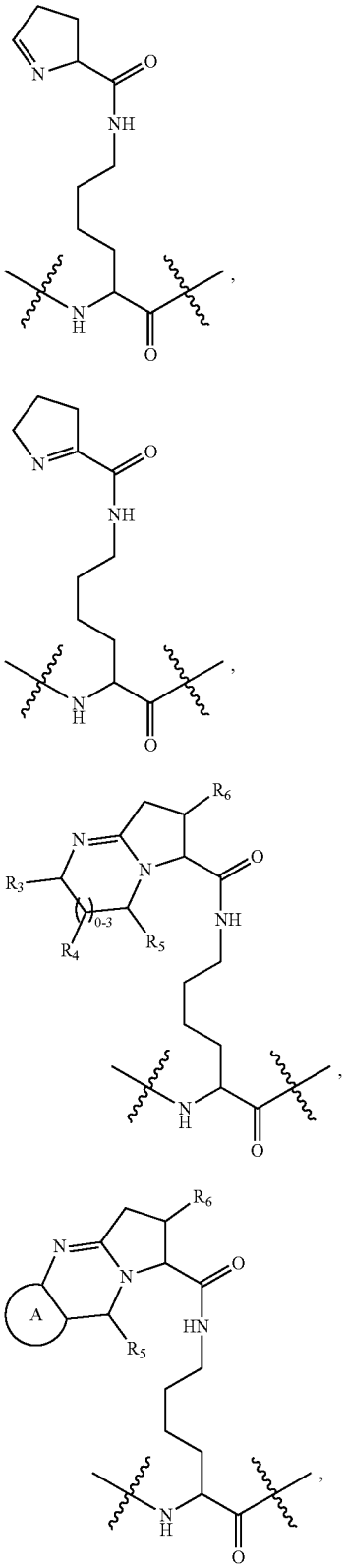
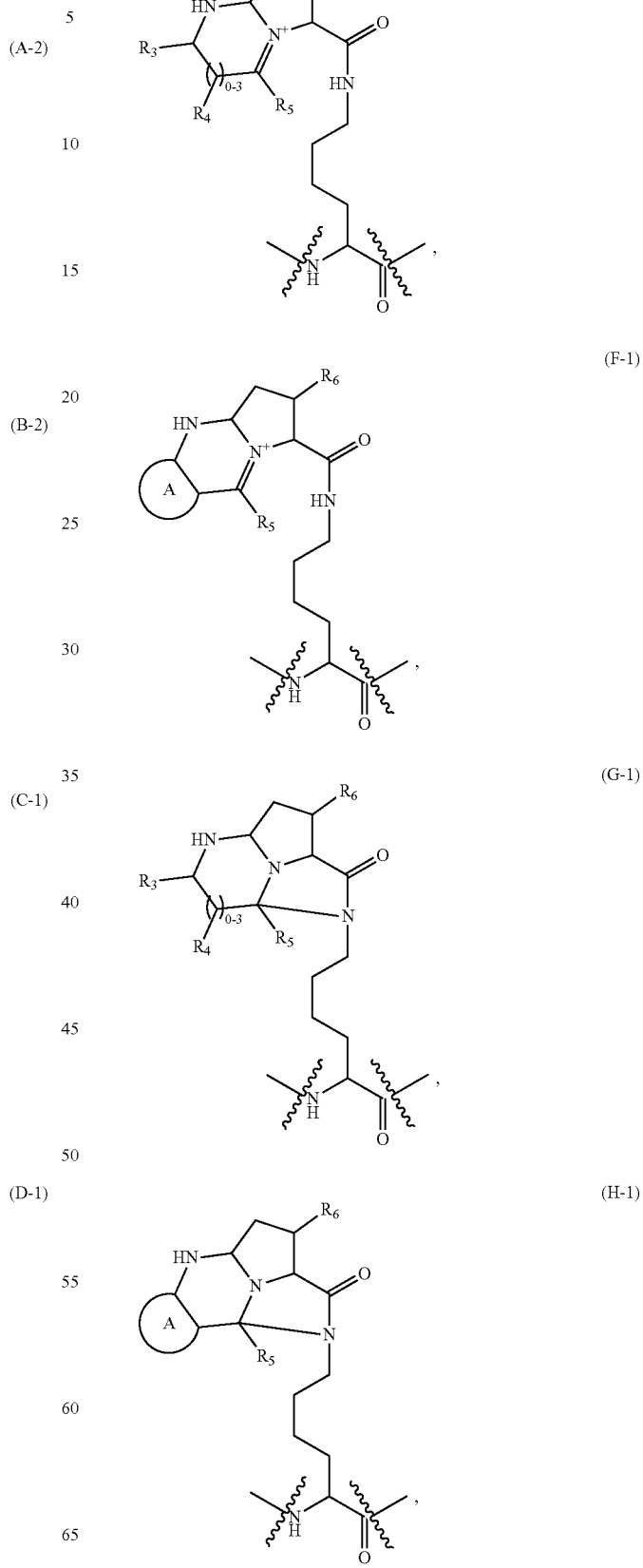

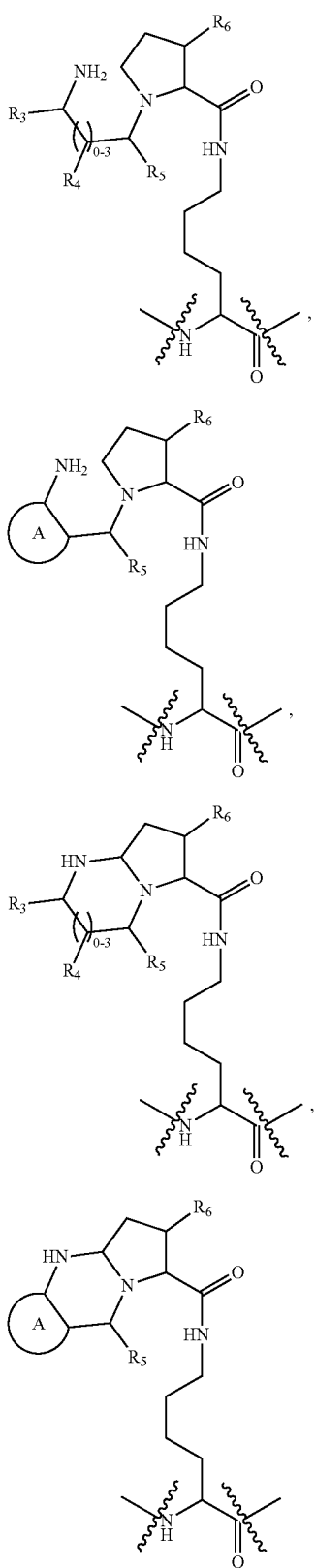

wherein:
R₃, R₅ and each R₄ is independently selected from H, —OH, —NO₂, halo, $C_{1-8}$alkyl, halo-substituted-$C_{1-8}$alkyl, hydroxy-substituted-$C_{1-8}$alkyl, aryl, heteroaryl, heterocycloalkyl or cycloalkyl and -$LX^1$;

$R_6$ is H or $C_1$alkyl;

A is a $C_3$-$C_8$cycloalkyl, $C_3$-$C_8$ heterocycloalkyl, a 5-6 membered monocyclic aryl, a 5-6 membered monocyclic heteroaryl, a 9-10 membered fused bicyclic ring or a 13-14 membered fused tricyclic ring, wherein A is optionally substituted with 1 to 5 substituents independently selected from —OH, —NO₂, halo, $C_{1-8}$alkyl, halo-substituted-$C_{1-8}$alkyl, hydroxy-substituted-$C_{1-8}$alkyl, aryl, heteroaryl, heterocycloalkly or cycloalkyl and -$LX^1$;

L is selected from a bond, $C_{1-8}$alkylene, halo-substituted-$C_{1-8}$alkylene, hydroxy-substituted-$C_{1-8}$alkylene, $C_{2-8}$alkenylene, halo-substituted-$C_{2-8}$alkenylene, hydroxy-substituted-$C_{2-8}$alkenylene, a polyalkylene glycol, a poly(ethylene glycol), —O(CR¹¹R¹²)$_k$—, —S(CR¹¹R¹²)$_k$—, —S(O)$_k$(CR¹¹R¹²)$_k$—, —O(CR¹¹R¹²)$_k$—NR¹¹C(O)—, —O(CR¹¹R¹²)$_k$C(O)NR¹¹—, —C(O)—, —C(O)(CR¹¹R¹²)$_k$—, —C(S)—, —C(S)(CR¹¹R¹²)$_k$—, —C(O)NR¹¹—, —NR¹¹C(O)—, —NR¹¹(CR¹¹R¹²)$_k$—, —CONR¹¹(CR¹¹R¹²)$_k$—, —N(R¹¹)CO(CR¹¹R¹²)$_k$—, —C(O)NR¹¹(CR¹¹R¹²)$_k$—, —NR¹¹C(O)(CR¹¹R¹²)$_k$—, where each $R^{11}$ and $R^{12}$ are independently H, $C_{1-8}$alkyl, halo-substituted-$C_{1-8}$alkyl, or hydroxy-substituted-$C_{1-8}$alkyl, and k is an integer from 1 to 12, and $X^1$ is selected from a label, a dye, a polymer, a water-soluble polymer, a polyalkylene glycol, a poly(ethylene glycol), a derivative of poly(ethylene glycol), a sugar, a lipid, a photocrosslinker, a cytotoxic compound, a drug, an affinity label, a photoaffinity label, a reactive compound; a resin, a peptide, a second protein or polypeptide or polypeptide analog, an antibody or antibody fragment, a metal chelator, a cofactor, a fatty acid, a carbohydrate, a polynucleotide, a DNA, a RNA, a PCR probe, an antisense polynucleotide, a ribo-oligonucleotide, a deoxyribo-oligonucleotide, phosphorothioate-modified DNA, modified DNA and RNA, a peptide nucleic acid, a saccharide, a disaccharide, an oligosaccharide, a polysaccharide, a water-soluble dendrimer, a cyclodextrin, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a ligand, a photoisomerizable moiety, biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chromophoric group, a chemiluminescent group, a fluorescent moiety, an electron dense group, a magnetic group, an intercalating group, a chelating group, a chromophore, an energy transfer agent, a biologically active agent, a detectable label, a small molecule, an inhibitory ribonucleic acid, an siRNA, a radionucleotide, a neutron-capture agent, a derivative of biotin, quantum dot(s), a nanotransmitter, a radiotransmitter, an abzyme, an enzyme, an activated complex activator, a virus, a toxin, an adjuvant, a TLR2 agonist, a TLR4 agonist, a TLR7 agonist, a TLR9 agonist, a TLR8 agonist, a T-cell epitope, a phospho-lipid, a LPS-like molecule, keyhole limpet hemocyanin (KLH), an immunogenic hapten, an aglycan, an allergen, an angiostatin, an antihormone, an antioxidant, an aptamer, a guide RNA, a saponin, a shuttle vector, a macromolecule, a mimotope, a receptor, a reverse micelle, detergents, immune response potentiators, fluorescence dyes, FRET reagents, radio-imaging probes, other spectroscopy probe, prodrugs, toxins for immunotherapy, a solid support, —CH$_2$CH$_2$—(OCH$_2$CH$_2$O)$_p$—OX$^2$, —O—(CH$_2$CH$_2$O)$_p$CH$_2$CH$_2$—X$^2$, and any combination thereof, wherein p is 1 to 10,000 and X$^2$ is H, a C$_{1-8}$alkyl, a protecting group or a terminal functional group, and wherein at least one AA is a pyrrolysine analogue amino acid residue having the structure of Formula (A-2) or Formula (B-2), or at least one BB is a pyrrolysine analogue amino acid residue having the structure of Formula (C-1) or Formula (D-1) or Formula (E-1) or Formula (F-1) or Formula (G-1) or Formula (H-1) or Formula (I-1) or Formula (J-1) or Formula (K-1) or Formula (L-1).

In certain embodiments of such compounds, ring A is selected from furan, thiophene, pyrrole, pyrroline, pyrrolidine, dioxolane, oxazole, thiazole, imidazole, imidazoline, imidazolidine, pyrazole, pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, piperazine, triazine, trithiane, indolizine, indole, isoindole, indoline, benzofuran, benzothiophene, indazole, benzimidazole, benzthiazole, purine, quinolizine, quinoline, isoquinoline, cinnoline, phthalazine, quinazoline, quinoxaline, naphthyridine, pteridine, quinuclidine, carbazole, acridine, phenazine, phenthiazine, phenoxazine, phenyl, indene, naphthalene, azulene, fluorene, anthracene, phenanthracene, norborane and adamantine.

In other embodiments of such compounds, ring A is selected from phenyl, furan, thiophene, pyrrole, pyrroline, pyrrolidine, dioxolane, oxazole, thiazole, imidazole, imidazoline, imidazolidine, pyrazole, pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, piperazine, triazine and trithiane.

In still other embodiments of such compounds, ring A is selected from indolizine, indole, isoindole, indoline, benzofuran, benzothiophene, indazole, benzimidazole, benzthiazole, purine, quinolizine, quinoline, isoquinoline, cinnoline, phthalazine, quinazoline, quinoxaline, naphthyridine, pteridine, quinuclidine, carbazole, acridine, phenazine, phenthiazine, phenoxazine, indene, naphthalene, azulene, fluorene, anthracene, phenanthracene, norborane and adamantine.

In certain embodiments of such compounds, ring A is selected from phenyl, naphthalene and pyridine.

In certain embodiments of such compounds, each BB is independently selected from an amino acid residue, a pyrrolysine analogue amino acid residue having the structure of Formula (A-2), a pyrrolysine analogue amino acid residue having the structure of Formula (B-2), a pyrrolysine analogue amino acid residue having the structure of Formula (C-1), a pyrrolysine analogue amino acid residue having the structure of Formula (D-2), a pyrrolysine analogue amino acid residue having the structure of Formula (E-1), a pyrrolysine analogue amino acid residue having the structure of Formula (F-2), a pyrrolysine analogue amino acid residue having the structure of Formula (G-1), a pyrrolysine analogue amino acid residue having the structure of Formula (H-2), a pyrrolysine analogue amino acid residue having the structure of Formula (I-1), a pyrrolysine analogue amino acid residue having the structure of Formula (J-2), a pyrrolysine analogue amino acid residue having the structure of Formula (K-1) and a pyrrolysine analogue amino acid residue having the structure of Formula (L-2);

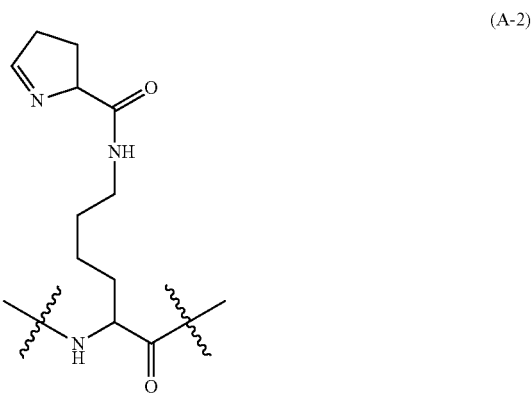

(A-2)

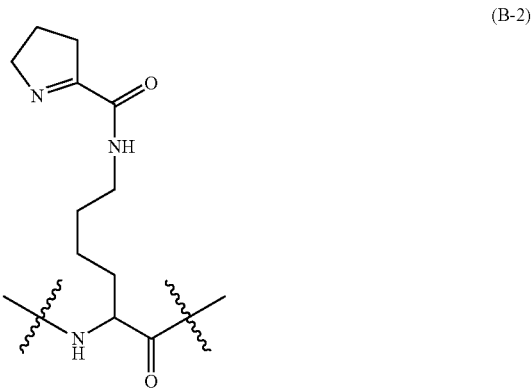

(B-2)

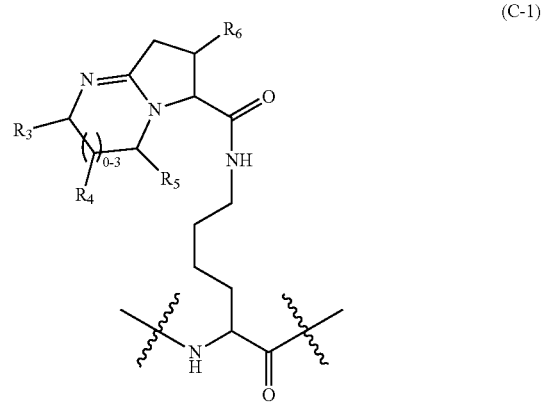

(C-1)

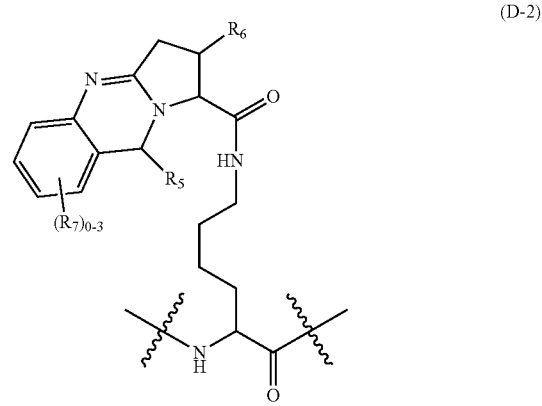

(D-2)

-continued
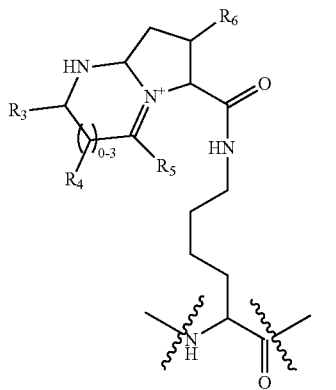
(E-1)
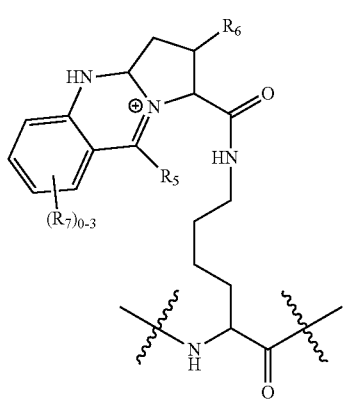
(F-2)
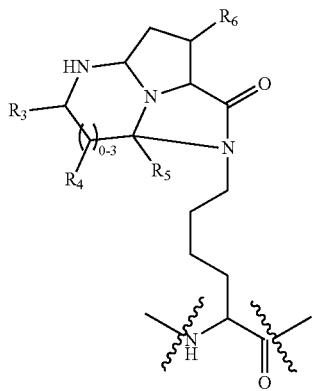
(G-1)
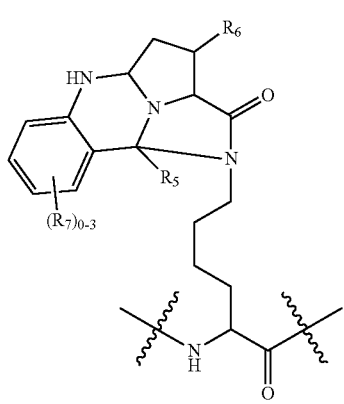
(H-2)
-continued
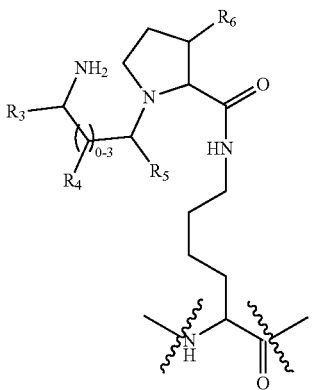
(I-1)
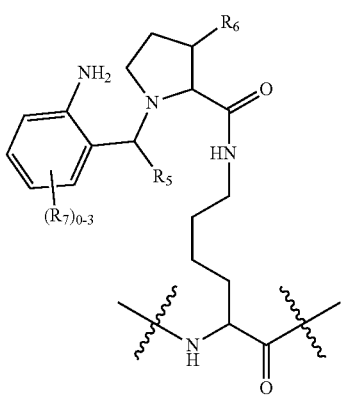
(J-2)
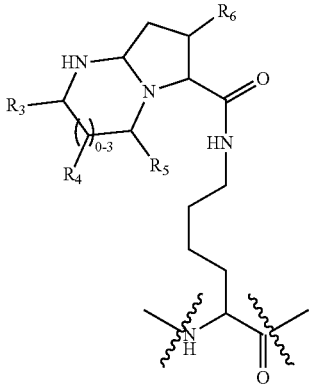
(K-1)
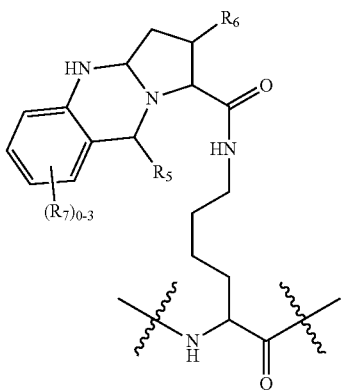
(L-2)
wherein,
$R_3$, $R_5$ and each $R_4$ is independently selected from H, —OH, —NO$_2$, halo, C$_{1-8}$alkyl, halo-substituted- $C_{1-8}$alkyl, hydroxy-substituted-$C_{1-8}$alkyl, aryl, heteroaryl, heterocycloalkly or cycloalkyl and -LX$^1$;

$R_6$ is H or $C_1$alkyl;

when present each $R_7$ is independently selected from —OH, —NO$_2$, halo, $C_{1-8}$alkyl, halo-substituted-$C_{1-8}$alkyl, hydroxy-substituted-$C_{1-8}$alkyl, aryl, heteroaryl, heterocycloalkly or cycloalkyl and -LX$^1$;

L is selected from a bond, $C_{1-8}$alkylene, halo-substituted-$C_{1-8}$alkylene, hydroxy-substituted-$C_{1-8}$alkylene, $C_{2-8}$alkenylene, halo-substituted-$C_{2-8}$alkenylene, hydroxy-substituted-$C_{2-8}$alkenylene, a polyalkylene glycol, a poly(ethylene glycol), —O(CR$^{11}$R$^{12}$)$_k$—, —S(CR$^{11}$R$^{12}$)$_k$—, —S(O)$_k$(CR$^{11}$R$^{12}$)$_k$—, —O(CR$^{11}$R$^{12}$)$_k$—NR$^{11}$C(O)—, —O(CR$^{11}$R$^{12}$)$_k$C(O)NR$^{11}$—, —C(O)—, —C(O)(CR$^{11}$R$^{12}$)$_k$—, —C(S)—, —C(S)(CR$^{11}$R$^{12}$)$_k$—, —C(O)NR$^{11}$—, —NR$^{11}$C(O)—, —NR$^{11}$(CR$^{11}$R$^{12}$)$_k$—, —CONR$^{11}$(CR$^{11}$R$^{12}$)$_k$—, —N(R$^{11}$)CO(CR$^{11}$R$^{12}$)$_k$—, —C(O)NR$^{11}$(CR$^{11}$R$^{12}$)$_k$—, —NR$^{11}$C(O)(CR$^{11}$R$^{12}$)$_k$—, where each R$^{11}$ and R$^{12}$ are independently H, $C_{1-8}$alkyl, halo-substituted-$C_{1-8}$alkyl, or hydroxy-substituted-$C_{1-8}$alkyl, and k is an integer from 1 to 12, and X$^1$ is selected from a label, a dye, a polymer, a water-soluble polymer, a polyalkylene glycol, a poly(ethylene glycol), a derivative of poly(ethylene glycol), a sugar, a lipid, a photocrosslinker, a cytotoxic compound, a drug, an affinity label, a photoaffinity label, a reactive compound; a resin, a peptide, a second protein or polypeptide or polypeptide analog, an antibody or antibody fragment, a metal chelator, a cofactor, a fatty acid, a carbohydrate, a polynucleotide, a DNA, a RNA, a PCR probe, an antisense polynucleotide, a ribo-oligonucleotide, a deoxyribo-oligonucleotide, phosphorothioate-modified DNA, modified DNA and RNA, a peptide nucleic acid, a saccharide, a disaccharide, an oligosaccharide, a polysaccharide, a water-soluble dendrimer, a cyclodextrin, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a ligand, a photoisomerizable moiety, biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chromophoric group, a chemiluminescent group, a fluorescent moiety, an electron dense group, a magnetic group, an intercalating group, a chelating group, a chromophore, an energy transfer agent, a biologically active agent, a detectable label, a small molecule, an inhibitory ribonucleic acid, an siRNA, a radionucleotide, a neutron-capture agent, a derivative of biotin, quantum dot(s), a nanotransmitter, a radiotransmitter, an abzyme, an enzyme, an activated complex activator, a virus, a toxin, an adjuvant, a TLR2 agonist, a TLR4 agonist, a TLR7 agonist, a TLR9 agonist, a TLR8 agonist, a T-cell epitope, a phospho-lipid, a LPS-like molecule, keyhole limpet hemocyanin (KLH), an immunogenic hapten, an aglycan, an allergen, an angiostatin, an antihormone, an antioxidant, an aptamer, a guide RNA, a saponin, a shuttle vector, a macromolecule, a mimotope, a receptor, a reverse micelle, detergents, immune response potentiators, fluorescence dyes, FRET reagents, radio-imaging probes, other spectroscopy probe, prodrugs, toxins for immunotherapy, a solid support, —CH$_2$CH$_2$—(OCH$_2$CH$_2$O)$_p$—OX$^2$, —O—(CH$_2$CH$_2$O)$_p$CH$_2$CH$_2$—X$^2$, and any combination thereof, wherein p is 1 to 10,000 and X$^2$ is H, a $C_{1-8}$alkyl, a protecting group or a terminal functional group.

In certain embodiments of such compounds, $R_6$ is H, while in other embodiments of such compounds, $R_6$ is $C_1$alkyl.

In certain embodiments of such compounds, $R_5$ is -LX$^1$. In certain embodiments of such compounds, $R_7$ is -LX$^1$. In certain embodiments of such compounds, X$^1$ a sugar, a polyethylene glycol, a fluorescent moiety, an immunomodulator, a ribonucleic acid, a deoxyribonucleic acid, a protein, a peptide, a biotin, a phospholipid, a TLR7 agonist, an immunogenic hapten or a solid support. In certain embodiments of such compounds, L is a poly(alkyleneglycol), a poly(ethyleneglycol), $C_{1-8}$alkylene, halo-substituted-$C_{1-8}$alkylene or hydroxy-substituted-$C_{1-8}$alkylene.

Another aspect provided herein is a method for derivatizing a protein, wherein the protein has the structure according to Formula (I), the method comprising contacting the protein with a reagent of Formula (III) or Formula (IV); where Formula (I) corresponds to:

$$R_1\text{-}(AA)_n\text{-}R_2 \qquad (I)$$

wherein:
$R_1$ is H or an amino terminus modification group;
$R_2$ is OH or a carboxy terminus modification group;
n is an integer from 1 to 5000;
each AA is independently selected from an amino acid residue, a pyrrolysine amino acid residue, a pyrrolysine analogue amino acid residue having the structure of Formula (A-1) and a pyrrolysine analogue amino acid residue having the structure of Formula (B-1);

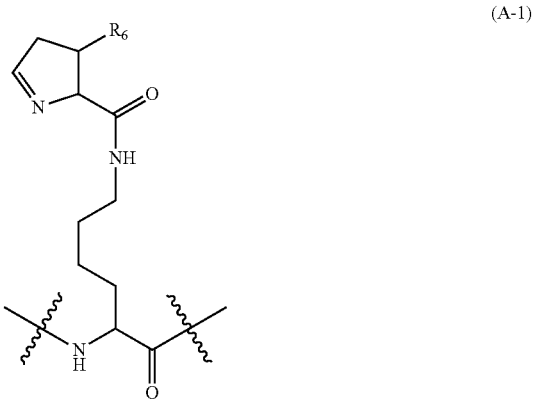

(A-1)

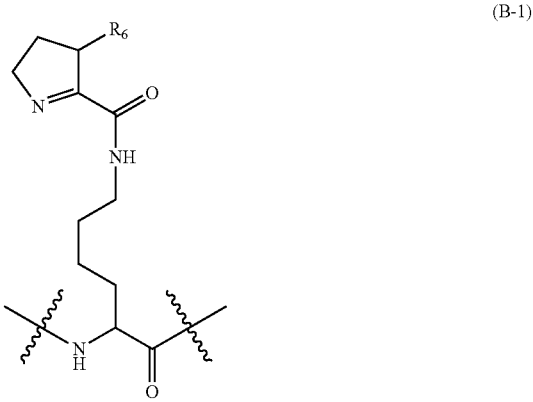

(B-1)

$R_6$ is H or $C_1$alkyl, and at least one AA is a pyrrolysine amino acid residue or pyrrolysine analogue amino acid residue having the structure of Formula (A-1) or Formula (B-1);

and where Formula (II) and Formula (III) correspond to:

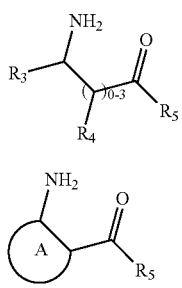

(III)

(IV)

wherein:

$R_3$, $R_5$ and each $R_4$ is independently selected from H, —OH, —$NO_2$, halo, $C_{1-8}$alkyl, halo-substituted-$C_{1-8}$alkyl, hydroxy-substituted-$C_{1-8}$alkyl, aryl, heteroaryl, heterocycloalkly or cycloalkyl and -$LX^1$;

A is a $C_3$-$C_8$cycloalkyl, $C_3$-$C_8$ heterocycloalkyl, a 5-6 membered monocyclic aryl, a 5-6 membered monocyclic heteroaryl, a 9-10 membered fused bicyclic ring or a 13-14 membered fused tricyclic ring, wherein A is optionally substituted with 1 to 5 substituents independently selected from —OH, —$NO_2$, halo, $C_{1-8}$alkyl, halo-substituted-$C_{1-8}$alkyl, hydroxy-substituted-$C_{1-8}$alkyl, aryl, heteroaryl, heterocycloalkly or cycloalkyl and -$LX^1$;

L is selected from a bond, $C_{1-8}$alkylene, halo-substituted-$C_{1-8}$alkylene, hydroxy-substituted-$C_{1-8}$alkylene, $C_{2-8}$alkenylene, halo-substituted-$C_{2-8}$alkenylene, hydroxy-substituted-$C_{2-8}$alkenylene, a polyalkylene glycol, a poly(ethylene glycol), —$O(CR^{11}R^{12})_k$—, —$S(CR^{11}R^{12})_k$—, —$S(O)_k(CR^{11}R^{12})_k$—, —$O(CR^{11}R^{12})_k$—$NR^{11}C(O)$—, —$O(CR^{11}R^{12})_kC(O)NR^{11}$—, —$C(O)$—, —$C(O)(CR^{11}R^{12})_k$—, —$C(S)$—, —$C(S)(CR^{11}R^{12})_k$—, —$C(O)NR^{11}$—, —$NR^{11}C(O)$—, —$NR^{11}(CR^{11}R^{12})_k$—, —$CONR^{11}(CR^{11}R^{12})_k$—, —$N(R^{11})CO(CR^{11}R^{12})_k$—, —$C(O)NR^{11}(CR^{11}R^{12})_k$—, —$NR^{11}C(O)(CR^{11}R^{12})_k$—, where each $R^{11}$ and $R^{12}$ are independently H, $C_{1-8}$alkyl, halo-substituted-$C_{1-8}$alkyl, or hydroxy-substituted-$C_{1-8}$alkyl, and k is an integer from 1 to 12, and $X^1$ is selected from a label, a dye, a polymer, a water-soluble polymer, a polyalkylene glycol, a poly(ethylene glycol), a derivative of poly(ethylene glycol), a sugar, a lipid, a photocrosslinker, a cytotoxic compound, a drug, an affinity label, a photoaffinity label, a reactive compound; a resin, a peptide, a second protein or polypeptide or polypeptide analog, an antibody or antibody fragment, a metal chelator, a cofactor, a fatty acid, a carbohydrate, a polynucleotide, a DNA, a RNA, a PCR probe, an antisense polynucleotide, a ribo-oligonucleotide, a deoxyribo-oligonucleotide, phosphorothioate-modified DNA, modified DNA and RNA, a peptide nucleic acid, a saccharide, a disaccharide, an oligosaccharide, a polysaccharide, a water-soluble dendrimer, a cyclodextrin, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a ligand, a photoisomerizable moiety, biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chromophoric group, a chemiluminescent group, a fluorescent moiety, an electron dense group, a magnetic group, an intercalating group, a chelating group, a chromophore, an energy transfer agent, a biologically active agent, a detectable label, a small molecule, an inhibitory ribonucleic acid, an siRNA, a radionucleotide, a neutron-capture agent, a derivative of biotin, quantum dot(s), a nanotransmitter, a radiotransmitter, an abzyme, an enzyme, an activated complex activator, a virus, a toxin, an adjuvant, a TLR2 agonist, a TLR4 agonist, a TLR7 agonist, a TLR9 agonist, a TLR8 agonist, a T-cell epitope, a phospho-lipid, a LPS-like molecule, keyhole limpet hemocyanin (KLH), an immunogenic hapten, an aglycan, an allergen, an angiostatin, an antihormone, an antioxidant, an aptamer, a guide RNA, a saponin, a shuttle vector, a macromolecule, a mimotope, a receptor, a reverse micelle, detergents, immune response potentiators, fluorescence dyes, FRET reagents, radio-imaging probes, other spectroscopy probe, prodrugs, toxins for immunotherapy, a solid support, —$CH_2CH_2$—$(OCH_2CH_2O)_p$—$OX^2$, —$O$—$(CH_2CH_2O)_pCH_2CH_2$—$X^2$, and any combination thereof, wherein p is 1 to 10,000 and $X^2$ is H, a $C_{1-8}$alkyl, a protecting group or a terminal functional group.

In certain embodiments of the aforementioned method, the amino acid residue of Formula (A-1) is an amino acid residue having the structure of Formula (A-2) or Formula (A-3):

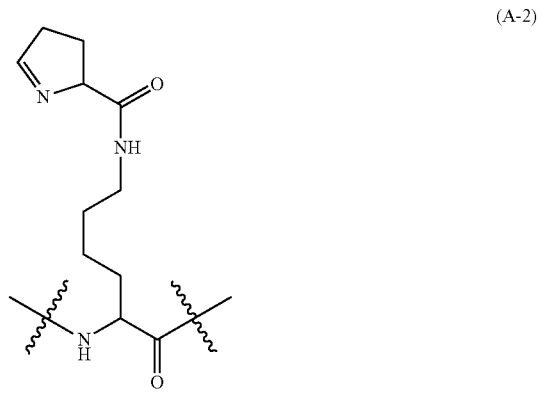

(A-2)

-continued

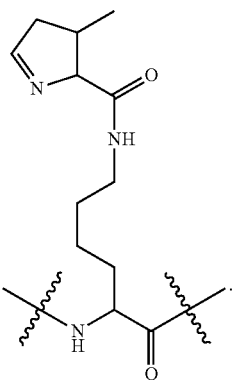
(A-3)

In certain embodiments of the aforementioned method, the amino acid residue of Formula (B-1) is an amino acid residue having the structure of Formula (B-2) or Formula (B-3):

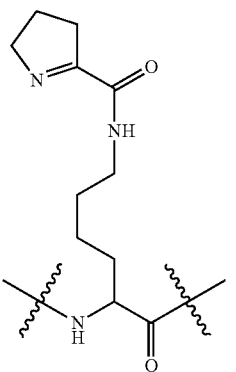
(B-2)

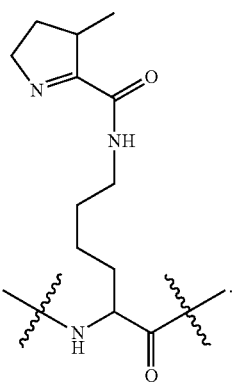
(B-3)

In certain embodiments of the aforementioned method, the amino acid residue of Formula (A-1) is a residue of an amino acid of Formula (V) and the amino acid residue of Formula (B-1) is a residue of an amino acid of Formula (VI):

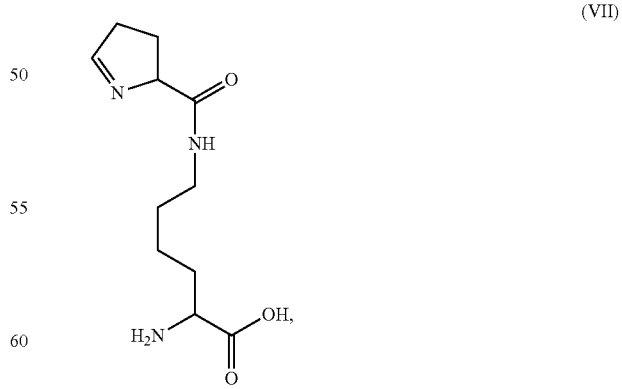

wherein $R_6$ is H or $C_1$alkyl

In certain embodiments the amino acid of Formula (V) or Formula (VI) is biosynthetically generated within a cell comprising a pylB gene, a pylC gene and a pylD gene, and the cell is in contact with a growth medium comprising a precursor. In other embodiments, the amino acid of Formula (V) or Formula (VI) is biosynthetically generated within a cell comprising a pylC gene and a pylD gene, and the cell is in contact with a growth medium comprising a precursor.

In certain embodiments, the amino acid of Formula (V) is an amino acid having the structure of Formula (VII):

and the precursor is ornithine, arginine, D-ornithine, D-arginine, (2S)-2-amino-6-(2,5-diaminopentanamido)hexanoic acid or (2S)-2-amino-6-((R)-2,5-diaminopentanamido)hexanoic acid.

In certain embodiments, the amino acid of Formula (VI) is an amino acid having the structure of Formula (VIII) and the precursor is ornithine or arginine:

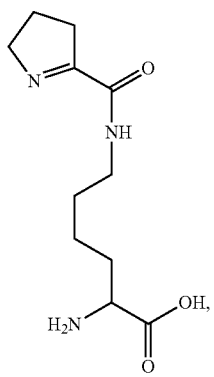

(VIII)

and the precursor is ornithine, arginine, D-ornithine, D-arginine, (2S)-2-amino-6-(2,5-diaminopentanamido)hexanoic acid or (2S)-2-amino-6-((R)-2,5-diaminopentanamido)hexanoic acid.

In certain embodiments the amino acid of Formula (V) is an amino acid having the structure of Formula (VII) and the precursor is D-ornithine or D-arginine. In certain embodiments, the amino acid of Formula (VI) is an amino acid having the structure of Formula (VIII) and the precursor is D-ornithine or D-arginine. In certain embodiments, the amino acid of Formula (V) is an amino acid having the structure of Formula (VII) and the precursor is (2S)-2-amino-6-(2,5-diaminopentanamido)hexanoic acid. In certain embodiments, the amino acid of Formula (V) is an amino acid having the structure of Formula (VII) and the precursor is (2S)-2-amino-6-((R)-2,5-diaminopentanamido)hexanoic acid. In certain embodiments, the amino acid of Formula (VI) is an amino acid having the structure of Formula (VIII) and the precursor is (2S)-2-amino-6-(2,5-diaminopentanamido)hexanoic acid. In certain embodiments, the amino acid of Formula (VI) is an amino acid having the structure of Formula (VIII) and the precursor is (2S)-2-amino-6-((R)-2,5-diaminopentanamido)hexanoic acid.

In certain embodiments the amino acid of Formula (V) is an amino acid having the structure of Formula (IX) and the precursor is ornithine, arginine, D-ornithine, D-arginine or 2,5-diamino-3-methylpentanoic acid:

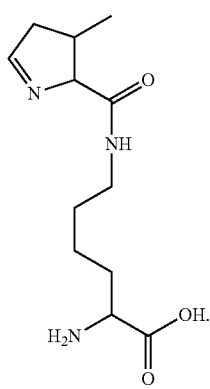

(IX)

In certain embodiments the amino acid of Formula (V) is an amino acid having the structure of Formula (X) and the precursor is ornithine, arginine, D-ornithine, D-arginine or 2,5-diamino-3-methylpentanoic acid:

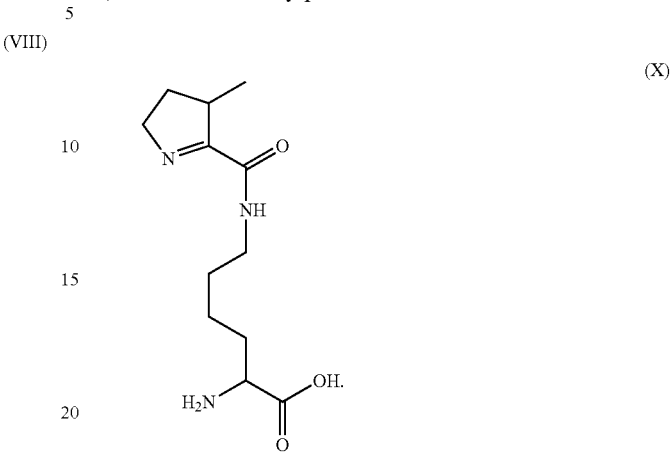

(X)

In certain embodiments the amino acid of Formula (V) is an amino acid having the structure of Formula (IX) and the precursor is D-2,5-diamino-3-methylpentanoic acid. In certain embodiments the amino acid of Formula (V) is an amino acid having the structure of Formula (X) and the precursor is D-2,5-diamino-3-methylpentanoic acid.

In certain embodiments the amino acid of Formula (V) is an amino acid having the structure of Formula (IX) and the precursor is (2R,3S)-2,5-diamino-3-methylpentanoic acid. In certain embodiments the amino acid of Formula (V) is an amino acid having the structure of Formula (X) and the precursor is (2R,3S)-2,5-diamino-3-methylpentanoic acid.

In certain embodiments the amino acid of Formula (V) is an amino acid having the structure of Formula (IX) and the precursor is (2R,3R)-2,5-diamino-3-methylpentanoic acid. In certain embodiments the amino acid of Formula (V) is an amino acid having the structure of Formula (X) and the precursor is (2R,3R)-2,5-diamino-3-methylpentanoic acid. In certain embodiments the amino acid of Formula (V) is an amino acid having the structure of Formula (IX) and the precursor is D-ornithine or D-arginine or (2S)-2-amino-6-((R)-2,5-diaminopentanamido)hexanoic acid. In certain embodiments the amino acid of Formula (V) is an amino acid having the structure of Formula (X) and the precursor is D-ornithine or D-arginine or (2S)-2-amino-6-((R)-2,5-diaminopentanamido)hexanoic acid.

In certain embodiments of the aforementioned methods, the amino acid of Formula (V), Formula (VI), Formula (VII), Formula (VII), Formula (IX) or Formula (X) is incorporated into a protein within the cell by an orthogonal tRNA (O-tRNA) and an orthogonal aminoacyl tRNA synthetase (O-RS), wherein the O-RS aminoacylates the O-tRNA with the amino acid of Formula (V) or Formula (VI) and the O-tRNA recognize at least one selector codon of a mRNA in the cell.

In certain embodiments of the aforementioned methods, the cell further comprises a pylS gene and a pylT gene and the amino acid of Formula (V), Formula (VI), Formula (VII), Formula (VII), Formula (IX) or Formula (X) is incorporated into a protein within the cell by an aminoacyl tRNA synthetase and a tRNA which recognizes at least one selector codon of a mRNA in the cell, wherein the aminoacyl tRNA synthetase is a gene product of the pylS gene and the tRNA is a gene product of the pylT gene.

In certain embodiments of the aforementioned methods, the selector codon is an amber codon (TAG).

In certain embodiments of the aforementioned methods, the cell is a prokaryotic cell, while in other embodiments the cell is a eukaryotic cell. In certain embodiments, the cell is an *Escherichia coli* cell, while in other embodiments the cell is a mammalian cell, a yeast cell or an insect cell. In certain embodiments, the yeast cell is a *Saccharomyces cerevisiae* or *Pichia pastoralis* cells. In certain embodiments, the mammalian cell is a CHO cell, a HeLa cell or a HEK293F cell. In certain embodiments, the insect cell is a sf9 cell.

Another aspect provided herein are derivatized proteins obtained using the aforementioned methods, wherein such derivatized proteins have the structure according to Formula (II):

$$R_1—(BB)_n—R_2 \quad (II)$$

wherein:

$R_1$ is H or an amino terminus modification group;

$R_2$ is OH or a carboxy terminus modification group;

n is an integer from 1 to 5000;

each BB is independently selected from an amino acid residue, a pyrrolysine analogue amino acid residue having the structure of Formula (A-1), a pyrrolysine analogue amino acid residue having the structure of Formula (B-1), a pyrrolysine analogue amino acid residue having the structure of Formula (C-1), a pyrrolysine analogue amino acid residue having the structure of Formula (D-1), a pyrrolysine analogue amino acid residue having the structure of Formula (E-1), a pyrrolysine analogue amino acid residue having the structure of Formula (F-1), a pyrrolysine analogue amino acid residue having the structure of Formula (G-1), a pyrrolysine analogue amino acid residue having the structure of Formula (H-1), a pyrrolysine analogue amino acid residue having the structure of Formula (I-1), a pyrrolysine analogue amino acid residue having the structure of Formula (J-1), a pyrrolysine analogue amino acid residue having the structure of Formula (K-1) and a pyrrolysine analogue amino acid residue having the structure of Formula (L-1);

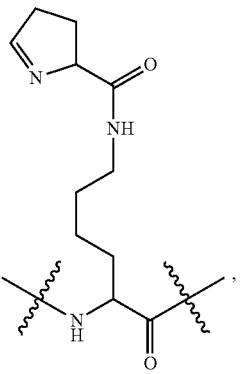

(A-2)

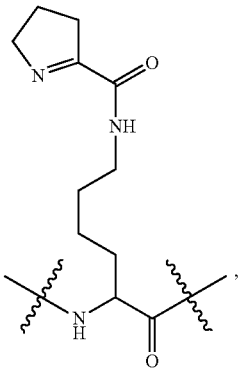

(B-2)

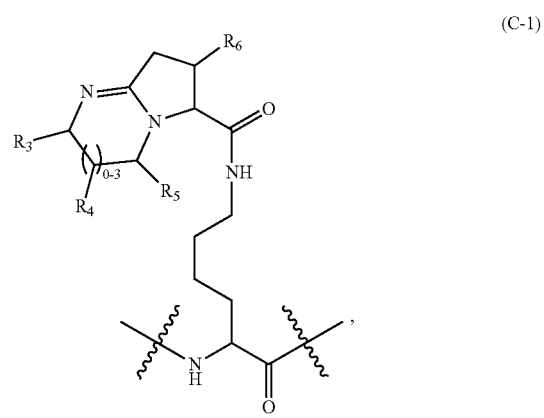

(C-1)

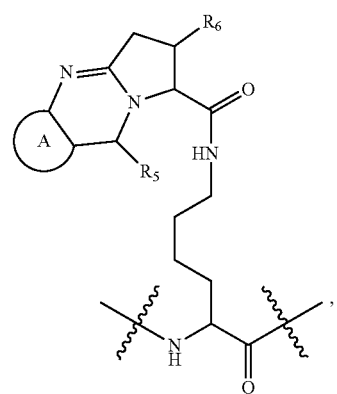

(D-1)

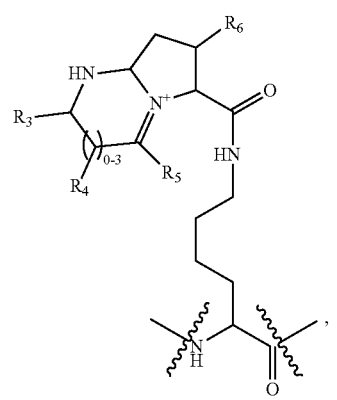

(E-1)

-continued (F-1)
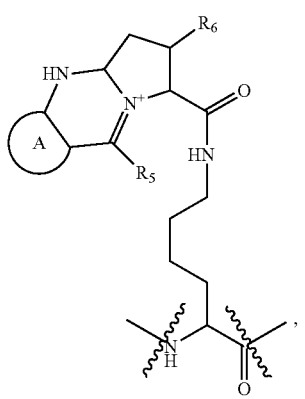

(G-1)
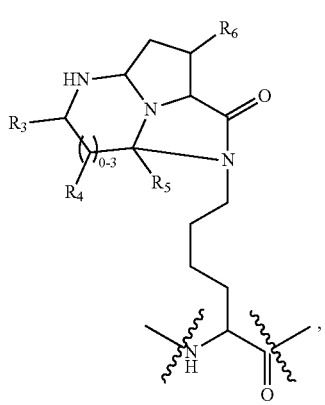

(H-1)
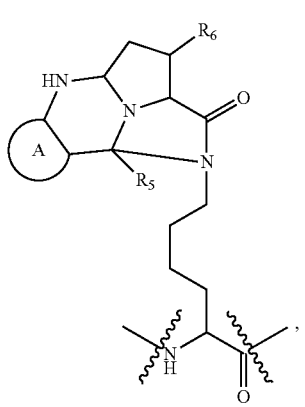

(I-1)
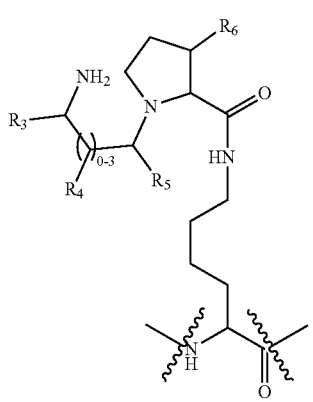

-continued (J-1)
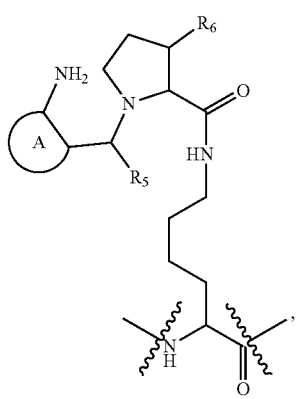

(K-1)
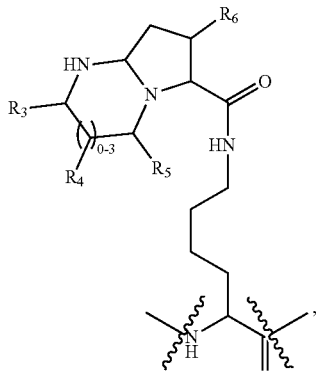

(L-1)
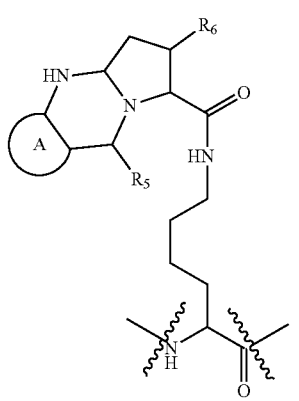

where at least one BB is a pyrrolysine analogue amino acid residue having the structure of Formula (C-1) or Formula (D-1) or Formula (E-1) or Formula (F-1) or Formula (G-1) or Formula (H-1) or Formula (I-1) or Formula (J-1) or Formula (K-1) or Formula (I-L).

In certain embodiments of the aforemention methods and such derivatized proteins, ring A is selected from furan, thiophene, pyrrole, pyrroline, pyrrolidine, dioxolane, oxazole, thiazole, imidazole, imidazoline, imidazolidine, pyrazole, pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, piperazine, triazine, trithiane, indolizine, indole, isoindole, indoline, benzofuran, benzothiophene, indazole, benzimidazole, benzthiazole, purine, quinolizine, quinoline, isoquinoline, cinnoline, phthalazine, quinazoline, quinoxaline, naphthyridine, pteridine, quinuclidine, carbazole, acridine, phenazine, phenthiazine, phenoxazine, phenyl, indene, naphthalene, azulene, fluorene, anthracene, phenanthracene, norborane and adamantine.

In certain embodiments of the aforemention methods and such derivatized proteins, ring A is selected from phenyl, furan, thiophene, pyrrole, pyrroline, pyrrolidine, dioxolane, oxazole, thiazole, imidazole, imidazoline, imidazolidine, pyrazole, pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, piperazine, triazine and trithiane.

In certain embodiments of the aforemention methods and such derivatized proteins, ring A is selected from indolizine, indole, isoindole, indoline, benzofuran, benzothiophene, indazole, benzimidazole, benzthiazole, purine, quinolizine, quinoline, isoquinoline, cinnoline, phthalazine, quinazoline, quinoxaline, naphthyridine, pteridine, quinuclidine, carbazole, acridine, phenazine, phenthiazine, phenoxazine, indene, naphthalene, azulene, fluorene, anthracene, phenanthracene, norborane and adamantine.

In certain embodiments of the aforemention methods and such derivatized proteins, ring A is selected from phenyl, naphthalyl and pyridyl.

In certain embodiments of the aforemention methods each BB is independently selected from an amino acid residue, a pyrrolysine analogue amino acid residue having the structure of Formula (A-2), a pyrrolysine analogue amino acid residue having the structure of Formula (B-2), a pyrrolysine analogue amino acid residue having the structure of Formula (C-1), a pyrrolysine analogue amino acid residue having the structure of Formula (D-2), a pyrrolysine analogue amino acid residue having the structure of Formula (E-1), a pyrrolysine analogue amino acid residue having the structure of Formula (F-2), a pyrrolysine analogue amino acid residue having the structure of Formula (G-1), a pyrrolysine analogue amino acid residue having the structure of Formula (H-2), a pyrrolysine analogue amino acid residue having the structure of Formula (I-1), a pyrrolysine analogue amino acid residue having the structure of Formula (J-2), a pyrrolysine analogue amino acid residue having the structure of Formula (K-1) and a pyrrolysine analogue amino acid residue having the structure of Formula (L-2);

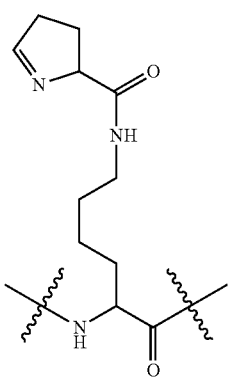

(A-2)

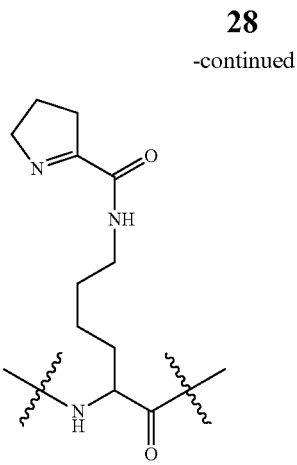

(B-2)

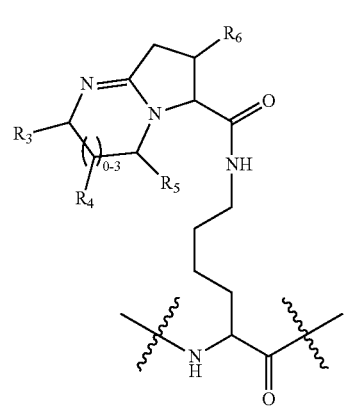

(C-1)

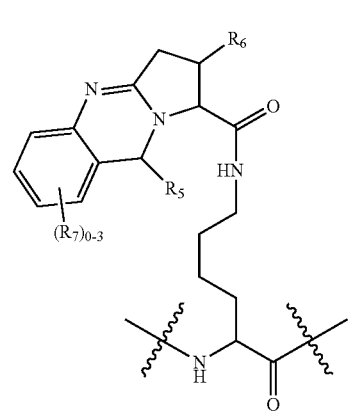

(D-2)

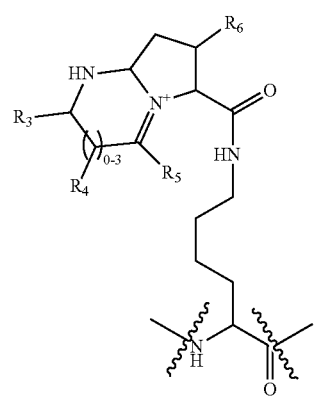

(E-1)

-continued (F-2)
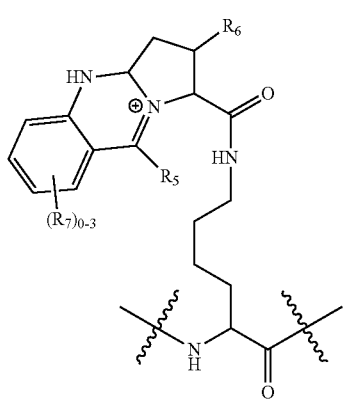

(G-1)

(H-2)

(I-1)
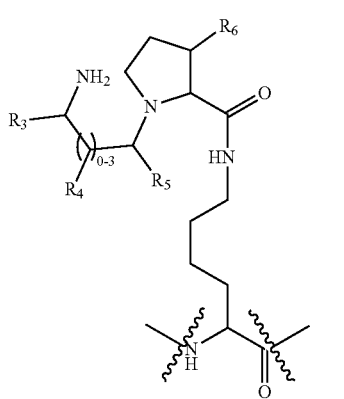

-continued (J-2)
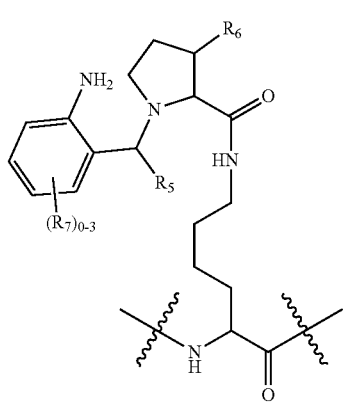

(K-1)
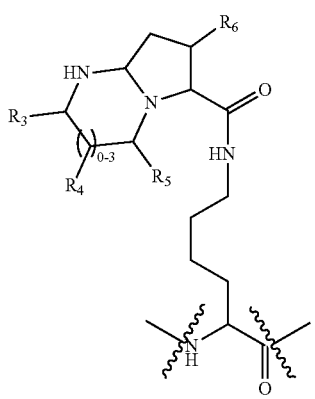

(L-2)
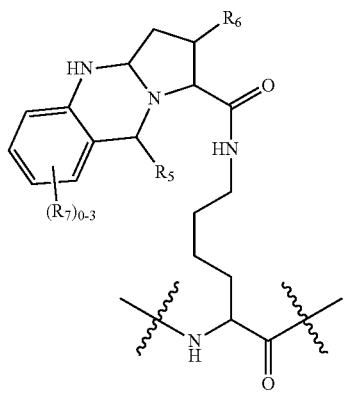

wherein,
$R_3$, $R_5$ and each $R_4$ is independently selected from H, —OH, —NO$_2$, halo, C$_{1-8}$alkyl, halo-substituted-C$_{1-8}$alkyl, hydroxy-substituted-C$_{1-8}$alkyl, aryl, heteroaryl, heterocycloalkly or cycloalkyl and -LX$^1$;

$R_6$ is H or C$_1$alkyl;

when present each $R_7$ is independently selected from —OH, —NO$_2$, halo, C$_{1-8}$alkyl, halo-substituted-C$_{1-8}$alkyl, hydroxy-substituted-C$_{1-8}$alkyl, aryl, heteroaryl, heterocycloalkly or cycloalkyl and -LX$^1$;

L is selected from a bond, C$_{1-8}$alkylene, halo-substituted-C$_{1-8}$alkylene, hydroxy-substituted-C$_{1-8}$alkylene, C$_{2-8}$alkenylene, halo-substituted-C$_{2-8}$alkenylene, hydroxy-substituted-C$_{2-8}$alkenylene, a polyalkylene glycol, a poly(ethylene glycol), —O(CR$^{11}$R$^{12}$)$_k$—, —S(CR$^{11}$R$^{12}$)$_k$—, —S(O)$_k$(CR$^{11}$R$^{12}$)$_k$—, —O(CR$^{11}$R$^{12}$)$_k$—NR$^{11}$C(O)—, —O(CR$^{11}$R$^{12}$)$_k$C(O)NR$^{11}$—, —C(O)—, —C(O)

$-(CR^{11}R^{12})_k-$, $-C(S)-$, $-C(S)(CR^{11}R^{12})_k-$, $-C(O)NR^{11}-$, $-NR^{11}C(O)-$, $-NR^{11}(CR^{11}R^{12})_k-$, $-CONR^{11}(CR^{11}R^{12})_k-$, $-N(R^{11})CO(CR^{11}R^{12})_k-$, $-C(O)NR^{11}(CR^{11}R^{12})_k-$, $-NR^{11}C(O)(CR^{11}R^{12})_k-$, where each $R^{11}$ and $R^{12}$ are independently H, $C_{1-8}$alkyl, halo-substituted-$C_{1-8}$alkyl, or hydroxy-substituted-$C_{1-8}$alkyl, and k is an integer from 1 to 12, and $X^1$ is selected from a label, a dye, a polymer, a water-soluble polymer, a polyalkylene glycol, a poly(ethylene glycol), a derivative of poly(ethylene glycol), a sugar, a lipid, a photocrosslinker, a cytotoxic compound, a drug, an affinity label, a photoaffinity label, a reactive compound; a resin, a peptide, a second protein or polypeptide or polypeptide analog, an antibody or antibody fragment, a metal chelator, a cofactor, a fatty acid, a carbohydrate, a polynucleotide, a DNA, a RNA, a PCR probe, an antisense polynucleotide, a ribo-oligonucleotide, a deoxyribo-oligonucleotide, phosphorothioate-modified DNA, modified DNA and RNA, a peptide nucleic acid, a saccharide, a disaccharide, an oligosaccharide, a polysaccharide, a water-soluble dendrimer, a cyclodextrin, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a ligand, a photoisomerizable moiety, biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chromophoric group, a chemiluminescent group, a fluorescent moiety, an electron dense group, a magnetic group, an intercalating group, a chelating group, a chromophore, an energy transfer agent, a biologically active agent, a detectable label, a small molecule, an inhibitory ribonucleic acid, an siRNA, a radionucleotide, a neutron-capture agent, a derivative of biotin, quantum dot(s), a nanotransmitter, a radiotransmitter, an abzyme, an enzyme, an activated complex activator, a virus, a toxin, an adjuvant, a TLR2 agonist, a TLR4 agonist, a TLR7 agonist, a TLR9 agonist, a TLR8 agonist, a T-cell epitope, a phospho-lipid, a LPS-like molecule, keyhole limpet hemocyanin (KLH), an immunogenic hapten, an aglycan, an allergen, an angiostatin, an antihormone, an antioxidant, an aptamer, a guide RNA, a saponin, a shuttle vector, a macromolecule, a mimotope, a receptor, a reverse micelle, detergents, immune response potentiators, fluorescence dyes, FRET reagents, radio-imaging probes, other spectroscopy probe, prodrugs, toxins for immunotherapy, a solid support, $-CH_2CH_2-(OCH_2CH_2O)_p-OX^2$, $-O-(CH_2CH_2O)_pCH_2CH_2-X^2$, and any combination thereof, wherein p is 1 to 10,000 and $X^2$ is H, a $C_{1-8}$alkyl, a protecting group or a terminal functional group.

In certain embodiments of the aforemention methods and such derivatized proteins, $R_6$ is H, while in other embodiments of $R_6$ is $C_1$alkyl.

In certain embodiments of the aforemention methods and such derivatized proteins, $R_5$ is -$LX^1$. In certain embodiments of the aforemention methods and such derivatized proteins, $X^1$ is a sugar, a polyethylene glycol, a fluorescent moiety, an immunomodulator, a ribonucleic acid, a deoxyribonucleic acid, a protein, a peptide, a biotin, a phospholipid, a TLR7 agonist, an immunogenic hapten or a solid support. In certain embodiments, L is poly(alkyleneglycol), a poly(ethyleneglycol), $C_{1-8}$alkylene, halo-substituted-$C_{1-8}$alkylene or hydroxy-substituted-$C_{1-8}$alkylene.

In certain embodiments of the aforementioned methods, the reagent of Formula (IV) is

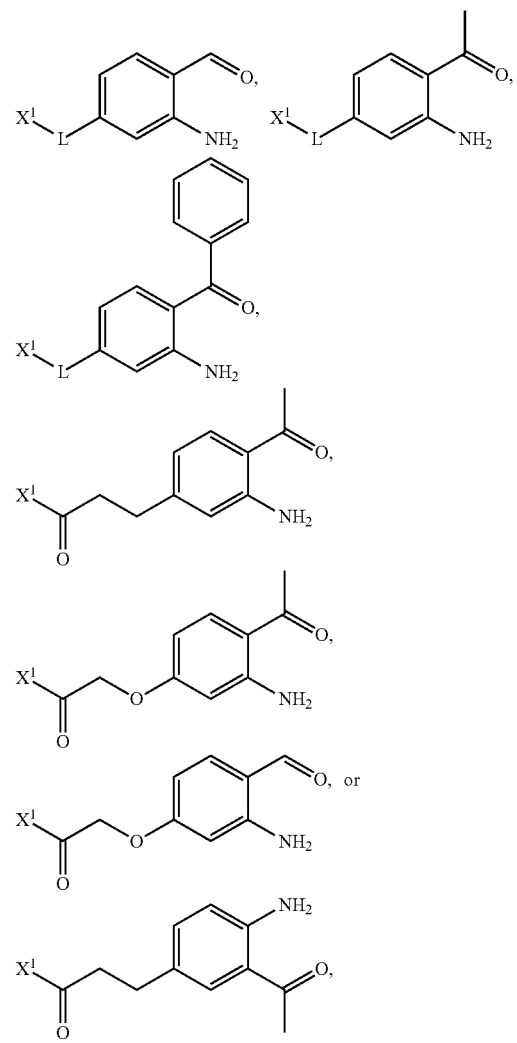

wherein L and $X^1$ are as described herein.

In certain embodiments of such reagents, L is a bond and $X^1$ is a polyethylene glycol.

In certain embodiments of the reagent of Formula (IV) is

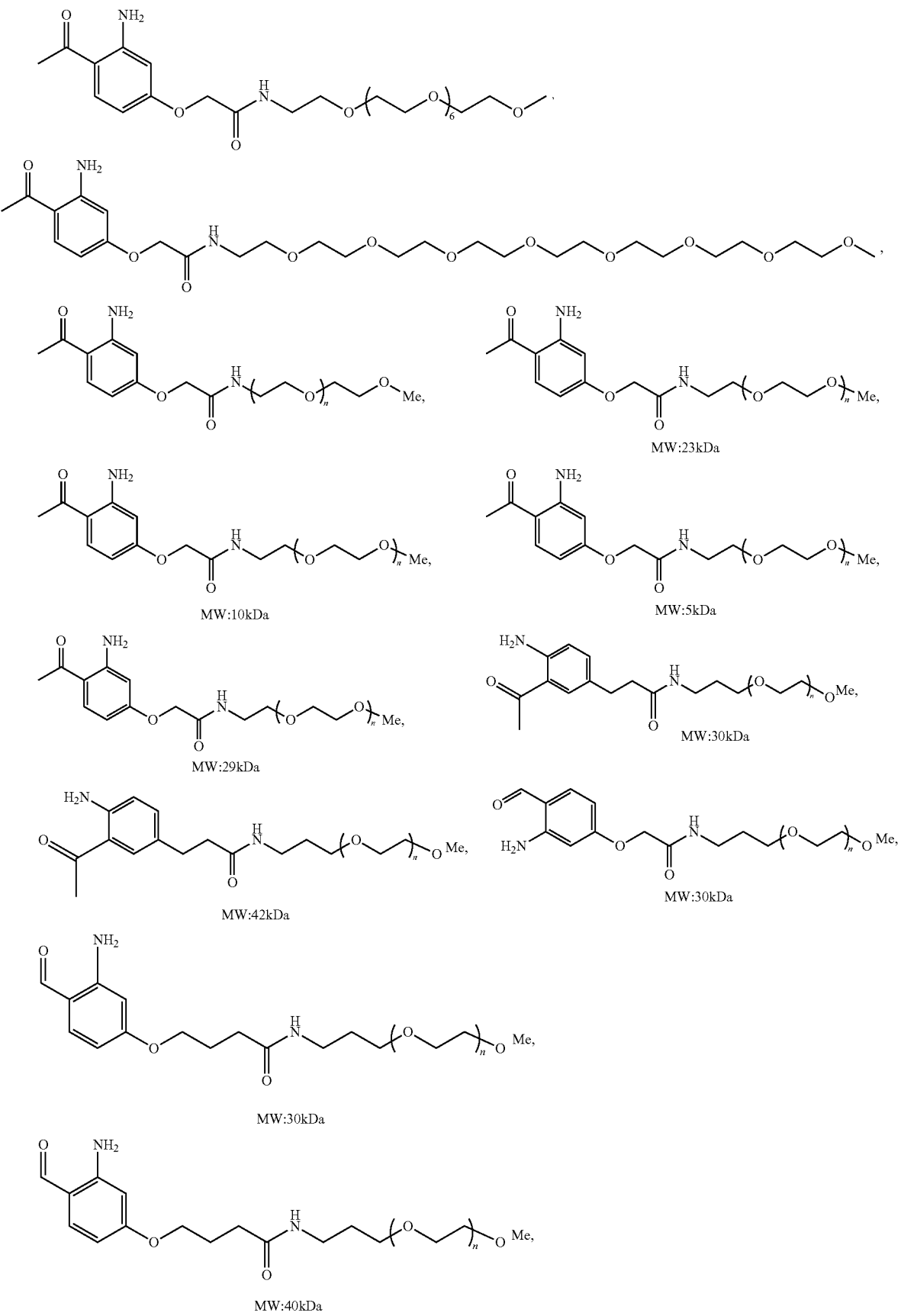

-continued
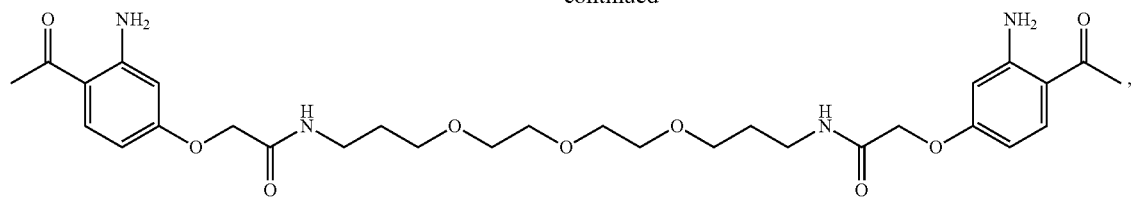
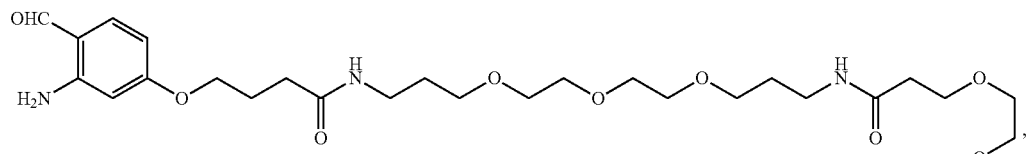
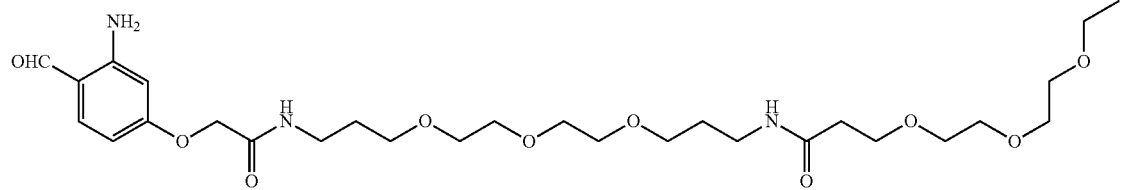
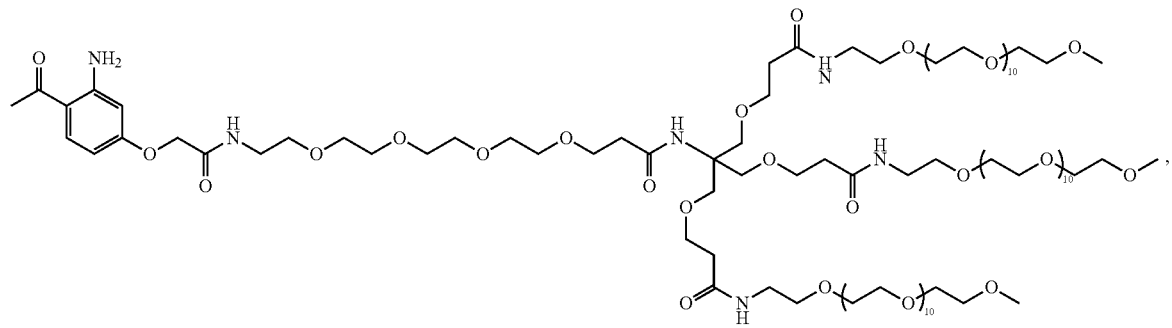
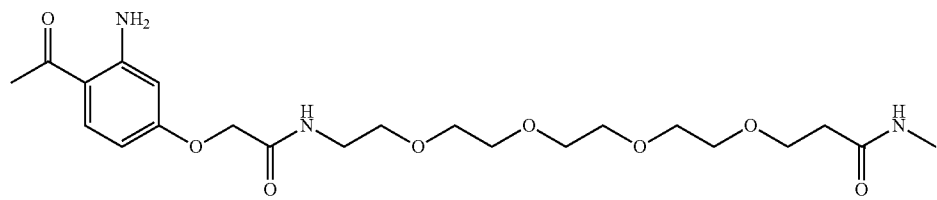
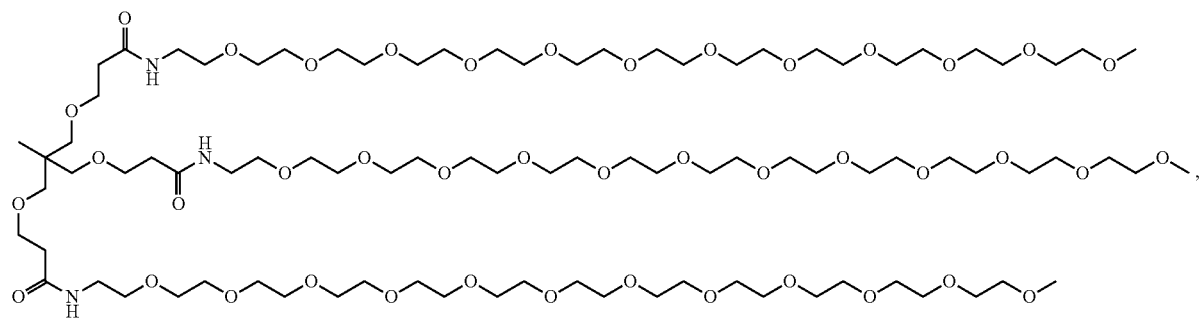
MW: 2.4kDa -continued
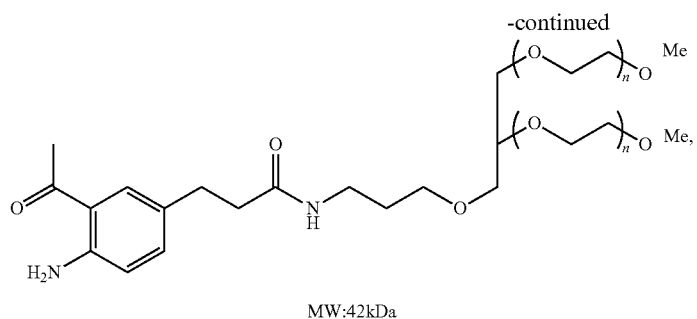
MW:42kDa
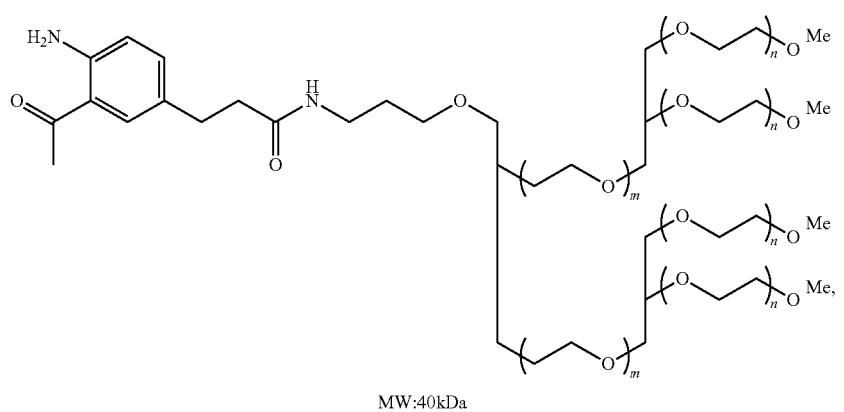
MW:40kDa
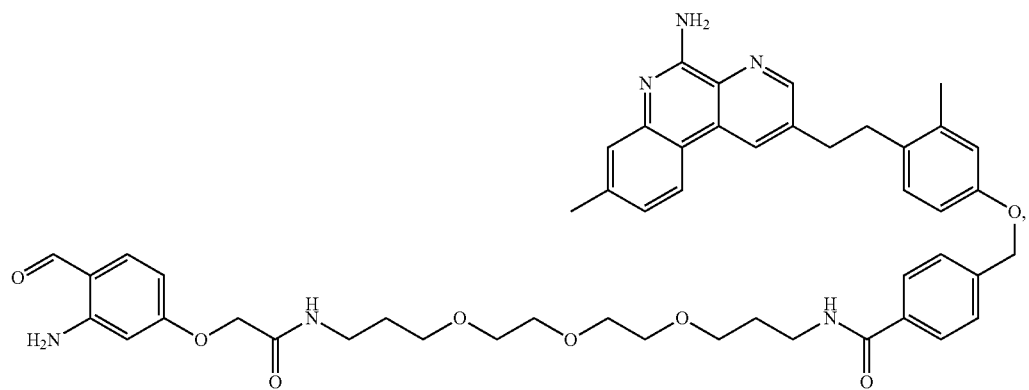
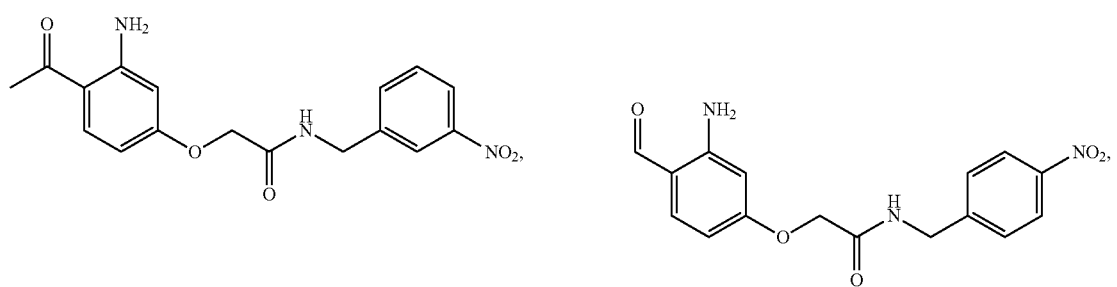

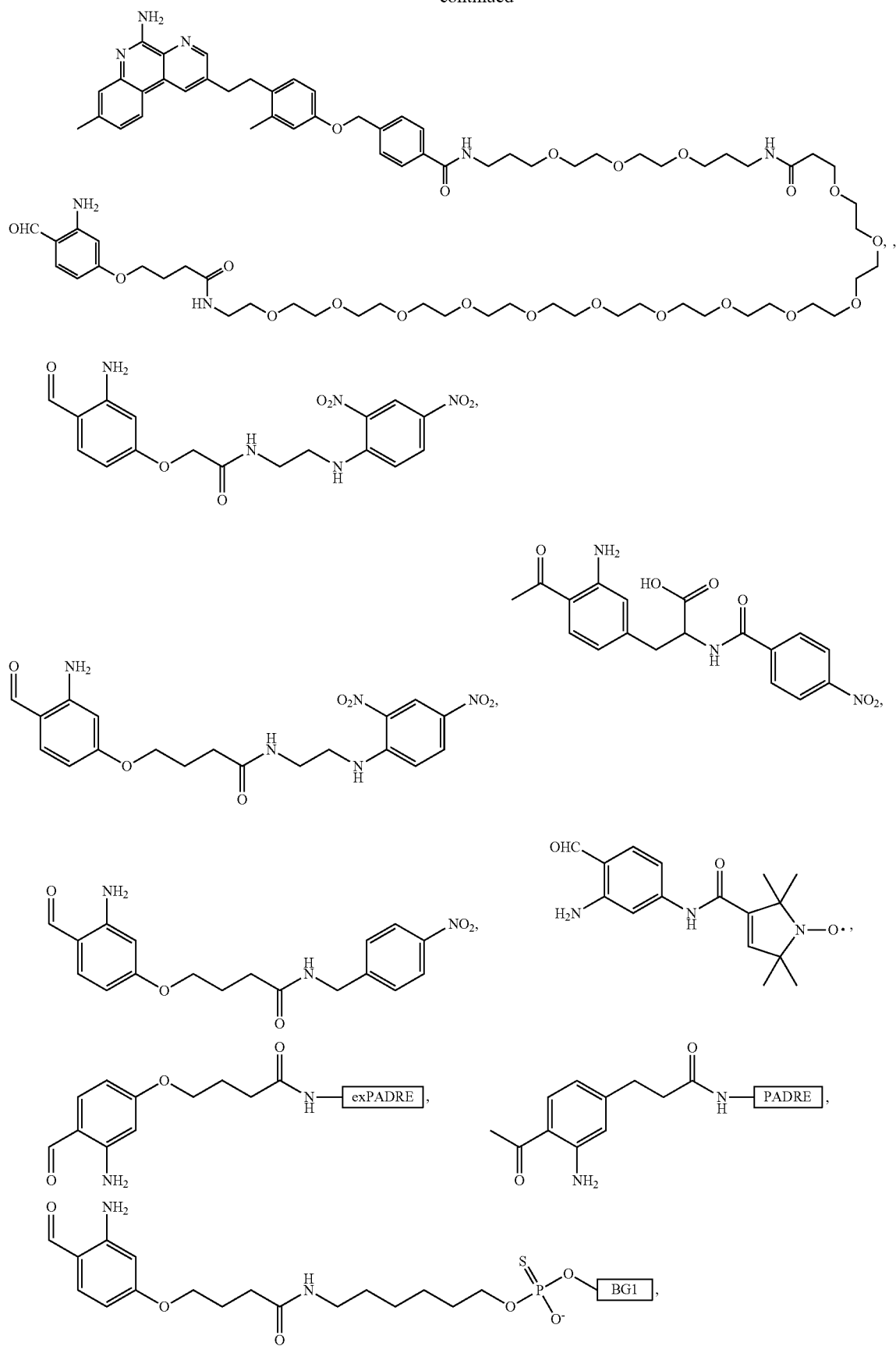

-continued

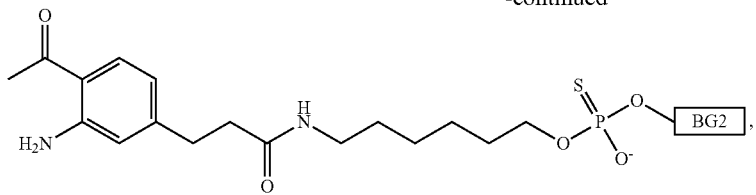

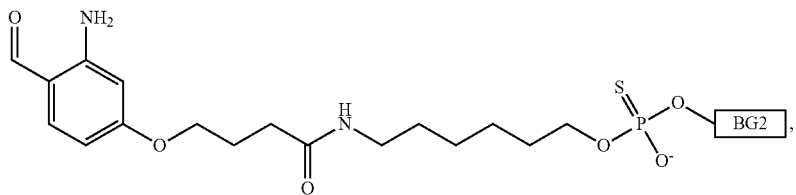

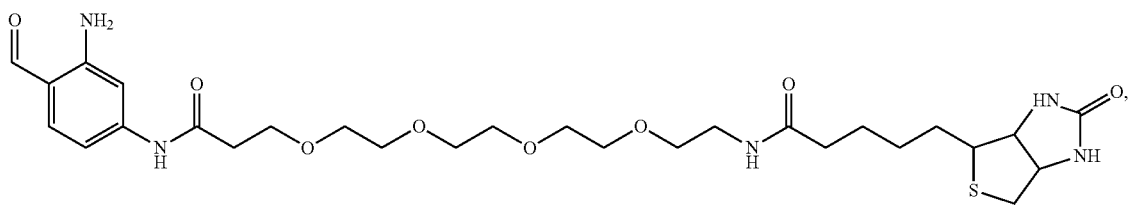

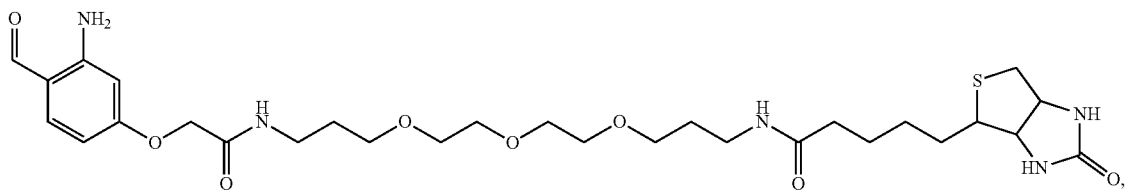

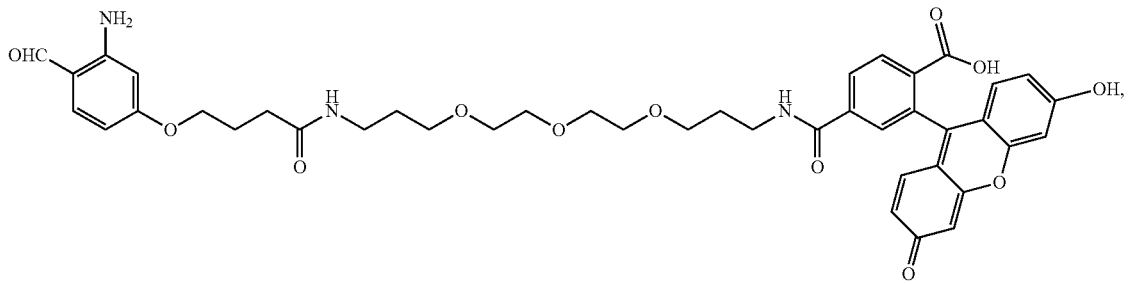

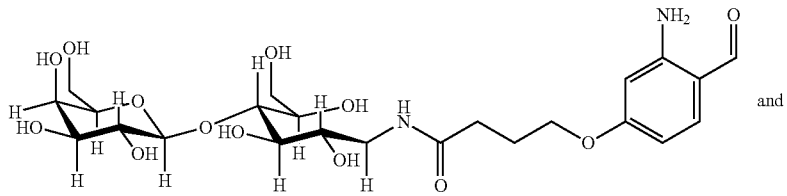

and

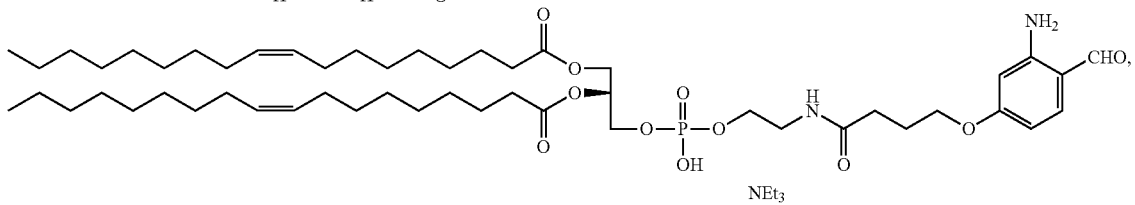

wherein the compounds having one or more polyethyleneglycol (PEG) moieties have an average molecular weight in the range from 1000 Da to 50 kDa, and n is from 20 to 1200 and wherein exPADRE is AlaGlySerArgSerGly(DAla)LysChaValAlaAlaTrpThrLeuLysAla(D-Ala)Gly-OH, PADRE is Gly(DAla)LysChaValAlaAlaTrpThrLeuLysAla(D-Ala)Gly-OH, BG1 is 5'*T*C*C*A*T*G*A*C*G*T*T*C*C*T*G*A*C*G*T*T-3' and BG2 is 5'*T*C*G*T*C*G*T*T*T*T*C*G*G*C*G*C*G*C*G*C*C*G-3', and where * denotes a phosphothioate linkage.

In certain embodiments of the reagent of Formula (IV) is a compound having the following structure:

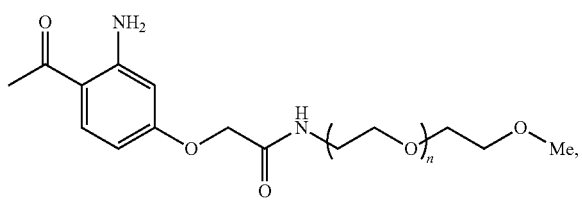

wherein the compound has an average molecular weight in the range from 1000 Da to 30 kDa, and n is from 20 to 679. In another embodiment, the reagent of Formula (IV) is a compound having the following structure:

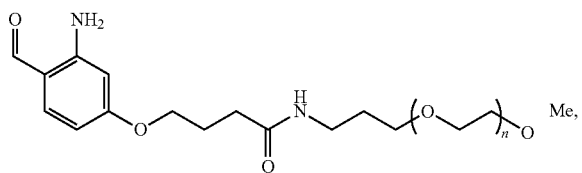

wherein the compound has an average molecular weight in the range from 1000 Da to 45 kDa, and n is from 20 to 1018.

Another aspect provided herein are compounds having the structure of Formula (VII) or Formula (VIII):

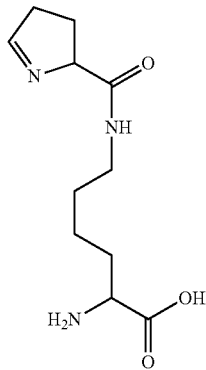
(VII)

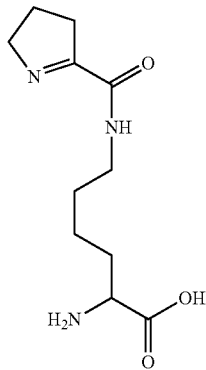
(VIII)

wherein the compound of Formula (VII) or Formula (VIII) is biosynthetically generated within a cell comprising a pylC gene, and a pylD gene, and the cell is in contact with a growth medium comprising a precursor.

In certain embodiments of such compounds, the cell comprises a pylB gene, a pylC gene and a pylD gene.

In certain embodiments of such compounds, the precursor is ornithine or arginine, while in other embodiments the precursor is D-ornithine or D-arginine or (2S)-2-amino-6-((R)-2,5-diaminopentanamido)hexanoic acid.

In certain embodiments of such compounds, the compound of Formula (VII) or Formula (VIII) is incorporated into a protein within the cell by an orthogonal tRNA (O-tRNA) and an orthogonal aminoacyl tRNA synthetase (O-RS), wherein the O-RS aminoacylates the O-tRNA with the compound of Formula (V) or Formula (VI) and the O-tRNA recognized at least one selector codon of a mRNA in the cell.

In certain embodiments of such compounds, the cell further comprises a pylS gene and a pylT gene and the compound of Formula (V) or Formula (VI) is incorporated into a protein within the cell by an aminoacyl tRNA synthetase and a tRNA which recognizes at least one selector codon of a mRNA in the cell, wherein the aminoacyl tRNA synthetase is a gene product of the pylS gene and the tRNA is a gene product of the pylT gene.

In certain embodiments the selector codon is an amber codon (TAG). In certain embodiments, the cell is a prokaryotic cell, while in other embodiments the cell is a eukaryotic cell. In certain embodiments, the cell is an *Escherichia coli* cell, while in other embodiments the cell is a mammalian cell, a yeast cell or an insect cell. In certain embodiments, the yeast cell is a *Saccharomyces cerevisiae* or *Pichia pastoralis* cell. In certain embodiments, the mammalian cell is a CHO cell, a HeLa cell or a HEK293F cell. In certain embodiments, the insect cell is a sf9 cell.

Another aspect provide herein are compounds having the structure of Formula (V) or Formula (VI):

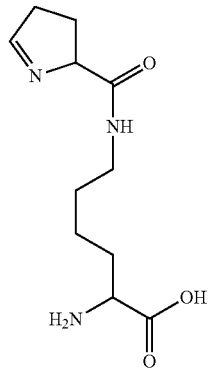
(VII)

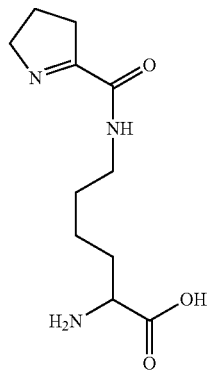
(VIII)

wherein the compound of Formula (VII) or Formula (VIII) is biosynthetically generated and secreted by a first cell in contact with a growth medium comprising a precursor and a second cell, and wherein the first cell is a feeder cell comprising a pylC gene and a pylD gene.

In certain embodiments of such compounds, the first cell comprises a pylB gene, a pylC gene and a pylD gene.

In certain embodiments of such compounds, the precursor is ornithine or arginine. In other embodiments of such compounds, the precursor is D-ornithine or D-arginine. In other embodiments of such compounds, the precursor is (2S)-2-amino-6-(2,5-diaminopentanamido)hexanoic acid. In other embodiments of such compounds, the precursor is (2S)-2-amino-6-((R)-2,5-diaminopentanamido)hexanoic acid.

In certain embodiments of such compounds, the compound of Formula (VII) or Formula (VIII) is incorporated into a protein in the second cell by an orthogonal tRNA (O-tRNA) and an orthogonal aminoacyl tRNA synthetase (O-RS), wherein the O-RS aminoacylates the O-tRNA with the compound of Formula (VII) or Formula (VIII) and the O-tRNA recognized at least one selector codon of a mRNA in the second cell.

In certain embodiments of such compounds, the second cell comprises a pylS gene and a pylT gene and the compound of Formula (VII) or Formula (VIII) is incorporated into a protein within the second cell.

In certain embodiments of such compounds, the compound of Formula (VII) or Formula (VIII) is incorporated into the protein within the second cell by an aminoacyl tRNA synthetase and a tRNA which recognizes at least one selector codon of a mRNA in the cell, wherein the aminoacyl tRNA synthetase is a gene product of the pylS gene and the tRNA is a gene product of the pylT gene.

In certain embodiments of such compounds, the selector codon is an amber codon (TAG).

In certain embodiments of such compounds, the first cell or the second cell is a prokaryotic cell. In certain embodiments of such compounds, the first cell and the second cell is a prokaryotic cell. In certain embodiments of such compounds, the first cell or the second cell is a eukaryotic cell. In certain embodiments of such compounds, the first cell and the second cell is a eukaryotic cell.

In certain embodiments the prokaryotic cell is an *Escherichia coli* cell. In certain embodiments, the eukaryotic cell is a mammalian cell, a yeast cell or an insect cell. In certain embodiments, the yeast cell is a *Saccharomyces cerevisiae* or *Pichia pastoralis* cell. In certain embodiments, the mammalian cell is a CHO cell, a HeLa cell or a HEK293F cell. In certain embodiments, insect cell is a sf9 cell.

Another aspect provided herein is a compound having the structure of Formula (IX):

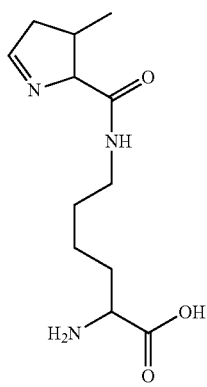

(IX)

wherein the compound of Formula (IX) is biosynthetically generated within a cell comprising a pylC gene, and a pylD gene, and the cell is in contact with a growth medium comprising 2,5-diamino-3-methylpentanoic acid or D-2,5-diamino-3-methylpentanoic acid.

In certain embodiments of such a compound, the 2,5-diamino-3-methylpentanoic acid is (2R,3S)-2,5-diamino-3-methylpentanoic acid.

In certain embodiments of such a compound, the 2,5-diamino-3-methylpentanoic acid is (2R,3R)-2,5-diamino-3-methylpentanoic acid.

In certain embodiments of such a compound, the cell comprises a pylB gene, a pylC gene and a pylD gene, and the cell is in contact with a growth medium comprising ornithine, arginine, D-ornithine, D-arginine, (2S)-2-amino-6-(2,5-diaminopentanamido)hexanoic acid 2,5-diamino-3-methylpentanoic acid or D-2,5-diamino-3-methylpentanoic acid.

In certain embodiments of such a compound, the compound of Formula (IX) is incorporated into a protein within the cell by an orthogonal tRNA (O-tRNA) and an orthogonal aminoacyl tRNA synthetase (O-RS), wherein the O-RS aminoacylates the O-tRNA with the compound of Formula (IX) and the O-tRNA recognized at least one selector codon of a mRNA in the cell.

In certain embodiments of such a compound, the cell further comprises a pylS gene and a pylT gene and the compound of Formula (IX) is incorporated into a protein within the cell by an aminoacyl tRNA synthetase and a tRNA which recognizes at least one selector codon of a mRNA in the cell, wherein the aminoacyl tRNA synthetase is a gene product of the pylS gene and the tRNA is a gene product of the pylT gene.

In certain embodiments, the selector codon is an amber codon (TAG). In certain embodiments, the cell is a prokaryotic cell, while in other embodiments, the cell is a eukaryotic cell. In certain embodiments, the prokaryotic cell is an *Escherichia coli* cell. In certain embodiments, the eukaryotic cell is a mammalian cell, a yeast cell or an insect cell. In certain embodiments, the yeast cell is a *Saccharomyces cerevisiae* or *Pichia pastoralis* cell. In certain embodiments, the mammalian cell is a CHO cell, a HeLa cell or a HEK293F cell. In certain embodiments, the insect cell is a sf9 cell.

Another aspect provided herein is a compound having the structure of Formula (IX):

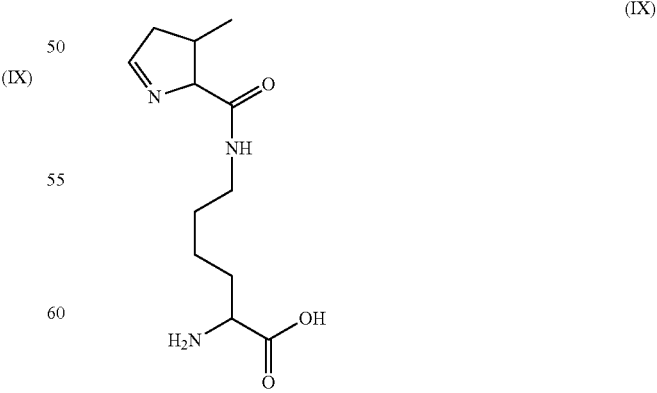

(IX)

wherein the compound of Formula (IX) is biosynthetically generated and secreted by a first cell in contact with a growth medium comprising 2,5-diamino-3-methylpentanoic acid or D-2,5-diamino-3-methylpentanoic acid, and a second cell, and wherein the first cell is a feeder cell comprising a pylC gene and a pylD gene.

In certain embodiments of such a compound, the 2,5-diamino-3-methylpentanoic acid is (2R,3S)-2,5-diamino-3-methylpentanoic acid.

In certain embodiments of such a compound, the 2,5-diamino-3-methylpentanoic acid is (2R,3R)-2,5-diamino-3-methylpentanoic acid.

In certain embodiments of such a compound, the cell comprises a pylB gene, a pylC gene and a pylD gene, and the cell is in contact with a growth medium comprising ornithine, arginine, D-ornithine, D-arginine, (2S)-2-amino-6-(2,5-diaminopentanamido)hexanoic acid 2,5-diamino-3-methylpentanoic acid or D-2,5-diamino-3-methylpentanoic acid.

In certain embodiments of such a compound, the compound of Formula (IX) is incorporated into a protein in the second cell by an orthogonal tRNA (O-tRNA) and an orthogonal aminoacyl tRNA synthetase (O-RS), wherein the O-RS aminoacylates the O-tRNA with the compound of Formula (IX) and the O-tRNA recognized at least one selector codon of a mRNA in the second cell.

In certain embodiments of such a compound, the second cell comprises a pylS gene and a pylT gene and the compound of Formula (IX) is incorporated into a protein within the second cell.

In certain embodiments of such a compound, the compound of Formula (IX) is incorporated into the protein within the second cell by an aminoacyl tRNA synthetase and a tRNA which recognizes at least one selector codon of a mRNA in the cell, and wherein the aminoacyl tRNA synthetase is a gene product of the pylS gene and the tRNA is a gene product of the pylT gene.

In certain embodiments, the selector codon is an amber codon (TAG).

In certain embodiments, the first cell or the second cell is a prokaryotic cell. In certain embodiments, the first cell and the second cell is a prokaryotic cell. In certain embodiments, the first cell or the second cell is a eukaryotic cell. In certain embodiments, the first cell and the second cell is a eukaryotic cell. In certain embodiments, the prokaryotic cell is an *Escherichia coli* cell. In certain embodiments the eukaryotic cell is a mammalian cell, a yeast cell or an insect cell. In certain embodiments, the yeast cell is a *Saccharomyces cerevisiae* or *Pichia pastoralis* cell. In certain embodiments, the mammalian cell is a CHO cell, a HeLa cell or a HEK293F cell. In certain embodiments, the insect cell is a sf9 cell.

Another aspect provided herein are the following compounds of Formula (IV):

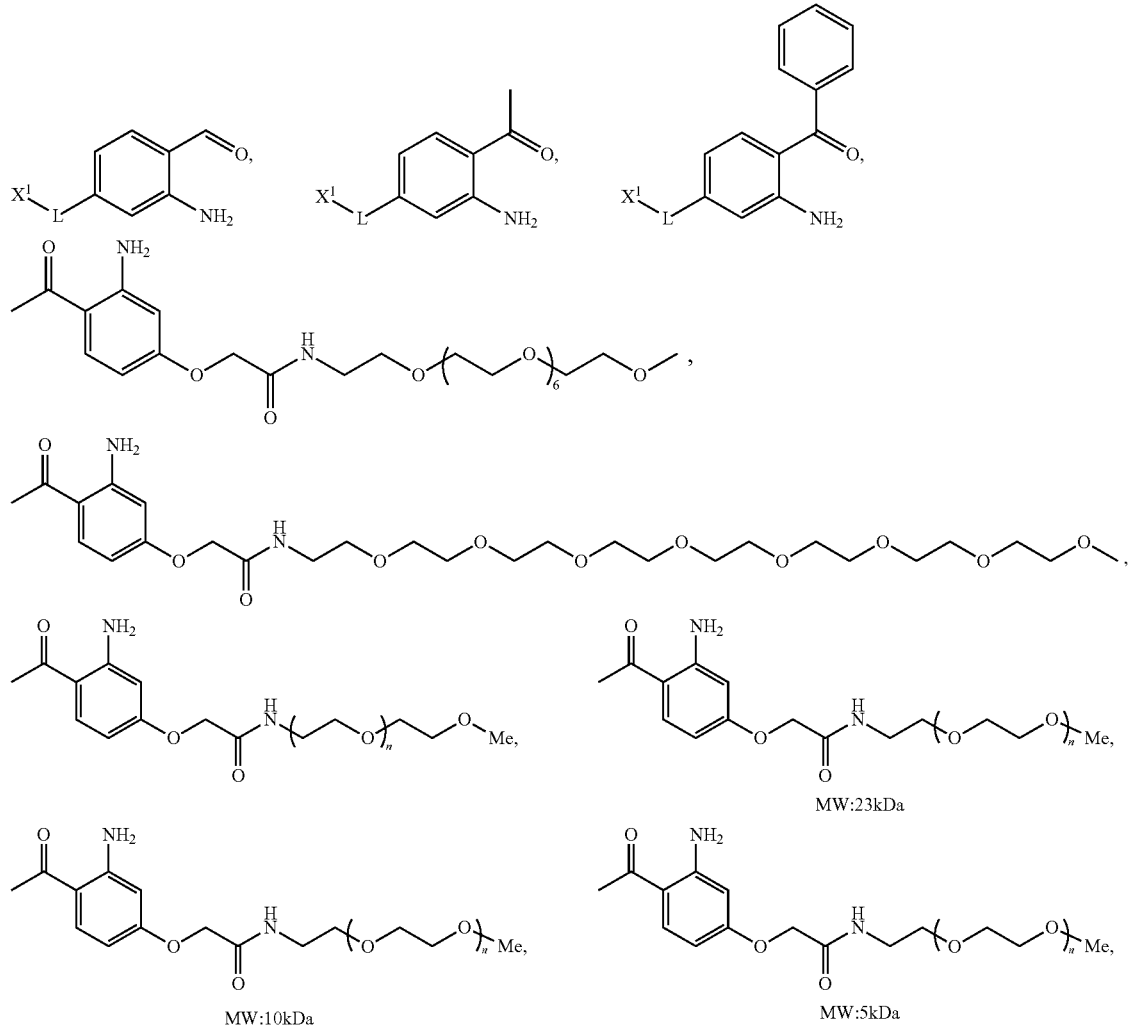

-continued
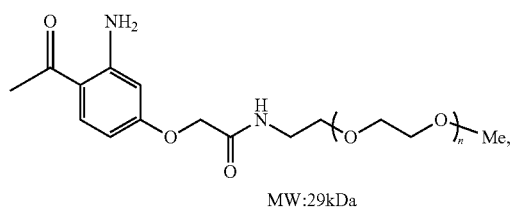
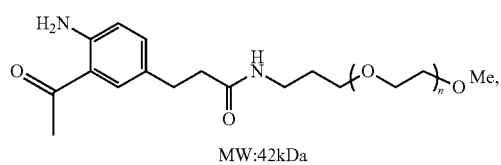
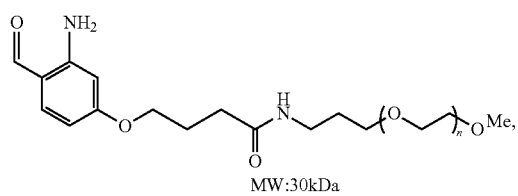
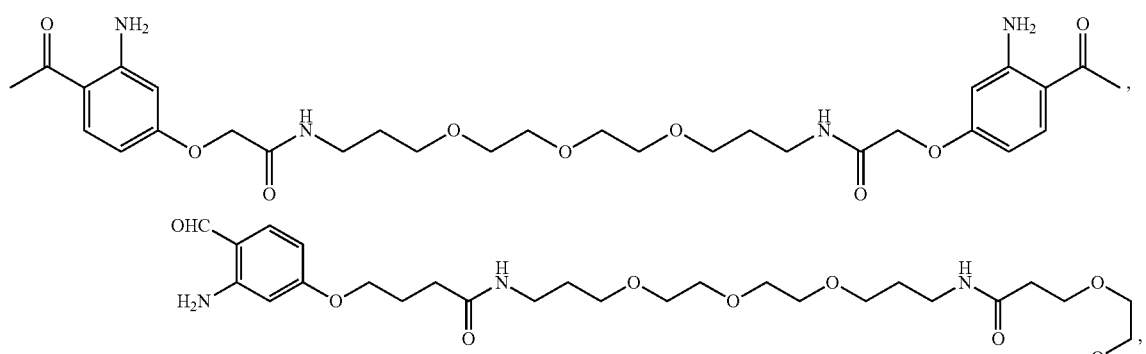
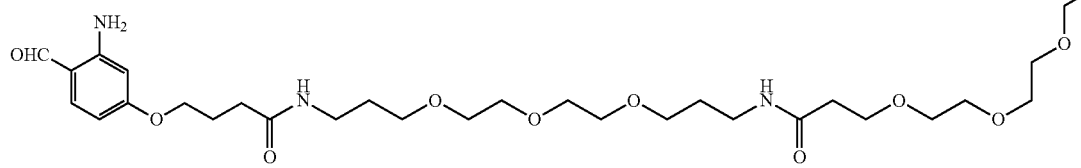
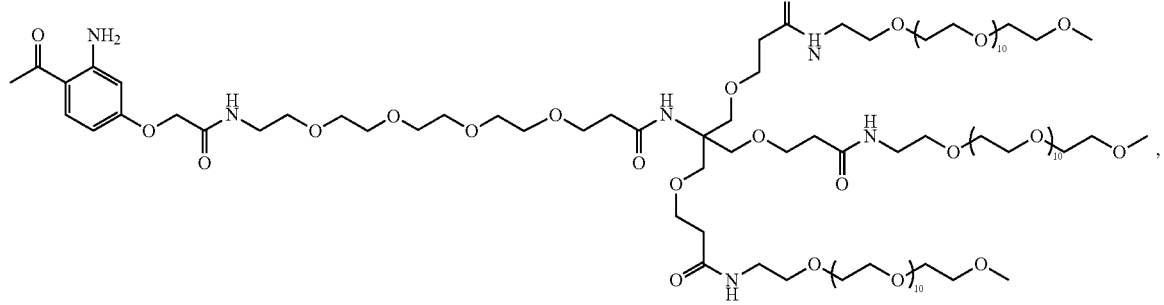
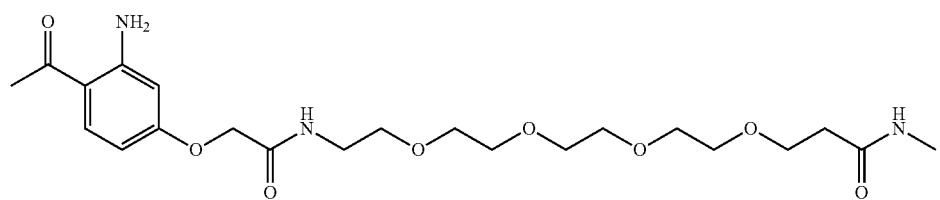

-continued
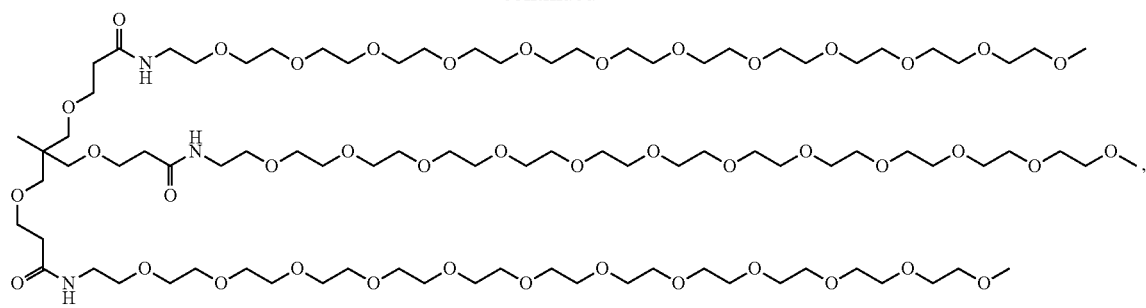
MW: 2.4kDa
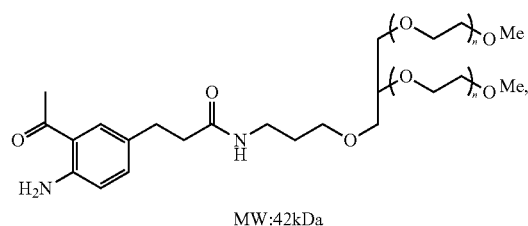
MW: 42kDa
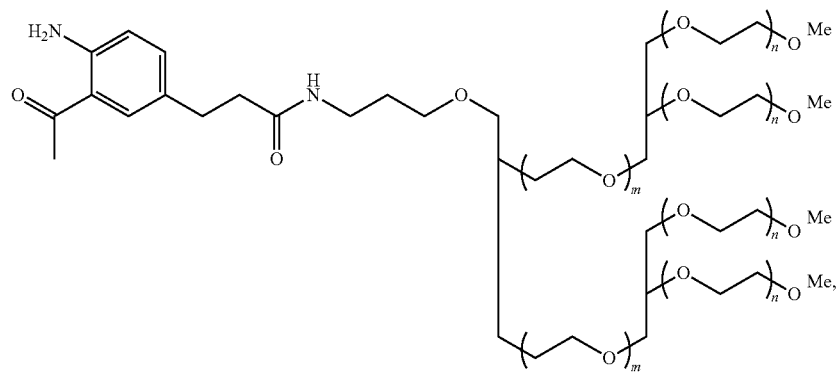
MW: 40kDa
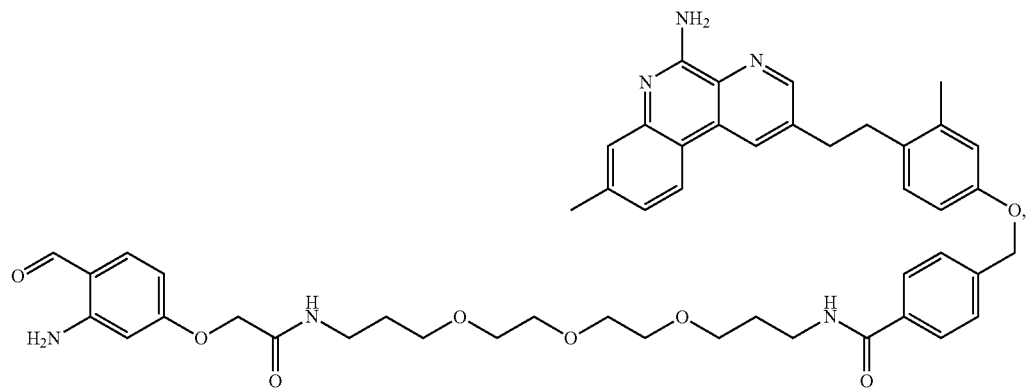
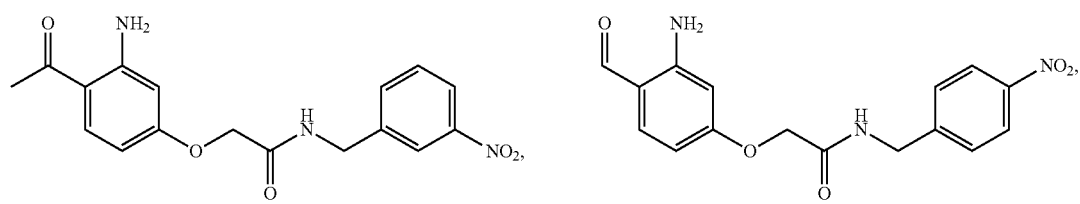

-continued
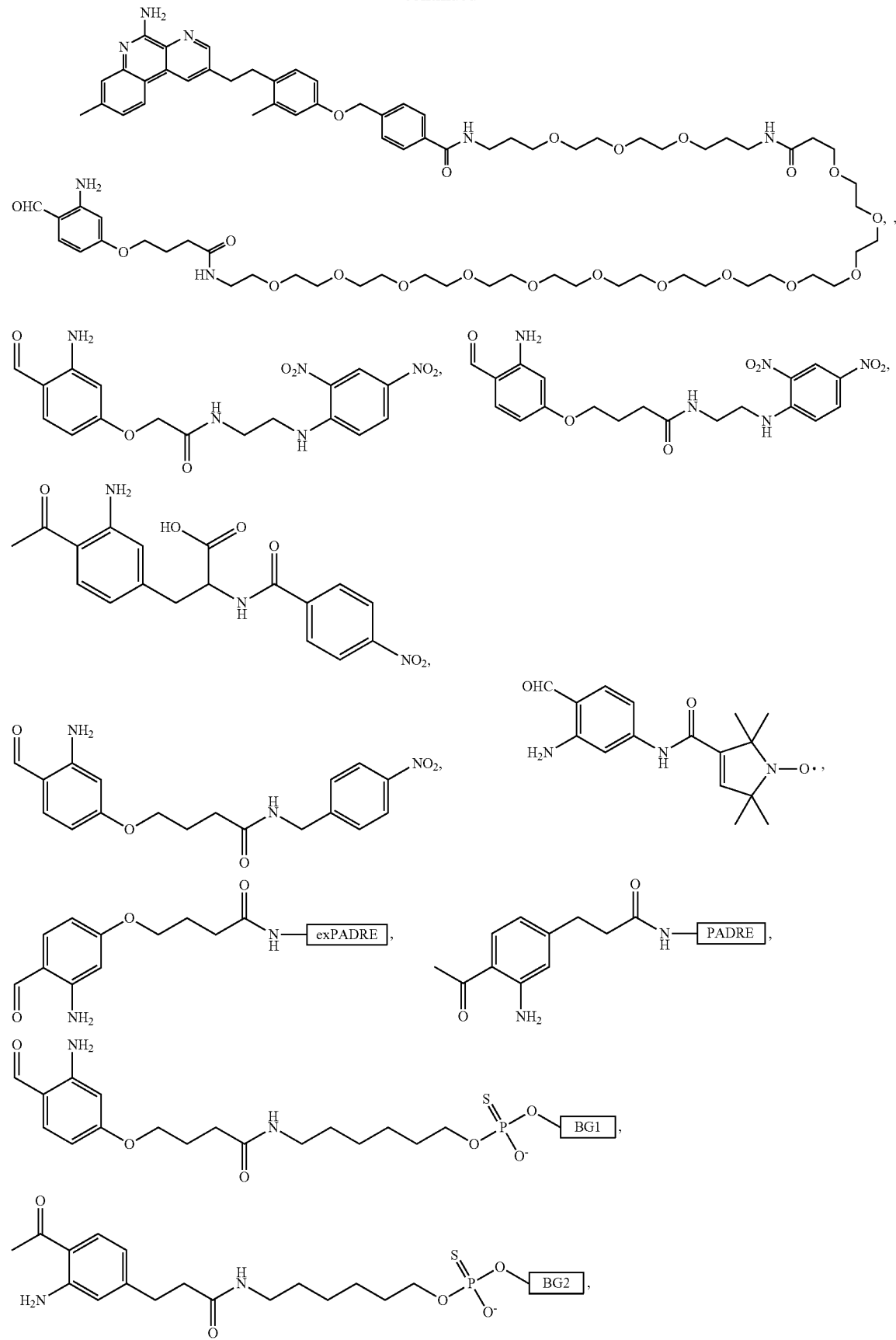

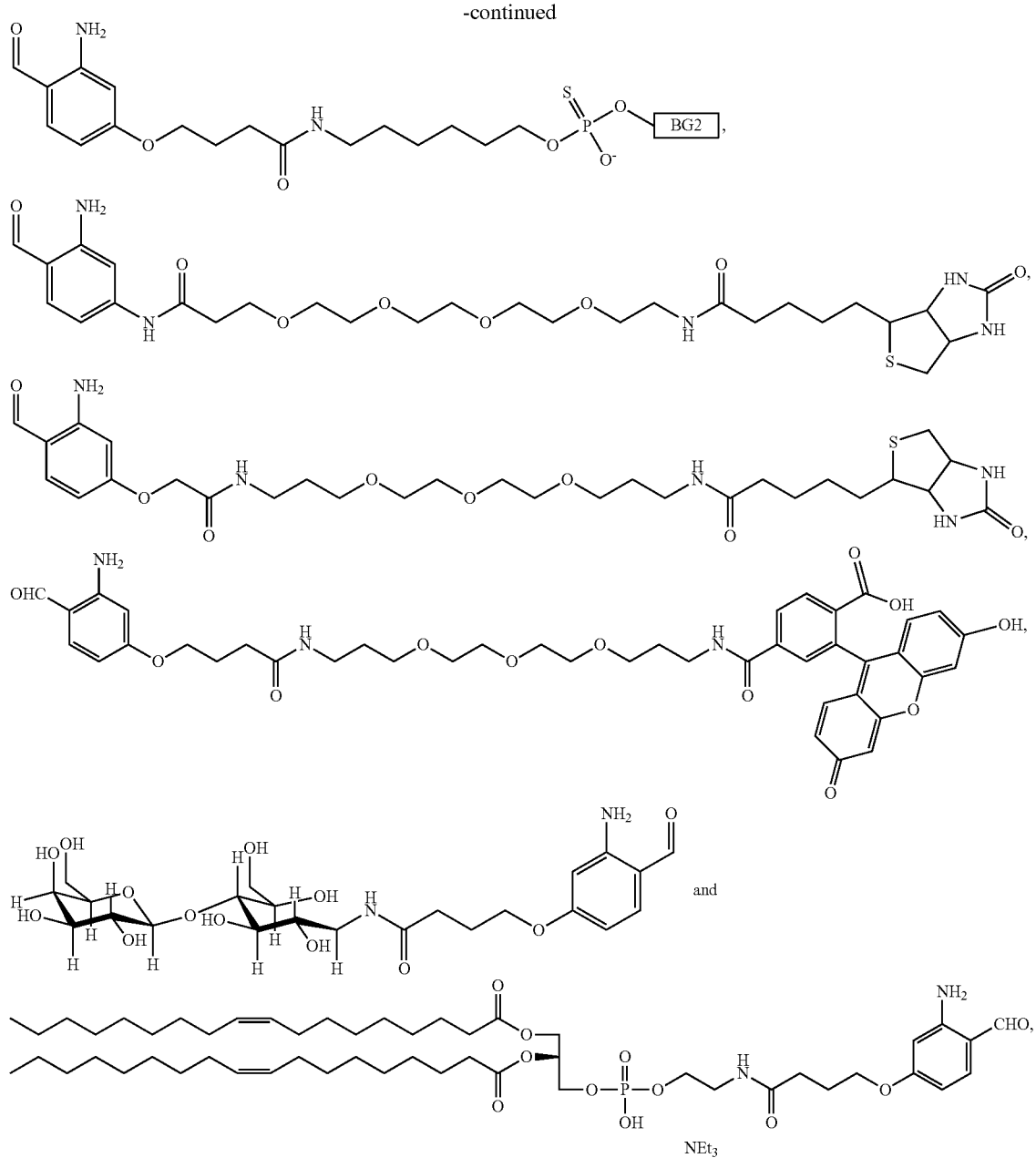

wherein compounds having one or more polyethyleneglycol (PEG) moieties have an average molecular weight in the range from 1000 Da to 50 kDa, and n is from 20 to 1200 and wherein exPADRE is AlaGlySerArgSerGly(DAla)LysChaValAlaAlaTrpThrLeuLysAla(D-Ala)Gly-OH, PADRE is Gly(DAla)LysChaValAlaAlaTrpThrLeuLysAla(D-Ala)Gly-OH, BG1 is 5'*T*C*C*A*T*G*A*C*G*T*T*C*C*T*G*A*C*G*T*T-3' and BG2 is 5'*T*C*G*T*C*G*T*T*T*T*C*G*G*C*G*C*G*C*G*C*C*G-3', and where * denotes a phosphothioate linkage.

DETAILED DESCRIPTION OF THE INVENTION

Provided herein are methods and compositions used to site-specifically modify proteins, polypeptides and/or peptides, wherein such methods involve site-specific modification of genetically encoded pyrrolysine or pyrroline-carboxylysine (PCL) residues wherein the pyrrolysine and PCL amino acids have been biosynthetically generated. Provided herein are various types of molecules that are site specifically coupled to proteins, polypeptides and/or peptides having one or more PCL moieties or pyrrolysine biosynthetically incorporated therein. In certain embodiments, such site-specific modifications are used to site-specifically label proteins, polypeptides and/or peptides. In certain embodiments, the label is a fluorescent moiety, a phosphorescent moiety, a chemiluminescent moiety, a chelating moiety, an intercalating moiety, a radioactive moiety, a chromophoric moiety, radioactive moiety, a spin-labeled moiety, a NMR-active moiety, a PET or MRI imaging reagents. In certain embodiments, such site-specific modifications are used to attach immune modulators to proteins, polypeptides and/or peptides. In other embodiments, such site-specific modifications are used to attach poly(ethylene glycol) (PEG) to proteins, polypeptides and/or peptides. In other embodiments, such site-specific modifications are used to attach sugars (glycosylate) to proteins, polypeptides and/or peptides.

In other embodiments, such site-specific modifications are used to site-specifically cross-link proteins, polypeptides and/or peptides thereby forming hetero-oligomers including, but not limited to, heterodimers and heterotrimers. In certain embodiments, such site-specific modifications are used to site-specifically cross-link antibodies to proteins, polypeptides and/or peptides. In other embodiments, such site-specific modifications are used to site-specifically cross-link proteins, polypeptides and/or peptides thereby forming protein-protein conjugates, protein-polypeptide conjugates, protein-peptide conjugates, polypeptide-polypeptide conjugates, polypeptide-peptide conjugates or peptide-peptide conjugates.

In other embodiments, such site-specific modifications are used to site-specifically link antibodies to proteins, in which the protein is a toxic protein provided herein, thereby forming antibody-drug conjugates. In other embodiments, such site-specific modifications are used to site-specifically link antibodies to proteins, in which the antibodies are coupled to low-molecular weight drugs, thereby forming antibody-drug conjugates.

In other embodiments, such site-specific modifications are used to site-specifically link receptor-ligands to proteins, in which the protein is a toxic protein provided herein, thereby forming receptor-ligand-drug conjugates. In other embodiments, such site-specific modifications are used to site-specifically link receptor-ligands to proteins, in which the receptor-ligand is coupled to low-molecular weight drugs, thereby forming receptor-ligand-drug conjugates.

Provided herein are proteins, polypeptides and/or peptides having pyrrolysine and/or PCL incorporated therein using the methods provided. Such proteins include, but are not limited to, is erythropoietin (EPO), fibroblast growth factor 21 (FGF21), interferon alpha (INF-α), interleukin 2 (IL-2), interleukin 4 (IL-4), interleukin 6 (IL-6), interleukin 10 (IL-10), interleukin 17 (IL-17), insulin-like growth factor 1 (IGF-1), and interferon beta (INF-β).

Provided herein are proteins, polypeptides and/or peptides having pyrrolysine and/or PCL incorporated therein using the methods provided herein and further derivatized using the methods provided herein. Such derivatization includes, but is not limited to, PEGylation. Such proteins include, but are not limited to, is erythropoietin (EPO), fibroblast growth factor 21 (FGF21), interferon alpha (INF-α), interleukin 2 (IL-2), interleukin 4 (IL-4), interleukin 6 (IL-6), interleukin 10 (IL-10), interleukin 17 (IL-17), insulin-like growth factor 1 (IGF-1), and interferon beta (INF-β).

Further provided herein are proteins, polypeptides and/or peptides having pyrrolysine and/or PCL incorporated therein, wherein such proteins, polypeptides and/or peptides are crosslinked using the methods provided herein. Such proteins include, but are not limited to, is erythropoietin (EPO), fibroblast growth factor 21 (FGF21), interferon alpha (INF-α), and interferon beta (INF-β).

In other embodiments, such sitespecific modifications are used to produce proteins, polypeptides and/or peptides wherein the position of the site specifically incorporated pyrrolysine or PCL allows for controlled orientation and attachment of such proteins, polypeptides and/or peptides onto a surface of a solid support. In certain embodiments, such solid support is a plastic microtiter plate, a glass slide, a silica surface, a polymer bead, a gold particles or a nano-particles either coated or uncoated. In certain embodiments, such controlled orientation and attachment is used in the analysis of proteins, polypeptides and peptides by ELISA or other antibody assays. In certain embodiments, such controlled orientation and attachment is used to purify and/or identify ligands of the immobilized proteins, polypeptide and/or peptides. In certain embodiments, such controlled orientation and attachment is used in the analysis of proteins, polypeptides and peptides and their interactions by evanescent wave analysis, including but not limited to label-free analysis using surface plasmon resonance analysis. In certain embodiments, such controlled orientation and attachment onto surfaces is used in the analysis of proteins, polypeptides and peptides and their interactions using microbalances (electrical, optical and/or mechanical), infrared spectroscopy, Raman spectroscopy including surface enhance Raman spectroscopy, evanescence resonance, fluorescence, interferometry, mass spectrometry and other spectroscopy methods. Such analysis methods are used to investigate interactions of the immobilized proteins, polypeptide and/or peptides with other proteins, polypeptides, peptides, nucleic acids, DNA, RNA, small molecules, drugs, metabolites, sugars, carbohydrates, oligosaccharides, polysaccharides and/or other molecules including conformational changes induced by such interactions. Such analysis methods are also used to investigate interactions of immobilized proteins, polypeptide and/or peptides with multiple subunit protein complexes, study native, recombinant, synthetic or tagged recombinant molecules, discover new interaction partners in body fluids, cell culture supernatants or crude extracts, study the interaction of small molecules, such as drug candidates, with their targets, study membrane biochemistry or membrane-bound receptor interactions using native membranes, artificial membranes or vesicles, investigate replication, transcription and translation, determine molecular relationships during the formation of protein complexes and their interaction with DNA, study hybridization of DNA and RNA, study interactions involving whole cells or viruses, study the effects of glycosylation on molecular interactions, and determine specific recognition properties of cell surface carbohydrates.

In other embodiments, such site-specific modifications are used to site-specifically attach nucleic acids to proteins. In certain embodiments, such site-specific modifications are used to site-specifically attach nucleic acids to antibodies or antibody fragments. In certain embodiments, the nucleic acid attached to the protein or antibody is used to immobilize the protein or antibody at defined locations onto a DNA array via hybridization. In certain embodiments, the nucleic acid attached to the protein or antibody is used to detect protein or antibody binding via PCR, strand displacement amplification (SDA), ligase chain reaction (LCR), proximity ligation immuno-PCR, rolling circle amplification, transcription-mediated amplification, NEN's tyramide signal amplification or other signal amplification methods. In certain embodiments, such site-specifical attachment of a PCR probe to an antibody is used to generate a reagent for immuno-PCR reactions (See, M. Adler, R. Wacker, Ch. M. Niemeyer, Sensitivity by combination: Immuno-PCR and related technologies, Analyst, 2008, 133, 702-718). In certain embodiments, the nucleic acid attached to the protein or antibody enables immuno-PCR or other immuno-as says of many analytes in parallel (multiplexed immuno-PCR or multiplexed immuno-assays).

In certain embodiments, the nucleic acid attached to the protein or antibody mediates the formation of homo- and heterodimers.

DEFINITIONS

The term "alkyl," as used herein, refers to a saturated branched or straight chain hydrocarbon. As used herein, the terms "$C_1$-$C_3$alkyl", "$C_1$-$C_4$alkyl", "$C_1$-$C_5$alkyl", "$C_1$-$C_6$alkyl", "$C_1$-$C_7$alkyl" and "$C_1$-$C_8$alkyl" refer to an alkyl group containing at least 1, and at most 3, 4, 5, 6, 7 or 8 carbon atoms, respectively. Non-limiting examples of alkyl groups as used herein include methyl, ethyl, n-propyl, isopropyl, n-butyl, isobutyl, sec-butyl, t-butyl, n-pentyl, isopentyl, hexyl, heptyl, octyl, nonyl, decyl and the like.

The term "alkylene," as used herein, refers to a saturated branched or straight chain divalent hydrocarbon radical, wherein the radical is derived by the removal of one hydrogen atom from each of two carbon atoms. As used herein, the terms "$C_1$-$C_3$alkylene", "$C_1$-$C_4$alkylene", "$C_1$-$C_5$alkylene", and "$C_1$-$C_6$alkylene" refer to an alkylene group containing at least 1, and at most 3, 4, 5 or 6 carbon atoms respectively. Non-limiting examples of alkylene groups as used herein include, methylene, ethylene, n-propylene, isopropylene, n-butylene, isobutylene, sec-butylene, t-butylene, n-pentylene, isopentylene, hexylene and the like.

The term "alkoxy," as used herein, refers to the group —OR$_a$, where R$_a$ is an alkyl group as defined herein. As used herein, the terms "$C_1$-$C_3$alkoxy", "$C_1$-$C_4$alkoxy", "$C_1$-$C_5$alkoxy", "$C_1$-$C_6$alkoxy", "$C_1$-$C_7$alkoxy" and "$C_1$-$C_8$alkoxy" refer to an alkoxy group wherein the alkyl moiety contains at least 1, and at most 3, 4, 5, 6, 7 or 8, carbon atoms. Non-limiting examples of alkoxy groups, as used herein, include methoxy, ethoxy, n-propoxy, isopropoxy, n-butoxy, t-butoxy, pentoxy, hexoxy, heptoxy, and the like.

The term "amino terminus modification group," as used herein, refers to any molecule that forms a linkage with a terminal amine group. By way of example, such terminal amine groups include, but are not limited to, amine protecting groups, the end of polymeric molecules, wherein such polymeric molecules include, but are not limited to, polypeptides, polynucleotides, and polysaccharides. Amino terminus modification groups also include but are not limited to, various water soluble polymers, peptides or proteins. By way of example only, terminus modification groups include polyethylene glycol or serum albumin. Certain amino terminus modification groups are used to modify therapeutic characteristics of proteins, including but not limited to increasing the serum half-life.

The term "aryl," as used herein, refers to monocyclic, bicyclic, and tricyclic ring systems having a total of five to fourteen ring members, wherein at least one ring in the system is aromatic and wherein each ring in the system contains 3 to 7 ring members. An aryl group are "optionally substituted", wherein such aryl groups contain one or more substituents. Unless otherwise defined herein, suitable substituents are generally selected from halogen, —R, —OR, —SR, —NO$_2$, —CN, —N(R)$_2$, —NRC(O)R, —NRC(S)R, —NRC(O)N(R)$_2$, —NRC(S)N(R)$_2$, —NRCO$_2$R, —NRNRC(O)R, —NRNRC(O)N(R)$_2$, —NRNRCO$_2$R, —C(O)C(O)R, —C(O)CH$_2$C(O)R, —CO$_2$R, —C(O)R, —C(S)R, —C(O)N(R)$_2$, —C(S)N(R)$_2$, —OC(O)N(R)$_2$, —OC(O)R, —C(O)N(OR)R, —C(NOR)R, —S(O)$_2$R, —S(O)$_3$R, —SO$_2$N(R)$_2$, —S(O)R, —NRSO$_2$N(R)$_2$, —NRSO$_2$R, —N(OR)R, —C(=NH)—N(R)$_2$, —P(O)$_2$R, —PO(R)$_2$, —OPO(R)$_2$, —(CH$_2$)$_{0-2}$NHC(O)R, phenyl (Ph) optionally substituted with R, —O(Ph) optionally substituted with R, —(CH$_2$)$_{1-2}$(Ph) optionally substituted with R, or —CH=CH(Ph), optionally substituted with R, wherein each independent occurrence of R is selected from hydrogen, optionally substituted $C_1$-$C_6$alkyl, optionally substituted $C_1$-$C_6$alkoxy, an unsubstituted 5-6 membered heteroaryl, phenyl, —O(Ph), or —CH$_2$(Ph), or two independent occurrences of R, on the same substituent or different substituents, taken together with the atom(s) to which each R is bound, to form an optionally substituted 3-12 membered saturated, partially unsaturated, or fully unsaturated monocyclic or bicyclic ring having 0-4 heteroatoms independently selected from nitrogen, oxygen, or sulfur. Non-limiting examples of aryl groups, as used herein, include phenyl, naphthyl, fluorenyl, indenyl, azulenyl, anthracenyl, phenanthracenyl and the like.

The term "arylene," as used means a divalent radical derived from an aryl group.

A "bi-functional linker," also referred to as a "bi-functional polymer," as used herein, refers to a linker comprising two functional groups that are capable of reacting specifically with other moieties to form covalent or non-covalent linkages. Such moieties include, but are not limited to, the amino acid side chain groups. By way of example only, a bi-functional linker has a functional group reactive with a group on a first peptide, and another functional group which is reactive with a group on a second peptide, whereby forming a conjugate that includes the first peptide, the bi-functional linker and the second peptide. A bi-functional linker is of any desired length or molecular weight, and is selected to provide a particular desired spacing or conformation.

A "multi-functional linker," also referred to as a "multi-functional polymer," as used herein, refers to a linker comprising two or more functional groups that are capable of reacting with other moieties to form covalent or non-covalent linkages. Such moieties include, but are not limited to, the amino acid side chain groups. A multi-functional linker is of any desired length or molecular weight, and is selected to provide a particular desired spacing or conformation.

The term "cyano," as used herein, refers to a —CN group.

The term "cycloalkyl," as used herein, refers to a saturated or partially unsaturated, monocyclic, fused bicyclic, fused tricyclic or bridged polycyclic ring assembly. As used herein, the terms "$C_3$-$C_5$ cycloalkyl", "$C_3$-$C_6$ cycloalkyl", "$C_3$-$C_7$ cycloalkyl", "$C_3$-$C_8$ cycloalkyl, "$C_3$-$C_9$ cycloalkyl and "$C_3$-$C_{10}$ cycloalkyl refer to a cycloalkyl group wherein the saturated or partially unsaturated, monocyclic, fused bicyclic or bridged polycyclic ring assembly contain at least 3, and at most 5, 6, 7, 8, 9 or 10, carbon atoms. Non-limiting examples of cycloalkyl groups, as used herein, include cyclopropyl, cyclobutyl, cyclopentyl, cyclohexyl, cycloheptyl, cyclooctyl, cyclononyl, cyclodecyl, cyclopentenyl, cyclohexenyl, decahydronaphthalenyl, 2,3,4,5,6,7-hexahydro-1H-indenyl and the like.

The term "cyclodextrin," as used herein, refers to cyclic carbohydrates consisting of at least six to eight glucose molecules in a ring formation. The outer part of the ring contains water soluble groups; at the center of the ring is a relatively nonpolar cavity able to accommodate small molecules.

The term "halogen," as used herein, refers to fluorine (F), chlorine (Cl), bromine (Br), or iodine (I).

The term "halo," as used herein, refers to the halogen radicals: fluoro (—F), chloro (—Cl), bromo (—Br), and iodo (—I).

The term "haloacyl," as used herein, refers to acyl groups which contain halogen moieties, including, but not limited to, —C(O)CH$_3$, —C(O)CF$_3$, —C(O)CH$_2$OCH$_3$, and the like.

The terms "haloalkyl" or "halo-substituted alkyl," as used herein, refers to an alkyl group as defined herein, substituted with at least one halo group or combinations thereof. Non-limiting examples of such branched or straight chained haloalkyl groups, as used herein, include methyl, ethyl, propyl, isopropyl, isobutyl and n-butyl substituted with one or more halo groups or combinations thereof, including, but not limited to, trifluoromethyl, pentafluoroethyl, and the like.

The term "haloalkoxy," as used herein, refers to an alkoxy group as defined above, substituted with one or more halo group or combinations thereof. Non-limiting examples of such branched or straight chained haloalkynyl groups, as used herein, include methoxy, ethoxy, n-propoxy, isopropoxy, n-butoxy, t-butoxy, pentoxy, hexoxy, heptoxy and the like substituted with one or more groups or combinations thereof.

The term "heteroalkyl," as used herein, refers to an alkyl group as defined herein wherein one or more carbon atoms are independently replaced by one or more of oxygen, sulfur, nitrogen, or combinations thereof.

The term "heteroalkylene," as used herein, refers to a divalent radical derived from a heteroalkyl.

The term "heteroaryl," as used herein, refers to monocyclic, bicyclic, and tricyclic ring systems having a total of five to fourteen ring members, wherein at least one ring in the system is aromatic, at least one ring in the system contains one or more heteroatoms selected from nitrogen, oxygen and sulfur, and wherein each ring in the system contains 3 to 7 ring members. Unless otherwise defined above and herein, suitable substituents on the unsaturated carbon atom of a heteroaryl group are generally selected from halogen; —R, —OR, —SR, —NO$_2$, —CN, —N(R)$_2$, —NRC(O)R, —NRC(S)R, —NRC(O)N(R)$_2$, —NRC(S)N(R)$_2$, —NRCO$_2$R, —NRNRC(O)R, —NRNRC(O)N(R)$_2$, —NRNRCO$_2$R, —C(O)C(O)R, —C(O)CH$_2$C(O)R, —CO$_2$R, —C(O)R, —C(S)R, —C(O)N(R)$_2$, —C(S)N(R)$_2$, —OC(O)N(R)$_2$, —OC(O)R, —C(O)N(OR)R, —C(NOR)R, —S(O)$_2$R, —S(O)$_3$R, —SO$_2$N(R)$_2$, —S(O)R, —NRSO$_2$N(R)$_2$, —NRSO$_2$R, —N(OR)R, —C(=NH)—N(R)$_2$, —P(O)$_2$R, —PO(R)$_2$, —OPO(R)$_2$, —(CH$_2$)$_{0-2}$NHC(O)R, phenyl (Ph) optionally substituted with R, —O(Ph) optionally substituted with R, —(CH$_2$)$_{1-2}$(Ph), optionally substituted with R, or —CH=CH(Ph), optionally substituted with R, wherein each independent occurrence of R is selected from hydrogen, optionally substituted C$_1$-C$_6$alkyl, optionally substituted C$_1$-C$_6$alkoxy, an unsubstituted 5-6 membered heteroaryl, phenyl, —O(Ph), or —CH$_2$(Ph), or two independent occurrences of R, on the same substituent or different substituents, taken together with the atom(s) to which each R is bound, to form an optionally substituted 3-12 membered saturated, partially unsaturated, or fully unsaturated monocyclic or bicyclic ring having 0-4 heteroatoms independently selected from nitrogen, oxygen, or sulfur. Non-limiting examples of heteroaryl groups, as used herein, include benzofuranyl, benzofurazanyl, benzoxazolyl, benzopyranyl, benzthiazolyl, benzothienyl, benzazepinyl, benzimidazolyl, benzothiopyranyl, benzo[1,3]dioxole, benzo[b]furyl, benzo[b]thienyl, cinnolinyl, furazanyl, furyl, furopyridinyl, imidazolyl, indolyl, indolizinyl, indolin-2-one, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidyl, pyrimidinyl, quinoxalinyl, quinolinyl, quinazolinyl, 4H-quinolizinyl, thiazolyl, thiadiazolyl, thienyl, triazinyl, triazolyl and tetrazolyl.

The term "heterocycloalkyl," as used herein, refers to a cycloalkyl, as defined herein, wherein one or more of the ring carbons are replaced by a moiety selected from —O—, —N=, —NR—, —C(O)—, —S—, —S(O)— or —S(O)$_2$—, wherein R is hydrogen, C$_1$-C$_4$alkyl or a nitrogen protecting group, with the proviso that the ring of said group does not contain two adjacent O or S atoms. Non-limiting examples of heterocycloalkyl groups, as used herein, include morpholino, pyrrolidinyl, pyrrolidinyl-2-one, piperazinyl, piperidinyl, piperidinylone, 1,4-dioxa-8-aza-spiro[4.5]dec-8-yl, 2H-pyrrolyl, 2-pyrrolinyl, 3-pyrrolinyl, 1,3-dioxolanyl, 2-imidazolinyl, imidazolidinyl, 2-pyrazolinyl, pyrazolidinyl, 1,4-dioxanyl, 1,4-dithianyl, thiomorpholinyl, azepanyl, hexahydro-1,4-diazepinyl, tetrahydrofuranyl, dihydrofuranyl, tetrahydrothienyl, tetrahydropyranyl, dihydropyranyl, tetrahydrothiopyranyl, thioxanyl, azetidinyl, oxetanyl, thietanyl, oxepanyl, thiepanyl, 1,2,3,6-tetrahydropyridinyl, 2H-pyranyl, 4H-pyranyl, dioxanyl, 1,3-dioxolanyl, dithianyl, dithiolanyl, dihydropyranyl, dihydrothienyl, dihydrofuranyl, imidazolinyl, imidazolidinyl, 3-azabicyclo[3.1.0]hexanyl, and 3-azabicyclo[4.1.0]heptanyl.

The term "heteroatom," as used herein, refers to one or more of oxygen, sulfur, nitrogen, phosphorus, or silicon.

The term "hydroxyl," as used herein, refers to the group —OH.

The term "hydroxyalkyl," as used herein refers to an alkyl group as defined herein substituted with at least one hydroxyl, hydroxyl being as defined herein. Non-limiting examples of branched or straight chained "C$_1$-C$_6$ hydroxyalkyl groups as used herein include methyl, ethyl, propyl, isopropyl, isobutyl and n-butyl substituted independently with one or more hydroxyl groups.

The term "optionally substituted," as used herein, means that the referenced group may or may not be substituted with one or more additional group(s) individually and independently selected from alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and the protected derivatives thereof. Non-limiting examples of optional substituents include, halo, —CN, —OR, —C(O)R, —OC(O)R, —C(O)OR, —OC(O)NHR, —C(O)N(R)$_2$, —SR—, —S(=O)R, —S(=O)$_2$R, —NHR, —N(R)$_2$, —NHC(O)—, NHC(O)O—, —C(O)NH—, S(=O)$_2$NHR, —S(O)$_2$N(R)$_2$, —NHS(=O)$_2$, —NHS(O)$_2$R, C$_1$-C$_6$ alkyl, C$_1$-C$_6$ alkoxy, aryl, heteroaryl, cycloalkyl, heterocycloalkyl, halo-substituted C$_1$-C$_6$alkyl, halo-substituted C$_1$-C$_6$alkoxy, where each R is independently selected from H, halo, C$_1$-C$_6$ alkyl, C$_1$-C$_6$ alkoxy, aryl, heteroaryl, cycloalkyl, heterocycloalkyl, halo-substituted C$_1$-C$_6$alkyl, halo-substituted C$_1$-C$_6$alkoxy.

The term "affinity label," as used herein, refers to a label which reversibly or irreversibly binds another molecule.

The terms "amber codon," as used herein, refer to incorporation sites of pyrrolysine, PCL and other pyrrolysine analogues and correspond to UAG, the nucleotide triplet within messenger RNA. The nucleotide sequence TAG is encoded in DNA and transcribed to UAG in RNA that is translated into protein. The TAG and UAG codon are used interchangeably herein to refer to the incorporation site of pyrrolysine, PCL and other pyrrolysine analogues.

The term "amino acid," as used herein, refers to naturally occurring amino acids, unnatural amino acids, amino acid analogues and amino acid mimetics that function in a manner similar to the naturally occurring amino acids, all in their D and L stereoisomers if their structure allows such stereoisomeric forms. Amino acids are referred to herein by either their name, their commonly known three letter symbols or by the one-letter symbols recommended by the IUPAC-IUB Biochemical Nomenclature Commission. Natural occurring amino acids are those amino acids that are encoded by the genetic code, as well as those encoded amino acids that are later modified. Natural occurring amino acids include, but are not limited to, alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr), valine (Val), pyrrolysine (Pyl), selenocycteine (Sec) and pyrroline-carboxy-lysine (PCL). Modified encoded amino acids include, but are not limited to, hydroxyproline, γ-carboxyglutamate, O-phosphoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminoproprionic acid, N-ethylglycine, N-methylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. The term amino acid also includes naturally occurring amino acids that are metabolites in certain organisms but are not encoded by the genetic code for incorporation into proteins. Such amino acids include, but are not limited to, ornithine, D-ornithine, and D-arginine.

The term "amino acid analogue," as used herein, refers to compounds that have the same basic chemical structure as a naturally occurring amino acid, by way of example only, an α-carbon that is bound to a hydrogen, a carboxyl group, an amino group, and an R group. Amino acid analogues include the natural and unnatural amino acids which are chemically blocked, reversibly or irreversibly, or their C-terminal carboxy group, their N-terminal amino group and/or their side-chain functional groups are chemically modified. Such analogues include, but are not limited to, methionine sulfoxide, methionine sulfone, S-(carboxymethyl)-cysteine, S-(carboxymethyl)-cysteine sulfoxide, S-(carboxymethyl)-cysteine sulfone, aspartic acid-(beta-methyl ester), N-ethylglycine, alanine carboxamide, homoserine, norleucine, and methionine methyl sulfonium. Certain blocking agents include, but are not limited to, t-butyloxycarbonyl (Boc) and 9-Fluorenylmethyloxycarbonyl (Fmoc).

The term "amino acid mimetics," as used herein, refers to chemical compounds that have a structure that is different from the general chemical structure of an amino acid, but functions in a manner similar to a naturally occurring amino acid.

The term "unnatural amino acid", as used herein, is intended to represent amino acid structures that cannot be generated biosynthetically in any organism using unmodified or modified genes from any organism, whether the same or different. In addition, it is understood that such "unnatural amino acids" require a modified tRNA and a modified tRNA synthetase (RS) for incorporation into a protein. These "selected" orthogonal tRNA/RS pair are specific for the unnatural amino acid and are generated by a selection process as developed by Schultz et al. or a similar procedure. As way of example, pyrroline-carboxy-lysine is a "natural amino acid" as it is generated biosynthetically by genes transferred from one organism into the host cells and as it is incorporated into proteins by using natural tRNA and tRNA synthetase genes, while p-aminophenylalanine (see, Generation of a bacterium with a 21 amino acid genetic code, Mehl R A, Anderson J C, Santoro S W, Wang L, Martin A B, King D S, Horn D M, Schultz P G. J Am Chem Soc. 2003 Jan. 29; 125(4):935-9) is an "unnatural amino acid" because, although generated biosynthetically, it is incorporated into proteins by a "selected" orthogonal tRNA/tRNA synthetase pair.

The term "amino acid residue," as used herein, refers to moieties having the structure:

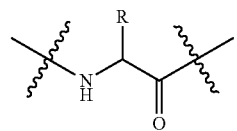

wherein such moieties are derived from amino acids and the R group is the side chain of any amino acid described herein. Such amino acid residues include, but are not limited to alaninyl, argininyl, asparaginyl, aspartyl, cysteinyl, glutaminyl, glutamyl, glycinyl, histidinyl, isoleucinyl, leucinyl, lysinyl, methioninyl, phenylalaninyl, prolinyl, serinyl, threoninyl, tryptophanyl, tyrosinyl, valinyl, pyroglutamate, formylmethionine, pyrroglycinyl and selenocysteinyl.

The term "amino terminus modification group" refers to any molecule that can be attached to a terminal amino group. Such amino terminus modification groups include, but are not limited to, amine protecting groups, the end of polymeric molecules, wherein such polymeric molecules include, but are not limited to, polypeptides, polynucleotides, and polysaccharides. Terminus modification groups also include but are not limited to, various water soluble polymers, peptides or proteins. By way of example only, amino terminus modification groups include polyethylene glycol or serum albumin. Certain amino terminus modification groups are used to modify therapeutic characteristics of a protein, polypeptide or peptide, including but not limited, to increasing the serum half-life such proteins, polypeptides or peptides.

The term "antibody fragment," as used herein, refers to any form of an antibody other than the full-length form. Antibody fragments herein include antibodies that are smaller components that exist within full-length antibodies, and antibodies that have been engineered. Antibody fragments include but are not limited to Fv, Fc, Fab, and (Fab')$_2$, single chain Fv (scFv), diabodies, triabodies, tetrabodies, bi-functional hybrid antibodies, CDR1, CDR2, CDR3, combinations of CDR's, variable regions, framework regions, constant regions, heavy chains, light chains, and variable regions, and alternative scaffold non-antibody molecules, bispecific antibodies, and the like. Another functional substructure is a single chain Fv (scFv), comprised of the variable regions of the immunoglobulin heavy and light chain, covalently connected by a peptide linker. These small (MW<25,000 Da) proteins generally retain specificity and affinity for antigen in a single polypeptide and can provide a convenient building block for larger, antigen-specific molecules. Unless specifically noted otherwise, statements and claims that use the term "antibody" or "antibodies" also include "antibody fragment" and "antibody fragments".

The term "bioavailability," as used herein, refers to the rate and extent to which a substance or its active moiety is delivered from a pharmaceutical dosage form and becomes available at the site of action or in the general circulation. Increases in bioavailability refers to increasing the rate and extent a substance or its active moiety is delivered from a pharmaceutical dosage form and becomes available at the site of action or in the general circulation. By way of example, an increase in bioavailability may be indicated as an increase in concentration of the substance or its active moiety in the blood when compared to other substances or active moieties.

The terms "biologically active molecule," "biologically active moiety" or "biologically active agent," as used herein, refers to any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include but are not limited to any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, DNA, RNA, small molecule drugs, hard drugs, soft drugs, polysaccharides, oligosaccharides, disaccharides, carbohydrates, inorganic atoms or molecules, dyes, lipids, nucleosides, radionuclides, oligonucleotides, toxins, cells, viruses, liposomes, microparticles and micelles. Classes of biologically active agents that are suitable for use with the methods and compositions described herein include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

The term "modulating biological activity," as used herein, refers to increasing or decreasing the concentration or the reactivity of a protein, polypeptide, peptide, DNA, RNA, saccharides, sugars, metabolites, precursors, cofactors or other biologically active chemicals or entities, altering the selectivity of the protein, polypeptide, peptide, DNA, RNA, saccharides, sugars, metabolites, precursors, cofactors or other biologically active chemicals or entities, or enhancing or decreasing the substrate selectivity of the protein, polypeptide, peptide, DNA, RNA, saccharides, sugars, metabolites, precursors, cofactors or other biologically active chemicals or entities.

The term "biomaterial," as used herein, refers to a biologically-derived material, including but not limited to material obtained from bioreactors and/or from recombinant methods and techniques.

The term "biophysical probe," as used herein, refers to probes that allow detection of or monitor structural changes in molecules by physical detection methods. Such molecules include, but are not limited to, proteins, polypeptide, peptides, DNA or RNA. Such "biophysical probe" is also used to detect or monitor interaction of proteins, polypeptides, peptides, DNA or RNA with other molecules, including but not limited to, macromolecules. Examples of biophysical probes include, but are not limited to, molecular mass, nuclear spins, UV absorbance, fluorescence, circular dichroism, heat capacity, melting temperature or other intrinsic molecular properties. Examples of biophysical probes also include labels that are added to the molecule. Such probes include, but are not limited to, spin-labels, fluorophores, isotope labels, and photoactivatible groups.

The term "biosynthetically generated," as used herein, refers to any method utilizing a cell or enzymes to generate an amino acid. Such methods include the use of at least one of the following components: a precursor and an enzyme. In certain embodiments, such amino acids are then incorporated into a protein. In certain embodiments, the biosynthesis and incorporation of the amino acid occurs in the same cell, while in other embodiments the amino acid is biosynthetically generated in a separate cell ("feeder cell"), or in a separate cell culture, and the amino acid is incorporated into a protein in another cell. In the latter case, the amino acid is optionally purified from the separate cell culture, and the purified amino acid is then added to the media of the cell culture that incorporates the amino acid into the protein The term "biotin analogue," or also referred to as "biotin mimic," as used herein, is any molecule, other than biotin, which bind with high affinity to avidin and/or streptavidin.

The term "carboxy terminus modification group" refers to any molecule that can be attached to a terminal carboxy group. Such carboxy terminus groups include, but are not limited to, carboxylate protecting groups, the end of polymeric molecules, wherein such polymeric molecules include, but are not limited to, polypeptides, polynucleotides, and polysaccharides. Terminus modification groups also include but are not limited to, various water soluble polymers, peptides or proteins. By way of example only, terminus modification groups include polyethylene glycol or serum albumin. Certain carboxy terminus modification groups are used to modify therapeutic characteristics of a protein, polypeptide or peptide, including but not limited, to increasing the serum half-life.

The term "chemically cleavable group," also referred to as "chemically labile," as used herein, refers to a group which breaks or cleaves upon exposure to acid, base, oxidizing agents, reducing agents, chemical initiators, or radical initiators.

The term "chemiluminescent group," as used herein, refers to a group which emits light as a result of a chemical reaction without the addition of heat. By way of example only, luminol (5-amino-2,3-dihydro-1,4-phthalazinedione) reacts with oxidants like hydrogen peroxide ($H_2O_2$) in the presence of a base and a metal catalyst to produce an excited state product (3-aminophthalate, 3-APA) subsequently resulting in the release of detectable light.

The term "chromophore," as used herein, refers to a molecule which absorbs light of visible wavelengths, UV wavelengths or IR wavelengths.

The term "cofactor," as used herein, refers to an atom or molecule essential for the action of a large molecule. Cofactors include, but are not limited to, inorganic ions, coenzymes, proteins, or some other factor necessary for the activity of enzymes.

The term "cofolding," as used herein, refers to refolding processes, reactions, or methods which employ at least two molecules which interact with each other and result in the transformation of unfolded or improperly folded molecules to properly folded molecules. By way of example only, "cofolding," employ at least two polypeptides which interact with each other and result in the transformation of unfolded or improperly folded polypeptides to native, properly folded polypeptides.

The term "cytotoxic," as used herein, refers to a compound which harms cells.

The term "denaturing agent" or "denaturant," as used herein, refers to any compound or material which will cause a reversible unfolding of a protein. The strength of a denaturing agent or denaturant will be determined both by the properties and the concentration of the particular denaturing agent or denaturant. By way of example, denaturing agents or denaturants include, but are not limited to, chaotropes, detergents, organic, water miscible solvents, phospholipids, or a combination thereof. Non-limiting examples of chaotropes include, but are not limited to, urea, guanidine, and sodium thiocyanate. Non-limiting examples of detergents may include, but are not limited to, strong detergents such as sodium dodecyl sulfate, or polyoxyethylene ethers (e.g. Tween or Triton detergents), Sarkosyl, mild non-ionic detergents (e.g., digitonin), mild cationic detergents such as N-2,3-(Dioleyoxy)-propyl-N,N,N-trimethylammonium, mild ionic detergents (e.g. sodium cholate or sodium deoxycholate) or zwitterionic detergents including, but not limited to, sulfobetaines (Zwittergent), 3-(3-chlolamidopropyl)dimethylammonio-1-propane sulfate (CHAPS), and 3-(3-chlolamidopropyl)dimethylammonio-2-hydroxy-1-propane sulfonate (CHAPSO). Non-limiting examples of organic, water miscible solvents include, but are not limited to, acetonitrile, lower alkanols (especially $C_2$-$C_4$ alkanols such as ethanol or isopropanol), or lower alkandiols ($C_2$-$C_4$ alkandiols such as ethylene-glycol) may be used as denaturants. Non-limiting examples of phospholipids include, but are not limited to, naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

The term "detectable label," as used herein, refers to a label which is observable using analytical techniques including, but not limited to, fluorescence, chemiluminescence, electron-spin resonance, ultraviolet/visible absorbance spectroscopy, infrared spectroscopy, mass spectrometry, nuclear magnetic resonance, magnetic resonance, radiometric and electrochemical methods.

The term "drug," as used herein, refers to any substance used in the prevention, diagnosis, alleviation, treatment, or cure of a disease or condition.

The term "dye," as used herein, refers to a soluble, coloring substance which contains a chromophore.

The term "electron dense group," as used herein, refers to a group that scatters electrons when irradiated with an electron beam. Such groups include, but are not limited to, ammonium molybdate, bismuth subnitrate cadmium iodide, 99%, carbohydrazide, ferric chloride hexahydrate, hexamethylene tetramine, 98.5%, indium trichloride anhydrous, lanthanum nitrate, lead acetate trihydrate, lead citrate trihydrate, lead nitrate, periodic acid, phosphomolybdic acid, phosphotungstic acid, potassium ferricyanide, potassium ferrocyanide, ruthenium red, silver nitrate, silver proteinate (Ag Assay: 8.0-8.5%) "Strong", silver tetraphenylporphin (S-TPPS), sodium chloroaurate, sodium tungstate, thallium nitrate, thiosemicarbazide (TSC), uranyl acetate, uranyl nitrate, and vanadyl sulfate.

The term "energy transfer agent," as used herein, refers to a molecule which can either donate or accept energy from another molecule. By way of example only, fluorescence resonance energy transfer (FRET) is a dipole-dipole coupling process by which the excited-state energy of a fluorescence donor molecule is non-radiatively transferred to an unexcited acceptor molecule which then fluorescently emits the donated energy at a longer wavelength.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

The term "eukaryotic" refers to material originating from organisms belonging to the phylogenetic domain Eucarya, including but not limited to animals (including but not limited to, mammals, insects, reptiles, and birds), ciliates, plants (including but not limited to, monocots, dicots, and algae), fungi, yeasts, flagellates, microsporidia, and protists.

The term "fatty acid," as used herein, refers to carboxylic acids with about $C_6$ or longer hydrocarbon side chain.

The term "fluorophore," as used herein, refers to a molecule which upon excitation emits photons and is thereby fluorescent.

The terms "functional group", "active moiety", "activating group", "leaving group", "reactive site", "chemically reactive group" and "chemically reactive moiety," are somewhat synonymous in the chemical arts and are used herein to indicate the portions of molecules that perform some function or activity and are reactive with other molecules.

The term "identical," as used herein, refers to two or more sequences or subsequences which are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences may be "substantially identical" if the sequential units are about 60% identical, about 65% identical, about 70% identical, about 75% identical, about 80% identical, about 85% identical, about 90% identical, or about 95% identical over a specified region. Such percentages to describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 85% identical, about 90% identical, or about 95% identical over a specified region. The identity can exist over a region that is at least about 75-100 amino acids in length, over a region that is about 50 amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75-100 nucleic acids in length, over a region that is about 50 nucleic acids in length, or, where not specified, across the entire sequence of a polynucleotide sequence.

The term "immunogenicity," as used herein, refers to an antibody response to administration of a therapeutic drug. The immunogenicity toward therapeutic proteins, polypeptides and peptides provided herein is obtained using quantitative and qualitative assays for detection of antibodies against said therapeutic proteins, polypeptides and peptides in biological fluids. Such assays include, but are not limited to, Radioimmunoassay (RIA), Enzyme-linked immunosorbent assay (ELISA), luminescent immunoassay (LIA), and fluorescent immunoassay (FIA). Analysis of such immunogenicity involves comparing the antibody response upon administration of therapeutic proteins, polypeptides and peptides provided herein to the antibody response upon administration of a control therapeutic protein, polypeptide or peptide or of the delivery vehicle or delivery buffer.

The term "intercalating agent," also referred to as "intercalating group," as used herein, refers to a molecule or group that inserts into the intramolecular space of another molecule or the intermolecular space between molecules. By way of example only an intercalating agent or group may be a molecule which inserts into the stacked bases of the DNA double helix.

The term "label," as used herein, refers to a substance which is incorporated into a compound and is readily detected, whereby its physical distribution may be detected and/or monitored.

The term "linkage," as used herein, refers to a bond or chemical moiety formed from a chemical reaction between the functional group of a first molecule with the functional group of a second molecule. Such bonds include, but are not limited to, covalent linkages and non-covalent bonds, while such chemical moieties include, but are not limited to, esters, carbonates, imines phosphate esters, hydrazones, acetals, orthoesters, peptide linkages, oligonucleotide linkages and those given in Table 1 herein. "Hydrolytically stable linkages" means that the linkages are substantially stable in water and do not react with water at useful pH values, including but not limited to, under physiological conditions for an extended period of time. "Hydrolytically unstable or degradable linkages" means that the linkages are degradable in water or in aqueous solutions, including for example, blood. "Enzymatically unstable or degradable linkages" means that the linkages are degraded by one or more enzymes. By way of example only, certain PEG and related polymers include degradable linkages in the polymer backbone or in a linker group between the PEG polymer backbone and one or more of the terminal functional groups of protein, polypeptide or peptide provided herein. Such degradable linkages include, but are not limited to, ester linkages formed by the reaction of PEG carboxylic acids or activated PEG carboxylic acids with alcohol groups on a biologically active agent, wherein such ester groups generally hydrolyze under physiological conditions to release the biologically active agent. Other hydrolytically degradable linkages include but are not limited to carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The terms "medium" or "media," as used herein, refer to any culture medium used to grow and harvest cells and/or products expressed and/or secreted by such cells. Such "medium" or "media" include, but are not limited to, solution, solid, semi-solid, or rigid supports that may support or contain any host cell, including, by way of example, bacterial host cells, yeast host cells, insect host cells, plant host cells, eukaryotic host cells, mammalian host cells, CHO cells, prokaryotic host cells, *Escherichia coli*, or *Pseudomonas* host cells, and cell contents. Such "medium" or "media" includes, but is not limited to, medium or media in which the host cell has been grown into which a polypeptide has been secreted, including medium either before or after a proliferation step. Such "medium" or "media" also includes, but is not limited to, buffers or reagents that contain host cell lysates, by way of example a polypeptide produced intracellularly and the host cells are lysed or disrupted to release the polypeptide.

The term "metal chelator," as used herein, refers to a molecule which forms a complex with metal ions. By way of example, such molecules form two or more coordination bonds with a central metal ion and optionally form ring structures.

The term "metal-containing moiety," as used herein, refers to a group which contains a metal ion, atom or particle. Such moieties include, but are not limited to, cisplatin, chelated metals ions (such as nickel, iron, and platinum), and metal nanoparticles (such as nickel, iron, and platinum).

The term "moiety incorporating a heavy atom," as used herein, refers to a group which incorporates an ion of atom which is usually heavier than carbon. Such ions or atoms include, but are not limited to, silicon, tungsten, gold, lead, and uranium.

The term "modified," as used herein refers to the presence of a change to an amino acid or amino acid residue, wherein such changes, or modifications, are obtained by chemical or biochemical processes.

As used herein, the term "modulated serum half-life" refers to positive or negative changes in the circulating half-life of a modified biologically active molecule relative to its non-modified form. By way of example, the modified biologically active molecules include, but are not limited to, compounds provided herein. By way of example, serum half-life is measured by taking blood samples at various time points after administration of the biologically active molecule or modified biologically active molecule, and determining the concentration of that molecule in each sample. Correlation of the serum concentration with time allows calculation of the serum half-life. By way of example, modulated serum half-life may be an increased in serum half-life, which may enable an improved dosing regimens or avoid toxic effects. Such increases in serum may be at least about two fold, at least about three-fold, at least about five-fold, or at least about ten-fold.

The term "nanoparticle," as used herein, refers to a particle which has a particle size between about 500 nm to about 1 nm.

The term "near-stoichiometric," as used herein, refers to the ratio of the moles of compounds participating in a chemical reaction being about 0.75 to about 1.5.

As used herein, the term "non-eukaryote" refers to non-eukaryotic organisms. By way of example, a non-eukaryotic organism belong to the Eubacteria phylogenetic domain, which includes but is not limited to, *Escherichia coli, Thermus thermophilus*, or *Bacillus stearothermophilus, Pseudomonas fluorescens, Pseudomonas aeruginosa, Pseudomonas putida*, or the Archaea phylogenetic domain, which includes, but is not limited to, *Methanococcus jannaschii, Methanobacterium thermoautotrophicum, Archaeoglobus fulgidus, Pyrococcus furiosus, Pyrococcus horikoshii, Aeuropyrum pernix*, or *Halobacterium* such as *Haloferax volcanii* and *Halobacterium* species NRC-1.

The term "nucleic acid," as used herein, refers to deoxyribonucleotides, deoxyribonucleosides, ribonucleosides or ribonucleotides and polymers thereof in either single- or double-stranded form. By way of example only, such nucleic acids and nucleic acid polymers include, but are not limited to, (i) analogues of natural nucleotides which have similar properties as a reference nucleic acid; (ii) oligonucleotide analogues including, but are not limited to, PNA (peptidonucleic acid), analogues of DNA used in antisense technology (phosphorothioates, phosphoroamidates, and the like); (iii) conservatively modified variants thereof (including but not limited to, degenerate codon substitutions) and complementary sequences and sequence explicitly indicated. By way of example, degenerate codon substitutions may be achieved by generating sequences in which the third position of one or more selected (or all) codons is substituted with mixed-base and/or deoxyinosine residues.

The term "oxidizing agent," as used herein, refers to a compound or material which is capable of removing an electron from a compound being oxidized. By way of example oxidizing agents include, but are not limited to, oxidized glutathione, cystine, cystamine, oxidized dithiothreitol, oxidized erythreitol, and oxygen. A wide variety of oxidizing agents are suitable for use in the methods and compositions described herein.

The term "photoaffinity label," as used herein, refers to a label with a group, which, upon exposure to light, forms a linkage with a molecule for which the label has an affinity. By way of example only, such a linkage may be covalent or non-covalent.

The term "photocaged moiety," as used herein, refers to a group which, upon illumination at certain wavelengths, covalently or non-covalently binds ions or other molecules.

The term "photocleavable group," as used herein, refers to a group which breaks upon exposure to light.

The term "photocrosslinker," as used herein, refers to a compound comprising two or more functional groups which, upon exposure to light, are reactive and form a covalent or non-covalent linkage with two or more monomeric or polymeric molecules.

The term "photoisomerizable moiety," as used herein, refers to a group wherein upon illumination with light changes from one isomeric form to another.

The term "polyalkylene glycol," as used herein, refers to linear or branched polymeric polyether polyols. Such polyalkylene glycols, including, but are not limited to, polyethylene glycol, polypropylene glycol, polybutylene glycol, and derivatives thereof.

The term "polymer," as used herein, refers to a molecule composed of repeated subunits. Such molecules include, but are not limited to, proteins, polypeptides, peptides, polynucleotides, or polysaccharides or polyalkylene glycols.

The terms "polypeptide," "peptide" and "protein" are used interchangeably herein to refer to a polymer of amino acid residues. That is, a description directed to a polypeptide applies equally to a description of a peptide and a description of a protein, and vice versa. Amino acid residues include residues resulting from natural and unnatural amino acids. The terms apply to naturally occurring amino acid polymers as well as amino acid polymers in which one or more amino acid residues is a compound provided herein. Additionally, such "polypeptides," "peptides" and "proteins" include amino acid chains of any length, including full length proteins, wherein the amino acid residues are linked by covalent peptide bonds or other linkages.

The term "post-translationally modified" refers to any modification of an amino acid which occurs after such an amino acid has been translationally incorporated into a polypeptide chain. Such modifications include, but are not limited to, post-translational in vivo modifications, and post-translational in vitro modifications.

The term "protected," as used herein, refers to the presence of a "protecting group" or moiety that prevents reaction of the chemically reactive functional group under certain reaction conditions. The protecting group will vary depending on the type of chemically reactive group being protected. By way of example only, (i) if the chemically reactive group is an amine or a hydrazide, the protecting group may be selected from tert-butyloxycarbonyl (t-Boc) and 9-fluorenylmethoxycarbonyl (Fmoc); (ii) if the chemically reactive group is a thiol, the protecting group may be orthopyridyldisulfide; and (iii) if the chemically reactive group is a carboxylic acid, such as butanoic or propionic acid, or a hydroxyl group, the protecting group may be benzyl or an alkyl group such as methyl, ethyl, or tert-butyl. By way of example only, blocking/protecting groups are also selected from: acetamide, allyloxycarbonyl, allyl ether, benzyl, benzylamine, benzylideneamine, benzyl carbamate, benzyl esters, methyl ester, t-butyl ester, S-t-butyl ester, 2-alkyl-1,3-oxazoline, dimethyl acetal, 1,3-dioxane, 1,3-dithiane, N,N-dimethylhydrazone, phtalimide, trityl, p-methoxybenzyl ether, Carbobenzyloxy, p-toluenesulfonamide, trifluoracetamide, triphenylmethylamine, t-butyl ether, benzyl ether, t-butyldimethylsilyl ether, t-butyldiphenylsilyl ether, 2-(trimethylsilyl)ethoxycarbonyl, acetic acid ester, pivalic acid ester, benzoic acid ester, acetonide, benzylidene acetal, and photolabile groups such as Nvoc and MeNvoc.

The term "radioactive moiety," as used herein, refers to a group whose nuclei spontaneously release nuclear radiation, such as alpha, or beta particles, or gamma radiation.

The term "reactive compound," as used herein, refers to a compound which under appropriate conditions is reactive toward another atom, molecule or compound.

The term "recombinant host cell," also referred to as "host cell," refers to a cell which includes an exogenous polynucleotide, wherein the methods used to insert the exogenous polynucleotide into a cell include, but are not limited to, direct uptake, transduction, f-mating, or other methods known in the art to create recombinant host cells. By way of example only, such exogenous polynucleotide may be a nonintegrated vector, including but not limited to a plasmid, or may be integrated into the host genome.

The term "redox-active agent," as used herein, refers to a molecule which oxidizes or reduces another molecule, whereby the redox active agent becomes reduced or oxidized. Examples of redox active agent include, but are not limited to, ferrocene, quinones, $Ru^{2+/3+}$ complexes, $Co^{2+/3+}$ complexes, and $Os^{2+/3+}$ complexes.

The term "reducing agent," as used herein, refers to a compound or material which is capable of adding an electron to a compound being reduced. By way of example reducing agents include, but are not limited to, dithiothreitol (DTT), 2-mercaptoethanol, dithioerythritol, cysteine, cysteamine (2-aminoethanethiol), and reduced glutathione. Such reducing agents may be used, by way of example only, to maintain sulfhydryl groups in the reduced state and to reduce intra- or intermolecular disulfide bonds.

The term "refolding," as used herein describes any process, reaction or method which transforms an improperly folded or unfolded state to a native or properly folded conformation. By way of example only, refolding transforms disulfide bond containing proteins or polypeptides from an improperly folded or unfolded state to a native or properly folded conformation with respect to disulfide bonds. Such disulfide bond containing proteins or polypeptides include proteins or polypeptides having incorporated therein compounds provided herein. Refolding is often initiated by removal of chaotropic agents such as urea or guanidinium hydrochloride previously added to protein solutions in order to solubilize and unfold said proteins.

The term "resin," as used herein, refers to high molecular weight, insoluble polymer beads. By way of example only, such beads may be used as supports for solid phase peptide synthesis, or sites for attachment of molecules prior to purification.

The term "saccharide," as used herein, refers to a series of carbohydrates including but not limited to sugars, monosaccharides, oligosaccharides, and polysaccharides.

The term "spin label," as used herein, refers to molecules which contain an atom or a group of atoms exhibiting an unpaired electron spin (i.e. a stable paramagnetic group) that can be detected by electron spin resonance spectroscopy and can be attached to another molecule. Such spin-label molecules include, but are not limited to, nitryl radicals and nitroxides, and may be single spin-labels or double spin-labels.

The term "stoichiometric," as used herein, refers to the ratio of the moles of compounds participating in a chemical reaction being about 0.9 to about 1.1.

The term "substantially purified," as used herein, refers to a component of interest that is substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater. By way of example only, a protein, polypeptide or peptide containing a compound provided herein is purified from a native cell or host cell. By way of example only, a preparation of a protein, polypeptide or peptide containing a compound provided herein is "substantially purified" when the preparation contains less than about 30%, less than about 25%, less than about 20%, less than about 15%, less than about 10%, less than about 5%, less than about 4%, less than about 3%, less than about 2%, or less than about 1% (by dry weight) of contaminating material. By way of example only, when a protein, polypeptide or peptide containing a compound provided herein is recombinantly produced by host cells, the protein, polypeptide or peptide containing a compound provided herein is present at about 30%, about 25%, about 20%, about 15%, about 10%, about 5%, about 4%, about 3%, about 2%, or about 1% or less of the dry weight of the cells. By way of example only, when a protein, polypeptide or peptide containing a compound provided herein is recombinantly produced by host cells, the protein, polypeptide or peptide containing a compound provided herein is present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less. By way of example only, a "substantially purified" protein, polypeptide or peptide containing a compound provided herein has a purity level of about 30%, about 35%, about 40%, about 45%, about 50%, about 55%, about 60%, about 65%, about 70%, about 75%, about 80%, about 85%, about 90, about 95%, about 99% or greater as determined by appropriate methods, including, but not limited to, SDS/PAGE analysis, RP-HPLC, SEC, and capillary electrophoresis.

The term "toxic moiety," as used herein, refers to a compound which can cause harm or death.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, the term "water soluble polymer" refers to any polymer that is soluble in aqueous solvents. Such water soluble polymers include, but are not limited to, polyethylene glycol, polyethylene glycol propionaldehyde, mono $C_1$-$C_{10}$ alkoxy or aryloxy derivatives thereof monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, serum albumin, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. By way of example only, coupling of such water soluble polymers to proteins, polypeptides or peptide containing a compound provided herein result in changes including, but not limited to, increased water solubility, increased or modulated serum half-life, increased or modulated therapeutic half-life relative to the unmodified form, increased bioavailability, modulated biological activity, extended circulation time, modulated immunogenicity, modulated physical association characteristics including, but not limited to, aggregation and multimer formation, altered receptor binding, altered binding to one or more binding partners, and altered receptor dimerization or multimerization.

Other objects, features and advantages of the methods, compositions and combinations described herein will become apparent from the following detailed description. It should be understood, however, that the detailed description and the specific examples, while indicating specific embodiments, are given by way of illustration only.

Site Specific Incorporation of Biosynthetically Generated Pyrrolysine and PCL

Pyrrolysine (PYL) is the $22^{nd}$ natural, genetically encoded amino acid found in certain methanogenic Archaea of the family Methanosarcinaceae and two unrelated bacterial species. Specifically, pyrrolysine is found in MtmB1, the monomethylamine (MMA) methyltransferase which initiates methane formation in such Archaea bacteria, (see Srinivasan, G., James, C. M., and Krzycki, J. A. (2002), "Pyrrolysine encoded by UAG in Archaea: charging of a UAG-decoding specialized tRNA," *Science*, 296, 1459-62; Soares, J. A., Zhang, L., Pitsch, R. L., Kleinholz, N. M., Jones, R. B., Wolff, J. J., Amster, J., Green-Church, K. B., and Krzycki, J. A. (2005), "The residue mass of L-pyrrolysine in three distinct methylamine methyltransferases," *Journal of Biological Chemistry*, 280, 36962-9; Hao, B., Gong, W., Ferguson, T. K., James, C. M., Krzycki, J. A., and Chan, M. K., (2002), "A new UAG-encoded residue in the structure of a methanogen methyltransferase", *Science*, 296, 1462-6; Krzycki, J. A., (2005), "The direct genetic encoding of pyrrolysine," *Current Opinion in Microbiology*, 8, 706-12; Krzycki, J. A., (2004), "Function of genetically encoded pyrrolysine in corrinoid-dependent methylamine methyltransferases," *Current Opinion in Chemical Biology*, 8, 484-91, and Ambrogelly, A., Palioura, S., and Soll, D., (2007), "Natural expansion of the genetic code," *Nature Chemical Biology* 3, 29-35). Pyrrolysine is considered a dipeptide wherein the ε-amine of lysine is linked to the D-isomer of 4-methyl-pyrroline-5-carboxylate via an amide bond (see, Polycarpo, C. R., Herring, S., Berube, A., Wood, J. L., Soll, D., and Ambrogelly, A., (2006), "Pyrrolysine analogues as substrates for pyrrolysyl-tRNA synthetase," *FEBS Letters*, 580, 6695-700). The structure of pyrrolysine (FIG. 1) was deduced from the crystal structure of MtmB1 and from the residue's mass (see, J. Biol. Chem. 2005, 44, 36962-36969; PNAS, 2007, 104, 1021-1026).

The mtmB1 gene encoding MtmB1 possesses an in-frame amber (TAG) codon, which is normally a canonical stop codon. However, in mtmB1 mRNA the UAG codon, encoded as TAG on the DNA level, does not terminate translation during production of the MtmB1 protein, but instead the UAG codon encodes pyrrolysine which is incorporated into the protein. Pyrrolysine is endogenously synthesized and is then co-translationally incorporated at such in-frame UAG codons as the free amino acid.

The biosynthesis and incorporation of pyrrolysine is facilitated by the natural genes pylT, pylS, pylB, pylC and pylD. pylT encodes pyrrolysyl-tRNA, pylS encodes pyrrolysyl-tRNA synthetase while pylB, pylC and pylD encode proteins required for the biosynthesis of pyrrolysine. These genes have been derived from *Methanosarcina mazei*, (see, Longstaff, D. G., Larue, R. C., Faust, J. E., Mahapatra, A., Zhang, L., Green-Church, K. B., and Krzycki, J. A., (2007), "A natural genetic code expansion cassette enables transmissible biosynthesis and genetic encoding of pyrrolysine," *Proceedings of the National Academy of Sciences of the United States of America*, 104, 1021-6, and Namy, O., Zhou, Y., Gundllapalli, S., Polycarpo, C. R., Denise, A., Rousset, J. P., Soll, D., and Ambrogelly, A., (2007), "Adding pyrrolysine to the *Escherichia coli* genetic code," *FEBS Letters*, 581, 5282-8). The pylT and pylS genes along with pylB, pylC and pylD genes form a pylTSBCD gene cluster which is a natural genetic code expansion cassette whose transfer allows the UAG codon to be translated as pyrrolysine, an endogenously synthesized free amino acid, which is incorporated into a protein at the UAG site.

The biosynthesis of pyrrolysine was suggested to be facilitated by the gene products of the natural genes pylB, pylC and pylD, with D-ornithine proposed as a precursor (see, Namy, O., Zhou, Y., Gundllapalli, S., Polycarpo, C. R., Denise, A., Rousset, J. P., Soll, D., and Ambrogelly, A., (2007), "Adding pyrrolysine to the *Escherichia coli* genetic code," *FEBS Letters*, 581, 5282-8). Although various precursors for pyrrolysine have been proposed, such as D-glutamate, D-isoleucine, D-proline and D-ornithine, D-ornithine was stated to be the most effective precursor for pyrrolysine biosynthesis in *Escherichia coli* transformed with a plasmid carrying the natural genes pylT, pylS, pylB, pylC and pylD. This study used readthrough at the TAG incorporation or truncation signal, i.e. the production of full-length protein, as the demonstration that pyrrolysine was biosynthesized and incorporated into proteins produced within *Escherichia coli* transformed with a plasmid carrying the natural genes pylT, pylS, pylB, pylC and pylD and using D-ornithine as a precursor. Incorporation of pyrrolysine was not verified directly by mass spectrometry but the conclusion was supported by previous mass spectrometry data that in the absence of added D-ornithine, pyrrolysine is biosynthesized and incorporated, albeit at low levels, into proteins produced within *Escherichia coli* transformed with a plasmid carrying the natural genes pylT, pylS, pylB, pylC and pylD (see, Longstaff, D. G., Larue, R. C., Faust, J. E., Mahapatra, A., Zhang, L., Green-Church, K. B., and Krzycki, J. A., (2007), "A natural genetic code expansion cassette enables transmissible biosynthesis and genetic encoding of pyrrolysine," *Proceedings of the National Academy of Sciences of the United States of America*, 104, 1021-6).

However, as provided herein, it was found that introduction of the pylT, pylS, pylB, pylC and pylD genes into *Escherichia coli* or mammalian cells, and the addition of D-ornithine into the growth media resulted in the biosynthesis and incorporation of a "demethylated pyrrolysine" (FIG. 1, PCL-A and PCL-B), as identified using mass spectrometry. This observation is surprising and not predictable in view of the results presented by Longstaff et al. Thus provided herein is a pyrrolysine analogue, pyrroline-carboxy-lysine (PCL) that is naturally encoded, biosynthetically generated and incorporated into proteins using the natural genes, pylT, pylS, pylB, pylC and pylD, and D-ornithine as a precursor. In other embodiments, as D-arginine is a precursor to D-ornithine, also provided herein is a pyrrolysine analogue that is naturally encoded, biosynthetically generated and incorporated into proteins using the natural genes, pylT, pylS, pylB, pylC and pylD, and D-arginine as a precursor.

The formation of the pyrroline ring of pyrrolysine from D-ornithine was initially thought to be analogous to the formation of proline from L-ornithine (see, Longstaff, D. G., Larue, R. C., Faust, J. E., Mahapatra, A., Zhang, L., Green-Church, K. B., and Krzycki, J. A., (2007), "A natural genetic code expansion cassette enables transmissible biosynthesis and genetic encoding of pyrrolysine," *Proceedings of the National Academy of Sciences of the United States of America*, 104, 1021-6). A number of bacteria convert L-ornithine into L-proline via the 1-pyrroline-5-carboxylate intermediate. The formation of 1-pyrroline-5-carboxylate from ornithine is the first step of a two step process in the biosynthesis of L-proline. Formation of 1-pyrroline-5-carboxylate from L-ornithine can occur via two pathways; the first wherein formation of 1-pyrroline-5-carboxylate results from cyclodeamination of L-ornithine, and a second via formation of L-glutamate semialdehyde by L-ornithine amino transferase. Glutamate semialdehyde then forms 1-pyrroline-5-carboxylate. Reduction of 1-pyrroline-5-carboxylate by pyrroline-5-carboxylate reductase results in the formation of L-proline.

Figure 2:
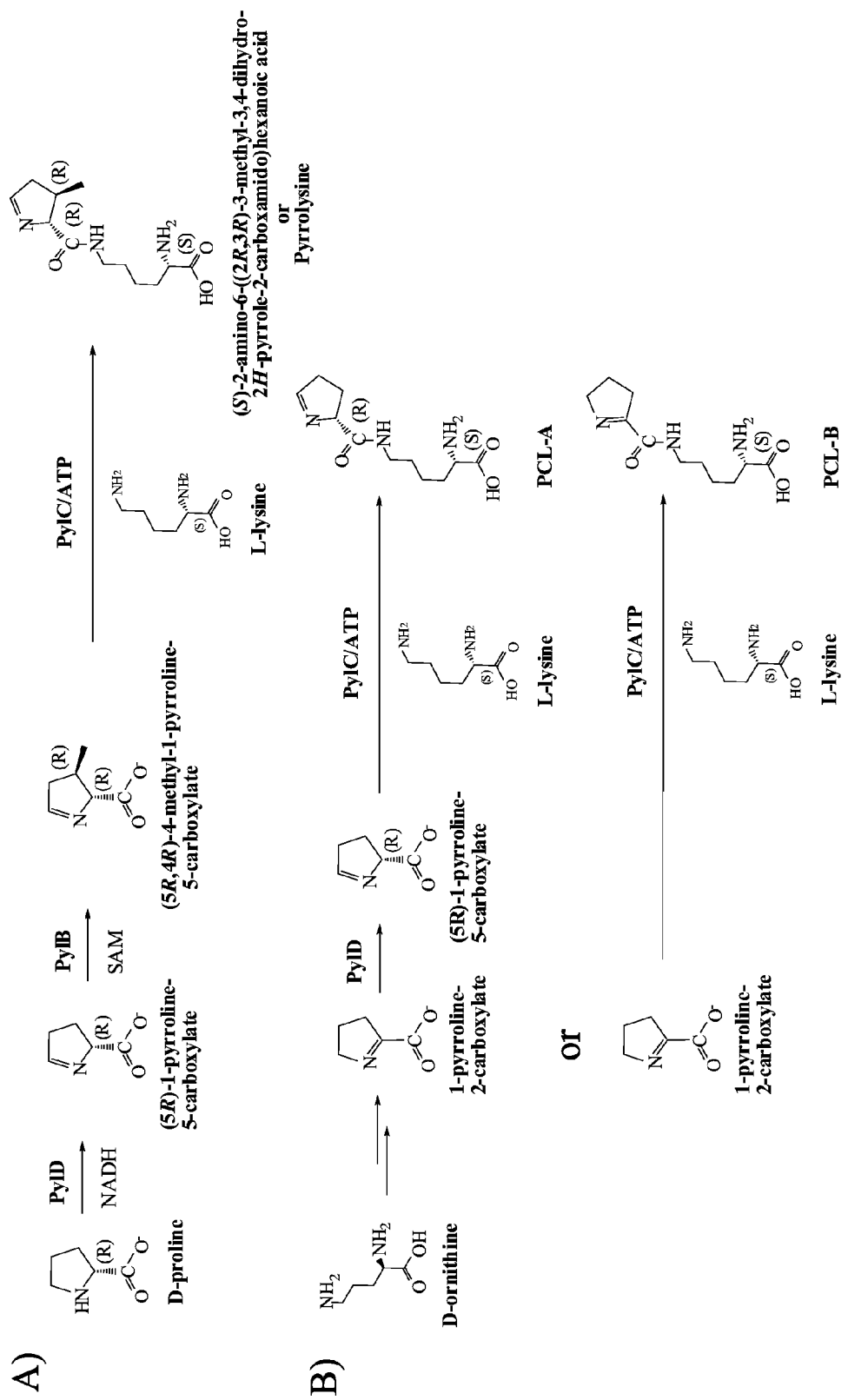
FIG. 2. Comparison of possible biosynthetic routes for pyrrolysine (A) and PCL (B).

At present no homology to L-ornithine amino transferase has been identified in the formation of pyrrolysine in methanogenic archaea. However it is anticipated to involve an analogous enzyme. The biosynthesis of pyrrolysine is thought to be a concerted process using a cellular precursor and the concerted action of the products of the pylB, pylC and pylD genes, wherein the proposed scheme for the biosynthesis of pyrrolysine from D-proline via 1-pyrroline-5-carboxylate is shown in FIG. 2A (see, Longstaff, D. G., Larue, R. C., Faust, J. E., Mahapatra, A., Zhang, L., Green-Church, K. B., and Krzycki, J. A., (2007), "A natural genetic code expansion cassette enables transmissible biosynthesis and genetic encoding of pyrrolysine," *Proceedings of the National Academy of Sciences of the United States of America*, 104, 1021-6). The pylB, pylD and pylD gene products are members of several protein families. PylB possesses signature residues of the Fe—S radical SAM enzyme family which are known to mediate radical-catalyzed reactions. Also, PylB shares some sequence homology with biotin synthase, therefore it has been suggested that PylB is involved in the formation or methylation of the pyrrolysine pyrroline ring. The pylD gene product PylD possesses the NADH-binding domain of several families of dehydrogenases, which suggests that PylD is involved in the formation of the 1-pyrroline imine bond. PylC is similar to carbamoylphosphate synthetase and D-alanyl-D-alanine ligases, which suggests a role in the formation of the pyrrolysine amide bond between lysine and the D-isomer of 4-methyl-1-pyrroline-5-carboxylate. Thus, the putative pylB, pylC and pylD gene products have the respective similarity to radical SAM proteins, proteins forming amides and amino acid dehydrogenases and thereby are thought to participate in similar pathways for the biosynthesis of pyrrolysine.

However, as provided herein, attempts to biosynthesize pyrrolysine in Escherichia coli and HEK293F cells using D-ornithine as a precursor did not result in the formation of pyrrolysine, but rather a "demethylated pyrrolysine" referred to herein as pyrroline-carboxy-lysine (PCL) (PCL-A or PCL-B: see FIG. 1). As presented herein, the biosynthesis of PCL-A or PCL-B does not require the presence of the pylB gene and therefore one possible scheme for the biosynthesis of PCL-A or PCL-B is shown in FIG. 2B. Without being held to any particular theory, this possible pathway involves the convertion of D-ornithine to 5-amino-2-oxopentanoic acid via an endogenous D-amino-acid oxidase (E.C. 1.4.3.3), and spontaneous cyclization of 5-amino-2-oxopentanoic acid to 1-pyrroline-2-carboxylate and water. This precursor, which is accessible in most organisms, could be converted into D-1-pyrroline-5-carboxylate by rearrangement of the double bond, possibly assisted by enzyme PylD. Ligation of D-1-pyrroline-5-carboxylate to the epsilon amine of L-lysine by PylC and ATP would result in pyrroline-carboxy-lysine (PCL: PCL-A). Alternatively, ligation of 1-pyrroline-2-carboxylate could result in PCL-B that is equal in molecular mass to PCL-A. The observation that both PylD and PylC are required for PCL incorporation and the inability of PylS to accept as substrate pyrrolysine analogues with a sp2 carbon at positions equivalent to the C-5 position of the 1-pyrroline ring of PCL (as presented herein), initially suggested that PCL is likely incorporated into proteins primarily in the form of PCL-A. Without being held to any particular theory it is thought that the demethylated PCL-A or PCL-B are obtained in the presence of the added D-ornithine as a result of either the deactivation of PylB, the absence of a methyl donating PylB substrate, the absence of required cofactor(s) or combinations thereof. However, this does not preclude the presence of an alternative mechanism. In fact, incorporation tests with several intermediates (as presented herein) suggest a different biosynthetic pathway for PCL-A or PCL-B than suggested in FIG. 2B. This alternative pathway is presented herein.

Figure 3:
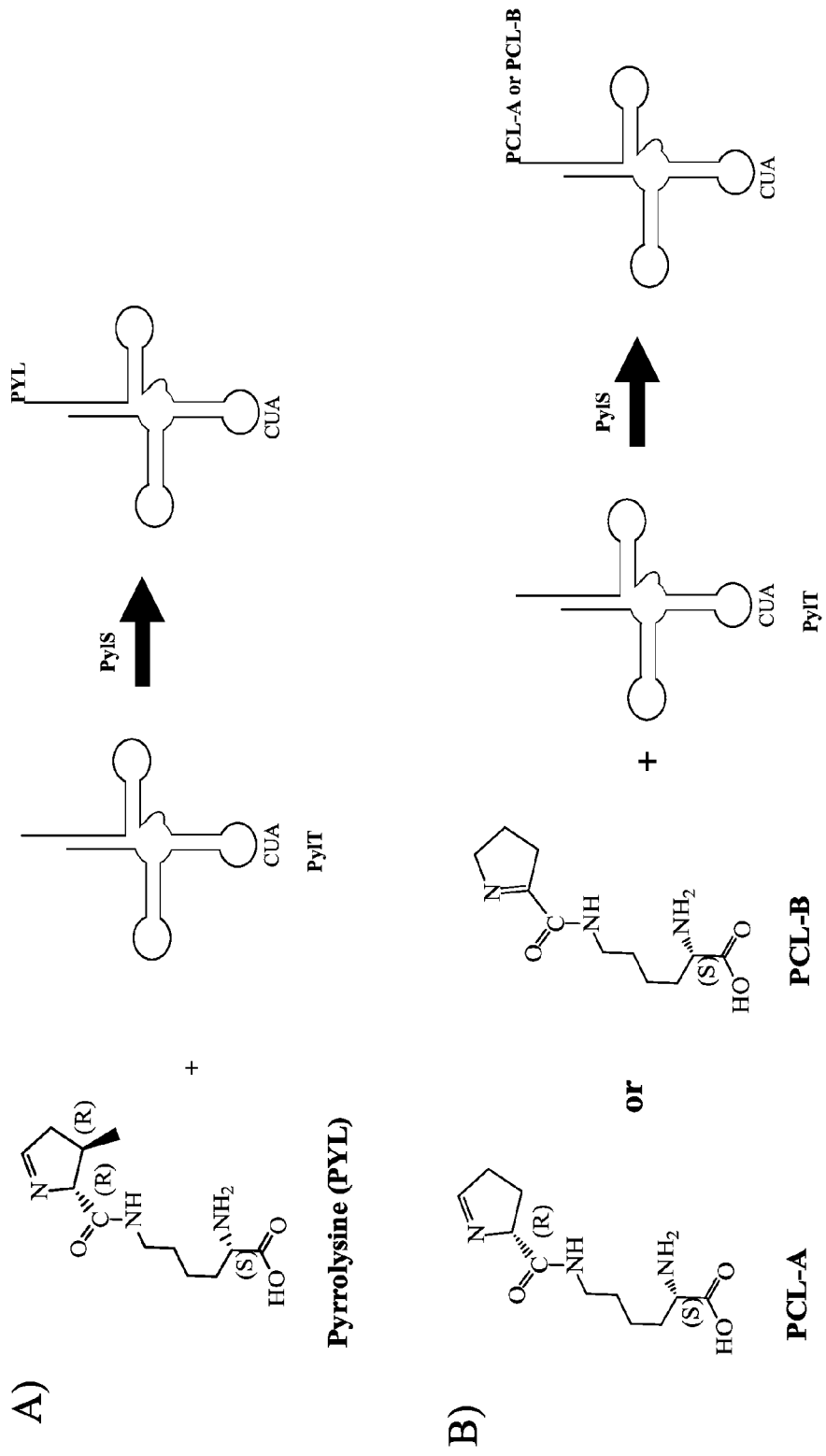
FIG. 3. Aminoacylation of pylT tRNA with pyrrolysine (A) and PCL (B).

The incorporation of pyrrolysine into a protein in response to the UAG codon has been shown to be facilitated by the natural genes pylT and pylS, wherein the UAG translation as pyrrolysine requires aminoacylation of the amber-decoding tRNA$^{pyl}$ with pyrrolysine by pyrrolysyl-tRNA synthetase (PylS) (FIG. 3A). The pylT gene encodes the dedicated natural suppressor tRNA$^{pyl}$ (PylT), whose CUA anticodon complements the UAG sense codon corresponding to pyrrolysine. The pylS gene encodes the pyrrolysyl-tRNA synthetase (PylS), a specific class II tRNA synthetase which charges tRNA$^{pyl}$ with pyrrolysine (chemically or biosynthetically synthesized) and also carries out pyrrolysine-dependent ATP:pyrophosphate exchange reactions. Similarly, the incorporation of pyrrolysine analogues PCL-A or PCL-B into a protein in response to the UAG codon is thought to be facilitated by the natural genes pylT and pylS (FIG. 3B).

Biosynthesis and Site-Specific Incorporation of Pyrrolysine and PCL into Proteins Expressed by Prokaryotic and Eukaryotic Cells Provided herein are methods for the site specific incorporation of biosynthetically generated pyrrolysine and/or pyrroline-carboxy-lysine ((S)-2-amino-6-(3,4-dihydro-2H-pyrrole-2-carboxamido)hexanoic acid (PCL-A) or (S)-2-amino-6-(3,4-dihydro-2H-pyrrole-5-carboxamido)hexanoic acid (PCL-B)). The pyrrolysine analogues PCL-A and PCL-B, both referred to herein as PCL, lack the methyl group of pyrrolysine (PYL) (FIG. 1). In certain embodiments of such methods, the eukaryotic cell is a mammalian cell, a yeast cell, an insect cell, a fungal cell or a plant cell. In other embodiments, the mammalian cells used in the methods provided herein include, but are not limited to, human embryonic kidney (HEK293F) cells, human epitheloid carcinoma (HeLa and GH3) cells, monkey kidney (COS) cells, rat C6 glioma cells, baby hamster kidney (BHK-21) cells and chinese hamster ovary (CHO) cells. In certain embodiments, the yeast cells used in the methods provided herein include, but are not limited to, Saccharomyces cerevisiae and Pichia pastoris cells. In other embodiments, the insect cells used in the methods provided herein include, but are not limited to, Spodoptera frugiperda (sf9 and sf21) cells, Trichoplusia ni (BTI TN-5B1-4 or High-Five™) cells and Mammestra brassicae cells. In certain embodiments, the prokaryotic cell is a bacterium, while in other embodiments, the bacterium used in the methods provided herein include, but are not limited to, Escherichia coli, Mycobacterium smegmatis, Lactococcus lactis and Bacillus subtilis.

In certain embodiments such methods for the site specific incorporation of biosynthetically generated pyrrolysine and PCL involves introducing the genes pylT, pylS, pylB, pylC and pylD, and the gene for the desired protein, into prokaryotic cells and/or eukaryotic cells, and optionally adding a precursor for pyrrolysine or PCL to the growth media of the transfected cells. In certain embodiments, the precursor is D-ornithine, while in other embodiments the precursor is L-ornithine. In certain embodiments, the precursor is D,L-ornithine. In certain embodiments, the precursor is D-arginine, while in other embodiments the precursor is L-arginine. In certain embodiments, the precursor is D,L-arginine. In certain embodiments, the precursor is

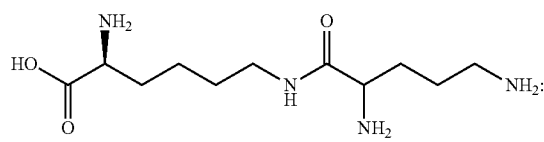

(2S)-2-amino-6-(2,5-diaminopentanamido)hexanoic acid. In certain embodiments, the precursor

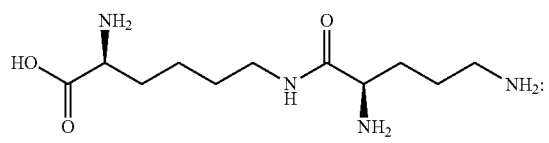

(2S)-2-amino-6-((R)-2,5-diaminopentanamido)hexanoic acid. In certain embodiments, the precursor is

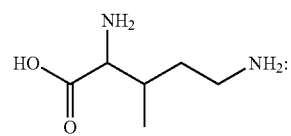

2,5-diamino-3-methylpentanoic acid. In certain embodiments, the precursor is (2R,3R)-2,5-diamino-3-methylpentanoic acid. In certain embodiments, the eukaryotic cell is a mammalian cell, a yeast cell, an insect cell, a fungal cell or a plant cell. In other embodiments, the mammalian cells used in the methods provided herein include, but are not limited to, human embryonic kidney HEK293F cells, human epitheloid carcinoma HeLa and GH3 cells, monkey kidney COS cells, rat C6 glioma cells, baby hamster kidney BHK-21 cells and chinese hamster ovary CHO cells. In certain embodiments, the yeast cells used in the methods provided herein include, but are not limited to, *Saccharomyces cerevisiae* and *Pichia pastoris* cells. In other embodiments, the insect cells used in the methods provided herein include, but are not limited to, *Spodoptera frugiperda* sf9 and sf21 cells, *Trichoplusia ni* (BTI TN-5B1-4 or High-Five™) cells and *Mammestra brassicae* cells. In certain embodiments, the prokaryotic cell is a bacterium, while in other embodiments, the bacterium used in the methods provided herein include, but are not limited to, *Escherichia coli, Mycobacterium smegmatis, Lactococcus lactis* and *Bacillus subtilis*.

In certain embodiments such methods for the site specific incorporation of biosynthetically generated pyrrolysine and PCL involves introducing the genes pylT, pylS, pylB, pylC and pylD, and the gene for the desired protein, into prokaryotic cells and/or eukaryotic cells, and adding a precursor for pyrrolysine or PCL to the growth media of the transfected cells. In certain embodiments, the precursor is D-ornithine, while in other embodiments the precursor is L-ornithine. In certain embodiments, the precursor is D,L-ornithine. In certain embodiments, the precursor is D-arginine, while in other embodiments the precursor is L-arginine. In certain embodiments, the precursor is D,L-arginine. In certain embodiments, the precursor is (2S)-2-amino-6-(2,5-diaminopentanamido)hexanoic acid. In certain embodiments, the precursor is (2S)-2-amino-6-((R)-2,5-diaminopentanamido)hexanoic acid. In certain embodiments, the precursor is 2,5-diamino-3-methylpentanoic acid. In certain embodiments, the precursor is (2R,3R)-2,5-diamino-3-methylpentanoic acid. In certain embodiments, the eukaryotic cell is a mammalian cell, a yeast cell, an insect cell, a fungal cell or a plant cell. In other embodiments, the mammalian cells used in the methods provided herein include, but are not limited to, human embryonic kidney HEK293F cells, human epitheloid carcinoma HeLa and GH3 cells, monkey kidney COS cells, rat C6 glioma cells, baby hamster kidney BHK-21 cells and chinese hamster ovary CHO cells. In certain embodiments, the yeast cells used in the methods provided herein include, but are not limited to, *Saccharomyces cerevisiae* and *Pichia pastoris* cells. In other embodiments, the insect cells used in the methods provided herein include, but are not limited to, *Spodoptera frugiperda* sf9 and sf21 cells, *Trichoplusia ni* (BTI TN-5B1-4 or High-Five™) cells and *Mammestra brassicae* cells. In certain embodiments, the prokaryotic cell is a bacterium, while in other embodiments, the bacterium used in the methods provided herein include, but are not limited to, *Escherichia coli, Mycobacterium smegmatis, Lactococcus lactis* and *Bacillus subtilis*.

In certain embodiments, such methods for the site specific incorporation of biosynthetically generated PCL involves introducing the genes pylT, pylS, pylC and pylD, and the gene for the desired protein, into prokaryotic cells and/or eukaryotic cells, and adding D-ornithine to the growth media as a precursor for PCL. In certain embodiments, the eukaryotic cell is a mammalian cell, a yeast cell, an insect cell, a fungal cell or a plant cell. In other embodiments, the mammalian cells used in the methods provided herein include, but are not limited to, human embryonic kidney HEK293F cells, human epitheloid carcinoma HeLa and GH3 cells, monkey kidney COS cells, rat C6 glioma cells, baby hamster kidney BHK-21 cells and chinese hamster ovary CHO cells. In certain embodiments, the yeast cells used in the methods provided herein include, but are not limited to, *Saccharomyces cerevisiae* and *Pichia pastoris* cells. In other embodiments, the insect cells used in the methods provided herein include, but are not limited to, *Spodoptera frugiperda* sf9 and sf21 cells, *Trichoplusia ni* (BTI TN-5B1-4 or High-Five™) cells and *Mammestra brassicae* cells. In certain embodiments, the prokaryotic cell is a bacterium, while in other embodiments, the bacterium used in the methods provided herein include, but are not limited to, *Escherichia coli, Mycobacterium smegmatis, Lactococcus lactis* and *Bacillus subtilis*. In such embodiments wherein the natural genes pylT, pylS, pylC and pylD are used, rather than pyrrolysine being biosynthetically generating and incorporating, instead the demethylated pyrrolysine analogue PCL is biosynthetically generated and incorporated.

In certain embodiments, such methods for the site specific incorporation of biosynthetically generated pyrrolysine and PCL involves introducing the genes pylT, pylS, pylC and pylD and the gene for the desired protein, into prokaryotic cells and/or eukaryotic cells, and adding D-ornithine, L-ornithine, D,L-ornithine, D-arginine, L-arginine, D,L-arginine, (2S)-2-amino-6-(2,5-diaminopentanamido)hexanoic acid, (2S)-2-amino-6-((R)-2,5-diaminopentanamido)hexanoic acid or 2,5-diamino-3-methylpentanoic acid or (2R,3R)-2,5-diamino-3-methylpentanoic acid to the growth media as a precursor for pyrrolysine and/or PCL. In certain embodiments, the eukaryotic cell is a mammalian cell, a yeast cell, an insect cell, a fungal cell or a plant cell. In other embodiments, the mammalian cells used in the methods provided herein include, but are not limited to, human embryonic kidney HEK293F cells, human epitheloid carcinoma HeLa and GH3 cells, monkey kidney COS cells, rat C6 glioma cells, baby hamster kidney BHK-21 cells and chinese hamster ovary CHO cells. In certain embodiments, the yeast cells used in the methods provided herein include, but are not limited to, *Saccharomyces cerevisiae* and *Pichia pastoris* cells. In other embodiments, the insect cells used in the methods provided herein include, but are not limited to, *Spodoptera frugiperda* sf9 and sf21 cells, *Trichoplusia ni* (BTI TN-5B1-4 or High-Five™) cells and *Mammestra brassicae* cells. In certain embodiments, the prokaryotic cell is a bacterium, while in other embodiments, the bacterium used in the methods provided herein include, but are not limited to, *Escherichia coli, Mycobacterium smegmatis, Lactococcus lactis* and *Bacillus subtilis*. In such embodiments wherein the natural genes pylT, pylS, pylC and pylD are used, rather than pyrrolysine being biosynthetically generating and incorporating, instead the demethylated pyrrolysine analogue PCL is biosynthetically generated and incorporated.

In certain embodiments, such methods for the site specific incorporation of biosynthetically generated pyrrolysine involves introducing the genes pylT, pylS, pylC and pylD, and the gene for the desired protein, into prokaryotic cells and/or eukaryotic cells, and adding 2,5-diamino-3-methylpentanoic acid or (2R,3R)-2,5-diamino-3-methylpentanoic acid to the growth media as a precursor for pyrrolysine. In certain embodiments, the eukaryotic cell is a mammalian cell, a yeast cell, an insect cell, a fungal cell or a plant cell. In other embodiments, the mammalian cells used in the methods provided herein include, but are not limited to, human embryonic kidney HEK293F cells, human epitheloid carcinoma HeLa and GH3 cells, monkey kidney COS cells, rat C6 glioma cells, baby hamster kidney BHK-21 cells and chinese hamster ovary CHO cells. In certain embodiments, the yeast cells used in the methods provided herein include, but are not limited to,

*Saccharomyces cerevisiae* and *Pichia pastoris* cells. In other embodiments, the insect cells used in the methods provided herein include, but are not limited to, *Spodoptera frugiperda* sf9 and sf21 cells, *Trichoplusia ni* (BTI TN-5B1-4 or High-Five™) cells and *Mammestra brassicae* cells. In certain embodiments, the prokaryotic cell is a bacterium, while in other embodiments, the bacterium used in the methods provided herein include, but are not limited to, *Escherichia coli, Mycobacterium smegmatis, Lactococcus lactis* and *Bacillus subtilis*.

Figure 4:
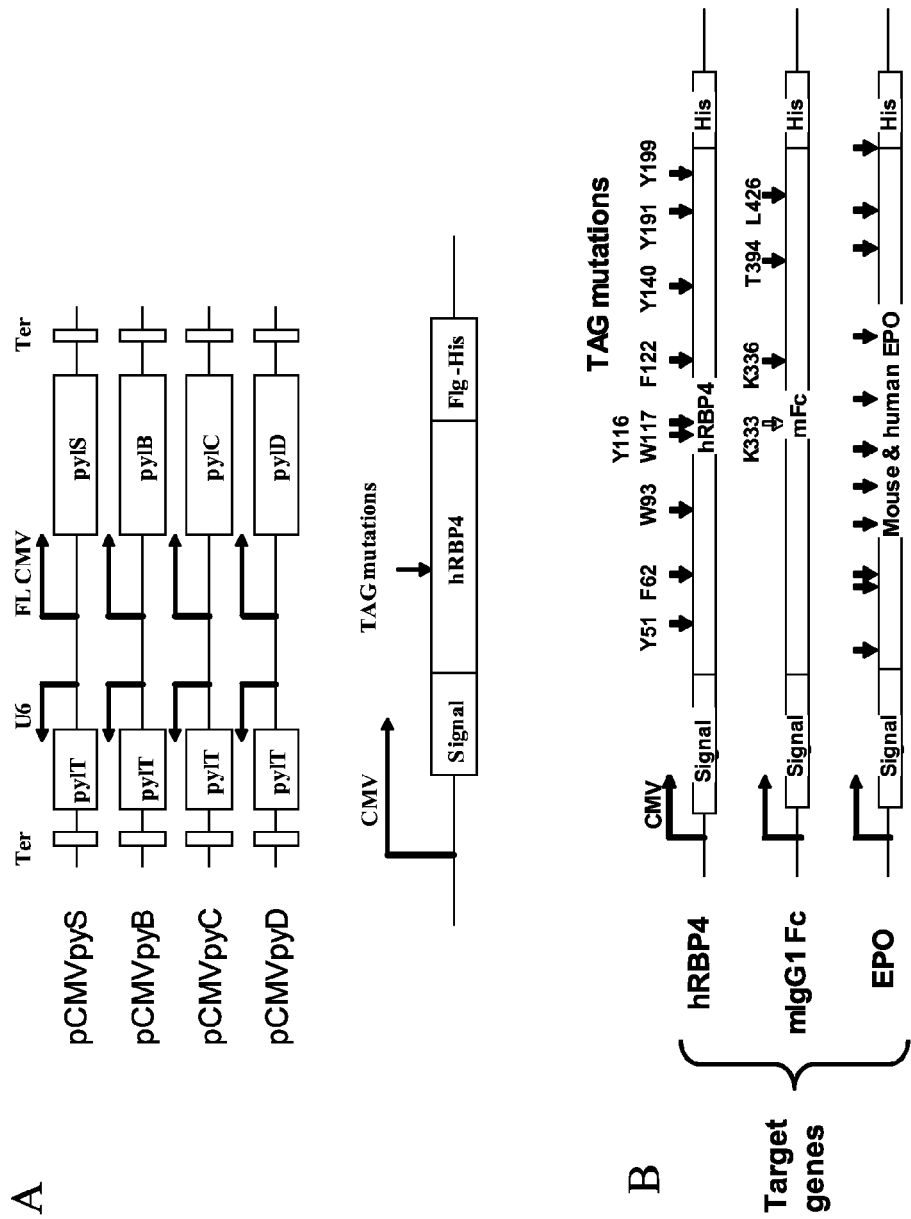
FIG. 4A. Plasmids carrying pylT, pylS, pylB, pylC and pylD for the incorporation of biosynthetically derived PCL or pyrrolysine in mammalian cells, and carrying a single site TAG mutant gene construct for the model protein hRBP4.
FIG. 4B. Single site TAG mutant gene constructs for hRBP4, mEPO, hEPO, and mIgG1. The single sites are indicated by arrows.
Figure 5:
FIG. 5. A plasmid carrying pylT, pylS, pylB, pylC and pylD for the incorporation of biosynthetically derived PCL or pyrrolysine in *Escherichia coli* cells.

The site specific incorporation of biosynthetically generated PCL at TAG encoded sites in a model protein (hRBP4) has been accomplished in mammalian cells using the natural genes pylT, pylS, pylB, pylC and pylD and D-ornithine added to the growth media as a precursor (see Example 2). In one embodiment, the site specific incorporation of PCL into the model protein, hRBP4, was achieved by co-transfecting HEK293F cells with DNA encoding the UAG-recognizing tRNA PylT, its specific aminoacyl-tRNA synthetase PylS, the biosynthetic genes pylB, pylC and pylD as well as DNA encoding the target protein with the incorporation site encoded by TAG. The gene constructs used for such in vivo biosynthesis and incorporation in mammalian cells into the model protein hRBP4 at single sites specified by TAG codons is shown in FIG. 4A. Other gene constructs for use in mammalian for the expression of various single site TAG mutants of hRBP4, mEPO, hEPO, and the Fc domain of mIgG1 are shown in FIG. 4B. A plasmid carrying pylT, pylS, pylB, pylC and pylD for the incorporation of biosynthetically derived PCL or pyrrolysine in *Escherichia coli* cells is shown in FIG. 5.

When D-ornithine, the putative precursor for the biosynthesis of pyrrolysine, is added to the culture media of HEK293F cells transfected with pylT, pylS, pylB, pylC and pylD as well as DNA encoding the target protein, PCL is incorporated into hRBP4 at the site of the TAG codon, rather than pyrrolysine (see Example 2, FIG. 6A). The incorporation efficiency varies for the different incorporation sites as seen in FIG. 6A.

The site specific incorporation of biosynthetically generated PCL at TAG encoded sites in a model protein (hRBP4) has been accomplished in mammalian cells using the natural genes pylT, pylS, pylC and pylD and D-ornithine added to the growth media as a precursor (see Example 2). In one embodiment, the site specific incorporation of PCL into the model protein, hRBP4, was achieved by co-transfecting HEK293F cells with DNA encoding the UAG-recognizing tRNA PylT, its specific aminoacyl-tRNA synthetase PylS, the biosynthetic genes pylC and pylD as well as DNA encoding the target protein with the incorporation site encoded by TAG. When D-ornithine, the putative precursor for the biosynthesis of pyrrolysine, is added to the culture media of the transfected HEK293F cells, PCL is incorporated into hRBP4 at the site of the TAG codon, rather than pyrrolysine. FIG. 6B shows the SDS-PAGE and FIG. 6C shows the mass spectrum of purified hRBP4 Phe62PCL (mutant #2) produced in HEK293F cells in the absence (B, lane 1) or presence (B, lane 2) of D-ornithine. The arrow indicates full length hRBP4 and the mass obtained was 23166.0 Da, close to the expected mass of 23168 Da. Mass spectrometry data shown in FIGS. 7-9 further illustrate that PCL, and not pyrrolysine, is incorporated at the TAG site, at residue 62 of hRBP4 (see Example 2).

Figure 7:
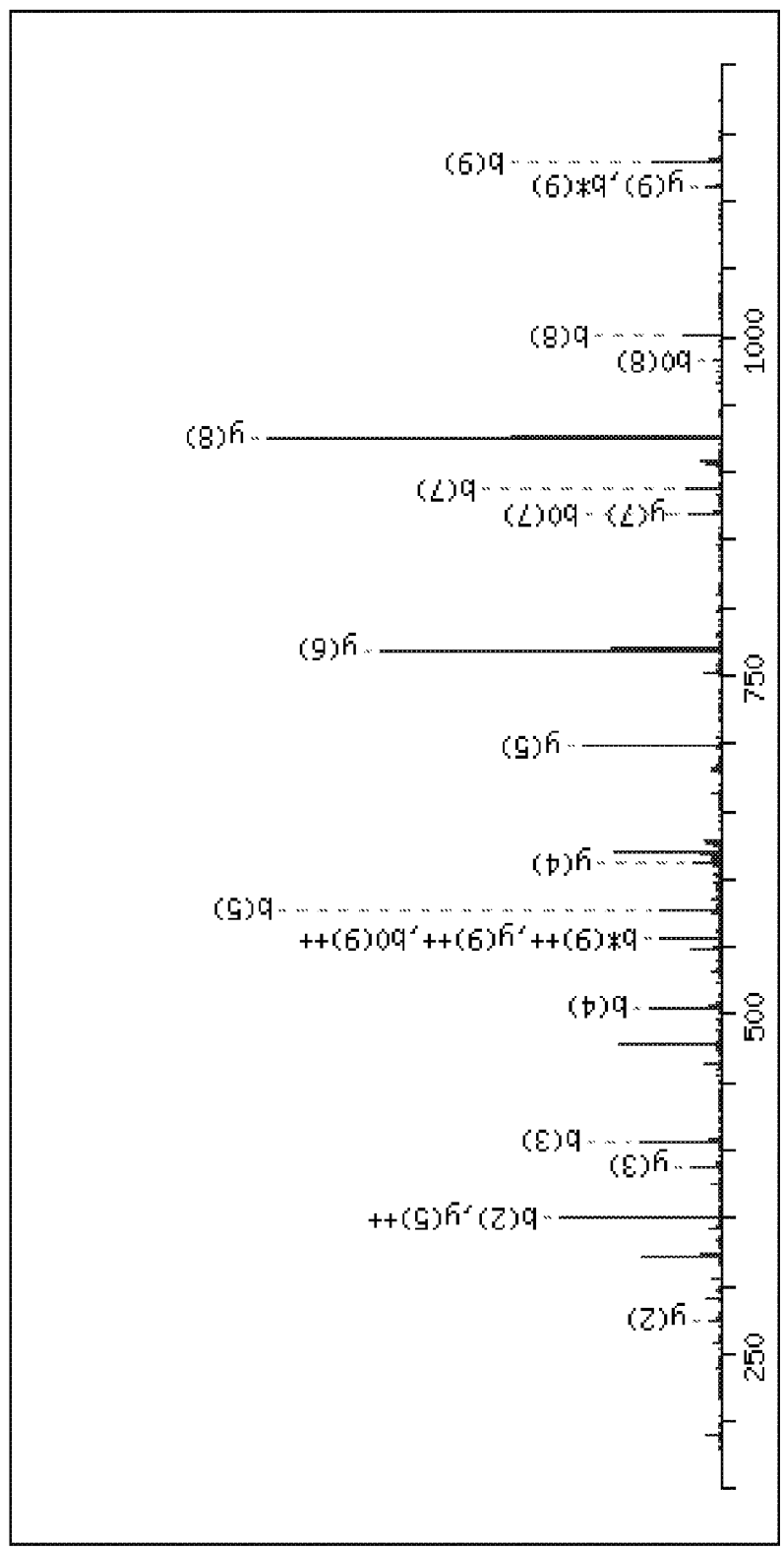
FIG. 7. Mass spectrometric analysis of a tryptic digest of hRBP4 Phe122PCL indicates incorporation of PCL at the target Phe122TAG site. Assigned MS/MS spectrum of YWGVASF*LQK (F*=PCL) (SEQ ID NO:17)
Figure 8:
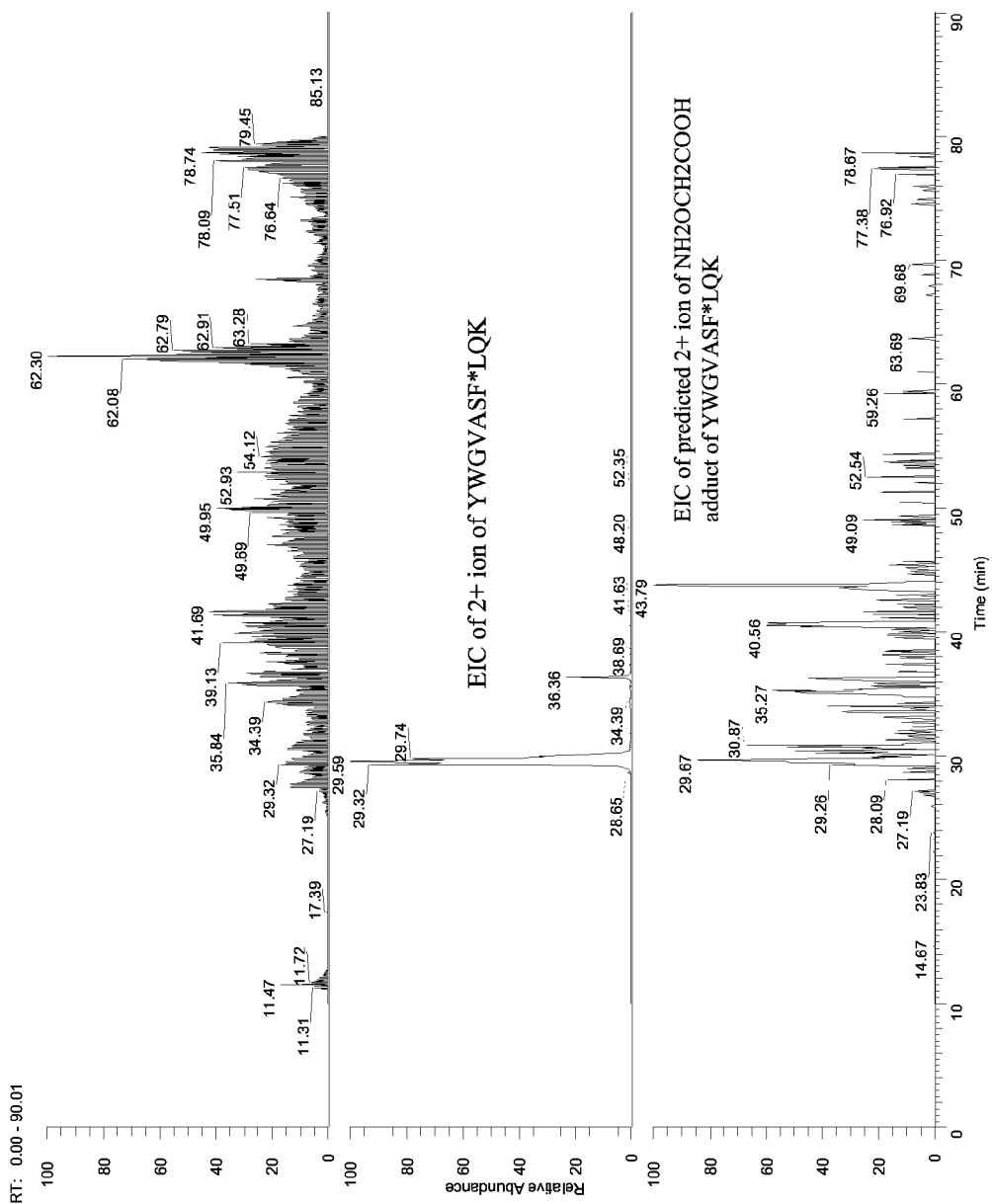
FIG. 8. Mass spectrum spectrometric analysis (TIC and EIC of 2+ ions of YWGVASF*LQK) (SEQ ID NO:17) of a tryptic digest of hRBP4 Phe122PCL indicates incorporation of PCL at the target Phe122TAG site.
Figure 9:
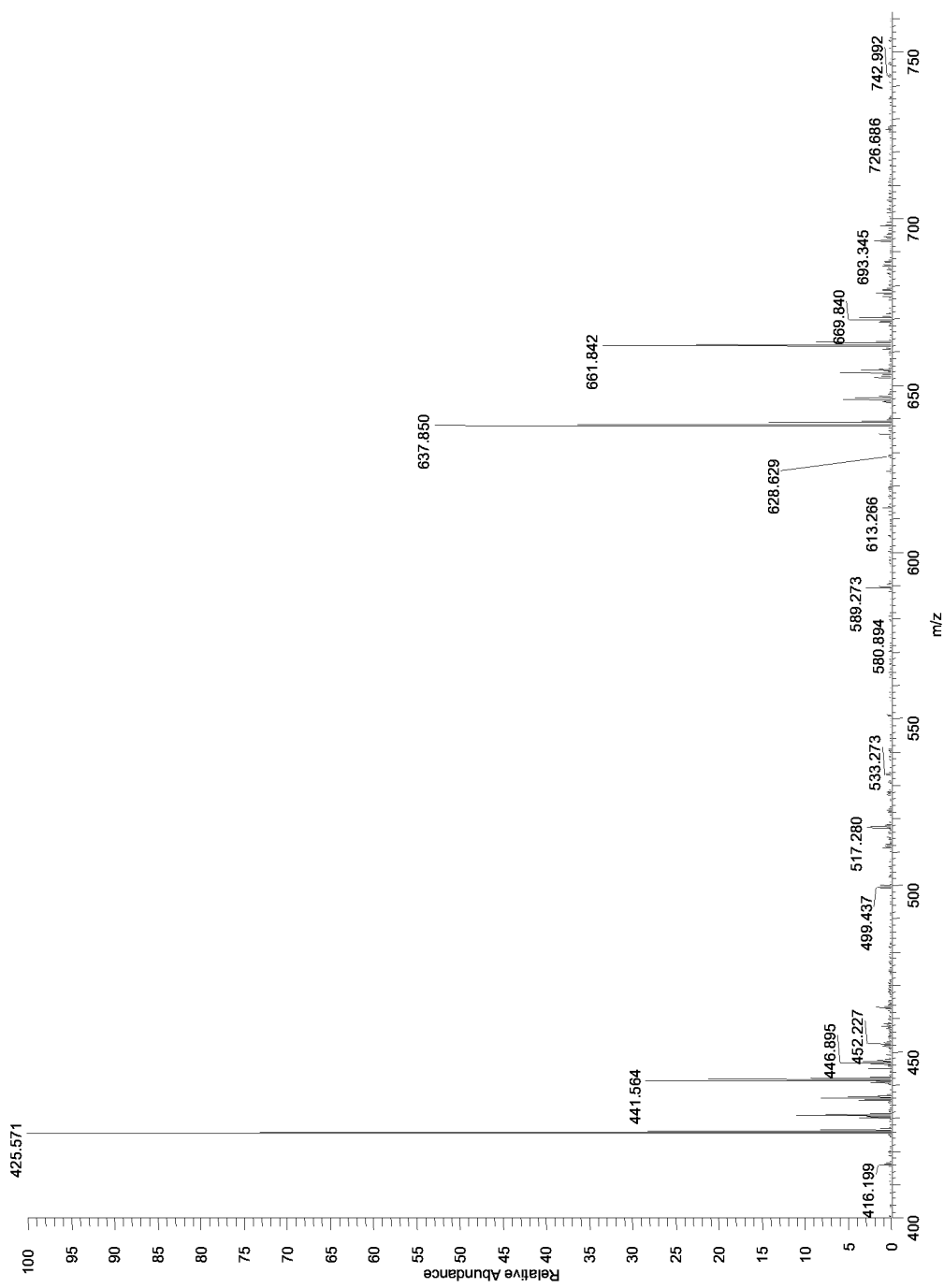
FIG. 9. Mass spectrometric analysis of a tryptic digest of hRBP4 Phe122PCL. The mass spectrum shows 3+ and 2+ precursors of YWGVASF*LQK (SEQ ID NO:17) indicating incorporation of PCL at the target Phe122TAG site.
Figure 10:
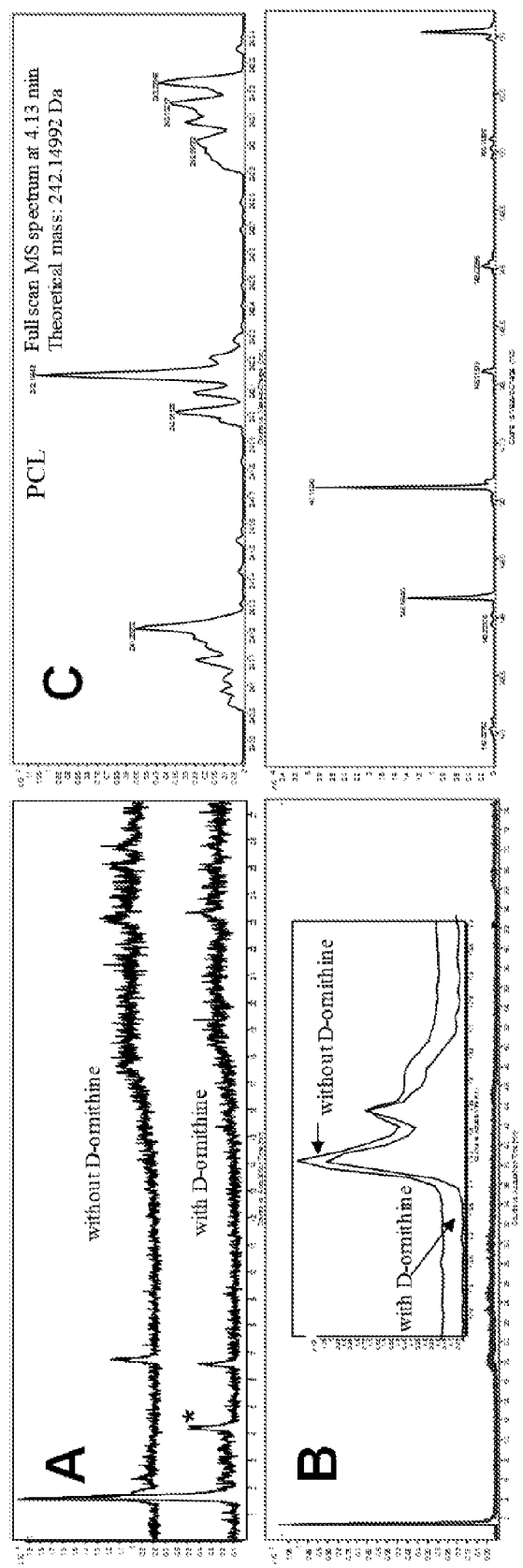
FIG. 10. Detection of PCL, biosynthesized from D-ornithine, in lysate from HEK293F cells.

FIG. 1 shows the structures of pyrrolysine (PYL) and the demethylated pyrrolysine analogue, pyrroline-carboxy-lysine (PCL) (structure PCL-A or the alternative structure PCL-B). The structure of PCL-A (or the alternative structure PCL-B) was distinguished from pyrrolysine with the use of high-precision mass spectrometric analysis of a peptide fragment of an incorporation site (FIGS. 7-9). In addition the structure of PCL was distinguished from pyrrolysine by the detection of PCL by mass spectrometry as a free amino acid in cell lysate (FIG. 10, see Example 3). Also, the observation of PCL in the cell lysate demonstrates that PCL is biosynthetically generated as a free amino acid, rather than being formed by a post-translational modification. FIGS. 10A and 10C shows the detection of PCL, in lysate from HEK293F cells biosynthesized from D-ornithine. FIG. 10A, is the HPLC trace of lysate from cells transfected with the biosynthetic genes pylB, pylC and pylD and grown in the presence of D-ornithine (bottom trace) and in the absence of D-ornithine (top trace). The lysate chromatogram obtained from cells grown in the presence of D-ornithine features a peak at 4.13 min elution time (marked with an asterisk) that is absent in lysate of identical cells cultured in the absence of D-ornithine. FIG. 10C is the full scan mass spectrum of the HPLC peak at 4.13 min wherein the mass obtained (m+1) is consistent with the theoretical mass for PCL. FIG. 10B is an HPLC chromatogram showing that lysine is equally abundant in both samples and a full scan mass (m+1) spectrum of the lysine HPLC at 1.44 min (FIG. 10D) illustrates the accuracy of the method.

Figure 11:
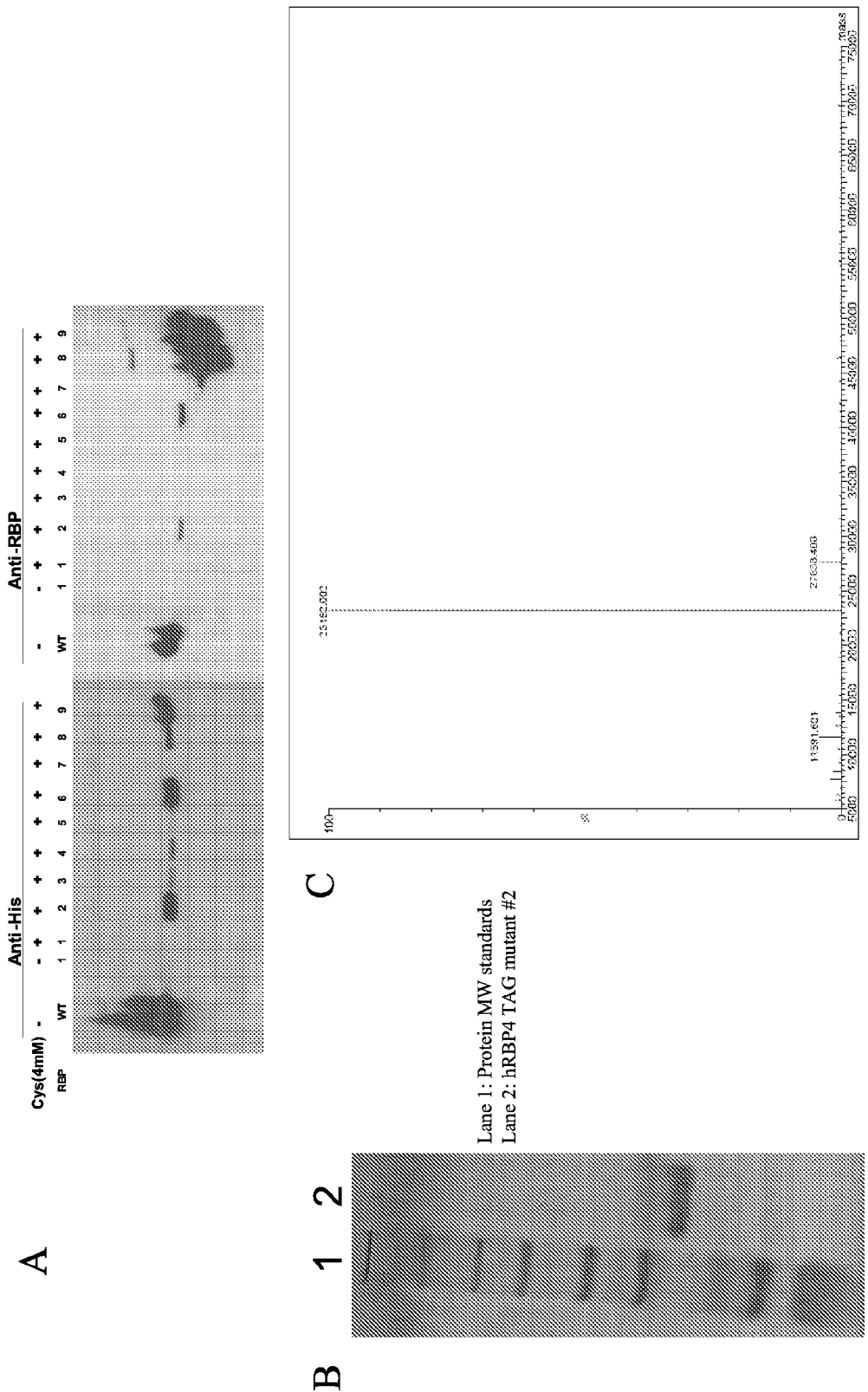
FIG. 11. Incorporation of N-ϵ-cyclopentyloxycarbonyl-L-lysine (CYC) into various hRBP4 TAG mutant proteins in HEK293F cells.
Figure 12:
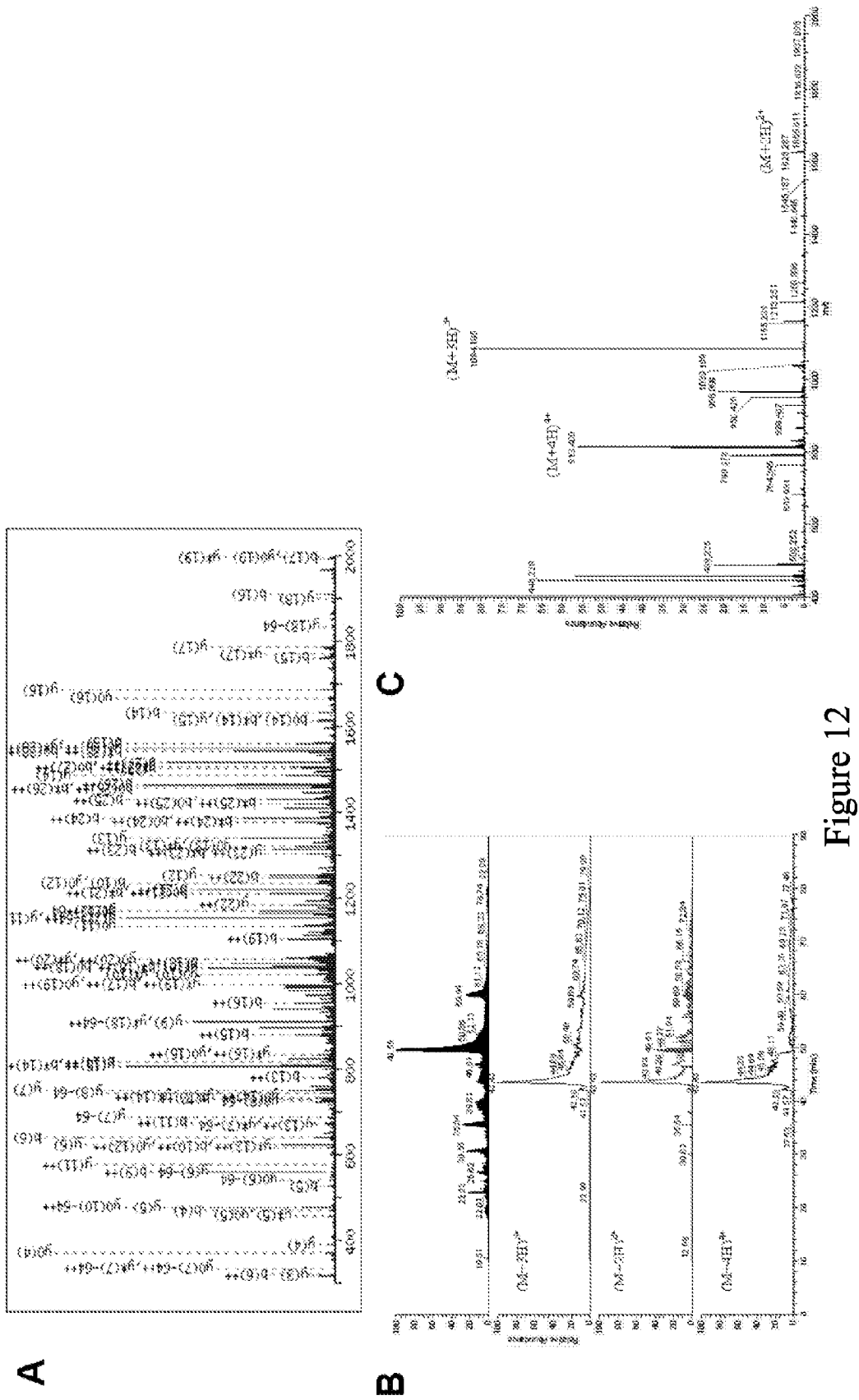
FIG. 12. Mass spectrometric verification of CYC incorporation at the TAG site of the hRBP4 mutant Phe62CYC.

FIG. 11 shows the incorporation of N-ε-cyclopentyloxy-carbonyl-L-lysine (CYC) into various hRBP4 TAG mutant proteins in HEK293F cells. FIG. 12 shows mass spectrometric verification of CYC incorporation at the TAG site of the hRBP4 mutant Phe62TAG. FIG. 13A and FIG. 13B (see Example 4) show PCL incorporation as a function of various precursors as listed in the table and shown in FIG. 14A. FIG. 13A and FIG. 13B also show direct incorporation of various pyrrolysine analogues (including CYC) into hRBP4 TAG mutant protein using HEK293F cells. To demonstrate that D-ornithine is a precursor for the biosynthesis of PCL, potential precursors for PCL (FIG. 14A) were added to the growth media of HEK293F cells transfected with the pyrrolysine biosynthetic pylB, pylC and pylD genes, the pylT/pylS tRNA/pyrrolysyl-tRNA synthetase pair and the hRBP4 TAG mutant DNA. In addition, the various pyrrolysine analogues, added to the growth media of HEK293F cells transfected with only the pylT/pylS tRNA/aa-tRNA synthetase pair and hRBP4 TAG mutant DNA, are shown in FIG. 14B. FIG. 13A is a Western blot of full-length hRBP4 protein with an anti-His-tag antibody, while FIG. 13B is an SDS-PAGE of the same samples after Ni-NTA purification. As shown D-ornithine (lane 2) is the better precursor for PCL biosynthesis, although D-arginine (lane 4), which can be metabolized to D-ornithine, gives above background protein production. Of the pyrrolysine analogues, only CYC results in protein production to a level similar to D-ornithine, while the 3-oxobutanoic acid analog TU3000-016 shows measurable but much lower incorporation. Description of the synthesis of various analogues is given in Example 33. All lanes show low-level production of full-length protein possibly because of low endogenous levels of D-ornithine and of metabolites or media components acceptable as PylS substrates.

Figure 13:
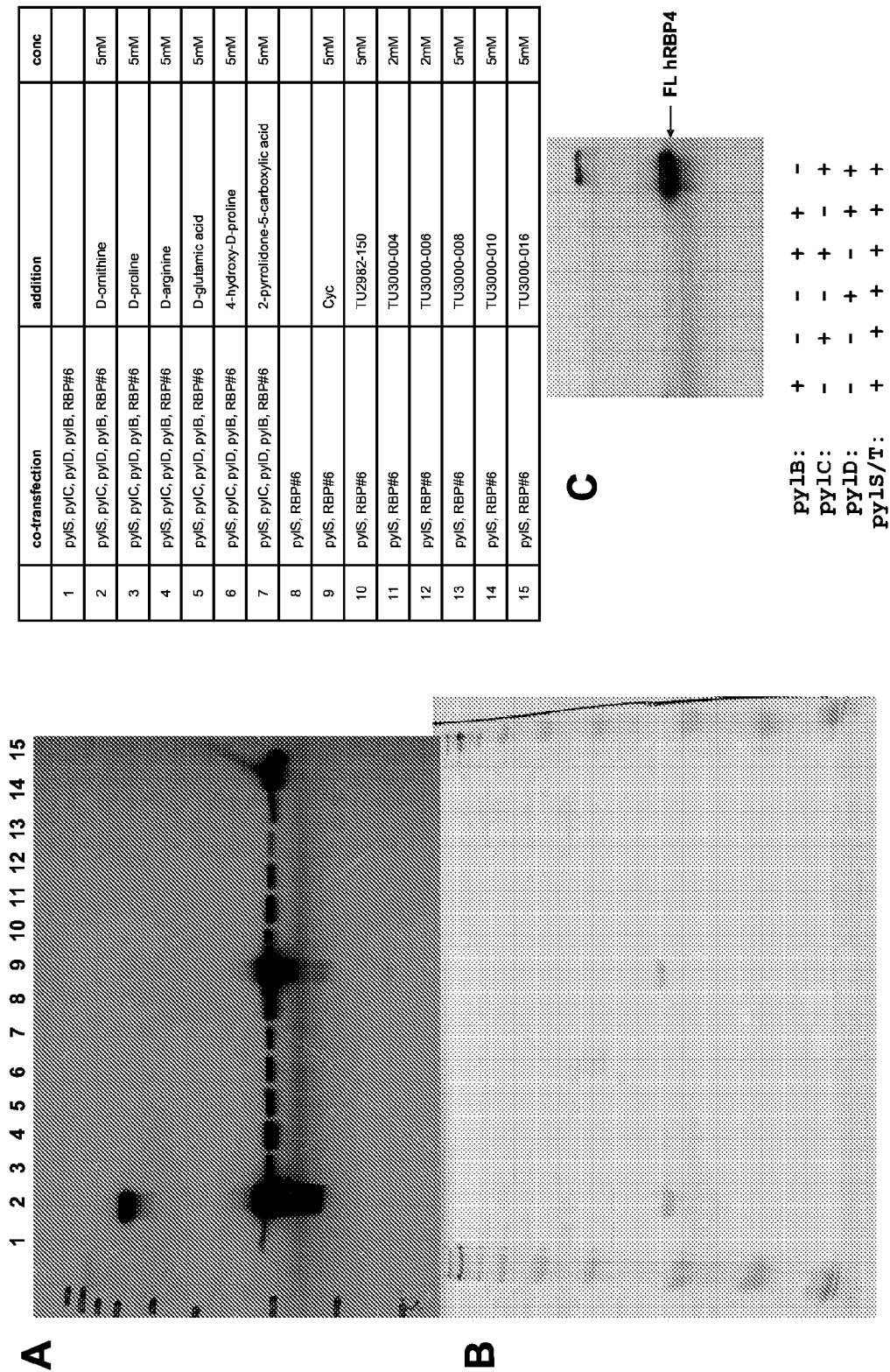
FIG. 13. PCL incorporation as a function of various precursors and direct incorporation of various pyrrolysine analogues (including CYC) into hRBP4 TAG mutant protein using HEK293F cells (FIG. 13A and FIG. 13B), and PCL incorporation using different combinations of the biosynthetic genes pylB, pylC and pylD (FIG. 13C).

The incorporation of PCL was evaluated using different combinations of the biosynthetic genes pylB, pylC and pylD (FIG. 13C). The data shows that only the genes pylC and pylD are essential for PCL biosynthesis and subsequent protein incorporation. Most notably D-proline, as other D-proline analogs and D-glutamic acid (FIGS. 13 and 14) did not result in full-length protein production above background. This suggests that the biosynthesis of PCL-A and PCL-B does not follow the pathway suggested in FIG. 2A. However, incorporation tests with 3,4-dihydro-2H-pyrrole-5-carboxylate (P2C) and 1-pyrroline-5-carboxylate (P5C) also failed to produce full-length protein in *Escherichia coli*, whereas synthetic PCL-A and PCL-B both incorporated with high efficiency (FIG. 15A, Example 15). Thus, the biosynthetic pathway suggested in FIG. 2B is also likely not the prominent pathway.

Figure 15:
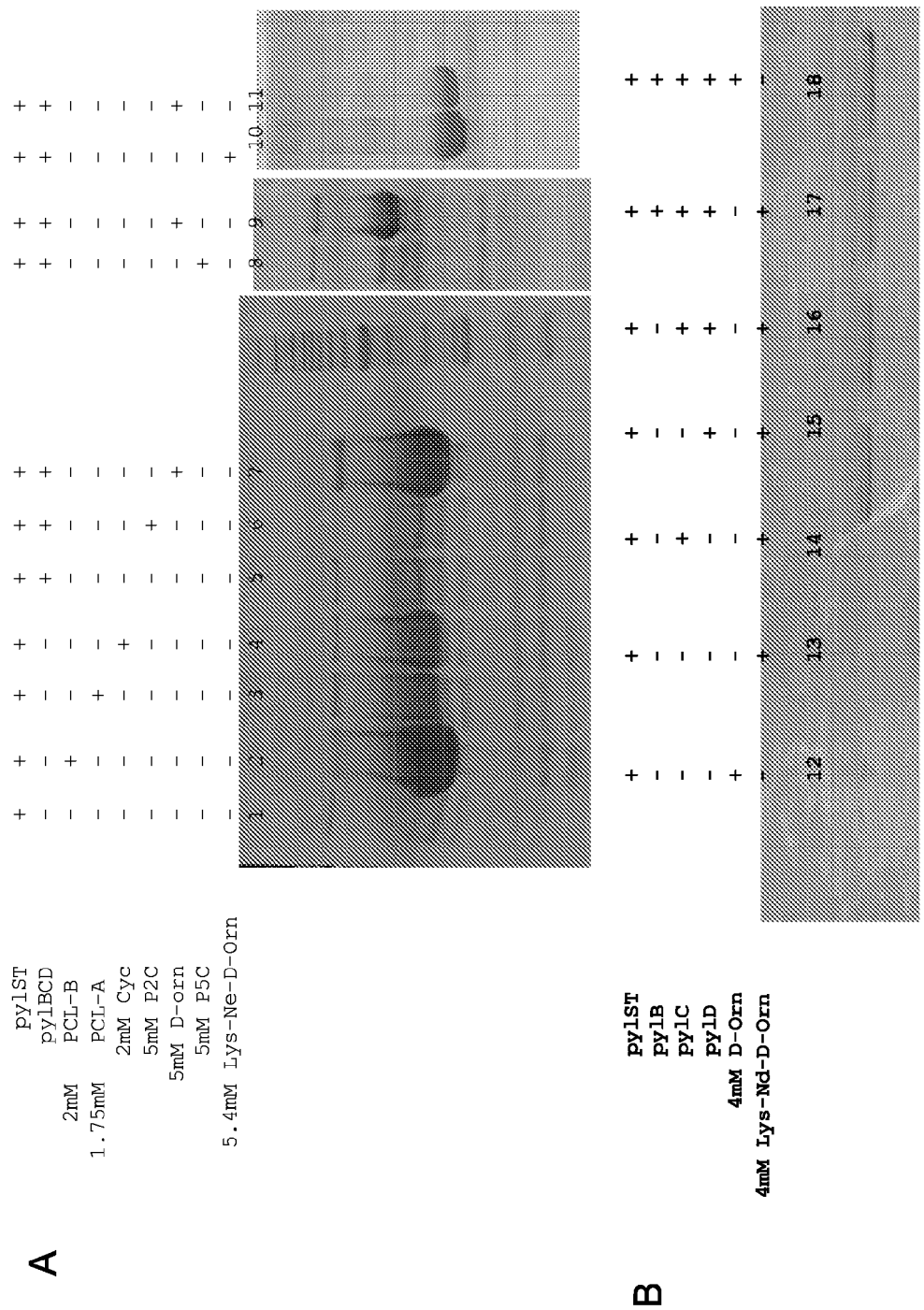
FIG. 15. Evaluation of various precursors and gene combinations for the incorporation of PCL into FASTE in HK100 cells.
Figure 16:
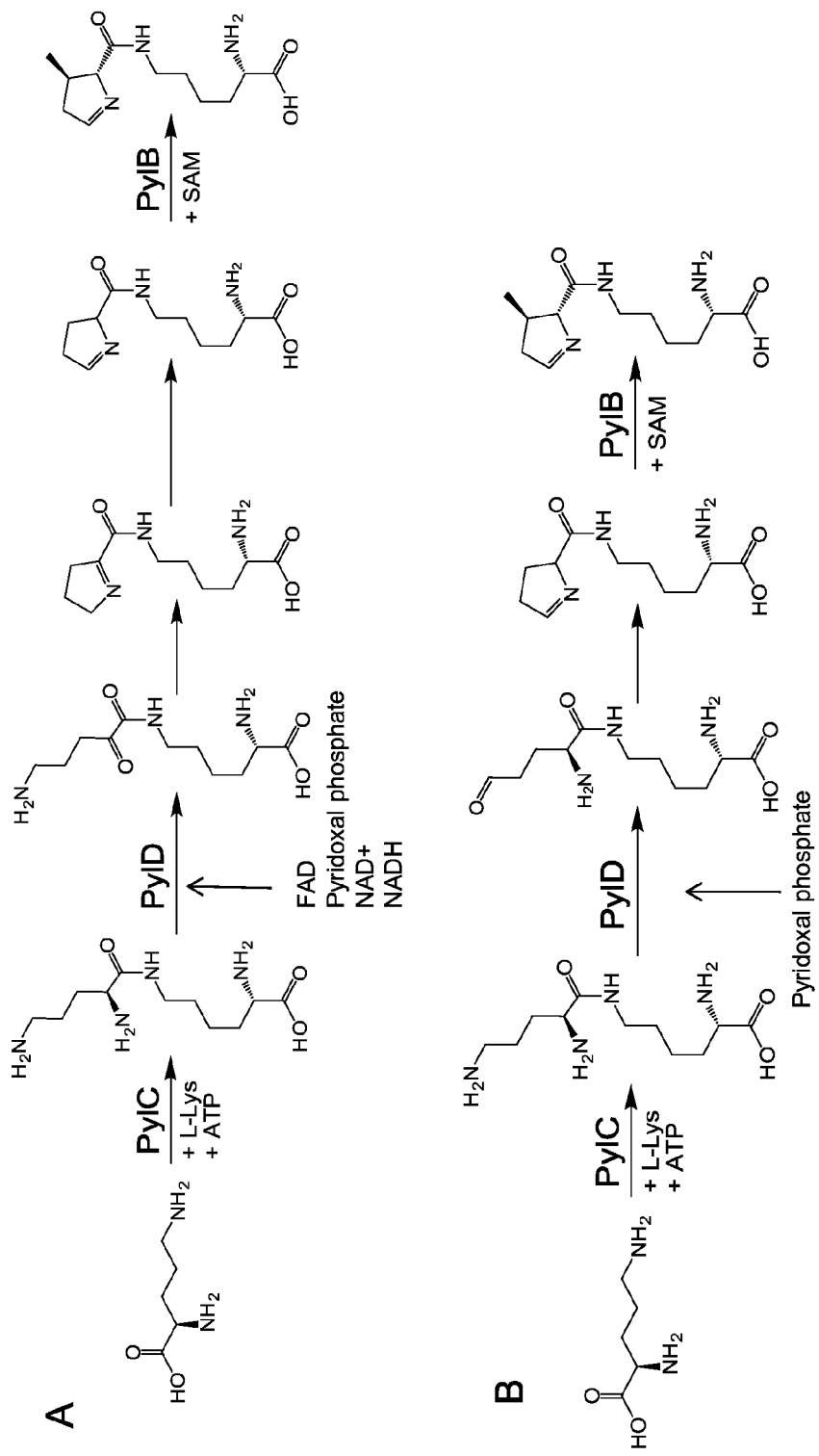
FIG. 16. Potential biosynthetic scheme for PCL (PCL-A) formation.

Incorporation of the precursor (2S)-2-amino-6-((R)-2,5-diaminopentanamido)hexanoic acid (also referred to as Lys-Nε-D-orn) yielded substantial amounts of full-length protein (FIG. 15A, Example 15). In addition, it was found that incorporation of (2S)-2-amino-6-((R)-2,5-diaminopentanamido)hexanoic acid only requires the presence of pylS, pylT and PylD genes (FIG. 15B, Example 15). Taken together, these observations suggest the alternative pathways shown in FIGS. 16A and 16B. These pathways are based on the concept that D-ornithine, with the help of PylC, a putative D-alanyl-D-alanine ligase, is first coupled to the epsilon amino group of L-lysine to form (2S)-2-amino-6-((R)-2,5-diaminopentanamido)hexanoic acid. In FIG. 16A, the (2S)-2-amino-6-((R)-2,5-diaminopentanamido)hexanoic acid intermediate is activated by a D-ornithine:oxygen oxidoreductase (EC 1.4.3.3) or D-amino-transaminase (EC 2.6.1.21) resulting in spontaneous cyclization to form PCL-B. Alternatively, in FIG. 16B the (2S)-2-amino-6-((R)-2,5-diaminopentanamido)hexanoic acid intermediate is activated by a D-ornithine:2-oxoglutarate 5-transaminase (EC 2.6.1.13) resulting in spontaneous cyclization to form PCL-A. Both of the cyclization reactions are similar to that of D-glutamate 5-semialdehyde. Either of the activation steps prior to cyclization could putatively be catalyzed by PylD, the second required enzyme for the biosynthesis of PCL. As shown in FIG. 16, it is proposed that the methylation of PCL-A by PylB completes the biosynthesis of PYL. Note that in case of the pathway in FIG. 16A, this would likely require the presence of another, yet to be discovered Pyl enzyme which forms PCL-A from PCL-B. However, this additional enzyme would not required for the alternative pathway shown in FIG. 16B. PCL-A formed after activation by PylD and spontaneous cyclization could be methylated by PylB directly to form pyrrolysine. Alternatively, any of the intermediates or D-ornithine could be the substrate for methylation by PylB if subsequent enzymes tolerate such modification of the substrate.

Figure 14:
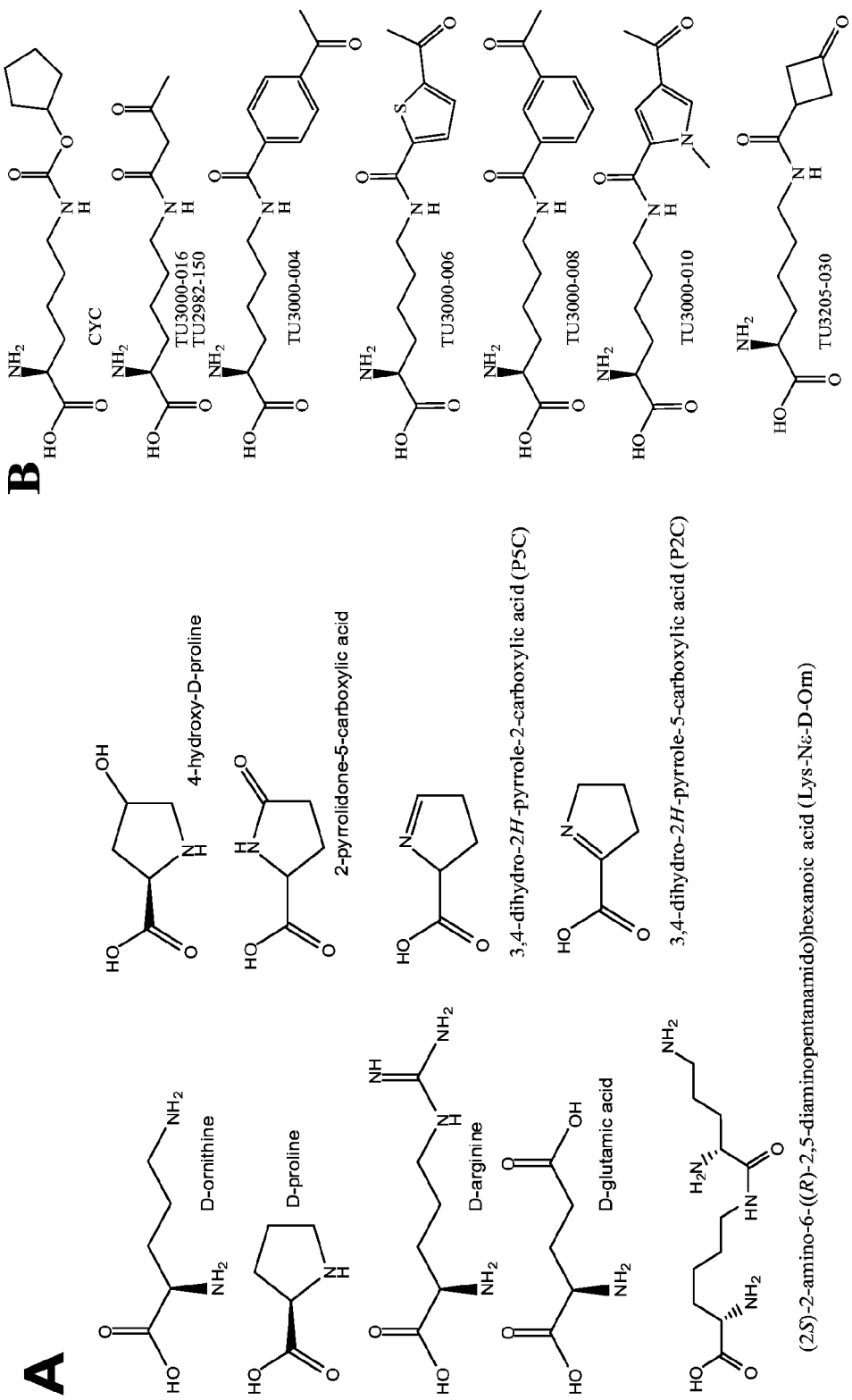
FIG. 14. Potential precursors for PCL biosynthesis (A) and various pyrrolysine analogues (B).

The pyrrolysyl-tRNA synthetase PylS has been shown to accept several pyrrolysine analogues for charging to tRNA$^{Pyl}$. However, such studies also indicated the importance of the pyrrolysine ring C-5 stereocenter for recognition of the synthetase PylS, wherein the D-conformation is required (see, Polycarpo, C. R., Herring, S., Berube, A., Wood, J. L., Soll, D., and Ambrogelly, A., (2006), "Pyrrolysine analogues as substrates for pyrrolysyl-tRNA synthetase," *FEBS Letters*, 580, 6695-700). As provided herein, and consistent with this interpretation, attempts to incorporate various pyrrolysine analogues (FIG. 13), including aromatic five and six-membered ring pyrrolysine analogues, demonstrated that such aromatic five and six-membered ring analogues are not acceptable substrates for PylS (FIG. 14). This is possibly because of the lack of the C-5 chiral center, or in certain cases because of the larger size of the analogues. As indicated, N-ε-cyclopentyloxycarbonyl-L-lysine (CYC), a known substrate for PylS, and the 3-oxobutanoic acid analogue, TU3000-016, were incorporated using the PylT/PylS tRNA/pyrrolysyl-tRNA synthetase pair (FIG. 14). However, analogues evaluated that are similar in size and bulkiness to N-ε-cyclopentyloxycarbonyl-L-lysine (CYC) were not incorporated possibly because they lacked the C-5 stereocenter. Thus, PylS appears to be selective for the chirality at the attachment point of the pyrroline ring. However, synthetic PCL-B was also incorporated with high efficiency suggesting that the sp2, achiral carbon at position C-5 does not in all cases disfavour incorporation. Currently, the low reactivity of synthetic PCL-B with 2-ABA when compared with synthetic PCL-A (Example 44, FIGS. 56 and 58 and the absence of a known enzyme for the PCL-B to PCL-A conversion in FIG. 16A favors the assignment of the incorporated the pyrrolysine analog as PCL-A.

Figure 19:
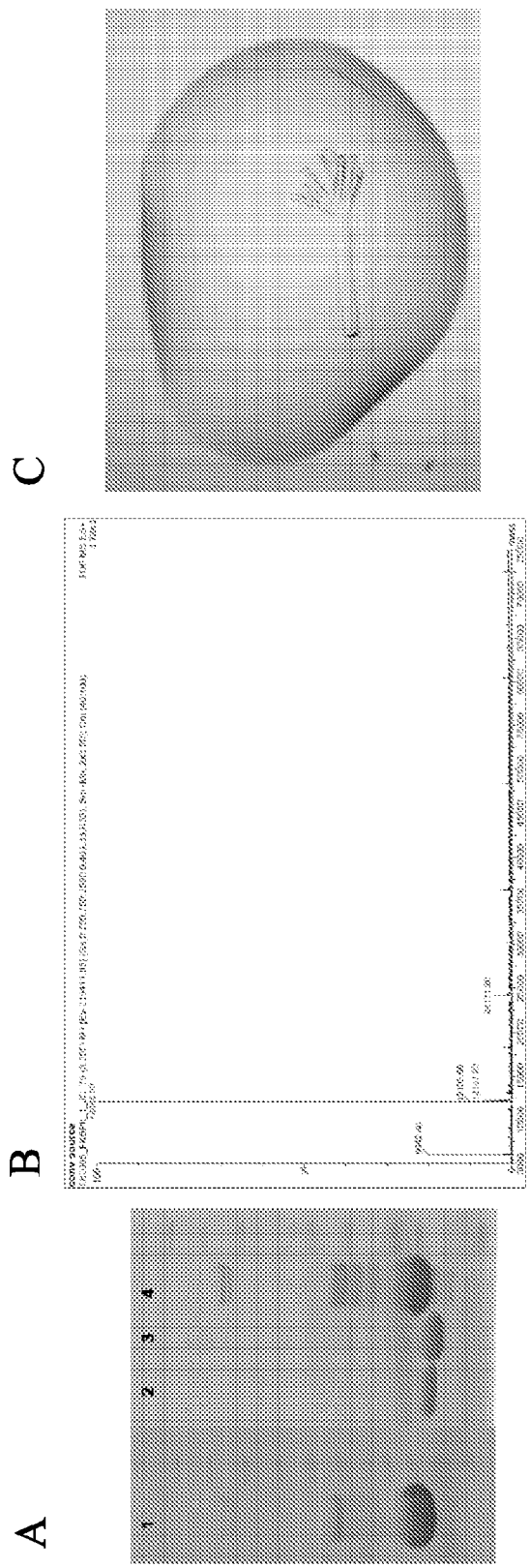
FIG. 19. Site specific incorporation of biosynthetically generated PCL at single TAG encoded sites (one site) in FKBP-12.
Figure 20:
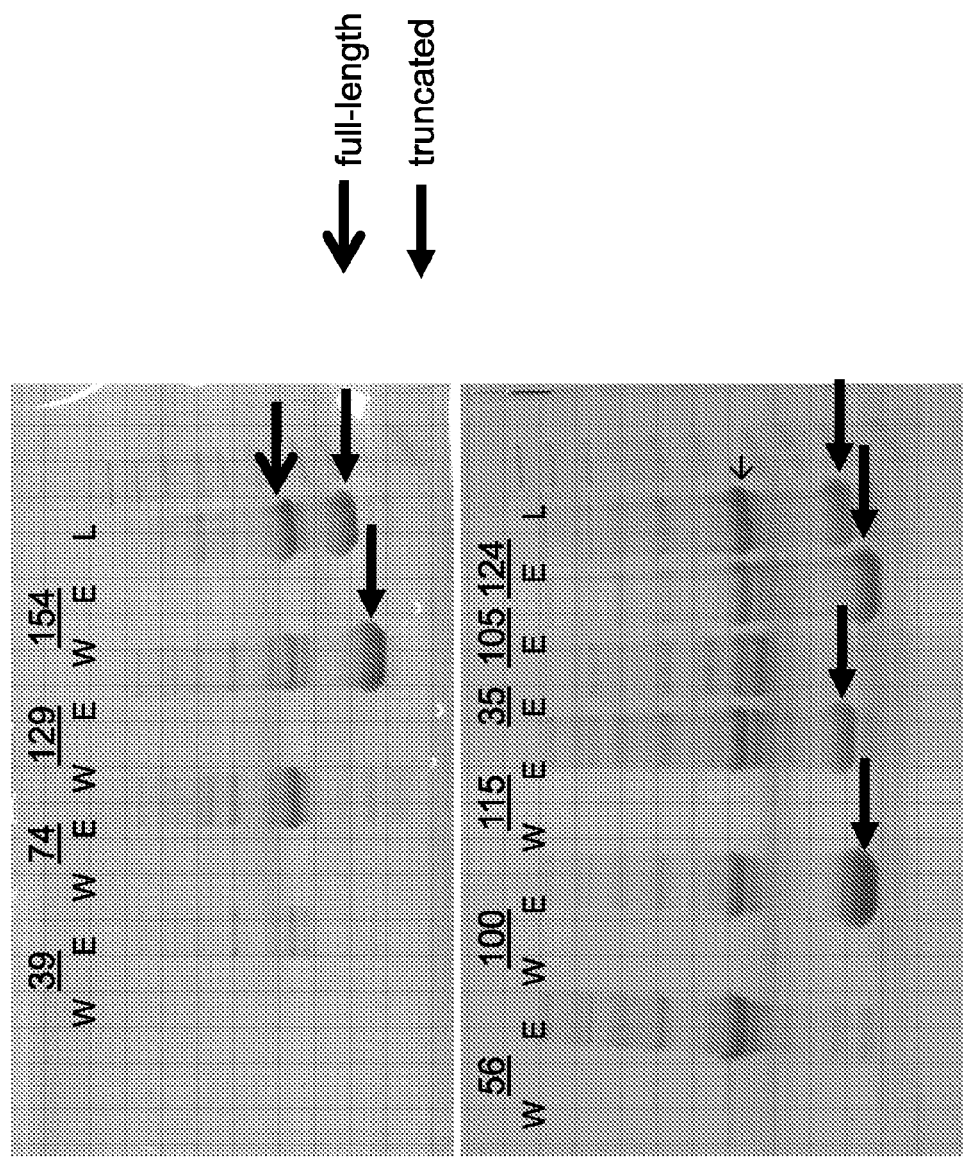
FIG. 20. Site specific incorporation of biosynthetically generated PCL at single TAG encoded sites (twenty sites) in fibroblast growth factor 21 (FGF21). SDS-PAGE shows incorporation of PCL at multiple sites into FGF21.

As provided herein, in certain embodiments it was found that when D-ornithine is added to the growth medium as a precursor the use of the natural genes pylB, pylC and pylD for the biosynthesis of pyrrolysine in mammalian cells (Examples 2) and bacterial cells (Examples 8, 9 and 10) resulted in the generation of PCL rather than pyrrolysine. In addition, evaluation of the biosynthesis of PCL using either the natural genes pylB and pylC, the natural genes pylB and pylD or the natural genes pylC and pylD, resulted in generation of PCL, only when pylC and pylD gene products were present. This suggests that the gene product of pylB is not needed in the biosynthesis of PCL, when D-ornithine is added to the growth medium as a precursor (FIG. 13C, see Example 4). This is supported by the incorporation of PCL into three model proteins, hRBP4 (FIG. 6, see Example 2), mIgG1 Fc domain (FIG. 17A, see Example 5) and mEPO (FIG. 17B, see Example 6) which was accomplished without cotransfecting the gene pylB into mammalian cells. In *Escherichia coli*, FAS-TE, FGF21 and FKBP are examples wherein using the natural genes pylB, pylC and pylD, resulted in generation of PCL exclusively (FIGS. 18B, 19 and 20, Examples 8, 9 and 10).

The biosynthesis of PCL requires the presence of biosynthetic genes pylC and pylD, but not pylB, to the host cells. In the biosynthesis of pyrrolysine within *Methanosarcina*, it has been suggested that PylD contains the NADH-binding domain of dehydrogenases and thereby generates D-1-pyrroline-5-carboxylate from D-proline. However, adding D-proline to the growth media does not result in significant PCL incorporation (FIG. 13). Addition of 3,4-dihydro-2H-pyrrole-5-carboxylate (also referred to herein as 1-pyrroline-2-carboxylate; P2C) and D-1-pyrroline-5-carboxylate (P5C) to the growth media also fails to produce full-length proteins while (2S)-2-amino-6-((R)-2,5-diaminopentanamido)hexanoic acid yields PCL containing protein. PylC has sequence homology with D-alanyl-D-alanine ligases and in the biosynthesis of PCL or pyrrolysine, could catalyze the attachment of D-ornithine to the epsilon-amino group of lysine to give (2S)-2-amino-6-((R)-2,5-diaminopentanamido)hexanoic acid. Thus, it is postulated herein and without being bound by any theory, the biosynthesis of PCL from D-ornithine within mammalian or *Escherichia coli* cells likely involves conversion of D-ornithine to (2S)-2-amino-6-((R)-2,5-diaminopentanamido)hexanoic acid by PylC (FIG. 16B). PylD is likely involved in the activation of (2S)-2-amino-6-((R)-2,5-diaminopentanamido)hexanoic acid into the semialdeyhdye ((S)-2-amino-6-((R)-2-amino-5-oxopentanamido)hexanoic acid) that spontaneously cyclizes to PCL-A as shown in FIG. 16B. Alternatively, PCL-B would form spontaneously if PylD has D-amino-acid transaminase or D-ornithine:oxygen oxidoreductase like activity (FIG. 16A).

Figure 21:
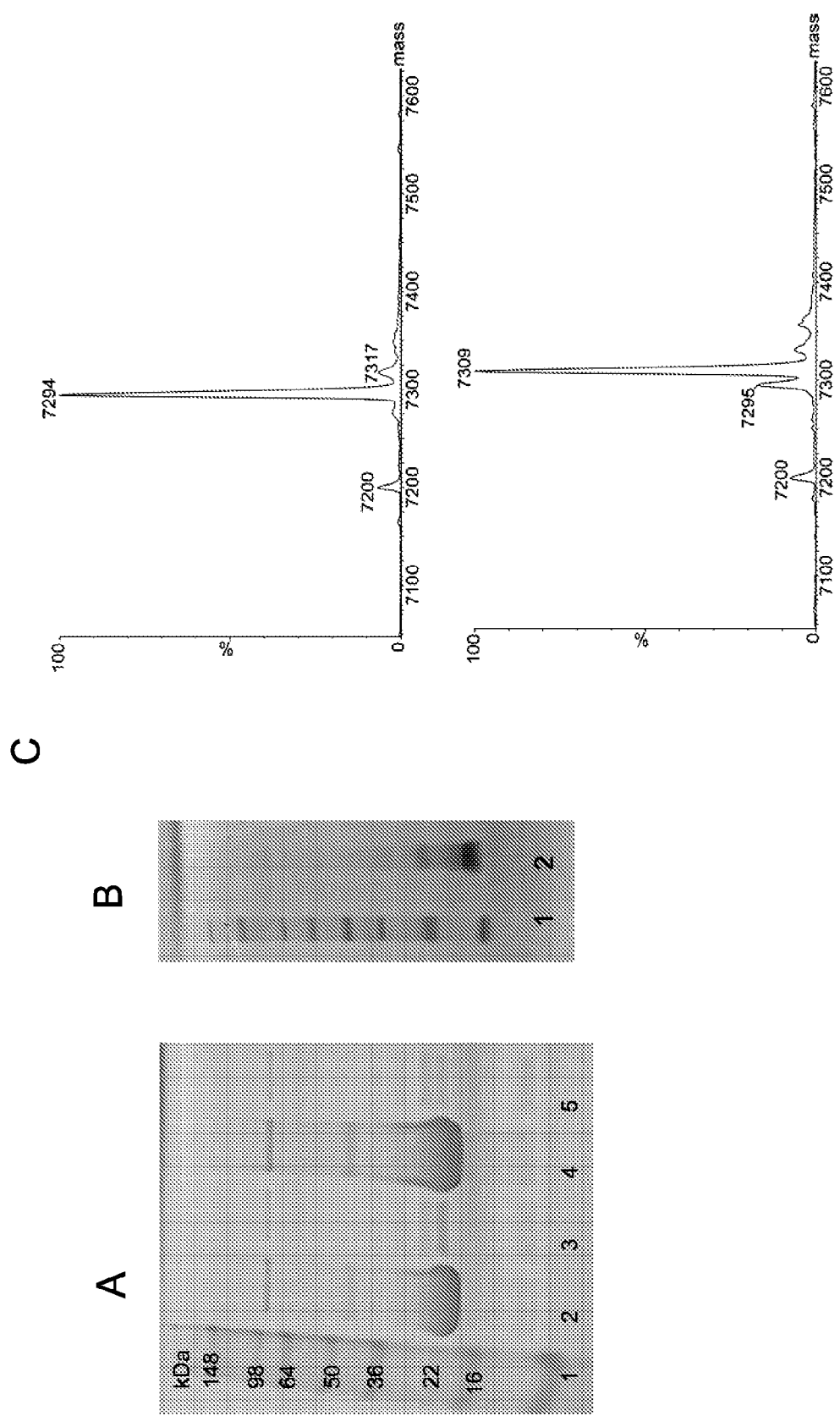
FIG. 21.

In other embodiments, expression of mouse EGF and mouse TNF-α in *Escherichia coli* (FIG. 21 and Examples 13 and 14) resulted in protein mixtures with either PCL or pyrrolysine incorporated at the TAG site. Incorporation of pyrrolysine was dependent on the presence of the pylB gene, whereas homogenous preparations of PCL containing proteins were observed in the absence of pylB (FIG. 21 and Examples 11 and 12). This therefore experimentally verifies PylB as the methyltransferase in the biosynthesis of pyrrolysine. Even in the presence of the pylB gene, the relative amounts of PCL and pyrrolysine containing proteins varied from fermentation to fermentation with PCL protein typically being more prominent. These observations suggest that the methyltransferase activity or the methyl-donating substrate or required co-factors are limiting for efficient pyrrolysine biosynthesis in Escherichia coli and mammalian cells.

In addition, the gene product of pylB may not be expressed efficiently. Therefore, in certain embodiments, modified pylB genes are used in the biosynthesis of pyrrolysine or other pyrrolysine analogues. Thus, provided herein are methods for the biosynthesis of pyrrolysine, PCL and other pyrrolysine analogues in Escherichia coli, mammalian and other host cells wherein one or more of the pylB, pylC and pylD genes are modified. Such modifications may include using homologous genes from other organisms, including but not limited to other species of Methanosarcinae, or mutated genes. In certain embodiments, site-directed mutagenesis is used, while in other embodiments random mutagenesis combined with selection is used. Such methods also include the addition of the DNA of the desired protein and the inclusion of the pylT and pylS genes to incorporate the pyrrolysine, PCL or pyrrolysine analogues into the protein. In a certain embodiment, a modified pylB gene, the natural pylC, pylD, pylT and pylS genes are used to biosynthetically generate and incorporate pyrrolysine. In other embodiments modified pylB and pylC genes, the natural pylD, pylT and pylS genes are used to biosynthetically generate and incorporate a pyrrolysine analogue other than PCL. In other embodiments modified pylB and pylD genes, the natural pylC, pylT and pylS genes are used to biosynthetically generate and incorporate a pyrrolysine analogue other than PCL. In other embodiments pylT, pylS, pylB, pylC and pylD genes are optionally modified, to improve incorporation of pyrrolysine, PCL or other pyrrolysine analogues into proteins.

In addition, for certain embodiments, the formation of intermediates in the biosynthesis of pyrrolysine, PCL and/or other pyrrolysine analogues from D-ornithine or the biosynthesis of pyrrolysine may be limited by the function of host enzymes and proteins. In certain embodiments, low activity or concentration of one or more host enzymes may be limiting the formation of intermediates required in the biosynthesis of pyrrolysine, PCL or other pyrrolysine analogues. In certain embodiments, the activity of host enzymes may divert the intermediates from the pathway leading to pyrrolysine, PCL or other pyrrolysine analogues to other metabolic pathways, or may be inhibiting the formation of such intermediates. Thus, provided herein are methods for the biosynthesis of pyrrolysine, PCL and other pyrrolysine analogues in Escherichia coli, mammalian or other host cells wherein one or more host enzyme is modified. Such methods include, but are not limited to, the overexpression, activation, suppression or inhibition of such host enzyme by genetic or chemical means, the addition of the DNA encoding such host enzymes, the addition of silencing RNA (siRNA) to suppress mRNA translation, and the addition of cofactors required for the formation of said intermediates from D-ornithine.

Figure 17:
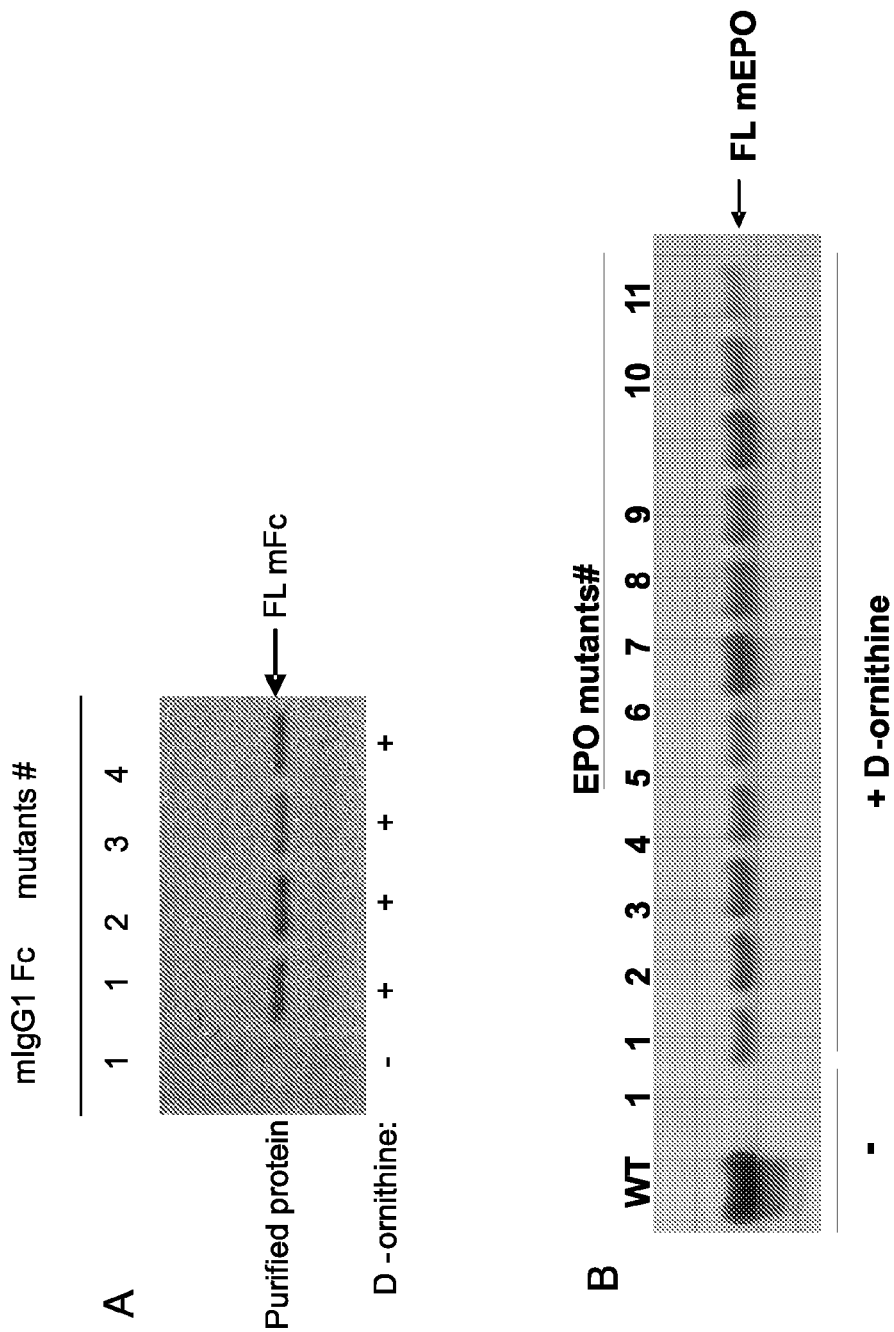
FIG. 17A. Site specific incorporation of biosynthetically generated PCL at single TAG encoded sites (four sites) in the Fc domain of mouse IgG1.
FIG. 17B. Site specific incorporation of biosynthetically generated PCL at single TAG encoded sites (eleven sites) in erythropoietin (EPO) as detected by SDS-PAGE.

The site specific incorporation of biosynthetically generated PCL at TAG encoded sites has also been accomplished at four sites in the Fc domain of mouse IgG1 (see Example 5 and FIG. 17A) and eleven sites in erythropoietin (EPO) (see Example 6 and FIG. 17B). PCL incorporation for both sets of proteins was achieved in HEK293F mammalian cells transfected with the natural genes pylT, pylS, pylC and pylD and using D-ornithine added as precursor to the media. FIG. 17A is the SDS-PAGE showing the four full length (FL) mFc proteins, wherein PCL has been incorporated into four sites of mouse IgG1 Fc domain using HEK293F cells co-transfected with the respective TAG mutant constructs of mFc, pCMVpylT, pCMVpylS, pCMVpylC and pCMVpylD (FIG. 4A) and the cells grown in the presence of D-ornithine. FIG. 17B is the SDS-PAGE showing eleven full length (FL) mEPO proteins, wherein PCL has been incorporated into eleven sites of mouse EPO using HEK293F cells co-transfected with TAG mutant constructs of mEPO, pCMVpylT, pCMVpylS, pCMVpylC and pCMVpylD and the cells grown in the presence of D-ornithine.

Site specific incorporation of biosynthetically generated PCL at TAG encoded sites has also been accomplished using Escherichia coli cells (see Example 7). A plasmid, pARA-pylSTBCD, encoding pylB, pylC, pylD, pylS and pylT was constructed (FIG. 6A). PCL-A (or PCL-B) incorporation at two sites into the thioesterase domain of human fatty acid synthetase (FAS-TE) (see Examples 8 and FIG. 18), one site of FKBP-12 (see Examples 9 and FIG. 19) and 20 sites of fibroblast growth factor 21 (FGF21) (see Examples 10 and FIG. 20) were accomplished by transforming Escherichia coli cells with pARA-pylSTBCD and a second expression plasmid with the gene for the protein of interest and adding D-ornithine to the growth media during protein expression.

Figure 18:
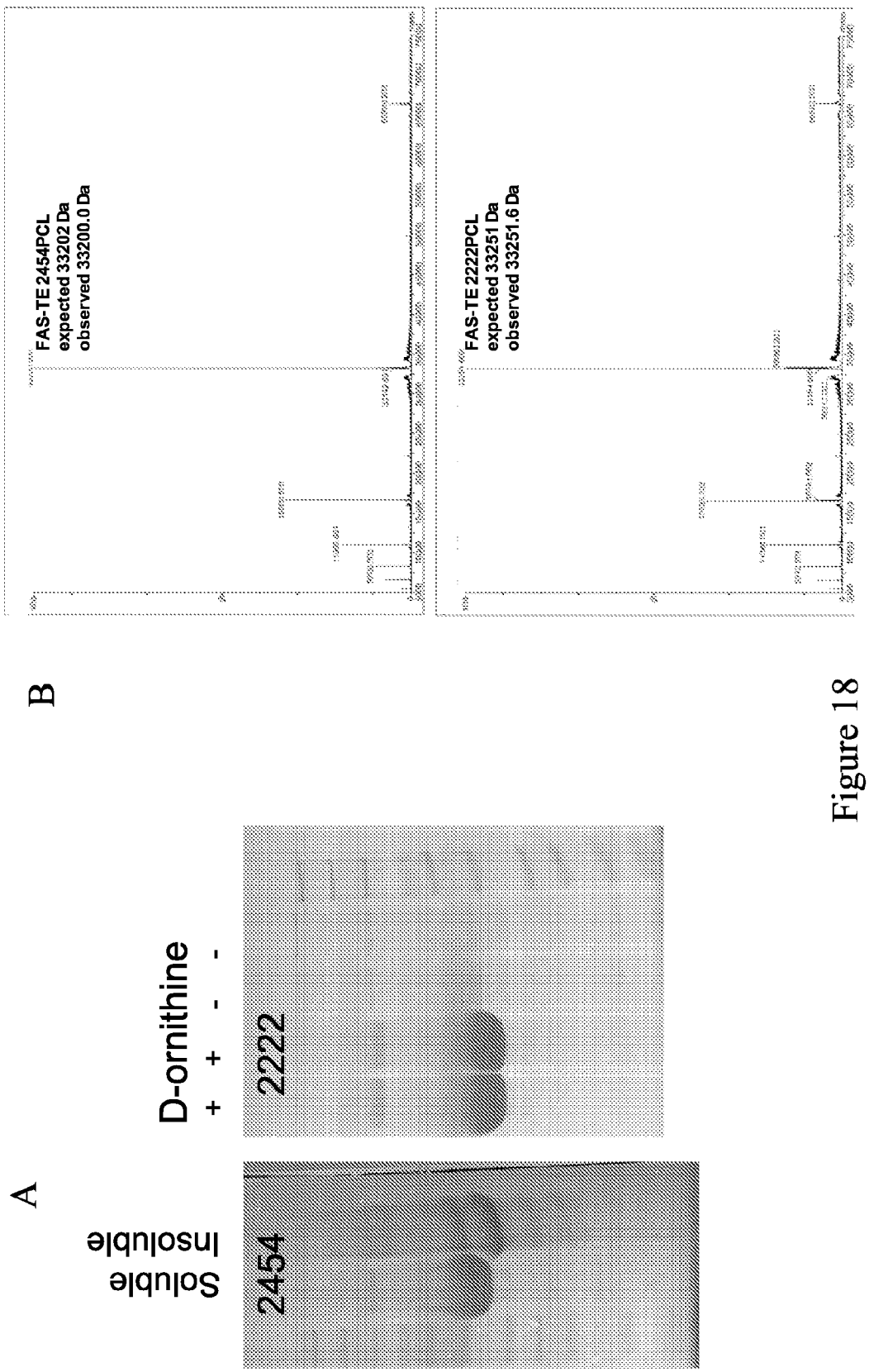
FIG. 18. Site specific incorporation of biosynthetically generated PCL at single TAG encoded sites (two sites) in the thioesterase domain of human fatty acid synthetase (FASTE).

FIG. 18 shows the SDS-PAGE and the mass spectra for PCL incorporation at two sites in the thioesterase of human fatty acid synthetase (FAS-TE). FAS-TE Tyr2454PCL was expressed, and both the soluble and insoluble protein fractions were purified by Ni-NTA. FAS-TE Leu2222PCL/Leu2223Ile was expressed with and without D-ornithine in duplicate cultures. Ni-NTA elutions are shown on the gels. The mass obtained for each is consistent with that expected. FIG. 19 shows the SDS-PAGE and the mass spectra for PCL incorporation at one site of FKBP-12. The mass obtained (12085.6 Da) is consistent with that expected (12084 Da) for single site incorporation of PCL. Also, shown in FIG. 19 is a crystal of FKBP12-Ile90PCL. FIG. 20 shows a SDS-PAGE showing incorporation of PCL at multiple sites into FGF21.

The incorporation of pyrrolysine (Pyl) and PCL was found to be dependent on the presence of the pylB gene in the expression system. FIG. 21A shows SDS-PAGE analysis of Pyl- or PCL-incorporation into mTNF-α with the codon of Gln21 (CAA) mutated to a TAG stop codon (Example 13). Lanes 2 and 4 show similar protein expression levels in the presence and absence of pylB, respectively when D-ornithine is present. Lane 3 (pylB present) and 5 (pylB absent) show that no protein is expressed in the absence of D-ornithine.

In addition, mEGF Tyr10TAG was expressed in the presence of the pylB, pylC, pylD, pylT and pylS genes in Escherichia coli using D-ornithine as precursor (Example 14). Intact MS spectra (FIG. 21C, bottom) suggested a mixture of proteins with PYL and PCL incorporated. The MS peak of the Pyl-containing mEGF at 7309 Da is approximately 6 times as large as that of the PCL-containing mEGF at 7295 Da. The incorporation of the PYL and PCL at the TAG position was verified by tandem MS spectra of the N-terminal peptide MNSYPGCPSS(PCL)DGYCLNGGVCM (SEQ ID NO:32) and MNSYPGCPSS(Pyl)DGYCLNGGVCM (SEQ ID NO:33) of mEGF Tyr10TAG mutant protein. Quantitation from relative precursor mass abundance of different peptides reveals that PYL is 5 to 10 times more abundant than PCL, which is in approximate agreement with intact mass measurements (FIG. 21C, bottom). When mEGF Tyr10TAG was expressed in the presence of pylB, the intact MS spectra (FIG. 21C, top) suggested a only PCL incorporation.

Similarly, when mTNF-α Gln21TAG was expressed in the presence of pylB, pylC, pylD, pylT and pylS genes in

*Escherichia coli* using D-ornithine tandem MS verified PYL and PCL incorporation in the peptide NH(Pyl)VE-EQLEWLSQR (SEQ ID NO:34) and NH(PCL)VE-EQLEWLSQR (SEQ ID NO:35) of mTNF Gln21PCL. In contrast to mEGF Tyr10TAG, quantitation from relative precursor mass abundance of different peptides identified with tandem MS reveals that PCL is 7 times more abundant than PYL in the mTNF-α Gln21TAG protein. The mTNF-α Gln21TAG was expressed in the absence of pylB gene, quantitation from relative precursor mass abundance of different peptides in tandem MS measurements shows only PCL protein within the dynamic range of the experiment. These experiments clearly indicate that PYL incorporation depends strictly on the presence of pylB, the putative methyltransferase in the biosynthesis of Pyl. The relative ratios of PCL and PYL incorporated into proteins in the presence of the pylB gene, however appear to vary from protein to protein and from fermentation experiment to experiment and therefore likely depend on the type of expression vector, the growth conditions and/or other properties of the host cell culture.

Provided herein are amino acids having the structure of Formula (V) and Formula (VI)

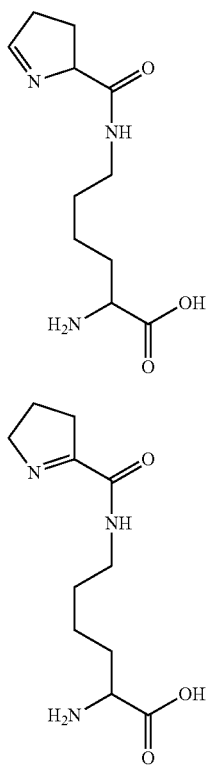

wherein such compounds of Formula (V) or Formula (VI) are biosynthetically generated within a cell comprising a pylB gene, a pylC gene, and a pylD gene, and the cell is in contact with a growth medium comprising a precursor. While in other embodiments, such compounds of Formula (V) or Formula (VI) are biosynthetically generated within a cell comprising a pylC gene and a pylD gene and the cell is in contact with a growth medium comprising a precursor. In certain embodiments of such biosynthesis, the precursor is ornithine or arginine. In certain embodiments of such biosynthesis, the precursor is D-ornithine or D-arginine. In certain embodiments of such biosynthesis, the precursor is (2S)-2-amino-6-((R)-2,5-diaminopentanamido)hexanoic acid. In other embodiments of such biosynthesis, the precursor is (2S)-2-amino-6-(2,5-diaminopentanamido)hexanoic acid.

Also provided herein, the cells wherein the compounds of Formula (V) and (VI) are biosynthesized, further comprise a pylS gene and a pylT gene and the compounds of Formula (V) or Formula (VI) are incorporated into a protein within the cell by an aminoacyl tRNA synthetase and a tRNA which recognizes at least one selector codon of a mRNA in the cell. Such an aminoacyl tRNA synthetase is a gene product of the pylS gene and the tRNA is a gene product of the pylT gene. In certain embodiments, such compounds of Formula (V) or Formula (VI) are incorporated into a protein within the cell by an orthogonal tRNA (O-tRNA) and an orthogonal aminoacyl tRNA synthetase (O-RS), wherein the O-RS aminoacylates the O-tRNA with the compound of Formula (V) or Formula (VI) and the O-tRNA recognized at least one selector codon of a mRNA in the cell.

The selector codon for the incorporation of pyrrolysine, PCL and/or other pyrrolysine analogues, including compounds of Formula (V) and Formula (VI), is an amber codon (TAG).

The cells used for the biosynthesis and/or incorporation of pyrrolysine, PCL and/or other pyrrolysine analogues, including compounds of Formula (V) and Formula (VI), are either prokaryotic cells or eukaryotic cells. In certain embodiments, the prokaryotic cells include, but are not limited to, *Escherichia coli*, *Mycobacterium smegmatis*, *Lactococcus lactis* and *Bacillus subtilis* cells. In other embodiments the eukaryotic cells include, but are not limited to, mammalian cells, yeast cells, fungal cells, plant cells or insect cells. Such mammalian cells include, but are not limited to, human embryonic kidney (HEK293F) cells, human epitheloid carcinoma (HeLa and GH3) cells, monkey kidney (COS) cells, rat C6 glioma cells, baby hamster kidney (BHK-21) cells and chinese hamster ovary (CHO) cells. In certain embodiments, the yeast cells include, but are not limited to, *Saccharomyces cerevisiae* and *Pichia pastoris* cells. In other embodiments, the insect cells include, but are not limited to, *Spodoptera frugiperda* sf9 and sf21 cells, *Trichoplusia ni* (BTI TN-5B1-4 or High-Five™) cells and *Mammestra brassicae* cells.

In another aspect provided herein, pyrrolysine, PCL and/or other pyrrolysine analogues, including compounds of Formula (V) and Formula (VI) are biosynthesized in feeder cells in contact with a growth medium comprising a precursor, and the feeder cells contain a pylB gene, a pylC gene and a pylD gene. In other embodiments, pyrrolysine, PCL and/or pyrrolysine analogues, including compounds of Formula (V) and Formula (VI), are biosynthesized in feeder cells in contact with a growth medium comprising a precursor, and the feeder cells contain a pylC gene and a pylD gene. Such biosynthesized pyrrolysine, PCL and/or other pyrrolysine analogues, including compounds of Formula (V) and Formula (VI), are secreted from the feeder cells into the growth medium whereby they are taken in by a second cell and subsequently incorporated into a protein synthesized within the second cell. Such second cells contain a pylS gene and a pylT gene. The pyrrolysine, PCL and/or other pyrrolysine analogues, including compounds of Formula (V) and Formula (VI), are incorporated into the protein within the second cell by an aminoacyl tRNA synthetase and a tRNA which recognizes at least one selector codon of a mRNA in the second cell. Such aminoacyl tRNA synthetase is a gene product of the pylS gene and the tRNA is a gene product of the pylT gene. In certain embodiments, such compounds of Formula (V) or Formula (VI) are incorporated into the protein within the second cell by an orthogonal tRNA (O-tRNA) and an orthogonal aminoacyl tRNA synthetase (O-RS), wherein the O-RS aminoacylates the O-tRNA with the compound of Formula (V) or Formula (VI) and the O-tRNA recognized at least one selector codon of a mRNA in the second cell.

In certain embodiments of such biosynthesis using feeder cells, the precursor is ornithine or arginine. In certain embodiments of such biosynthesis, the precursor is D-ornithine or D-arginine. In certain embodiments, the precursor is (2S)-2-amino-6-(2,5-diaminopentanamido)hexanoic acid. In certain embodiments, the precursor is (2S)-2-amino-6-((R)-2,5-diaminopentanamido)hexanoic acid.

The selector codon for the incorporation of pyrrolysine, PCL and/or other pyrrolysine analogues, including compounds of Formula (V) and Formula (VI) biosynthesized using feeder cells, is an amber codon (TAG).

In certain embodiments, the second cell is the same type of cell as the feeder cell, while in other embodiments, the second cell is a different cell type than the feeder cell. The cells used for such biosynthesis and/or incorporation of pyrrolysine, PCL and/or other pyrrolysine analogues, including compounds of Formula (V) and Formula (VI), are either prokaryotic cells or eukaryotic cells. In certain embodiments, the prokaryotic cells include, but are not limited to, *Escherichia coli, Mycobacterium smegmatis, Lactococcus lactis* and *Bacillus subtilis* cells. In other embodiments the eukaryotic cells include, but are not limited to, mammalian cells, yeast cells, fungal cells, plant cells or insect cells. Such mammalian cells include, but are not limited to, human embryonic kidney (HEK293F) cells, human epitheloid carcinoma (HeLa and GH3) cells, monkey kidney (COS) cells, rat C6 glioma cells, baby hamster kidney (BHK-21) cells and chinese hamster ovary (CHO) cells. In certain embodiments, the yeast cells include, but are not limited to, *Saccharomyces cerevisiae* and *Pichia pastoris* cells. In other embodiments, the insect cells include, but are not limited to, *Spodoptera frugiperda* sf9 and sf21 cells, *Trichoplusia ni* (BTI TN-5B1-4 or High-Five™) cells and *Mammestra brassicae* cells.

In another aspect provided herein, pyrrolysine, PCL and/or other pyrrolysine analogs, including compounds of Formula (V) and Formula (VI) are biosynthesized in feeder cells and such biosynthesized pyrrolysine and/or PCL, including compounds of Formula (V) and Formula (VI) are then purified from the feeder cell culture and added to the growth media of a second culture containing a second cell. Such purified pyrrolysine, PCL and/or other pyrrolysine analogs are then incorporated into a protein synthesized within the second cell. In certain embodiments, the pyrrolysine, PCL and/or other pyrrolysine analogs, including compounds of Formula (V) and Formula (VI) are biosynthesized in feeder cells in contact with a growth medium comprising a precursor, and the feeder cells contain a pylB gene, a pylC gene and a pylD gene. In other embodiments, pyrrolysine, PCL and/or other pyrrolysine analogs, including compounds of Formula (V) and Formula (VI), are biosynthesized in feeder cells in contact with a growth medium comprising a precursor, and the feeder cells contain a pylC gene and a pylD gene. The second cells used in this aspect contain a pylS gene and a pylT gene. The pyrrolysine, PCL and/or other pyrrolysine analogs, including compounds of Formula (V) and Formula (VI), are incorporated into the protein within the second cell by an aminoacyl tRNA synthetase and a tRNA which recognizes at least one selector codon of a mRNA in the second cell. Such aminoacyl tRNA synthetase is a gene product of the pylS gene and the tRNA is a gene product of the pylT gene. In certain embodiments, such compounds of Formula (V) or Formula (VI) are incorporated into the protein within the second cell by an orthogonal tRNA (O-tRNA) and an orthogonal aminoacyl tRNA synthetase (O-RS), wherein the O-RS aminoacylates the O-tRNA with the compound of Formula (V) or Formula (VI) and the O-tRNA recognized at least one selector codon of a mRNA in the second cell.

In certain embodiments of such biosynthesis using feeder cells, the precursor is ornithine or arginine. In certain embodiments of such biosynthesis, the precursor is D-ornithine or D-arginine. In certain embodiments, the precursor is (2S)-2-amino-6-(2,5-diaminopentanamido)hexanoic acid. In certain embodiments, the precursor is (2S)-2-amino-6-((R)-2,5-diaminopentanamido)hexanoic acid.

The selector codon for the incorporation of pyrrolysine, PCL and/or other pyrrolysine analogs, including compounds of Formula (V) and Formula (VI) biosynthesized using feeder cells, is an amber codon (TAG).

In certain embodiments, the second cell is the same type of cell as the the feeder cell, while in other embodiments, the second cell is a different cell type than the feeder cell. The cells used for such biosynthesis and/or incorporation of pyrrolysine, PCL and/or other pyrrolysine analogs, including compounds of Formula (V) and Formula (VI), are either prokaryotic cells or eukaryotic cells. In certain embodiments, the prokaryotic cells include, but are not limited to, *Escherichia coli, Mycobacterium smegmatis, Lactococcus lactis* and *Bacillus subtilis* cells. In other embodiments the eukaryotic cells include, but are not limited to, mammalian cells, yeast cells, fungal cells, plant cells or insect cells. Such mammalian cells include, but are not limited to, human embryonic kidney (HEK293F) cells, human epitheloid carcinoma (HeLa and GH3) cells, monkey kidney (COS) cells, rat C6 glioma cells, baby hamster kidney (BHK-21) cells and chinese hamster ovary (CHO) cells. In certain embodiments, the yeast cells include, but are not limited to, *Saccharomyces cerevisiae* and *Pichia pastoris* cells. In other embodiments, the insect cells include, but are not limited to, *Spodoptera frugiperda* sf9 and sf21 cells, *Trichoplusia ni* (BTI TN-5B1-4 or High-Five™) cells and *Mammestra brassicae* cells.

Also provided herein are amino acids having the structure of Formula (VII);

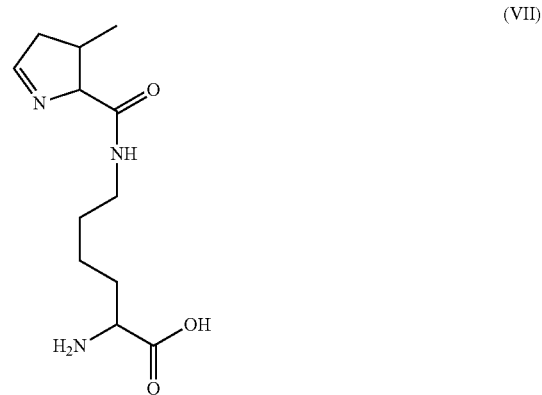 [SMILES: CC1CC=NC1C(=O)NCCCCC(N)C(=O)O]

(VII)

wherein the compound of Formula (VII), or isomers or tautomers thereof, is biosynthetically generated within a cell containing a pylB gene, a pylC gene, and a pylD gene, and the cell is in contact with a growth medium containing D-ornithine or D-arginine or (2S)-2-amino-6-((R)-2,5-diaminopentanamido)hexanoic acid or 2,5-diamino-3-methylpentanoic acid or (2S)-2-amino-6-(2,5-diaminopentanamido)hexanoic acid. While in other embodiments, such a compound of Formula (VII) is biosynthetically generated within a cell containing a pylC gene and a pylD gene and the cell is in contact with a growth medium containing 2,5-diamino-3-methylpentanoic acid. In certain embodiments, the cell is in contact with a growth medium comprising D-2,5-diamino-3-methylpentanoic acid. In certain embodiments the 2,5-diamino-3-methylpentanoic acid is (2R,3S)-2,5-diamino-3-methylpentanoic acid. In certain embodiments the 2,5-diamino-3-methylpentanoic acid is (2R,3R)-2,5-diamino-3-methylpentanoic acid.

The cells wherein the compound of Formula (VII) is biosynthetically generated, further comprise a pylS gene and a pylT gene and the compound of Formula (VII) is incorporated into a protein within the cell by an aminoacyl tRNA synthetase and a tRNA which recognizes at least one selector codon of a mRNA in the cell. Such aminoacyl tRNA synthetase is a gene product of the pylS gene and the tRNA is a gene product of the pylT gene. In certain embodiments, such compound of Formula (VII) is incorporated into a protein within the cell by an orthogonal tRNA (O-tRNA) and an orthogonal aminoacyl tRNA synthetase (O-RS), wherein the O-RS aminoacylates the O-tRNA with the compound of Formula (VII) and the O-tRNA recognized at least one selector codon of a mRNA in the cell.

The selector codon for the incorporation of a compound of Formula (VII) is an amber codon (TAG).

The cells used for the biosynthesis and/or incorporation of a compound of Formula (VII), are either prokaryotic cells or eukaryotic cells. In certain embodiments, the prokaryotic cells include, but are not limited to, *Escherichia coli, Mycobacterium smegmatis, Lactococcus lactis* and *Bacillus subtilis* cells. In other embodiments the eukaryotic cells include, but are not limited to, mammalian cells, yeast cells, fungal cells, plant cells or insect cells. Such mammalian cells include, but are not limited to, human embryonic kidney (HEK293F) cells, human epitheloid carcinoma (HeLa and GH3) cells, monkey kidney (COS) cells, rat C6 glioma cells, baby hamster kidney (BHK-21) cells and chinese hamster ovary (CHO) cells. In certain embodiments, the yeast cells include, but are not limited to, *Saccharomyces cerevisiae* and *Pichia pastoris* cells. In other embodiments, the insect cells include, but are not limited to, *Spodoptera frugiperda* sf9 and sf21 cells, *Trichoplusia ni* (BTI TN-5B1-4 or High-Five™) cells and *Mammestra brassicae* cells.

In certain embodiments, one or more pyrrolysine, PCL and/or other pyrrolysine analogs are incorporated into proteins, polypeptides and/or peptides using the methods provides herein, and such pyrrolysine and/or PCL are derivatized using the methods provides herein.

Derivatization of PCL and Pyrrolysine

Provided herein are proteins, polypeptides or peptides having the structure according to Formula (I):

$$R_1\text{-}(AA)_n\text{-}R_2 \tag{I}$$

wherein:
$R_1$ is H or an amino terminus modification group;
$R_2$ is OH or a carboxy terminus modification group;
n is an integer from 1 to 5000;
each AA is independently selected an amino acid residue, a moiety having the structure of Formula (A-1) and a moiety having the structure of Formula (B-1);

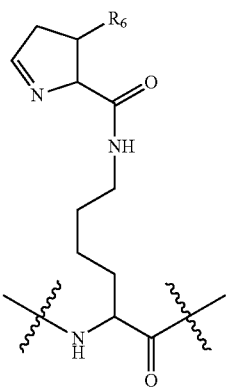

(A-1)

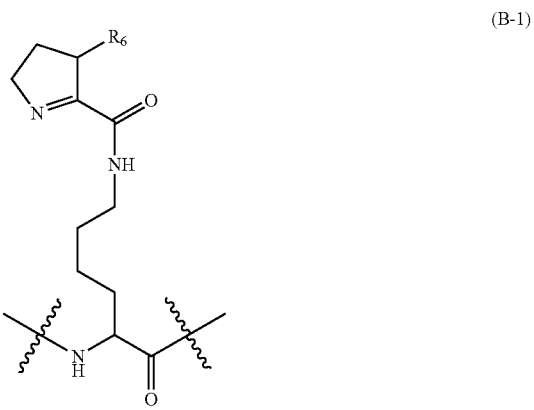

(B-1)

where $R_6$ is H or $C_1$ alkyl and at least one AA is a pyrrolysine or pyrrolysine analogue having the structure of Formula (A-1) or Formula (B-1), or isomers thereof.

In certain embodiments of such compounds of Formula (I), $R_6$ is H and the moiety having the structure of Formula (A-1) and a moiety having the structure of Formula (B-1) have the structure of Formula (A-2) and Formula (B-2), respectively, or isomers thereof;

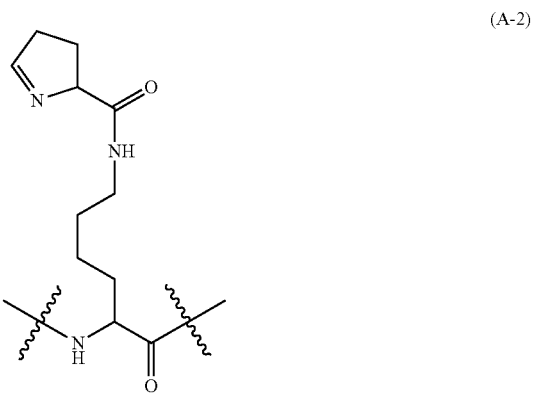

(A-2)

-continued (B-2)

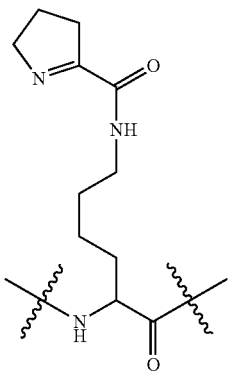

Thus, also provided herein are proteins, polypeptides or peptides having the structure according to Formula (I):

$$R_1\text{-}(AA)_n\text{-}R_2 \qquad (I)$$

wherein:
$R_1$ is H or an amino terminus modification group;
$R_2$ is OH or a carboxy terminus modification group;
n is an integer from 1 to 5000;
each AA is independently selected an amino acid residue, a moiety having the structure of Formula (A-2) and a moiety having the structure of Formula (B-2);
and at least one AA is a pyrrolysine or pyrrolysine analogue having the structure of Formula (A-2) or Formula (B-2), or isomers thereof.

In certain embodiments, n is an integer from 1 to 4000. In certain embodiments n is an integer from 1 to 3000. In certain embodiments n is an integer from 1 to 2000. In certain embodiments n is an integer from 1 to 1000. In certain embodiments n is an integer from 1 to 700. In certain embodiments n is an integer from 1 to 800. In certain embodiments n is an integer from 1 to 600. In certain embodiments n is an integer from 1 to 500. In certain embodiments n is an integer from 1 to 400. In certain embodiments n is an integer from 1 to 300. In certain embodiments n is an integer from 1 to 200. In certain embodiments n is an integer from 1 to 100. In certain embodiments n is an integer from 1 to 90. In certain embodiments n is an integer from 1 to 80. In certain embodiments n is an integer from 1 to 70. In certain embodiments n is an integer from 1 to 60. In certain embodiments n is an integer from 1 to 50. In certain embodiments n is an integer from 1 to 40. In certain embodiments n is an integer from 1 to 30. In certain embodiments n is an integer from 1 to 20. In certain embodiments n is an integer from 1 to 10. In certain embodiments n is an integer from 1 to 5.

Also, provided herein are methods for the site specific labeling of proteins, polypeptides and/or peptides of Formula (I), wherein the method involves admixing such proteins, polypeptides and/or peptides that contain one or more pyrrolysine and/or PCL residues with a reagent having the structure of Formula (III):

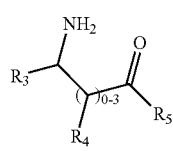

(III)

wherein:
$R_3$, $R_5$ and each $R_4$ are independently is selected from H, —OH, —$NO_2$, halo, $C_{1-8}$alkyl, halo-substituted-$C_{1-8}$alkyl, hydroxy-substituted-$C_{1-8}$alkyl, aryl, heteroaryl, heterocycloalkyl or cycloalkyl and -$LX^1$;
L is selected from a bond, $C_{1-8}$alkylene, halo-substituted-$C_{1-8}$alkylene, hydroxy-substituted-$C_{1-8}$alkylene, $C_{2-8}$alkenylene, halo-substituted-$C_{2-8}$alkenylene, hydroxy-substituted-$C_{2-8}$alkenylene, a polyalkylene glycol, a poly(ethylene glycol), —$O(CR^{11}R^{12})_k$—, —$S(CR^{11}R^{12})_k$—, —$S(O)_k(CR^{11}R^{12})_k$—, —$O(CR^{11}R^{12})_k$—$NR^{11}C(O)$—, —$O(CR^{11}R^{12})_kC(O)NR^{11}$—, —$C(O)$—, —$C(O)(CR^{11}R^{12})_k$—, —$C(S)$—, —$C(S)(CR^{11}R^{12})_k$—, —$C(O)NR^{11}$—, —$NR^{11}C(O)$—, —$NR^{11}(CR^{11}R^{12})_k$—, —$CONR^{11}(CR^{11}R^{12})_k$—, —$N(R^{11})CO(CR^{11}R^{12})_k$—, —$C(O)NR^{11}(CR^{11}R^{12})_k$—, —$NR^{11}C(O)(CR^{11}R^{12})_k$—, where each $R^{11}$ and $R^{12}$ are independently H, $C_{1-8}$alkyl, halo-substituted-$C_{1-8}$alkyl, or hydroxy-substituted-$C_{1-8}$alkyl, and k is an integer from 1 to 12;
$X^1$ is selected from a label, a dye, a polymer, a water-soluble polymer, a polyalkylene glycol, a poly(ethylene glycol), a derivative of poly(ethylene glycol), a sugar, a lipid, a photocrosslinker, a cytotoxic compound, a drug, an affinity label, a photoaffinity label, a reactive compound; a resin, a peptide, a second protein or polypeptide or polypeptide analog, an antibody or antibody fragment, a metal chelator, a cofactor, a fatty acid, a carbohydrate, a polynucleotide, a DNA, a RNA, a PCR probe, an antisense polynucleotide, a ribo-oligonucleotide, a deoxyribo-oligonucleotide, phosphorothioate-modified DNA, modified DNA and RNA, a peptide nucleic acid, a saccharide, a disaccharide, an oligosaccharide, a polysaccharide, a water-soluble dendrimer, a cyclodextrin, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a ligand, a photoisomerizable moiety, biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chromophoric group, a chemiluminescent group, a fluorescent moiety, an electron dense group, a magnetic group, an intercalating group, a chelating group, a chromophore, an energy transfer agent, a biologically active agent, a detectable label, a small molecule, an inhibitory ribonucleic acid, an siRNA, a radionucleotide, a neutron-capture agent, a derivative of biotin, quantum dot(s), a nanotransmitter, a radiotransmitter, an abzyme, an enzyme, an activated complex activator, a virus, a toxin, an adjuvant, a TLR2 agonist, a TLR4 agonist, a TLR7 agonist, a TLR9 agonist, a TLR8 agonist, a T-cell epitope, a phospho-lipid, a LPS-like molecule, keyhole limpet hemocyanin (KLH), an immunogenic hapten, an aglycan, an allergen, an angiostatin, an antihormone, an antioxidant, an aptamer, a guide RNA, a saponin, a shuttle vector, a macromolecule, a mimotope, a receptor, a reverse micelle, detergents, immune response potentiators, fluorescence dyes, FRET reagents, radio-imaging probes, other spectroscopy probe, prodrugs, toxins for immunotherapy, a solid support, —$CH_2CH_2$—$(OCH_2CH_2O)_p$—$OX^2$, —O—$(CH_2CH_2O)_pCH_2CH_2$—$X^2$, and any combination thereof, wherein p is 1 to 10,000 and $X^2$ is H, a $C_{1-8}$alkyl, a protecting group or a terminal functional group.

Further provided herein are methods for the site specific labeling of proteins, polypeptides and/or peptides of Formula (I), wherein the method involves admixing and reacting under appropriate conditions, such proteins, polypeptides and/or peptides that contain one or more pyrrolysine and/or PCL residues with a reagent having the structure of Formula (IV):

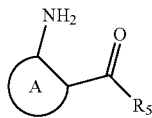

(IV)

wherein:
$R_5$ is selected from —OH, —NO$_2$, halo, $C_{1-8}$alkyl, halo-substituted-$C_{1-8}$alkyl, hydroxy-substituted-$C_{1-8}$alkyl, aryl, heteroaryl, heterocycloalkyl or cycloalkyl and -LX$^1$;

A is a $C_3$-$C_8$cycloalkyl, $C_3$-$C_8$ heterocycloalkyl, a 5-6 membered monocyclic aryl, a 5-6 membered monocyclic heteroaryl, a 9-10 membered fused bicyclic ring or a 13-14 membered fused tricyclic ring, wherein A is optionally substituted with 1 to 5 substituents independently selected from —OH, —NO$_2$, halo, $C_{1-8}$alkyl, halo-substituted-$C_{1-8}$alkyl, hydroxy-substituted-$C_{1-8}$alkyl, aryl, heteroaryl, heterocycloalkyl or cycloalkyl and -LX$^1$;

L is selected from a bond, $C_{1-8}$alkylene, halo-substituted-$C_{1-8}$alkylene, hydroxy-substituted-$C_{1-8}$alkylene, $C_{2-8}$alkenylene, halo-substituted-$C_{2-8}$alkenylene, hydroxy-substituted-$C_{2-8}$alkenylene, a polyalkylene glycol, a poly(ethylene glycol), —O(CR$^{11}$R$^{12}$)$_k$—, —S(CR$^{11}$R$^{12}$)$_k$—, —S(O)$_k$(CR$^{11}$R$^{12}$)$_k$—, —O(CR$^{11}$R$^{12}$)$_k$—NR$^{11}$C(O)—, —O(CR$^{11}$R$^{12}$)$_k$C(O)NR$^{11}$—, —C(O)—, —C(O)(CR$^{11}$R$^{12}$)$_k$—, —C(S)—, —C(S)(CR$^{11}$R$^{12}$)$_k$—, —C(O)NR$^{11}$—, —NR$^{11}$C(O)—, —NR$^{11}$(CR$^{11}$R$^{12}$)$_k$—, —CONR$^{11}$(CR$^{11}$R$^{12}$)$_k$—, —N(R$^{11}$)CO(CR$^{11}$R$^{12}$)$_k$—, —C(O)NR$^{11}$(CR$^{11}$R$^{12}$)$_k$—, —NR$^{11}$C(O)(CR$^{11}$R$^{12}$)$_k$—, where each R$^{11}$ and R$^{12}$ are independently H, $C_{1-8}$alkyl, halo-substituted-$C_{1-8}$alkyl, or hydroxy-substituted-$C_{1-8}$alkyl, and k is an integer from 1 to 12;

$X^1$ is selected from a label, a dye, a polymer, a water-soluble polymer, a polyalkylene glycol, a poly(ethylene glycol), a derivative of poly(ethylene glycol), a sugar, a lipid, a photocrosslinker, a cytotoxic compound, a drug, an affinity label, a photoaffinity label, a reactive compound; a resin, a peptide, a second protein or polypeptide or polypeptide analog, an antibody or antibody fragment, a metal chelator, a cofactor, a fatty acid, a carbohydrate, a polynucleotide, a DNA, a RNA, a PCR probe, an antisense polynucleotide, a ribo-oligonucleotide, a deoxyribo-oligonucleotide, phosphorothioate-modified DNA, modified DNA and RNA, a peptide nucleic acid, a saccharide, a disaccharide, an oligosaccharide, a polysaccharide, a water-soluble dendrimer, a cyclodextrin, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a ligand, a photoisomerizable moiety, biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chromophoric group, a chemiluminescent group, a fluorescent moiety, an electron dense group, a magnetic group, an intercalating group, a chelating group, a chromophore, an energy transfer agent, a biologically active agent, a detectable label, a small molecule, an inhibitory ribonucleic acid, an siRNA, a radionucleotide, a neutron-capture agent, a derivative of biotin, quantum dot(s), a nanotransmitter, a radiotransmitter, an abzyme, an enzyme, an activated complex activator, a virus, a toxin, an adjuvant, a TLR2 agonist, a TLR4 agonist, a TLR7 agonist, a TLR9 agonist, a TLR8 agonist, a T-cell epitope, a phospho-lipid, a LPS-like molecule, keyhole limpet hemocyanin (KLH), an immunogenic hapten, an aglycan, an allergen, an angiostatin, an antihormone, an antioxidant, an aptamer, a guide RNA, a saponin, a shuttle vector, a macromolecule, a mimotope, a receptor, a reverse micelle, detergents, immune response potentiators, fluorescence dyes, FRET reagents, radio-imaging probes, other spectroscopy probe, prodrugs, toxins for immunotherapy, a solid support, —CH$_2$CH$_2$—(OCH$_2$CH$_2$O)$_p$—OX$^2$, —O—(CH$_2$CH$_2$O)$_p$CH$_2$CH$_2$—X$^2$, and any combination thereof, wherein p is 1 to 10,000 and X$^2$ is H, a $C_{1-8}$alkyl, a protecting group or a terminal functional group.

In certain embodiments k is an integer from 1 to 11. In certain embodiments k is an integer from 1 to 10. In certain embodiments k is an integer from 1 to 9. In certain embodiments k is an integer from 1 to 8. In certain embodiments k is an integer from 1 to 7. In certain embodiments k is an integer from 1 to 6. In certain embodiments k is an integer from 1 to 5. In certain embodiments k is an integer from 1 to 4. In certain embodiments k is an integer from 1 to 3. In certain embodiments k is an integer from 1 to 2.

In certain embodiments p is an integer from 1 to 8000. In certain embodiments p is an integer from 1 to 7000. In certain embodiments p is an integer from 1 to 6000. In certain embodiments p is an integer from 1 to 5000. In certain embodiments p is an integer from 1 to 4000. In certain embodiments p is an integer from 1 to 3000. In certain embodiments p is an integer from 1 to 2000. In certain embodiments p is an integer from 1 to 1000. In certain embodiments p is an integer from 1 to 500. In certain embodiments p is an integer from 1 to 400. In certain embodiments p is an integer from 1 to 300. In certain embodiments p is an integer from 1 to 200. In certain embodiments p is an integer from 1 to 100. In certain embodiments p is an integer from 1 to 90. In certain embodiments p is an integer from 1 to 80. In certain embodiments p is an integer from 1 to 70. In certain embodiments p is an integer from 1 to 60. In certain embodiments p is an integer from 1 to 50. In certain embodiments p is an integer from 1 to 40. In certain embodiments p is an integer from 1 to 30. In certain embodiments p is an integer from 1 to 20. In certain embodiments p is an integer from 1 to 10. In certain embodiments p is an integer from 1 to 5.

Non-limiting example of compounds of Formula (IV) include:

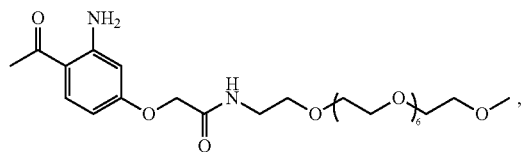
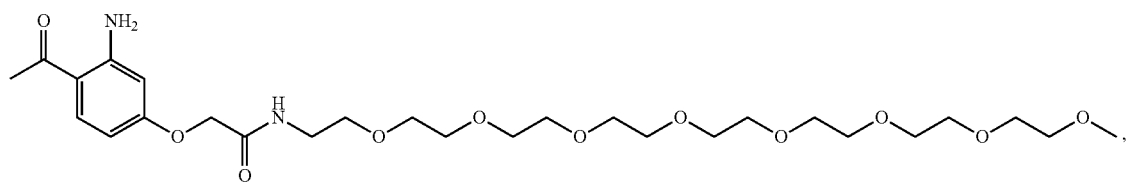
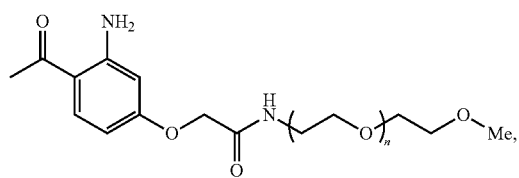 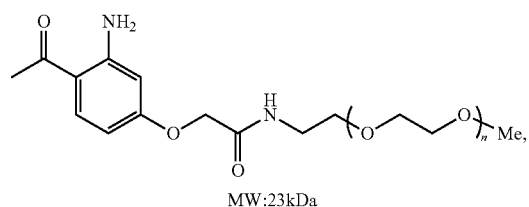
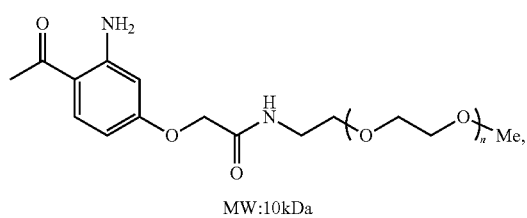 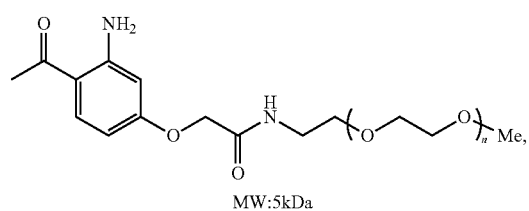
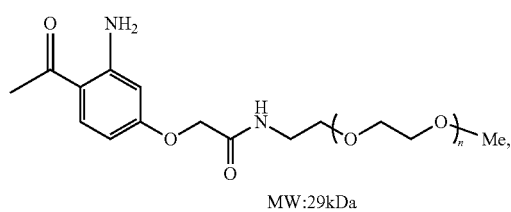 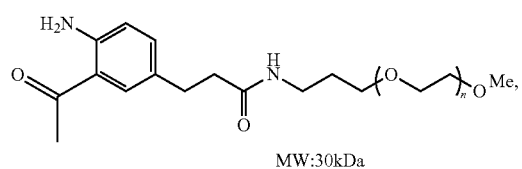
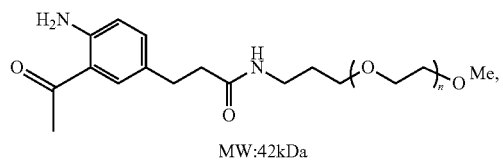 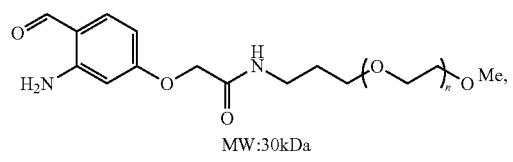
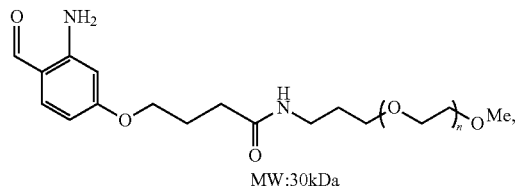 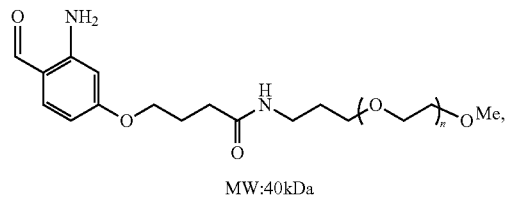
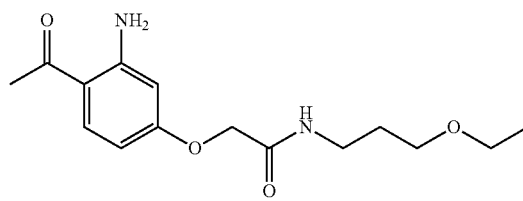 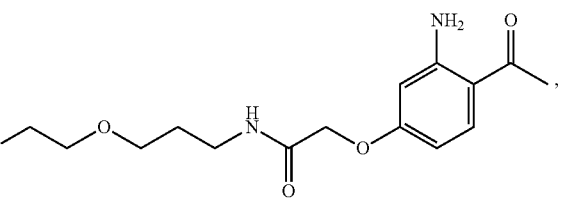

-continued
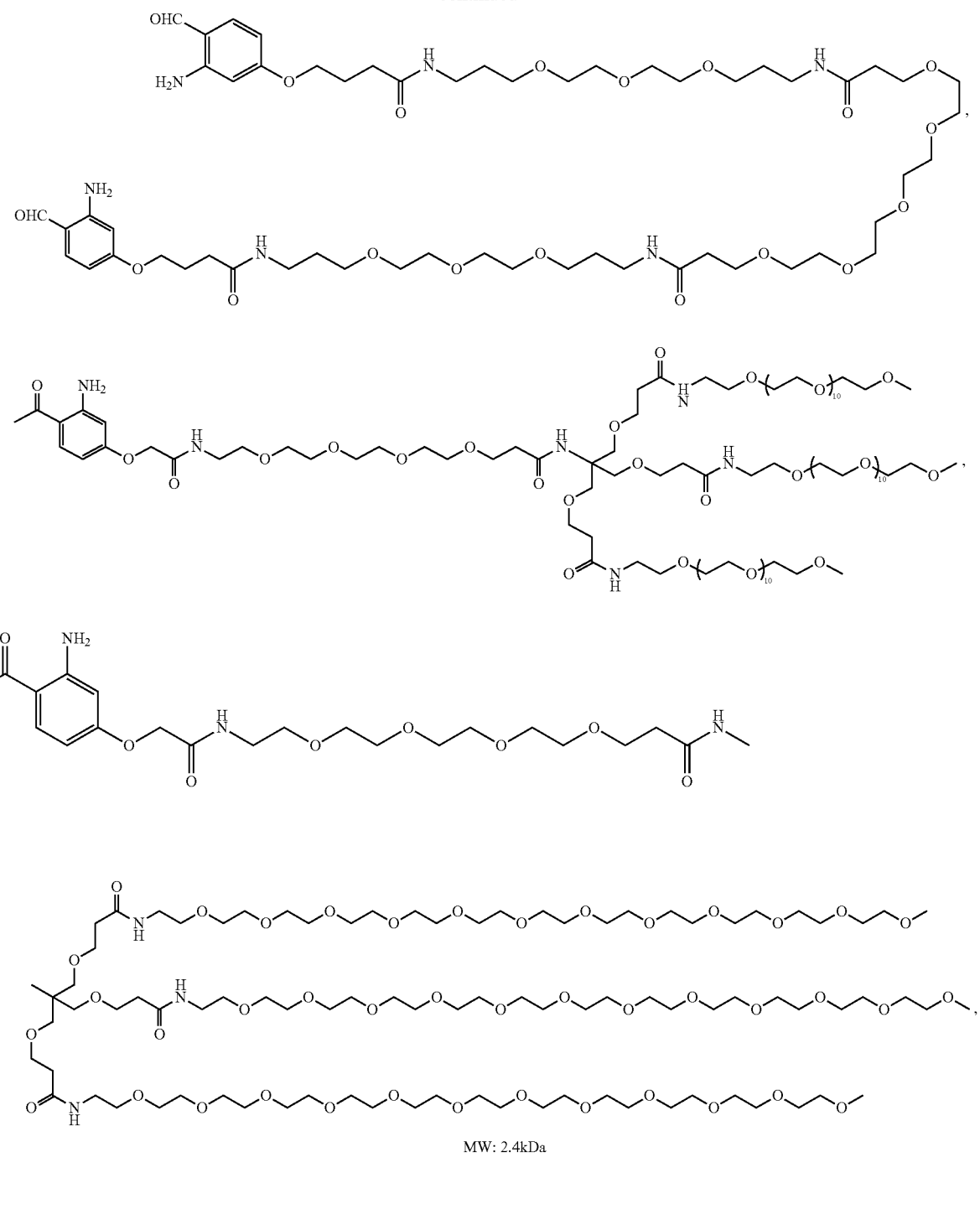
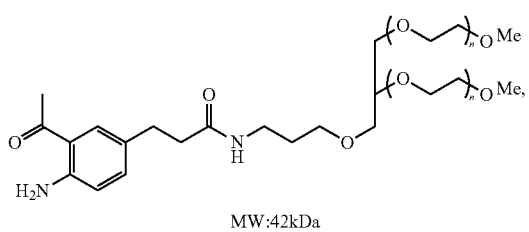
MW: 42kDa

101                                              102
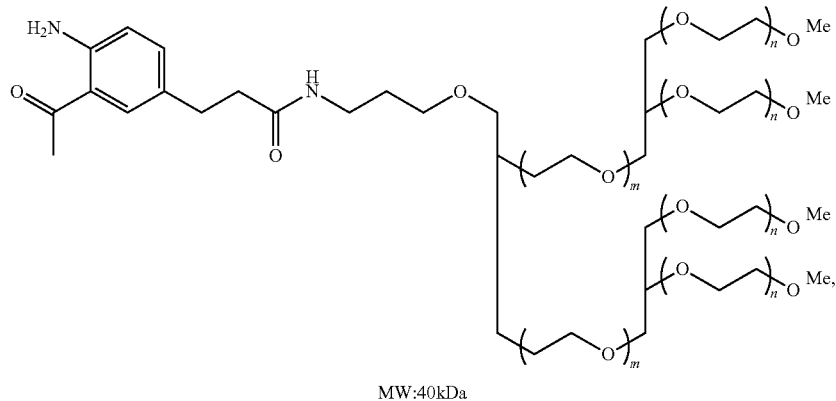
MW:40kDa
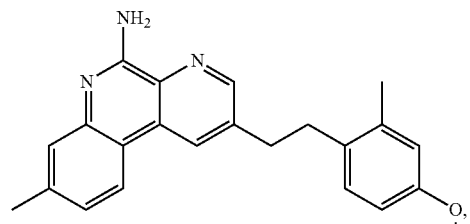
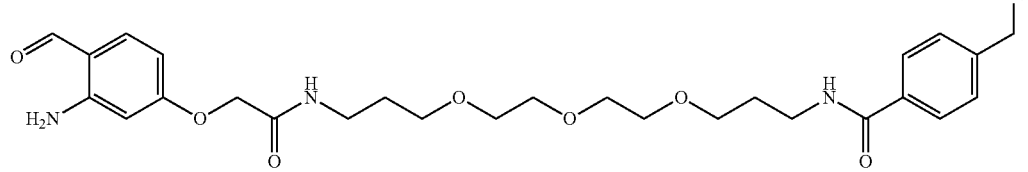
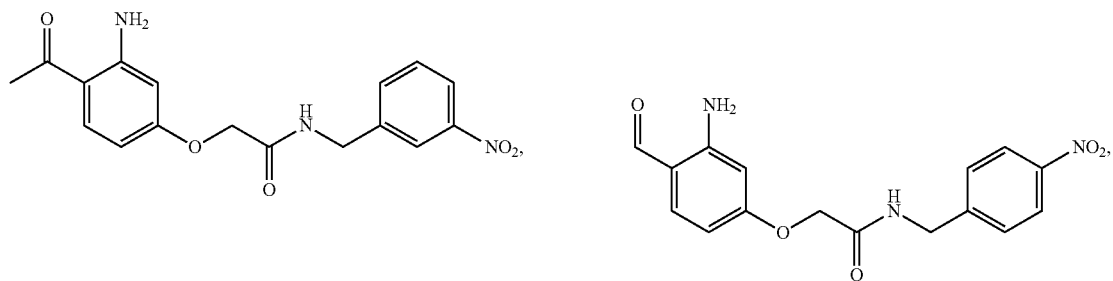
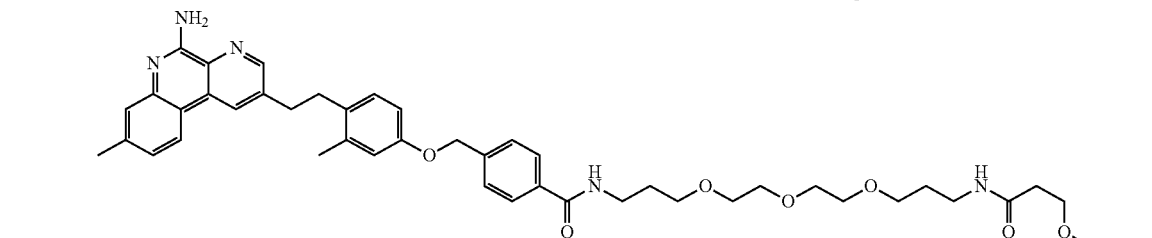
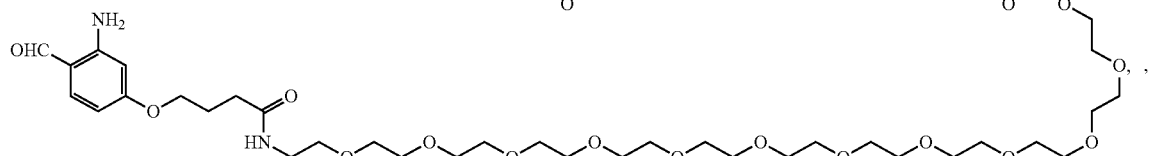
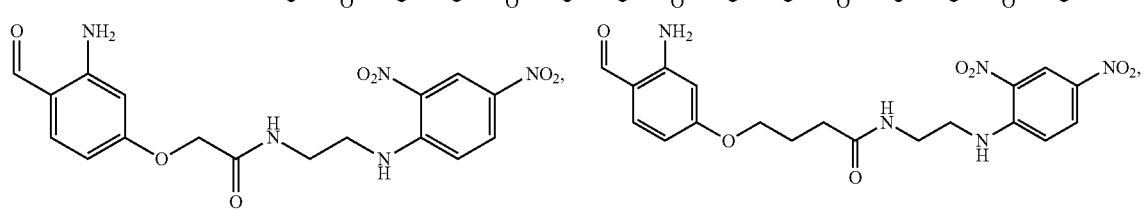

103
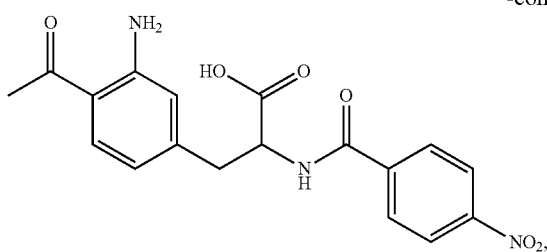
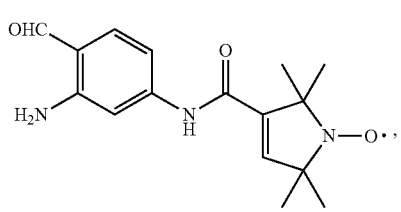
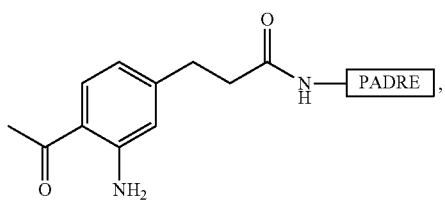
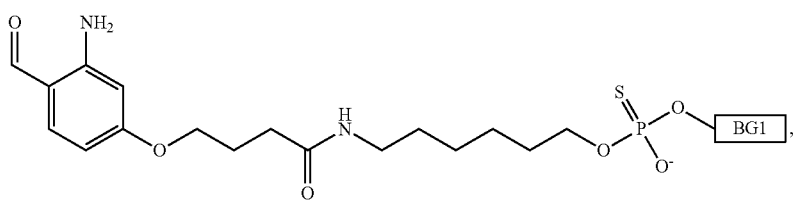
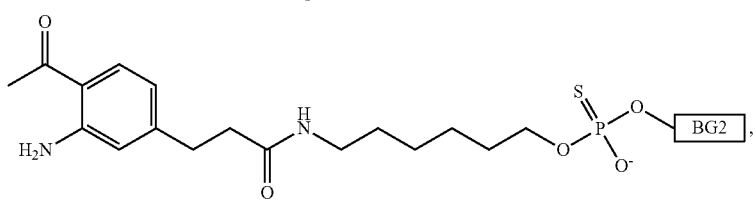
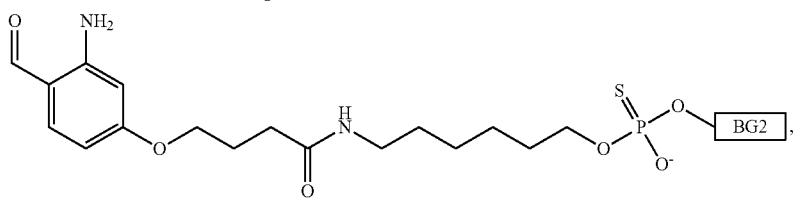
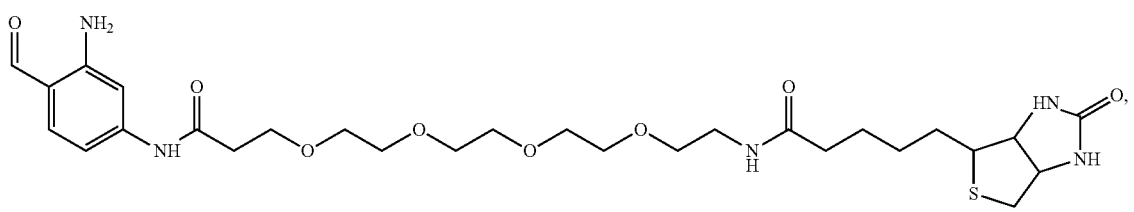
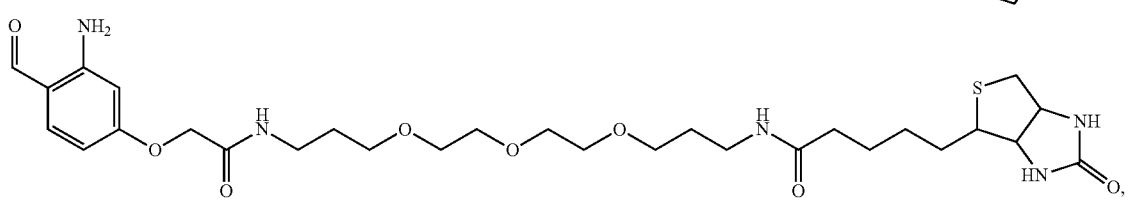
104
-continued
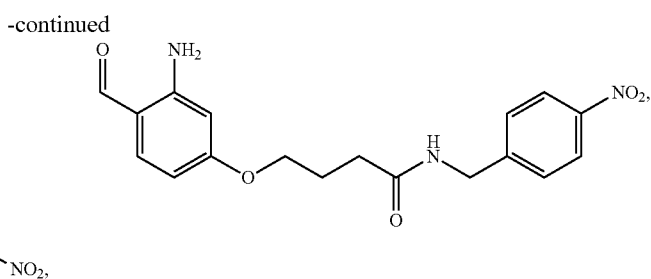
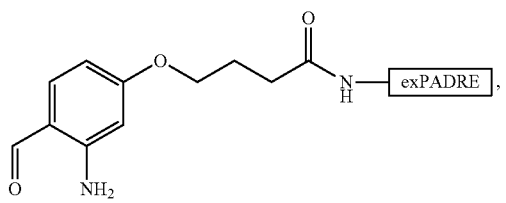

-continued

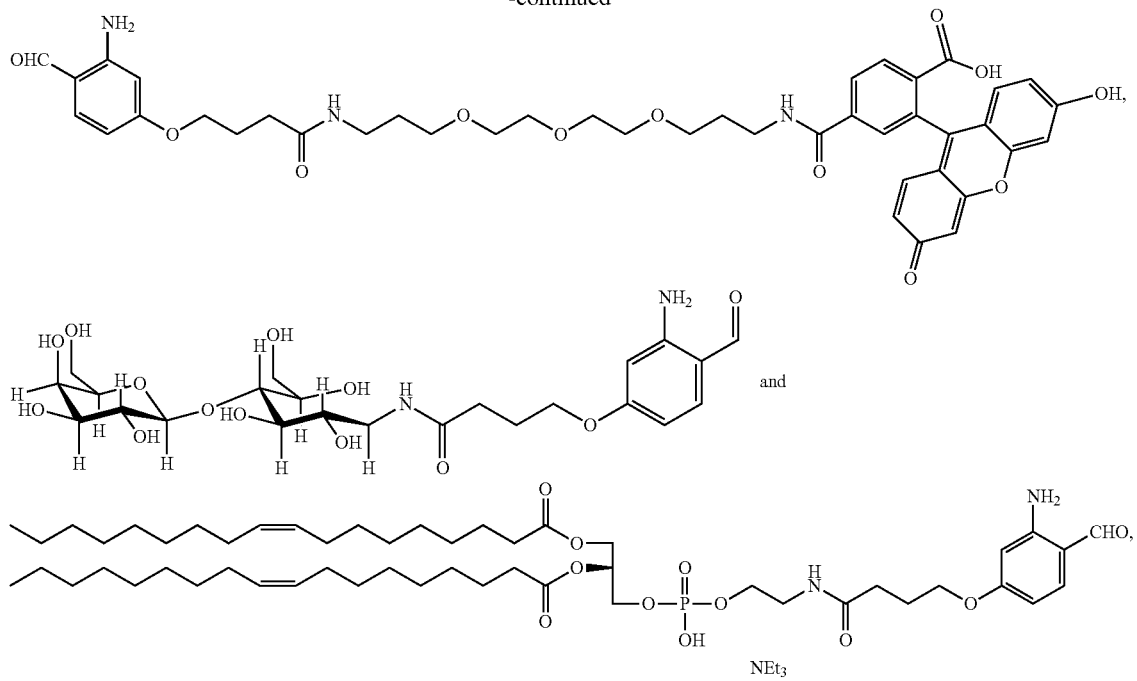

wherein compounds having one or more polyethyleneglycol (PEG) moieties have an average molecular weight in the range from 1000 Da to 50 kDa, and n is from 20 to 1200 and wherein exPADRE is AlaGlySerArgSerGly(DAla)LysChaValAlaAlaTrpThrLeuLysAla(D-Ala)Gly-OH, PADRE is Gly(DAla)LysChaValAlaAlaTrpThrLeuLysAla(D-Ala)Gly-OH, BG1 is 5'*T*C*C*A*T*G*A*C*G*T*T*C*C*T*G*A*C*G*T*T-3' and BG2 is 5'*T*C*G*T*C*G*T*T*T*T*C*G*G*C*G*C*G*C*G*C*C*G-3', and where * denotes a phosphothioate linkage.

In certain embodiments the proteins, polypeptides and/or peptides containing one or more pyrrolysine and/or PCL derivatized using the methods provided herein have the structure of Formula (II):

$R_1$-(BB)$_n$-$R_2$     (II)

wherein:
R$_1$ is H or an amino terminus modification group;
R$_2$ is OH or a carboxy terminus modification group;
n is an integer from 1 to 5000;
each BB is independently selected from an amino acid residue, a pyrrolysine analogue amino acid residue having the structure of Formula (A-2), a pyrrolysine analogue amino acid residue having the structure of Formula (B-2), a pyrrolysine analogue amino acid residue having the structure of Formula (C-1), a pyrrolysine analogue amino acid residue having the structure of Formula (D-1), a pyrrolysine analogue amino acid residue having the structure of Formula (E-1), a pyrrolysine analogue amino acid residue having the structure of Formula (F-1), a pyrrolysine analogue amino acid residue having the structure of Formula (G-1), a pyrrolysine analogue amino acid residue having the structure of Formula (H-1), a pyrrolysine analogue amino acid residue having the structure of Formula (I-1), a pyrrolysine analogue amino acid residue having the structure of Formula (J-1), a pyrrolysine analogue amino acid residue having the structure of Formula (K-1) and a pyrrolysine analogue amino acid residue having the structure of Formula (L-1), or isomers thereof;

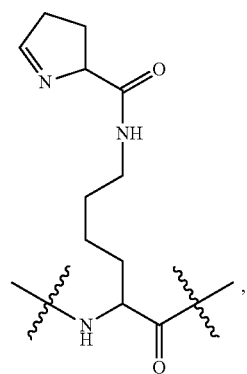

(A-2)

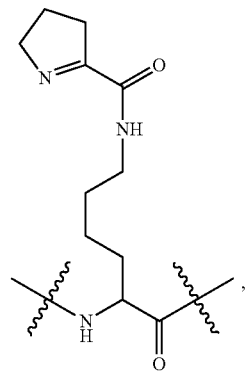

(B-2)

107
-continued
(C-1)
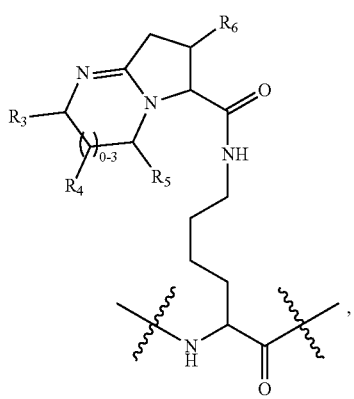
(D-1)
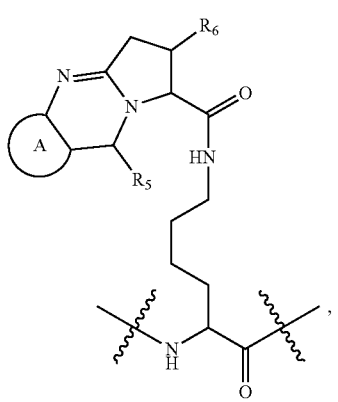
(E-1)
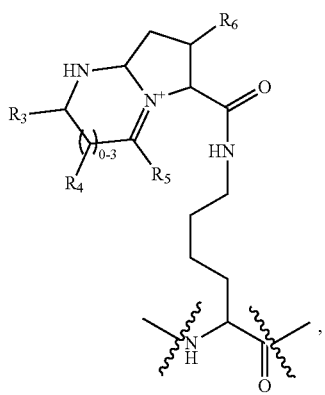
(F-1)
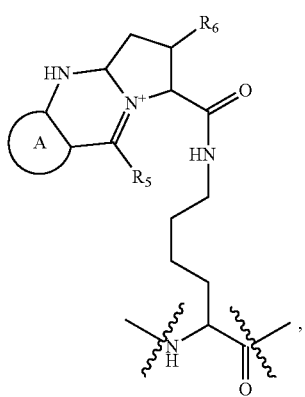
108
-continued
(G-1)
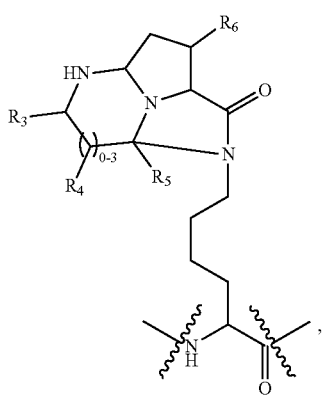
(H-1)
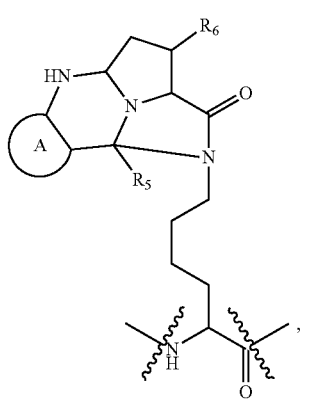
(I-1)
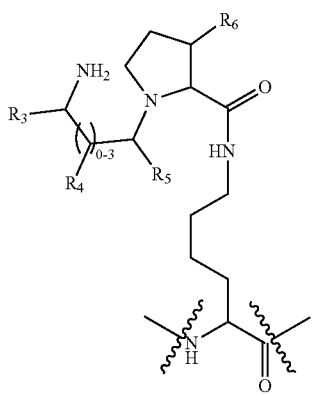
(J-1)
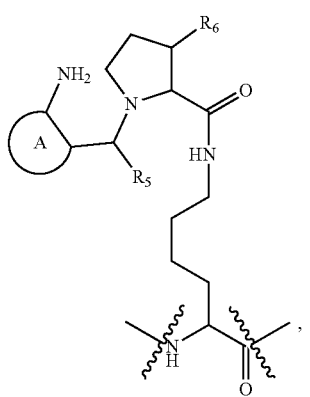

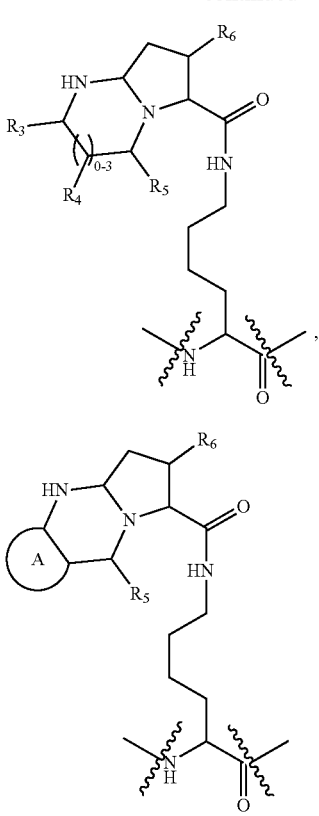

wherein:
R₃, R₅ and each R₄ is independently selected from H, —OH, —NO₂, halo, $C_{1-8}$alkyl, halo-substituted-$C_{1-8}$alkyl, hydroxy-substituted-$C_{1-8}$alkyl, aryl, heteroaryl, heterocycloalkyl or cycloalkyl and $LX^1$;

R₆ is H or $C_1$alkyl;

A is a $C_3$-$C_8$cycloalkyl, $C_3$-$C_8$ heterocycloalkyl, a 5-6 membered monocyclic aryl, a 5-6 membered monocyclic heteroaryl, a 9-10 membered fused bicyclic ring or a 13-14 membered fused tricyclic ring, wherein A is optionally substituted with 1 to 5 substituents independently selected from —OH, —NO₂, halo, $C_{1-8}$alkyl, halo-substituted-$C_{1-8}$alkyl, hydroxy-substituted-$C_{1-8}$alkyl, aryl, heteroaryl, heterocycloalkyl or cycloalkyl and -$LX^1$;

L is selected from a bond, $C_{1-8}$alkylene, halo-substituted-$C_{1-8}$alkylene, hydroxy-substituted-$C_{1-8}$alkylene, $C_{2-8}$alkenylene, halo-substituted-$C_{2-8}$alkenylene, hydroxy-substituted-$C_{2-8}$alkenylene, a polyalkylene glycol, a poly(ethylene glycol), —O(CR¹¹R¹²)$_k$—, —S(CR¹¹R¹²)$_k$—, —S(O)$_k$(CR¹¹R¹²)$_k$—, —O(CR¹¹R¹²)$_k$—NR¹¹C(O)—, —O(CR¹¹R¹²)$_k$C(O)NR¹¹—, —C(O)—, —C(O)(CR¹¹R¹²)$_k$—, —C(S)—, —C(S)(CR¹¹R¹²)$_k$—, —C(O)NR¹¹—, —NR¹¹C(O)—, —NR¹¹(CR¹¹R¹²)$_k$—, —CONR¹¹(CR¹¹R¹²)$_k$—, —N(R¹¹)CO(CR¹¹R¹²)$_k$—, —C(O)NR¹¹(CR¹¹R¹²)$_k$—, —NR¹¹C(O)(CR¹¹R¹²)$_k$—, where each R¹¹ and R¹² are independently H, $C_{1-8}$alkyl, halo-substituted-$C_{1-8}$alkyl, or hydroxy-substituted-$C_{1-8}$alkyl, and k is an integer from 1 to 12, and $X^1$ is selected from a label, a dye, a polymer, a water-soluble polymer, a polyalkylene glycol, a poly(ethylene glycol), a derivative of poly(ethylene glycol), a sugar, a lipid, a photocrosslinker, a cytotoxic compound, a drug, an affinity label, a photoaffinity label, a reactive compound; a resin, a peptide, a second protein or polypeptide or polypeptide analog, an antibody or antibody fragment, a metal chelator, a cofactor, a fatty acid, a carbohydrate, a polynucleotide, a DNA, a RNA, a PCR probe, an antisense polynucleotide, a ribo-oligonucleotide, a deoxyribo-oligonucleotide, phosphorothioate-modified DNA, modified DNA and RNA, a peptide nucleic acid, a saccharide, a disaccharide, an oligosaccharide, a polysaccharide, a water-soluble dendrimer, a cyclodextrin, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a ligand, a photoisomerizable moiety, biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chromophoric group, a chemiluminescent group, a fluorescent moiety, an electron dense group, a magnetic group, an intercalating group, a chelating group, a chromophore, an energy transfer agent, a biologically active agent, a detectable label, a small molecule, an inhibitory ribonucleic acid, an siRNA, a radionucleotide, a neutron-capture agent, a derivative of biotin, quantum dot(s), a nanotransmitter, a radiotransmitter, an abzyme, an enzyme, an activated complex activator, a virus, a toxin, an adjuvant, a TLR2 agonist, a TLR4 agonist, a TLR7 agonist, a TLR9 agonist, a TLR8 agonist, a T-cell epitope, a phospho-lipid, a LPS-like molecule, keyhole limpet hemocyanin (KLH), an immunogenic hapten, an aglycan, an allergen, an angiostatin, an antihormone, an antioxidant, an aptamer, a guide RNA, a saponin, a shuttle vector, a macromolecule, a mimotope, a receptor, a reverse micelle, detergents, immune response potentiators, fluorescence dyes, FRET reagents, radio-imaging probes, other spectroscopy probe, prodrugs, toxins for immunotherapy, a solid support, —CH₂CH₂—(OCH₂CH₂O)$_p$—OX², —O—(CH₂CH₂O)$_p$CH₂CH₂—X², and any combination thereof, wherein p is 1 to 10,000 and $X^2$ is H, a $C_{1-8}$alkyl, a protecting group or a terminal functional group, and wherein at least one AA is a pyrrolysine analogue amino acid residue having the structure of Formula (A-2) or Formula (B-2), or at least one BB is a pyrrolysine analogue amino acid residue having the structure of Formula (C-1) or Formula (D-1) or Formula (E-1) or Formula (F-1) or Formula (G-1) or Formula (H-1) or Formula (I-1) or Formula (J-1) or Formula (K-1) or Formula (L-1), or isomers thereof.

In certain embodiments k is an integer from 1 to 11. In certain embodiments k is an integer from 1 to 10. In certain embodiments k is an integer from 1 to 9. In certain embodiments k is an integer from 1 to 8. In certain embodiments k is an integer from 1 to 7. In certain embodiments k is an integer from 1 to 6. In certain embodiments k is an integer from 1 to 5. In certain embodiments k is an integer from 1 to 4. In certain embodiments k is an integer from 1 to 3. In certain embodiments k is an integer from 1 to 2.

In certain embodiments p is an integer from 1 to 8000. In certain embodiments p is an integer from 1 to 7000. In certain embodiments p is an integer from 1 to 6000. In certain embodiments p is an integer from 1 to 5000. In certain embodiments p is an integer from 1 to 4000. In certain embodiments p is an integer from 1 to 3000. In certain embodiments p is an integer from 1 to 2000. In certain embodiments p is an integer from 1 to 1000. In certain embodiments p is an integer from 1 to 500. In certain embodiments p is an integer from 1 to 400. In certain embodiments p is an integer from 1 to 300. In certain embodiments p is an integer from 1 to 200. In certain embodiments p is an integer from 1 to 100. In certain embodiments p is an integer from 1 to 90. In certain embodiments p is an integer from 1 to 80. In certain embodiments p is an integer from 1 to 70. In certain embodiments p is an integer from 1 to 60. In certain embodiments p is an integer from 1 to 50. In certain embodiments p is an integer from 1 to 40. In certain embodiments p is an integer from 1 to 30. In certain embodiments p is an integer from 1 to 20. In certain embodiments p is an integer from 1 to 10. In certain embodiments p is an integer from 1 to 5.

In certain embodiments n is an integer from 1 to 4000. In certain embodiments n is an integer from 1 to 3000. In certain embodiments n is an integer from 1 to 2000. In certain embodiments n is an integer from 1 to 1000. In certain embodiments n is an integer from 1 to 700. In certain embodiments n is an integer from 1 to 800. In certain embodiments n is an integer from 1 to 600. In certain embodiments n is an integer from 1 to 500. In certain embodiments n is an integer from 1 to 400. In certain embodiments n is an integer from 1 to 300. In certain embodiments n is an integer from 1 to 200. In certain embodiments n is an integer from 1 to 100. In certain embodiments n is an integer from 1 to 90. In certain embodiments n is an integer from 1 to 80. In certain embodiments n is an integer from 1 to 70. In certain embodiments n is an integer from 1 to 60. In certain embodiments n is an integer from 1 to 50. In certain embodiments n is an integer from 1 to 40. In certain embodiments n is an integer from 1 to 30. In certain embodiments n is an integer from 1 to 20. In certain embodiments n is an integer from 1 to 10. In certain embodiments n is an integer from 1 to 5.

In certain embodiments, the compounds of Formula (III) used in the derivatization methods provided herein include, but are not limited to, amino sugars. In certain embodiments, such amino sugars include, but are not limited to, D-mannosamine and D-galactosamine.

In certain embodiments, the compounds of Formula (IV) used in the derivatization methods provided herein include, but are not limited to, 2-amino-benzaldehyde (2-ABA), derivatives of 2-amino-benzaldehyde (2-ABA), derivatives of 2-amino-benzaldehyde (2-ABA) provided herein, 2-amino-acetophenone (2-AAP), derivatives of 2-amino-acetophenone (2-AAP), derivatives of 2-amino-acetophenone (2-AAP) provided herein, 2-amino-5-nitro-benzophenone (2-ANBP), derivatives of 2-amino-5-nitro-benzophenone (2-ANBP) and derivatives of 2-amino-5-nitro-benzophenone (2-ANBP) provided herein.

Figure 22:
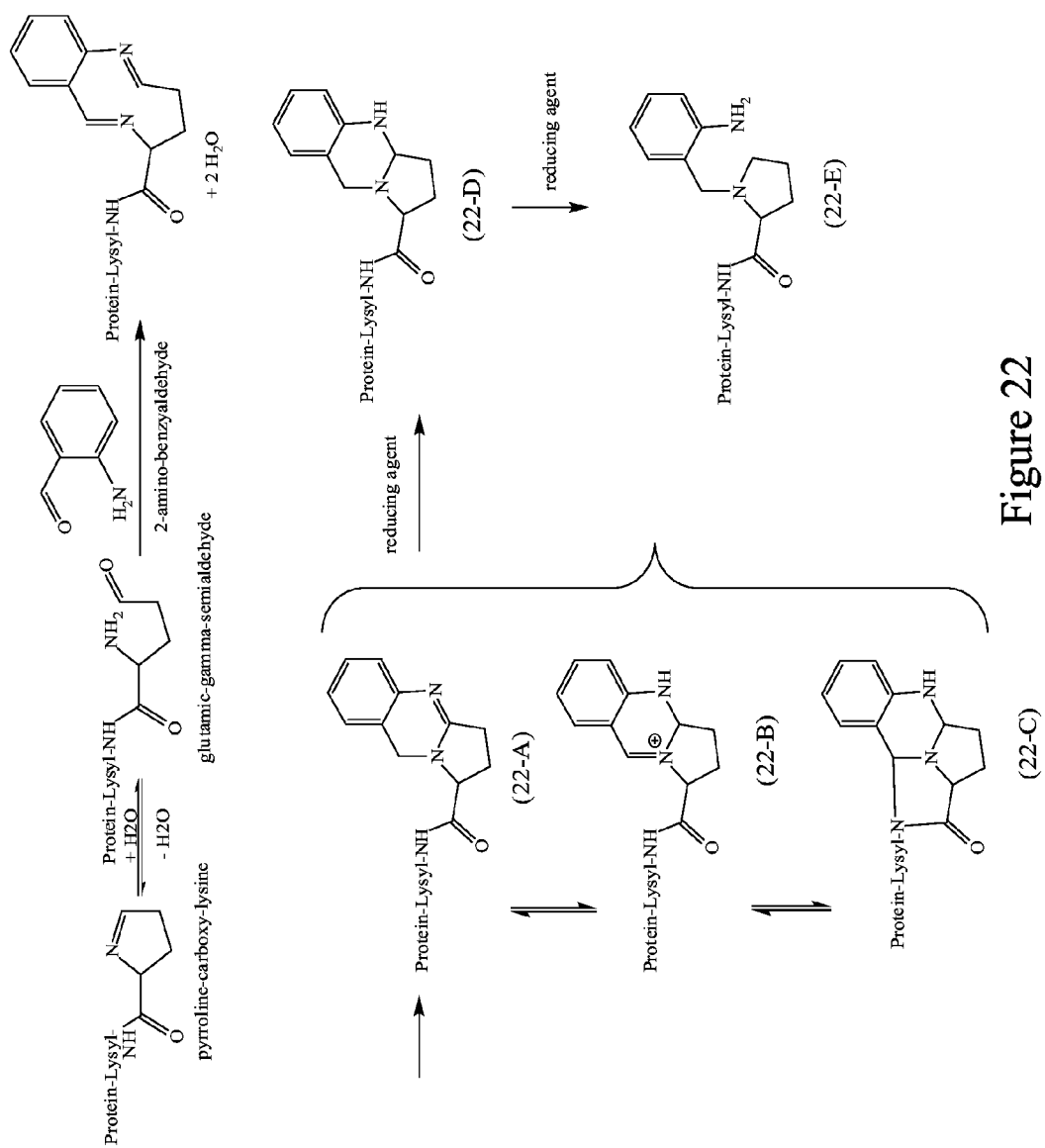
FIG. 22. Possible reaction schemes for the chemical derivatization of PCL with 2-amino-benzaldehyde.

FIG. 22 shows a reaction scheme for the chemical derivatization of PCL-A with 2-amino-benzaldehyde (2-ABA), wherein one or more PCL-A has been site-specifically incorporated into the protein. The cyclization reaction of the semialdehyde with 2-ABA is a Friedlaender-type reaction that results in the formation of a quinazoline-type moiety (22-A or 22-B), which can be further reduced with an appropriate reducing agent to form tetrahydroquinazoline type moieties (22-D) or substituted anilines (22-E). Alternatively, further reaction of quinazoline-type moiety 22-B results in the formation of the fused ring moiety (22-C). Suitable reducing agents for the reduction of the quinazoline-type moieties include, but are not limited to, sodium cyanoborohydride and sodium borohydride.

Figure 23:
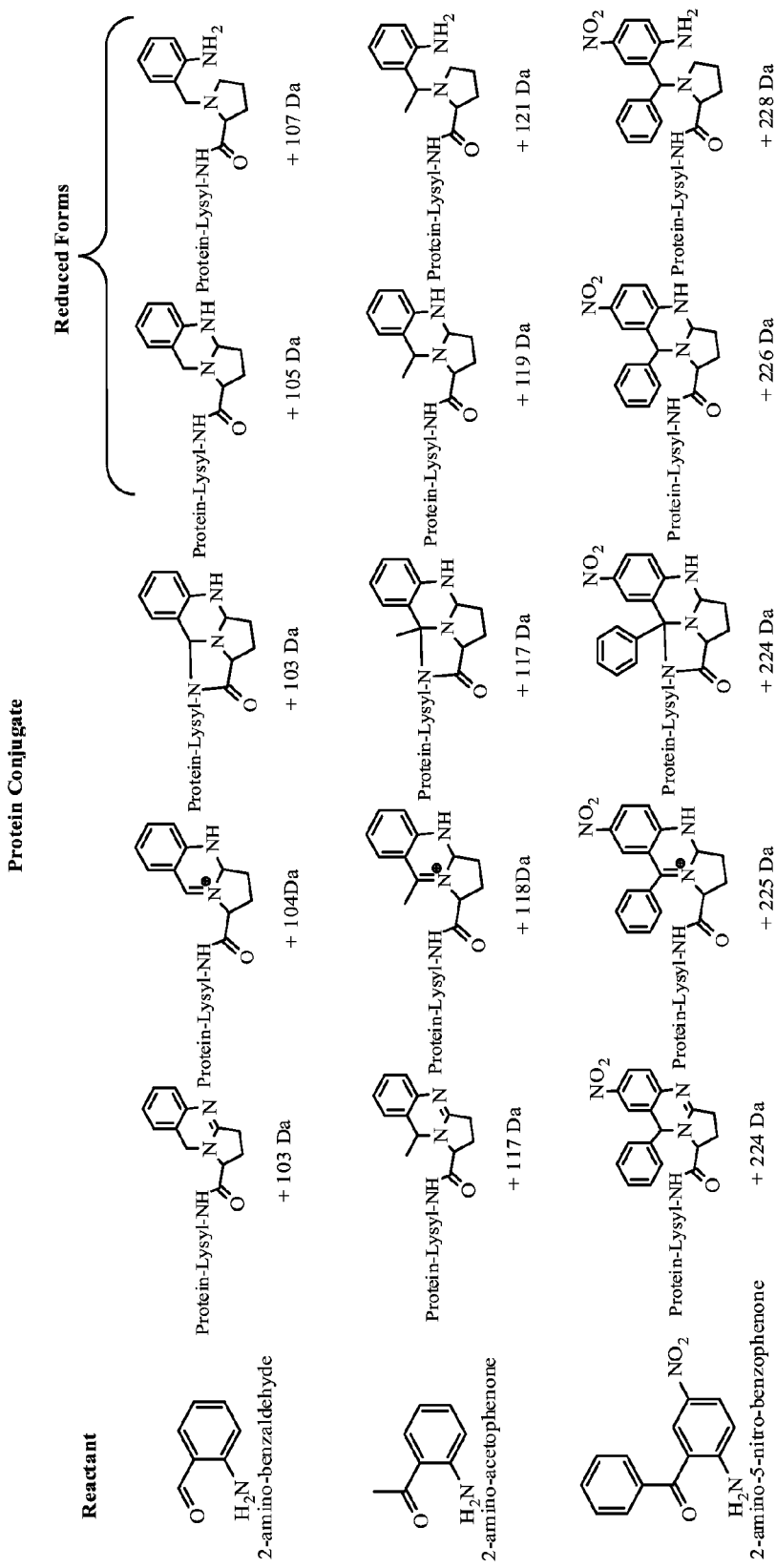
FIG. 23. Protein conjugates and mass change postulated after derivatization of PCL with 2-amino benzaldehyde, 2-aminoacetophenone and 2-amino-5-nitro-benzophenone.

In addition, FIG. 23 shows the various structures of the protein conjugates formed after reaction of PCL-A with either 2-ABA, 2-AAP or 2-ANBP. The expected mass increase due to the attachment of such groups is also shown. The structures obtained using such groups were characterized using NMR spectroscopy (see Example 45). Also, NaCNBH$_3$ reduction was found to stabilize PCL-based protein conjugates and to prevent dissociation of the PCL-ABA and PCL-AAP linkage even at high temperatures (see Example 44).

The reaction of 2-ABA with $\Delta^1$-pyrroline-5-carboxylic acid (L-1-pyrroline-5-carboxylic acid) (see Strecker, H. J., (1971), *Methods in Enzymology* 27B, 254-257; Vogel, H. J., and Davis, B. D. (1953), "Glutamic gamma-semialdehyde and delta1-pyrroline-5-carboxylic acid, intermediates in the biosynthesis of proline," *J. Am. Chem. Soc.* 74, 109-112; and Schoepf, C., and Oechler, F., (1936), *Ann. Chem.* 523, 1), and other pyrrolines (see Schoepf, C., and Oechler, F., (1936), *Ann. Chem.* 523, 1; and Schoepf, C., and Steuer, H., (1947), *Ann. Chem.* 558, 124) have been used as a colorimetric assay in studies of the role of $\Delta^1$-pyrroline-5-carboxylic acid in proline metabolism and biosynthesis (see Vogel, H. J., and Davis, B. D. (1953), "Glutamic gamma-semialdehyde and $\Delta^1$-pyrroline-5-carboxylic acid, intermediates in the biosynthesis of proline," *J. Am. Chem. Soc.* 74, 109-112; Strecker, H. J., (1960), "The interconversion of glutamic acid and proline," *J. Biol. Chem.* 235, 2045-2050; Mezl, V. A., and Knox, W. E., (1976), "Properties and analysis of a stable derivative of pyrroline-5-carboxylic acid for use in metabolic studies," *Analytical Biochemistry* 74, 430-40; Wu, G. Y., and Seifter, S., (1975), "A new method for the preparation of delta 1-pyrroline 5-carboxylic acid and proline," *Analytical Biochemistry* 67, 413-21; Williams, I., and Frank, L., (1975), "Improved chemical synthesis and enzymatic assay of $\Delta^1$-pyrroline-5-carboxylic acid," *Anal. Biochem.* 64, 85-97, and Strecker, H. J., (1957), "The interconversion of glutamic acid and proline," *J. Biol. Chem.* 225, 825). Although the reaction scheme shows the formation of the glutamic-gamma-semialdehyde intermediate, the reaction may proceed directly from pyrroline-carboxy-lysine without the formation of such an intermediate.

Figure 24:
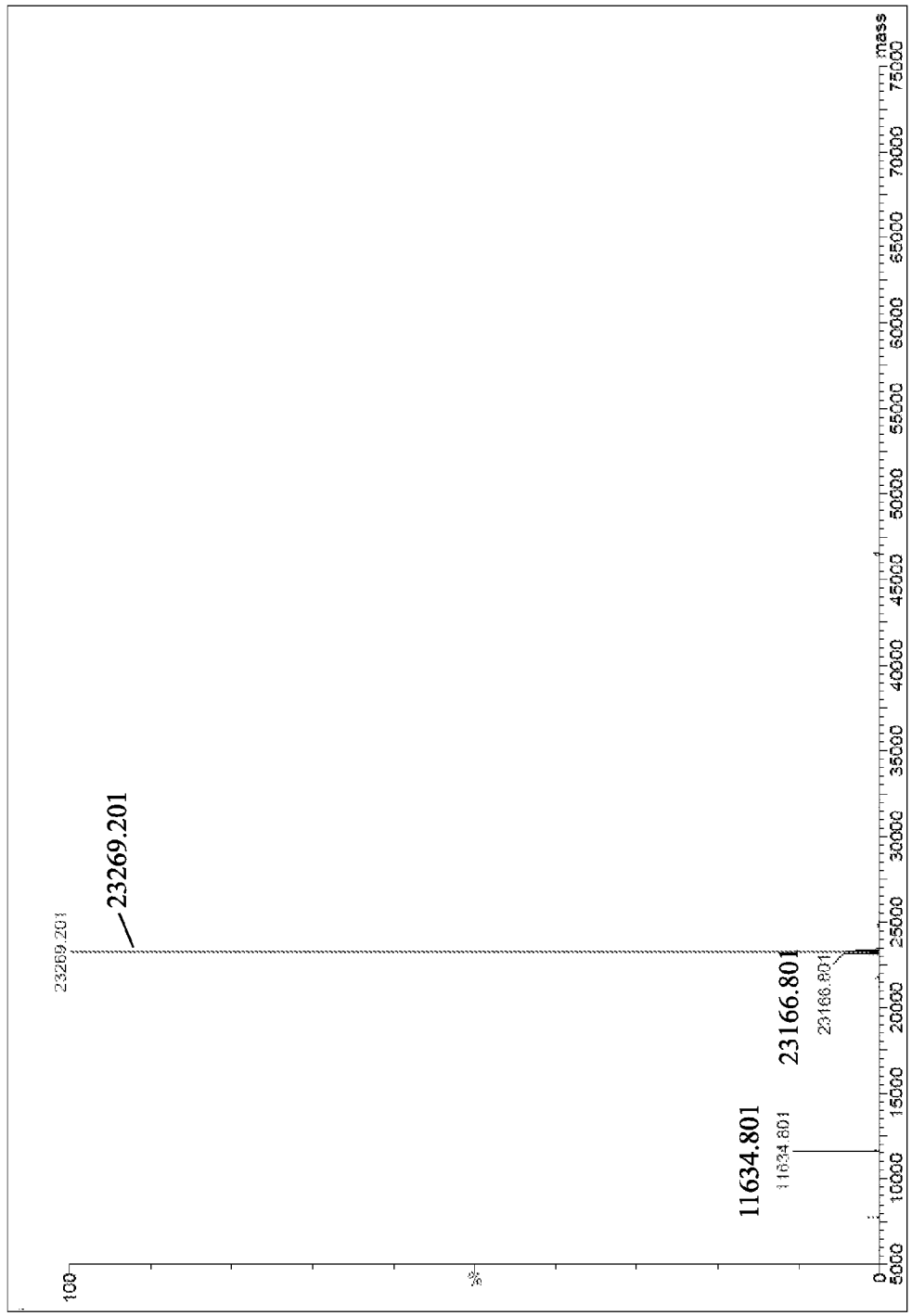
FIG. 24. Mass spectrometric analysis of hRBP4 Phe122PCL derivatized with 2-amino-benzaldehyde (2-ABA).
Figure 25:
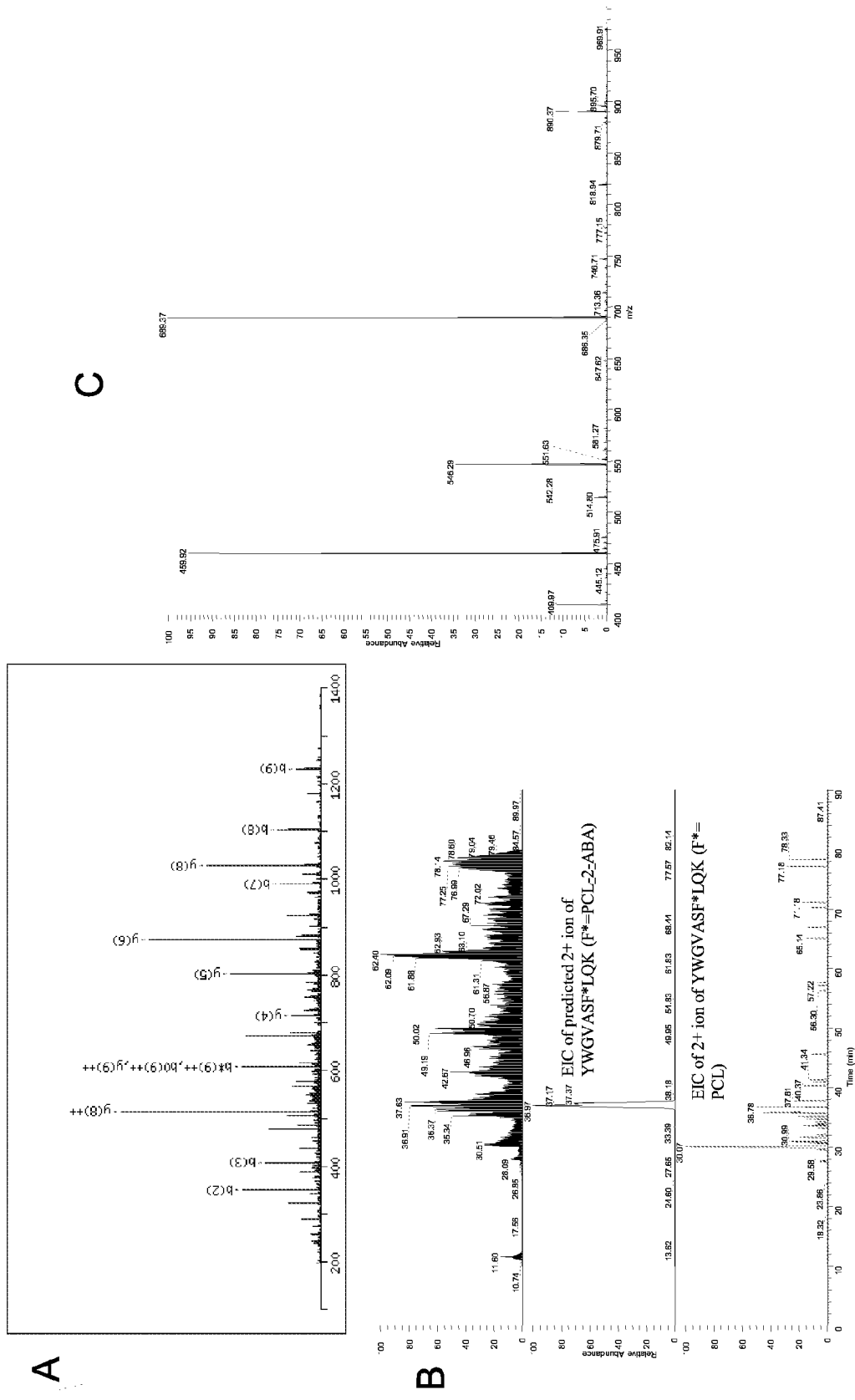
FIG. 25. Mass spectrometric analysis of a tryptic digest of the 2-ABA-derivatized hRBP4 Phe122PCL protein verifies derivatization of the PCL residue incorporated at the TAG site. YWGVASF*LQK peptide (SEQ ID NO:17)
Figure 26:
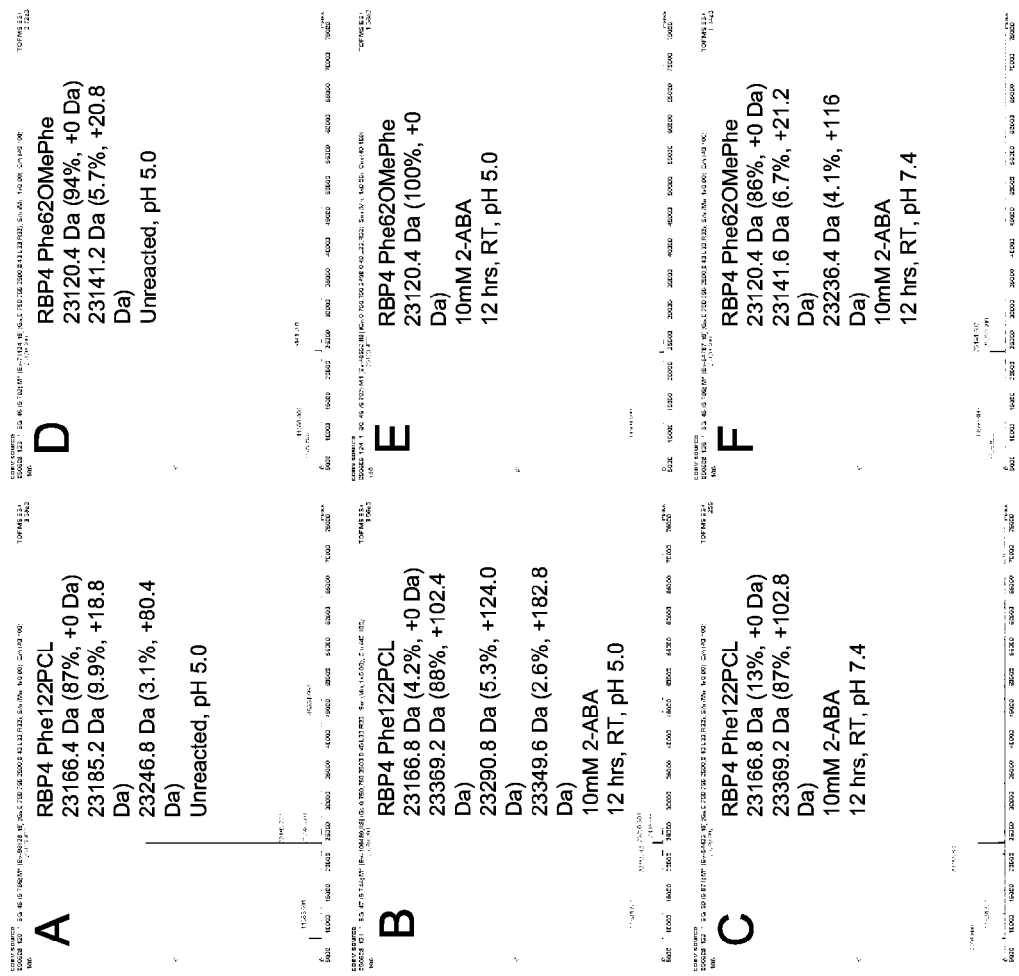
FIG. 26. Evaluation of the pH dependence of the derivatization of hRBP4 Phe122PCL with 2-ABA.

High-resolution mass spectrometric studies of the model protein hRBP4 verified the chemical derivatization of the PCL residue with 2-ABA, wherein the PCL was site specifically incorporated into the protein hRBP4 (FIGS. 25-26, see Example 11). FIG. 24 shows mass spectrometric analysis of hRBP4 Phe122PCL derivatized with 2-ABA, wherein the protein derivatized with 2-ABA results in the major peak at 23269.2 Da and a minimal amount of unmodified protein is detected at 23166.8 Da. The mass increase of 102.4 Da for the derivatized protein is consistent with the expected increase of 103 Da for the attachment of the 2-ABA moiety as shown in FIG. 23. Thus demonstrating that a protein with site specific incorporation of PCL is site-specifically modified at the PCL site. The MS/MS analysis (FIG. 25) obtained after LC-MS analysis of the tryptic digest of the 2-ABA-derivatized hRBP4 Phe122PCL protein identified the expected YWGVASF*LQK peptide, wherein F* has a mass consistent with that of an 2-ABA-modified PCL. FIG. 25A is the fragmentation pattern of the YWGVASF*LQK peptide, wherein F* has a mass consistent with that of a 2-ABA-modified PCL. FIG. 25B is the TIC (total ion chromatogram) and EIC (extracted ion chromatogram) of 2+ ions of YWGVASF*LQK (F*=PCL and PCL-2-ABA adduct), wherein comparison of the EICs for derivatized and underivatized (not detectable) species indicates completion of the reaction. FIG. 25C is the mass spectrometric analysis of hRBP4 Phe122PCL derivatized with 2-ABA showing 3+ and 2+ precursors of YWGVASF*LQK at m/z 459.92 (3+) and 689.37 (2+) respectively (F*=PCL-2-ABA adduct), thereby demonstrating that the observed reactions with 2-ABA occurs site-specifically with the PCL residue incorporated at the desired TAG site at residue 122.

Evaluation of the pH dependence of the derivatization is shown in FIG. 26. The mass spectrum of hRBP4 with PCL incorporated at position 122 (hRBP4 Phe122PCL) is shown in FIG. 26A, wherein the hRBP4 Phe122PCL has not been reacted with 2-ABA, while FIG. 26B and FIG. 26C are the mass spectra of hRBP4 Phe122PCL after reaction with 10 mM 2-ABA in acetate buffer, pH 5.0, and with 10 mM 2-ABA in phosphate buffer, pH 7.4, respectively. The reaction of the PCL residue of hRBP4 protein with 2-ABA proceeds rapidly with up to 95% completeness at room temperature in aqueous buffer adjusted to pH 5, and to a slightly lower extent, to approximately 87% at pH 7.4. The reaction with 2-ABA is selective for the PCL residue as seen in FIGS. 27D-F, wherein no reaction with 2-ABA was observed for hRBP4 labeled with O-methyl-phenylalanine (OMePhe), an inert unnatural amino acid, at position 62, and with a wild-type phenylalanine (Phe) residue at position 122.

Figure 27:
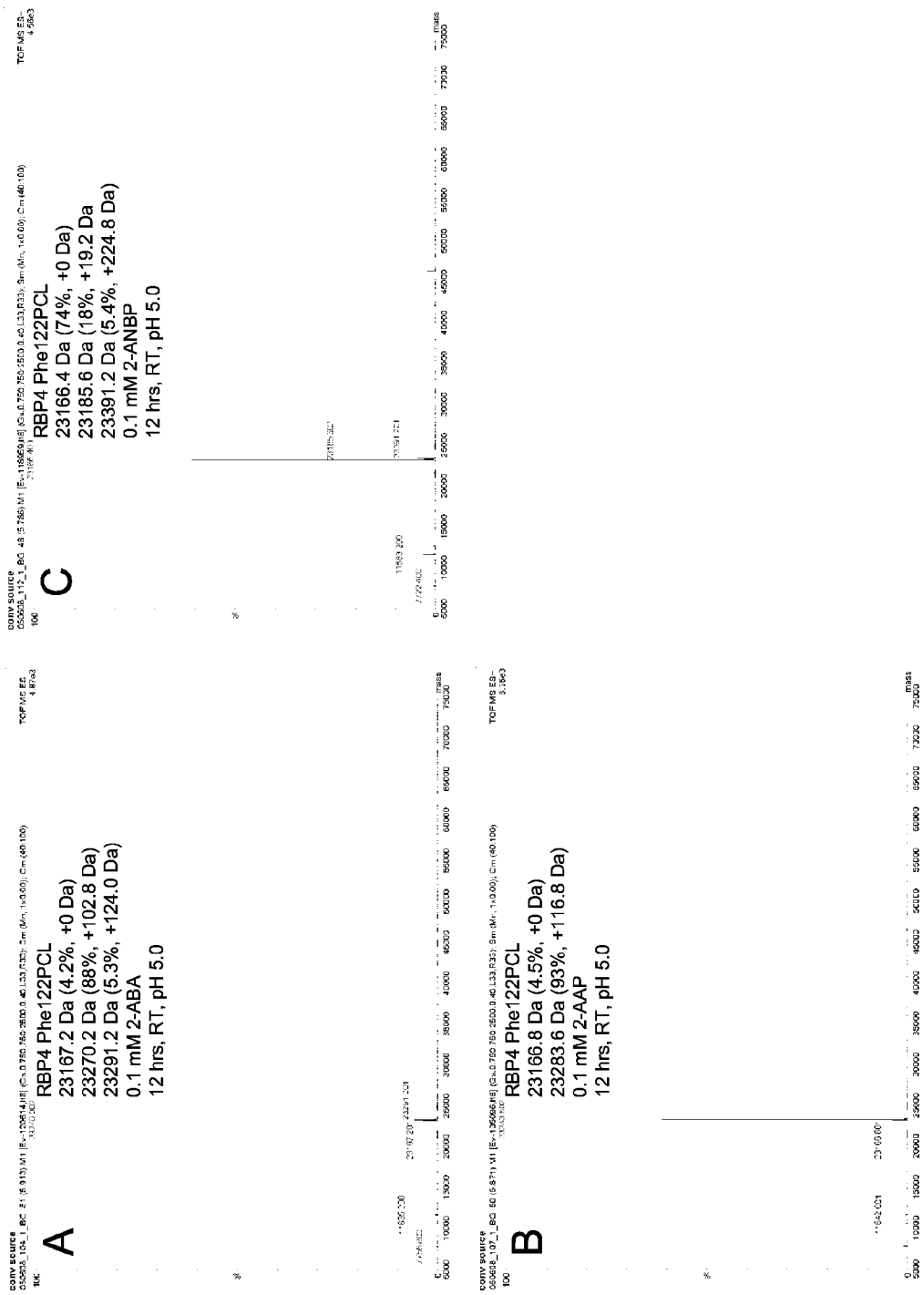
FIG. 27. Evaluation of the reaction efficiency as a function of the reactant to protein concentration ratio, and the reactivity with 2-ABA, 2-ANBP and 2-AAP.

Evaluation of the reaction efficiency as a function of the reactant to protein concentration ratio, and the reactivity with 2-ABA-like reactants is shown in FIG. 27. The mass spectra of hRBP4 with PCL incorporated at position 122 (hRBP4 Phe122PCL) after reaction with 0.1 mM 2-amino-benzaldehyde (2-ABA) is shown in FIG. 27A, while the mass spectra for hRBP4 Phe122PCL after reaction with 0.1 mM 2-amino-acetophenone (2-AAP) and 0.1 mM 2-amino-5-nitro-benzophenone (2-ANBP) are shown if FIG. 27B and FIG. 27C, respectively. All reactions were performed in 200 mM sodium acetate, pH 5.0. The protein conjugates are detected at the correct mass and with the expected mass increase as given in FIG. 23. In addition, yields of greater than 88% conversion for 2-ABA and 2-AAP were achieved, although because of low solubility a yield of about 5% was obtained for 2-ANBP. However, this demonstrates that 2-ABA analogues react efficiently at the PCL incorporation site at reactant to protein concentration ratios of 6 to 1. The extent of the reactions is only slightly lower than those performed at reactant to protein ratios of 600 to 1 (FIG. 26).

Figure 28:
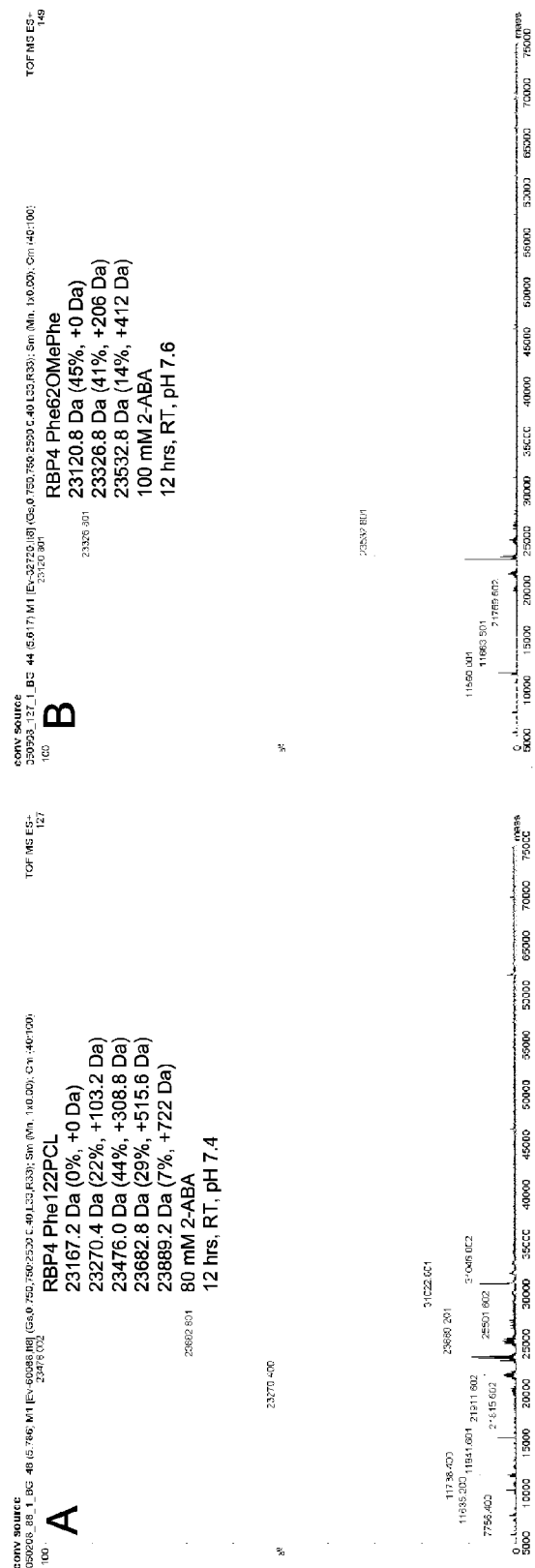
FIG. 28. Derivatization at molar ratios larger than 4700 (A: 4700 fold excess of 2-ABA over protein) and for OMePhe incorporated hRBP4 (B: 15400 fold excess).

When the derivatization agents were added at a final concentration range between 0.1 and 10 mM, corresponding to between 6 to 600 fold molar excess over protein, there was no significant improvement in the extent of derivatization. In addition, at molar ratios larger than 4700, additional protein residues, presumably lysines, are derivatized by 2-ABA (FIG. 28). In FIG. 28, a large excess of 2-ABA over protein in 10×PBS results in conjugation at additional sites for PCL incorporated hRBP4 (A, ~17 µM, 4700 fold excess of 2-ABA over protein) and for OMePhe incorporated hRBP4 (B, ~6.5 µM, 15400 fold excess) illustrating that conjugation at these additional sites is mediated by residues other than PCL.

Figure 29:
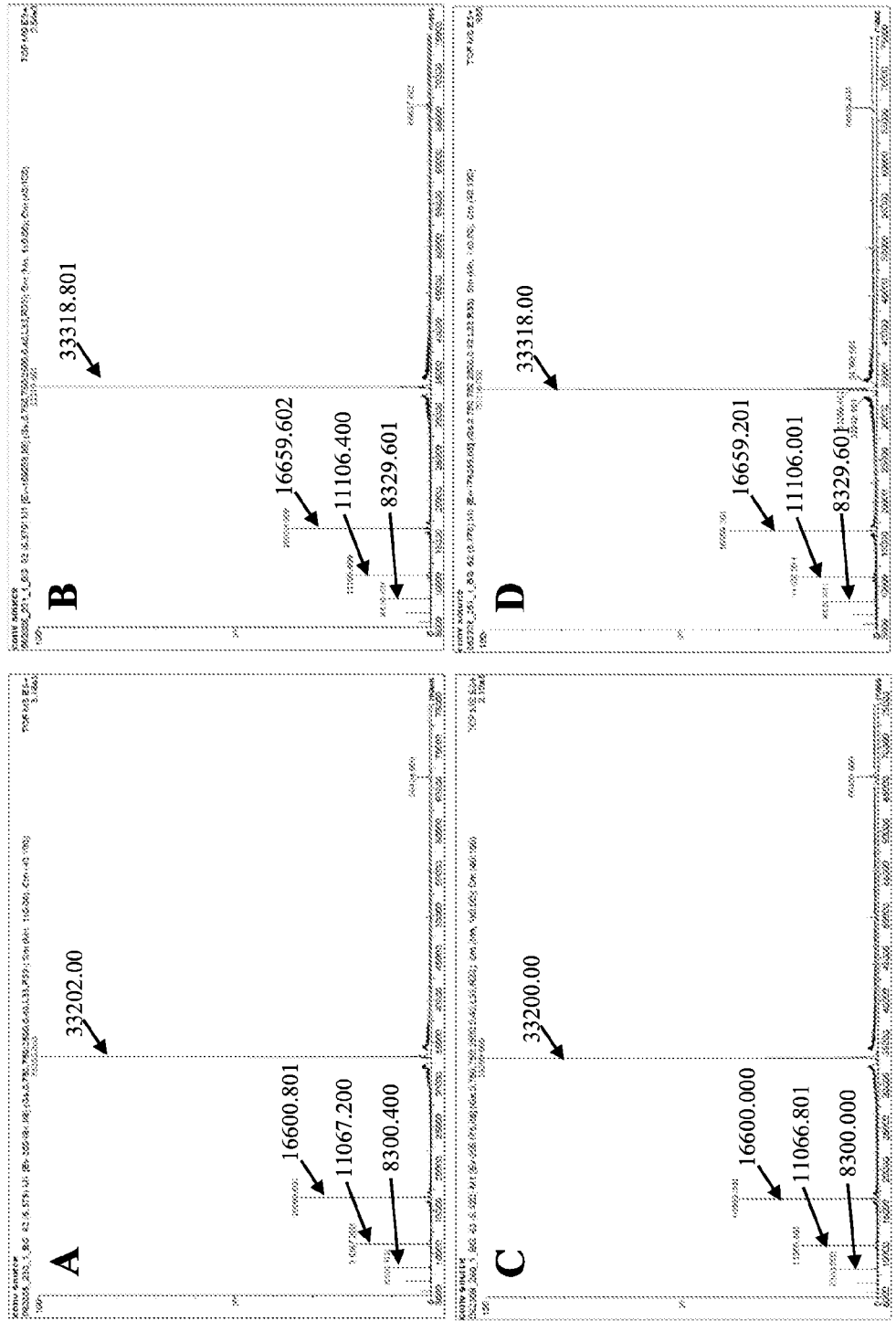
FIG. 29. Derivatization of FAS-TE Tyr2454PCL with 2-amino-acetophenone (2-AAP). Mass spectra of unreacted samples (A and C) and samples derivatized with 2-AAP at pH 5.0 (B) and pH 7.4 (D).

To further illustrate the utility of the methods provided herein, FIG. 29 shows the mass spectra before and after derivatization of PCL incorporated into FAS-TE with 2-amino-acetophenone (2-AAP) at pH 5.0 and pH 7.4 (see, Example 12). FIG. 29A shows the mass spectrum of unreacted FAS-TE Tyr2454PCL, while FIG. 29B shows the mass spectrum of the reaction mixture at pH 5.0. Here 100% of the observable peak intensity occurs at 33318.8 Da, which is 116.8 Da larger than that of unreacted material, as expected for the 117 Da mass increase anticipated for 2-AAP modified FAS-TE Tyr2454PCL. Similarly, at pH 7.4 the reaction goes to 95% completion (FIG. 29C (unreacted) and FIG. 29D (reacted)).

Figure 30:
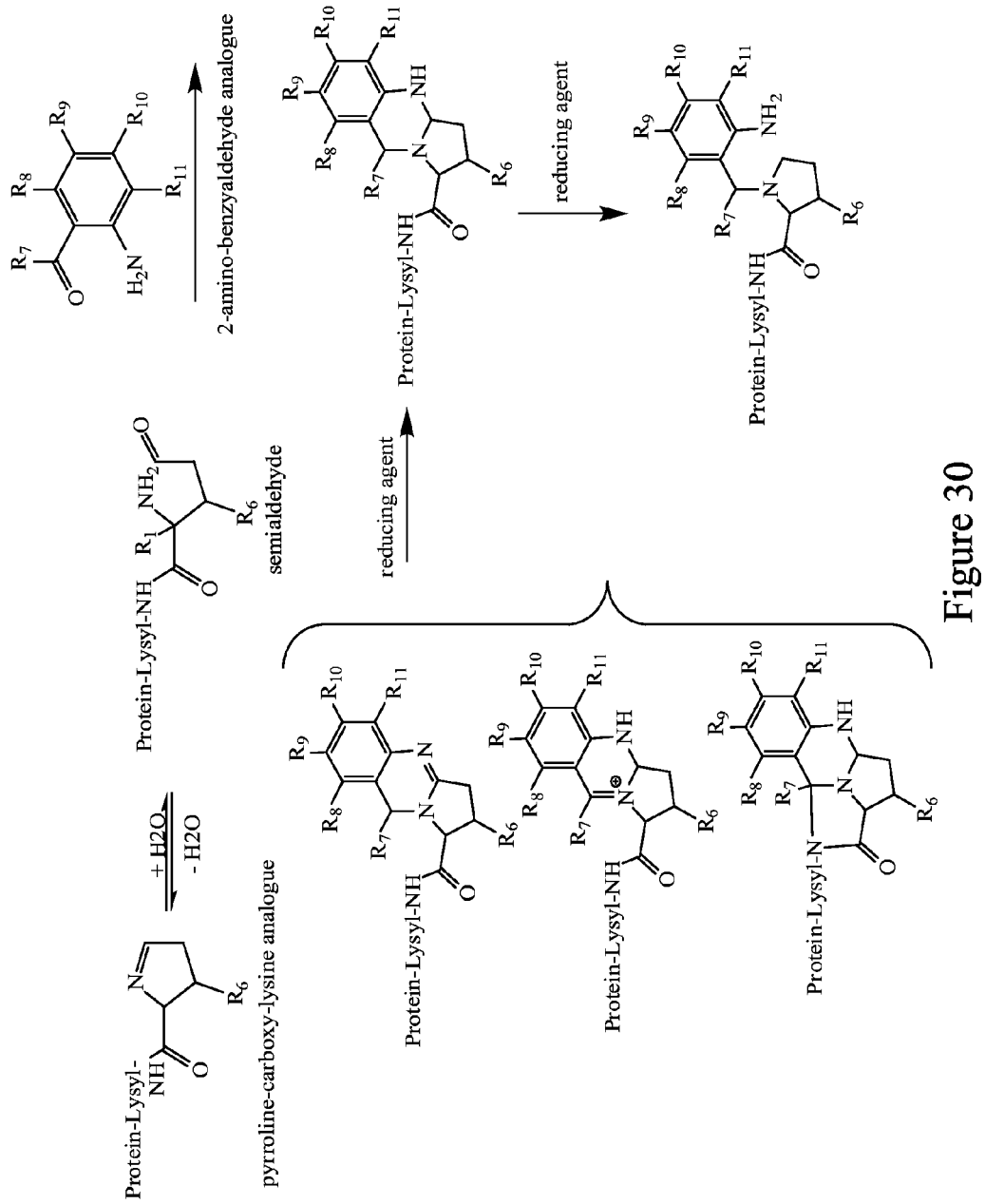
FIG. 30. General reaction scheme for site-specific modification of proteins via chemical derivatization of pyrrolysine and/or PCL with 2-amino-benzaldehyde or 2-amino-benzaldehyde analogues.

FIG. 30 is a general reaction scheme for site-specific modification of proteins via chemical derivatization of pyrrolysine and/or PCL with 2-amino-benzaldehyde or 2-amino-benzaldehyde analogues. Certain embodiments of such analogues are provided herein. The reaction of the pyrroline ring of pyrrolysine and PCL with 2-ABA is similar to the reaction of $\Delta^1$-pyrroline-5-carboxylic acid with 2-ABA. Similarly, reactions of pyrrolysine and PCL with 2-AAP and 2-ANBP result in proteins modified with the respective substituted moieties of FIG. 23.

In certain embodiments, the 2-ABA functionality is used to site-specifically attach various groups to proteins, polypeptides and/or peptides having pyrrolysine or PCL incorporated therein. Such groups include, but is not limited to, a label, a dye, a polymer, a water-soluble polymer, a polyalkylene glycol, a poly(ethylene glycol), a derivative of poly(ethylene glycol), a sugar, a lipid, a photocrosslinker, a cytotoxic compound, a drug, an affinity label, a photoaffinity label, a reactive compound; a resin, a peptide, a second protein or polypeptide or polypeptide analog, an antibody or antibody fragment, a metal chelator, a cofactor, a fatty acid, a carbohydrate, a polynucleotide, a DNA, a RNA, a PCR probe, an antisense polynucleotide, a ribo-oligonucleotide, a deoxyribo-oligonucleotide, phosphorothioate-modified DNA, modified DNA and RNA, a peptide nucleic acid, a saccharide, a disaccharide, an oligosaccharide, a polysaccharide, a water-soluble dendrimer, a cyclodextrin, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a ligand, a photoisomerizable moiety, biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chromophoric group, a chemiluminescent group, a fluorescent moiety, an electron dense group, a magnetic group, an intercalating group, a chelating group, a chromophore, an energy transfer agent, a biologically active agent, a detectable label, a small molecule, an inhibitory ribonucleic acid, an siRNA, a radionucleotide, a neutron-capture agent, a derivative of biotin, quantum dot(s), a nanotransmitter, a radiotransmitter, an abzyme, an enzyme, an activated complex activator, a virus, a toxin, an adjuvant, a TLR2 agonist, a TLR4 agonist, a TLR7 agonist, a TLR9 agonist, a TLR8 agonist, a T-cell epitope, a phospho-lipid, a LPS-like molecule, keyhole limpet hemocyanin (KLH), an immunogenic hapten, an aglycan, an allergen, an angiostatin, an antihormone, an antioxidant, an aptamer, a guide RNA, a saponin, a shuttle vector, a macromolecule, a mimotope, a receptor, a reverse micelle, detergents, immune response potentiators, fluorescence dyes, FRET reagents, radio-imaging probes, other spectroscopy probe, prodrugs, toxins for immunotherapy, a solid support, —$CH_2CH_2$—($OCH_2CH_2O)_p$—$OX^2$, —O—($CH_2CH_2O)_pCH_2CH_2$—$X^2$, and any combination thereof, wherein p is 1 to 10,000 and $X^2$ is H, a $C_{1-8}$alkyl, a protecting group or a terminal functional group.

In certain embodiments, the 2-AAP functionality is used to site-specifically attach various groups to proteins, polypeptides and/or peptides having pyrrolysine or PCL incorporated therein. Such groups include, but is not limited to, a label, a dye, a polymer, a water-soluble polymer, a polyalkylene glycol, a poly(ethylene glycol), a derivative of poly(ethylene glycol), a sugar, a lipid, a photocrosslinker, a cytotoxic compound, a drug, an affinity label, a photoaffinity label, a reactive compound; a resin, a peptide, a second protein or polypeptide or polypeptide analog, an antibody or antibody fragment, a metal chelator, a cofactor, a fatty acid, a carbohydrate, a polynucleotide, a DNA, a RNA, a PCR probe, an antisense polynucleotide, a ribo-oligonucleotide, a deoxyribo-oligonucleotide, phosphorothioate-modified DNA, modified DNA and RNA, a peptide nucleic acid, a saccharide, a disaccharide, an oligosaccharide, a polysaccharide, a water-soluble dendrimer, a cyclodextrin, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a ligand, a photoisomerizable moiety, biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chromophoric group, a chemiluminescent group, a fluorescent moiety, an electron dense group, a magnetic group, an intercalating group, a chelating group, a chromophore, an energy transfer agent, a biologically active agent, a detectable label, a small molecule, an inhibitory ribonucleic acid, an siRNA, a radionucleotide, a neutron-capture agent, a derivative of biotin, quantum dot(s), a nanotransmitter, a radiotransmitter, an abzyme, an enzyme, an activated complex activator, a virus, a toxin, an adjuvant, a TLR2 agonist, a TLR4 agonist, a TLR7 agonist, a TLR9 agonist, a TLR8 agonist, a T-cell epitope, a phospho-lipid, a LPS-like molecule, keyhole limpet hemocyanin (KLH), an immunogenic hapten, an aglycan, an allergen, an angiostatin, an antihormone, an antioxidant, an aptamer, a guide RNA, a saponin, a shuttle vector, a macromolecule, a mimotope, a receptor, a reverse micelle, detergents, immune response potentiators, fluorescence dyes, FRET reagents, radio-imaging probes, other spectroscopy probe, prodrugs, toxins for immunotherapy, a solid support, —$CH_2CH_2$—($OCH_2CH_2O)_p$—$OX^2$, —O—($CH_2CH_2O)_pCH_2CH_2$—$X^2$, and any combination thereof, wherein p is 1 to 10,000 and $X^2$ is H, a $C_{1-8}$alkyl, a protecting group or a terminal functional group.

In certain embodiments, the 2-ANPA functionality is used to site-specifically attach various groups to proteins, polypeptides and/or peptides having pyrrolysine or PCL incorporated therein. Such groups include, but is not limited to, a label, a dye, a polymer, a water-soluble polymer, a polyalkylene glycol, a poly(ethylene glycol), a derivative of poly(ethylene glycol), a sugar, a lipid, a photocrosslinker, a cytotoxic compound, a drug, an affinity label, a photoaffinity label, a reactive compound; a resin, a peptide, a second protein or polypeptide or polypeptide analog, an antibody or antibody fragment, a metal chelator, a cofactor, a fatty acid, a carbohydrate, a polynucleotide, a DNA, a RNA, a PCR probe, an antisense polynucleotide, a ribo-oligonucleotide, a deoxyribo-oligonucleotide, phosphorothioate-modified DNA, modified DNA and RNA, a peptide nucleic acid, a saccharide, a disaccharide, an oligosaccharide, a polysaccharide, a water-soluble dendrimer, a cyclodextrin, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a ligand, a photoisomerizable moiety, biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chromophoric group, a chemiluminescent group, a fluorescent moiety, an electron dense group, a magnetic group, an intercalating group, a chelating group, a chromophore, an energy transfer agent, a biologically active agent, a detectable label, a small molecule, an inhibitory ribonucleic acid, an siRNA, a radionucleotide, a neutron-capture agent, a derivative of biotin, quantum dot(s), a nanotransmitter, a radiotransmitter, an abzyme, an enzyme, an activated complex activator, a virus, a toxin, an adjuvant, a TLR2 agonist, a TLR4 agonist, a TLR7 agonist, a TLR9 agonist, a TLR8 agonist, a T-cell epitope, a phospho-lipid, a LPS-like molecule, keyhole limpet hemocyanin (KLH), an immunogenic hapten, an aglycan, an allergen, an angiostatin, an antihormone, an antioxidant, an aptamer, a guide RNA, a saponin, a shuttle vector, a macromolecule, a mimotope, a receptor, a reverse micelle, detergents, immune response potentiators, fluorescence dyes, FRET reagents, radio-imaging probes, other spectroscopy probe, prodrugs, toxins for immunotherapy, a solid support, —$CH_2CH_2$—($OCH_2CH_2O)_p$—$OX^2$, —O—($CH_2CH_2O)_pCH_2CH_2$—$X^2$, and any combination thereof, wherein p is 1 to 10,000 and $X^2$ is H, a $C_{1-8}$alkyl, a protecting group or a terminal functional group.

Any of the attachment points $R_7$ to $R_{11}$ shown in FIG. 30 are used to attach any of these aforementioned groups to 2-ABA, 2-AAP and 2-ANPA. In other embodiments the benzene ring is replaced by any other ring structure provided herein, including but not limited to naphthalene. In other embodiments the benzene ring is replaced by sugars.

The concentration of the derivatization agent used in the methods provided herein for the derivatization of pyrrolysine and PCL, incorporated into proteins, polypeptides and/or peptides, is in the range of about 0.005 mM to about 50 mM. In certain embodiments, the concentration of the derivatization agent used in the methods provided herein for the derivatization of pyrrolysine or PCL is in the range of about 0.005 mM to about 25 mM. In certain embodiments, the concentration of the derivatization agent used in the methods provided herein for the derivatization of pyrrolysine or PCL is in the range of about 0.005 mM to about 10 mM. In certain embodiments, the concentration of the derivatization agent used in the methods provided herein for the derivatization of pyrrolysine or PCL is in the range of about 0.005 mM to about 5 mM. In certain embodiments, the concentration of the derivatization agent used in the methods provided herein for the derivatization of pyrrolysine or PCL is in the range of about 0.005 mM to about 2 mM. In certain embodiments, the concentration of the derivatization agent used in the methods provided herein for the derivatization of pyrrolysine or PCL is in the range of about 0.005 mM to about 1 mM.

In the derivatization methods provided herein, the molar ratio of the derivatization agent to the proteins, polypeptides or peptides having one or more pyrrolysine or PCL incorporated therein, is in the range of about 0.05 to about 10000. In certain embodiments, the molar ratio of the derivatization agent to such proteins, polypeptides or peptides is in the range of about 0.05 to about 8000. In certain embodiments, the molar ratio of the derivatization agent to such proteins, polypeptides or peptides is in the range of about 0.05 to about 6000. In certain embodiments, the molar ratio of the derivatization agent to such proteins, polypeptides or peptides is in the range of about 0.05 to about 4000. In certain embodiments, the molar ratio of the derivatization agent to such proteins, polypeptides or peptides is in the range of about 0.05 to about 2000. In certain embodiments, the molar ratio of the derivatization agent to such proteins, polypeptides or peptides is in the range of about 0.05 to about 1000. In certain embodiments, the molar ratio of the derivatization agent to such proteins, polypeptides or peptides is in the range of about 0.05 to about 800. In certain embodiments, the molar ratio of the derivatization agent to such proteins, polypeptides or peptides is in the range of about 0.05 to about 600. In certain embodiments, the molar ratio of the derivatization agent to such proteins, polypeptides or peptides is in the range of about 0.05 to about 400. In certain embodiments, the molar ratio of the derivatization agent to such proteins, polypeptides or peptides is in the range of about 0.05 to about 200. In certain embodiments, the molar ratio of the derivatization agent to such proteins, polypeptides or peptides is in the range of about 0.05 to about 100. In certain embodiments, the molar ratio of the derivatization agent to such proteins, polypeptides or peptides is in the range of about 0.05 to about 50. In certain embodiments, the molar ratio of the derivatization agent to such proteins, polypeptides or peptides is in the range of about 0.05 to about 25. In certain embodiments, the molar ratio of the derivatization agent to such proteins, polypeptides or peptides is in the range of about 0.05 to about 10. In certain embodiments, the molar ratio of the derivatization agent to such proteins, polypeptides or peptides is in the range of about 0.05 to about 1.

In still other embodiments, the molar ratio of the derivatization agent to such proteins, polypeptides or peptides is in the range of about 1.5 to about 10000. In certain embodiments, the molar ratio of the derivatization agent to such proteins, polypeptides or peptides is in the range of about 1.5 to about 8000. In certain embodiments, the molar ratio of the derivatization agent to such proteins, polypeptides or peptides is in the range of about 1.5 to about 6000. In certain embodiments, the molar ratio of the derivatization agent to such proteins, polypeptides or peptides is in the range of about 1.5 to about 4000. In certain embodiments, the molar ratio of the derivatization agent to such proteins, polypeptides or peptides is in the range of about 1.5 to about 2000. In certain embodiments, the molar ratio of the derivatization agent to such proteins, polypeptides or peptides is in the range of about 1.5 to about 1000. In certain embodiments, the molar ratio of the derivatization agent to such proteins, polypeptides or peptides is in the range of about 1.5 to about 800. In certain embodiments, the molar ratio of the derivatization agent to such proteins, polypeptides or peptides is in the range of about 1.5 to about 600. In certain embodiments, the molar ratio of the derivatization agent to such proteins, polypeptides or peptides is in the range of about 1.5 to about 400. In certain embodiments, the molar ratio of the derivatization agent to such proteins, polypeptides or peptides is in the range of about 1.5 to about 200. In certain embodiments, the molar ratio of the derivatization agent to such proteins, polypeptides or peptides is in the range of about 1.5 to about 100. In certain embodiments, the molar ratio of the derivatization agent to such proteins, polypeptides or peptides is in the range of about 1.5 to about 50. In certain embodiments, the molar ratio of the derivatization agent to such proteins, polypeptides or peptides is in the range of about 1.5 to about 25. In certain embodiments, the molar ratio of the derivatization agent to such proteins, polypeptides or peptides is in the range of about 1.5 to about 10. In certain embodiments, the molar ratio of the derivatization agent to such proteins, polypeptides or peptides is in the range of about 6 to about 600.

The pH of the buffer solution used in the derivatization of proteins, polypeptides and/or peptides using the methods and compositions provided herein is from about pH 2 to about pH 10. In certain embodiments, the pH is from about pH 4 to about pH 8. In certain embodiments, the pH is from about pH 4 to about pH 7.5. In certain embodiments, the pH is from about pH 4 to about pH 7. In certain embodiments, the pH is from about pH 4 to about pH 6.5. In certain embodiments, the pH is from about pH 4 to about pH 6. In certain embodiments, the pH is from about pH 4 to about pH 5.5. In certain embodiments, the pH is from about pH 4 to about pH 5. In certain embodiments, the pH is from about pH 4 to about pH 4.5. In certain embodiments, the pH is from about pH 6 to about pH 8. In certain embodiments, the pH is from about pH 6 to about pH 7.5. In certain embodiments, the pH is from about pH 6 to about pH 7. In certain embodiments, the pH is from about pH 6 to about pH 6.5. In certain embodiments, the pH is from about pH 7 to about pH 8. In certain embodiments, the pH is from about pH 7 to about pH 7.5.

The derivatization methods provided herein are useful for the derivatization of pyrrolysine or PCL site specifically incorporated into proteins. In certain embodiments, such derivatization methods are used for derivatization of a PCL residue incorporated at a single site in a protein, polypeptide and/or peptide. In other embodiments, such derivatization methods are used for derivatization of a PCL residue incorporated at multiple sites in a protein, polypeptide and/or peptide. In certain embodiments, the protein, polypeptide or peptides derivatized using the methods and compositions provided herein contain 1, 2, 3, 4, 5, 6, 7, 6, 9, 10, 11, 12, 13, 14, 15 or more pyrrolysine or pyrrolysine analogues.

In another aspect provided herein, the proteins, polypeptides and peptides having one or more pyrrolysine or PCL incorporated therein are derivatized by at least one co-translational or post-translational modification. Non-limiting examples of such co-translational or post-translational modifications include, but are not limited to, glycosylation, acetylation, acylation, methylation, nitration, sulfation, lipid-modification, palmitoylation, palmitate addition, phosphorylation, glycolipid-linkage modification, and the like. Also included with this aspect are methods for producing, purifying, characterizing and using such proteins, polypeptides and peptides containing at least one such co-translational or post-translational modification.

Biotherapeutics with Site-Specific Modifications
Macromolecular Polymers Coupled to PCL and Pyrrolysine Incorporated into Proteins, Polypeptides and/or Peptides In certain embodiments, the compositions, methods, techniques and strategies described herein, are used to add macromolecular polymers to pyrrolysine or PCL residues incorporated into proteins, polypeptides and/or peptides. A wide variety of macromolecular polymers can be coupled to pyrrolysine and PCL residues incorporated into proteins, polypeptides and/or peptides described herein. Such modifications are used to modulate the biological properties of such proteins, polypeptides and/or peptides, and/or provide new biological properties to such proteins, polypeptides and/or peptides. In certain embodiments, the macromolecular polymers are coupled to the proteins, polypeptides and/or peptides provided herein via direct coupling to the pyrrolysine or PCL residue(s) incorporated into such proteins, polypeptides and/or peptides. In other embodiments, the macromolecular polymers are coupled to the proteins, polypeptides and/or peptides provided herein via bi-, tri-, tetra-, and polyfunctional linkers coupled to the pyrrolysine or PCL residue(s). In other embodiments, the macromolecular polymers are coupled to the proteins, polypeptides and/or peptides provided herein via bi-functional linkers coupled to the pyrrolysine or PCL residue(s). In certain embodiments, such bi-, tri-, tetra- and polyfunctional linkers are monofunctional linkers wherein all termini are substituents that are specific for reaction with pyrrolysine or PCL residues. In certain embodiments, such bi-, tri-, tetra- and polyfunctional linkers are heterobifunctional linkers wherein one or more termini are a substituent that is specific for reaction with pyrrolysine or PCL residue(s), while the other termini are another functional substituent that does not react with pyrrolysine or PCL residue(s). Certain substituents that are pyrrolysine or PCL specific reactive groups are provided herein, and the other functional substituent and the resulting linkages, that are used in such bi-, tri, tetra- and polyfunctional linkers include, but are not limited to, those listed in Table 1.

TABLE 1

| Electrophile | Nucleophile | Covalent Linkage |
| --- | --- | --- |
| Activated esters | Amines/anilines | Carboxamides |
| Acyl azides | Amines/anilines | Carboxamides |
| Acyl halides | Amines/anilines | Carboxamides |
| Acyl halides | Alcohols/phenols | Esters |
| Acyl nitriles | Alcohols/phenols | Esters |
| Acyl nitriles | Amines/anilines | Carboxamides |
| Aldehydes | Amines/anilines | Imines |
| Aldehydes or ketones | Hydrazines | Hydrazones |
| Aldehydes or ketones | Hydroxylamines | Oximes |
| Alkyl halides | Amines/anilines | Alkyl amines |
| Alkyl halides | Carboxylic acids | Esters |
| Alkyl halides | Thiols | Thioethers |
| Alkyl halides | Alcohols/phenols | Ethers |
| Alkyl sulfonates | Thiols | Thioethers |
| Alkyl sulfonates | Carboxylic acids | Esters |
| Alkyl sulfonates | Alcohols/phenols | Ethers |
| Anhydrides | Alcohols/phenols | Esters |
| Anhydrides | Amines/anilines | Carboxamides |
| Aryl halides | Thiols | Thiophenols |
| Aryl halides | Amines | Aryl amines |
| Azindines | Thiols | Thioethers |
| Boronates | Glycols | Boronates esters |
| Carboxylic acids | Amines/anilines | Carboxamides |
| Carboxylic acids | Alcohols | Esters |
| Hydrazides | Carboxylic acids | Hydrazines |
| Carbodiimides | Carboxylic acids | N-acylureas or anhydrides |
| Diazoalkanes | Carboxylic acids | Esters |
| Epoxides | Thiols | Thioethers |
| Haloacetamides | Thiols | Thioethers |
| Halotriazines | Amines/anilines | Aminotriazines |
| Halotriazines | Alcohols/phenols | Triazinyl ethers |
| Imido esters | Amines/anilines | Amidines |
| Isocyanates | Amines/anilines | Ureas |
| Isocyanates | Alcohols/phenols | Yrethanes |
| Isothiocyanates | Amines/anilines | Thioureas |
| Maleimides | Thiols | Thioethers |
| Phosphoramidites | Alcohols | Phosphate esters |
| Silyl halides | Alcohols | Silyl ethers |
| Sulfonate esters | Amines/anilines | Alkyl amines |
| Sulfonate esters | Thiols | Thioethers |
| Sulfonate esters | Carboxylic acids | Esters |
| Sulfonate esters | Alcohols | Ethers |
| Sulfonyl halides | Amines/anilines | Sulfonamides |
| Sulfonyl halides | Alcohols/phenols | Sulfonate esters |

The covalent attachment of macromolecular polymers to a biologically active molecule, such the proteins, polypeptides and/or peptides provided herein, represents an approach to increasing water solubility (such as in a physiological environment), bioavailability, increasing serum half-life, increasing therapeutic half-life, modulating immunogenicity, modulating biological activity, or extending the circulation time of such biologically active molecules. Important features of such macromolecular polymers include biocompatibility, lack of toxicity, and lack of immunogenicity, and for therapeutic uses of the proteins, polypeptides and/or peptides provided herein that are coupled to macromolecular polymers via pyrrolysine or PCL residue, such macromolecular polymers are pharmaceutically acceptable.

Certain macromolecular polymers coupled to the pyrrolysine or PCL residue(s) incorporated into proteins, polypeptides and/or peptides described herein are water-soluble polymers. In certain embodiments, such water-soluble polymers are coupled via pyrrolysine or PCL residue(s) incorporated into proteins, polypeptides and/or peptides provided herein, while in other embodiments such water-soluble polymers are coupled to the proteins, polypeptides and/or peptides provided herein via any functional group or substituent coupled to pyrrolysine or PCL residue(s) incorporated into such proteins, polypeptides and/or peptides. In some embodiments, the proteins, polypeptides and/or peptides provided herein include one or more PCL residues coupled to water-soluble polymers and one or more naturally-occurring amino acids linked to water-soluble polymers.

The structural forms of the macromolecular polymers coupled to pyrrolysine or PCL residues incorporated into proteins, polypeptides and/or peptides include, but are not limited to, linear, forked or branched polymers. In certain embodiments, the backbones of such branched or forked water-soluble polymers have from 2 to about 300 termini. In certain embodiments, each terminus of such multi-functional polymer derivatives, including, but not limited to, linear polymers having two termini, includes a functional group. In certain embodiments such functional groups are the same, while in other embodiments such functional groups are different. Non-limiting examples of such terminal functional groups include, but are not limited to, N-succinimidyl carbonates, amines, hydrazides, succinimidyl propionates and succinimidyl butanoates, succinimidyl succinates, succinimidyl esters, benzotriazole carbonates, glycidyl ethers, oxycarbonylimidazoles, p-nitrophenyl carbonates, aldehydes, maleimides, orthopyridyl-disulfides, acrylols and vinylsulfones. In other embodiments, the functional groups include those listed in Table 1.

The covalent attachment of water-soluble polymers (also referred to herein as hydrophilic polymers) to a biologically active molecule, such the proteins, polypeptides and/or peptides provided herein, represents an approach for increasing water solubility (such as in a physiological environment), bioavailability, increasing serum half-life, increasing therapeutic half-life, modulating immunogenicity, modulating biological activity, or extending the circulation time of such biologically active molecules. Important features of such water soluble polymers include biocompatibility, lack of toxicity, and lack of immunogenicity, and for therapeutic uses of the proteins, polypeptides and/or peptides provided herein that are coupled to water-soluble polymers via pyrrolysine or PCL residues, such macromolecular polymers are pharmaceutically acceptable.

Hydrophilic polymers coupled to proteins, polypeptides and/or peptides via pyrrolysine or PCL residues include, but are not limited to, polyalkyl ethers and alkoxy-capped analogues thereof, polyvinylpyrrolidones, polyvinylalkyl ethers, polyoxazolines, polyalkyl oxazolines, polyhydroxyalkyl oxazolines, polyacrylamides, polyalkyl acrylamides, polyhydroxyalkyl acrylamides, polyhydroxyalkyl acrylates, polysialic acids and analogues thereof, hydrophilic peptide sequences; polysaccharides and their derivatives, cellulose and its derivatives, chitin and its derivatives, hyaluronic acid and its derivatives, starches, alginates, chondroitin sulfate, albumin, pullulan, carboxymethyl pullulan, polyaminoacids and derivatives thereof, maleic anhydride copolymers, polyvinyl alcohols and copolymers thereof, polyvinyl alcohols and terpolymers thereof, and combinations thereof.

Such polyalkyl ethers and alkoxy-capped analogues thereof include, but are not limited to, polyoxyethylene glycol (also known as poly(ethylene glycol) or PEG), polyoxyethylene/propylene glycol, and methoxy or ethoxy-capped analogues thereof. Such polyhydroxyalkyl acrylamides include, but are not limited to, polyhydroxypropylmethacrylamide and derivatives thereof. Such polysaccharides and derivatives thereof include, but are not limited to, dextran and dextran derivatives (such as, by way of example only, carboxymethyldextran, dextran sulfates and aminodextran). Such cellulose and derivatives thereof include, but are not limited to, carboxymethyl cellulose and hydroxyalkyl celluloses. Such chitin and derivatives thereof include, but are not limited to, chitosan, succinyl chitosan, carboxymethylchitin and carboxymethylchitosan. Such polyaminoacids and derivatives thereof, include, but are not limited to, polyglutamic acids, polylysines, polyaspartic acids and polyaspartamides. Such maleic anhydride copolymers include, but are not limited to, styrene maleic anhydride copolymer and divinylethyl ether maleic anhydride copolymer.

In some embodiments, the water-soluble polymer coupled directly or indirectly to a proteins, polypeptides and/or peptides provided herein via pyrrolysine or PCL residue(s) incorporated into such proteins, polypeptides and/or peptides is a poly(ethylene glycol) (PEG). Poly(ethylene glycol) is considered to be biocompatible, wherein PEG is capable of coexistence with living tissues or organisms without causing harm. PEG is also substantially non-immunogenic and therefore does not tend to produce an immune response in the body. PEG is a hydrophilic polymer that has been used extensively in pharmaceuticals, on artificial implants, and in other applications where biocompatibility, lack of toxicity, and lack of immunogenicity are of importance. PEG conjugates tend not to produce a substantial immune response or cause clotting or other undesirable effects. Thus, when attached to a molecule having some desirable function in the body, such as a biologically active agent, PEG tends to mask the agent and can reduce or eliminate any immune response so that an organism can tolerate the presence of the agent.

In some embodiments, the poly(ethylene glycol) coupled directly or indirectly to a proteins, polypeptides and/or peptides provided herein via pyrrolysine or PCL residue(s) incorporated into such proteins, polypeptides and/or peptides is a straight chain polymer, while in other embodiments such PEG polymers are branched polymers. The molecular weight or molecular weight distribution of such straight chain and branched PEG polymers is between about 100 Da and about 100,000 Da or more. In some embodiments, the molecular weight or molecular weight distribution of such PEG polymers is between about 100 Da and 50,000 Da. In some embodiments, the molecular weight or molecular weight distribution of such PEG polymers is between about 100 Da and 40,000 Da. In some embodiments, molecular weight or molecular weight distribution of such PEG polymers is between about 1,000 Da and 40,000 Da. In some embodiments, the molecular weight or molecular weight distribution of such PEG polymers is between about 5,000 Da and 40,000 Da. In some embodiments, the molecular weight or molecular weight distribution of such PEG polymers is between about 10,000 Da and 40,000 Da. In certain embodiments the molecular weight of such PEG polymers is 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, or 100 Da.

The structural forms of the PEG polymers coupled to pyrrolysine or PCL residue(s) incorporated into proteins, polypeptides and/or peptides include, but are not limited to, linear, forked or branched. In certain embodiments, the backbones of such branched or forked PEG polymers have from 2 to about 300 termini. In certain embodiments, each terminus of such multi-functional polymer derivatives, including, but not limited to, linear polymers having two termini, includes a functional group. In certain embodiments such functional groups are the same, while in other embodiments at least one of such functional groups is different. In still other embodiments such functional groups are different.

In certain embodiments prior to coupling to proteins, polypeptides and/or peptides, one or more termini of the PEG polymer include a functional group. In certain embodiments, the PEG is a linear polymer with one terminus having a functional group, wherein in other embodiments the PEG is a linear polymer with each terminus having a functional group, thereby forming a bi-functional PEG polymer. In other embodiments, the PEG is a forked polymer with one terminus having a functional group, wherein in other embodiments the PEG is a forked polymer with two or more termini having a functional group. In still other embodiments, the PEG is a forked polymer with each terminus having a functional group, thereby forming a multi-functional PEG polymer. In other embodiments, the PEG is a branched polymer with one terminus having a functional group, wherein in other embodiments the PEG is a branched polymer with two or more termini having a functional group. In still other embodiments, the PEG is a branched polymer with each terminus having a functional group, thereby forming a multi-functional PEG polymer. In certain embodiments of such aforementioned PEG polymers the functional groups are the same, while in other embodiments of such functional groups at least one functional group is different. In still other embodiments of such aforementioned PEG polymers the functional groups are different. However, at least one terminus of the PEG polymers is available for reaction with at least one pyrrolysine or PCL residue incorporated into a protein, polypeptide and/or peptide.

Non-limiting examples of terminal functional groups include, but are not limited to, N-succinimidyl carbonates, amines, hydrazides, succinimidyl propionates, succinimidyl butanoates, succinimidyl succinates, succinimidyl esters, benzotriazole carbonates, glycidyl ethers, oxycarbonylimidazoles, p-nitrophenyl carbonates, aldehydes, maleimides, orthopyridyl-disulfides, acrylols, vinylsulfones, activated carbonates (including but not limited to, p-nitrophenyl ester), activated esters (including but not limited to, N-hydroxysuccinimide, p-nitrophenyl ester), oximes, carbonyls, dicarbonyls, hydroxylamines, hydroxyl, methoxy, benzaldehydes, acetophenones, 2-amino-benzaldehydes, 2-amino-acetophenones and 2-amino-5-nitro-benzophenones.

Figure 31:
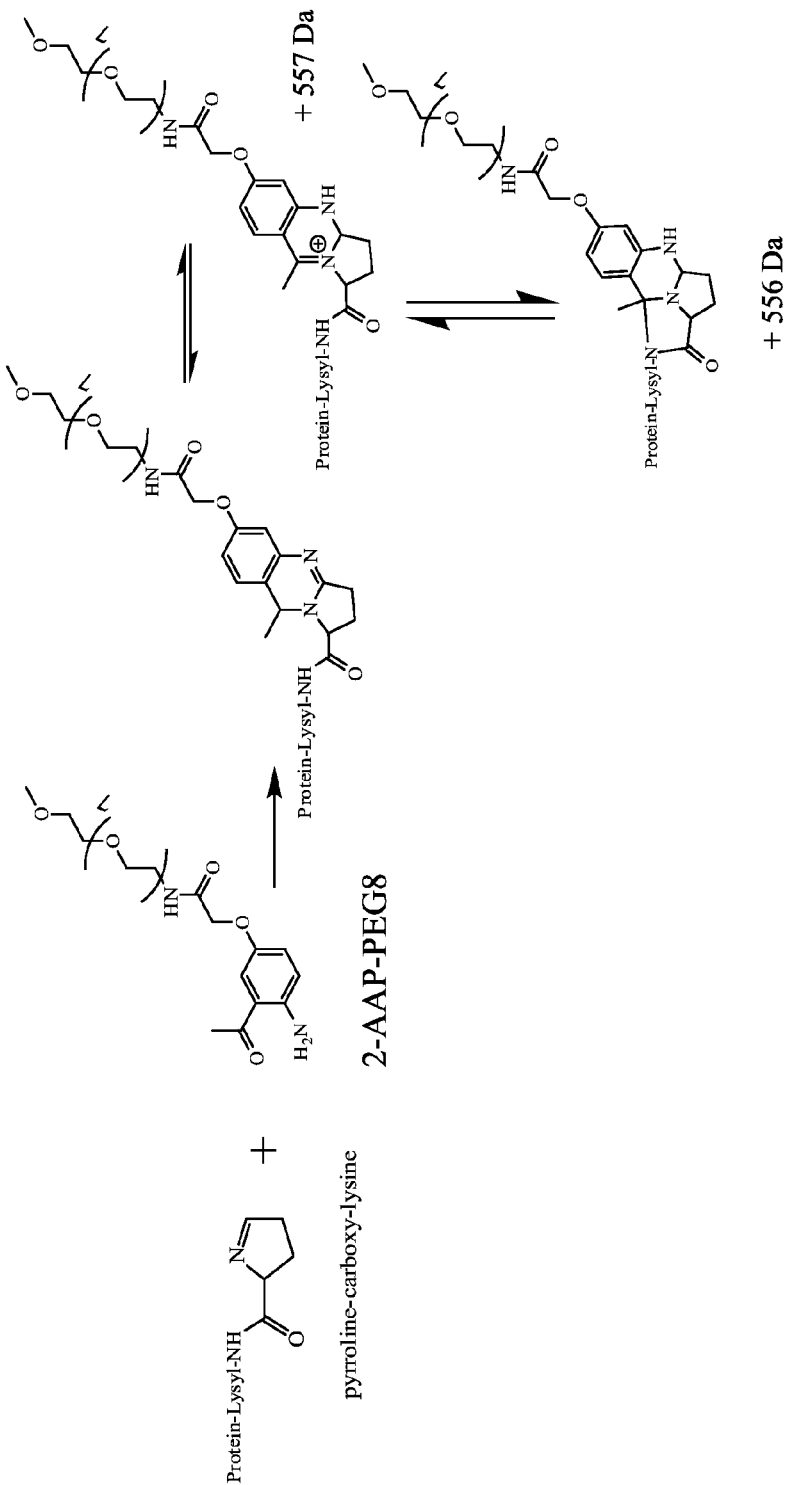
FIG. 31. Illustration of one embodiment of a functionalized PEG polymer, 2-amino-acetophenones-PEG$_8$ (2-AAP-PEG8; TU3205-044), coupled to proteins via a PCL residue incorporated into a protein.

FIG. 31 illustrates one embodiment of a functionalized PEG polymer, 2-amino-acetophenones-$PEG_8$ (2-AAP-PEGS; TU3205-044), coupled to proteins via at least one PCL residue incorporated into such proteins. As shown the 2-amino-acetophenone moiety of 2-AAP-PEG8 forms a quinazoline-type moiety as a spacer between the $PEG_8$ and the protein. This quinazoline-type moiety can further react to form the fused ring structure. In the case of the coupling of 2-AAP-PEG8, such a derivatization adds 556 Da to the mass of the protein. Other functionalized PEGs used in the methods provide herein include, but are not limited to, those given in Example 20.

Figure 32:
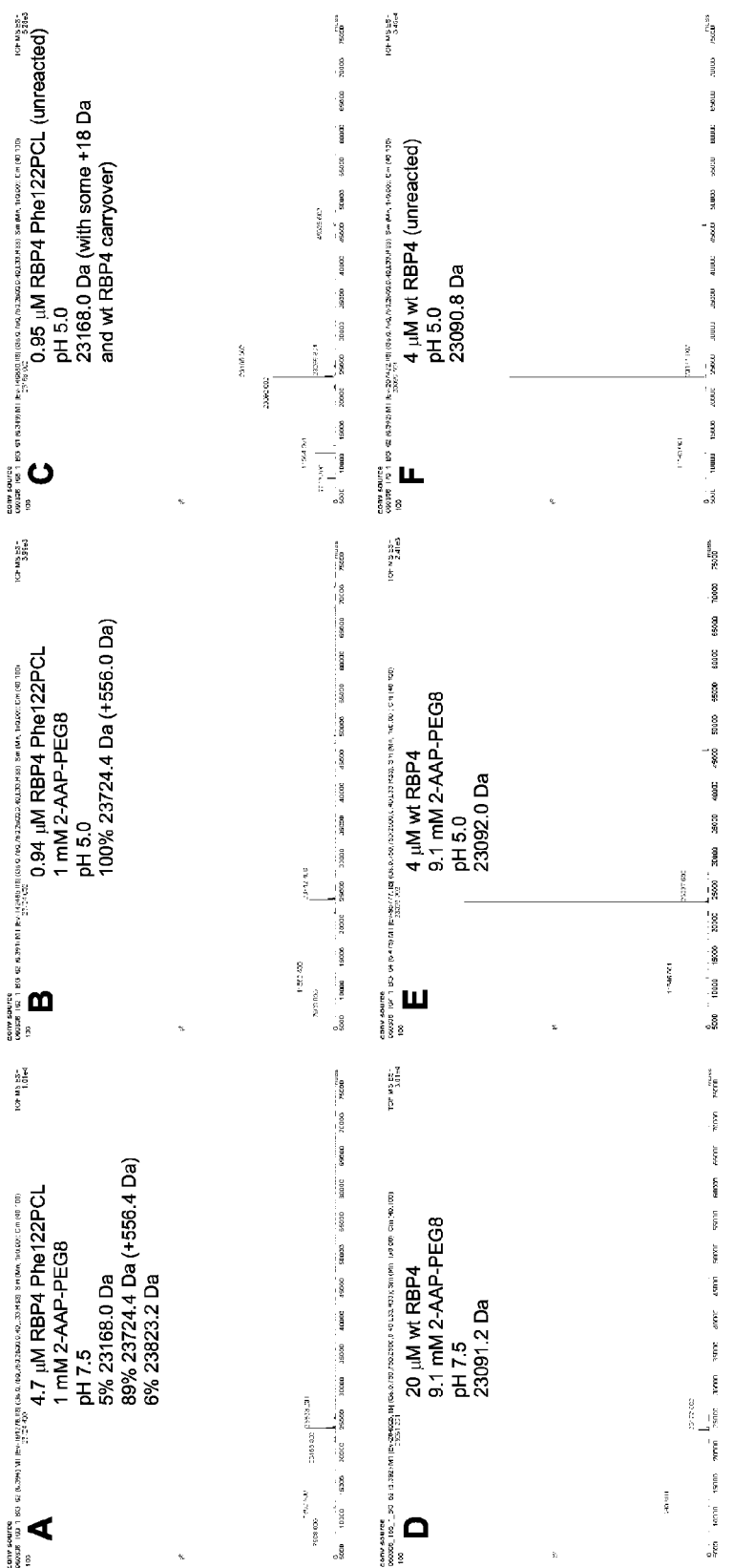
FIG. 32. Derivatization of hRBP4 Phe122PCL with 2-AAP-PEG8. Mass spectra of hRBP4 with PCL incorporated at position 122 after derivatization with 2-AAP-PEG8 at pH 7.5 (A) and pH 5.0 (B) compared to that of unreacted hRBP4 Phe122PCL protein (C) and wild-type hRBP4 with (D and E) and without 2-AAP-PEG8 added (F).

FIG. 32 is the mass spectra of hRBP4 with PCL incorporated at position 122 (hRBP4 Phe122PCL) before and after derivatization with 2-AAP-PEG8 at pH 7.5 (FIG. 32A) and pH 5.0 (FIG. 32B). These coupling reactions were conducted at pH 7.5 and pH 5, wherein 89 to 100% conversion occurs resulting in the expected mass increase of 556 Da relative to unreacted protein (FIG. 32C). Wild-type hRBP4 does not react with a 450 or 2300 fold excess of 2-AAP-PEG8 (FIG. 32D-F). This further illustrates the specificity of the coupling reaction between PCL and 2AAP-PEG8, as no coupling is observed when PCL is absent.

Figure 33:
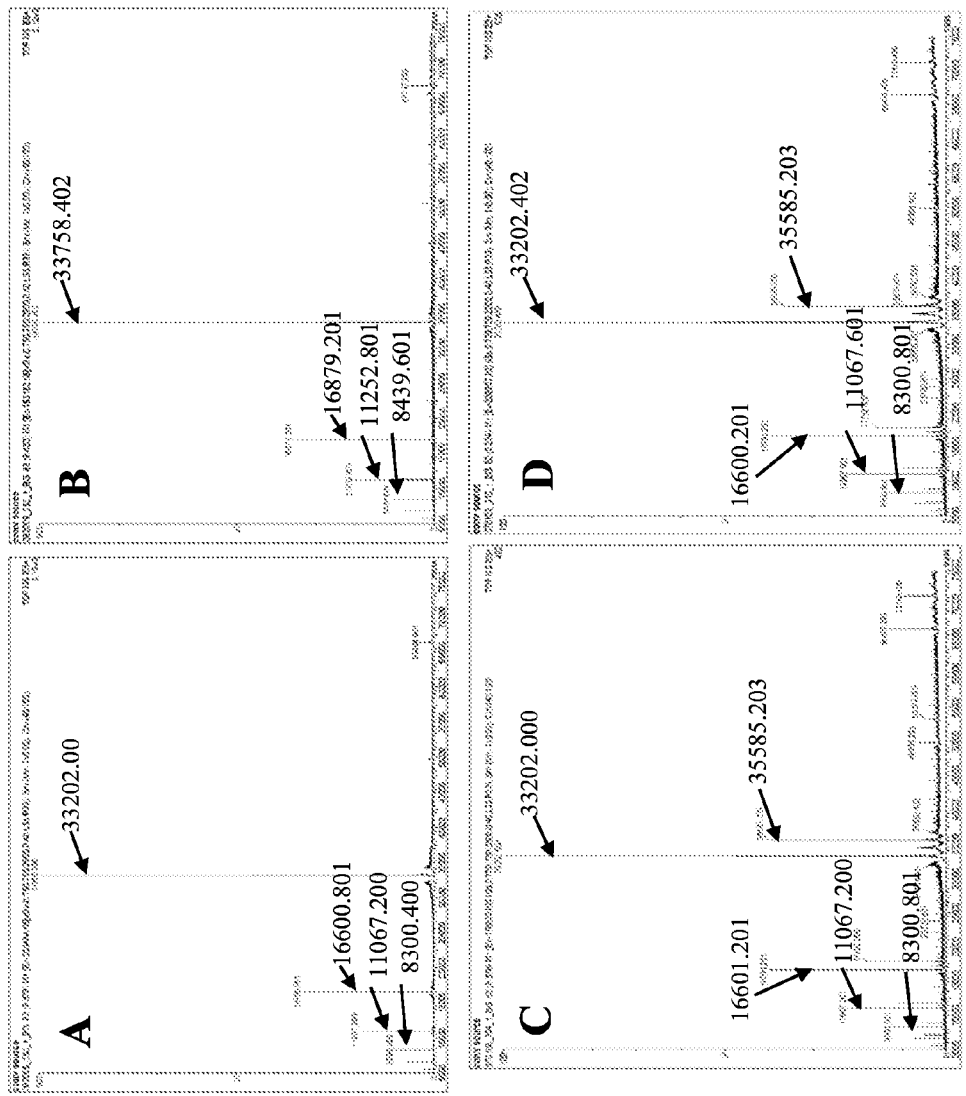
FIG. 33. Derivatization of FAS-TE Tyr2454PCL with 2-AAP-PEG8. Mass spectrum for unreacted protein (A) and for FAS-TE Tyr2454PCL protein reacted with 2-AAP-PEG8 (TU3205-044) (B).

To further illustrate the utility of this labeling method, thioesterase domain of human fatty acid synthetase (FAS-TE) with PCL incorporated at position 2454 (FAS-TE Tyr2454PCL) produced in *Escherichia coli* was derivatized with 2-AAP-PEG8 (FIG. 33, see Example 14). FIG. 33A shows the mass spectrum for unreacted protein (mass 33202 Da), while FIG. 33B shows the mass spectrum for FAS-TE Tyr2454PCL reacted to completeness with 2-AAP-PEG8 (TU3205-044) giving the expected mass of 33756 Da. Further illustration is provided in FIG. 33C and FIG. 33D which shows the mass spectra for FAS-TE with PCL incorporated at position 2454 (FAS-TE Tyr2454PCL) produced in *Escherichia coli* derivatized with 2.4 kDa 2-AAP-PEG (TU3205-048) at room temperature (FIG. 33C) and at 4° C. (FIG. 33D). Under the conditions used only approximately 25% conversion occurred to obtain the protein with the expected mass of 35585 Da.

Figure 34:
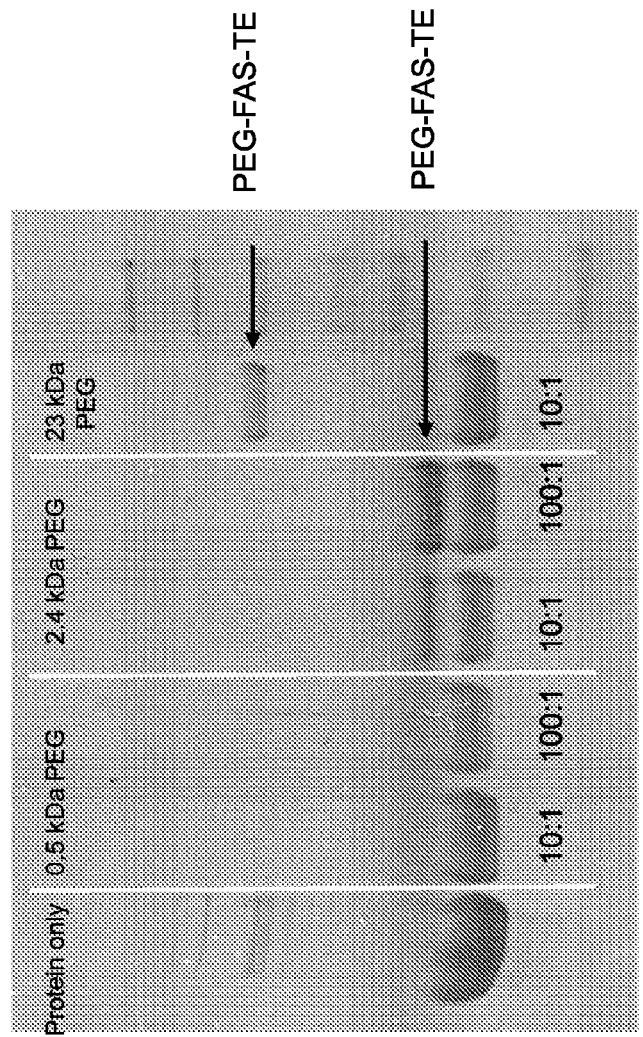
FIG. 34. PEGylation of FAS-TE Tyr2454PCL with 0.5 kDa 2-AAP-PEG (2-AAP-PEG8), 2.4 kDa 2-AAP-PEG and 23 kDa 2-AAP-PEG at the molar ratios shown.

In addition, FIG. 34 shows the PEGylation of FAS-TE Tyr2454PCL with 2.4 kDa 2-AAP-PEG and 23 kDa 2-AAP-PEG at the molar ratios shown. The 0.5 kDa 2-AAP-PEG (2-AAP-PEGS) pegylated product was not resolvable using SDS-PAGE, however it was verified using mass spectroscopy.

Figure 35:
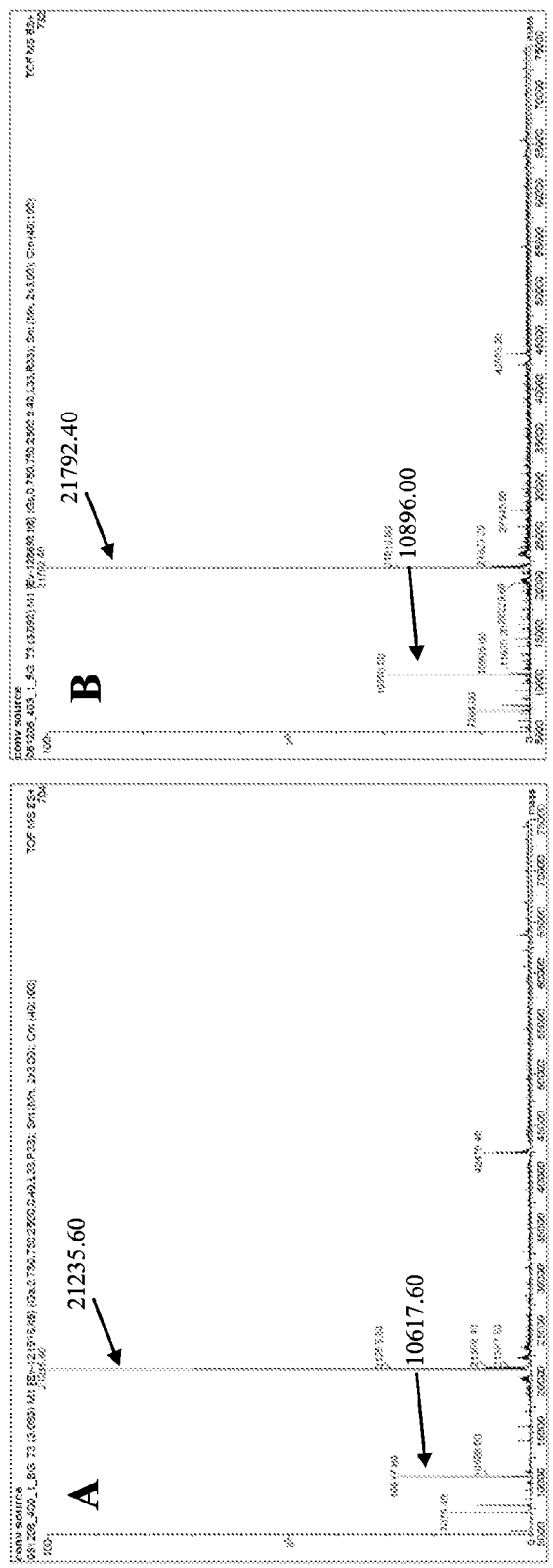
FIG. 35. Derivatization of FGF21 Lys81PCL with 2-AAP-PEG8. Mass spectra of unreacted FGF21 Lys84PCL (A) and of FGF21 Lys84PCL after derivatization with 2-AAP-PEG8 (B).
Figure 36:
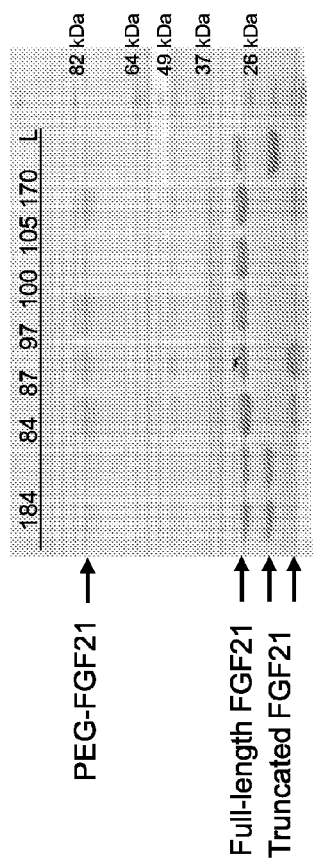
FIG. 36. PEGylation of FGF21 proteins. SDS-PAGE results obtained after derivatization of seven of the FGF21 PCL mutants with a 23 kDa 2-AAP-PEG showing PEG-FGF21, full length (FL) FGF21-PCL and truncated (TR) FGF21-PCL before (A) and after partial purification (B).
Figure 36:
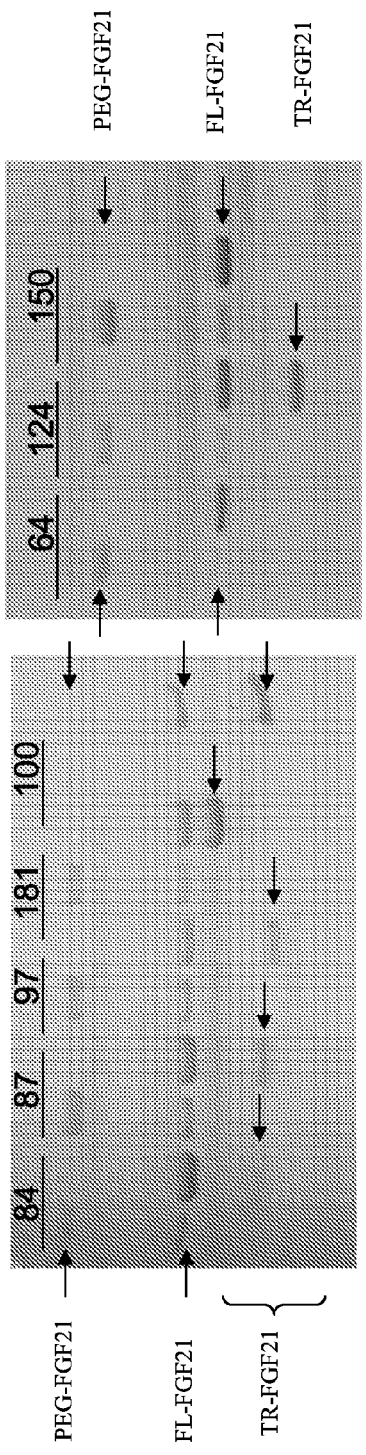

The methods provided herein have been used to incorporate PCL into twenty positions in fibroblast growth factor 21 (FGF-21) and subsequently used to PEGylate the corresponding PCL residues (see, Example 15). FIG. 35 shows the mass spectra obtained before and after derivatization of FGF21 Lys84PCL with 2-AAP-PEGS. FIG. 35A is the mass spectrum of unreacted FGF21 Lys84PCL (21235.6 Da), while FIG. 35B is the mass spectrum of FGF21 Lys84PCL reacted with 2-AAP-PEGS. The PEGylation reaction proceeded to completion and yielded a protein with 21792.4 Da. The increase of 556.8 Da is in agreement with the 556 Da increase expected for the derivatization. FIG. 36 shows SDS-PAGE results obtained after derivatization of seven of the FGF21 PCL mutants with 23 kDa 2-AAP-PEG. FIG. 36A is the SDS gel of reaction mixtures of FGF21 PCL mutants (between 0.1 and 0.4 mM) reacted with 23 kDa 2-AAP-PEG (pH 7.4, 4° C., 60 hours) and shows the PEG-FGF21, the full length (FL) FGF21-PCL and truncated (TR) FGF21-PCL. FIG. 36B shows SDS-PAGE results of eight FGF21 PCL mutants after partial purification of PEG-FGF21, full-length (FL) and truncated (TR) FGF21.

Figure 37:
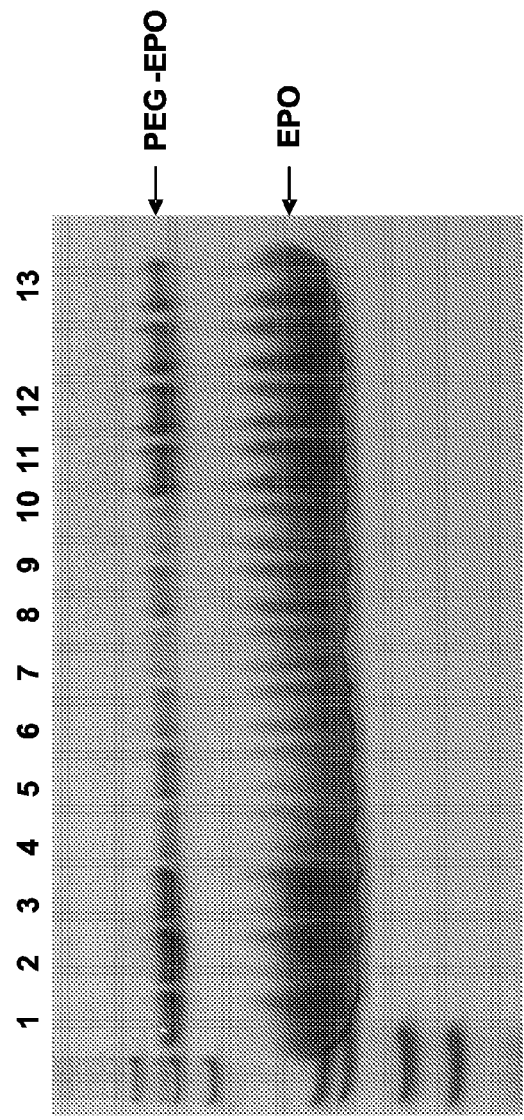
FIG. 37. PEGylations of EPO proteins. SDS-PAGE after derivatization of mouse EPO PCL mutants with 23 kDa 2-AAP-PEG.

The methods provided herein have been used to incorporate PCL into eleven positions in mouse erythropoietin (EPO) and subsequently used to PEGylate the corresponding PCL residues for three of the EPO PCL mutants (see, Example 6). FIG. 37 is an SDS gel obtained after PEGylation of mouse EPO PCL mutants. Mouse EPO with PCL incorporated in HEK293F cells at three different positions was reacted with 2-AAP-mPEG23k (TU3205-052). PEGylated EPO and non-PEGylated EPO are indicated by arrows.

In certain embodiments, bi-functional or multi-functional PEG polymers linked to a protein, polypeptide and/or peptide via PCL residue(s) are further derivatized or substituted using the remaining functional groups on the unreacted termini. In certain embodiments, bi-functional or multi-functional PEG polymers linked to a protein, polypeptide and/or peptide via reaction of a benzaldehyde, benzophenone or acetophenone moiety with PCL residue(s) are further derivatized or substituted using the remaining functional groups on the unreacted termini.

The methods and compositions described herein provide a highly efficient method for the selective modification of proteins, polypeptides and peptides with PEG derivatives, which involves the selective incorporation of the amino acid PCL or pyrrolysine into proteins in response to a selector codon and the subsequent modification of the corresponding amino acid residues with a suitably functionalized PEG derivative. Thus, provided herein are proteins, polypeptides and/or peptides having PCL or pyrrolysine residue(s) incorporated therein, and also provided herein are such proteins, polypeptides and/or peptides linked to water soluble polymers, such as poly (ethylene glycol)s (PEGs), via such PCL or pyrrolysine residue(s).

The extent of PEGylation to a protein, polypeptide and/or peptide (that is the number of PEG polymers linked to a protein, polypeptide and/or peptide) described herein is adjustable to provide an altered pharmacologic, pharmacokinetic or pharmacodynamic characteristic. In certain embodiments, such alterations are increases in such characteristics, while in other embodiments, such alterations are decreases in such characteristics. In certain embodiments, such a characteristic is in-vivo half-life. In some embodiments, the half-life of a protein, polypeptide and/or peptide PEGylated using the method and compositions provided herein is increased at least about 10, 20, 30, 40, 50, 60, 70, 80, 90 percent, two fold, five-fold, 10-fold, 50-fold, 100-fold or at least about 200-fold over an unmodified protein, polypeptide and/or peptide.

In certain embodiments, the proteins, polypeptides and/or peptides PEGylated using the methods and compositions provided herein are purified using methods including, but not limited to, hydrophobic chromatography, affinity chromatography; anion exchange chromatography, cation exchange chromatography, Q quaternary ammonium resin, DEAE SEPHAROSE, chromatography on silica; reverse phase HPLC, gel filtration (using, including but not limited to, SEPHADEX G-75, Sephacryl S-100, SUPERDEX 75, 100 and 200), hydrophobic interaction chromatography, size-exclusion chromatography, metal-chelate chromatography; ultrafiltration/diafiltration, ethanol precipitation, chromatofocusing, displacement chromatography, electrophoretic procedures (including but not limited to preparative isoelectric focusing), differential solubility (including but not limited to ammonium sulfate precipitation), and extraction.

In other aspects the PEG polymers used in the methods provided herein have weak or degradable linkages in the backbone. By way of example only, such PEG polymers have ester linkages in the polymer backbone that are subject to hydrolysis, and this hydrolysis results in cleavage of the linkage to release the protein, the polypeptide or the peptide to which the PEG was attached.

In other aspects, the methods and compositions described herein are used to produce substantially homogenous preparations of polymer-protein conjugates. "Substantially homogenous" as used herein means that polymer:protein conjugate molecules are observed to be greater than half of the total protein. The polymer:protein conjugate has biological activity and the present "substantially homogenous" PEGylated polypeptide preparations provided herein are those which are homogenous enough to display the advantages of a homogenous preparation, such as, by way of example only, ease in clinical application in predictability of lot to lot pharmacokinetics.

In other aspects, the methods and compositions described herein are used to produce substantially homogenous preparations of polymer:protein conjugates. "Substantially homogenous" as used herein means that polymer:protein conjugate molecules are observed to be greater than half of the total protein. The polymer:protein conjugate has biological activity and the present "substantially homogenous"

PEGylated polypeptide preparations provided herein are those which are homogenous enough to display the advantages of a homogenous preparation, such as, by way of example only, ease in clinical application in predictability of lot to lot pharmacokinetics.

In another aspect the methods and compositions described herein are used to prepare a mixture of polymer-protein conjugate molecules, and the advantage provided herein is that the proportion of mono-polymer:protein conjugate to include in the mixture is selectable. Thus, in certain embodiments a mixture of various proteins with various numbers of polymer moieties attached (i.e., bi-, tri-, tetra-, etc.) are prepared and these conjugates optionally combined with mono-polymer-protein conjugate prepared using the methods described herein, thereby giving a mixture with a predetermined proportion of mono-polymer:protein conjugates.

The proportion of poly(ethylene glycol) molecules to protein molecules will vary, as will their concentrations in the reaction mixture. In certain embodiments, the optimum ratio (in terms of efficiency of reaction in that there is minimal excess unreacted protein or polymer) is determined by the molecular weight of the poly(ethylene glycol) selected and on the number of reactive groups available. The higher the molecular weight of the polymer, the fewer number of polymer molecules that are attached to the protein. Similarly, in other embodiments the branching of a PEG polymer is taken into account when optimizing these parameters. In this instance, the higher the molecular weight (or the more branches) the higher the polymer:protein ratio.

Figure 38:
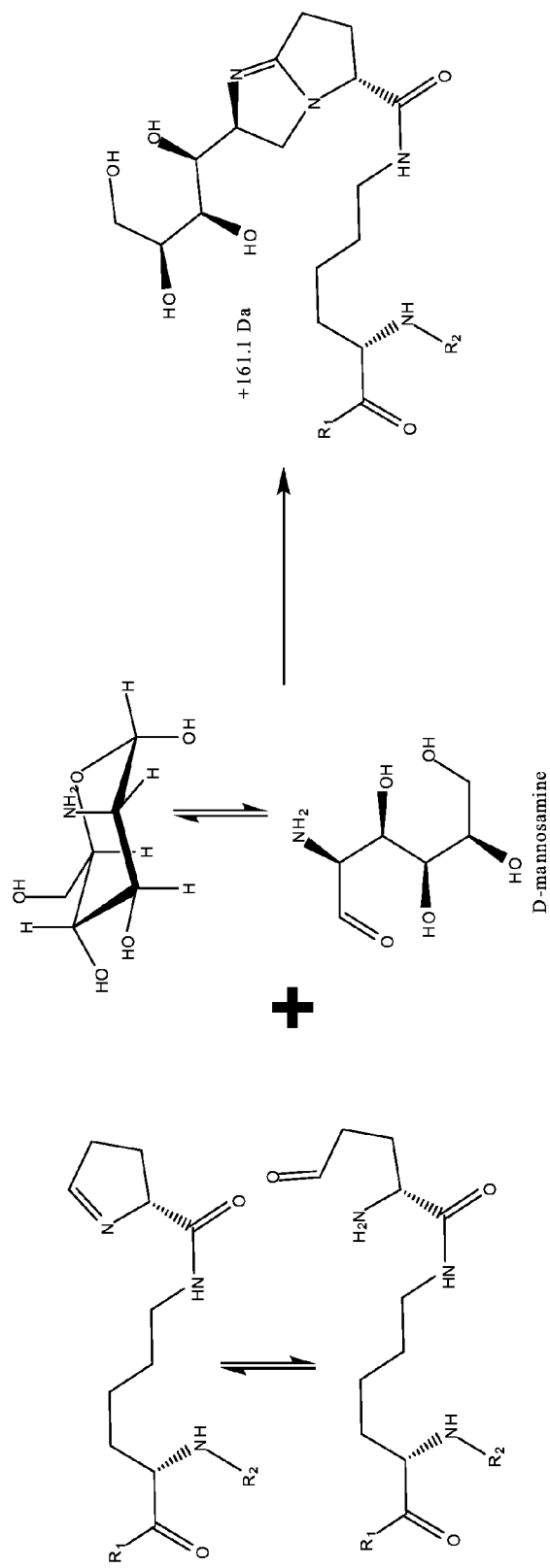
FIG. 38. Derivatization of PCL with amino sugars. Generalized reaction scheme wherein D-mannosamine is coupled to a protein (illustrated as $R_1$) having PCL incorporated therein.
Figure 39:
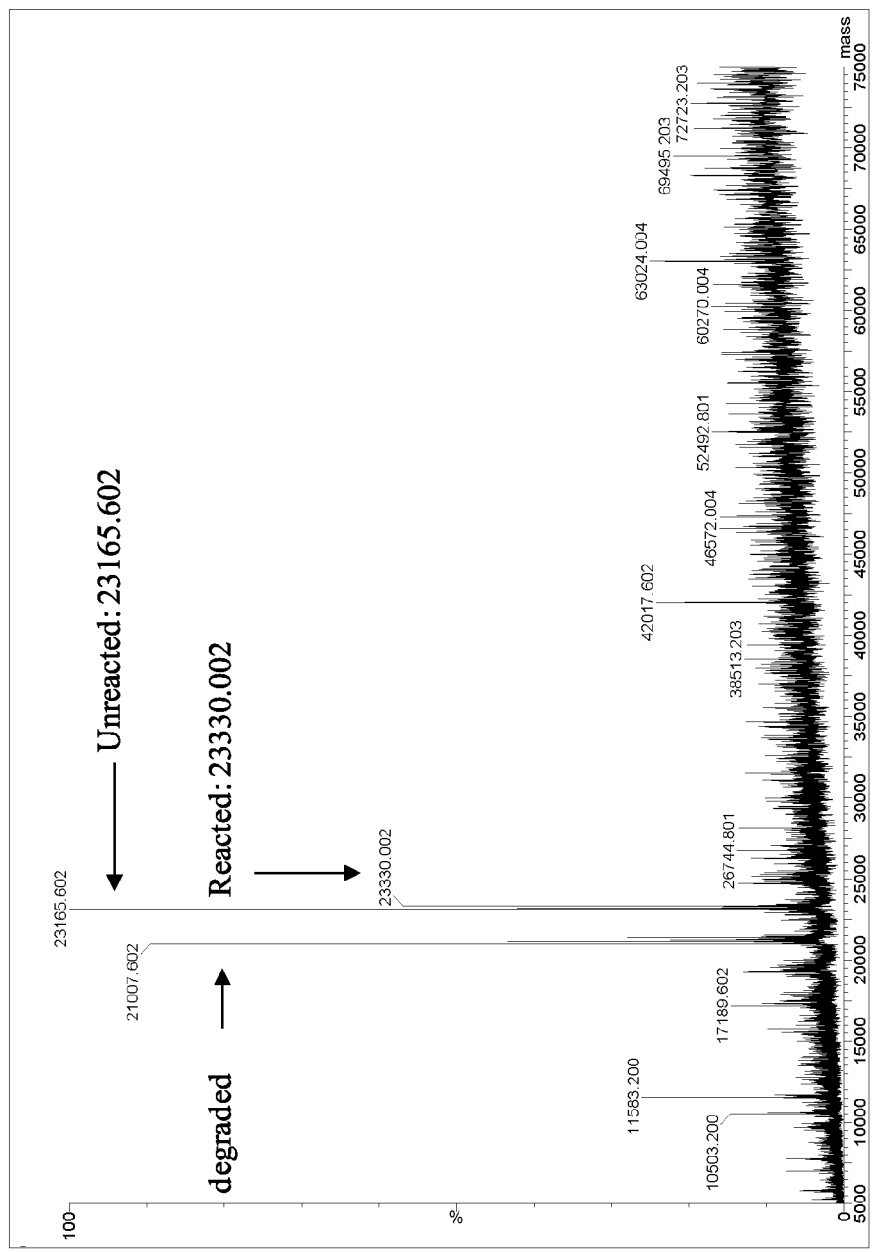
FIG. 39. Derivatization of hRBP4 Phe122PCL with D-mannosamine. Mass spectrum of hRBP4 with PCL incorporated at position 122 after reaction with mannosamine.
Figure 40:
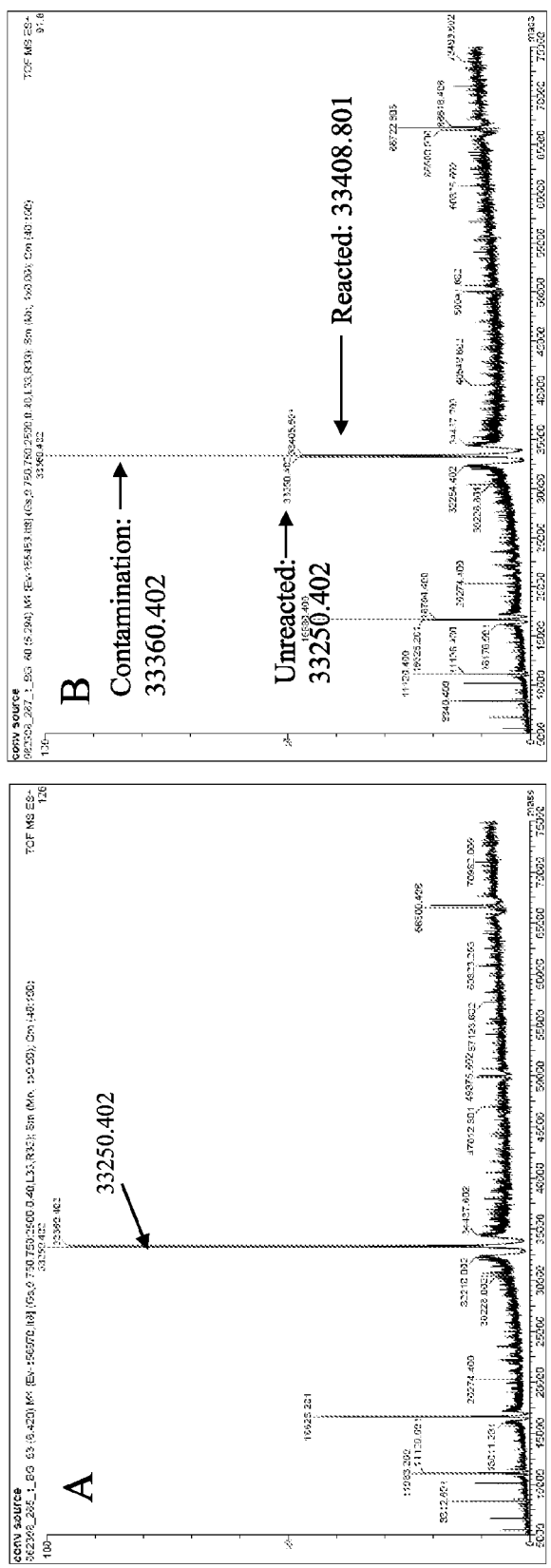
FIG. 40. Derivatization of FAS-TE Leu2222PCL with D-mannosamine. Mass spectrum of unreacted human fatty acid synthetase (FAS-TE) with PCL incorporated at position 2222 (FAS-TE Leu2222PCL/Leu2223Ile) (A) and of protein reacted with mannosamine (B).

Direct Coupling of Amino Sugars to Pyrrolysine and/or PCL Incorporated into Proteins, Polypeptides and/or Peptides In another aspect provided herein, proteins, polypeptides and/or peptides having one or more pyrrolysines and/or PCL residue(s) incorporated therein are derivatized with amino sugars. FIG. 38 shows a generalized reaction scheme wherein D-mannosamine is coupled to a protein (illustrated as $R_1$) having PCL incorporated therein. In such an embodiment the aminoaldehyde moiety of D-mannosamine reacts with the PCL residue thereby increasing the mass of the protein by 161 Da. Other aminosugars used in such embodiments include, but are not limited to, mannosamine, galactosamine, and glucosamine. FIG. 39 shows the mass spectrum of hRBP4 with PCL incorporated at position 122 (hRBP4 Phe122PCL) after reaction with mannosamine, while FIG. 40 shows the mass spectrum of human fatty acid synthetase (FAS-TE) with PCL incorporated at position 2222 (FAS-TE Leu2222PCL/Leu2223Ile) before (FIG. 40A) and after (FIG. 40B) reaction with mannosamine.

Glycosylation of Proteins, Polypeptides and/or Peptides Via Coupling to Pyrrolysine and PCL Incorporated into such Proteins, Polypeptides and/or Peptides The methods and compositions described herein are used to obtain proteins, polypeptides and peptides with one or more pyrrolysine and/or PCL residue bearing saccharide residues. The saccharide residues may be either natural (including but not limited to, N-acetylglucosamine and D-mannosamine) or non-natural (including but not limited to, 3-fluorogalactose). In certain embodiments the saccharides are linked to the pyrrolysine and/or PCL residue by a non-natural linkage including, but not limited to, by formation of a quinazoline-type moiety. In certain embodiments the saccharides are linked to the pyrrolysine and/or PCL residue by a non-natural linkage including, but not limited to, by formation of a quinazoline-type moiety that has been further reduced with a reducing agent. In certain embodiments the saccharides are linked to the pyrrolysine and/or PCL residue by a non-natural linkage including, but not limited to, by formation of a quinazoline-type moiety that has further reacted thereby forming the fused ring system as provided herein (see FIGS. 22, 23 and 30). In certain embodiments, the addition of a saccharide or saccharides, including, but not limited to, glycosyl moieties are added to proteins, polypeptides and peptides having one or more pyrrolysine and/or PCL incorporated therein occurs in-vivo. In other embodiments, the addition of a saccharide or saccharides, including, but not limited to, glycosyl moieties which are added to proteins, polypeptides and peptides having one or more pyrrolysine and/or PCL incorporated therein occurs in-vitro. In other embodiments, once attached to the pyrrolysine and/or PCL residue, the saccharide is further modified by treatment with glycosyltransferases and/or other enzymes to generate an oligosaccharide bound to the protein, polypeptide or peptide having one or more pyrrolysine pyrrolysine and/or PCL incorporated therein.

Figure 41:
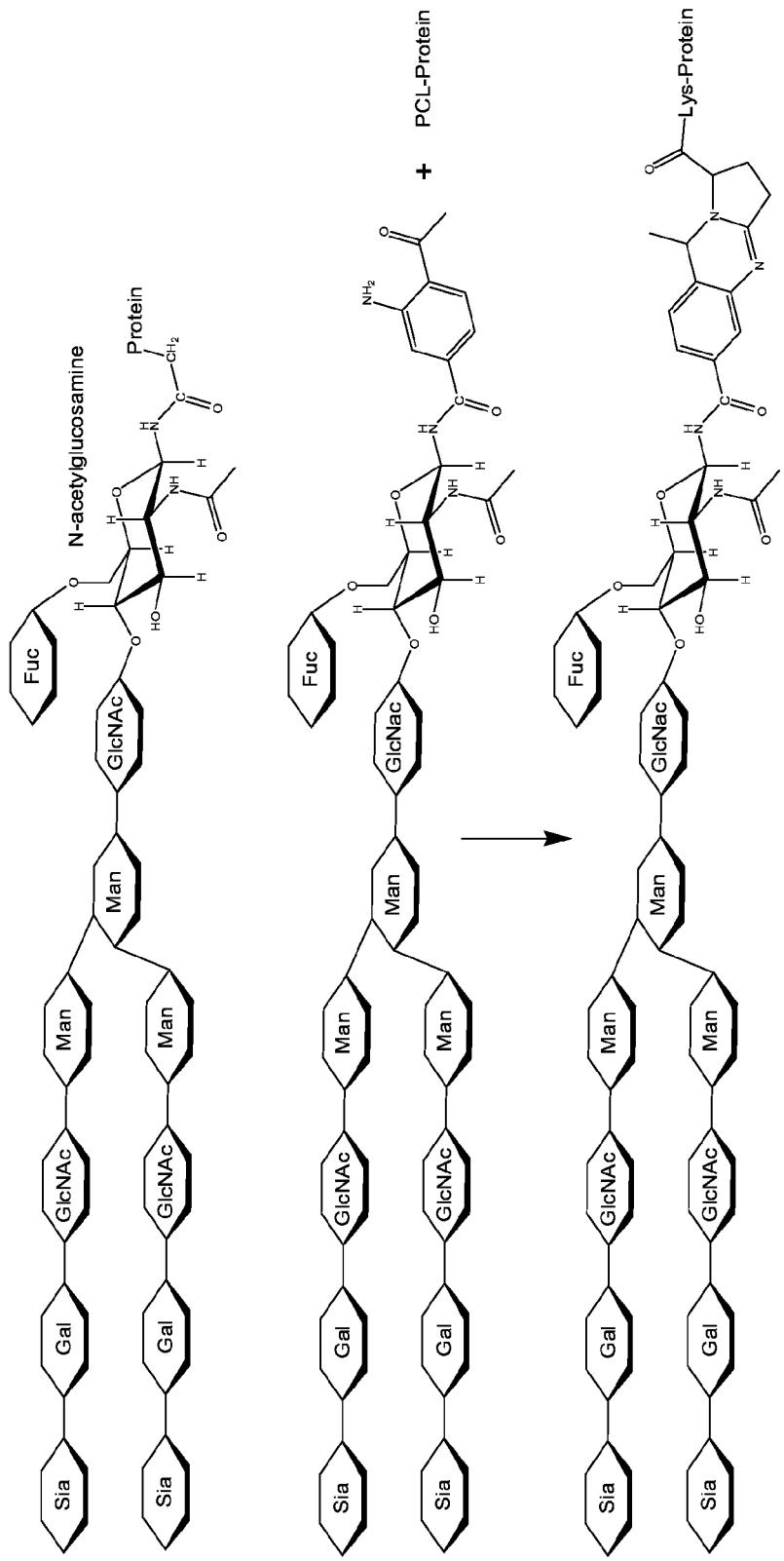
FIG. 41. Illustration of an embodiment for the site specific attachment of an oligosaccharide to a protein via reacting a 2-ABA moiety linked to the oligosaccharide with PCL incorporated into the protein.

FIG. 41 illustrates an embodiment wherein the co-translational or post-translational modification comprises attachment of an oligosaccharide to a protein, polypeptide or peptide by formation of a quinazoline-type moiety. In certain embodiments the saccharides are linked to the pyrrolysine and/or PCL residue by a non-natural linkage including, but not limited to, by formation of a quinazoline-type moiety that has been further reduced with a reducing agent. In certain embodiments the saccharides are linked to the pyrrolysine and/or PCL residue by a non-natural linkage including, but not limited to, by formation of a quinazoline-type moiety that has further reacted thereby forming the fused ring system as provided herein (FIGS. 22, 23 and 30). In such embodiments, by way of example only, the oligosaccharide comprises the (GlcNAc-Man)$_2$-Man-GlcNAc-GlcNAc core linked to 2-amino-acetophenone (2-AAP) is conjugated to a pyrrolysine and/or PCL residue incorporated into the protein, polypeptide or peptide. In other embodiments the oligosaccharide comprises the (GlcNAc-Man)$_2$-Man-GlcNAc-GlcNAc core linked to 2-amino-benzaldehyde (2-ABA) and the protein conjugate is formed by reaction of the 2-ABA with a pyrrolysine and/or PCL residue incorporated into the protein, polypeptide or peptide. In still other embodiments the oligosaccharide comprises the (GlcNAc-Man)$_2$-Man-GlcNAc-GlcNAc core linked to 2-amino-benzophenone (2-ABP) and the protein conjugate is formed by reaction of the 2-ABP with a pyrrolysine and/or PCL residue incorporated into the protein, polypeptide or peptide. Other oligosaccharides used in such embodiments possess 2-ABA, 2-AAP or 2-ANBP moieties.

Oriented Covalent Attachment of Proteins in Hetero-Dimers, Hetero-Trimers, Hetero-Multimers, Homo-Dimers, Homo-Trimers, Homo-Multimers, Unsymmetric Homo-Dimers, Unsymmetric Homo-Trimers and Unsymmetric Homo-Multimers.

Figure 42:
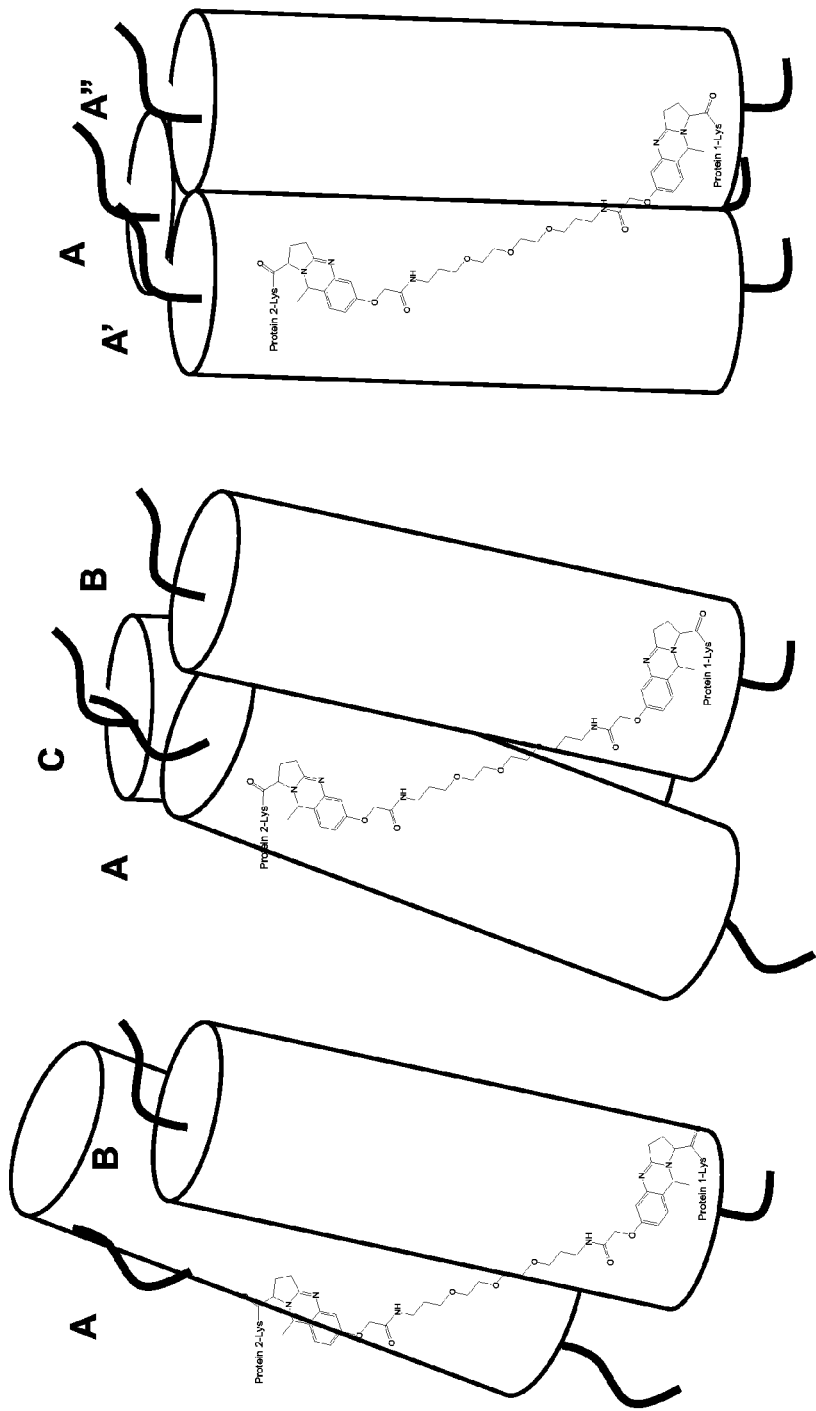
FIG. 42. Illustration of certain embodiments of protein-protein conjugate (hetero-dimers, hetero-trimers, homo-trimers) formed by crosslinking proteins having PCL incorporated therein.

In another aspect using the methods provided herein, the site-specific incorporation of one or more pyrrolysine and/or PCL into proteins, polypeptides and/or peptides is used to form protein-protein conjugates including, but not limited to, hetero-dimers, hetero-trimers, hetero-multimers, homo-dimers, homo-trimers, homo-multimers, unsymmetric homo-dimers, unsymmetric homo-trimers and unsymmetric homo-multimers. Such protein-protein conjugate formation is accomplished using site-specific crosslinking between proteins having pyrrolysine and PCL residue(s) incorporated therein. FIG. 42 illustrates certain embodiments (hetero-dimers, hetero-trimers, homo-trimers) of such protein-protein conjugate formation, wherein proteins having PCL residue(s) incorporated therein are crosslinked. In FIG. 42, the protein conjugate linkage formed by such crosslinking is a quinazoline-type moiety that links the proteins together, however in other embodiments the linkage is a reduced form of the quinazoline-type moiety (FIGS. 22, 23 and 30). In other embodiments, the linkage is the fused ring moiety (FIGS. 22, 23 and 30).

Non-limiting examples of such protein-protein conjugates include, but are not limited to, protein-protein conjugates a cytokine, a growth factor, a growth factor receptor, an interferon, an interleukin, an inflammatory molecule, an oncogene product, a peptide hormone, a signal transduction molecule, a steroid hormone receptor, a transcriptional activator, a transcriptional suppressor, erythropoietin (EPO), fibroblast growth factors, fibroblast growth factor 21 (FGF21), leptin, insulin, human growth hormone, epithelial Neutrophil Activating Peptide-78, GROα/MGSA, GROβ, GROγ, MIP-1α, MIP-16, MCP-1, hepatocyte growth factor, insulin-like growth factor, leukemia inhibitory factor, oncostatin M, PD-ECSF, PDGF, pleiotropin, SCF, c-kit ligand, VEGF, G-CSF, IL-1, IL-2, IL-8, IGF-I, IGF-II, FGF (fibroblast growth factor), PDGF, TNF, TGF-α, TGF-β, EGF (epidermal growth factor), KGF (keratinocyte growth factor), CD40L/CD40, VLA-4/VCAM-1, ICAM-1/LFA-1, hyalurin/CD44, Mos, Ras, Raf, Met; p53, Tat, Fos, Myc, Jun, Myb, Rel, estrogen receptor, progesterone receptor, testosterone receptor, aldosterone receptor, LDL receptor, and/or corticosterone. In another set of embodiments, the protein is homologous to a therapeutic or other protein such as: an Alpha-1 antitrypsin, an Angiostatin, an Antihemolytic factor, an antibody, an Apolipoprotein, an Apoprotein, an Atrial natriuretic factor, an Atrial natriuretic polypeptide, an Atrial peptide, a C—X—C chemokine, T39765, NAP-2, ENA-78, a Gro-a, a Gro-b, a Gro-c, an IP-10, a GCP-2, an NAP-4, an SDF-1, a PF4, a MIG, a Calcitonin, a c-kit ligand, a cytokine, a CC chemokine, a Monocyte chemoattractant protein-1, a Monocyte chemoattractant protein-2, a Monocyte chemoattractant protein-3, a Monocyte inflammatory protein-1 alpha, a Monocyte inflammatory protein-1 beta, RANTES, 1309, R83915, R91733, HCC1, T58847, D31065, T64262, a CD40, a CD40 ligand, a C-kit Ligand, a Collagen, a Colony stimulating factor (CSF), a Complement factor 5a, a Complement inhibitor, a Complement receptor 1, a cytokine, an epithelial Neutrophil Activating Peptide-78, a GROα/MGSA, a GROβ, a GROγ, a MIP-1α, a MIP-16, a MCP-1, an Epidermal Growth Factor (EGF), an epithelial Neutrophil Activating Peptide, an Exfoliating toxin, a Factor IX, a Factor VII, a Factor VIII, a Factor X, a Fibroblast Growth Factor (FGF), a Fibrinogen, a Fibronectin, a G-CSF, a GM-CSF, a Glucocerebrosidase, a Gonadotropin, a growth factor, a growth factor receptor, a Hedgehog protein, a Hemoglobin, a Hepatocyte Growth Factor (HGF), a Hirudin, a Human serum albumin, an ICAM-1, an ICAM-1 receptor, an LFA-1, an LFA-1 receptor, an Insulin, an Insulin-like Growth Factor (IGF), an IGF-I, an IGF-II, an interferon, an IFN-α, an IFN-β, an IFN-γ, an interleukin, an IL-1, an IL-2, an IL-3, an IL-4, an IL-5, an IL-6, an IL-7, an IL-8, an IL-9, an IL-10, an IL-11, an IL-12, a Keratinocyte Growth Factor (KGF), a Lactoferrin, a leukemia inhibitory factor, a Luciferase, a Neurturin, a Neutrophil inhibitory factor (NIF), an oncostatin M, an Osteogenic protein, an oncogene product, a Parathyroid hormone, a PD-ECSF, a PDGF, a peptide hormone, a Human Growth Hormone, a Pleiotropin, a Protein A, a Protein G, a Pyrogenic exotoxins A, B, or C, a Relaxin, a Renin, an SCF, a Soluble complement receptor I, a Soluble I-CAM 1, a Soluble interleukin receptors, a Soluble TNF receptor, a Somatomedin, a Somatostatin, a Somatotropin, a Streptokinase, a Superantigens, a Staphylococcal enterotoxins, an SEA, an SEB, an SEC 1, an SEC2, an SEC3, an SED, an SEE, a steroid hormone receptor, a Superoxide dismutase, a Toxic shock syndrome toxin, a Thymosin alpha 1, a Tissue plasminogen activator, a tumor growth factor (TGF), a TGF-α, a TGF-β, a Tumor Necrosis Factor, a Tumor Necrosis Factor alpha, a Tumor necrosis factor beta, a Tumor necrosis factor receptor (TNFR), a VLA-4 protein, a VCAM-1 protein, a Vascular Endothelial Growth Factor (VEGF), a Urokinase, a Mos, a Ras, a Raf, a Met; a p53, a Tat, a Fos, a Myc, a Jun, a Myb, a Rel, an estrogen receptor, a progesterone receptor, a testosterone receptor, an aldosterone receptor, an LDL receptor, and/or a corticosterone.

Figure 43:
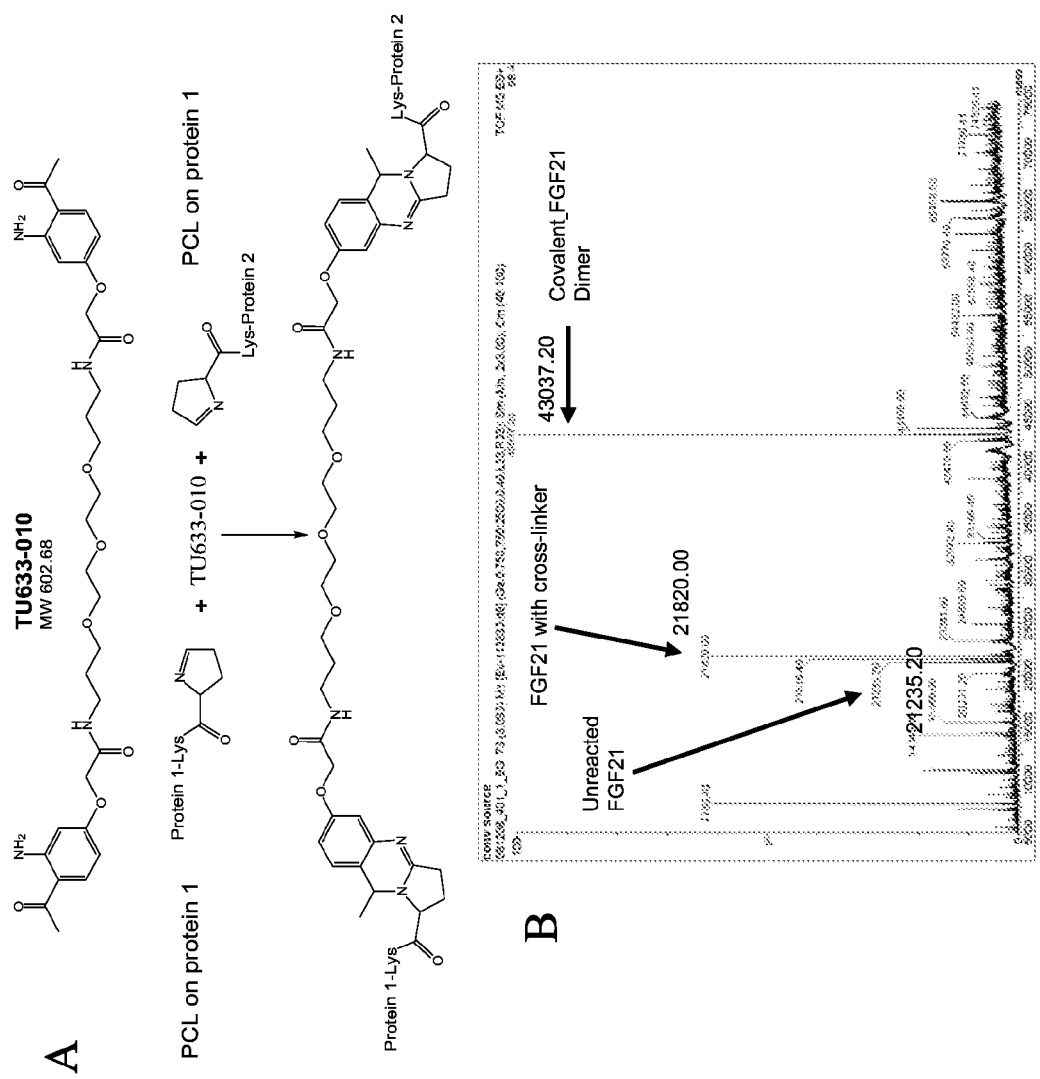
FIG. 43. Homodimer formation with a PCL specific, bi-functional crosslinker as illustrated for FGF21 Lys84PCL protein. A non limiting example of a bi-functional crosslinker used to form a homodimer is shown in A, and the mass spectrum of the reaction mixture of crosslinked FGF-21 Lys84PCL using this bi-functional linker is shown in B.

Crosslinkers used to form protein-protein conjugates including, but not limited to, hetero-dimers, hetero-trimers, hetero-multimers, homo-dimers, homo-trimers, homo-multimers, unsymmetric homo-dimers, unsymmetric homo-trimers and unsymmetric homo-multimers, possess benzaldehyde, acetophenone and/or benzophenone moieties on their respective termini. Such moieties react with pyrrolysine and/or PCL residue(s) incorporated into proteins using the methods provided herein, and such proteins include those provided herein. A non limiting example of a bi-functional crosslinker used to form a homodimer is shown in FIG. 43A. This bifunctional linker was used to crosslink fibroblast growth factor 21 (FGF-21) with a PCL residue incorporated at position 84 (FGF21 Lys84PCL). FIG. 43B is the mass spectrum of the reaction mixture, wherein the peak for the covalent FGF21 Lys48PCL dimer at the expected mass of 43037.2 Da is the dominant species. Unreacted FGF21 Lys84PCL is detected at 21235.2 Da, while some monomeric FGF21 modified with one end of the cross-linker attached is detected at 21820.0 Da. Modification of the reaction conditions allowed for complete reaction of the FGF21 Lys84PCL. In FIG. 43, the protein conjugate linkage formed by such crosslinking is a quinazoline-type moiety, however in other embodiments the linkage is a reduced form of the quinazoline-type moiety (FIGS. 22, 23 and 30). In other embodiments, the linkage is the fused ring moiety (FIGS. 22, 23 and 30).

Figure 44:
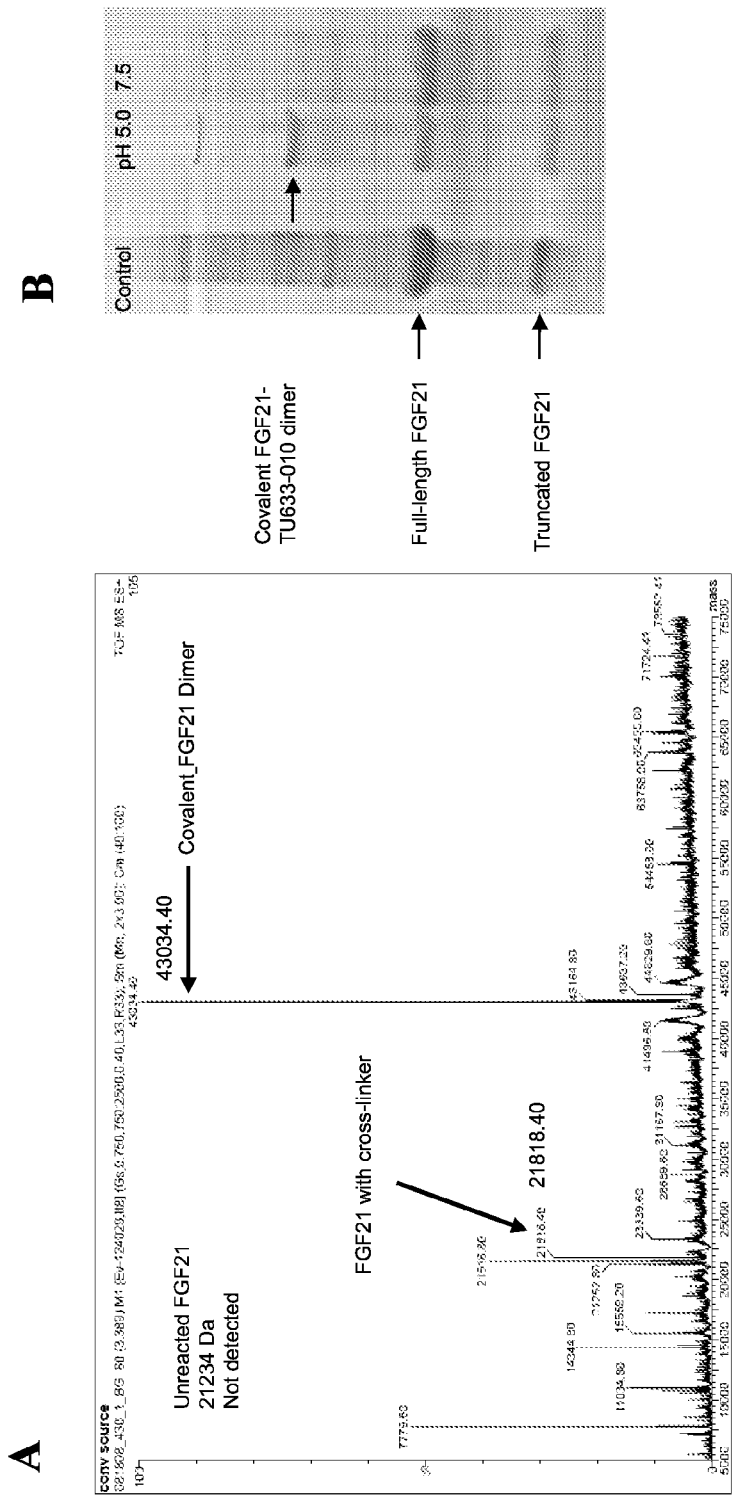
FIG. 44. Homodimer formation of FGF-21 PCL mutant protein with a bi-functional crosslinker.
Figure 45:
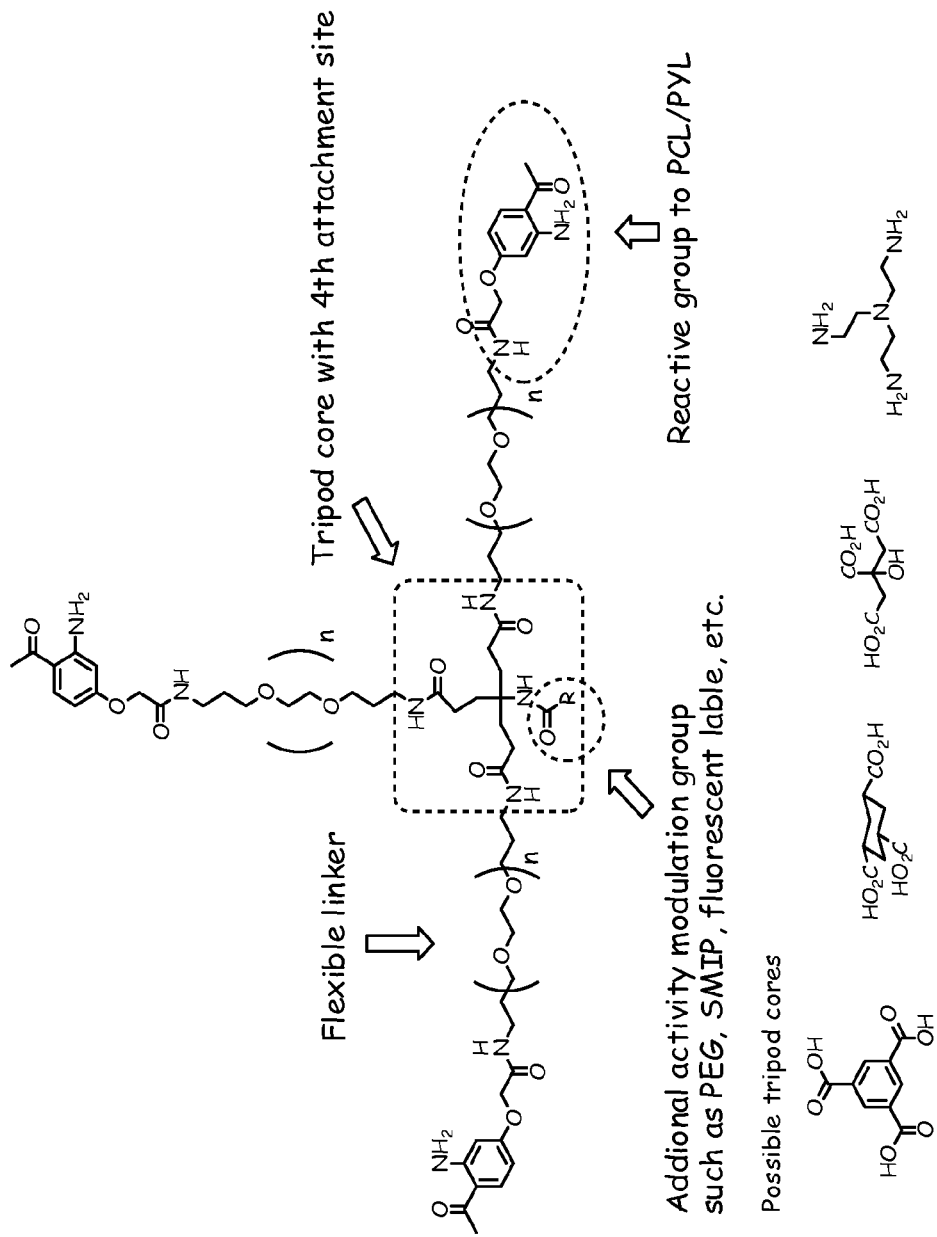
FIG. 45. An embodiment for a crosslinker used to form trimers.

FIG. 44A shows the mass spectrum of the reaction mixture, wherein the peak of the covalent FGF21 dimer at the expected mass of 43034 Da is the dominant species. Unreacted FGF21 Lys84PCL is not detected at 21234 Da, while some monomeric FGF21 modified with one end of the cross-linker attached is detected at 21818 Da. FIG. 43B is the SDS-PAGE of the reactions at pH 5.0 and pH 7.5, indicating better conversion at pH 5.0. PCL-specific cross-linking has been used to make dimers of FGF21. However the methodology is applicable to any of the proteins listed above and can be used to form dimers, trimers, and multimers. Such crosslinking is used to potentiate the activity of biologically active proteins. In addition, this approach is used to stabilize complexes for structural studies and/or stabilize receptor decoys. FIG. 45 shows an embodiment for a crosslinker used to form trimers.

Site-Specific Labeling

In another aspect using the methods provided herein, the site-specific incorporation of one or more pyrrolysine and/or PCL into proteins, polypeptides and/or peptides is used to allow for site-specific labeling of such proteins, polypeptides and/or peptides. Such labelling results from reaction of pyrrolysine and/or PCL residue(s) with a label derivatized with a functional group that reacts selectively with the pyrrolysine and/or PCL residue(s). The label used includes, but is not limited to, a dye, an antibody or antibody fragment, a metal chelator, a spin label, a fluorophore, a metal-containing moiety, a radioactive moiety, an actinic radiation excitable moiety, a ligand, biotin, a biotin analogue, a redox-active agent, an isotopically labeled moiety, a biophysical probe, a phosphorescent group, a chemiluminescent group, an electron dense group, a magnetic group, an intercalating group, a chromophore; an energy transfer agent, quantum dot(s), fluorescence dyes, FRET reagents, and any combination thereof. The label is also any $X^1$ as defined herein.

In embodiments of such site-specific labeling of such proteins, polypeptides and/or peptides containing one or more pyrrolysine and/or PCL residues is the reaction of the pyrrolysine and/or PCL residue(s) with a label derivatized with benzaldehyde, acetophenone or benzophenone moieties. The label used includes, but is not limited to, a dye, an antibody or antibody fragment, a metal chelator, a spin label, a fluorophore, a metal-containing moiety, a radioactive moiety, an actinic radiation excitable moiety, a ligand, biotin, a biotin analogue, a redox-active agent, an isotopically labeled moiety, a biophysical probe, a phosphorescent group, a chemiluminescent group, an electron dense group, a magnetic group, an intercalating group, a chromophore; an energy transfer agent, quantum dot(s), fluorescence dyes, FRET reagents, and any combination thereof. The label is also any $X^1$ as defined herein.

In a further aspect of such site specific labeling provided herein, the reaction of the pyrrolysine and/or PCL residue(s) with a label derivatized with a moiety that reacts selectively with the pyrrolysine and/or PCL residue(s) allows for increased detection sensitivity. Specifically, such reactions form a detectable moiety that has spectral properties different from those of the reactants present prior to the reaction, and thereby enhancing the signal to noise ratio by minimizing the background signal in relation to the detectable moiety signal. In certain embodiments of such site specific labeling provided herein, the reaction of the pyrrolysine or PCL residue(s) with a label derivatized with benzaldehyde, acetophenone or benzophenone moieties forms a quinazoline-type moiety (FIGS. 22, 23 and 30) which has spectral properties different from the benzaldehyde, acetophenone or benzophenone moieties. In certain embodiments of such site specific labeling provided herein, the reaction of the pyrrolysine or PCL residue(s) with a label derivatized with benzaldehyde, acetophenone or benzophenone moieties forms a reduced quinazoline-type moiety (FIGS. 22, 23 and 30) which has spectral properties different from the benzaldehyde, acetophenone or benzophenone moieties. In certain embodiments of such site specific labeling provided herein, the reaction of the pyrrolysine or PCL residue(s) with a label derivatized with benzaldehyde, acetophenone or benzophenone moieties forms a fused ring moiety (FIGS. 22, 23 and 30) which has spectral properties different from the benzaldehyde, acetophenone or benzophenone moieties.

In certain embodiments, such labeled proteins, polypeptides and/or peptides are used for diagnostics and imaging, while in other embodiments such labeled proteins, polypeptides and/or peptides are used in High-Throughput Screening. In other embodiments, such labeled proteins, polypeptides and/or peptides are used to evaluate transport properties, while in other embodiments such labeled proteins, polypeptides and/or peptides are used in localization studies.

Figure 46:
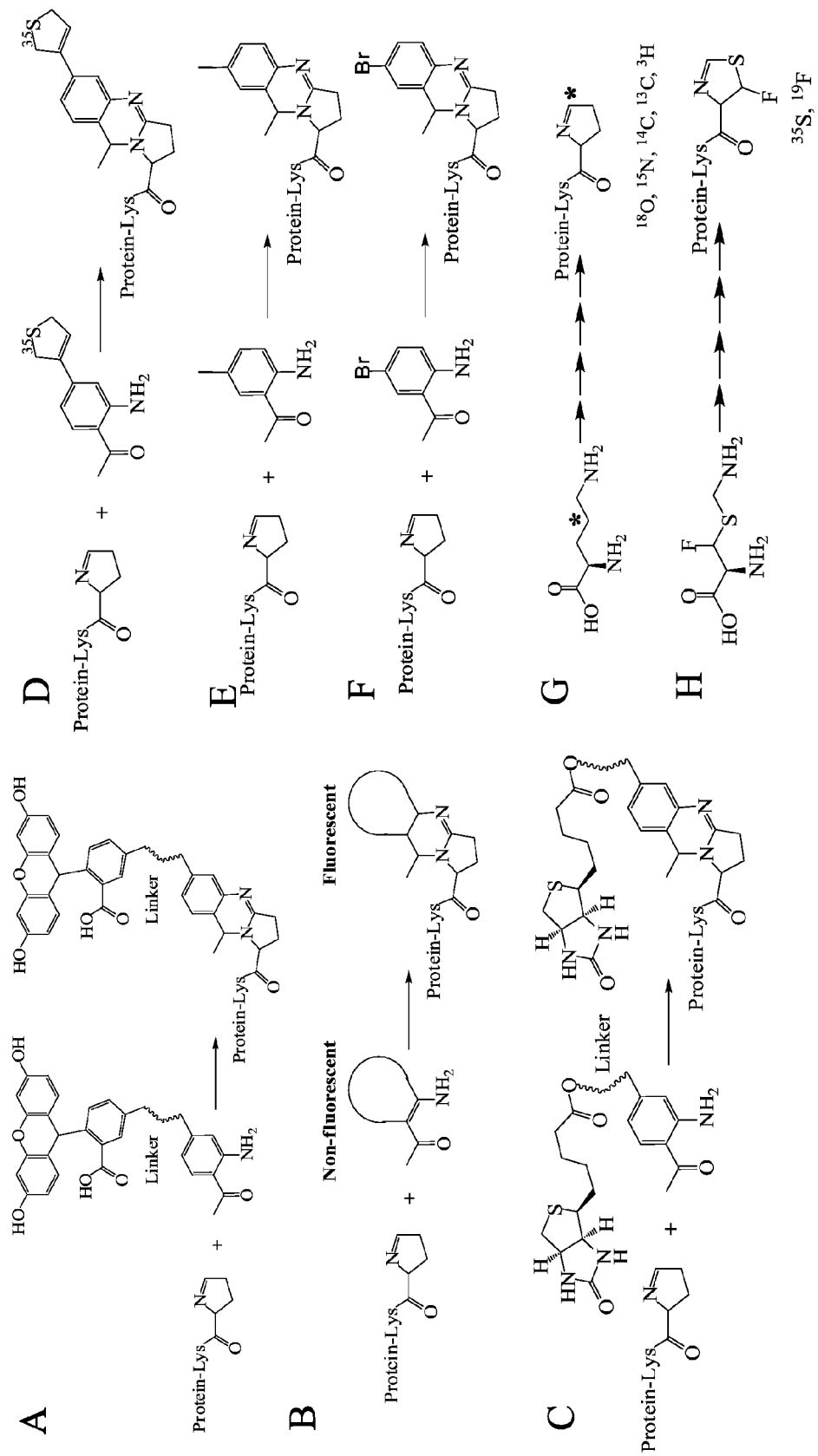
FIG. 46. Illustration of various embodiments of site-specific labels and labeling using the methods provided herein.

FIG. 46 illustrates certain embodiments of such site-specific labeling. FIG. 46A illustrates labeling with a fluorescent moiety. FIG. 46B illustrates reacting a PCL residue with a non-fluorescent moiety that upon reaction becomes fluorescent. FIG. 46C illustrates biotinylation of a protein. FIG. 46D illustrates labeling with a radioactive moiety. FIG. 46E illustrates labeling with 1-(2-amino-5-iodophenyl)ethanone and FIG. 46F illustrates labeling with 1-(2-amino-5-bromophenyl)ethanone; both can be used to obtain phasing information for the process of determining X-ray crystal structures of proteins. 1-(2-amino-5-iodophenyl)ethanone can also be used for labeling proteins with a radioactive moiety. In FIG. 46, the protein conjugate linkage formed by such labelling is a quinazoline-type moiety, however in other embodiments the linkage is a reduced form of the quinazoline-type moiety (FIGS. 22, 23 and 30). In other embodiments, the linkage is the fused ring moiety (FIGS. 22, 23 and 30).

In embodiments of such site-specific labeling of such proteins, polypeptides and/or peptides containing one or more pyrrolysine and/or PCL residue(s), the pyrrolysine or PCL residue(s) itself can be labeled by using a labeled precursor. FIG. 46G and FIG. 46H illustrate, by way of example only, labeling with radioactive or stable isotopes from differently labeled precursors.

Another aspect of the present invention provides for the production of proteins that are homologous to any available protein, but comprising one or more pyrrolysine or PCL residue(s). For example, in certain embodiments therapeutic proteins are made that comprise one or more pyrrolysine or PCL and are homologous to one or more therapeutic protein. For example, in one aspect, the protein is homologous to a therapeutic or other protein such as: a cytokine, a growth factor, a growth factor receptor, an interferon, an interleukin, an inflammatory molecule, an oncogene product, a peptide hormone, a signal transduction molecule, a steroid hormone receptor, a transcriptional activator, a transcriptional suppressor, erythropoietin (EPO), fibroblast growth factors, fibroblast growth factor 21 (FGF21), leptin, insulin, human growth hormone, epithelial Neutrophil Activating Peptide-78, GROα/MGSA, GROβ, GROγ, MIP-1α, MIP-16, MCP-1, hepatocyte growth factor, insulin-like growth factor, leukemia inhibitory factor, oncostatin M, PD-ECSF, PDGF, pleiotropin, SCF, c-kit ligand, VEGF, G-CSF, IL-1, IL-2, IL-8, IGF-I, IGF-II, FGF (fibroblast growth factor), PDGF, TNF, TGF-α, TGF-β, EGF (epidermal growth factor), KGF (keratinocyte growth factor), CD40L/CD40, VLA-4/VCAM-1, ICAM-1/LFA-1, hyalurin/CD44, Mos, Ras, Raf, Met; p53, Tat, Fos, Myc, Jun, Myb, Rel, estrogen receptor, progesterone receptor, testosterone receptor, aldosterone receptor, LDL receptor, and/or corticosterone. In another set of embodiments, the protein is homologous to a therapeutic or other protein such as: an Alpha-1 antitrypsin, an Angiostatin, an Antihemolytic factor, an antibody, an Apolipoprotein, an Apoprotein, an Atrial natriuretic factor, an Atrial natriuretic polypeptide, an Atrial peptide, a C—X—C chemokine, T39765, NAP-2, ENA-78, a Gro-α, a Gro-β, a Gro-γ, an IP-10, a GCP-2, an NAP-4, an SDF-1, a PF4, a MIG, a Calcitonin, a c-kit ligand, a cytokine, a CC chemokine, a Monocyte chemoattractant protein-1, a Monocyte chemoattractant protein-2, a Monocyte chemoattractant protein-3, a Monocyte inflammatory protein-1 alpha, a Monocyte inflammatory protein-1 beta, RANTES, 1309, R83915, R91733, HCC1, T58847, D31065, T64262, a CD40, a CD40 ligand, a C-kit Ligand, a Collagen, a Colony stimulating factor (CSF), a Complement factor 5a, a Complement inhibitor, a Complement receptor 1, a cytokine, an epithelial Neutrophil Activating Peptide-78, a GROα/MGSA, a GROβ, a GROγ, a MIP-1α, a MIP-16, a MCP-1, an Epidermal Growth Factor (EGF), an epithelial Neutrophil Activating Peptide, interferon alpha (INF-α), or interferon beta (INF-β), an Exfoliating toxin, a Factor IX, a Factor VII, a Factor VIII, a Factor X, a Fibroblast Growth Factor (FGF), a Fibrinogen, a Fibronectin, a G-CSF, a GM-CSF, a Glucocerebrosidase, a Gonadotropin, a growth factor, a growth factor receptor, a Hedgehog protein, a Hemoglobin, a Hepatocyte Growth Factor (HGF), a Hirudin, a Human serum albumin, an ICAM-1, an ICAM-1 receptor, an LFA-1, an LFA-1 receptor, an Insulin, an Insulin-like Growth Factor (IGF), an IGF-I, an IGF-II, an interferon, an IFN-α, an IFN-β, an IFN-γ, an interleukin, an IL-1, an IL-2, an IL-3, an IL-4, an IL-5, an IL-6, an IL-7, an IL-8, an IL-9, an IL-10, an IL-11, an IL-12, a Keratinocyte Growth Factor (KGF), a Lactoferrin, a leukemia inhibitory factor, a Luciferase, a Neurturin, a Neutrophil inhibitory factor (NIF), an oncostatin M, an Osteogenic protein, an oncogene product, a Parathyroid hormone, a PD-ECSF, a PDGF, a peptide hormone, a Human Growth Hormone, a Pleiotropin, a Protein A, a Protein G, a Pyrogenic exotoxins A, B, or C, a Relaxin, a Renin, an SCF, a Soluble complement receptor I, a Soluble I-CAM 1, a Soluble interleukin receptors, a Soluble TNF receptor, a Somatomedin, a Somatostatin, a Somatotropin, a Streptokinase, a Superantigens, a Staphylococcal enterotoxins, an SEA, an SEB, an SEC 1, an SEC2, an SEC3, an SED, an SEE, a steroid hormone receptor, a Superoxide dismutase, a Toxic shock syndrome toxin, a Thymosin alpha 1, a Tissue plasminogen activator, a tumor growth factor (TGF), a TGF-α, a TGF-β, a Tumor Necrosis Factor, a Tumor Necrosis Factor alpha, a Tumor necrosis factor beta, a Tumor necrosis factor receptor (TNFR), a VLA-4 protein, a VCAM-1 protein, a Vascular Endothelial Growth Factor (VEGF), a Urokinase, a Mos, a Ras, a Raf, a Met; a p53, a Tat, a Fos, a Myc, a Jun, a Myb, a Rel, an estrogen receptor, a progesterone receptor, a testosterone receptor, an aldosterone receptor, an LDL receptor, and/or a corticosterone.

In one aspect, the compositions herein comprise a protein, including, any of the proteins noted above, comprising one or more pyrrolysine or PCL residue(s) and a pharmaceutically acceptable excipient.

In certain embodiments, the protein is a therapeutic protein, while in other embodiments the therapeutic protein is erythropoietin (EPO), fibroblast growth factor 21 (FGF21), interferon alpha (INF-α), or interferon beta (INF-β). In certain embodiments, the therapeutic protein is an antibody or antibody fragment, including but not limited to Fab's. In certain embodiments, the therapeutic protein is produced as a fusion protein wherein the fusion partner is modified. In certain embodiments, the therapeutic protein is a fusion with Fc domain.

Homology to the protein or polypeptide can be inferred by performing a sequence alignment, e.g., using BLASTN or BLASTP, e.g., set to default parameters. For example, in one embodiment, the protein is at least about 50%, at least about 75%, at least about 80%, at least about 90% or at least about 95% identical to a known therapeutic protein (e.g., a protein present in Genebank or other available databases).

Figure 47:
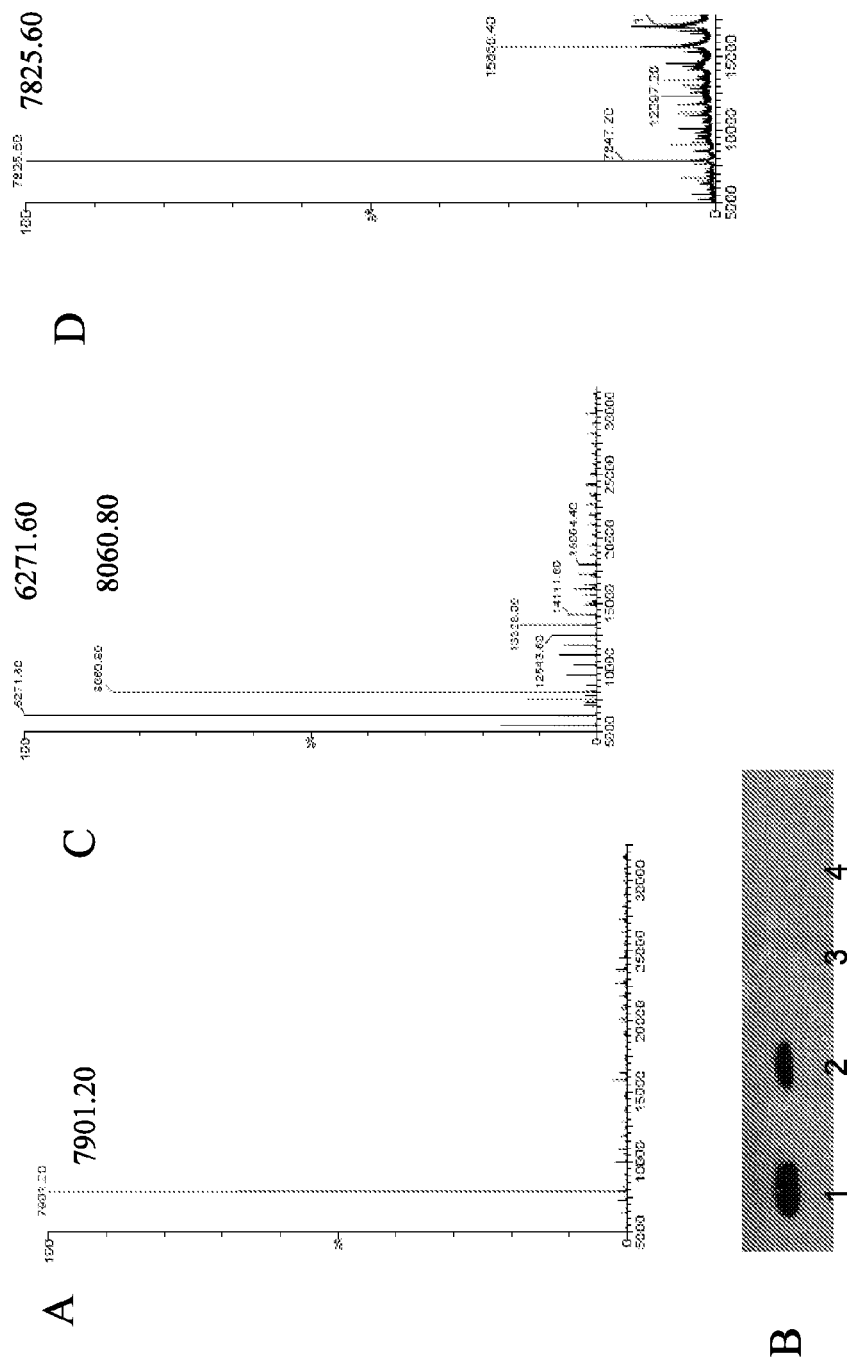
FIG. 47.

To demonstrate site-specific labeling, PCL was incorporated into mEGF using the methods provided herein (see Example 12), and the PCL moiety was coupled to a biotin via a polyether functionalized with an ABA moiety (see X3626-140, Example 40). FIG. 47A shows the ESI mass spectrometric analysis of mEGF-Tyr10PCL conjugated with biotin (see Example 24)). FIG. 47B shows the Western blot of mEGF-Tyr10PCL-ABA-biotin conjugate using a horseradish peroxidase (HRP) conjugated goat anti-biotin antibody. Uncoupled mEGF-Tyr10PCL and fluorescein-conjugated mEGF-Tyr10PCL served as negative controls.

To further demonstrate site-specific labeling, PCL was incorporated into mEGF using the methods provided herein (see Example 12), and the PCL moiety was coupled to fluorescein via a polyether functionalized with an ABA moiety (see X3757-48, Example 41). FIG. 47C shows the ESI mass spectrometric analysis of mEGF-Tyr10PCL conjugated with fluorescein (see Example 25)). In addition, PCL was incorporated into mEGF using the methods provided herein (see Example 12), and the PCL moiety was coupled to a disaccharide functionalized with an ABA moiety (see 3793-050, Example 42). FIG. 47D shows the ESI mass spectrometric analysis of mEGF-Tyr10PCL conjugated with the disaccharide (see Example 26). It is understood that the coupling chemistry used for the attachment of the disaccharide can readily be applied to the coupling of other sugars and complex oligo and polysaccharides.

Coupling of Immune Modulators to Pyrrolysine and/or Pyrrolysine Analogues Incorporated into Proteins, Polypeptides and/or Peptides & Enhanced Immunogenicity Via such Coupling In another aspect provided herein, proteins, polypeptides and/or peptides having one or more pyrrolysine and/or PCL incorporated therein are derivatized with one or more immune modulator. Using the methods provided herein immune stimulating moieties can easily be coupled to proteins, polypeptides and/or peptides via pyrrolysine and/or PCL residue(s). Such immune stimulating moieties include but are not limited to, one or more nitro groups, lipids, phospho-lipids, LPS-like molecules, adjuvants, adjuvant-like molecules, a TLR2 agonist, a TLR4 agonist, a TLR7 agonist, a TLR9 agonist, a TLR8 agonist, T-cell epitopes, keyhole limpet hemocyanin (KLH), immunogenic haptens, halogens, aryl groups, heteroaryl groups, cycloalkyl groups or heterocycloalkyl groups. In certain embodiments, the immune modulator attached to pyrrolysine and/or PCL is used to stimulate an immune response against self-antigen in a way similar to p-nitro-phenylalanine incorporated into proteins (Grünewald J, Tsao M L, Perera R, Dong L, Niessen F, Wen B G, Kubitz D M, Smider V V, Ruf W, Nasoff M, Lerner R A, Schultz P G, Immunochemical termination of self-tolerance, Proc Natl Acad Sci USA. 2008 Aug. 12; 105(32):11276-80). In certain embodiments, a self-antigen with an immune modulator attached to pyrrolysine and/or PCL is used as a cancer vaccine. In other embodiments, the antigen with an immune modulator attached to pyrrolysine and/or PCL is used as a vaccine for infectious diseases. In other embodiments, the antigen with an immune modulator attached to pyrrolysine and/or PCL is used as a vaccine for diseases that involve the formation of amyloids, including but not limited to, Alzheimer's disease.

In one embodiment a library of immune stimulating moieties is generated by creating a library of 2-aminobenzaldehyde compounds, coupling this library to pyrrolysine or PCL incorporated into an antigen of interest and then screening the coupled product for the generation of high-titer antibodies against the modified and unmodified antigen. In such an embodiment the 2-aminobenzaldehyde moiety is substituted with various substituents including, but not limited to, one or more nitro groups, lipids, phospho-lipids, LPS-like molecules, adjuvants, adjuvant-like molecules, a TLR2 agonist, a TLR4 agonist, a TLR7 agonist, a TLR9 agonist, a TLR8 agonist, T-cell epitopes, keyhole limpet hemocyanin (KLH), immunogenic haptens, halogens, aryl groups, heteroaryl groups, cycloalkyl groups or heterocycloalkyl groups.

In another embodiment a library of immune stimulating moieties is generated by creating a library of 2-amino-acetophenone compounds, coupling this library to pyrrolysine or PCL incorporated into an antigen of interest and then screening the coupled product for the generation of high-titer antibodies against the modified and unmodified antigen. In such an embodiment the 2-amino-acetophenone moiety is substituted with various substituents including, but not limited to, one or more nitro groups, lipids, phospho-lipids, LPS-like molecules, adjuvants, adjuvant-like molecules, a TLR2 agonist, a TLR4 agonist, a TLR7 agonist, a TLR9 agonist, a TLR8 agonist, T-cell epitopes, keyhole limpet hemocyanin (KLH), immunogenic haptens, halogens, aryl groups, heteroaryl groups, cycloalkyl groups or heterocycloalkyl groups.

In another embodiment a library of immune stimulating moieties is generated by creating a library of 2-amino-5-nitro-benzophenone compounds, coupling this library to pyrrolysine or PCL incorporated into an antigen of interest and then screening the coupled product for the generation of high-titer antibodies against the modified and unmodified antigen. In such an embodiment the 2-amino-5-nitro-benzophenone moiety is substituted with various substituents including, but not limited to, one or more nitro groups, lipids, phospho-lipids, LPS-like molecules, adjuvants, adjuvant-like molecules, a TLR2 agonist, a TLR4 agonist, a TLR7 agonist, a TLR9 agonist, a TLR8 agonist, T-cell epitopes, keyhole limpet hemocyanin (KLH), immunogenic haptens, halogens, aryl groups, heteroaryl groups, cycloalkyl groups or heterocycloalkyl groups.

Figure 48:
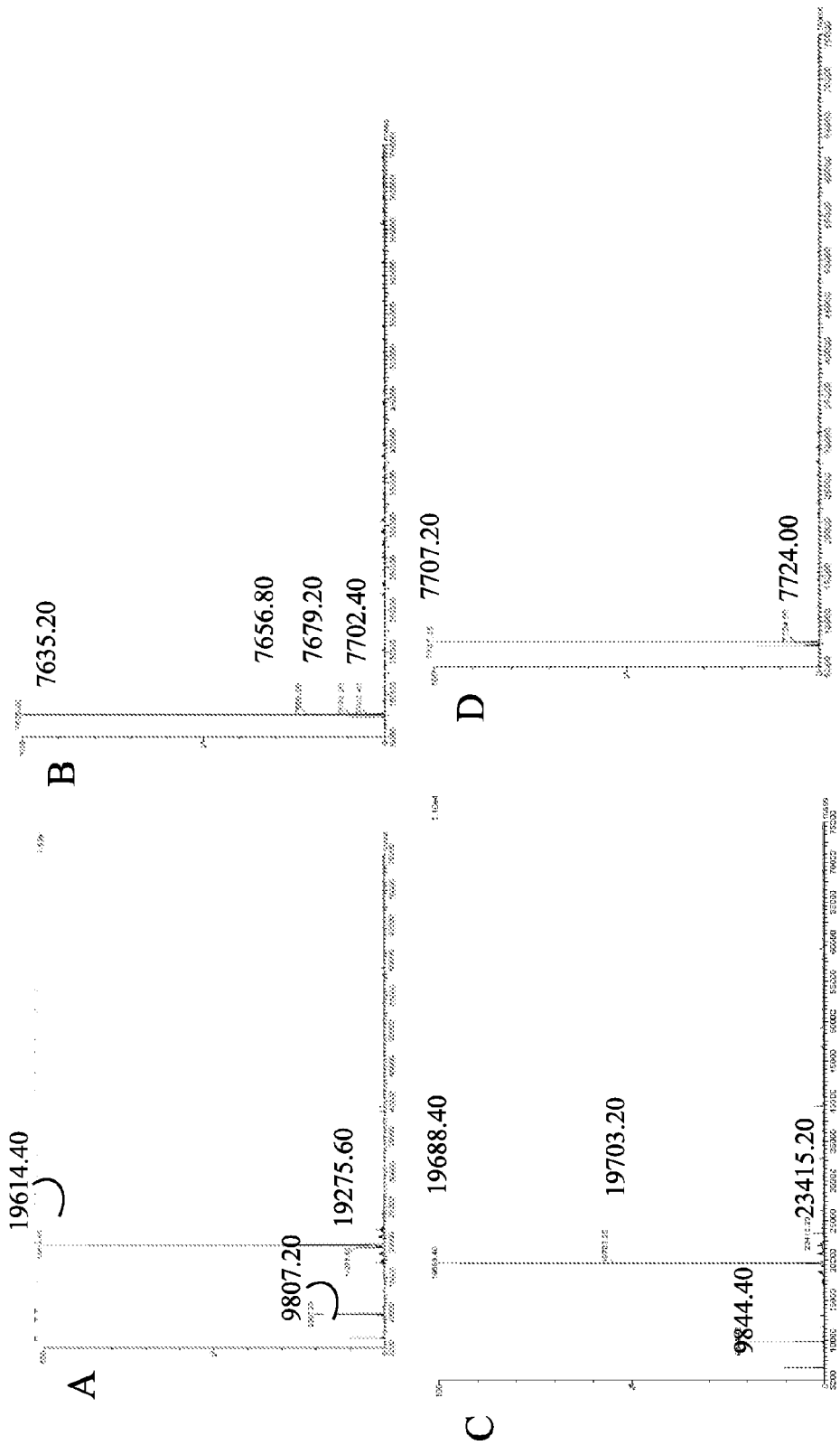
FIG. 48.

To demonstrate this aspect PCL was incorporated into mTNF-α and mEGF using the methods provided herein (see Examples 11 and 12), and the PCL moiety was coupled to a hapten containing one or more nitrophenyl groups (see Examples 27 and 28). FIG. 48A and FIG. 48B demonstrates the attachment of a mono-nitrophenyl hapten (see 3793-001, Example 38-8) at the site of PCL incorporation in mTNF-Gln21PCL (FIG. 48A) and mEGF-Tyr10PCL (FIG. 48B). FIG. 48C and FIG. 48D shows the attachment of a di-nitrophenyl hapten (TU3627-088, Example 38-7) at the site of PCL incorporation into mTNF-α (FIG. 48C) and mEGF (FIG. 48D).

Figure 49:
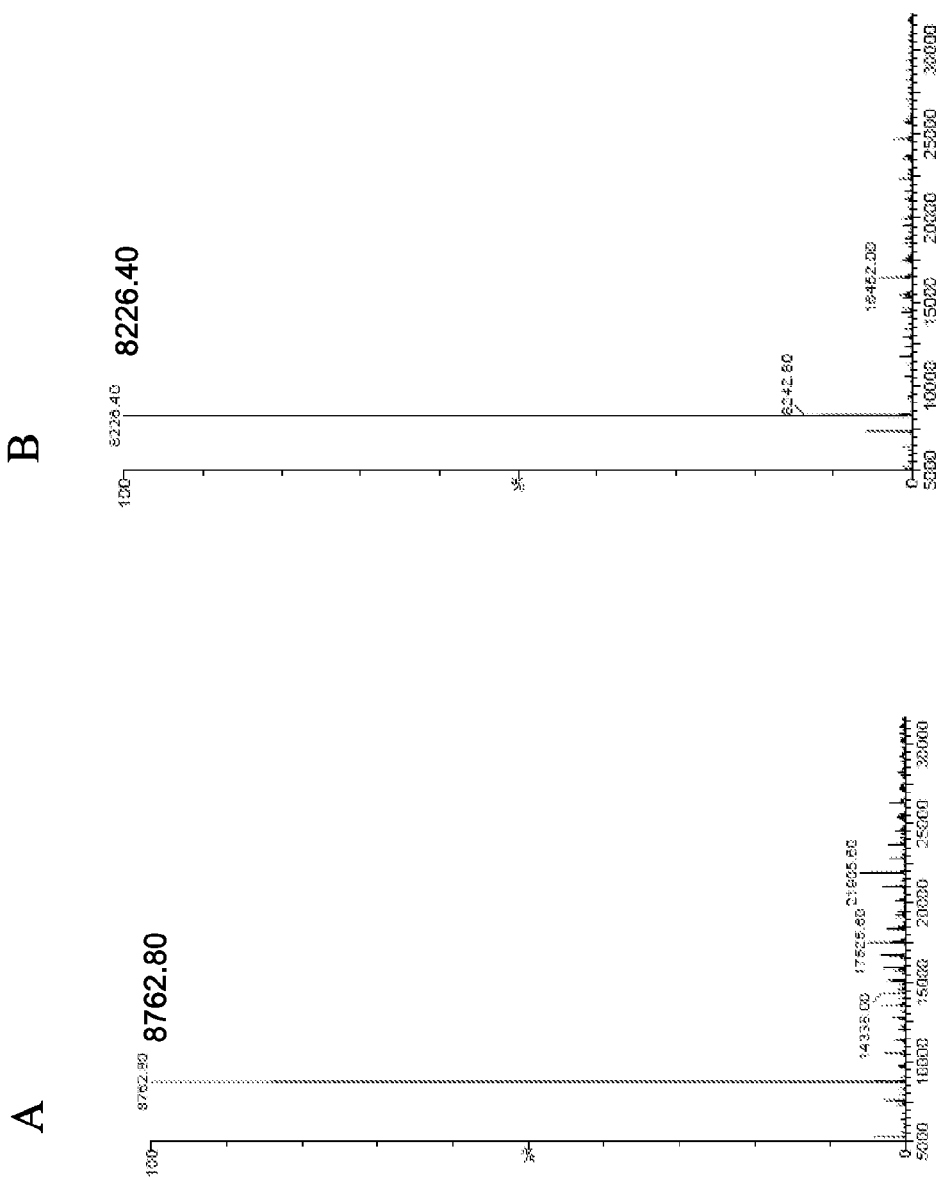
FIG. 49.

FIG. 49A demonstrate the attachment of a TLR7 agonist (see X3678-114; Example 38-3) at the site of PCL incorporation in mEGF-Tyr10PCL (see Example 29). FIG. 49B demonstrate the attachment of a phospholipid (see TU3627-092; Example 43-1) at the site of PCL incorporation in mEGF-Tyr10PCL (see Example 31).

Figure 50:
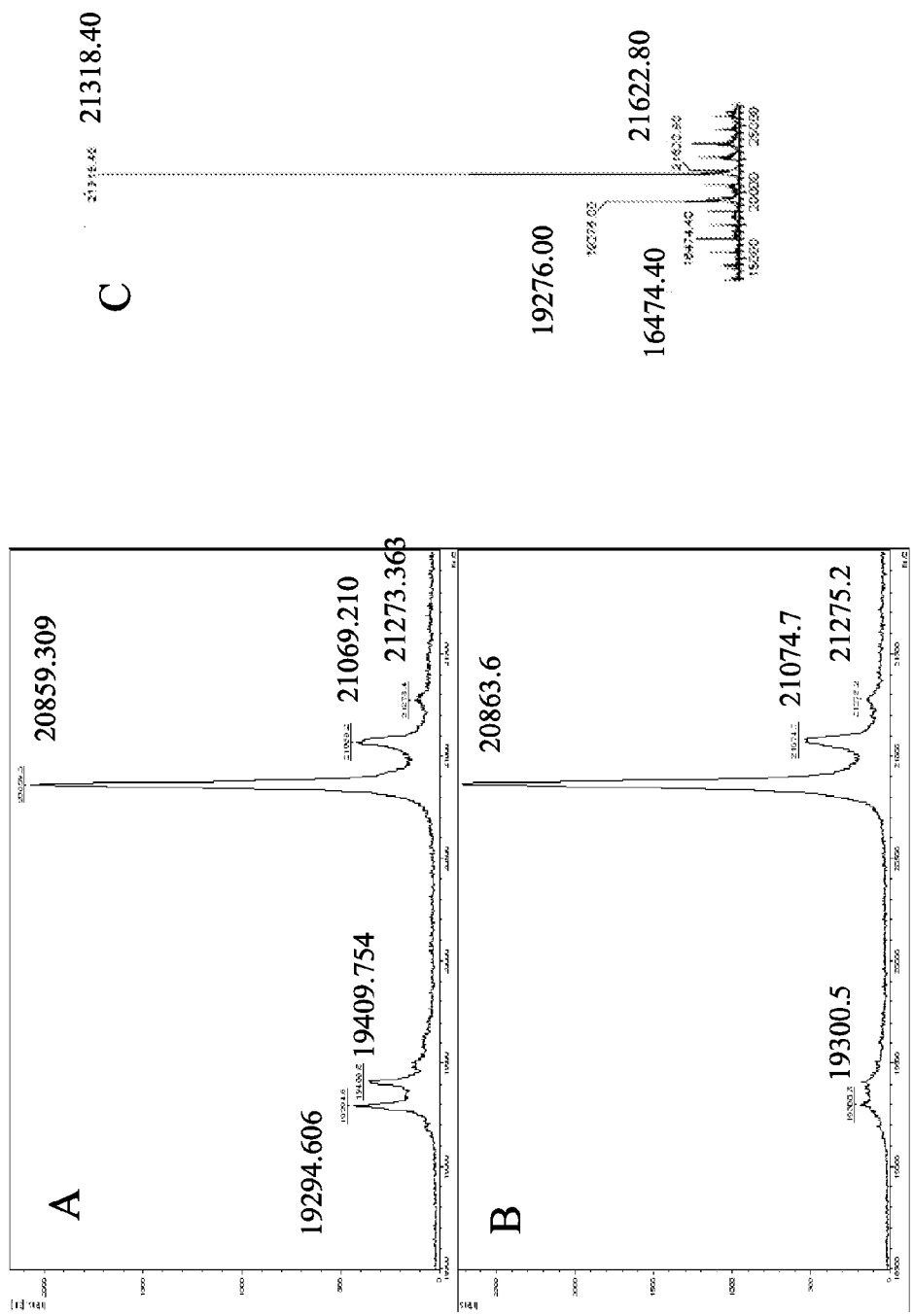
FIG. 50.
Figure 51:
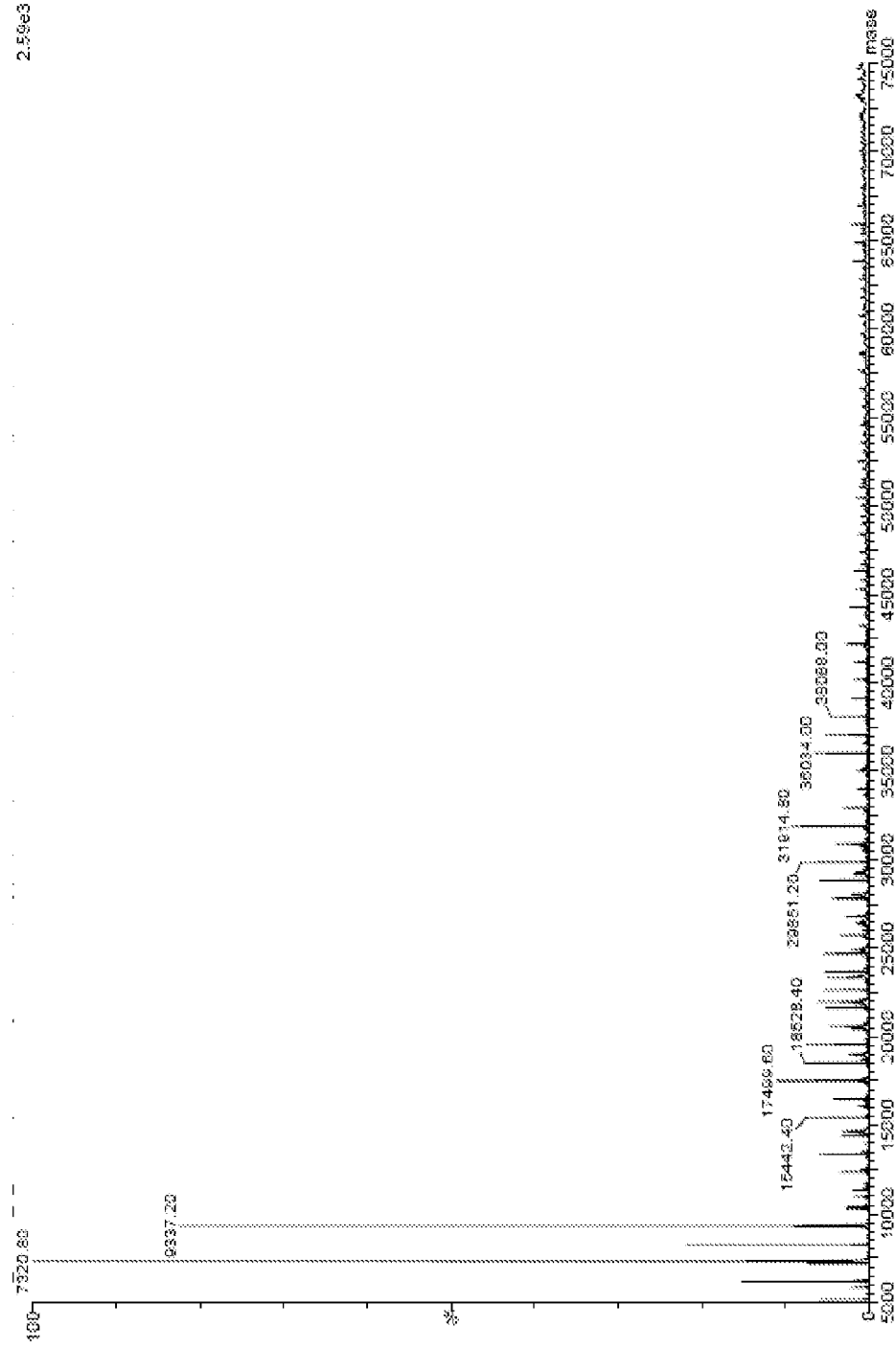
FIG. 51.

FIGS. 50-51 demonstrate the conjugation of PADRE peptides: PX2-PADRE (MW=1585) (see 3465-143; Example 38-11), and BHA-exPADRE (MW=2060) (see 3647-104; Example 38-10) to either mTNF-Gln21PCL or mEGF-Tyr10PCL. FIG. 50A and FIG. 50B show the MALDI-TOF mass spectrometric analysis of mTNF-Gln21PCL conjugation reaction with PX2-PADRE at two different pH values (see Example 30), while FIG. 50C shows the ESI mass spectrometric analysis of mTNF-Gln21PCL conjugation reaction with BHA-exPADRE (see Example 30). FIG. 51 shows the coupling of BHA-exPADRE to mEGF-Tyr10PCL (see Example 30). The sequence of the PADRE peptide (SEQ ID NO:28) is is Gly(DAla)LysXValAlaAlaTrpThrLeuLysAla(D-Ala)Gly-OH, where X is cyclohexyl-alanine. The sequence of the exPADRE peptide (SEQ ID NO:29) is Ala-GlySerArgSerGly(DAla)LysXValAlaAlaTrpThrLeuLysAla(D-Ala)Gly-OH, where X is cyclohexyl-alanine. In certain embodiments, known immunogenic peptide epitopes will be coupled to antigens in order to enhance the immunogenicity of said antigen. In certain embodiments, peptides derived from an antigen will be coupled to an immunogenic carrier protein. In certain embodiments, the immunogenic carrier protein is KLH. It is understood that the coupling chemistry used for the attachment of PADRE peptides can be readily applied to the coupling of other peptides to PCL and pyrrolysine.

Immuno-PCR: Coupling of DNA and other Oligonucleotides to Pyrrolysine and/or Pyrrolysine Analogues Incorporated into Proteins, Polypeptides and/or Peptides In another aspect provided herein, proteins, polypeptides and/or peptides having one or more pyrrolysine and/or PCL incorporated therein are derivatized with DNA using the methods provided herein. The DNA is modified to have terminal 2-amino-benzaldehyde, 2-amino-acetophenone or 2-amino-5-nitro-benzophenone moieties that react with pyrrolysine and/or PCL incorporated into the protein, polypeptide and/or peptide, there the DNA is coupled to the protein, polypeptide and/or peptide via a quinazoline-type linkage, reduced quinazoline linkage or the fused ring linkage (see FIGS. 22, 23 and 30).

Figure 52:
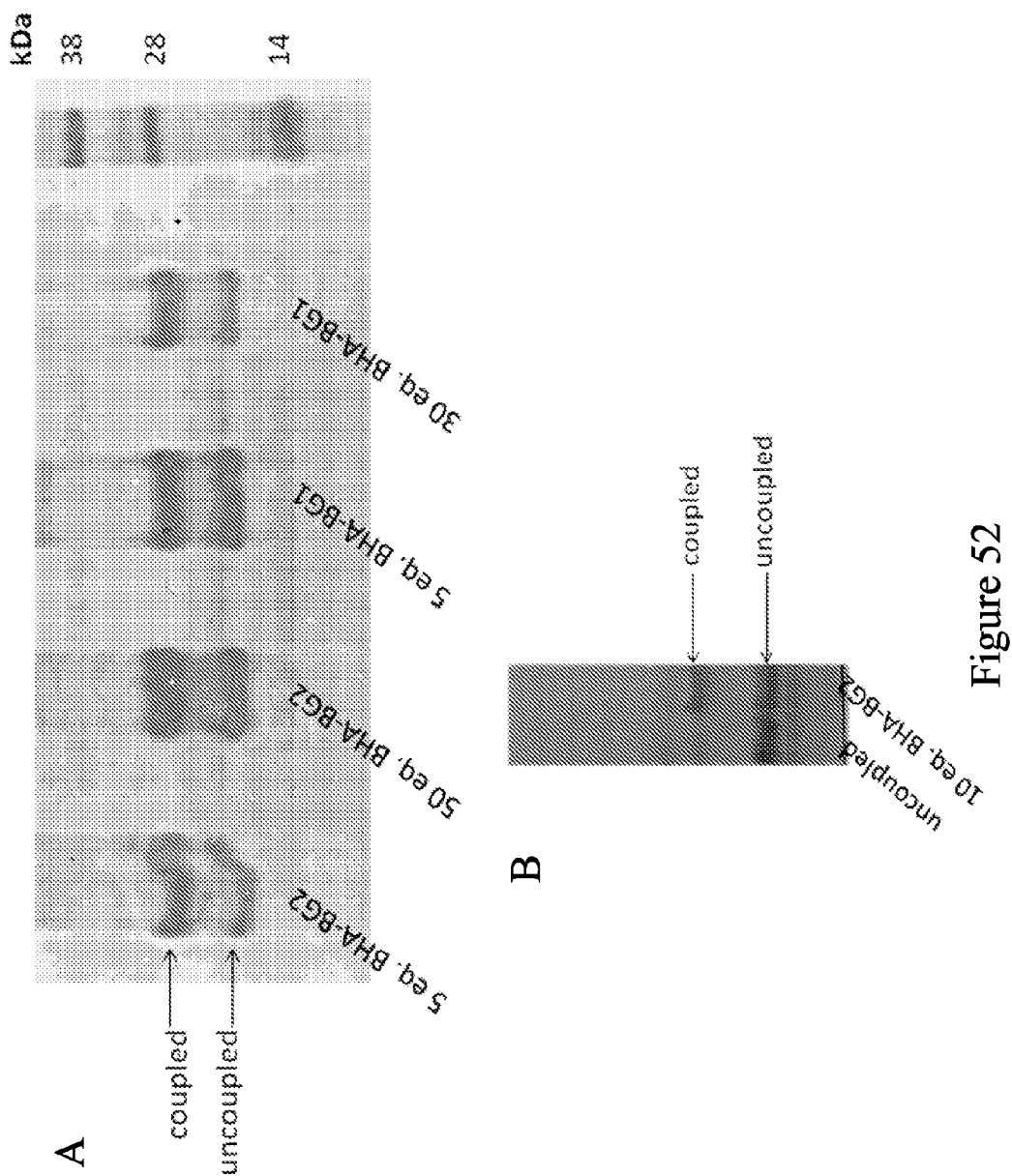
FIG. 52.

To demonstrate the attachment of DNA to PCL, PCL was incorporated into mTNF-α and mEGF using the methods provided herein (see Examples 11 and 12), and the PCL moiety was coupled to a CpG oligonucleotide that is also an immune stimulating moiety (see Examples 32). BHA-BG1 (see 3647-057; Example 38-12) and BHA-BG2(see 3597-167; Example 38-14) were the CpG reagent used to attach the CpG to mTNF-Gln21PCL and mEGF-Tyr10PCL at the site of PCL incorporation. The coupling of BHA-BG1 (7.4 kDa) and BHA-BG2 (7.4 kDa) to mTNF-Gln21PCL (19.3 kDa) was confirmed by gel shift assay (FIG. 52A) as was the coupling of BHA-BG2 (7.4 kDa) to mEGF-Tyr10PCL (7.2 kDa) (FIG. 52B). The sequence of BG1 (SEQ ID NO:30) is 5'*T*C*C*A*T*G*A*C*G*T*T*C*C*T*G*A*C*G*T*T-3', where * denotes a phosphothioate linkage. The sequence of BG2 (SEQ ID NO:31) is 5'*T*C*G*T*C*G*T*T*T*T*C*G*G*C*G*C*G*C*G*C*C*G-3', where * denotes a phosphothioate linkage. In certain embodiments, the oligonucleotide to be coupled will be a deoxyribonucleic acid, a ribonucleic acid, a peptide nucleic acid or other modified oligonucleotide. Initially coupled to pyrrolysine or PCL as a single-stranded oligonucleotide, double-stranded DNA, RNA, PNA or hybrid polymers can readily be prepared by hybridization with a complementary strand. It is understood that the coupling chemistry used for the attachment of CpG oligonucleotides can readily be applied to the coupling of other oligonucleotides.

In certain embodiments the proteins, polypeptides and/or peptides are antibodies and such antibodies having linked DNA are used to perform immuno-PCR analysis. Immuno-PCR is performed by linking DNA to an antibody using the methods described herein, and then binding the DNA linked antibody with a target antigen. After binding the DNA is amplified using DNA amplification techniques and the resulting amplification product is analyzed using electrophoretic techniques, microplate methods or real-time PCR.

Site-Specific and Oriented Attachment

Figure 53:
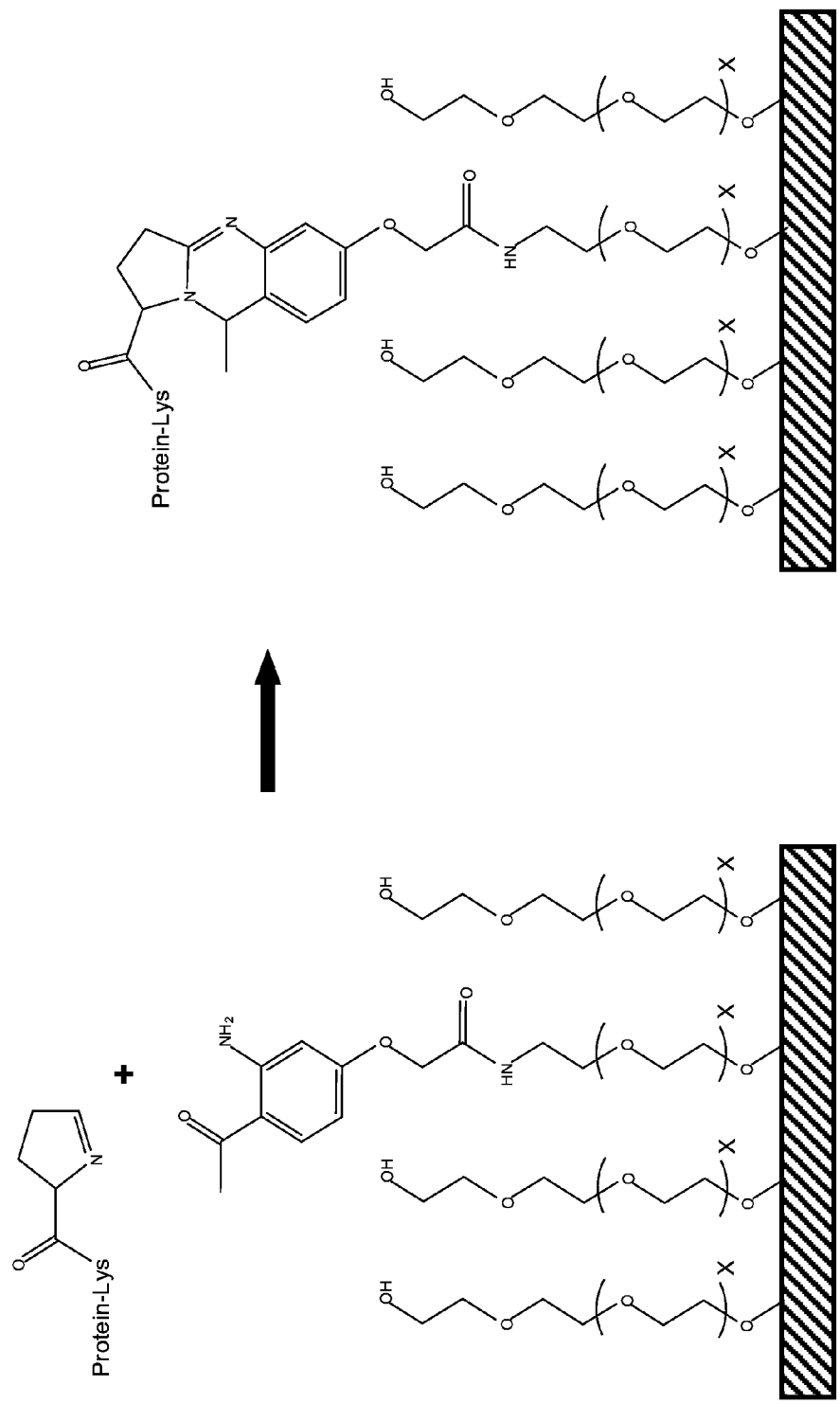
FIG. 53.

In another aspect provided herein, the site-specific incorporation of one or more pyrrolysine and/or PCL into proteins, polypeptides and/or peptides is used to control the orientation of such proteins, polypeptides and/or peptides upon attachment to the surface of a support. Such attachment results from reaction of the pyrrolysine or PCL residues with a surface derivatized with benzaldehyde moieties, acetophenone moieties, benzophenone moieties or combinations thereof, thereby forming a quinazoline moiety linking and orienting the protein on the surface. By incorporating pyrrolysine and/or PCL at specific positions within the protein, the orientation of the protein on a surface is controlled. Such control of the orientation of protein attachment is used as a component of a protein engineering tool kit for evaluation of protein properties. FIG. 53 illustrates an embodiment of such site-specific oriented attachment, wherein a surface is derivatized with 20amino-acetophenone moieties that reacts with a PCL residues incorporated into a protein thereby attaching the protein to the surface via a quinazoline-type linkage. In FIG. 53, the protein conjugate linkage formed is a quinazoline-type moiety, however in other embodiments the linkage is a reduced form of the quinazoline-type moiety (see FIGS. 22, 23 and 30). In other embodiments, the linkage is the fused ring moiety (see FIGS. 22, 23 and 30).

Non-limiting examples of support include, but are not limited to, solid and semi-solid matrixes, such as aerogels and hydrogels, resins, beads, biochips (including thin film coated biochips), microfluidic chip, a silicon chip, multi-well plates (also referred to as microtitre plates or microplates), membranes, cells, conducting and nonconducting metals, glass (including microscope slides) and magnetic supports. Other non-limiting examples of solid supports used in the methods and compositions described herein include silica gels, polymeric membranes, particles, derivatized plastic films, derivatized glass, derivatized silica, glass beads, cotton, plastic beads, alumina gels, polysaccharides such as Sepharose, poly (acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like. In certain embodiments, the supports used in the methods and compositions described herein are supports used for surface analysis such as surface acoustic wave devices or devices utilizing evanescent wave analysis, such as surface plasmon resonance analysis.

The surfaces of the solid supports used for the attachment of proteins, polypeptides and/or peptides having pyrrolysine and/or pyrrolysine analogues incorporated therein have reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide and sulfoxide. Such functional groups are used to covalently attach the 2-amino-benzaldehyde moieties, 2-amino-acetophenone moieties and/or 2-amino-5-nitro-benzophenone moieties that react with the pyrrolysine or pyrrolysine analogues to form the quinazoline moiety. In certain embodiments, such 2-amino-benzaldehyde moieties, 2-amino-acetophenone moieties and 2-amino-5-nitro-benzophenone moieties are part of a polymeric linker coupled to the solid support by reaction with a solid support reactive functional group, such as, but not limited to, hydroxyl, carboxyl, amino, thiol, aldehyde, halogen, nitro, cyano, amido, urea, carbonate, carbamate, isocyanate, sulfone, sulfonate, sulfonamide and sulfoxide.

In other embodiments, the surfaces of the solid supports have streptavidin or avidin attached thereto, and are used for the attachment of proteins, polypeptides and/or peptides having pyrrolysine and/or pyrrolysine analogues incorporated therein, wherein the pyrrolysine and/or pyrrolysine analogues are used to site specifically attached biotin to the proteins, polypeptides and/or peptides.

Other supports used in the methods and compositions described herein include, resins used in peptide synthesis such as, by way of example only, polystyrene, PAM-resin, POLYHIPE™ resin, polyamide resin, polystyrene resin grafted with poly(ethylene glycol), polydimethyl-acrylamide resin and PEGA beads.

In certain embodiments, proteins, polypeptides and/or peptides having pyrrolysine and/or PCL incorporated therein are deposited onto a solid support in an array format. In certain embodiments, such deposition is accomplished by direct surface contact between the support surface and a delivery mechanism, such as a pin or a capillary, or by ink jet technologies which utilize piezoelectric and other forms of propulsion to transfer liquids from miniature nozzles to solid surfaces. In the case of contact printing, robotic control systems and multiplexed printheads allow automated microarray fabrication. For contactless deposition by piezoelectric propulsion technologies, robotic systems also allow for automatic microarray fabrication using either continuous or drop-on-demand devices.

EXAMPLES

It is understood that the embodiments described herein and the following examples are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for the purposes as indicated.

Example 1

Site Specific Incorporation of Biosynthetically Generated PCL into Proteins Using Mammalian Cells This example provides a description of the gene constructs that when transfected into mammalian cells enable the incorporation of PCL into TAG encoded sites in a target protein. Although simultaneous incorporation at multiple sites is possible, all examples herein, illustrate incorporation of PCL at a single site per protein molecule only. This example also describes the general procedures for PCL incorporation into proteins using mammalian cells.

Constructs:

Full length pylT and coding regions of pylS, pylT, pylB, pylC and pylD were amplified from genomic DNA of *Methanosarcina mazei* Go1 by PCR with primers designed based on nucleotide sequences of pylS, pylT, pylB, pylC and pylD from *Methanosarcina mazei* Go1 (NC_003901, see below. The initiation codon of the genes was changed to ATG. PylT was cloned upstream of the CMV promoter into the pCMV vector. Transcription is under the control of a U6 promoter to form vector pCMVU6. pylS, pylB, pylC and pylD were similarly cloned into pCMVU6. Transcription of pylS, pylB, pylC and pylD is under the control of the CMV promoter (FIG. 4A).

Coding regions of target genes, human retinol binding protein (hRBP4), human and mouse erythropoietin (EPO), and mIgG1 Fc (mFc) were cloned into pRS vector under the control of a CMV promoter with a His tag in the C-terminal (FIG. 4B). Residues for mutation to a TAG codon were selected based on their solvent-exposure in existing structural models as indicated in Table 2. The TAG codons were introduced into the target genes by PCR methods.

TABLE 2

Single site TAG mutants introduced in proteins expressed in HEK293F cells.

| # | Human EPO | Mouse EPO | hRBP4 | Mouse IgG1 Fc |
|---|---|---|---|---|
| 1 | R31 | R30 | Y51 | K333 |
| 2 | A57 | A56 | F62 | K336 |
| 3 | N63 | N60 | W83 | T394 |
| 4 | K79 | K78 | Y116 | L426 |
| 5 | Q92 | Q91 | W117 | |
| 6 | R103 | Q102 | F122 | |
| 7 | W115 | P114 | Y140 | |
| 8 | K143 | K142 | Y191 | |
| 9 | A152 | T151 | Y199 | |
| 10 | R158 | R157 | | |
| 11 | R193 | R192 | | |

FIG. 4B shows the TAG mutant constructs of hRBP4, mEPO, hEPO, and mIgG1. The sites of the mutations are listed in Table 2 and indicated in FIG. 4B by arrows. For each construct a His tag is attached in the C-terminal as the purification and detection tool. Only the full length proteins can have the His tag. pylT, pylS, pylB, pylC, and pylD were cloned into pCMVU6 under the control of a CMV (FIG. 4A). They are used in co-transfection studies.

Cell Culture and Transfection:

HEK293F cells were grown in suspension in 293 Freestyle expression media at 37° C. under 5% $CO_2$. One day before transfection, cells were split to $0.7 \times 10^6$ cells/ml. Plasmid DNA was prepared using Qiagen Maxi plasmid preparation kit. Transfections were carried out by PEI method. PEI was mixed with plasmid DNA in a ratio of 2 to 1 in Opti-MEM and the DNA complex was added to HEK293F cells at 1 ug plasmid DNA/ml cell culture and the cells were cultured for four days in the presence of 5 mM Cyc or D-ornithine. When cells were co-transfected with several plasmids the ratio of PEI to total amount of plasmid DNA was always 2 to 1.

Protein Purification and Analysis:

Four days after transfection, cell cultures were centrifuged at 2000 g for 20 min and media were collected for purification of His tagged proteins. The media were loaded to Ni-NTA columns equilibrated previously with 20 mM TrisHCl (7.5), 150 mM NaCl containing 10 mM imidazole. The columns were washed with the same buffer and eluted with an elution buffer (20 mM TrisHCl 7.5, 150 mM NaCl, 300 mM Imidazol). Eluted proteins were assayed by Bradford method and SDS-PAGE. In some cases, media and purified proteins were analyzed by western Blot with antibody to His tag or to proteins.

The sequences of pyl genes cloned from genomic DNA from *Methanosarcina maize* are given below:

```
Sequence of pylS:                                                                          (SEQ ID NO: 1)

atggataaaaaaccactaaacactctgatatctgcaaccgggctctggatgtccaggaccggaacaattcataaaataaaacaccac gaagtctctcgaagcaaaatctatattgaaatggcatgcggagaccaccttgagtaaacaactccaggagcagcaggactgcaag agcgctcaggcaccacaaatacaggaagacctgcaaacgctgcagggtttcggatgaggatctcaataagttcctcacaaaggca aacgaagaccagacaagcgtaaaagtcaaggtcgtttctgccccgaccagaacgaaaaaggcaatgccaaaatccgttgcgaga gccccgaaacctcttgagaatacagaagcggcacaggctcaaccttctggatctaaattttcacctgcgataccggtttccacccaa gagtcagtttctgtcccggcatctgtttcaacatcaatatcaagcatttctacaggagcaactgcatccgcactggtaaagggaa tacgaacccattacatccatgtctgcccctgttcaggcaagtgcccccgcacttacgaagagccagactgacaggcttgaagtcc tgttaaacccaaaagatgagatttccctgaattccggcaagcctttcagggagcttgagtccgaattgctctctcgcagaaaaaa gacctgcagcagatctacgcggaagaaagggagaattatctggggaaactcgagcgtgaaattaccaggttctttgtggacagggg ttttctggaaataaaatccccgatcctgatccctcttgagtatatcgaaaggatgggcattgataatgataccgaactttcaaaaca gatcttcagggttgacaagaacttctgcctgagacccatgcttgctccaaacctttacaactacctgcgcaagcttgacagggccct gcctgatccaataaaatttttgaaataggcccatgctacagaaaagagtccgacggcaaagaacacctcgaagagtttaccatgct gaacttctgccagatgggatcgggatgcacacgggaaaatcttgaaagcataattacggacttcctgaaccacctgggaattgattt caagatcgtaggcgattcctgcatggtctatggggataccttgatgtaatgcacggagacctggaactacctctgcagtagtcgga cccataccgcttgaccgggaatgggtattgataaaccctggatagggcaggtttcgggctcgaacgccttctaaaggttaaacac gactttaaaaatatcaagagagctgcaaggtccgagtcttactataacgggatttctaccaacctgtaa Sequence of pylB:                                                                          (SEQ ID NO: 2)

atgatccagaaaatggcaaccgaagaacttgacaggttcggggagaaaattattgaaggttttaaattgtctgatgatgacctcagg gctcttctttctcttgaattcgaagaagagctggaaaagctttactatgtagctagaaaggtcagaaactattatttcggcaacagg gtgtttcttaactgttttatttatttctcaacttattgtaaaaaccagtgctcttttttgctactataactgtaaaaacgaaattaac cgctaccgcctgaccggtgaagaggaaaagagatgtgcaaagccctgaaaggtgcaggcatcacatgatcgacctgacaatgggaga ggatcccctattactatgatgaccctgaccgcttcgttgaacttgtcaggacagtaaaagaagaactcgggcttccaataatgatttc tccgggagttatggatgacagcaccctcctgaaagccagggaagaaggagcaaatttctttgcccttttatcaggagacttatgaccg cgaactttatggaaagctaagggtaggtcagtccttcgaaggaaggtttaatgcccgcaggtttgcaaaagaacagggggtactgtat agaagacggcattcaaccggcgtaggaaatgatatcgaatcaactcaatatccctgaaggggatgaaagcaaacaatcctgatatggt aagggtaatgacttttctgcctcaggaaggaactccgcttgaaggtttcagcgatagttcaaagctttcggagctgaaaatcatagcg attctcaggctcatgtttcctgaatgcctgataccggcttctcttgaccttgaaggcatagacggcatggtgcaccgtttaaatgccg gagcaaatattgtaacctccatcctcccagattcacgcctggaaggggagccaattacgaccgcggcatggaagagagggacagggacg ttacaagcgttgtcaaaaggctgaaggttatgggaatggaacctgcgccgcaggctgagtttgagagagtcctggggtgctaa
```

Sequence of pylC: (SEQ ID NO: 3)

atgagagagtcctggggtgctagcctgaaaacaatatgccaataggcgggaagctgcagggcacgaggctgcatacctatctaa gaaagccggaatgaaagtgcttgtaatagacaaaaacccgcaggcgcttataaggaattatgcggatgagttccagtgttttaacat aacgaagagccggaaaaactcgtcgcgatatcaaaaaatgagatgccatactgccggtaaatgaaaaccagaatgtatagaatt tctgaattctataaaagaaaaattctcctgcccggtacttttcgattttgaagcttacaggatcagcagggataagagaaatcaaa agaatacttcgcatccataggaaccccgaccccctcaggacaaaccgtcggaaccaccttatttttgtaaagcctccctgcgaaagcagc agtgtgggagcgagaataatccatgacaggaaagagcttaaagagcagagcccgggatgctcatagaagaatacgagaaggg gaagtggtctcacttgaggtcatagggggatggaaataattagctgtggtaaaggaaacccagtacatatcgatgacacctatgactg ccatatggtgacccctctccctctagaccccttccttcaggggaactatcctactcccttgcagcaaacctgcccttaaaaggaattat ggacgtggaagcgatttccggcccccctggggttaaaagttattgagatagatgcccgtttcccgagccagactccgactgcggtctat tattcttccgggatcaacctcatagaactcctgttccgggcttttaatggaggcatagaagagatcaaaactctccctgaagacaggt actgcatttacgaacatctcatgcttgcagaaaatggagtacttatccctgtgggagaacaggtcctgtccatgggaaatgattacgg caattattatgaagaacctggaatagagattacctgtgcaaaggagagaaccctgtattcaccctggattctggggcagagacaggg aagaagctgaagctagaaaaaacaaagggcatcgattctaaaaagccgatcggagctgctgcataa Sequence of pylD: (SEQ ID NO: 4)

atggcacttttaaccccagaagacctggaaaatattaacaaacagcttcaagaagctgattctactgtccgcagagttacagggcttg atataaaaggtatctgtaaagatttctacggcacaactccatgctgtgaaaaagtaggtatcgtgcctgtgacctcagggaacgggat cataggagctttttccgaatccctgaatgcaattgccgggtatttcgggtttgacagtttttattactgatatgcctgacgtcagcgga tattatgaggcagtaaagaacggagcccggatcatacttatggcagatgataataccaccagcccacaacctgaaaaatggaaaaatc gccaataaccagccgtgtacaggcataatttatgctgaaatagatcaagatacctgaaagccgattccaaagaagtgcagccgtg ggtcttgggaaggttggatttccgggagcagcccatctcgtacagaaaggcttcaaggtttacggatatgatgctgacagaaccctt ctagaaaaaagcgtttccagcctcggaattatacctttcaatcccgtcagccccgaaggcgacaggcaaaggaagttttccattatt ttcgaagcaaccccctgtgcagacacgattccggaatccgtaatttcggaaaactgtgtgatttctacccctgggatacctgtgca atctcaaaggagctgcaaaaaaagtgtggagttgaacttgtaatggaaccactggggataggtacagcatcaatgctgtattctgt actctaa Sequence of pylT: (SEQ ID NO: 5)

GGAAACCTGATCATGTAGATCGAATGGACTCTAAATCCGTTCAGCCGGGTTAGATTCCCGGGGTTTCCGCCA

Example 2

Site Specific Incorporation of Biosynthetically Generated PCL into hRBP4 Using Mammalian Cells This example demonstrates the site specific incorporation of PCL at TAG encoded sites in the model protein human RBP4 (human retinol binding protein 4). hRBP4 is a secreted protein and its structure has been characterized, and the solvent exposed residues in hRBP4 are well defined.

hRBP4 was cloned into the pRS vector with a Flag-His tag in the C-terminus (FIG. 4A). hRBP4 was expressed well in HEK293F cells using transient transfection. The TAG codon was introduced into nine positions in separate hRBP4 constructs as indicated in Table 2 and in the following sequences. Note that individual TAG codons were introduced at the codon of the underlined amino acid residues.

(A). hRBP4 amino acid sequence: (SEQ ID NO: 6)

MKTFILLLWVLLLWVIFLLPGATAQPERDCRVSSFRVKENFDKARFSGTWY51A

MAKKDPEGLF62LQDNIVAEFSVDETGQMSATAKGRVRLLNNW93DVCADMV

GTFTDTEDPAKFKMKY116W117GVASF122LQKGNDDHWIVDTDYDTY140AV

QYSCRLLNLDGTCADSYSFVFSRDPNGLPPEAQKIVRQRQEELCLARQY191RLI

VHNGY199CDGRSERNLLDYKDDDDKHHHHHH

Figure 6:
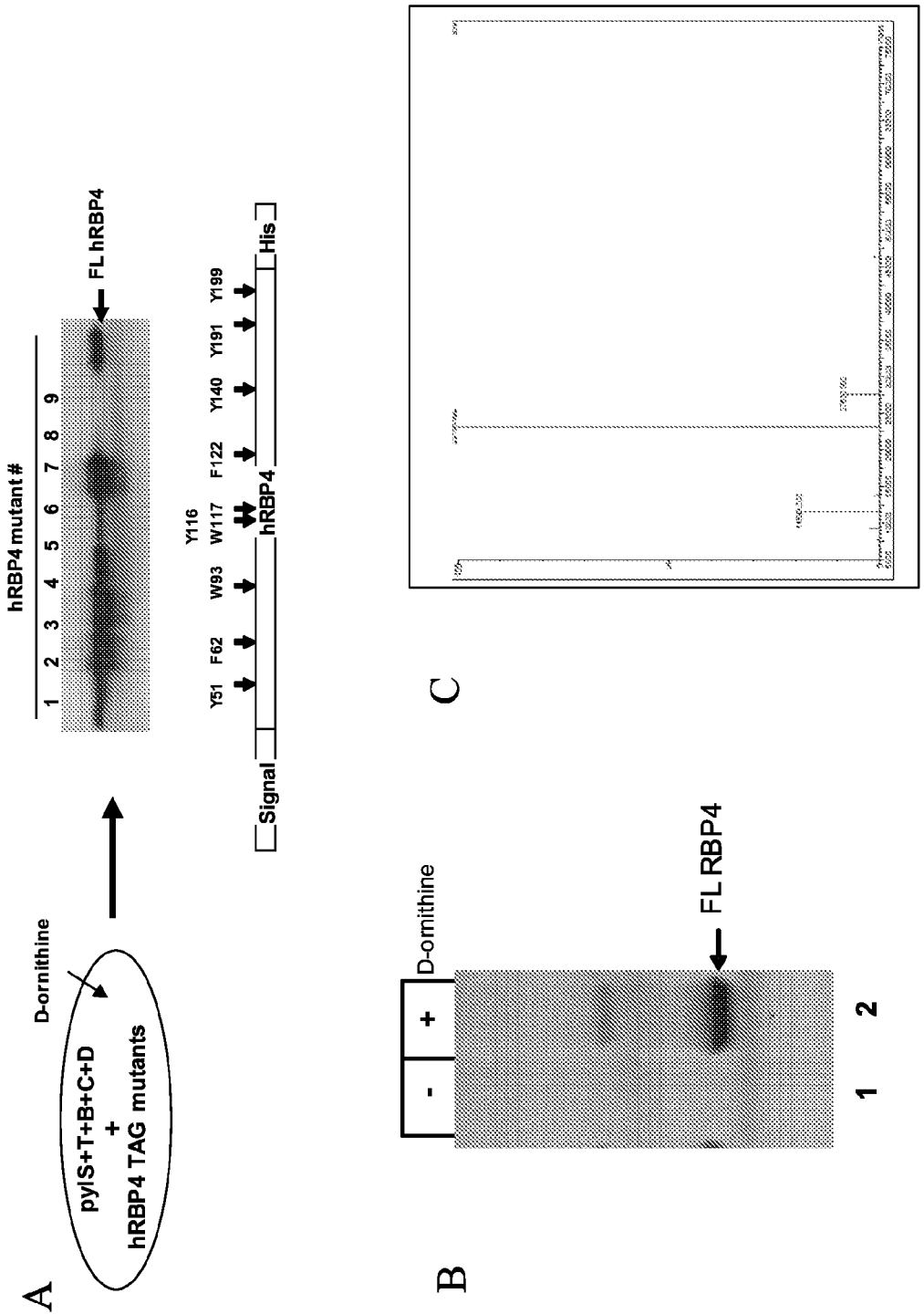
FIG. 6A. Expression of hRBP4 in HEK293F cells. TAG mutant constructs of hRBP4 (#1-9). SDS-PAGE followed by a Western blot with an anti-His antibody. The arrow at 26 kDa indicates full-length hRBP4.
FIGS. 6B and 6C. SDS-PAGE (A) and mass spectrum (B) of purified hRBP4 Phe62PCL produced in HEK293F cells in the presence of D-ornithine.

-continued (B). Nucleotide sequence of hRBP4 and TAG mutants
Wild-type hRBP4:
(SEQ ID NO:7)
ATGAAAACATTCATACTCCTGCTcTGGGTACTGCTGCTCTGGGTTatcttcctgcttc ccggtgccactgctcagcctgagcgcgactgccgagtgagcagcttccgagtcaagga gaacttcgacaaggctcgcttctctgggacctggTACgccatggccaagaaggacccc gagggcctcTTTctgcaggacaacatcgtcgcggagactccgtggacgagaccggcca gatgagcgccacagccaagggccgagtccgtcttttgaataacTGGgacgtgtgcgca gacatggtgggcaccacacagacaccgaggaccctgccaagttcaagatgaagTACTG GggcgtagcctccTTTctccagaaaggaaatgatgaccactggatcgtcgacacagac tacgacacgTATgccgtgcagtactcctgccgcctcctgaacctcgatggcacctgtg ctgacagctactccttcgtgttttcccgggaccccaacggcctgccccagaagcgca gaagattgtaaggcagcggcaggaggagctgtgcctggccaggcagTACaggctgatc gtccacaacggtTACtgcgatggcagatcagaaagaaacctttggactataaagacg atgacgataagcatcaccatcaccatcacTAA hRBP4 mutant 1:
(SEQ ID NO: 8)
ATGAAAACATTCATACTCCTGCTcTGGGTACTGCTGCTCTGGGTTatcttcctgcttc ccggtgccactgctcagcctgagcgcgactgccgagtgagcagcttccgagtcaagga gaacttcgacaaggctcgcttctctgggacctgg<u>TAG</u>gccatggccaagaaggacccc gagggcctcTTTctgcaggacaacatcgtcgcggagactccgtggacgagaccggcca gatgagcgccacagccaagggccgagtccgtcttttgaataacTGGgacgtgtgcgca gacatggtgggcaccacacagacaccgaggaccctgccaagttcaagatgaagTACTG GggcgtagcctccTTTctccagaaaggaaatgatgaccactggatcgtcgacacagac tacgacacgTATgccgtgcagtactcctgccgcctcctgaacctcgatggcacctgtg ctgacagctactccttcgtgttttcccgggaccccaacggcctgccccagaagcgca gaagattgtaaggcagcggcaggaggagctgtgcctggccaggcagTACaggctgatc gtccacaacggtTACtgcgatggcagatcagaaagaaacctttggactataaagacg atgacgataagcatcaccatcaccatcacTAA hRBP4 mutant 2:
(SEQ ID NO: 9)
ATGAAAACATTCATACTCCTGCTcTGGGTACTGCTGCTCTGGGTTatcttcctgcttc ccggtgccactgctcagcctgagcgcgactgccgagtgagcagcttccgagtcaagga gaacttcgacaaggctcgcttctctgggacctggTACgccatggccaagaaggacccc gagggcctc<u>TAG</u>ctgcaggacaacatcgtcgcggagactccgtggacgagaccggcca gatgagcgccacagccaagggccgagtccgtcttttgaataacTGGgacgtgtgcgca gacatggtgggcaccacacagacaccgaggaccctgccaagttcaagatgaagTACTG GggcgtagcctccTTTctccagaaaggaaatgatgaccactggatcgtcgacacagac tacgacacgTATgccgtgcagtactcctgccgcctcctgaacctcgatggcacctgtg ctgacagctactccttcgtgttttcccgggaccccaacggcctgccccagaagcgca gaagattgtaaggcagcggcaggaggagctgtgcctggccaggcagTACaggctgatc gtccacaacggtTACtgcgatggcagatcagaaagaaacctttggactataaagacg atgacgataagcatcaccatcaccatcacTAA -continued hRBP4 mutant 3:
(SEQ ID NO: 10)
ATGAAAACATTCATACTCCTTGCTcTGGGTACTGCTGCTCTGGGTTatcttcctgcttc ccggtgccactgctcagcctgagcgcgactgccgagtgagcagcttccgagtcaaggag aacttcgacaaggctcgcttctctgggacctggTACgccatggccaagaaggaccccga gggcctcTTTctgcaggacaacatcgtcgcggagttctccgtggacgagaccggccaga tgagcgccacagccaagggccgagtccgtcttttgaataacTAGgacgtgtgcgcagac atggtgggcaccttcacagacaccgaggaccctgccaagttcaagatgaagTACTGGgg cgtagcctccTTTctccagaaaggaaatgatgaccactggatcgtcgacacatacgaca cgTATgccgtgcagtactcctgccgcctcctgaacctcgatggcacctgtgctgacagc tactccttcgtgttttcccgggaccccaacggcctgcccccagaagcgcagaagattgt aaggcagcggcaggaggagctgtgcctggccaggcagTACaggctgatcgtccacaacg gtTACtgcgatggcagatcagaaagaaaccttttgactataaagacgatgacgataagc atcaccatcaccatcacTAA hRBP4 mutant 4:
(SEQ ID NO: 11)
ATGAAAACATTCATACTCCTTGCTcTGGGTACTGCTGCTCTGGGTTatcttcctgcttc ccggtgccactgctcagcctgagcgcgactgccgagtgagcagcttccgagtcaaggag aacttcgacaaggctcgcttctctgggacctggTACgccatggccaagaaggaccccga gggcctcTTTctgcaggacaacatcgtcgcggagttctccgtggacgagaccggccaga tgagcgccaagggccgagtccgtcttttgaataacTGGgacgtgtgcgcagacatggtg ggcaccttcacagacaccgaggaccctgccaagttcaagatgaagTAGTGGggcgtagc ctccTTTctccagaaaggaaatgatgaccactggatcgtcgacacagactacgacacgT ATgccgtgcagtactcctgccgcctcctgaacctcgatggcacctgtgctgacagctac tccttcgtgttttcccgggaccccaacggcctgcccccagaagcgcagaagattgtaag gcagcggcaggaggagctgtgcctggccaggcagTACaggctgatcgtccacaacggtT ACtgcgatggcagatcagaaagaaaccttttggactataaagacgatgacgataagcat caccatcaccatcacTAA hRBP4 mutant 5:
(SEQ ID NO: 12)
ATGAAAACATTCATACTCCTTGCTcTGGGTACTGCTGCTCTGGGTTatcttcctgcttc ccggtgccactgctcagcctgagcgcgactgccgagtgagcagcttccgagtcaaggag aacttcgacaaggctcgcttctctgggacctggTACgccatggccaagaaggaccccga gggcctcTTTctgcaggacaacatcgtcaggacaacatcgtcgcggagttctccgtggac gagaccggccagatgagcgccacagccaagggccgagtccgtcttttgaataacTGGga cgtgtgcgcagacatggtgggcaccttcacagacaccgaggaccctgccaagttcaaga tgaagTACTAGggcgtagcctccTTTctccagaaaggaaatgatgaccactggatcgtc gacacagactacgacacgTATgccgtgcagtactcctgccgcctcctgaacctcgatgg cacctgtgctgacagctactccttcgtgttttcccgggaccccaacggcctgcccccag aagcgcagaagattgtaaggcagcggcaggaggagctgtgcctggccaggcagTACagg ctgatcgtccacaacggtTACtgcgatggcagatcagaaagaaaccttttggactataa agacgatgacgataagcatcaccatcaccatcacTAA -continued hRBP4 mutant 6:
(SEQ ID NO: 13)
ATGAAAACATTCATACTCCTGCTcTGGGTACTGCTGCTCTGGGTTatcttcctgcttc ccggtgccactgctcagcctgagcgcgactgccgagtgagcagcttccgagtcaaggag aacttcgacaaggctcgcttctctgggacctggTACgccatggccaagaaggaccccga gggcctcTTCctgcaggacaacatcgtcgcggagttctccgtggacgagaccggccaga tgagcgccacagccaagggccgagtccgtcttttgaataacTGGgacgtgtgcgcgcag acatggtgggccacttcacagacaccgaggaccctgccaagtcaagatgaagTACTGGg gcgtagcctccTAGctccagaaaggaaatgatgaccactggatcgtcgacacagactac gacacgTATgccgtgcagtactcctgccgcctcctgaacctcgatggcacctgtgctga cagctactccttcgtgttttcccgggaccccaacggcctgccccagaagcgcagaaga ttgtaaggcagcggcaggaggagctgtgcctggccaggcagTACaggctgatcgtccac aacggtTACtgcgatggcagatcagaaagaaacctttTggactataaagacgatgacga taagcatcaccatcaccatcacTAA hRBP4 mutant7:
(SEQ ID NO: 14)
ATGAAAACATTCATACTCCTGCTcTGGGTACTGCTGCTCTGGGTTatcttcctgcttc ccggtgccactgctcagcctgagcgcgactgccgagtgagcagcttccgagtcaaggag aacttcgacaaggctcttctctgggacctggTACgccatggccaagaaggaccccgagg gcctcTTTctgcaggacaacatcgtcgcggagttctccgtggacgagaccggccagatg agcgccacagccaagggccgagtccgtcttttgaataacTGGgacgtgtgcgcgcagacat ggtgggccacttcacagacaccgaggaccctgccaagttcaagatgaagTACTGGggcg tagcctccTTTctccagaaaggaaatgatgaccactggatcgtcgacacagactacgac acgTAGgccgtgcagtactcctgccgcctcctgaacctcgatggcacctgtggacagct actccttcgtgttttcccgggaccccaacggcctgccccagaagcgcagaagattgta aggcagcggcaggaggagctgtgcctggccaggcagTACaggctgatcgtccacaacgg tTACtgcgatggcagatcagaaagaaaccattggactataaagacgatgacgataagca tcaccatcaccatcacTAA hRBP4 mutant 8:
(SEQ ID NO: 15)
ATGAAAACATTCATACTCCTGCTcTGGGTACTGCTGCTCTGGGTTatcttcctgcttc ccggtgccactgctcagcctgagcgcgactgccgagtgagcagcttccgagtcaaggag aacttcgacaaggctcgcttctctgggacctggTACgccatggccaagaaggaccccga gggcctcTTTctgcaggacaacatcgtcgcggagactccgtggacgagaccggccagat gagcgccacagccaagggccgagtccgtcttttgaataacTGGgacgtgtgcgcagaca tggtgggccacacagacaccgaggaccctgccaagttcaagatgaagTACTGGggcg tagcctccTTTctccagaaaggaaatgatgaccactggatcgtcgacacagactacgac acgTATgccgtgcagtactcctgccgcctcctgaacctcgatggcacctgtgctgacag ctactccttcgtgttttcccgggaccccaacggcctgccccagaagcgcagaagattg taaggcagcggcaggaggagctgtgcctggccaggcagTAGaggctgatcgtccacaac ggtTACtgcgatggcagatcagaaagaaaccttttggactataaagacgatgacgataa gcatcaccatcaccatcacTAA -continued hRBP4 mutant 9:
(SEQ ID NO: 16)
ATGAAAACATTCATACTCCTGCTcTGGGTACTGCTGCTCTGGGTTatcttcctgcttc ccggtgccactgctcagcctgagcgcgactgccgagtgagcagcttccgagtcaaggag aacttcgacaaggctcgcttctctgggacctggTACgccatggccaagaaggacccga gggcctcTTTctgcaggacaacatcgtcgcggagactccgtggacgagaccggccagat gagcgccacagccaagggccgagtccgtcttttgaataacTGGgacgtgtgcgcagaca tggtgggcaccacacagacaccgaggaccctgccaagttcaagatgaagTACTGGggcg tagcctccTTTctccagaaaggaaatgatgaccactggatcgtcgacacagactacgac acgTATgccgtgcagtactcctgccgcctcctgaacctcgatggcacctgtgctgacag ctactccttcgtgttttcccgggaccccaacggcctgccccagaagcgcagaagattg taaggcagcggcaggaggagctgtgcctggccaggcagTACaggctgatcgtccacaac ggtTAGtgcgatggcagatcagaaagaaacctttttggactataaagacgatgacgataa gcatcaccatcaccatcacTAA Tyr108 and Phe54 line the retinol binding site of hRBP4 while all other TAG mutations are at solvent exposed protein residues. When expressed in mammalian cells, termination of translation at these TAG sites would result in a truncated protein lacking the C-terminal His tag. Consequently, truncated protein will not be recognized by anti-His antibody. A read-through translation would create a full length product with a His tag. Therefore, detection with anti-His antibody serves as an indicator for read-through activity.
Expression of hRBP4:
pRSRBP was co-transfected into HEK293F cells with pCMVpyS, pCMVpyB, pCMVpyC and pCMVpyD and cells were grown in the presence of 5 mM D-ornithine as described in Example 1. His-tagged hRBP4 was then analyzed using Western blot and anti-His antibody, and because truncated hRBP4 did not contain the His tag, only full length hRBP4 with PCL incorporated at the TAG codon was detected by the Western blot. Thus the presence of full length hRBP4 demonstrates PCL incorporation. As indicated in FIG. 6A, anti-His antibody detected a band at 26 kDa, the expected size for full length hRBP4, indicating an incorporation of PCL at the mutated TAG codon. PCL was incorporated in nine hRBP4 constructs (Table 2) at different rates with #2, #6 and #9 mutant constructs at a higher rate and #7 and #8 mutant constructs at a lower rate. The protein yield for #2, #6 and #9 were between 4 and 8 mg/L, about 20% of the yield for wild-type hRBP4. These proteins were purified and subjected to mass spectrometric (MS) analysis. The mass obtained for the proteins was consistent with that expected for the incorporation of PCL, and tandem MS analysis confirmed the incorporation of PCL at the expected site (FIG. 6A to 11).

FIG. 6B shows the SDS-PAGE and FIG. 6C shows the mass spectrum of hRBP4 produced in HEK293F cells in which PCL is incorporated into the hRBP4. hRBP4 was purified from the media of co-transfected HEK293F cells in the absence (A, lane 1) or presence (A, lane 2) of D-ornithine and analyzed on SDS-PAGE. The arrow indicates full length hRBP4. The purified protein was analyzed by mass spectrometry (B): The observed mass is 23166.0 Da, close to the expected mass of 23168 Da.
Mass Spectrometric Detection of PCL Site-Specifically Incorporated into hRBP4:
A 500 ml culture of HEK293F cells transfected with the pylS, pylT, pylC and pylD genes and DNA for hRBP4 mutant #6 (Table 2: hRBP4 Phe122PCL) was grown in media supplemented with 5 mM D-ornithine. The media was run over two Ni-NTA columns to capture all full length hRBP4 protein. The elution fractions when pooled contained 4.3 mg total protein. The observed mass of the protein was 23166.8 Da (expected 23168 Da) consistent with the incorporation of a single PCL residue (data not shown). An aliquot of the sample was subjected to tryptic digestion and LC-MS analysis. The MS/MS spectrum in FIG. 7 could be assigned to the peptide YWGVASF*LQK (SEQ ID NO:17) whereby the residue F* had a mass consistent with that of PCL confirming site-specific incorporation of PCL at the desired TAG site at residue 122. The assignments for the peptide YWGVASF*LQK are given below:

Assignments for YWGVASF*LQK at m/z 647.86 (F* = PCL)

Monoisotopic mass of neutral peptide Mr(calc): 1273.6819
Variable modifications:
F7: PCL at F (F)
Ions Score: 60 Expect: 0.0013
Matches (Bold): 22/74 fragment ions using 32 most intense peaks

| # | b | b++ | b* | b*++ | b° | b°++ | Seq. | y |
|---|---|---|---|---|---|---|---|---|
| 1 | 164.0706 | 82.5389 | | | | | Y | |
| 2 | 350.1499 | 175.5786 | | | | | W | 1111.6259 |
| 3 | 407.1714 | 204.0893 | | | | | G | 925.5465 |
| 4 | 506.2398 | 253.6235 | | | | | V | 868.5251 |
| 5 | 577.2769 | 289.1421 | | | | | A | 769.4567 |

Assignments for YWGVASF*LQK at m/z 647.86 (F* = PCL)

Monoisotopic mass of neutral peptide Mr(calc): 1273.6819
Variable modifications:
F7: PCL at F (F)
Ions Score: 60 Expect: 0.0013
Matches (Bold): 22/74 fragment ions using 32 most intense peaks

| # | | | | | | | | | |
|---|---|---|---|---|---|---|---|---|---|
| 6 | 664.3089 | 332.6581 | | | 646.2984 | 323.6528 | S | 698.4195 | |
| 7 | 887.4410 | 444.2241 | | | 869.4304 | 435.2189 | F | 611.3875 | |
| 8 | 1000.5251 | 500.7662 | | | 982.5145 | 491.7609 | L | 388.2554 | |
| 9 | 1128.5837 | 564.7955 | 1111.5571 | 556.2822 | 1110.5731 | 555.7902 | Q | 275.1714 | |
| 10 | | | | | | | K | 147.1128 | |

| # | $y^{++}$ | $y^*$ | $y^{*++}$ | $y^0$ | $y^{0++}$ | # |
|---|---|---|---|---|---|---|
| 1 | | | | | | 10 |
| 2 | 556.3166 | 1094.5993 | 547.8033 | 1093.6153 | 547.3113 | 9 |
| 3 | 463.2769 | 908.5200 | 454.7636 | 907.5360 | 454.2716 | 8 |
| 4 | 434.7662 | 851.4985 | 426.2529 | 850.5145 | 425.7609 | 7 |
| 5 | 385.2320 | 752.4301 | 376.7187 | 751.4461 | 376.2267 | 6 |
| 6 | 349.7134 | 681.3930 | 341.2001 | 680.4090 | 340.7081 | 5 |
| 7 | 306.1974 | 594.3610 | 297.6841 | | | 4 |
| 8 | 194.6314 | 371.2289 | 186.1181 | | | 3 |
| 9 | 138.0893 | 258.1448 | 129.5761 | | | 2 |
| 10 | 74.0600 | 130.0863 | 65.5468 | | | 1 |

FIG. 8 shows the mass spectrometric analysis (TIC and EIC of 2+ ions of YWGVASF*LQK) of a tryptic digest of human RBP4 Phe122PCL, and indicates incorporation of PCL at the target Phe122TAG site. FIG. 9 shows the mass spectrometric analysis of a tryptic digest of human RBP4 Phe122PCL. The mass spectrum shows 3+ and 2+ precursors of YWGVASF*LQK at m/z 425.57 (3+) and 637.85 (2+) respectively. (F*=PCL), further indicating the incorporation of PCL at the target Phe122TAG site.

Example 3

Detection of Biosynthetically Generated PCL in Lysate from Mammalian Cells

This example demonstrates that PCL is generated biosynthetically in mammalian cells and is detectable as free amino acid in the lysate of such cells. This example therefore suggests that PCL is incorporated like pyrrolysine and the other 20 naturally occurring amino acids and that PCL incorporation is not the result of posttranslational protein modifications.

Detection of PCL in Cell Lysate 60 ml cultures of HEK293F cells were grown with 5 mM or without D-ornithine and with the pylT, pylS, pylB, pylC and pylD genes. The cells were harvested and lysed by sonication in 250 μl double-deionized $H_2O$. The cellular debris was pelleted by centrifugation. Protein was precipitated by adding cold methanol to a final concentration of 80% and removed by centrifugation. The soluble lysate was then concentrated by speedvac and analyzed by high pressure liquid chromatography combined with mass spectrometry to show the presence of PCL.

Dried samples were first reconstituted in 100 μl 98/2 Mobile phase A/Mobile phase B (mobile phase A: water with 0.1% formic acid; mobile phase B: acetonitrile with 0.1% formic acid). The samples were then diluted 20 times and 2 μL were injected into the HPLC. Analyte separation was accomplished on an Agilent zorbax 300SB_C18 reverse HPLC column using the following solution gradient: 0 min 2% B; 5 min 2% B; 60 min 100% B; Flow rate: 0.25 ml/min. Comparison of the HPLC traces (FIG. 10A) shows a peak at 4.13 min (indicated by asterisk) that is present in lysate from cells transfected with the biosynthetic genes pylB, pylC and pylD and grown in the presence of the D-ornithine (bottom EIC (extracted ion chromatogram) trace) but not in lysate from cells grown in the absence of D-ornithine (top EIC trace). A full scan mass spectrum (FIG. 10C) of the 4.13 min HPLC peak indicates a mass of 242.14943 Da consistent with the theoretical mass for PCL (242.14992 Da), the demethylated version of PYL. Lysine (HPLC peak at 1.44 min) is equally abundant in both samples (FIG. 10B) and a full mass spectrum of lysine (FIG. 10D) serves as an internal calibration and illustrate the accuracy of the method. This analysis indicates that PCL is generated from D-ornithine as a free amino acid detectable in cell lysate.

Example 4

Incorporation Test with Putative PCL and Pyrrolysine Precursors, with Synthetic Pyrrolysine Analogues, and with Different Combinations of Biosynthetic Genes This example demonstrates that D-ornithine is a preferred precursor for the biosynthesis of PCL as measured by its site specific incorporation into human RBP4. Also illustrated in this example is the site specific incorporation of certain pyrrolysine analogues, including CYC, at TAG encoded sites in the model protein human RBP4, human retinol binding protein 4 using mammalian cells. This example also provides insight into the substrate specificity of the pylS tRNA synthetase.

N-ε-cyclopentyloxycarbonyl-L-lysine (CYC) Incorporation

DNA constructs for nine hRBP4 TAG mutants (Table 3) were individually co-transfected into HEK293F cells together with pylT/pylS DNA as described in Example 2 and cultured in the absence or presence of 4 mM N-ε-cyclopentyloxycarbonyl-L-lysine (CYC), a pyrrolysine analogue. Culture media were harvested and analyzed by Western Blot with anti-His and anti-hRBP4 antibodies (FIG. 11A). Western Blot with anti-His antibody revealed a protein of 24 kDa for six of nine hRBP4 TAG mutant constructs. The size of the protein is equivalent to the size of wild-type hRBP4, indicating the production of full length protein via the read-through translation. The read-through activity varied among hRBP4 mutant constructs (Table 3) and was dependent on CYC and pylS. In particular, full-length hRBP4 protein could not be detected for mutant #1, 5 and 7. High yields of full-length protein were observed for mutants #2, 6 and 9 similar to the results seen for PCL incorporation (Example 2, FIG. 6A).

TABLE 3 hRBP4 mutants and qualitative results of CYC incorporation

| hRBP4 mutant | Mutant Number | CYC Incorporation |
|---|---|---|
| Tyr51TAG | 1 | Not detected by Western |
| Phe62TAG | 2 | Strong |
| Trp93TAG | 3 | Very weak |
| Tyr116TAG | 4 | Weak |
| Trp117TAG | 5 | Detectable |
| Phe122TAG | 6 | Strong |
| Tyr140TAG | 7 | Not detected |
| Tyr191TAG | 8 | Medium |
| Tyr199TAG | 9 | Strong |

The expressed proteins containing CYC were purified from the media by Ni-NTA chromatography and analyzed by SDS-PAGE followed by Coomassie blue staining. FIG. 11B shows the SDS-PAGE analysis of purified hRBP4 TAG mutant #2. The purified preparation exhibited a single protein band with a size of 24 kDa. The mass spectrum of the purified protein was consistent with a single site incorporation of CYC (FIG. 11C). The expected molecular weight for single-site CYC incorporation instead of Phe62 was (23114.6 Da (wild-type)−165.2 Da (Phe)+258.3 Da (CYC)) 23208.7 Da, and the observed 23182.0 Da. The observed mass suggests cyclization of the N-terminal Q residue to pyrrolidone carboxylic acid resulting in abstraction of 18 Da and the presence of three intact disulphide bonds resulting in abstraction of 6 Da (23208.7 Da−6 Da−18 Da=23184.7 Da). Tandem MS analysis of the purified protein demonstrated that CYC was incorporated into the designated TAG site in the hRBP4 construct (FIG. 12). The protein yield from the transient transfection was estimated to be approximately 5 mg/L. The MS/MS fragmentation of KDPEGLFLQDNIVAEFSVDETGQMSATAK (SEQ ID NO:18) is Monoisotopic mass of neutral peptide Mr(calc): 3248.5646 Variable modifications:
F7: Cyc at F (F)
Q9: Deamidated (NQ)
N11: Deamidated (NQ)
M24: Oxidation (M), with neutral losses 0.0000 (shown in table), 63.9983
Ions Score: 113 Expect: 4.6e−009
Matches (Bold): 110/498 fragment ions using 156 most intense peaks

| # | b | $b^{++}$ | b* | b*++ | $b^0$ | $b^{0++}$ | Seq. | y |
|---|---|---|---|---|---|---|---|---|
| 1 | 129.1022 | 65.0548 | 112.0757 | 56.5415 | | | K | |
| 2 | 244.1292 | 122.5682 | 227.1026 | 114.0550 | 226.1186 | 113.5629 | D | 3121.4769 |
| 3 | 341.1819 | 171.0946 | 324.1554 | 162.5813 | 323.1714 | 162.0893 | P | 3006.4500 |
| 4 | 470.2245 | 235.6159 | 453.1980 | 227.1026 | 452.2140 | 226.6106 | E | 2909.3972 |
| 5 | 527.2460 | 264.1266 | 510.2195 | 255.6134 | 509.2354 | 255.1214 | G | 2780.3546 |
| 6 | 640.3301 | 320.6687 | 623.3035 | 312.1554 | 622.3195 | 311.6634 | L | 2723.3332 |
| 7 | 878.4982 | 439.7527 | 861.4716 | 431.2395 | 860.4876 | 430.7475 | F | 2610.2491 |
| 8 | 991.5823 | 496.2948 | 974.5557 | 487.7815 | 973.5717 | 487.2895 | L | 2372.0810 |
| 9 | 1120.6248 | 560.8161 | 1103.5983 | 552.3028 | 1102.6143 | 551.8108 | Q | 2258.9969 |
| 10 | 1235.6518 | 618.3295 | 1218.6252 | 609.8163 | 1217.6412 | 609.3243 | D | 2129.9543 |
| 11 | 1350.6787 | 675.8430 | 1333.6522 | 667.3297 | 1332.6682 | 666.8377 | N | 2014.9274 |
| 12 | 1463.7628 | 732.3850 | 1446.7362 | 723.8718 | 1445.7522 | 723.3798 | I | 1899.9004 |
| 13 | 1562.8312 | 781.9192 | 1545.8047 | 773.4060 | 1544.8206 | 772.9140 | V | 1786.8164 |
| 14 | 1633.8683 | 817.4378 | 1616.8418 | 808.9245 | 1615.8578 | 808.4325 | A | 1687.7480 |
| 15 | 1762.9109 | 881.9591 | 1745.8844 | 873.4458 | 1744.9003 | 872.9538 | E | 1616.7108 |
| 16 | 1909.9793 | 955.4933 | 1892.9528 | 946.9800 | 1891.9688 | 946.4880 | F | 1487.6683 |
| 17 | 1997.0114 | 999.0093 | 1979.9848 | 990.4960 | 1979.0008 | 990.0040 | S | 1340.5998 |
| 18 | 2096.0798 | 1048.5435 | 2079.0532 | 1040.0302 | 2078.0692 | 1039.5382 | V | 1253.5678 |
| 19 | 2211.1067 | 1106.0570 | 2194.0802 | 1097.5437 | 2193.0961 | 1097.0517 | D | 1154.4994 |
| 20 | 2340.1493 | 1170.5783 | 2323.1228 | 1162.0650 | 2322.1387 | 1161.5730 | E | 1039.4725 |
| 21 | 2441.1970 | 1221.1021 | 2424.1704 | 1212.5889 | 2423.1864 | 1212.0968 | T | 910.4299 |
| 22 | 2498.2184 | 1249.6129 | 2481.1919 | 1241.0996 | 2480.2079 | 1240.6076 | G | 809.3822 |
| 23 | 2626.2770 | 1313.6422 | 2609.2505 | 1305.1289 | 2608.2665 | 1304.6369 | Q | 752.3607 |
| 24 | 2773.3124 | 1387.1599 | 2756.2859 | 1378.6466 | 2755.3019 | 1378.1546 | M | 624.3021 |
| 25 | 2860.3445 | 1430.6759 | 2843.3179 | 1422.1626 | 2842.3339 | 1421.6706 | S | 477.2667 |
| 26 | 2931.3816 | 1466.1944 | 2914.3550 | 1457.6811 | 2913.3710 | 1457.1891 | A | 390.2347 |
| 27 | 3032.4293 | 1516.7183 | 3015.4027 | 1508.2050 | 3014.4187 | 1507.7130 | T | 319.1976 |
| 28 | 3103.4664 | 1552.2368 | 3086.4398 | 1543.7235 | 3085.4558 | 1543.2315 | A | 218.1499 |
| 29 | | | | | | | K | 147.1128 |

| # | $y^{++}$ | y* | y*++ | $y^0$ | $y^{0++}$ | # |
|---|---|---|---|---|---|---|
| 1 | | | | | | 29 |
| 2 | 1561.2421 | 3104.4504 | 1552.7288 | 3103.4664 | 1552.2368 | 28 |
| 3 | 1503.7286 | 2989.4234 | 1495.2154 | 2988.4394 | 1494.7233 | 27 |
| 4 | 1455.2022 | 2892.3707 | 1446.6890 | 2891.3867 | 1446.1970 | 26 |
| 5 | 1390.6810 | 2763.3281 | 1382.1677 | 2762.3441 | 1381.6757 | 25 |
| 6 | 1362.1702 | 2706.3066 | 1353.6569 | 2705.3226 | 1353.1649 | 24 |

-continued

Monoisotopic mass of neutral peptide Mr(calc): 3248.5646 Variable
modifications:
F7: Cyc at F (F)
Q9: Deamidated (NQ)
N11: Deamidated (NQ)
M24: Oxidation (M), with neutral losses 0.0000
(shown in table), 63.9983
Ions Score: 113 Expect: 4.6e-009
Matches (Bold): 110/498 fragment ions using 156 most intense peaks

|  |  |  |  |  |  |  |
|---|---|---|---|---|---|---|
| 7 | 1305.6282 | 2593.2226 | 1297.1149 | 2592.2385 | 1296.6229 | 23 |
| 8 | 1186.5441 | 2355.0544 | 1178.0308 | 2354.0704 | 1177.5388 | 22 |
| 9 | 1130.0021 | 2241.9704 | 1121.4888 | 2240.9863 | 1120.9968 | 21 |
| 10 | 1065.4808 | 2112.9278 | 1056.9675 | 2111.9438 | 1056.4755 | 20 |
| 11 | 1007.9673 | 1997.9008 | 999.4541 | 1996.9168 | 998.9620 | 19 |
| 12 | 950.4539 | 1882.8739 | 941.9406 | 1881.8899 | 941.4486 | 18 |
| 13 | 893.9118 | 1769.7898 | 885.3986 | 1768.8058 | 884.9065 | 17 |
| 14 | 844.3776 | 1670.7214 | 835.8643 | 1669.7374 | 835.3723 | 16 |
| 15 | 808.8591 | 1599.6843 | 800.3458 | 1598.7003 | 799.8538 | 15 |
| 16 | 744.3378 | 1470.6417 | 735.8245 | 1469.6577 | 735.3325 | 14 |
| 17 | 670.8036 | 1323.5733 | 662.2903 | 1322.5572 | 661.7983 | 13 |
| 18 | 627.2875 | 1236.5413 | 618.7743 | 1235.5572 | 618.2823 | 12 |
| 19 | 577.7533 | 1137.4729 | 569.2401 | 1136.4888 | 568.7481 | 11 |
| 20 | 520.2399 | 1022.4459 | 511.7266 | 1021.4619 | 511.2346 | 10 |
| 21 | 455.7186 | 893.4033 | 447.2053 | 892.4193 | 446.7133 | 9 |
| 22 | 405.1947 | 792.3556 | 396.6815 | 791.3716 | 396.1894 | 8 |
| 23 | 376.6840 | 735.3342 | 368.1707 | 734.3502 | 367.6787 | 7 |
| 24 | 312.6547 | 607.2756 | 304.1414 | 606.2916 | 303.6494 | 6 |
| 25 | 239.1370 | 460.2402 | 230.6237 | 459.2562 | 230.1317 | 5 |
| 26 | 195.6210 | 373.2082 | 187.1077 | 372.2241 | 186.6157 | 4 |
| 27 | 160.1024 | 302.1710 | 151.5892 | 301.1870 | 151.0972 | 3 |
| 28 | 109.5786 | 201.1234 | 101.0653 |  |  | 2 |
| 29 | 74.0600 | 130.0863 | 65.5468 |  |  | 1 |

Incorporation Test with Putative PCL and Pyrrolysine Precursors

The production of full-length hRBP4 Phe122PCL protein (mutant #6) was measured in the presence of the putative PCL precursor D-ornithine, D-proline, D-arginine, D-glutamic acid, 4-hydroxyl-D-proline and 2-pyrrolidone-5-carboxylic acid (FIGS. 13A and B, FIG. 14A). pRSRBP was co-transfected into HEK293F cells with pCMVpyS, pCMVpyB, pCMVpyC and pCMVpyD and cells were grown in the presence of 5 mM of the putative precursor (FIG. 14A) as described in Example 2. His-tagged and hence full-length hRBP4 with PCL incorporated was then analyzed using Western blot and anti-His antibody and SDS-PAGE. As shown in FIG. 13B, only D-ornithine gave rise to a measurable protein band on SDS-PAGE of Ni-NTA purified samples. Detection by Western blot of unpurified samples (FIG. 13A) indicates only low level formation of full-length hRBP4 protein in the presence of all other precursors clearly indicating that D-ornithine is the most efficient precursor for the biosynthesis and incorporation of PCL. From Western Blot and SDS-PAGE analysis it appears that biosynthetic generation of PCL from 5 mM D-ornithine (lane 2) and subsequent protein incorporation is more efficient than incorporation of the known PylS substrate CYC added at 5 mM (lane 9) to the medium of cells transfected with pCMVpyS. This example demonstrates that D-ornithine is the preferred precursor for the biosynthesis of PCL.

Incorporation Test with Synthetic Pyrrolysine Analogues

In parallel to the above experiment, the production of full-length hRBP4 Phe122PCL protein (mutant #6) was also measured in the presence of a series of synthetic pyrrolysine analogues designed with an acetyl moiety for chemical derivatization after protein incorporation (FIG. 14B). The synthetic analogues were prepared as described in Example 19. pRSRBP was co-transfected into HEK293F cells with pCMVpyS which supplies one gene copy of pylT tRNA and of pylS tRNA synthetase. Depending on solubility, the synthetic analogues were added to the media either at 2 or 5 mM final concentration. The detection of His-tagged and hence full-length hRBP4 with PCL incorporated was then analyzed using Western blot and anti-His antibody and SDS-PAGE. As shown in FIG. 13B, only CYC (lane 9) gave rise to a measurable protein band in the analysis of Ni-NTA purified samples. The Western blot analysis of unpurified samples (FIG. 13A) suggests that TU3000-016 (lane 15) is also a viable substrate for the pylS tRNA synthetase. However, incorporation efficiency is low and the compound is not stable as a different batch (TU2982-150) had degraded as measured by nuclear magnetic resonance spectroscopy, resulting in even lower incorporation into hRBP4 (lane 10). This example, in agreement with published reports, demonstrates that pyrrolysine analogues featuring a sp2 carbon at the attachment point of the ring moiety of the analog are not tolerated as substrates for pylS tRNA synthetase.

Incorporation Test with Different Combinations of Biosynthetic Genes

The production of full-length hRBP4 Phe122PCL was also tested with cell cultures with 5 mM D-ornithine and cotransfection with different combinations of the biosynthetic genes pylB, pylC and pylD (FIG. 13C). All cultures were cotransfected with pCMVpyS which supplies one gene copy of pylT tRNA and of pylS tRNA synthetase. Full-length hRBP4 protein is only detected by Western blot with anti-His-tag antibody when both pylC and pylD are cotransfected. pylB although likely required for PYL biosynthesis is not essential for PCL biosynthesis and subsequent incorporation. This observation is further confirmed by the production of full-length PCL mutants of mIgG1 Fc domain protein (Example 5) and mouse and human EPO (Example 6). All three examples illustrate that only the genes pylC and pylD are essential for PCL biosynthesis and protein incorporation.

Example 5

Site Specific Incorporation of Biosynthetically Generated PCL into Fc Domain of Mouse IgG1 using Mammalian Cells This example demonstrates that site specific incorporation of biosynthetically generated PCL in mammalian cells using the methods provided herein is general procedure and is not limited to the protein hRBP4.

Expression of mIgG1 Fc

Four TAG mutants were generated at K333 (mutant #1), K336 (mutant #2), T394 (mutant #3) and L426 (mutant #4) of the Fc domain of mouse IgG1 (Table 2 and FIG. 17A). pRSFc #1-4 (Table 2) were co-transfected into HEK293F cells with pCMVpyT, pCMVpyS, pCMVpyC and pCMVpyD and cells were grown in the presence of 5 mM D-ornithine (pCMVpyB was not added). His-tagged Fc domain protein was purified from the media by Ni-NTA chromatography and analyzed on SDS-PAGE. The sizes of the protein bands on the gel for each constructs are consistent with their expected size for full length proteins (FIG. 17A). The expression construct features a C-terminal His6 tag for purification and therefore only full-length protein is recovered. As FIG. 17A shows, expression of mutant #1 depends on the addition of D-ornithine to the growth media. The expression levels of all four mutants are similar. Mass spectrometric analysis was not performed due to glycosylation of the Fc domain when produced in HEK293F cells.

Example 6

Site Specific Incorporation of Biosynthetically Generated PCL into Erythropoietin (EPO) using Mammalian Cells In this example PCL is site specifically incorporated into erythropoietin, further demonstrates that the methods provided herein are a general procedure for the site specific incorporation of biosynthetically generated PCL into proteins within mammalian cells.

Expression of Mouse Erythropoietin (EPO)

PCL incorporation into EPO mutant proteins was accomplished in HEK293F cells. TAG mutations were introduced at eleven surface-exposed Lys or Arg residues facing away from EPO receptor binding interface. The sites of incorporation are shown in below and listed in Table 2. Mouse EPO protein was expressed as described in Example 1 except the pylB genes was not added: pRSEPO #1-11 (Table 2) were co-transfected into HEK293F cells with pCMVpyT, pCMVpyS, pCMVpyC and pCMVpyD and cells were grown in the presence of 5 mM D-ornithine. His-tagged EPO was purified from the media by Ni-NTA chromatography and analyzed on SDS-PAGE. The EPO constructs contain a C-terminal His-tag. Therefore only protein with successfully incorporated PCL will produce full-length protein, will be purified by Ni-NTA chromatography and therefore yield a detectable band on SDS-PAGE. SDS-PAGE of full-length mouse EPO indicates successful incorporation of PCL for all eleven mutants (FIG. 17B). The sizes of the protein bands on the gel for each constructs are consistent with their expected size for full length proteins. For mutant #1, it is illustrated that formation of full-length protein depends on D-ornithine. Expression levels of all eleven mutant proteins are similar and between 10 to 20% of wt protein that expresses at ~40 mg/L (FIG. 17B). Mass spectrometric analysis was not performed due to the glycosylation of EPO in HEK293F cells. The sequences of the mature human (SEQ ID NO:19) and mouse (SEQ ID NO:20) EPO proteins are given below, with the PCL incorporation sites in bold and the glycosylation sites underlined. Numbering of mutants starts form the N-terminal (see also Table 2).

```
        EPO
Human   APPRLICDSRVLERYLLEAKEAE NITTGCAEHCSLNENITVPDTKVNFYAW KRMEVGQQAVEVW QGLALLS
Mouse   APPRLICDSRVLERYILEAKEAE NVTMGCAEGPRLSENITVPDTKVNFYAW KRMEVEEQAIEVW QGLSLLS EAVLRGQALLVNSSQPWEPLQLHVDKAVSGLRSLTTLLRALGAQ KEAISPPDAASAAPLRTITADTFRKLF
        EAILQAQALLANSSQPPETLQLHIDKAISGLRSLTSLLRVLGAQ KELMSPPDTTPPAPLRTLTVDTFCKLF

RVYSNFLRGKLKLYTGEA CRTGDR
        RVYANFLRGKLKLYTGEVCRRGD R
```

Example 7

Plasmid for Incorporation of Biosynthetically Generated PCL into Proteins Using *Escherichia coli* Cells Provided in this example is a description of the plasmid that when transformed into *Escherichia coli* cells enables the incorporation of PCL into TAG encoded sites in a target protein expressed from a second plasmid cotransformed into the same *Escherichia coli* cell.

pAra-pylSTBCD Construction

A plasmid for the incorporation of PCL in *E. coli* cells is shown in FIG. 5 and was constructed as follows: A cassette encoding pylT under the proK promoter was synthesized by amplification of the promoter, tRNA, and 3' sequence from pSUP with overlapping primers. The three pieces were then mixed with end primers encoding restriction sites for ApaLI and XhoI in order to synthesize the full insert. After digestion with ApaLI and XhoI, the cassette was ligated into a pSUP backbone that had been prepared with the same enzymes to make pSUP-pylT. The coding sequences for pylS, pylB, pylC, and pylD from *M. mazei* were amplified from appropriate pCMVU6 plasmids previously prepared (Example 1) and inserted into pMH4 with no tags (see, Lesley S A, Kuhn P, Godzik A, Deacon A M, Mathews I, Kreusch A, Spraggon G, Klock H E, McMullan D, Shin T, Vincent J, Robb A, Brinen L S, Miller M D, McPhillips T M, Miller M A, Scheibe D, Canaves J M, Guda C, Jaroszewski L, Selby T L, Elsliger M A, Wooley J, Taylor S S, Hodgson K O, Wilson I A, Schultz P G, and Stevens R C, "Structural genomics of the *Thermotoga maritima* proteome implemented in a high-throughput structure determination pipeline", *Proc Natl Acad Sci USA* 2002; 99: 11664-11669). The entire promoter-CDS-terminator of each one was then amplified with primers with differing restriction sites (KpnI-pylS-SbfI, NdeI-pylD-BglII, BglII-pylB-XhoI, XhoI-pylC-KpnI). The pylS PCR product was digested with KpnI and SbfI and ligated into pSUP-pylT between the KpnI and PstI sites to give pAra-pylST. The pylB, pylC, and pylD products were cut with the respective enzymes and ligated into a plasmid backbone prepared with NdeI and KpnI. After verification of the plasmid product of this four-way ligation by sequencing and diagnostic PCR, the full cassette was then amplified with primers to add KpnI sites to both ends of the pylD-pylB-pylC cassette. This was digested with KpnI and ligated into pAra-pylST at the KpnI site to give the final pAra-pylSTBCD (FIG. 5). The final plasmid contains pylD, pylB, pylC, and pylS each under the control of separate arabinose-inducible and T7 hybrid promoters and with the rrnB terminator downstream of each one (identical to the pMH4 context) and the pylT gene under the proK promoter (similar to the pSUP/pSUPAR context with a single tRNA copy) (Cellitti et al., "In vivo incorporation of unnatural amino acids to probe structure, dynamics, and ligand binding in a large protein by nuclear magnetic resonance spectroscopy", J Am Chem Soc. 2008 Jul. 23; 130(29): 9268-81).

Example 8

Site Specific Incorporation of Biosynthetically Generated PCL into FAS-TE using *Escherichia coli* Cells This example provides description of the incorporation of PCL into TAG encoded sites of human fatty acid synthetase (FAS-TE) expressed from a second plasmid cotransformed into the same *Escherichia coli* cell.

The thioesterase domain encoding residues 2221 to 2502 of the human fatty acid synthetase (FAS-TE) is expressed from a pMH4 vector with an N-terminal tag (MGDSKIHH-HHHHENLYFQG) (SEQ ID NO:21) (see, Lesley S A, Kuhn P, Godzik A, Deacon A M, Mathews I, Kreusch A, Spraggon G, Klock H E, McMullan D, Shin T, Vincent J, Robb A, Brinen L S, Miller M D, McPhillips T M, Miller M A, Scheibe D, Canaves J M, Guda C, Jaroszewski L, Selby T L, Elsliger M A, Wooley J, Taylor S S, Hodgson K O, Wilson I A, Schultz P G, and Stevens R C, "Structural genomics of the *Thermotoga maritima* proteome implemented in a high-throughput structure determination pipeline", Proc Natl Acad Sci USA 2002; 99: 11664-11669). TAG codons were mutated using PIPE cloning (see, Klock, H E, Koesema E J, Knuth M W, and Lesley, S A, "Combining the polymerase incomplete primer extension method for cloning and mutagenesis with microscreening to accelerate structural genomics efforts", Proteins. 2008 May 1; 71(2):982-94) as described in detail in Cellitti et al., "In vivo incorporation of unnatural amino acids to probe structure, dynamics, and ligand binding in a large protein by nuclear magnetic resonance spectroscopy", J Am Chem Soc. 2008 Jul. 23; 130(29):9268-81. The mutants that were tested for PCL incorporation were Leu2222TAG/Leu2223Ile and Y2454TAG (FIG. 18A). HK100 cells were co-transformed with a pMH4-FAS-TE plasmid and pAra-pylSTBCD and selected on LB+Kan+Cm plates. Liquid cultures were grown at 37° C. in TB (Sigma)+Kan+Cm supplemented with 5 mM D-ornithine (Sigma or Nova Biochem) prior to induction. At OD$_{595}$=0.8, the cells were moved to 30° C. and induced 15-30 minutes later with 0.2% arabinose. Cells were grown for approximately 20 hours after induction before harvest by centrifugation. Cells were lysed in TBS+5% glycerol pH 8 by sonication. The soluble protein fraction was purified on Ni-NTA (Qiagen) chromatography according to the manufacturer's protocol. The yields are 46-80 mg/L for FAS-TE Leu2222PCL/Leu2223Ile and 155-186 mg/L for FAS-TE Tyr2454PCL, comparable to between 50 and 80% of the yields for wild-type protein. The molecular size on SDS-PAGE and molecular weight of the proteins as determined by mass spectrometry is consistent with single site incorporation of PCL at the desired location (FIG. 18B).

The sequence of FAS-TE (SEQ ID NO:22) with the two PCL incorporation sites (bold and underlined) is given below (for Leu2222PCL, residue Leu2223 is mutated to Ile2223):

MGSDKIHHHHHHENLYFQGS<u>L</u>LVNPEGPTLMRLNSVQSSERPLFLVHPI

EGSTTVFHSLASRLSIPTYGLQCTRAAPLDSIHSLAAYYIDCIRQVQPE

GPYRVAGYSYGACVAFEMCSQLQAQQSPAPTHNSLFLFDGSPTYVLAYT

QSYRAKLTPGSEAEAETEAICFFVQQFTDMEHNRVLEALLPLKGLEERV

AAAVDLIIKSHQGLDRQELSFAARSFYYKLRAAEQYTPKAKYHGNVMLL

RAKTGGA<u>Y</u>GEDLGADYNLSQVCDGKVSVHVIEGDHRTLLEGSGLESIIS

IIHSSLA

Example 9

Site Specific Incorporation of Biosynthetically Generated PCL into FKBP12 Using *Escherichia coli* Cells This example describes the incorporation of PCL into a TAG encoded site of FKBP12 expressed from a second plasmid cotransformed into the same *Escherichia coli* cell.

FKBP12 is expressed from a pET vector (Novagen) with an N-terminal tag (MGSSHHHHHHLEVLFQGP) (SEQ ID NO:23). A TAG codon was introduced at position Ile90 using PIPE cloning (see Klock, H E, Koesema E J, Knuth M W, Lesley, S A, "Combining the polymerase incomplete primer extension method for cloning and mutagenesis with microscreening to accelerate structural genomics efforts", Proteins. 2008 May 1; 71(2):982-94). BL21(DE3) cells (Invitrogen) were co-transformed with pET-FKBP12 and pAra-pylST-BCD and selected on LB+Kan+Cm plates. Liquid cultures were grown at 37° C. in TB+Kan+Cm supplemented with 5 mM D-ornithine. At OD$_{595}$=0.4, cells were moved to 30° C. and induced 30 minutes later with 1 mM IPTG. Cells were grown a further 20 hours before harvest. Cells were lysed and purified as for FAS-TE. The purified protein was then dialyzed into TBS and cut with HRV-3C protease (2 U per 1 mg FKBP12) for 48 hours at 4° C. to remove the His tag. The cut material was allowed to flow through a Ni-NTA column, collected, concentrated, and run over an S75 size exclusion column (GE Healthcare) for further purification. The final protein was further concentrated to 15-20 mg/ml before crystallization. The yield for FKBP Ile90PCL was 120 mg/L crude. The crystallized FKBP Ile90PCL is to be used to obtain an X-ray structure of a PCL-containing protein. FIG. 19A-C shows the SDS-PAGE and mass spectrometry data and crystallization results for PCL biosynthetically incorporated into FKBP12. The mass obtained was 12085.6 Da, which is consistent with the expected value of 12084 Da for the single site incorporation of PCL.

The sequence of FKBP12 (SEQ ID NO:24) with the PCL incorporation sites (bold and underlined) is given below:

MGSSHHHHHHLEVLFQGPGVQVETISPGDGRTFPKRGQTCVVHYTGMLE

DGKKFDSSRDRNKPFKFMLGKQEVIRGWEEGVAQMSVGQRAKLTISPDY

AYGATGHPG<u>I</u>IPPHATLVFDVELLKLE

Example 10

Site Specific Incorporation of Biosynthetically Generated PCL into Fibroblast Growth Factor 21(FGF21) using *Escherichia coli* Cells Provided in this example is the incorporation of PCL into 20 separately TAG encoded sites of human fibroblast growth factor, FGF21 expressed from a second plasmid cotransformed into the same *Escherichia coli* cell.

Fibroblast growth factor 21, FGF21 was expressed from the pSpeedET vector (see, Klock, H E, Koesema E J, Knuth M W, Lesley, S A, "Combining the polymerase incomplete primer extension method for cloning and mutagenesis with microscreening to accelerate structural genomics efforts", Proteins. 2008 May 1; 71(2):982-94) with an N-terminal tag (MGDSKIHHHHHHENLYFQG) (SEQ ID NO:21) and encoding residues 33-209 of the translated human protein. TAG codons for PYL analog incorporation and subsequent PEG attachment were introduced into the FGF21 (SEQ ID NO:25) aa33-209 construct at the following 20 individual positions: Ser35, Gln39, Arg47, Gln56, Arg64, Asp74, Lys84, Lys87, Lys97, Arg100, Arg105, His115, Arg124, Glu129, Lys150, Arg154, Leu167, Leu170, Leu181 and Gln184. The sequence of the FGF21 (33-209 aa) construct is shown below with the incorporation sites in the 20 separate constructs highlighted in bold and underlined.

```
MGSSHHHHHHS SGENLYFQGD SSPLLQFGGVRQRYLYTDD

AQQTEAHLEI REDGTVGGAA DQSPESLLQL KALKPGVIQI

LGVKTSRFLC QRPDGALYGS LHFDPEACSF RELLLEDGYN

VYQSEAHGLP LHLPGNKSPH RDPAPRGPAR FLPLPGLPPA

LPEPPGILAP QPPDVGSSDP LSMVGPSQGR SPSYAS
```

Either HK100 or BL21(DE3) cells were co-transformed with a pSpeedet-FGF21 plasmid and pAra-pylSTBCD and selected on LB+Kan+Cm. Liquid cultures were grown as in Example 8, with 5 mM D-ornithine was added prior to induction. The $OD_{595}$ for switching to 30° C. was tested between 0.2 and 1.0 with subsequent induction with 0.2% arabinose or 1 mM IPTG 15-30 minutes later and at OD595=0.4-2.0. Cells were grown approximately 20 hours post-induction before harvest. Cells were lysed in TBS with 5% glycerol, 1% Triton X-114, or 2.5% deoxycholate. The insoluble pellet was then resuspended in TBS+6M guanidine-HCl pH 8. Protein was purified on Ni-NTA resin and refolded either on the column or after elution from the column. The tag was subsequently removed with TEV protease, and the product was purified by Ni-NTA, ion exchange, and size exclusion chromatography.

Representative data showing incorporation of PCL into FGF21 is shown in FIG. 20. Preliminary expression yields are recorded in Table 4. Both full-length and truncated FGF21 proteins were purified due to the construct featuring a N-terminal His-tag. The extent to which the TAG codon is utilized as stop codon (yielding truncated protein) and utilized to incorporate PCL (yielding full-length protein) was dependent on the different incorporation site (FIG. 20). For three of the mutants (Table 4) no FGF21 protein could be detected, and for the remaining 17 mutants total yields of protein obtained varied between 5.7 and 143 mg/L with estimated yields of desired full-length proteins between 4 and 56 mg/L. For all mutants PCL incorporation was verified by mass spectrometry.

TABLE 4

| Mutant | Yield total protein [mg/L] | MS Verified? | % Truncation | Estimated yield full-length protein [mg/L] |
|---|---|---|---|---|
| R64 | 9 | yes | 15 | 7.7 |
| L181 | 48 | yes | 50 | 24.0 |
| S35 | 9 | yes | 30 | 6.3 |
| Q39 | 5.7 | no | 30 | not det. |
| R47 | 9 | yes | 30 | 6.3 |
| Q56 | 22 | yes | 10 | 19.8 |
| D74 | 16 | yes | 15 | 13.6 |
| R100 | 31 | yes | 75 | 7.6 |
| R105 | 10 | yes | 60 | 4.0 |
| H115 | 16 | yes | 50 | 8.0 |
| R124 | 25 | yes | 40 | 15.0 |
| E129 | 15 | no | 80 | not det. |
| R154 | 52 | yes | 50 | 26.0 |
| L167 | 143 | no | 90 | not det. |
| L170 | 47 | yes | 60 | 18.8 |
| Q184 | 75 | yes | 50 | 37.5 |
| K84 | 75 | yes | 30 | 52.5 |
| K87 | 21 | yes | 75 | 5.1 |
| K97 | 60 | yes | 10 | 54.0 |
| K150 | 113 | yes | 50 | 56.3 |

Example 11

Incorporation PCL into mTNF-α

To express the mTNF-α Gln21PCL mutant, *E. coli* BL21 (DE3) cells were cotransformed with pAra-pylSTBCD and the respective mutant mTNF-α gene on a pET22b plasmid vector. The transformed cells were grown in the presence of 5 mM D-ornithine in TB medium at 37° C. and induced with 1 mM IPTG and 0.2% (w/v) arabinose when the $OD_{600}$ reached 0.5. The cells were then continually shaken at 30° C. for 12-16 h and harvested. The cell pellet was stored at −20° C. until use. X-ray crystal structure of mTNF-α showed PCL incorporation sites Lys11 and Gln21 as indicated below in the protein sequence of recombinant mTNF-α containing an N-terminal $His_6$ tag followed by a factor Xa cleavage site (GIEGR) (SEQ ID NO:26):

```
       His₆ tag  Factor Xa cleavage site
MRGSHHHHHHGSGIEGR-L¹RSSSQNSSDK¹¹PVAH
VVANHQ²¹VEEQLEWLSQRANALLANGMDLKDNQ
LVVPADGLYLVYSQVLFKGQGCPDYVLLTHTVSRFAIS
YQEKVNLLSAVKSPCPKDTPEGAELKPWYEPIYLGG
VFQLEKGDQLSAEVNLPKYLDFAESGQVYFGVIAL
```

Example 12

Incorporation of PCL into mEGF

To express the mEGF-Tyr10PCL mutant, *E. coli* BL21 (DE3) cells were cotransformed with pAra-pylSTBCD and the respective mutant mEGF gene on a pET22b plasmid vector. The transformed cells were grown in the presence of 5 mM D-ornithine in TB medium at 37° C. and induced with 1 mM IPTG and 0.2% (w/v) arabinose when the $OD_{600}$ reached 0.5. The cells were then continually shaken at 30° C. for 12-16 h and harvested. The cell pellet was stored at −20° C. until use. X-ray crystal structure of mEGF showed PCL incorporation sites Tyr10 and Tyr29 as indicated below in the protein sequence of recombinant mEGF with a C-terminal $His_6$ tag is given (SEQ ID NO:27):

M-N₁SYPGCPSSY¹⁰DGYCLNGGVCMHIESLDSY²⁹

TCNCVIGYSGDRCQTRDLRWWELR-LE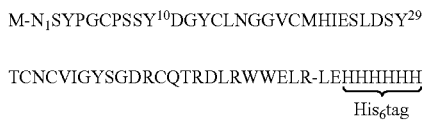

Example 13

Incorporation of Pyrrolysine (Pyl) or PCL into mTNF-α

To insert PYL into mTNF-α, E. coli BL21(DE3) cells were co-transformed with the mutant mTNF-α gene on a pET22b plasmid vector with the codon for Gln21 (CAA) mutated to a stop codon (TAG) as well as pAra-pylSTBCD containing M. mazei pylS, pylT, pylB, pylC, and pylD. To exclusively incorporate PCL into mutant mTNF-α pAra-pylSTBCD was substituted with pAra-pylSTCD, which lacks the gene for the putative methyltransferase pylB. The transformed cells were grown in the presence of 5 mM D-ornithine in TB medium at 37° C. and induced with 1 mM IPTG and 0.2% (w/v) arabinose when the OD$_{600}$ reached 0.5. The cells were then continually shaken at 30° C. for 12-16 hours and harvested. The cell pellet was stored at −20° C. After thawing the cell pellet for 15 minutes on ice, the cells were resuspended in lysis buffer (20 mM Tris/HCl, 50 mM NaCl, pH 8.0) at 3 ml per gram wet weight. Lysozyme was added to 1 mg/ml and the cells were sonicated for 2 minutes on ice. The lysate was centrifuged at 30,000×g for 20 minutes at 4° C. to pellet the cellular debris. 1 ml of 50% Ni-NTA slurry (Qiagen) was added to the cleared lysate and gently mixed by shaking at 4° C. for 60 minutes. The lysate-Ni-NTA mixture was loaded into a column and the flow-though was collected. After washing the resin with 20 mL of 25 mM imidazole in PBS (pH 8.0), the protein was eluted with 2.5 ml of 250 mM imidazole in PBS (pH 8.0) and buffer-exchanged into PBS, pH 7.4 by using a PD-10 column (GE Healthcare). The expression of mTNF-α Gln21TAG in the presence or absence of pylB as well as in the presence or absence of D-ornithine was analyzed by SDS-polyacrylamide gel electrophoresis (SDS-PAGE) (FIG. 21A). In FIG. 21A Lane 1 is the molecular weight standard SeeBlue Plus2 Pre-Stained Standard; Lane 2 is expression in the presence of both pylB and D-ornithine; Lane 3, expression in the presence of pylB with no D-ornithine added; Lane 4, expression in the absence of pylB with 5 mM of D-ornithine added; and Lane 5, expression in the absence of both pylB and D-ornithine. The data illustrates that expression of full-length mTNF-α depends on the presence of D-ornithine and is similar in the absence or presence of the pylB gene.

Example 14

Incorporation of Pyrrolysine (Pyl) or PCL into mEGF

E. coli BL21(DE3) cells were co-transformed with pAra-pylSTBCD and the respective mutant mEGF Tyr10TAG and Tyr29TAG genes on a pET22b plasmid vector. Both constructs were expressed in the presence of 5 mM D-ornithine in TB medium at 37° C. with addition of 1 mM IPTG and 0.2% (w/v) arabinose when the OD$_{600}$ reached 0.5. The temperature was then reduced to 30° C., and cells were harvested 16 hours after induction. The cell pellet was resuspended in 20 mL of 20 mM Tris/HCl (pH 8.5) and sonicated for 5 minutes. After centrifugation at 30,000×g for 20 minutes, the supernatant was discarded. The pellet was resuspended by sonication into 20 mL of 20 mM Tris/HCl (pH 8.5) containing 2% (v/v) Triton-X100. After another round of centrifugation at 30,000×g, for 20 minutes, the pellet was solubilized by sonication into 10 mL of 8 M urea, 20 mM Tris/HCl, 10 mM β-mercaptoethanol, pH 8.5. Insoluble cell debris was removed by centrifugation (30,000×g for 20 minutes) and the supernatant was diluted 2-fold with refolding buffer (100 mM Tris/HCl, 4 mM reduced glutathione, 0.4 mM oxidized glutathione, 20% (v/v) ethanol, pH 8.5). The diluted sample was then dialyzed against refolding buffer overnight at 4° C. by using a slide-a-lyzer dialysis cassette (3500 Da molecular weight cut off, Pierce). Insoluble protein was removed by centrifugation at 30,000×g for 20 minutes, and the supernatant was supplemented with β-mercaptoethanol to a final concentration of 2 mM. 1 ml of 50% Ni-NTA slurry (Qiagen) was added to the refolded protein and gently mixed by shaking at 4° C. for 60 minutes. The protein-Ni-NTA mixture was loaded into a column and the flow-though was collected. After washing the resin with 20 mL of 25 mM imidazole in PBS (pH 8.0), the protein was eluted with 2.5 ml of 250 mM imidazole in PBS (pH 8.0). Finally, the protein was buffer-exchanged into PBS (pH 7.4) by using a PD-10 column (GE Healthcare). The purity of the protein preparation was investigated by SDS-PAGE (FIG. 21B). In FIG. 21B, Lane 1 is the molecular weight standard SeeBlue Plus2 Pre-Stained Standard and Lane 2, mEGF Tyr10TAG mutant protein after Ni-NTA purification.

In addition, mEGF Tyr10TAG, ESI-MS spectra were obtained for protein obtained in the presence or absence of pylB expression, as obtained using the methods for mTNFα above. (FIG. 21C). The lower mass spectrum in FIG. 21C illustrates that PYL incorporation predominantly occurs in the presence of the pylB gene (expected mass of mEGF Tyr10Pyl=7310 Da), while the upper mass spectrum in FIG. 21C illustrates that only PCL incorporation occurs in the absence of pylB (expected mass of mEGF Tyr10Pyl=7296 Da). Thus the protein observed in FIG. 21B, Lane 2 is mEGF with PYL incorporated as confirmed further by LC-MS/MS analysis. Similarly, the protein observed in FIG. 21A, Lane 2 is likely mTNFcs with PYL incorporated, while Lane 4 is likely mTNFcs with PCL incorporated.

Additionally, quantitation of the PCL/PYL ratio from LC-MS/MS extracted ion chromatograms mass analysis of PCL and PYL incorporation into mEGF Tyr10TAG samples expressing all genes (M. mazei pylS, pylT, pylB, pylC, and pylD) and showed that PYL is 5 to 10 times more abundant than PCL, whereas quantitation of the PCL/PYL ratio from LC-MS/MS extracted ion chromatograms mass analysis of PCL and PYL incorporation into mTNF Gln21TAG samples expressing all genes (M. mazei pylS, pylT, pylB, pylC, and pylD) showed that PCL is about 7 times more abundant than Pyl. Quantitation in the absence of the pylB gene shows only PCL protein illustrating that PYL incorporation is strictly dependent on pylB which further suggests that pylB is indeed the methyltransferase required for the biosynthesis of Pyl.

Example 15

Incorporation of other Analogues and Precursors

HK100 cells (derived from Genehogs; Invitrogen) were co-transformed with pAra-pylSTBCD, pAra-pylSTCD, pAra-pylSTC, pAra-pylSTD, or pSUPAR-pylST and pMH4-FASTE-L2222TAG-L2223I. Cells were grown in 25 ml cultures of Terrific Broth (TB) (Sigma) at 37° C. to OD595~0.6. Cells were moved to 30° C. and the analogue or precursor compounds were added to each individual culture at the concentration indicated in FIG. 15. The compounds evaluated were N-ε-cyclopentyloxycarbonyl-L-lysine (CYC; Sigma), D-ornithine (Chem-Impex), PCL-A (see Example 36-1, compound 3647-125), PCL-B (see Example 36-2, compound 3793-011), P2C (see Example 36-2, compound 3647-164), P5C (see Example 35-1, compound 3793-007) and Lys-Nε-D-ornithine (see Example 35-2, compound 3793-031). The cells were then induced 20 minutes later with 0.2% arabinsoe. After 18-20 hours, the cells were harvested by centrifugation. Cells were lysed by sonication, purified on Ni-NTA (Qiagen) under native conditions and evaluated on an SDS-PAGE gel followed by Coomasie staining (0.25 ml Ni-NTA, 0.75 ml elution, 20 μl on gel). FIG. 15A shows purified protein (FAS-TE) from cells grown with the indicated pyl genes present (pylS/pylT or pylB/pylC/pylD/pylS/pylT) and fed the indicated compounds. Cyc and D-ornithine (D-Orn) were used as positive controls. Addition of no compound is presented as a negative control. Gel sample volumes in lanes 1-11 and in 12-18 are each internally consistent.

Lanes 2 and 3 show protein obtained from cells grown with only the pylS and pylT genes and either with PCL-B (Lys-P2C) or PCL-A (Lys-P5C), respectively. Both compounds were incorporated into proteins, thereby demonstrating the ability of PylS to utilize the two compounds. Lanes 5 to 11 show evaluation of protein synthesis in cells with the full set of pyl biosynthetic genes (pylB/pylC/pylD/pylS/pylT) in the presence of precursor Lys-Nε-D-Orn (Lane 10), or precursors having only a pyrroline ring: P2C (lane 6) and P5C (lane 8). The precursors having only a pyrroline ring: P2C (lane 6) and P5C (lane 8) were not sufficient to support PCL biosynthesis, which suggested that these are not intermediates in the pathway. However, Lys-Nε-D-Orn (lane 10) resulted in protein expression with PCL incorporated at the amber codon, demonstrating that this is an intermediate in the biosynthetic pathway of PCL. Table 5 gives the amount of protein obtained (Bradford), the observed mass and the ratio of PCL:PYL:CYC obtained.

TABLE 5

| Lane | Test | Bradford (mg/25 ml) | Intact mass LC-MS (observed) | Ratio PCL:PYL:CYC From LC-MS |
|---|---|---|---|---|
| 1 | negative | 0.071 | — | — |
| 2 | PCL-B (Lys-P2C) | 2.703 | 33270.8 | PCL only |
| 3 | PCL-A (Lys-P5C) | 0.539 | 33256.8 | PCL only |
| 4 | positive | 0.796 | 33272.8 | CYC only |
| 5 | negative | 0.131 | 33275.2 | 2:1:— |
| 6 | P2C | 0.103 | 33274.0 | 4:1:— |
| 7 | positive | 1.838 | 33257.2, 33368.4 | PCL only |
| 8 | P25 | 0.075 | Noise (33248) | |
| 9 | positive | 0.795 | 33248 (PCL), 33360 | |
| 10 | Lys-Nε-D-ornithine | 1.66 | 33248 (PCL) | |
| 11 | positive | 0.51 | 33248 (PCL) | |

To determine if Lys-Nε-D-Orn was an intermediate in the biosynthetic pathway upstream of any of the required genes (pylC and pylD), HK100 cells (derived from Genehogs; Invitrogen) were co-transformed with pSUPAR-pylST, pMH4-FASTE-L2222TAG-L2223I, and either pAra-pylSTB, pAra-pylSTC, pAra-pylSTD, pAra-pylSTCD or pAra-pylSTBCD. FIG. 15B shows that only pylD (lane 15) is required for formation of PCL from Lys-Ne-D-Orn, suggesting that it is an intermediate upstream of pylC in the biosynthetic pathway. Furthermore, NMR evaluation confirmed that Lys-Ne-D-Orn is a substrate for PylD.

Example 16

Derivatization of PCL Incorporated into hRBP4 with 2-amino benzaldehyde, 2-amino-acetophenone and 2-amino-5-nitro-benzophenone Provided in this example is labeling of PCL with 2-amino-benzaldehyde (2-ABA), 2-amino-acetophenone and 2-amino-5-nitro-benzophenone. The reaction is thought to follow the general scheme shown in FIG. 22. Mass spectrometry and NMR were used to evaluate the structures formed. FIG. 23 indicates the protein conjugates formed from the three different 2-amino-benzaldehyde moieties and presents the expected and observed mass changes.

Mass Spectrometric Detection of PCL Site-Specifically Modified by 2-ABA in hRBP4

Retinol binding protein (hRBP4) was expressed in HEK293F cells as described in Example 2. PCL was incorporated instead of Phe122 (hRBP4 mutant #6) as verified by mass spectrometry (FIG. 6A-11). 10 μl of hRBP4 Phe122PCL stock solution was mixed with 89 μl of 200 mM sodium acetate buffer, pH 5.0 and 1 μl of a 1 M 2-ABA solution and incubated for 16 hours at room temperature. The final concentrations in the reaction mixture were 17 μM hRBP4 Phe122PCL protein and 10 mM 2-amino-benzaldehyde (2-ABA). The mass spectrum of the derivatized hRBP4 is shown in FIG. 24, wherein the mass obtained corresponded to the 2-ABA adduct of PCL (23269.2 Da). The unmodified hRBP4 has a mass of 23166.8 Da and therefore the observed mass increase of 102.4 Da (expected+103 Da) demonstrates that the hRBP4 has been modified with 2-ABA. At least 96% of the peak intensities in the mass spectrum is due to 2-ABA adduct of PCL, which indicated that the reaction went to near completion.

The LC-MS analysis of the tryptic digest of the 2-ABA-derivatized hRBP4 Phe122PCL protein was performed and MS/MS analysis (FIG. 25A) identified the expected YWGVASF*LQK peptide (SEQ ID NO:17), wherein F* had a mass consistent with that of 2-ABA-modified PCL as shown in FIG. 23. The reaction was complete as the underivatized PCL residue was not detectable. The assigned MS/MS spectrum of YWGVASF*LQK (F*=PCL-2-ABA adduct) is given below:

Monoisotopic mass of neutral peptide Mr(calc): 1376.7241
Variable modifications:
F7: PCL-2-ABA adduct at F (F)
Ions Score: 44 Expect: 0.059
Matches (Bold): 13/74 fragment ions using 28 most intense peaks

| # | b | b++ | b* | b*++ | b⁰ | b⁰++ | Seq. | y |
|---|---|---|---|---|---|---|---|---|
| 1 | 164.0706 | 82.5389 | | | | | Y | |
| 2 | 350.1499 | 175.5786 | | | | | W | 1214.6681 |
| 3 | 407.1714 | 204.0893 | | | | | G | 1028.5887 |
| 4 | 506.2398 | 253.6235 | | | | | V | 971.5673 |
| 5 | 577.2769 | 289.1421 | | | | | A | 872.4989 |
| 6 | 664.3089 | 332.6581 | | | 646.2984 | 323.6528 | S | 801.4618 |
| 7 | 990.4832 | 495.7452 | | | 972.4727 | 486.7400 | F | 714.4297 |
| 8 | 1103.5673 | 552.2873 | | | 1085.5567 | 543.2820 | L | 388.2554 |
| 9 | 1231.6259 | 616.3166 | 1214.5993 | 607.8033 | 1213.6153 | 607.3113 | Q | 275.1714 |
| 10 | | | | | | | K | 147.1128 |

| | # | y++ | y* | y*++ | y⁰ | y⁰++ | # |
|---|---|---|---|---|---|---|---|
| | 1 | | | | | | 10 |
| | 2 | 607.8377 | 1197.6415 | 599.3244 | 1196.6575 | 598.8324 | 9 |
| | 3 | 514.7980 | 1011.5622 | 506.2847 | 1010.5782 | 505.7927 | 8 |
| | 4 | 486.2873 | 954.5407 | 477.7740 | 953.5567 | 477.2820 | 7 |
| | 5 | 436.2873 | 855.4723 | 428.2398 | 854.4883 | 427.7478 | 6 |
| | 6 | 401.2345 | 784.4352 | 392.7212 | 783.4512 | 392.2292 | 5 |
| | 7 | 357.7185 | 697.4032 | 349.2052 | | | 4 |
| | 8 | 194.6314 | 371.2289 | 186.1181 | | | 3 |
| | 9 | 138.0893 | 258.1448 | 129.5761 | | | 2 |
| | 10 | 74.0600 | 130.0863 | 65.5468 | | | 1 |

FIG. 25B is the TIC and EIC of 2+ ions of YWGVASF*LQK (F*=PCL and PCL-2-ABA adduct), wherein comparison of the EICs (extracted ion chromatogram) for derivatized and underivatized (not detectable) species indicates completion of the reaction. FIG. 25C is the mass spectrometric analysis of hRBP4 Phe122PCL derivatized with 2-ABA showing 3+ and 2+ precursors of YWGVASF*LQK at m/z 459.92 (3+) and 689.37 (2+) respectively. (F*=PCL-2-ABA adduct). This example demonstrates that the observed reactions with 2-ABA occurs site-specifically with the PCL residue incorporated at the desired TAG site at residue 122.

Reaction Efficiency as a Function of pH:

The reaction efficiency as a function of pH, (FIG. 26), was evaluated by reacting 17 µM hRBP4 PCL mutant protein with or without 10 mM 2-amino-benzaldehyde (2-ABA) at 200 mM sodium acetate buffer, pH 5.0, or with 10 mM 2-amino-benzaldehyde (2-ABA) 10× PBS buffer, pH 7.4 for 12 hours at room temperature. Mass spectra of the reaction mixtures showed that at least 87% of the total peak intensity corresponds to that of protein modified with one 2-ABA moiety (+102 Da as expected) (FIGS. 26A, B and C). The pH 7.4 reaction mixture contains approximately 13% unreacted protein (FIG. 26C) while only 4.2% unreacted protein is detected in the reaction at pH 5.0 (FIG. 26B) suggesting a slightly greater reactivity of PCL at pH 5.0 compared to pH 7.4. The reaction is specific for the presence of PCL, as hRBP4 with OMePhe incorporated instead of Phe62 was not modified by the presence of 10 mM 2-ABA (FIGS. 26D, E and F).

Reaction Efficiency as a Function of Reactant to Protein Concentration and with Other 2-ABA-Like Moieties:

The reaction efficiency as a function of the reactant to protein concentration ratio, and the reactivity with 2-ABA-like reactants was evaluated by reacting 17 µM hRBP4 PCL mutant protein with 0.1 mM 2-amino-benzaldehyde (2-ABA), 0.1 mM 2-amino-acetophenone (2-AAP) or 0.1 mM 2-amino-5-nitro-benzophenone (2-ANBP) in 200 mM sodium acetate buffer at pH 5.0. After 12 hours at room temperature, mass spectra of the reaction mixture showed the expected mass of conjugated protein (FIG. 27). For 2-ABA the relative intensity of the correctly conjugated peak was 88% of the total intensity; only 4.2% of the protein remained unreacted (FIG. 27A). For 2-AAP 93% appeared reacted; 4.5% unreacted (FIG. 27B). For 2-ANBP only 5.4% reacted (FIG. 27C) presumably because of the low solubility of the reactive reagent, as the 2-ANBP immediately precipitation upon addition to the solution containing the hRBP4 PCL mutant protein.

This example demonstrates that PCL modified proteins react with different 2-amino-benzaldehyde analogues and are derivatized at the site of the incorporated PCL. In all cases the measured mass of the modified protein was consistent with the expected mass for structures as drawn in FIG. 23. The data also demonstrate that the conjugation reactions proceed with high efficiency and to near completion at a low reactant to protein ratio of only 6 to 1. The data also demonstrates that each protein sample is derivatized only once. However, it was observed that the attachment of multiple reactant molecules was obtained (FIG. 28A) at very high reactant to protein ratios (4700-fold) and at pH 7.5. Precipitation of an identical sample at pH 5.0 suggests multiple reactions as well. Similarly hRBP4 modified with OMePhe instead of Phe62 (6.5 µM) showed a similar pattern of conjugates (FIG. 28B) to that observed in FIG. 28A when reacted with a 15400-fold molar excess of 2-ABA at pH 7.5. This demonstrates that under these conditions (large molar excess of reactant over protein) attachment does not depend on the presence of a PCL side chain but likely involves lysine side chains. However, the example reactions illustrate that PCL residues incorporated into proteins can be specifically and near quantitatively derivatized by reacted with 2-amino-benzaldehyde containing molecules added in small molar excess.

Example 17

Derivatization of PCL Incorporated into FAS-TE with 2-amino-acetophenone

16 µM of FAS-TE Tyr2454PCL produced in *Escherichia coli* as in Example 8 was reacted with 1 mM 2-AAP for 16 hours at room temperature and 24 hours at 4 degree ° C. at pH 5.0 in 200 mM sodium acetate buffer. FIG. 29A shows the mass spectrum of unreacted FAS-TE Tyr2454PCL while FIG. 29B shows the mass spectrum of the reaction mixture: 100% of the observable peak intensity occurs at 33318.8 Da, 116.8 Da larger than that of unreacted material and within errors of the 116 Da mass increase expected for 2-AAP modified FAS-TE Tyr2454PCL. Similarly, at pH 7.4 the reaction goes to 95% completion (FIG. 29C (unreacted) and FIG. 29D (reacted)).

Example 18

Derivatization of PCL Incorporated into hRBP4 with 2-amino-acetophenone-PEG8

This example demonstrates that PCL incorporated into hRBP4 can be derivatized to completeness at a single site with a polyethylene glycol (PEG) derivative of 2-amino-acetophenone. In this example the PEG contains 8 ethylene glycol units and its structure is shown in FIG. 31. The example also demonstrates that wild-type hRBP4 at pH 5.0 and pH 7.5 does not react with 2-AAP-PEG8 with reagent to protein ratios of up to 2300.

hRBP4 mutant #6 was prepared as in Example 2. The 2-amino-acetophenone PEG8 (TU3205-044) was prepared as described in Example 20. The reactions were allowed to proceed for 14 hours at room temperature and 72 hours at 4 degree ° C. before mass spectra were obtained of the reaction mixtures.

For reactions performed at pH 7.5, 10 µL of hRBP4 Phe122PCL (0.22 mg/mL, in PBS, pH 7.5) were diluted with 10 µl of 10×PBS. 0.2 µl or 2 µl of a 100 mM stock solution of 2-AAP-PEG8 (in water) were added to a final concentration of 1 and 9.1 mM respectively. The protein concentration was 4.7 µM and 4.3 µM, respectively, resulting in a 210 or 2100 molar excess of reactant to protein. FIG. 32A shows the mass spectra of the reaction mixture at the 210 to 1 ratio, indicating an approximate 95% completeness for the reaction and the observed mass increase of 556 Da was identical to the expected value (FIG. 31). 100% completeness was obtained for the reaction at 2100 molar excess (data not shown).

Similarly, reactions were performed at pH 5.0. In this case, 10 µL of hRBP4 Phe122PCL (0.22 mg/mL, in PBS, pH 7.5) were diluted with 90 µl of 200 mM sodium acetate buffer at pH 5.0. 1 µl or 10 µl of a 100 mM stock solution of 2-AAP-PEG8 (in water) were added to a final concentration of 1 and 9.1 mM respectively. The protein concentration was 0.94 and 0.86 µM, respectively, resulting in a 1050 or 10500 molar excess of reactant to protein. FIG. 32B shows the mass spectra of the reaction mixture at the 1050 to 1 ratio. 100% completeness was obtained for both reactions and the observed mass increase of 556 Da was identical to the expected value (FIG. 31).

To test the reactivity of 2-AAP-PEG8 with wild-type hRBP4 protein, test reactions were setup similarly to those above. For the pH 7.5 reactions the final wild-type protein concentration was 20 µM and the 2-AAP-PEG8 concentration was 1 or 9.1 mM resulting in a molar ratio of 46 and 460 to 1. The pH 5 reactions were performed at 4 µM protein concentration and 1 and 9.1 mM 2-AAP-PEG (230 and 2300 to 1 reactant to protein). In all four reactions only unmodified wild-type hRBP4 protein was observed at the expected mass (FIG. 32D-F). This example demonstrates that the coupling reaction of 2-AAP-PEG is highly specific for the presence of a PCL residue in the target protein.

Example 19

Derivatization of PCL Incorporated into FAS-TE with 2-amino-acetophenone-PEGs of Differing Molecular Weight This example demonstrates the generality of the reactivity of PCL side chains with 2-amino-acetophenone PEGs. This example further demonstrates that 2-AAP-PEGs of lengths sufficient to be useful for the modification of biotherapeutic proteins can be conjugated to PCL modified proteins.

16 µM of FAS-TE Tyr2454PCL produced in *Escherichia coli* as described in Example 8 was reacted with 1 mM TU3205-044 (2-AAP-PEGS) for 16 hours at room temperature at pH 5.0 in 200 mM sodium acetate buffer. FIG. 33A shows the mass spectrum of unreacted FAS-TE Tyr2454PCL, while FIG. 33B shows the mass spectrum of the reaction mixture: In FIG. 33B, 100% of the observable peak intensity occurs at 33758.4 Da, 556 Da larger than that of unreacted material. This mass difference is that expected for 2-AAP-PEG8 modified FAS-TE Tyr2454PCL (FIG. 31).

In a further example, PCL incorporated into FAS-TE at Tyr2454 was derivatized with three different 2-AAP-PEGs with MW of 0.5 kDa, 2.4 kDa and 23 kDa. The FAS-TE single-site PCL mutant was produced in *Escherichia coli* at a yield of approximately 160 mg/L (corresponding to ~80% of wt yield) as described in Example 8. Aliquotes of FAS-TE Tyr2454PCL (0.16 mM in PBS, pH 7.5) were reacted with TU3205-044 (0.5 kDa 2-AAP-PEG), TU3205-048 (2.4 kDa 2-AAP-PEG) and TU3205-052 (23 kDa 2-AAP-PEG) at molar ratios of 10:1 or 100:1 for 6 days at 4° C. or room temperature. The structures of the PEGs and their synthesis is described in Example 37.

Before SDS-PAGE analysis (FIG. 34) excess PEG reagents were removed by binding the His-tagged FAS-TE proteins to Ni-NTA beads and repeated washing of the beads with PBS buffer. For the gel and mass spectrometric analysis, excess buffer was removed from the Ni-NTA beads and protein was eluted with imidazole buffer. Specifically, 50 µL of Ni-NTA beads were added to 50 µL of reaction mixture, incubated for 2 hours and the reaction mixture and buffer were separated by centrifugation. The beads were then washed 3 times with 1 mL PBS; 70 µL of 250 mM imidazole buffer, 20 mM TRIS, pH 8 was added to the beads to elute the protein for gel and mass spectrometric analysis. PEGylation with the 0.5 kDa 2-AAP-PEG could not be resolved by SDS-PAGE but was verified by mass spectrometry. The extent of the reaction was approximately 57% for the 100:1 room temperature reaction and 43% for the 100:1 4° C. reaction (data not shown). For the larger 2-AAP-PEGs the PEGylated products can be resolved by SDS-PAGE (FIG. 34). All reactions were incomplete and proceeded to approximately 25-30% for the 2.4 kDa and the 23 kDa 2-AAP-PEG. Single site conjugation at the PCL site and the extent of the reaction was confirmed by mass spectrometry for the 2.4 kDa 2-AAP-PEG (FIG. 33). Mass spectrometric data for the 23 kDa 2-AAP-PEG derivatized protein could not be obtained because of the inhomogenity of the PEG.

The reported reaction yields are a lower estimate as the stringency of the Ni-NTA bead extraction may have favored the extraction of unreacted FAS-TE as the PEGylation may have lowered the affinity of the His-tag (as was the case for PEGylation of FAS-TE Leu2222PCL; data not shown). However, the detection of PEGylated material after the extraction demonstrates the stability of the PCL-2-AAP-PEG linkage.

Example 20

Derivatization of PCL Incorporated into FGF21 with 2-amino-acetophenone-PEGs of Differing Molecular Weight The example shows that FGF21 with PCL incorporated at various positions can be PEGylated with 2-AAP-PEG reagents. The example also shows that PEGylated FGF21 mutants can be separated from unreacted full-length FGF21 and truncated FGF21 by a combination of ion-exchange and size-exclusion chromatography.

FGF21 with PCL incorporated at the position of Lysine 84 was expressed in Escherichia coli and refolded and purified as described in Example 10 except the protein was not subjected to TEV protease cleavage. The protein stock was approximately 6.6 mg/mL in PBS and contained approximately 20% FGF21 protein truncated at residue 84. 5 μl of the FGF21 stock were mixed with 45 μl 200 mM sodium acetate buffer at pH 5.0 and 0.5 μl of a 100 mM TU3205-044 (2-AAP-PEGS, see Example 20) stock solution. The final molar ratio was 1 mM 2-AAP-PEG8 to approximately 30 μM FGF21. The reaction was allowed to proceed for 16 hours at room temperature and reached completion.

FIG. 35A shows the mass spectrum of unreacted FGF21, while FIG. 35B shows the mass spectrum of the reaction mixture: The PEGylation reaction proceeded to completion and yielded a protein of 21792.4 Da, 556 Da larger than that of unreacted material. This mass difference was expected for 2-AAP-PEG8 modified FGF21.

Various FGF21 PCL mutants (expressed and purified as in Example 10) were PEGylated with 23 kDa 2-AAP-PEG (TU3205-052, see Example 37-3). Typically, the protein concentrations were between 100 and 400 μM while the 23 kDa 2-AAP-PEG was added to a final concentration of 1 mM in PBS buffer, pH 7.4. The reactions were incubated at 4° C. for 3 days. The SDS-PAGE of the PEGylation reactions with seven representative FGF21 PCL mutants are shown in FIG. 36A, while eight purified PEGylated FGF21 proteins separated from full-length (FL) unreacted FGF21 and truncated (TR) FGF21 are shown in FIG. 36B.

Example 21

Derivatization of PCL Incorporated into EPO with 2-amino-acetophenone-PEGs

PCL was incorporated at various positions in mouse EPO as described in Example 6. After Ni-NTA purification, mEPO constructs (#6, #9 and #10 mutant constructs) were further purified by an S-300 gel filtration column in PBS. The purified mEPO proteins were concentrated to approximately 1 mg/ml. Activated 23 kDa 2-AAP-PEG (TU3205-052, see Example 37-3) was added to the purified proteins at 1 mM and incubated at the conditions as indicated in the table 6.

TABLE 6

| # | constructs | pH | temp |
|---|---|---|---|
| 1 | EPO6 | pH 7.5 | 4 C. |
| 2 | EPO6 | pH 5.5 | 4 C. |
| 3 | EPO6 | pH 8.5 | 4 C. |
| 4 | EPO9 | pH 7.5 | 4 C. |

TABLE 6-continued

| # | constructs | pH | temp |
|---|---|---|---|
| 5 | EPO9 | pH 5.5 | 4 C. |
| 6 | EPO9 | pH 8.5 | 4 C. |
| 7 | EPO10 | pH 7.5 | 4 C. |
| 8 | EPO10 | pH 5.5 | 4 C. |
| 9 | EPO10 | pH 8.5 | 4 C. |
| 10 | EPO6 | pH 7.5 | 4 C. |
| 11 | EPO6 | pH 7.5 | 22 C. |
| 12 | EPO6 | pH 7.5 | 30 C. |
| 13 | EPO6 | pH 7.5 | 37 C. |

All mEPO constructs were run as a monomer in the column. When 23 kDa 2-AAP-PEG was incubated with the purified proteins, mEPO were PEGylated at a single site, as they migrated as a 65 kDa band in SDS-PAGE (FIG. 37). The efficiency of the reaction varied from 10% to 15% depending on the conditions, with pH 5.5 resulting in a higher degree of PEGylation relative to pH 7 and pH 8.5. In addition, temperatures greater than 4° C. did not significantly increase the extent of PEGylation.

Example 22

Derivatization of PCL Incorporated into hRBP and FAS-TE with D-Mannosamine

This example demonstrates the direct coupling of an amino sugar, D-mannosomine, to PCL incorporated into two target proteins. This example suggests a general reaction scheme for the glycosylation of PCL containing proteins (FIG. 38).

Human RBP4 Phe122PCL (mutant #6) was prepared in HEK293F cells as in Example 2. 10 μL of 170 μM protein stock was added to 89 μL 10×PBS buffer, pH 7.5 and mixed with 1 μl of 1 M D-mannosamine. hRBP4 Phe122PCL protein (17 μM) was incubated with 10 mM D-mannosamine for 14 at room temperature (no reaction observed) followed by 48 hours at 37° C. FIG. 39 shows the mass spectrum of the reaction mixture after the 37° C. incubation period. In addition to the expected peak of unreacted hRBP4 at 23165.6 Da (expected 23166 Da), a peak putatively assigned to the D-mannosamine adduct is observed at 23300.0 Da. The mass increase of 164.4 Da is close but not identical to the 161.1 Da increase expected for the putative reaction product drawn in FIG. 38. In addition, part of the protein degraded to a species detected at 21007.8 Da.

In a second example, FAS-TE modified with PCL at position 2222 (11 μM) expressed in Escherichia coli and purified as in Example 8, was incubated with 10 mM D-mannosamine for 72 hours at room temperature. The mass spectrum of the unreacted sample is shown in FIG. 40A and contains the expected signal at 33250.4 Da corresponding to the unreacted protein and a peak at 33360.4 Da attributed to a contaminating protein in the sample. Mass spectrometry of the reaction mixture shows the expected signal at 33250.4 Da corresponding to the unreacted protein (FIG. 40B). An additional peak is visible at 33408.8 Da, 158.4 Da larger the starting material, presumably that of the reaction product shown in FIG. 37. Comparison of these two samples suggests a conversion of FAS-TE Leu2222PCL to the D-mannosamine adduct with a yield of approximately 50% under these reaction conditions.

Example 23

PCL Mediated Covalent Cross-Linking of FGF21

This example demonstrates that proteins can be covalently dimerized via a bi-functional PCL-specific cross-linker.

FGF21 with PCL incorporated at the position of Lysine 84 was expressed in *Escherichia coli* and refolded and purified as described in Example 10, except the protein was not subjected to TEV protease cleavage. FGF21 Lys84PCL was derivatized with the cross-linker TU633-010 (FIG. 43A; see Example 37-4 for synthesis). The protein stock was approximately 6.6 mg/mL in PBS and contained approximately 20% FGF21 protein truncated at residue 84. 5 µl of the FGF21 stock was mixed with 45 µl 200 mM sodium acetate buffer at pH 5.0. 0.1 µl of a 5 mM stock solution of cross-linker TU633-010 (in DMSO) was added to a final concentration of 10 µM cross-linker and approximately 30 µM FGF21. Similarly 50 µl of FGF21 stock solution in PBS, pH 7.4 was reacted with 1 µl of 5 mM TU633-010 at a concentration of 100 µM cross-linker and approximately 300 µM FGF21. A sample of FGF21 diluted into 200 mM sodium acetate buffer was prepared as control and treated identically. After 16 hours at room temperature, aliquots of the reactions and of the control sample were analyzed by mass spectrometry and SDS-PAGE analysis without purification. The mass spectrum obtained for the pH 5.0 sample (FIG. 43B) clearly shows a peak at the expected mass of the covalent dimer (43037.2 Da; relative intensity of all FGF21 peaks 53%), at the expected mass of FGF21 with one end of the cross-linker attached (21820.0 Da; 33%) and unreacted FGF21 (21235.2 Da; 14%). For the pH 7.4 sample, the covalent dimer is not detected; 28% of FGF21 is mono-reacted with cross-linker while most of the protein is unreacted (data not shown).

Adjustment of the reactant to protein concentration further increased the yield of covalent dimer. Specifically, 10 µl of the FGF21 stock was mixed with 90 µl 200 mM sodium acetate buffer at pH 5.0. 0.3 µl of a 5 mM stock solution of cross-linker TU633-010 (in DMSO) was added to a final concentration of 15 µM cross-linker and approximately 30 µM FGF21. One sample was incubated for 4 days at room temperature while a second sample was incubated at 4° C. Samples in 10×PBS, pH 7.5 were also prepared and incubated identically. For the pH 5.0 sample incubated at room temperature, the peak of the covalent FGF21 dimer at the expected mass of 43034.4 Da is the dominant species, while the unreacted FGF21 is not detected at 21233.6 Da. Some of FGF21 modified with one end of the cross-linker attached is detected at 21818.4 Da (FIG. 44A). The reaction did not progress to the same extent at pH 5.0 and 4° C. as approximately 19% of FGF21 remains unreacted; 40% is modified with one end of the cross-linker attached while approximately 41% of the mass spectra peak intensity is that of the covalent dimer. The reactions at pH 7.5 did not yield any covalent dimer as indicated by SDS-PAGE (FIG. 44B).

Site-Specific Modification of Pyrroline-Carboxy-Lysine (PCL) Containing Proteins with other Diverse Molecules.

In other embodiments, the coupling of the 2-aminobenzaldehyde (ABA) conjugates and 2-aminoacetophenone (AAP) conjugates provide herein to PCL-containing proteins was carried out in 10× phosphate buffered saline (PBS) at pH 7.0 and 25° C. The conjugation reaction was started by the addition of 10 µM PCL-containing protein and 100 µM ABA/AAP conjugate. Complete formation of the protein conjugate was verified by electrospray ionization-mass spectrometry (ESI-MS) or matrix-assisted laser desorption/ionization (MALDI). Coupling of ABA/AAP DNA conjugates was analyzed by gel shift assay using a NuPAGE 4-12% Bis-Tris Gel (Invitrogen, Carlsbad, Calif.). After quantitative coupling, the protein conjugate was dialyzed into 10 mM sodium phosphate buffer (pH 7.5) and concentrated to 100 µM using an Amicon Ultra-4 Centrifugal Filter Unit with 10 kDa cutoff (Millipore Corporation, Bedford, Mass.). A freshly prepared solution of 200 mM NaCNBH$_3$ (dissolved in 10 mM phosphate buffer, pH 7.5) was then added to a final concentration of 20 mM. After allowing the reduction reaction to proceed for 2-4 hours at 25° C., the reaction was quenched by the addition of six volumes of 10 mM sodium phosphate buffer (pH 7.5). Using a NAP-5 column or PD10 column (GE Healthcare, Piscataway, N.J.), the reduced protein conjugate was finally buffer exchanged into the desired buffer. Non-limiting examples of coupling of such 2-aminobenzaldehyde (ABA) conjugates and 2-aminoacetophenone (AAP) conjugates to various proteins is given below.

Example 24

Coupling of Biotin Reagent

To demonstrate that biotin can be coupled to proteins having one or more PCL moieties incorporated therein, mEGF-Tyr10PCL (see Example 12) was conjugated with biotin using an ABA-biotin reagent (X3626-140, Example 40). Coupling of biotin was carried out as follows, 500 µM the ABA-biotin was added to 10 µM mEGF-Tyr10PCL in phosphate buffered saline (PBS, pH 7.0) and 0.5% (v/v) DMSO and reacted at 25° C. for 16 hours. Complete formation of the biotin conjugate was verified by ESI-MS (FIG. 47A; expected mass of uncoupled protein=7296; expected mass of coupled protein=7902).

After quantitative coupling, a freshly prepared solution of 200 mM NaCNBH$_3$ (dissolved in PBS, pH 7.0) was added to a final concentration of 20 mM. After allowing the reduction reaction to proceed for 3 hours at 25° C., the reaction was quenched by the addition of six volumes of PBS (pH 7.0). Excessive NaCNBH$_3$ was removed by dialysis against PBS (pH 7.0) at 4° C. using a Slide-A-Lyzer dialysis cassette (3,500 Da molecular weight cutoff, Pierce). The reduced biotin conjugate was concentrated using an Amicon Ultra-4 Centrifugal Filter Unit with 3.5 kDa cutoff (Millipore Corporation). After electrophoresis through a NuPAGE 4-12% Bis-Tris gel (Invitrogen), the biotinylated protein was transferred on a polyvinylidene difluoride (PVDF) membrane using an iBlot Gel Transfer System (Invitrogen). The biotin conjugate was then detected with a horseradish peroxidase (HRP) conjugated goat anti-biotin antibody (1:100 dilution, Cell Signaling Technologies) and visualized using a Hyperfilm ECL (GE Healthcare) (FIG. 47B). Uncoupled mEGF-Tyr10PCL and fluorescein-conjugated mEGF-Tyr10PCL served as negative controls. Lane 1, 20 pmol mEGF-Tyr10PCL-ABA-biotin conjugate; lane 2, 8 pmol mEGF-Tyr10PCL-ABA-biotin conjugate; lane 3, 2 nmol mEGF-Y10PCL; lane 4, 20 pmol mEGF-Tyr10PCL-ABA-fluorescein conjugate.

Example 25

Coupling Fluorescent Molecules

To demonstrate that a fluorescent molecule can be coupled to proteins having one or more PCL moieties incorporated therein, mEGF-Tyr10PCL (see Example 12) was conjugated with fluorescein using an ABA-fluorescein reagent (see 3793-050, Example 42). Coupling of fluorescein was carried out as follows, 1 mM of the ABA-fluorescein was added to 10 µM mEGF-Tyr10PCL in phosphate buffered saline (PBS, pH 7.0) and 0.5% (v/v) DMSO and reacted at 25° C. for 16 hours. Formation of the fluorescein conjugate was verified by ESI-MS (FIG. 47C; expected mass of uncoupled protein=7296; expected mass of coupled protein=8062).

The fluorescein conjugate was reduced with 20 mM NaC-NBH$_3$ for 3 hours at 25° C. After quenching the reduction reaction with six volumes of PBS (pH 7.0), residual NaC-NBH$_3$ was removed by dialysis against PBS (pH 7.0) at 4° C. using a Slide-A-Lyzer dialysis cassette (3,500 Da molecular weight cutoff). The conjugate was then concentrated to 1 µM using an Amicon Ultra-4 Centrifugal Filter Unit with 3.5 kDa cutoff. Absorbance spectra in the range of 350-700 nm of 1 µM mEGF-Tyr10PCL-ABA-fluorescein and of 10 µM ABA-fluorescein were obtained using a SpectraMax Plus (Molecular Devices). Both gave an absorbance maximum at 500 nm.

Fluorescence spectra were then recorded on a SpectraMax GEMINI fluorometer (Molecular Devices). An emission spectrum for 1 µM mEGF-Tyr10PCL-ABA-fluorescein and of 10 µM ABA-fluorescein were obtained by maintaining the excitation wavelength at 490 nm, while scanning the emission wavelength from 510 nm to 750 nm using a step size of 2 nm. Both gave an emission maximum at 522 nm. In addition an excitation spectrum for 1 µM mEGF-Tyr10PCL-ABA-fluorescein and of 10 µM ABA-fluorescein were obtained by maintaining the emmission wavelength at 522 nm, while scanning the excitation wavelength from 300 nm to 510 nm using a step size of 2 nm.

Example 26

Coupling Polysaccharides

To demonstrate that polysaccharides can be coupled to proteins having one or more PCL moieties incorporated therein, mEGF-Tyr10PCL (see Example 12) was conjugated with a disaccharide using a ABA-disaccharide (3793-050; Example 42, MW 546.52). The coupling reaction was carried out by the addition of 1 mM ABA-disaccharide to 10 µM mEGF-Tyr10PCL mutant protein in PBS and 1% (v/v) DMSO at pH 7.0. The reaction was allowed to proceed at room temperature for 16 hours and analyzed by ESI-MS (FIG. 47D). The mass spectrum shows the major peak at the expected mass for the conjugated protein (7825 Da). The mass for the non-coupled protein is 7296 Da.

Example 27

Coupling of Immune Modulators: Mono-Nitrophenyl Hapten Conjugates

To demonstrate that immune modulators can be coupled to proteins having one or more PCL moieties incorporated therein, mTNF-Gln21PCL and mEGF-Tyr10PCL (see Examples 11 and 12) were conjugated with a mono-nitrophenyl hapten using an ABA-mono-nitrophenyl hapten reagent (3793-001, Example 38-8). Coupling of the mono-nitrophenyl hapten conjugate was carried out as described above. FIG. 48A is the ESI mas spectrum of of 3793-001 conjugated to mTNF-Gln21PCL (expected mass of uncoupled protein=19275; expected mass of coupled protein=19614), and FIG. 48B is the ESI mas spectrum of 3793-001 conjugated to mEGF-Tyr10PCL (expected mass of uncoupled protein=7296; expected mass of coupled protein=7635).

Example 28

Coupling of Immune Modulators: di-nitrophenyl Hapten Conjugates

To demonstrate that immune modulators can be coupled to proteins having one or more PCL moieties incorporated therein, mTNF-Gln21PCL and mEGF-Tyr10PCL (see Examples 11 and 12) were conjugated with a di-nitrophenyl hapten using the di-nitrophenyl hapten (TU3627-088, Example 38-7). Coupling of the di-nitrophenyl hapten conjugate was carried out as described above. FIG. 48C is the ESI mas spectrum of TU3627-088 conjugated to mTNF-Gln21PCL (expected mass of uncoupled protein=19275; expected mass of coupled protein=19688), and FIG. 48D is the ESI mas spectrum of TU3627-088 conjugated to mEGF-Tyr10PCL (expected mass of uncoupled protein=7296; expected mass of coupled protein=7709).

Example 29

Coupling of Immune Modulators: TLR7 Agonists

To demonstrate that immune modulators can be coupled to proteins having one or more PCL moieties incorporated therein, mEGF-Y10PCL (see Example 12) was conjugated with a TLR7 agonist using an ABATLR7 agonist reagent (see X3678-114; Example 38-3). The coupling reaction was carried out by the addition of 100 µM ABA-TLR7 agonist to 10 µM mEGF-Y10PCL mutant protein in 200 mM sodium acetate buffer and 1% (v/v) DMSO at pH 4.5. The reaction was allowed to proceed at room temperature for 16 hours and analyzed by ESI-MS (FIG. 49A). The mass spectrum shows the majore peak at the expected mass for the conjugated protein (8763 Da), with the mass of the uncoupled protein being 7296 Da.

Example 30

Coupling of Immune Modulators: PADRE Peptides

To demonstrate that immune modulators and that peptides can be coupled to proteins having one or more PCL moieties incorporated therein, mTNF-Gln21PCL and mEGF-Tyr10PCL (see Examples 11 and 12) were conjugated with PADRE peptides. Coupling of the PADRE peptides was carried out as described in the paragraph immediately following the subtitle "Site-Specific Modification of Pyrroline-Carboxy-Lysine (PCL) Containing Proteins with other diverse molecules". FIG. 50A is a MALDI-TOF mass spectrometric analysis of mTNF-Gln21PCL conjugated with PX2-PADRE (see 3465-143; Example 38-11) at pH 5.0, while FIG. 50B is a MALDI-TOF mass spectrometric analysis of mTNF-Q21PCL conjugated with PX2-PADRE at pH 7.5. The expected mass of uncoupled protein is 19275 Da and the expected mass of coupled protein is 20842 Da. FIG. 50C is an ESI mass spectrometric analysis of mTNF-Gln21PCL conjugated with BHA-exPADRE (see 3647-104; Example 38-10). Here the expected mass of uncoupled protein is 19275 Da and the expected mass of coupled protein is 21317 Da. In addition, FIG. 51 is an ESI mass spectrum showing the coupling of BHA-exPADRE to mEGF-Tyr10PCL (expected mass of uncoupled protein 7296 Da; expected mass of coupled protein 9338 Da).

Example 31

Coupling of Immune Modulators: Phospholipid

To demonstrate that immune modulators and phospholipids can be coupled proteins having one or more PCL moieties incorporated therein, mEGF-Tyr10PCL (see Example 12) was conjugated with a phospholipid (DOPE) using an ABA phospholipid reagent (TU3627-092; Example 43-1). Coupling of ABA-DOPE to mEGF-Tyr10PCL (MW=7296 Da) was carried out in 20 mM HEPES (pH 7.0) and 1% (v/v) DMSO at 25° C. for 16 hours. The conjugation reaction was initiated by the addition of 10 μM mEGF-Tyr10PCL and 100 μM ABA-DOPE. Formation of the protein conjugate was verified by electrospray ionization-mass spectrometry (ESI-MS) analysis of the conjugation of DOPE to mEGF-Y10PCL (FIG. 49B; expected mass of uncoupled protein=7296; expected mass of the conjugated protein=8227 Da).

Example 32

Coupling of Oligonucleotide to Protein: CpG Peptides

To demonstrate that oligonucleotides and CpG immune modulators can be coupled to proteins having one or more PCL moieties incorporated therein, mTNF-Gln21PCL and mEGF-Tyr10PCL (see Examples 11 and 12) were conjugated with CpG oligonucleotides using either CpG reagent BHA-BG1 (see 3647-057; Example 38-12) or CpG reagent BHA-BG2 (see 3597-167; Example 38-14). Coupling of the CpG oligonucleotide was carried out as described in the paragraph immediately following the subtitle "Site-Specific Modification of Pyrroline-Carboxy-Lysine (PCL) Containing Proteins with other diverse molecules". Coupling of BHA-BG1 (7.4 kDa) and BHA-BG2 (7.4 kDa) to mTNF-Gln21PCL (19.3 kDa) was confirmed by gel shift assay (FIG. 52A), and coupling of BHA-BG2 (7.4 kDa) to mEGF-Tyr10PCL (7.2 kDa) was also confirmed by gel shift assay (FIG. 52B).

Example 33

Synthesis of Reactive Pyrrolysine Analogues

Example 33-1

Synthesis of (S)-2-amino-6-(3-oxobutanamido)hexanoic acid hydrochloride (TU3000-016)

TU2982-126

TU3000-012

TU3000-016

(S)-methyl 6-amino-2-(2,2,2-trifluoroacetamido)hexanoate hydrochloride (TU2982-126) was prepared according to the procedure described in Bing Hao et al., ChemBio 2004, 11, 1317-24 & its supplemental material except that the removal of the Cbz group was preformed in the presence of HCl to afford the HCl salt.

To (S)-methyl 6-amino-2-(2,2,2-trifluoroacetamido)hexanoate hydrochloride (0.943 g, 3.22 mmol), N,N-diisopropyl ethylamine (DIEA, 1.39 mL) and dichloromethane (DCM, 10 mL) in a 40 mL glass vial was added diketene (0.37 mL) under $N_2$ atmosphere, and the reaction was stirred at ambient temperature for 16 hours. The reaction mixture was diluted with ethyl acetate (EtOA), washed successively with $H_2O$, 1 N HCl, $H_2O$, sat aq $Na_2CO_3$, and sat aq NaCl, dried over $Na_2SO_4$, filtered and concentrated under reduced pressure. The residue was purified by a $SiO_2$ flash chromatography, affording (S)-methyl-6-(3-oxobutanamido)-2-(2,2,2-trifluoroacetamido)hexanoate (TU3000-012) as a yellow oil. MS (ESI$^+$): calcd. 341.12. found 341.10 (MH$^+$). H-NMR (400 MHz, CDCl$_3$):1.33 (2H, m), 1.55 (2H, m), 1.89 (2H, m), 2.259(3H, s), 3.31 (2H, m), 3.410 (2H, s), 3.783 (3H, s), 4.543 (1H, dt, J=4.4, 8.0 Hz). 7.091 (1H, br.s), 7.279 (1H, br.d, J=7.6 Hz). F-NMR (376 MHz, CDCl$_3$): −75.609.

(S)-methyl_6-(3-oxobutanamido)-2-(2,2,2-trifluoroacetamido)hexanoate (0.736 g, 2.16 mmol) was treated with 1 N aq NaOH (6.5 mL) and 10 mL $H_2O$ at ambient temperature for 18 hours. LC-MS analysis was used to reveal the reaction was complete. The reaction mixture was concentrated under reduced pressure. The residue was treated with excess 1 N aq HCl, and concentrated to dryness under reduced pressure, affording (S)-2-amino-6-(3-oxobutanamido)hexanoic acid hydrochloride (TU3000-016). MS (ESI$^+$): calcd. 231.13. found 231.10 (MH$^+$).

Example 33-2

Synthesis of (S)-5-(4-acetylbenzamido)-1-carboxypentan-1-aminium chloride (TU3000-004)

TU2982-126

Example 33-3

Synthesis of ((S)-5-(5-acetylthiophene-2-carboxamido)-1-carboxypentan-1-aminium chloride (TU3000-006), (S)-5-(3-acetylbenzamido)-1-carboxypentan-1-aminium chloride (TU3000-008), and (S)-5-(4-acetyl-1-methyl-1H-pyrrole-2-carboxamido)-1-carboxypentan-1-aminium chloride (TU3000-010)

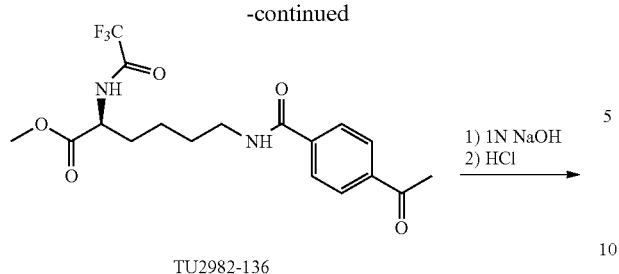

TU2982-136

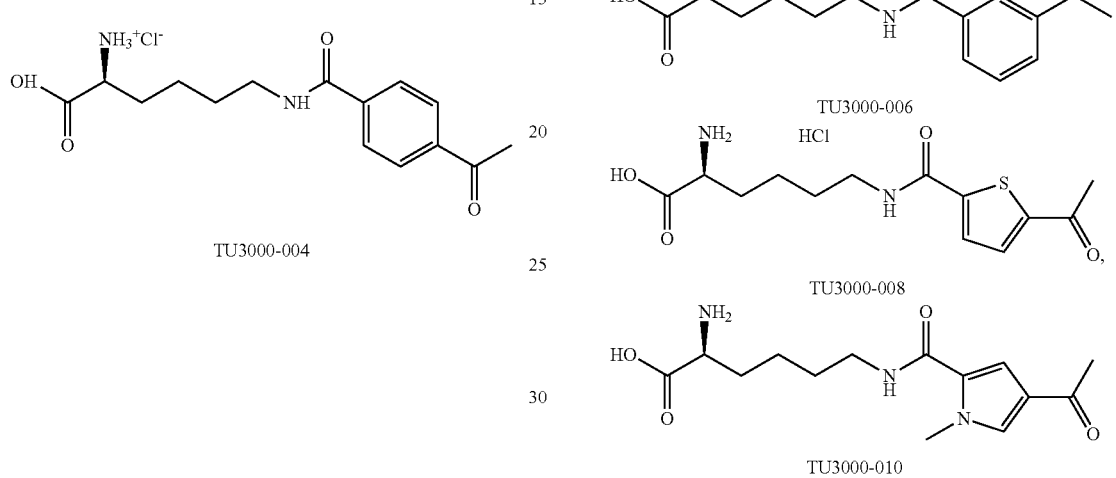

(S)-methyl 6-amino-2-(2,2,2-trifluoroacetamido)hexanoate hydrochloride (TU2982-126) (303 mg, 1.03 mmol), 4-acetylbenzoic acid (190 mg), HATU (418 mg), DIEA (523 µL) and DMF (8 mL) were combined and stirred at ambient temperature for 18 hours. The reaction mixture was diluted with EtOA, washed successively with H₂O, 1 N HCl, H₂O, sat aq Na₂CO₃, and sat aq NaCl, dried over Na₂SO₄, filtered and concentrated under reduced pressure. The residue was purified by a SiO₂ flash chromatography, affording (S)-methyl-6-amino-2-(2,2,2-trifluoroacetamido)hexanoate hydrochloride (TU2982-136). MS (ESI$^+$): calcd. 403.14. found 403.20 (MH$^+$). H-NMR (400 MHz, CDCl₃):1.44 (2H, m), 1.68 (2H, m), 1.90 (1H, m), 2.00 (1H,) 2.64 (3H, s), 3.31 (2H, m), 3.50 (2H, m), 3.80 (3H, s), 4.60 (1H, dt, J=4.8, 7.6 Hz). 6.35 (1H, br.s), 7.21 (2H, br.d, J=7.64 Hz), 7.86 (21H, d, J=8.4 Hz), 8.01 (2H, d, J=8.8 Hz). F-NMR (376 MHz, CDCl₃): −75.625.

(S)-methyl 6-(4-acetylbenzamido)-2-(2,2,2-trifluoroacetamido)hexanoate (TU2982-136) (0.473 g) was treated 1 N aq NaOH (2.36 mL) in 10 mL MeOH at ambient temperature for 18 hours. LC-MS analysis was used to reveal the complete hydrolysis of the methyl ester, while maintaining the trifluoroamide moiety intact. The reaction was heated at 60° C. for 5 hours, at which time the amide hydrolysis was almost complete, as indicated by LC-MS analysis. The reaction mixture was cooled and concentrated under reduced pressure. The residue was treated with excess 1 N aq HCl, and concentrated to dryness under reduced pressure, affording ((S)-5-(4-acetylbenzamido)-1-carboxypentan-1-aminium chloride (TU3000-004) as a slightly yellow solid. MS (ESI$^+$): calcd. 293.14. found 293.20 (MH$^+$).

(S)-5-(5-acetylthiophene-2-carboxamido)-1-carboxypentan-1-aminium chloride (TU3000-006), (S)-5-(3-acetylbenzamido)-1-carboxypentan-1-aminium chloride (TU3000-008), and (S)-5-(4-acetyl-1-methyl-1H-pyrrole-2-carboxamido)-1-carboxypentan-1-aminium chloride (TU3000-010) were prepared in the same way as in TU3000-004 but using the corresponding acids instead of 4-acetylbenzoic acid. The acid used was 4-acetyl-1-methyl-1H-pyrrole-2-carboxylic acid, 5-acetylthiophene-2-carboxylic acid and 3-acetylbenzoic acid for TU3000-006, TU3000-008, and TU3000-010, respectively. TU3000-006: MS (ESI+): m/z 293.20 (MH+); TU3000-008: MS (ESI+): m/z 299.10 (MH+); and TU3000-010: MS (ESI+): m/z 296.20 (MH+).

Example 33-4

Synthesis of (S)-2-Amino-6-(3-oxocyclobutanecarboxamido)hexanoic acid (TU3205-030)

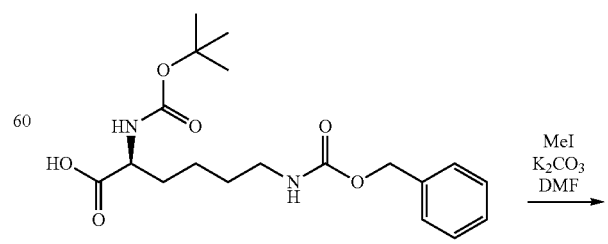

1

-continued

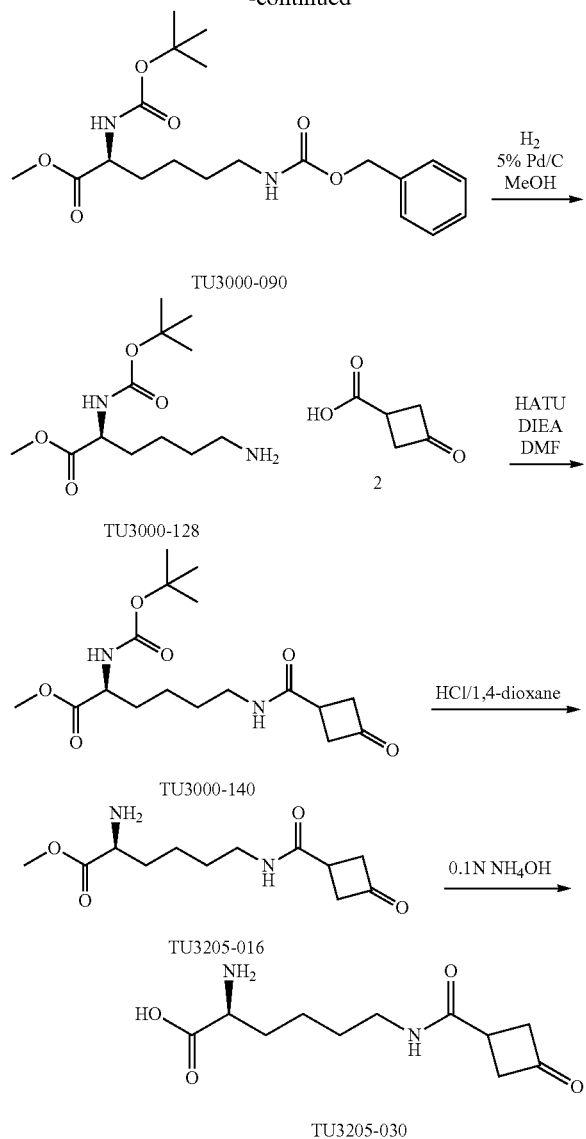

Iodomethane (2.0 mL), K₂CO₃ (5.60 g), (S)-6-(benzyloxycarbonylamino)-2-(tert-butoxycarbonylamino)hexanoic acid (1) (NovaBiochem, A29340), and anhydrous DMF (20 mL) were combined and stirred at ambient temperature for 2 hours. The reaction mixture was subjected to an aqueous work-up, affording (S)-methyl 6-(benzyloxycarbonylamino)-2-(tert-butoxycarbonylamino)hexanoate (TU3000-090) as clear oil. MS (ESI+): calcd. 417.20. found 417.20 (MNa+), calcd. 295.16. found 295.209((M-Boc)H+). H-NMR (400 MHz, CDCl₃):1.372 (2H, m), 1.425 (9H, s), 1.515 (2H, m), 1.623 (1H, m), 1.785 (1H, br.s), 3.175(2H, m), 3.723 (3H, s), 4.284 (1H, m), 4.848 (1H, br.s), 5.084 (3H, overlapping br.s and s), 7.344 (5H, m). C-NMR (100 MHz, CDCl3): 22.340, 28.268, 29.307, 32.313, 40.569, 52.272, 53.099, 66.597, 79.897, 128.061, 128.100, 128.471, 136.519, 155.435, 156.426, 173.230.

(S)-methyl 6-(benzyloxycarbonylamino)-2-(tert-butoxycarbonylamino)hexanoate (8.60 g) was hydrogenated in 150 mL MeOH over 5% palladium on activated carbon (1.08 g) under 1 atm hydrogen at ambient temperature for 3 hours. The spent catalyst was removed by vacuum filtration through a celite pad which was washed with MeOH. The combined filtrate and wash were concentrated under reduced pressure, affording (S)-methyl 6-amino-2-(tert-butoxycarbonylamino)hexanoate (TU3000-128) as clear viscous oil. MS (ESI+): calcd. 261.17. found 261.20 (MH+). H-NMR (600 MHz, CDCl3):1.328 (2H, m), 1.375 (9H, s), 1.390 (2H, m), 1.55 (1H, m), 1.74(1H, m), 2.623(2H, d, J=6.9 Hz), 3.671 (3H, s), 4.237 (1H, m), 5.007 (1H, m).

A 1M stock solution of (S)-methyl 6-amino-2-(tert-butoxycarbonylamino)hexanoate in 20 mL DMF was prepared, and used. A 2 mL aliquot of the (S)-methyl 6-amino-2-(tert-butoxycarbonylamino)hexanoate stock solution, 3-oxocyclobutanecarboxylic acid (2) (Parkway *BX-102, 283 mg), HATU (800 mg), DIEA (1.0 mL) and 8 mL DMF were combined in a 40 mL glass vial, and stirred at ambient temperature overnight. The LC-MS analysis revealed a complete reaction. The reaction mixture was diluted with EtOAc, washed successively with water, sat aq. NaCl, dried over MgSO₄, filtered and concentrated under reduced pressure. The crude material was purified by silica gel flash chromatography (hexanes/EtOAc), affording (S)-methyl 2-(tert-butoxycarbonylamino)-6-(3-oxocyclobutanecarboxamido)hexanoate (TU3000-140) as a clear viscous oil. MS (ESI+): calcd. 379.18. found 379.20 (MNa+), calcd. 257.15. found 257.20 ((M-Boc)H+). H-NMR (400 MHz, DMSO-d6):1.245 (4H, m), 1.371 (9H, s), 1.579 (2H, m), 3.065 (3H, m), 3.135 (4H, m), 3.608 (3H, s), 3.895 (1H, m), 7.209 (1 h, d, J=8.0 Hz), 8.123 (1H, t, J=5.4 Hz). C-NMR (100 MHz, DMSO-d6): 22.850, 27.185, 28.111, 28.551, 30.209, 38.276, 50.859, 51.639, 53.412, 53.529, 78.137, 155.507, 172.992, 173.167, 205.576.

(S)-methyl 2-(tert-butoxycarbonylamino)-6-(3-oxocyclobutanecarboxamido)hexanoate (0.501 g) was treated with 20 mL 4M HCl in 1,4-dioxane at ambient temperature for 20 minutes and the solvent was removed under reduced pressure. The resulting viscous oil was taken up in 10 mL CH₃CN, and seeded with small amount of crystals of the title compound prepared in a smaller scale. The resulting crystals were collected by vacuum filtration, washed with CH₃CN, and dried under reduced pressure, affording (S)-methyl 2-amino-6-(3-oxocyclobutanecarboxamido)hexanoate (TU3205-016) as color less solid. MS (ESI+): calcd. 257.15. found 257.20 (MH+). H-NMR (400 MHz, DMSO-d6):1.267 (1H, m), 1.419 (3H, m), 1.753 (2H, m), 3.114 (7H, m), 3.752 (3H, m), 4.023 (1H, t, J=6.4 Hz), 8.169 (1H, t, J=5.5 Hz), 8.365 (3H, br.s). C-NMR (100 MHz, DMSO-d6): 21.499, 27.160, 28.390, 29.548, 38.067, 50.858, 51.721, 52.727, 169.949, 173.034, 205.586.

(S)-methyl 2-amino-6-(3-oxocyclobutanecarboxamido)hexanoate (0.297 g) and 18 mL H₂O were put in a 40 mL glass vial. To the resulting clear solution was added 2.2 mL 1N NH4OH, and the reaction was shaken at ambient temperature for 22 hours, at which time the LCMS analysis revealed a complete reaction. The reaction mixture was frozen and lyophilized, affording (S)-2-amino-6-(3-oxocyclobutanecarboxamido)hexanoic acid (TU3205-030) as colorless crystals. MS (ESI+): m/z 243.20 (MH+).

Example 34

Synthesis of Reactive Pyrrolysine Intermediates

Example 34-1

Synthesis of Lithium 2-(4-acetyl-3-aminophenoxy)acetate (TU3205-042)

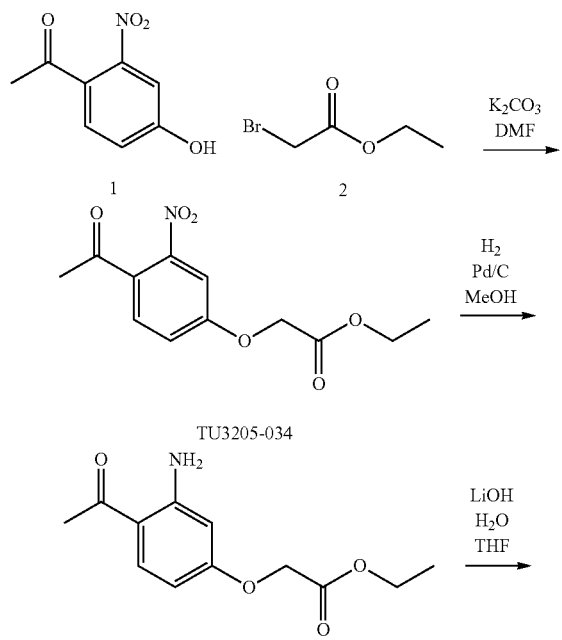

1-(4-Hydroxy-2-nitrophenyl)ethanone (Carbocore, 181 mg, 1.00 mmol), ethyl 2-bromoacetate (183 mg, 1.10 mmol), potassium carbonate (138 mg. 1.00 mmol) and DMF (5 mL) were combined in a 20 mL glass vial and stirred at 60° C. for 2 hours, at which point LC-MS analysis showed a clean complete reaction. The reaction mixture was diluted with water and extracted with EtOAc, washed with sat. NaCl aq. The reaction was repeated using 1-(4-Hydroxy-2-nitrophenyl)ethanone (0.802 g, 4.43 mmol), ethyl 2-bromoacetate (0.813 g, 4.87 mmol), potassium carbonate (0.612 g. 4.43 mmol) and DMF (25 mL), and worked up in the same way. The combined EtOAc extracts were dried over anhydrous $MgSO_4$, filtered and concentrated under reduced pressure, affording ethyl 2-(4-acetyl-3-nitrophenoxy)acetate (TU3205-034) as a dark yellow oil MS (ESI$^+$): calcd. 268.07. found 268.10 (MH$^+$). H-NMR (400 MHz, CDCl$_3$): 1.317 (3H, t, J=7.2 Hz), 2.512 (3H, s), 4.294 (2H, q, J=7.2 Hz), 4.722 (2H, s), 7.192 (1H, dd, J=8.4 Hz, 2.4 Hz), 7.455 (1H, d, J=8.4 Hz), 7.462 (1H, d, J=2.8 Hz). C-NMR (100 MHz, CDCl$_3$): 14.133, 29.695, 61.922, 65.499, 110.105, 119.735, 129.461, 130.154, 147.793, 159.356, 167.474, 198.352.

Ethyl 2-(4-acetyl-3-nitrophenoxy)acetate (TU3205-034) (111 mg) in MeOH (5 mL) was hydrogenated using 10% palladium on charcoal (11 mg) under atmospheric pressure of $H_2$ at ambient temperature. After 30 minutes LC-MS analysis revealed a clean complete reaction. The reaction was repeated using TU3205-034 (1.45 g), 10% palladium on charcoal (140 mg), and MeOH (80 mL). The two reaction mixtures were combined, and the spent catalyst was removed by filtration through a celite pad. The filtrate was concentrated under reduced pressure, affording ethyl 2-(4-acetyl-3-aminophenoxy)acetate (TU3205-036) as a dark yellow oil. MS (ESI$^+$): calcd. 238.10. found 238.10 (MH$^+$). H-NMR (400 MHz, CDCl$_3$): 1.295 (3H, t, J=7.0 Hz), 2.507 (3H, s), 4.269 (2H, q, J=7.2 Hz), 4.603 (2H, s), 6.047 (1H, d, J=2.8 Hz), 6.236 (1H, dd, J=8.8 Hz, 2.8 Hz), 6.396 (2H, br.s), 7.647 (1H, d, J=9.2 Hz). C-NMR (100 MHz, CDCl$_3$): 14.135, 27.658, 61.532, 64.939, 100.237, 104.030, 113.586, 134.286, 152.468, 162.294, 168.310, 199.055.

Ethyl 2-(4-acetyl-3-aminophenoxy)acetate (TU3205-036) (1.02 g) was dissolved in THF (17 mL) and treated with aqueous LiOH (1 M, 4.3 mL) at ambient temperature for 1 hour. LC-MS analysis showed a clean complete reaction. The reaction mixture was concentrated under reduced pressure, affording lithium 2-(4-acetyl-3-aminophenoxy)acetate (TU3205-042) as a yellowish solid. MS (ESI$^+$): calcd. for free acid 210.10. found 210.10 (MH$^+$).

Example 34-2

Synthesis of Lithium 2-(3-amino-4-formylphenoxy)acetate (TU3627-018)

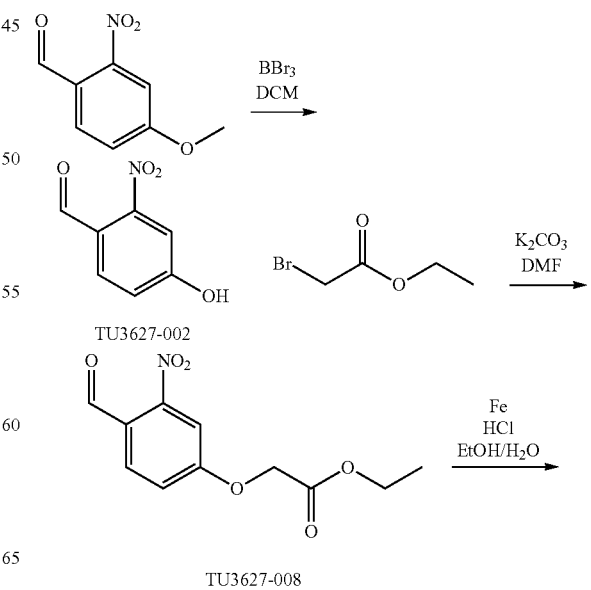

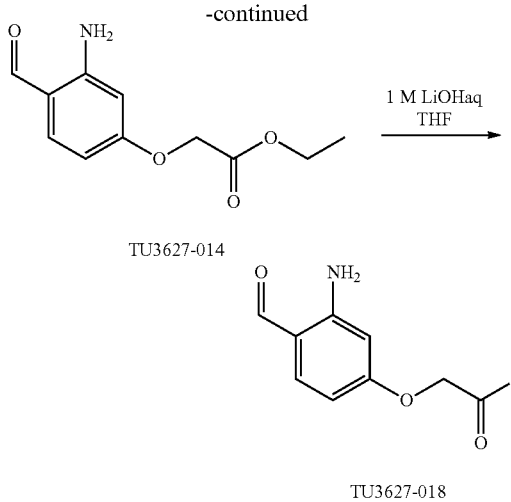

To 4-methoxy-2-nitrobenzaldehyde (CarboCore, CO-0119, 5.5 g) and 200 mL DCM in a 500 mL round-bottom flask was added borontribromide (24 g) dropwise with cooling in an ice bath. The reaction was stirred at the same temperature for 30 minutes and then at ambient temperature for 3 hours. The reaction mixture was carefully poured into ice water and let stand at ambient temperature for 3 days. The aqueous mixture was extracted with EtOAc, washed with sat. aq. NaCl, dried over $Na_2SO_4$, filtered and concentrated under reduced pressure. The crude material was purified by a $SiO_2$ gel flash chromatography using a linear gradient of 20 to 60% EtOAc in hexanes (Rf. 0.32, 50% EtOAc in hexanes), affording TU3627-002 as orange crystals. MS (ESI+): calcd. 168.02. found 168.10 (MH+). H-NMR (400 MHz, DMSO-d6): δ 7.211 (1H, dd, J=2.4, 8.4 Hz), 7.362 (1H, d, J=2.4 Hz), 7.866 (1H, d, 8.8 Hz), 9.998 (1H, s), 11.466 (1H, s). C-NMR (100 MHz, DMSO-d6): δ 110.726, 119.683, 120.770, 132.616, 151.225, 162.650, 187.885.

TU3627-002 (1.87 g), ethyl bromoacetate (Aldrich, 1.5 mL), potassium carbonate (2.32 g) and DMF were combined and stirred at ambient temperature for 18 hours. The reaction mixture was partitioned between EtOAc and water. The organic layer was separated, washed with sat aq. NaCl, dried over $MgSO_4$, filtered and concentrated under reduced pressure. The crude material was purified by a $SiO_2$ gel flash chromatography using a linear gradient of 5 to 35% EtOAc in hexanes (Rf. 0.32, 35% EtOAc in hexanes), affording TU3627-008 as dark yellow oil. MS (ESI+): calcd. 254.1. found 254.1 (MH+). H-NMR (400 MHz, CDCl3): δ 1.304 (3H, t, J=7.0 Hz), 4.285 (2H, q, J=7.2 Hz), 4.767 (2H, s), 7.233 (1H, dd, 2.0, 8.4 Hz), 7.522 (1H, d, J=2.4 Hz), 7.967 (1H, 8.4 Hz), 10.286 (1H, s). C-NMR (100 MHz, CDCl3): δ 14.082, 61.971, 65.482, 69.302, 110.427, 119.520, 124.321, 131.525, 151.286, 161.66, 167.172, 186.841.

TU3627-008 was reduced by the method described by Merlic (C. A. Merlic et al., *J. Org. Chem.*, 1995, 60, 3365-69). Specifically, TU3627-008 (1.717 g), iron powder (3.79 g), EtOH (45 mL), $H_2O$ (11 ml) and conc.HCl (180 µL) were combined and heated at reflux for 2 hours. The reaction mixture was filtered, and the filtrate was concentrated. The residue was purified by silica gel flash chromatography using a linear gradient of 5 to 60% solvent B in solvent A (solvent A: 5% $NEt_3$ in hexanes; solvent B: 5% $NEt_3$ in EtOAc) (Rf. 0.34, 35% EtOAc in hexanes), affording TU3627-014 as light yellow crystals. MS (ESI+): calcd. 224.10. found 224.10 (MH+). H-NMR (400 MHz, DMSO-d6): δ 1.216 (3 h, t, J=7.2 Hz), 4.173 (2H, q, 7.2 Hz), 4.777 (2H, s), 6.168 (1H, d, J=2.4 Hz), 6.248 (1H, dd, J=2.4, 8.8 Hz), 7.183 (2H, br.s), 7.441 (1H, d, J=8.4 hz), 9.646 (1H, s). C-NMR (100 MHz, DMSO-d6): δ 13.976, 60.711, 64.354, 98.521, 103.988, 113.256, 137.699, 152.665, 162.849, 168.176, 191.670.

TU3627-014 (0.608 g) in 5 mL THF was treated with a 2.72 mL aliquot of 1M aq. LiOH at ambient temperature. After 20 minutes the LC-MS analysis revealed a complete reaction. The reaction mixture was concentrated under reduced pressure to dryness, affording lithium 2-(3-amino-4-formylphenoxy)acetate (TU3627-018) as a yellow solid. MS (ESI+): m/z 196.1 (MH+). H-NMR (400 MHz, DMSO-d6): 4.132 (2H, s), 6.110 (1H, d, J=2.0 Hz), 6.145 (1H, dd, J=2.0, 8.8 Hz), 7.155 (2H, br.s), 7.33 (1H, d, J=8.8 hz), 9.576 (1H, s). C-NMR (100 MHz, DMSO-d6): 67.675, 98.354, 105.031, 112.386, 137.042, 152.914, 164.589, 169.349, 191.056.

Example 34-3

Synthesis of Lithium 4-(3-acetyl-4-aminophenoxy)butanoate (TU3627-064)

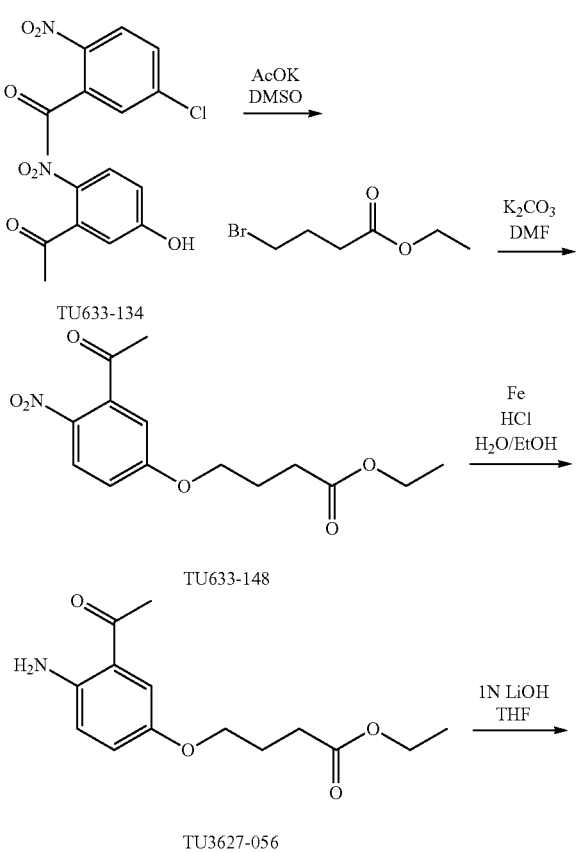

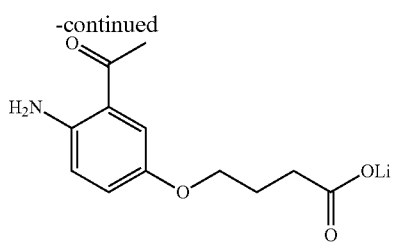

TU3627-064

A mixture of 4'-Chloro-2'-nitroacetophenone (Bionet cat #3W0333, 1.00 g), potassium acetate (4.91 g) and DMSO was heated at 170° C. for 20 minutes under microwave irradiation. The reaction mixture was partitioned between EtOAc and water. The organic layer was separated, washed with sat. aq. NaCl, dried over Na2SO4, filtered and concentrated under reduced pressure. Another reaction was performed in the same way, and the crude products from the two reactions were combined for purification by a silica gel flash chromatography (EtOAc). The title compound was obtained as orange solid. MS (ESI+): calcd. 182.15. found 182.10 (MH+). H-NMR (400 MHz, DMSO-d6): δ 2.474 (3H, s), 6.837 (1H, d, J=2.4 Hz), 6.973 (1H, dd, J=2.4, 8.8 Hz), 8.078 (1H, d, J=8.8 Hz), 11.307 (1H, s). C-NMR (100 MHz, DMSO-d6): δ 30.155, 113.264, 116.446, 127.386, 136.211, 140.986, 163.417, 200.099.

A mixture of 4'-Hydoxy-2'-nitroacetophenone (1.12 g), ethyl 4-bromobutanoate (1.33 g), potassium carbonate (0.94 g) and 4.mL DMF were stirred at 60° C. for 6.5 hours. The reaction mixture was partitioned between EtOAc and water. The organic layer was separated, washed with sat. aq. NaCl, dried over Na$_2$SO$_4$, filtered and concentrated under reduced pressure. The crude product was purified by a silica gel flash chromatography (hexanes/EtOAc), affording 1 the title compound as yellow crystals. MS (ESI+): calcd. 296.11. found 296.20 (MH+). H-NMR (400 MHz, CDCl3): δ 1.255 (3H, t, J=7.2 Hz), 2.141 (2H, quint, J=6.6 Hz), 2.506 (2H, t, J=7.2 Hz), 2.512 (3H, s), 4.116 (2H, t, J=6.0 Hz), 4.143 (2H, q, J=7.2 Hz), 6.757 (1H, d, J=2.8 Hz), 6.973 (1H, dd, J=2.8, 9.2 Hz), 8.125 (1H, d, J=8.8 Hz). C-NMR (100 MHz, CDCl3): δ 14.182, 24.136, 30.282, 30.360, 60.616, 67.907, 112.305, 115.150, 127.023, 138.036, 141.205, 163.580, 172.730, 200.054.

TU633-148 (1.48 g) was reduced by the method described by Merlic (C. A. Merlic et al., *J. Org. Chem.*, 1995, 60, 3365-69), as described herein. TU3627-056 was obtained as a light yellow oil after silica gel flash chromatography using a linear gradient of 5 to 60% solvent B in solvent A (solvent A: 5% NEt3 in hexanes; solvent B: 5% NEt3 in EtOAc). MS (ESI+): calcd. 266.13. found 266.20 (MH+). H-NMR (400 MHz, CDCl3): δ 1.258 (3H, t, J=7.2 Hz), 2.085 (2H, quint, J=6.8 Hz), 2.512 (2H, t, J=7.2 Hz), 2.556 (3H, s), 3.955 (2H, t, J=6.0 Hz), 4.146 (2H, q, J=7.2 Hz0, 6.066 (2H, br.s), 6.632 91H, d, J=8.8 Hz), 6.954 (1H, dd, J=2.8, 8.8 Hz), 7.186 (1H, d, J=2.8 Hz). C-NMR (400 MHz, CDCl3): δ 14.218, 24.688, 27.990, 30.729, 60.434, 67.790, 115.933, 118299, 118.621, 123.550, 144.593, 149.271, 173.213, 200.283.

TU3627-056 (0.50 g) in 3 mL THF was treated with a 1.9 mL aliquot of 1M aq. LiOH at ambient temperature for 18 hours. The LC-MS analysis revealed a clean complete reaction. The reaction mixture was concentrated under reduced pressure to dryness, affording lithium 4-(3-acetyl-4-aminophenoxy)butanoate (TU3627-064) as a yellow solid. MS (ESI+): m/z 238.10 (MH+). H-NMR (400 MHz, DMSO-d6): 1.823 (2H, quint, J=6.8 Hz), 2.008 (2H, t, J=6.8 Hz), 2.489 (3H, s), 3.871, (2H, t, J=6.8 Hz), 6.694 (1H, d, 9.2 Hz), 6.808 (2H, s), 6.962 (1H, dd, J=2.8, 8.8 Hz), 7.177 (1 h, d, J=2.8 Hz). C-NMR (100 MHz, DMSO-d6): 26.079, 28.014, 34.164, 68.394, 114.896, 116.388, 118.059, 123.861, 145.529, 147.995, 176.119, 199.756.

Example 34-4

Synthesis of Lithium 4-(3-amino-4-formylphenoxy)butanoate (TU3627-074)

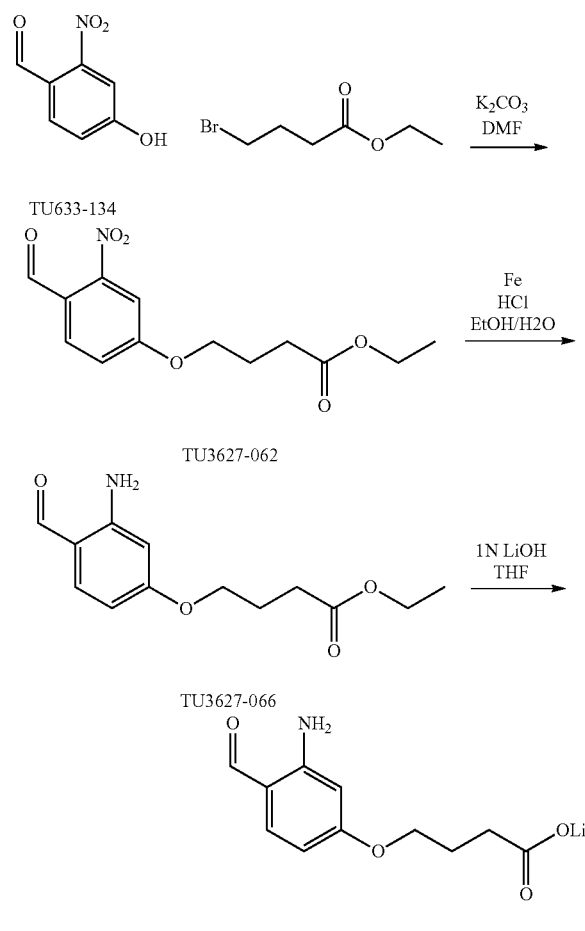

A mixture of 2-nitro-4-hydroxybenzaldehyde (2.85 g), ethyl 4-bromobutanoate (3.66 g), potassium carbonate (2.84 g) and DMF (20 mL) were stirred at ambient temperature for 50 hours. The reaction mixture was partitioned between H$_2$O and EtOAc. The organic layer was separated and washed with sat NaHCO$_3$aq. The combined aqueous layers were extracted with EtOAc. The combined organic layers were washed with dilute citric acid, sat NaClaq, dried over MgSO$_4$, filtered and concentrated. The residue was purified by silica gel flash chromatography using a linear gradient of 20 to 40% EtOAc in hexanes (Rf: 0.35, 35% EtOAc in hexanes), affording the title compound as yellow oil. MS (ESI+): calcd. 282.09. found 282.10 (MH+). H-NMR (400 MHz, CDCl3): δ 1.261 (3H, t, J=7.2 Hz), 2.170 (2H, quint, J=6.8 Hz), 2.528 (2H, t, J=7.2 Hz), 4.153 (2H, d, J=7.2 Hz), 4.167 (2H, t, 6.4 Hz), 7.217 (1H, dd, J=2.4, 8.4 Hz), 7.498 (1 h, d, J=2.4 Hz), 7.964 (1H, d, J=8.8 Hz), 10.277 (1H, s). C-NMR (100 MHz, CDCl3): δ 14.190, 24.112, 27.712, 30.291, 32.443, 32.771, 60.648, 68.075, 110.024, 119.397, 123.405, 131.455, 151.572, 162.916, 172.710, 186.943.

TU3627-062 (3.89 g) was reduced by the method described by Merlic (C. A. Merlic et al., *J. Org. Chem.*, 1995, 60, 3365-69), as described herein. TU3627-066 was obtained as a yellow solid after silica gel flash chromatography using a linear gradient of 20 to 60% solvent B in solvent A (solvent A: 5% NEt3 in hexanes; solvent B: 5% NEt3 in EtOAc). Rf: 0.51, 50% EtOAc in hexanes). MS (ESI+): calcd. 252.12. found 252.20 (MH+). H-NMR (400 MHz, DMSO-d6): δ 1.177 (3H, t, J=7.2 Hz), 1.962 (2H, quint, J=6.8 hz), 2.441 (2H, t, J=7.2 Hz), 3.979 (2 h, t, J=6.4 Hz), 4.064 (2H, q, J=7.2 Hz), 6.206 (1H, s), 6.219 (1H, d, J=8.8 Hz), 7.411 (1H, d, J=8.8 Hz), 9.623 (1H, s). C-NMR (100 MHz, DMSO-d6): δ 14.041, 24.028, 30.002, 59.837, 66.459, 98.075, 104.394, 112.822, 137.558, 152.871, 163.809, 172.404, 191.535.

TU3627-066 (1.00 g) in 6 mL THF was treated with 3.98 mL of 1M aqueous LiOH at ambient temperature for 4 hours. Most solvent was removed under reduced pressure, and the resulting cloudy mixture was diluted with doubly deionized water, frozen and lyophilized, affording lithium 4-(3-amino-4-formylphenoxy)butanoate (TU3627-074) as a dull yellow solid. MS (ESI+): m/z 224.20 (MH+). H-NMR (400 MHz, DMSO-d6): 1.852 (2H, quint, J=6.8 Hz), 2.040 (2H, t, 6.8 Hz), 3.949 (2H, t, J=6.8 Hz), 6.191 (1H, dd, 2.4, 8.8 Hz), 6.239 (1H, d, J=2.4 Hz), 7.208 (2H, br.s), 7.367 (1H, d, J=8.8 Hz), 9.597 (1H, s). C-NMR (100 MHz, DMSO-d6): 25.624, 33.706, 67.799, 97.997, 104.677, 112.589, 137.427, 153.003, 164.195, 176.575, 191.394.

Example 34-5

Synthesis of Lithium 3-(3-acetyl-4-aminophenyl)propanoate (X3547-1)

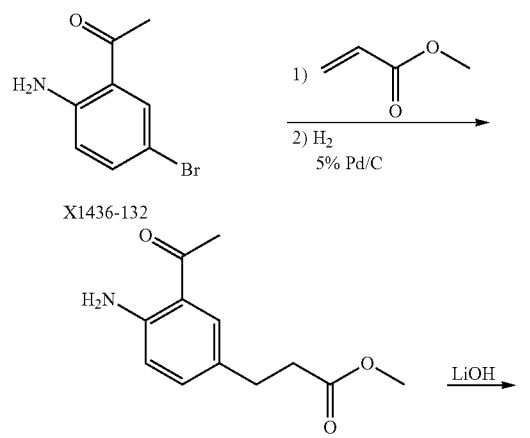

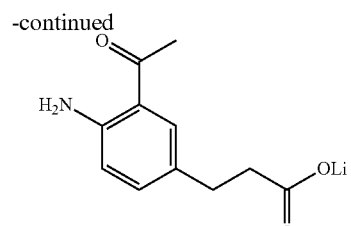

To a mixture of 1-(2-amino-5-bromophenyl)ethanone (642 mg), Pd(OAc)$_2$ (33.7 mg), and P(otolyl)$_3$ (137 mg) in anhydrous DMF(10 mL) in a pressure tube was added methyl crylate (351 μL) and TEA (1.4 mL). The mixture was flushed with N$_2$ for 3 minutes and then sealed and heated at 110° C. for 4 hours. The reaction mixture was cooled to ambient temperature and then partitioned between ethyl acetate and water. The aqueous layer was extracted once with ethyl acetate, and the combined organic layers were washed with brine, dried (Na$_2$SO$_4$), filtered, remove solvent in vacuo. The crude residue was purified by a silica gel flash chromatography (EtOAc/hexanes), affording the product. $^1$H NMR (400 MHz, MeOD): δ 7.96 (d, J=2.0 Hz, 1H), 7.63 (d, J=16.0 Hz, 1H), 6.67 (dd, J=8.8 Hz, J'=2.0 Hz, 1H), 6.77 (d, J=8.8 Hz, 1H), 6.29 (d, J=16.0 Hz, 1H), 3.76 (s, 3H), 2.59 (s, 3H); MS-ESI+220.24 (MH$^+$).

(E)-Methyl 3-(3-acetyl-4-aminophenyl)acrylate (219 mg) was reduced by 5% Pd/C (21.9 mg) in MeOH with hydrogen balloon at room temperature, affording the product (quantitative) after filtration and concentration. The product was used for the next step without further purification. $^1$H NMR (400 MHz, MeOD): δ 7.59 (d, J=2.0 Hz, 1H), 7.13 (dd, J=8.4 Hz, J'=2.0 Hz, 1H), 6.67 (d, J=8.4 Hz, 1H), 3.64 (s, 3H), 2.81 (dd, J=7.6 Hz, J'=7.6 Hz, 2H), 2.60 (dd, J=7.6 Hz, J'=7.6 Hz, 2H), 2.54 (s, 3H); MS-ESI+ 222.25 (MH$^+$).

Methyl 3-(3-acetyl-4-aminophenyl)propanoate (221 mg) and 4 M LiOH (0.275 mL) were added to 3 mL THF/water (v/v=3/1). The solvent was removed under reduced pressure after the reaction completed, affording lithium 3-(3-acetyl-4-aminophenyl)propanoate (X3547-1). $^1$H NMR (400 MHz, MeOD): δ 7.62 (d, J=2.0 Hz, 1H), 7.17 (dd, J=8.4 Hz, J'=2.0 Hz, 1H), 6.67 (d, J=8.4 Hz, 1H), 2.80 (dd, J=7.6 Hz, J'=9.0 Hz, 2H), 2.55 (s, 3H), 2.41 (dd, J=7.6 Hz, J'=9.0 Hz, 2H); MS-ESI+ 207.22 (MH$^+$).

Example 34-6

Synthesis of Lithium 3-(4-acetyl-3-aminophenyl)propanoate (X3547-8)

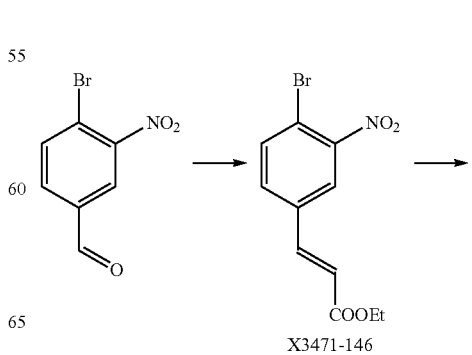

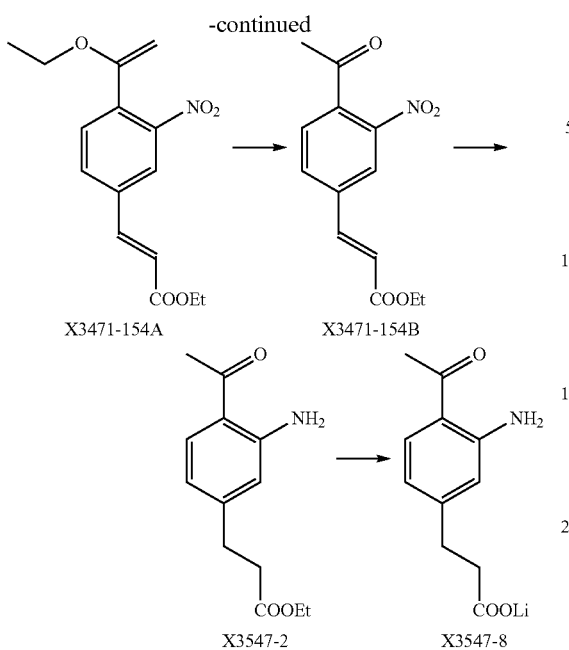

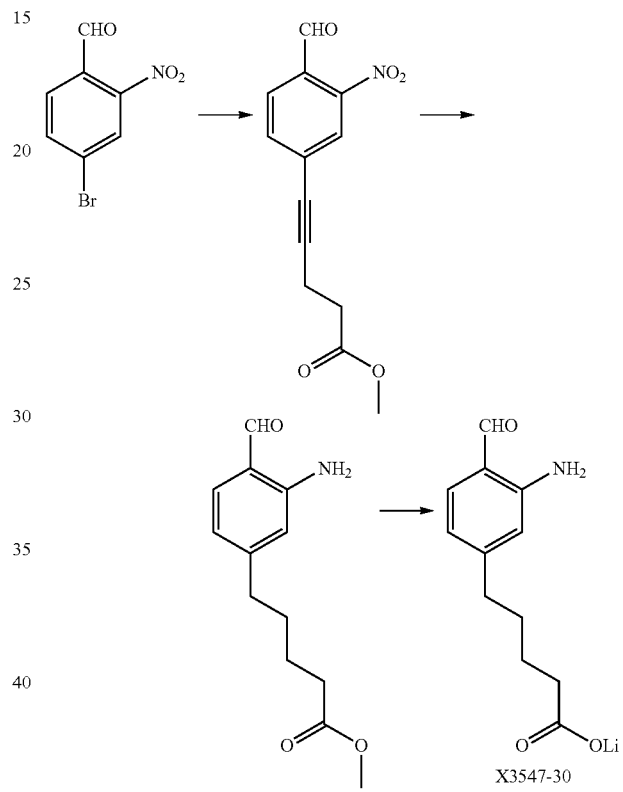

A solution of ethyl triphenylphosphoranylidine acetate (1.742 g) dissolved in CH₃CN (15 mL) was added with stirring to a CH₃CN solution (10 mL) containing 4-bromo-3-nitrobenzaldehyde (1.150 g). The reaction mixture was refluxed overnight. After the mixture was cooled, the solvent was removed under reduced pressure, affording a crude solid. The pure product X3471-146 was obtained as a white solid after silica gel flash column chromatography (hexanes/EtOAc, 9:1).

The product X3471-146 (632 mg) from the above step and PdCl$_2$(PPh$_3$)$_2$ (148 mg) were dissolved in DMF (5.0 mL) under N$_2$ in a Schlenk tube. Tributyl(1-ethoxyvinyl)stannane (711 μL) was added with stirring, The mixture was heated at 100° C. overnight. After the mixture was cooled, the solvent was removed under reduced pressure, diluted with DCM, washed with water and brine. After removal of DCM, the residue was purified by silica gel flash column chromatography (15%-25% EtOAc in hexanes) to give compound X3471-154.

Compound X3471-154A was treated with 20 mL 1N HCl at room temperature for 4 hours. The removal of the solvent afforded (E)-ethyl 3-(4-acetyl-3-nitrophenyl)acrylate X3471-154B. $^1$H NMR (400 MHz, MeOD): δ 8.31 (d, J=1.6 Hz, 1H), 8.04 (dd, J'=1.6 Hz, J"=8.0 Hz, 1H), 7.76 (d, J=16.0 Hz, 1H), 7.67 (d, J=8.0 Hz, 1H), 6.74 (d, J=16.0 Hz, 1H), 4.27 (q, J=7.2 Hz, 2H), 2.57 (s, 3H), 1.34 (t, J=7.2 Hz, 3H); ESI-MS (m/z) 264.07 (MH⁺).

Compound X3471-154B (263 mg) was reduced to ethyl 3-(4-acetyl-3-aminophenyl)propanoate X3547-2 with 5% Pd/C (26 mg) in 5.0 mL MeOH under hydrogen at 1 atm. ESI-MS (m/z) 236.30 (MH⁺).

Compound X3547-2 was treated with the mixture of 4 M LiOH (0.248 mL), THF (3.0 mL) and water (1.0 mL) at room temperature. After the reaction was complete, the reaction mixture was lyophilized, affording lithium 3-(4-acetyl-3-aminophenyl)propanoate (X3547-8). MS (ESI+): m/z 208.10 (MH⁺).

Example 34-7

Synthesis of Lithium 5-(3-amino-4-formylphenyl)pentanoate (X3547-30)

A mixture of 4-bromo-2-nitrobenzaldehyde (460 mg), Pd(PPh$_3$)$_2$Cl$_2$ (70 mg), and CuI (38 mg), methyl pent-4-ynoate (269 mg) in TEA(5.0 mL) was stirred at room temperature until the reaction was completed. The crude residue was purified by a silica gel flash chromatography (15% EtOAc in hexanes), affording methyl 5-(4-formyl-3-nitrophenyl)pent-4-ynoate. ESI-MS m/z 262.23 (MH⁺).

Methyl 5-(4-formyl-3-nitrophenyl)pent-4-ynoate (522 mg) was reduced by 5% Pd/C (53 mg) in MeOH with hydrogen balloon at room temperature. Filtration followed by concentration under reduced pressure afforded methyl 5-(3-amino-4-formylphenyl)pentanoate. MS-ESI m/z 236.28 (MH⁺).

Methyl 5-(3-amino-4-formylphenyl)pentanoate (447 mg) was treated with LiOH (88 mg) in 8.0 mL THF/water(v/v=3/1). Removal of the solvent after the reaction completed afforded lithium 5-(3-amino-4-formylphenyl)pentanoate (X3547-30). MS (ESI+): 222.10 (MH+). H NMR (400 MHz, MeOD): δ 9.72 (s, 1H), 7.37 (d, J=8.0 Hz, 1H), 6.57 (s, 1H), 6.55 (d, J=8.0 Hz, 1H), 2.56 (m, 2H), 2.19 (m, 2H), 1.64 (m, 4H).

Example 34-8

Synthesis of 3-(4-Acetyl-3-aminophenyl)-2-aminopropanoic acid (X3179-96)

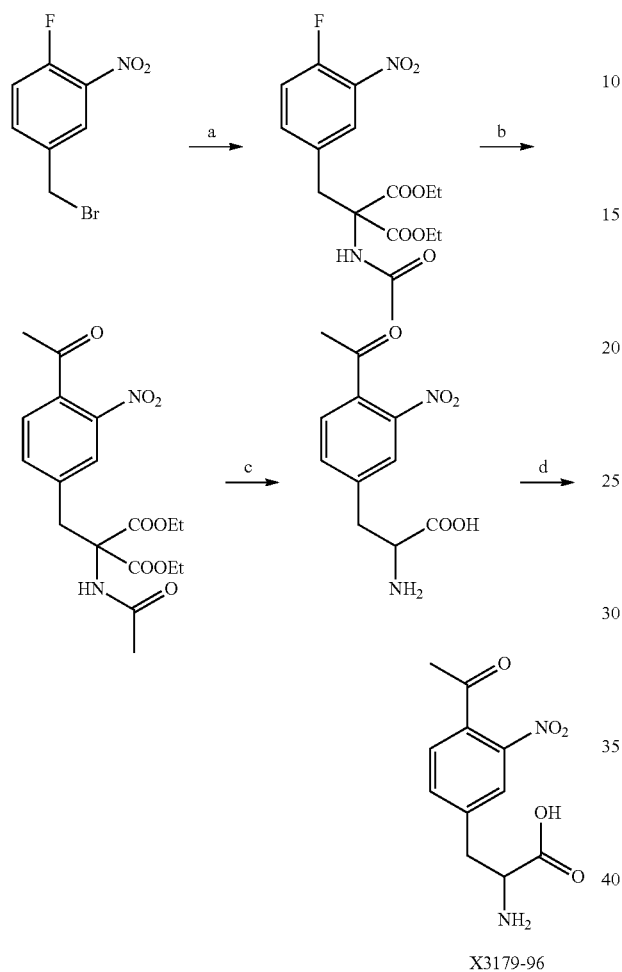

Sodium hydride (60% in mineral oil, 1.74 g) was washed with hexanes and suspended in DMF (12 ml). Diethyl acetamidomalonate (10.4 g) in DMF (30 ml) and 4-(bromomethyl)-1-fluoro-2-nitrobenzene (10.2 g) in DMF (10 ml) were added successively and the reaction mixture was stirred for 4 hours at room temperature, followed by removal of the solvent under reduced pressure. The residue was purified by silica gel flash chromatography (10-20% EtOAc in DCM), affording diethyl 2-acetamido-2-(4-fluoro-3-nitrobenzyl)malonate. $^1$H NMR (400 MHz, MeOD): δ 7.77 (d, J=8.4 Hz, 1H), 7.42 (s, 1H), 6.54 (d, J=8.4 Hz, 1H), 4.25 (q, J=7.2 Hz, 4H), 3.65 (s, 2H), 2.03 (s, 3H), 1.28 (t, J=7.2 Hz, 6H); $^{13}$C NMR: δ 172.95, 168.23, 157.33, 154.72, 138.68, 134.19, 128.45, 119.31, 68.64, 63.88, 38.04, 22.31, 14.38; ESI-MS (m/z) 371.33(MH$^+$).

To diethyl 2-acetamido-2-(4-fluoro-3-nitrobenzyl)malonate (7.41 g) and nitroethane (6.0 mL) in EtOAc was added DBU (9.0 mL) and the mixture was stirred at room temperature for 16 hours. The reaction mixture was concentrated and the residue was dissolved in methanol (35 mL). Aqueous H$_2$O$_2$ (30%, 10.2 mL) and 10% aqueous NaHCO$_3$ (10.2 mL) were added and the mixture was stirred at room temperature for 16 hours. The reaction mixture was concentrated under reduced pressure. The residue was dissolved in EtOAc, washed with 1 N HCl, brine, dried over MgSO4, filtered and concentrated under reduced pressure. The residue was purified by silica gel flash chromatography (10-20% EtOAc in DCM), affording diethyl 2-acetamido-2-(4-acetyl-3-nitrobenzyl)malonate. $^1$H NMR (400 MHz, MeOD): δ 7.73 (s, 1H), 7.55 (d, J=8.0 Hz, 1H), 7.47 (d, J=8.0 Hz, 1H), 4.25 (q, J=7.2 Hz, 4H), 3.72 (s, 2H), 2.53 (s, 3H), 2.03 (s, 3H), 1.28 (t, J=7.2 Hz, 6H); $^{13}$C NMR: δ 172.99, 168.22, 153.68, 147.48, 140.96, 137.31, 136.82, 128.99, 126.79, 68.62, 63.95, 54.01, 38.58, 22.32, 14.36; ESI-MS (m/z) 395.38(MH$^+$).

Diethyl 2-acetamido-2-(4-acetyl-3-nitrobenzyl)malonate (2.0 g) was dissolved in 10 mL 37% HCl, heated at 100° C. overnight, and cooled down. The resulting solid was collect by filtration, affording 3-(4-acetyl-3-nitrophenyl)-2-aminopropanoic acid. $^1$H NMR (400 MHz, D$_2$O): δ 8.01(s, 1H), 7.53 (d, J=7.6 Hz, 1H), 7.50 (d, J=7.6 Hz, 1H), 4.07 (m, 1H), 3.20-3.34 (m, 2H), 2.52 (s, 3H); $^{13}$C NMR: δ 201.39, 170.78, 174.89, 140.02, 137.84, 136.28, 129.59, 126.46, 54.46, 36.56, 30.01; ESI-MS (m/z) 253.22 (MH$^+$).

3-(4-acetyl-3-nitrophenyl)-2-aminopropanoic acid was reduced by 5% Pd on carbon in MeOH under 1 atm H$_2$. Filtration followed by concentration under reduced pressure afforded 3-(4-Acetyl-3-aminophenyl)-2-aminopropanoic acid (X3179-96). MS (ESI+): m/z 223.22 (MH$^+$). $^1$H NMR (400 MHz, MeOD): δ 7.78 (d, J=8.4 Hz, 1H), 6.66 (s, 1H), 6.54 (d, J=8.4 Hz, 1H), 4.25 (dd, J'=8.4 Hz, J"=5.2 Hz, 1H), 3.23 (dd, J'=14.4 Hz, J"=5.2 Hz, 1H), 3.02 (dd, J'=14.4 Hz, J"=8.4 Hz, 1H), 2.54 (s, 3H); $^{13}$C NMR: δ 202.14, 171.20, 152.93, 142.51, 134.40, 118.78, 118.23, 116.91, 54.63, 37.42, 27.90.

Example 34-9

Synthesis of 1-(2-Amino-5-bromophenyl)ethanone (X1436-132)

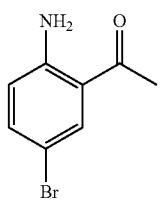

A flask charged with 1-(2-aminophenyl)ethanone (135 mg) and DCM (2.5 mL) was cooled to −10° C. and NBS (178 mg) was added in several portions over 30 min. The reaction mixture was diluted with 10 mL DCM, washed with sat. aqueous NaHCO$_3$, dried over Na$_2$SO$_4$, filtered and concentrated under reduced pressure, affording the title compound. MS (ESI+): m/z 215.06 (MH+). $^1$H NMR (400 MHz, CDCl$_3$): δ 7.79 (s, 1H), 7.31 (d, J=8.8 Hz, 1H), 6.54 (d, J=8.8 Hz, 1H), 6.30 (br, 2H), 2.55 (s, 3H).

Example 34-10

Synthesis of 1-(2-Amino-5-iodophenyl)ethanone (X1436-134)

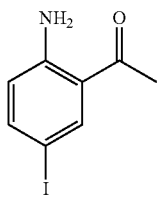

A flask charged with 1-(2-aminophenyl)ethanone (405 mg) and DCM (20 mL) was cooled in an ice/water bath and NIS (675 mg) was added in three portions. The reaction was stirred at 0° C. The reaction mixture was diluted with 30 mL DCM, washed with sat. aqueous $NaHCO_3$, dried over $Na_2SO_4$, filtered and concentrated under reduced pressure. The crude material was purified by preparative RP-HPLC, affording the title compound. MS (ESI+): m/z 262.06 (MH+). $^1$H NMR (400 MHz, $CDCl_3$): δ 7.94 (s, 1H), 7.44 (d, J=8.8 Hz, 1H), 6.43 (d, J=8.8 Hz, 1H), 6.32 (br, 2H), 2.53 (s, 3H).

Example 34-11

Synthesis of 2-Amino-4-bromobenzaldehyde (X3547-158)

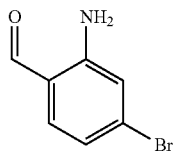

Iron powder (1.20 g), water (2.0 mL), and HCl (12 N, 40 μL) were added consecutively to a solution of 2-nitrobenzaldehyde (230 mg) in ethanol (8.0 mL). After stirring at 95° C. for 90 minutes, the reaction mixture was filtered hot. Following an ethanol wash, the filtrates were combined and the solvent was removed in vacuo. The crude material was purified by silica gel flash chromatography (40:55:5 hexandethyl acetate/triethylamine), affording 2-amino-4-bromobenzaldehyde as yellow crystals. MS (ESI+): m/z 199.96 (MH+). $^1$H NMR (400 MHz, MeOD): δ 9.77 (s, 1H), 7.40 (d, J=8.4 Hz, 1H), 6.95 (d, J=1.6 Hz, 1H), 6.78 (dd, J=8.4 Hz, J'=1.6 Hz, 1H).

Example 35

Synthesis of PCL and Pyrrolysine Biosyjthetic Precursors

Example 35-1

Synthesis of Ammonium DL-1-pyrroline-5-carboxylate (3793-007)

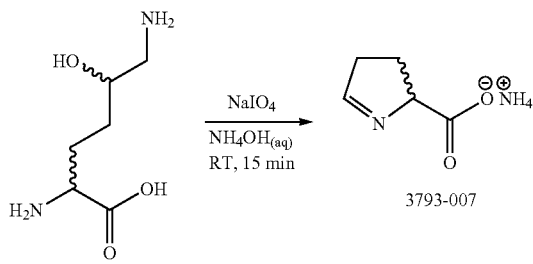

HCl salt of H-DL-δ-DL-hydroxyLys-OH (118 mg, 0.5 mmol) was applied to a cation exchange SPE cartridge, and the amino acid was eluted with ammonium hydroxide. $NaIO_4$ (107 mg) was added into the ammonium elute and the reaction mixture was stirred at room temperature for 30 minutes. The reaction mixture was lyophilized, and the crude product was acidified to pH 2.6 with HCl, and purified by cation exchange SPE. The first 10 mL $H_2O$ eluant was discarded and the following 30 ml $H_2O$ eluant was collected and neutralized immediately by 1 N $NH_4OH_{(aq)}$ (0.5 mL). After lyophilization, the desired product was obtained as light yellow powder. ESI-MS calculated for $C_5H_7NO_2$ $[MH]^+$: 114.1; observed: 114.1.

Example 35-2

Synthesis of H-L-Lys-N$^\epsilon$-(D-Orn)-OH (3793-031)

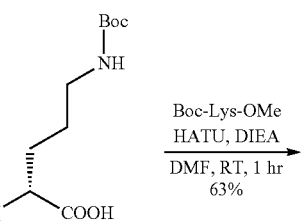

-continued

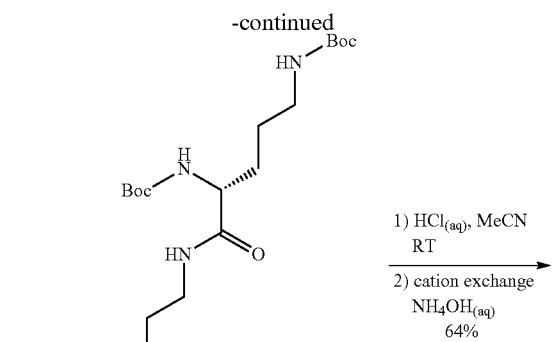

3793-026

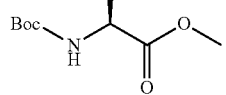

3793-031

Boc-D-Orn(Boc)-OH (1.097 g) was treated with HATU (1.255 g) and DIEA (1.53 mL) in DMF (5 mL) for 1 hour. A DMF solution (5 mL) of Boc-Lys-OMe (acetate salt, 1.057 g) and DIEA (627 µL) was then added to the reaction mixture, and the reaction was stirred at room temperature for 2 hours. The reaction mixture was partitioned between 10% NaCl$_{(aq)}$ (30 mL) and EtOAc (60 mL). The EtOAc layer was washed with 5% citric acid (30 mL), 10% NaHCO$_{3(aq)}$ (30 mL), and brine (30 mL). The EtOAc layer was dried over Na$_2$SO$_{4(s)}$, filtered and concentrated under reduced pressure. The residue was purified by silica gel flash column chromatography with a 80 g silica column and gradient elution of 0-15% MeOH/DCM, affording Boc-Lys(Boc-D-Orn(Boc))-OMe (3793-026) as a colorless oil. $^1$H NMR (400 MHz, CDCl$_3$): 6.54 (br s, 1H), 5.17 (br, 2H), 4.76 (br s, 1H), 4.24(quartet, J=6.7 Hz, 2H), 3.72 (s, 3H), 3.34-3.02 (m, 4H), 1.83-1.30 (m, 37H). $^{13}$C NMR (100 MHz, CDCl$_3$): 173.2, 172.3, 156.6, 155.8, 155.5, 79.8, 79.2, 53.3, 53.0, 52.3, 39.2, 38.8, 32.0, 30.4, 29.1, 28.4, 28.3, 26.4, 22.5. ESI-MS calculated for C$_{27}$H$_{50}$N$_4$O$_9$ [MH]$^+$: 575.4; observed: 575.4.

To a 65% acetonitrile aqueous solution (5 mL) of Boc-Lys(Boc-D-Orn(Boc))-OMe (214 mg) was added concentrated HCl (1 mL), and the reaction mixture was stirred vigorously for 2 hours. The reaction mixture was lyophilized, and purified by cation exchange chromatography using an SCX SPE cartridge with 1 N NH$_4$OH in 20% MeCN$_{(aq)}$. The methyl ester was hydrolyzed in the NH4OH eluate overnight. After lyophilization, H-L-Lys-N$^\epsilon$-(D-Orn)-OH (3793-031) was obtained as a white powder. $^1$H NMR (400 MHz, D$_2$O): 3.33-3.30 (m, 2H), 3.29-3.22 (m, 1H), 3.20-3.12 (m, 1H), 2.86(t, J=7.0 Hz, 2H), 1.65-1.48 (m, 8H), 1.36-1.25 (m, 2H). $^{13}$C NMR (100 MHz, D$_2$O): 181.5, 176.9, 55.5, 54.3, 39.4, 38.9, 33.2, 31.4, 28.1, 24.5, 22.1. ESI-MS calculated for C$_{11}$H$_{24}$N$_4$O$_3$ [MH]$^+$: 261.2; observed: 261.2.

Example 35-3

Synthesis of N-((6-chloropyridin-3-yl)methyl)-1-pyrrolin-5-carboxamide (3647-061)

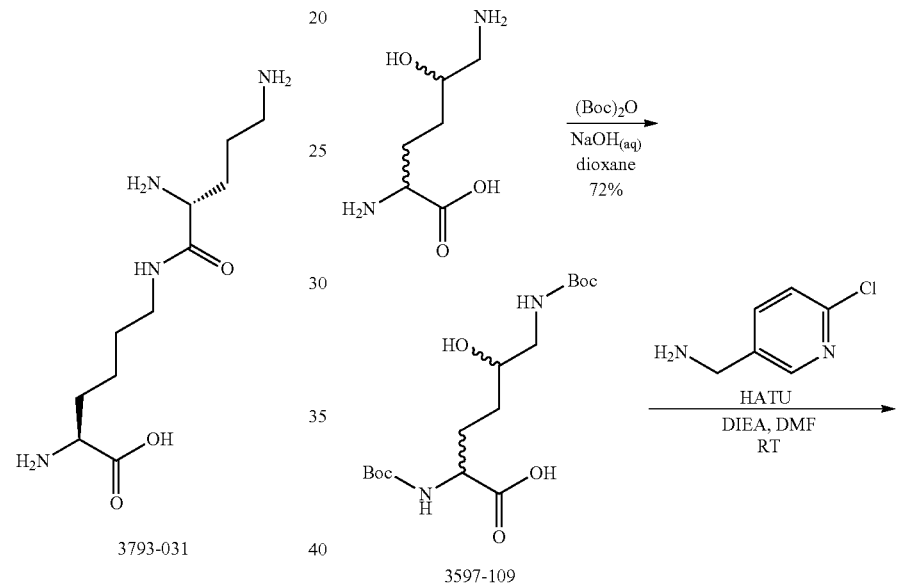

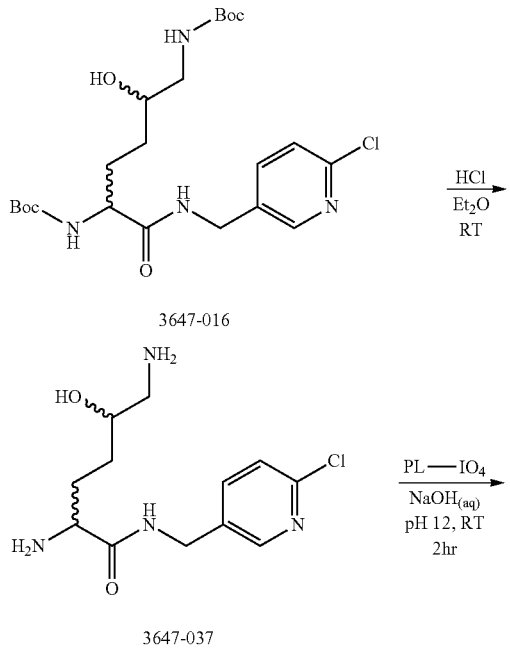

3647-037

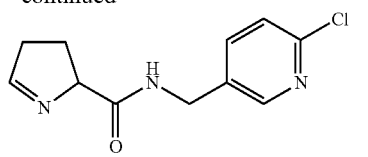

3647-061

Example 36

Synthesis of PCL Model Compounds

Example 36-1

Synthesis of H-L-Lys-Nε-(DL-1-pyrroline-5-carbonyl)-OH (3647-125)

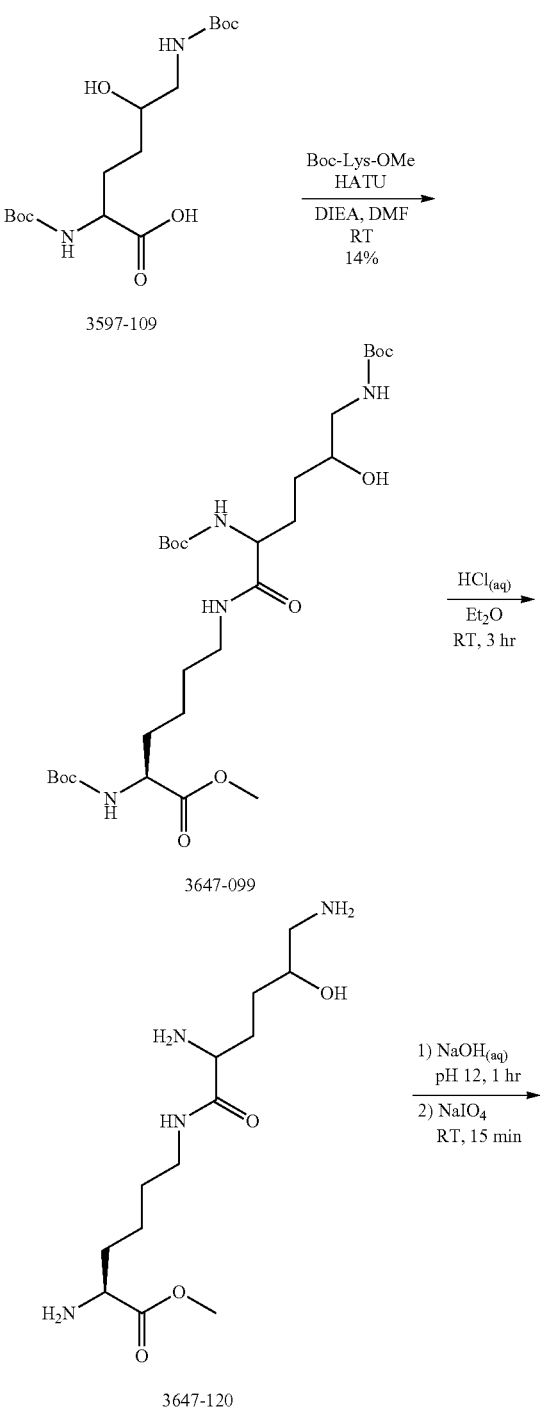

t-Butylpyrocarbonate (6.55 g) in dioxane (10 mL) was added dropwise to DL-δ-DL-hydroxyLys (1.99 g) in 1 N NaOH$_{(aq)}$ (50 mL) and the reaction was stirred at room temperature overnight. The reaction mixture was acidified to pH 3.0 with 1 N HCl$_{(aq)}$ and extracted with EtOAc (200 mL) twice. The EtOAc layers were combined, dried over Na$_2$SO$_{4(s)}$, filtered and concentrated under reduced pressure, affording the crude product. The crude product was purified by silica gel flash column chromatography with gradient elution of 0-10% MeOH/DCM, affording Boc-DL-δ-DL-hydroxyLys(Boc) (3597-109) as a white solid. ESI-MS calculated for C$_{16}$H$_{30}$N$_2$O$_7$ [MNa]$^+$: 385.2; observed: 385.2.

Boc-DL-δ-DL-hydroxyLys(Boc) (435 mg) was treated with HATU (456 mg) and DIEA (523 μL) in 3.5 mL DMF for 1 hour. The resulting solution was added to 6-chloropyridin-3-ylmethylamine (143 mg) in 1.5 mL DMF solution at room temperature and the reaction was stirred for 2 days. The reaction mixture was extracted with 10% NaCl$_{(aq)}$ (15 mL) and EtOAc (30 mL). The EtOAc layer was washed with 5% citric acid (15 mL), 10% NaHCO$_3$ (15 mL), and brine (15 mL). Then the EtOAc layer was dried over Na$_2$SO$_{4(s)}$, filtered and concentrated under reduced pressure, affording the crude product. The crude product was purified by silica gel flash column chromatography with gradient elution of 0-15% MeOH/DCM, affording the desired product (3647-016) as a white solid. ESI-MS calculated for C$_{22}$H$_{35}$N$_4$O$_6$Cl [MH]$^+$: 487.2; observed: 487.3.

The product (3647-016) (263 mg) from above was stirred in a solution of Et$_2$O (7 mL) and 1 N HCl$_{(aq)}$ (7 mL) at room temperature overnight. The reaction mixture was evaporated and lyophilized, and the residue was purified by a cation exchange SPE cartridge, affording the desired product (3647-037) as white solid. ESI-MS calculated for C$_{12}$H$_{19}$N$_4$O$_2$Cl [MH]$^+$: 287.1; observed: 287.2.

The product (3647-037) (69.6 mg) from above was dissolved in 2 mL H$_2$O (2 mL), and the pH was adjusted to 12 with 1 N NaOH$_{(aq)}$. PL-IO$_4$ resin (Varian, 381 mg, 0.48 mmol) was added and the reaction was stirred at room temperature for 2 hours. The resin was removed by filtration and half of the filtrate was purified by preparative HPLC, affording the desired product (3647-061) as white solid. ESI-MS calculated for C$_{11}$H$_{12}$N$_3$OCl [MH]$^+$: 238.1; observed: 238.1.

-continued

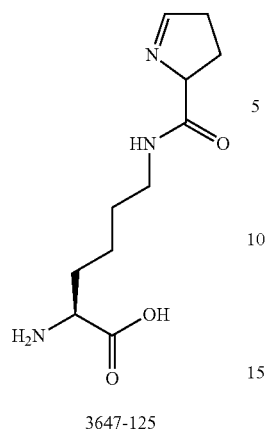

3647-125

Boc-DL-δ-DL-hydroxyLys(Boc) (3597-109) (886 mg) was activated by HATU (932 mg) in 3.0 mLDMF in the presence of DIEA (1068 µL) for 1 hour, and added to Boc-Lys-OMe (549 mg) in 3.0 mL DMF (3.0 mL). The reaction was stirred at room temperature for 36 hours. The reaction mixture was partitioned between 10% $NaCl_{(aq)}$ (30 mL) and EtOAc (60 mL). The EtOAc layer was washed with 5% citric acid (15 mL), 10% $NaHCO_3$ (15 mL), and brine (15 mL). The EtOAc layer was dried over $Na_2SO_{4(s)}$ filtered and concentrated under reduced pressue, affording the crude product. The crude product was purified by silica gel flash column chromatography with 0-15% MeOH/DCM, followed by RP-C18 SPE with elution of 25% and 65% $MeCN_{(aq)}$, affording the desired product (3647-099) as white solid. ESI-MS calculated for $C_{28}H_{52}N_4O_{10}$ [MH]$^+$: 605.4; observed: 605.4.

To Boc-Lys(Boc-DL-δ-DL-hydroxyLys(Boc))-OMe (3647-099) (84.1 mg) in 1 mL $Et_2O$ was added 4 N $HCl_{(aq)}$ (3 mL) and the reaction was stirred at room temperature for 3 hours. Removal of the solvent afforded 61.1 mg of the crude product (3647-120) as a white solid. ESI-MS calculated for $C_{13}H_{28}N_4O_4$ [MH]$^+$: 305.2; observed: 305.2.

The crude product (3647-120) (61.1 mg) from above was dissolved in 1 mL $H_2O$ and the pH was adjusted to 12 with 1 N $NaOH_{(aq)}$. The mixture was stirred at room temperature for 1 hour, resulting in the methyl ester hydrolysis. Then $NaIO_4$ (29.9 mg) was added to the reaction mixture and the reaction was stirred at room temperature for an additional 15 minutes. The reaction mixture was neutralized with 1 N $HCl_{(aq)}$ and loaded into cation exchange SPE for purification to give H-L-Lys-Nε-(DL-1-pyrroline-5-carbonyl)-OH (3647-125). ESI-MS calculated for $C_{11}H_{19}N_3O_3$ [MH]$^+$: 242.2; observed: 242.2.

Example 36-2

Synthesis of H-L-Lys-N$^\epsilon$-(DL-1-pyrroline-2-carbonyl)-OH (3793-011)

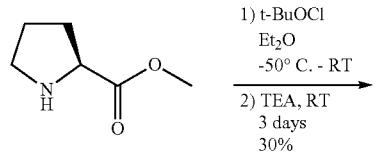

1) t-BuOCl
Et$_2$O
-50° C. - RT

2) TEA, RT
3 days
30%

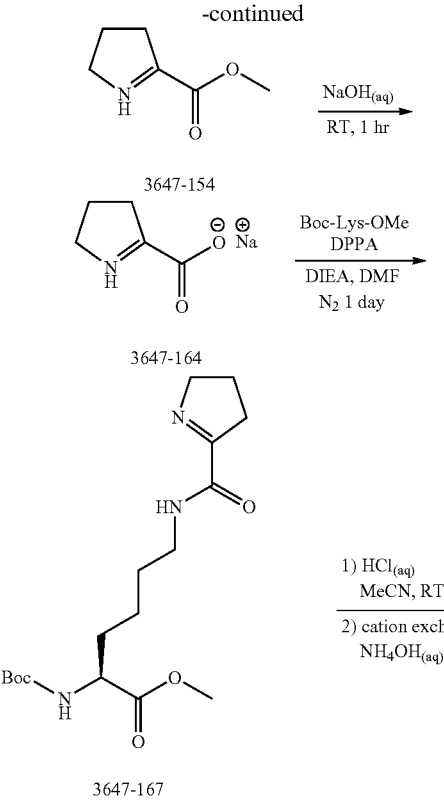

Sodium 1-pyrrolin-2-carboxylate (3647-164) was prepared by following the method described by György Szöllösi et al. (*Chirality*, 2001, 13(10), 619-624).

Triethylamine (8.4 mL) was added to H-Pro-OMe HCl (7.512 g) in ether (27 mL) and the reaction was stirred for 2 hours. The reaction mixture was filtered, and Et2O was removed by evaporation. The residue was purified by vacuum distillation, affording 4.119 g of H-Pro-OMe as colorless oil. t-BuOCl (3.59 mL) was added dropwise to an Et2O (100 mL) solution of H-Pro-OMe (4.089 g) and the reaction was stirred at −50° C. for 1 hour. The reaction mixture was warmed to room temperature and triethylamine (4.64 mL) was added to the reaction mixture, followed by stirring for 3 days. The reaction mixture was filtered, and concentrated under reduced pressure. The residue was purified by vacuum distillation to obtain Methyl pyrroline-2-carboxylate (3647-154) as a colorless oil. ESI-MS calculated for C6H9NO2 [MH]+: 128.1; observed: 128.2. 1H NMR (400 MHz, CDCl3): 4.09 (tt, J=7.6

Hz, 2.5 Hz, 2H), 3.85 (s, 3H), 2.81 (tt, J=8.2 Hz, 2.8 Hz, 2H), 1.97 (quintet, J=8.0 Hz, 2H). 13C NMR (100 MHz, CDCl3): 168.2, 163.1, 62.5, 52.5, 35.2, 22.1. ESI-MS calculated for $C_5H_7NO_2$ [MH]$^+$: 114.1; observed: 114.2. $^1$H NMR (400 MHz, D$_2$O): 3.84 (tt, J=7.4 Hz, 2.5 Hz, 2H), 2.73 (tt, J=8.2 Hz, 2.6 Hz, 2H), 1.92 (quintet, J=7.8 Hz, 2H). $^{13}$C NMR (100 MHz, D$_2$O): 175.5, 171.8, 60.1, 35.6, 21.8ESI-MS calculated for $C_5H_7NO_2$ [MH]$^+$: 114.1; observed: 114.2. $^1$H NMR (400 MHz, D$_2$O): 3.84 (tt, J=7.4 Hz, 2.5 Hz, 2H), 2.73 (tt, J=8.2 Hz, 2.6 Hz, 2H), 1.92 (quintet, J=7.8 Hz, 2H). $^{13}$C NMR (100 MHz, D$_2$O): 175.5, 171.8, 60.1, 35.6, 21.8.

Methyl pyrroline-2-carboxylate (2.265 g) was dissolved in 1 N NaOH$_{(aq)}$ (17.8 mL) and stirred at room temperature for 1 hour. The reaction mixture was lyophilized to give crude sodium pyrroline-2-carboxylate (3647-164) as a white powder. ESI-MS calculated for $C_5H_7NO_2$ [MH]$^+$: 114.1; observed: 114.2.

Sodium 1-pyrroline-2-carboxylate (459 mgl) and DPPA (886 μL) were added to Boc-Lys-OMe (acetate salt, 897 mg) and DIEA (1184 μL) in 20 mL DMF and the reaction was stirred at room temperature under N$_2$ for 24 hours. The reaction mixture was partitioned between 10% NaCl$_{(aq)}$ (50 mL) and EtOAc (100 mL). The EtOAc layer was dried over Na$_2$SO$_{4(s)}$, filtered and concentrated under reduced pressure, affording the crude product as light orange oil. The crude product was purified by silica gel flash column chromatography with gradient elution of 0-15% MeOH/DCM, followed by RP-C18 SPE, affording the desired product (3647-167) as a colorless oil. ESI-MS calculated for $C_{17}H_{29}N_3O_5$ [MH]$^+$: 356.2; observed: 356.0. $^1$H NMR (400 MHz, CDCl$_3$): 7.14 (s, 1H), 5.08 (d, d=4 Hz), 4.27 (quartet, J=5.2 Hz, 1H), 3.99 (td, J=7.2 Hz, 1.6 Hz, 2H), 3.72 (d, J=1.6 Hz, 3H), 3.31 (quartet, J=6.9 Hz, 2H), 2.83 (td, J=8.3 Hz, 1.3 Hz, 2H), 1.97 (quintet, J=8.2 Hz, 2H), 1.88-1.72 (m, 2H), 1.69-1.51 (m, 2H), 1.48-1.33 (m, 11H). $^{13}$C NMR (100 MHz, CDCl$_3$): 171.6, 162.4, 155.4, 129.7, 79.8, 61.7, 53.2, 52.3, 38.7, 34.0, 32.2, 29.0, 28.3, 22.6, 22.5.

HCl (conc, 1 mL) was added to a 50% MeCN(aq) solution (5 mL) of the product (3647-167) (49.3 mg) from above and the reaction was stirred at room temperature for 2 hours. After lyophilization, the residue was purified by cation exchange SPE cartridge. The methyl ester was hydrolyzed by NH$_4$OH$_{(aq)}$ in the eluant for overnight. After lyophilization, the desired product (3793-011) was obtained as a light yellow powder. ESI-MS calculated for $C_{11}H_{19}N_3O_3$ [MH]$^+$: 242.2; observed: 242.2. $^1$H NMR (400 MHz, D$_2$O): 3.94 (tt, J=7.6 Hz, 2.5 Hz, 2H), 3.65 (t, J=6.2 Hz, 1H), 3.30 (t, J=6.8 Hz, 2H), 2.78 (tt, J=8.4 Hz, 2.6 Hz, 2H), 1.97 (quintet, J=7.9 Hz, 2H), 1.87-1.77 (m, 2H), 1.59 (quintet, J=7.2 Hz, 2H), 1.46-1.34 (m, 2H). 13C NMR (100 MHz, D$_2$O): 175.7, 172.2, 165.1, 60.9, 54.7, 38.9, 34.3, 30.5, 27.9, 21.8, 21.7. Example 37: Synthesis of 2-AAP-PEG reagents The synthesis of different 2-AAP-PEG derivatives used in the examples provided herein are described below. 2-amino-acetophenone derivatives of PEGs with molecular weights of approximately 500, 2400, 23000 Da as well as 5000 and 10000 Da were synthesized as follows:

Example 37-1

Synthesis of TU3205-044 (0.5 kDa 2-AAP-mPEG)

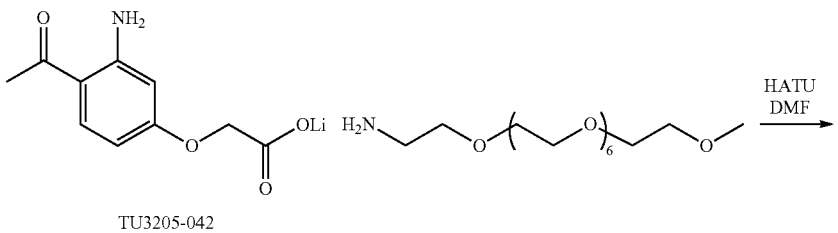

TU3205-042

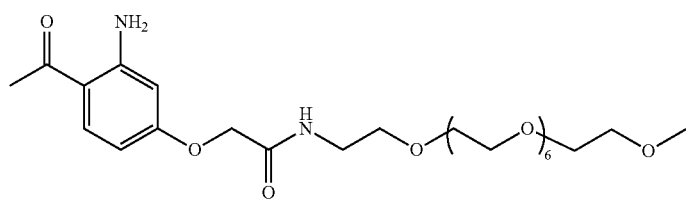

TU3205-044

Lithium 2-(4-acetyl-3-aminophenoxy)acetate (TU3205-042) (55.9 mg) was charged in a 10 mL round bottom flask, and DMF (3 mL) and HATU (98.9 mg) were added. The resulting slurry was stirred at ambient temperature for 40 minutes. The reaction turned into a yellow solution during this period. To the reaction was then added mPEG-amine (Quanta Biodesign, MW 383.5, 100 mg) in 2 mL DMF. After 5 minutes, LC-MS analysis showed a complete reaction. The reaction mixture was stirred for an additional 40 minutes and concentrated under reduced pressure. The residue was purified by a SiO$_2$ flash chromatography (3% MeOH in DCM), affording TU3205-044 (0.5 kDa 2-AAP-mPEG) as a yellow viscous oil. MS (ESI$^+$): calcd. 575.31. found 575.30 (MH$^+$). H-NMR (400 MHz, CDCl$_3$): 2.210 (3H, s), 3.370 (3H, s), 3.544 (4H, m), 3.650 (28H, m), 4.499 (2H, s), 6.172 (1H, d, J=2.4 Hz), 6.243 (1H, dd, J=8.8 Hz, 2.8 Hz), 6.540 (2H, br.s). 7.034 (1H, br.s), 7.649 (1H, d, J=8.8 Hz).

Example 37-2

Synthesis of TU3205-048 (2.4 kDa 2-AAP-PEG)

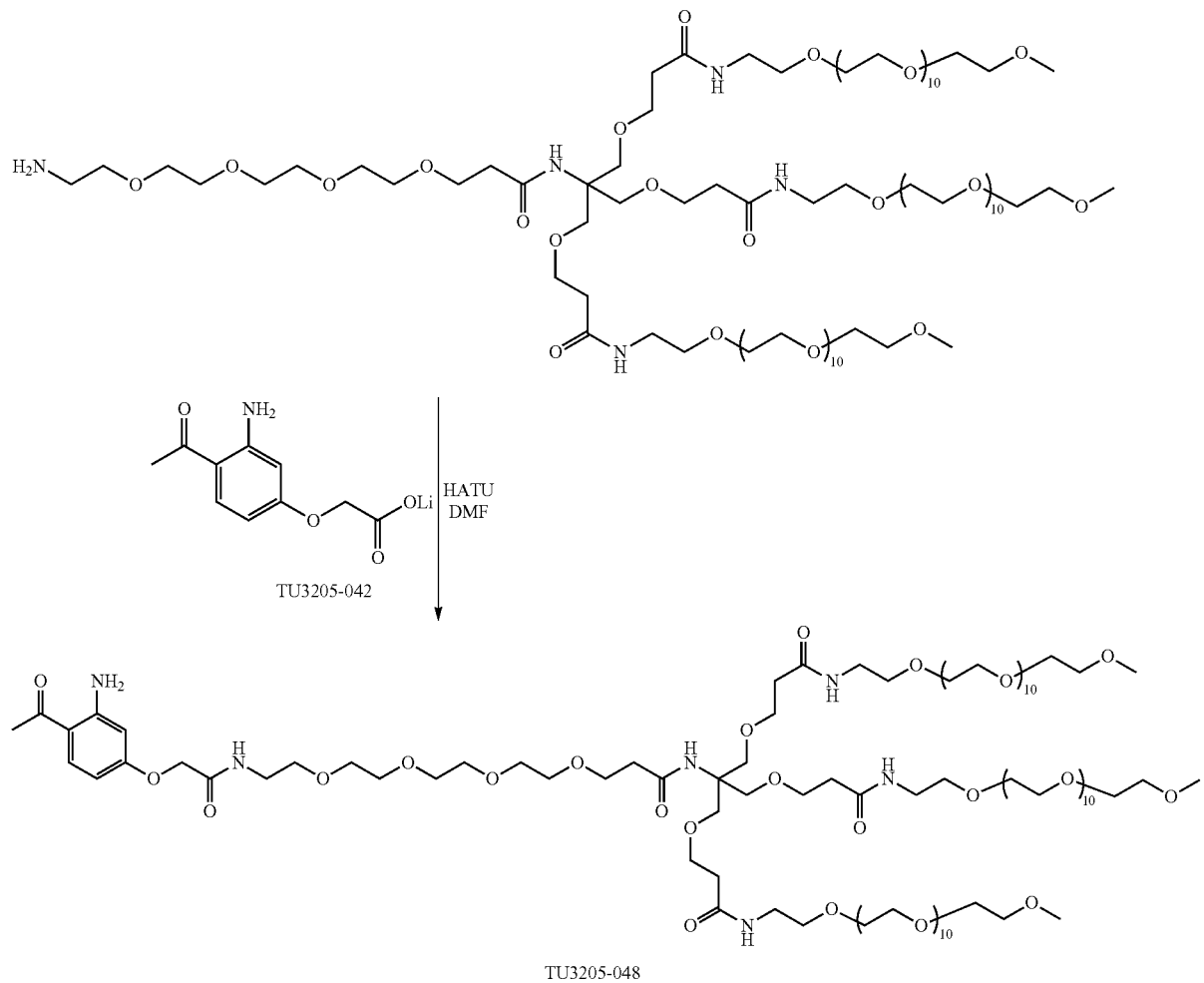

Lithium 2-(4-acetyl-3-aminophenoxy)acetate (TU3205-042) (12.2 mg) was charged in a 10 mL round bottom flask, and DMF (1 ml) and HATU (21.5 mg) were added. The resulting slurry was stirred at the ambient temperature for 35 minutes. The reaction turned into a yellow solution during this period. To the reaction was then added mPEG-amine (Quanta Biodesign, MW 2209, 100 mg) in 2 mL DMF. The reaction mixture was stirred for 18 hours and concentrated under reduced pressure. The residue was purified by a $SiO_2$ flash chromatography (MeOH in DCM), affording TU3205-048 (2.4 kDa 2-AAP-mPEG) as a yellow viscous oil. MS (ESI+): calcd. 800.8. found 800.5 ($M^{+3}H^+/3$), calcd. 600.9. found 600.7 ($M^{+4}H^+/4$).

Example 37-3

Synthesis of TU3205-052 (23 kDa 2-AAP-PEG)

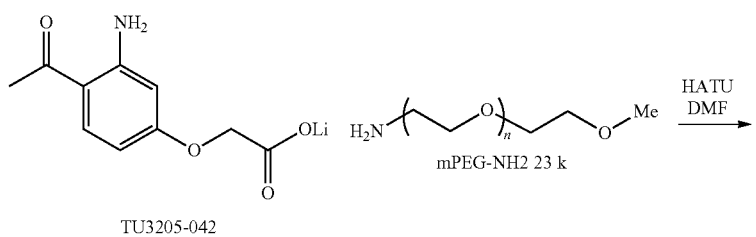

-continued

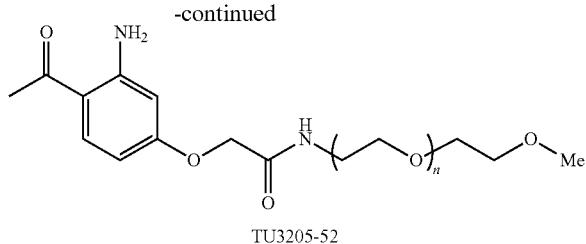

TU3205-52

Lithium 2-(4-acetyl-3-aminophenoxy)acetate (TU3205-042) (21.5 mg) and HATU (38.0 mg) were charged in a 10 mL round bottom flask, and DMF (0.5 mL) was added. The resulting slurry was stirred at the ambient temperature for 50 minutes. The resulting yellow solution was added to mPEG-NH$_2$ (Laysan Bio, average MW 23k, average n=520, 0.50 g) in 5 mL DMF in a 20 mL glass vial. The reaction was shaken at ambient temperature for 2.5 hours. The reaction mixture was then diluted with 10 mL water, and an aliquot of 2.5 mL each of the solution was applied to PD-10 columns (GE Healthtech) and the desired product was eluted with water according to the supplier's instruction. The pooled aqueous solutions were pooled, frozen, and lyophilized, affording TU3205-052 (23 kDa 2-AAP-mPEG) as a white solid. (Note; the chacterization of high MW PEG reagents was obtained only after they were conjugated to the PCL containing proteins.)

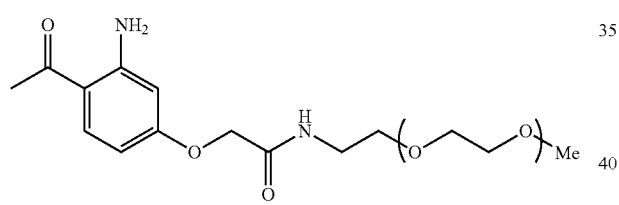

(TU633-006) (10 kDa 2-AAP-mPEG) and

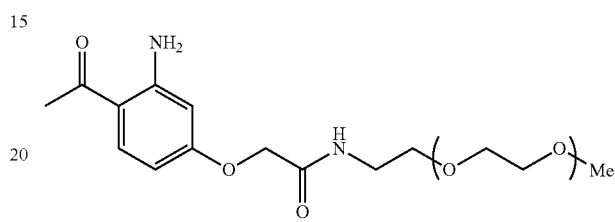

(TU633-008) (5 kDa 2-AAP-mPEG) were prepared in similar manners as TU3205-052 using the corresponding 10,000 (average n=225) and 5,000 (average n=111) MW mPEG-NH$_2$. (Note; the chacterization of high MW PEG reagents was obtained only after they were conjugated to the PCL containing proteins.)

Example 37-4

Synthesis of TU633-010: Bifunctional Linker

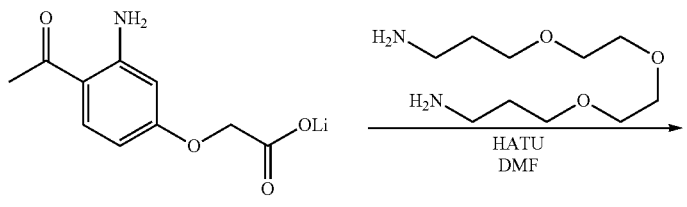

TU3205-042

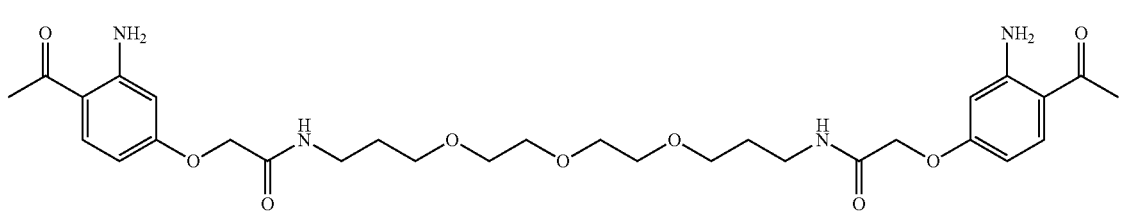

TU633-010

Lithium 2-(4-acetyl-3-aminophenoxy)acetate (TU3205-042) (94.6 mg) and HATU (167 mg) were charged in a 10 mL round bottom flask, and DMF (2 mL) was added. The resulting slurry was stirred at ambient temperature for 45 minutes. To the resulting yellow solution was added 4,7,10-trioxa-1,13-tridecanediamine (Fluka, 44 mg) in 1 mL DMF. The reaction mixture was stirred at ambient temperature for 18 hours, and concentrated under reduced pressure. The residue was purified by a SiO$_2$ flash chromatography (MeOH in DCM), followed by a preparative reverse phase LC purification. The LC purified material was dissolved in EtOAc and treated with sat. aqueous NaHCO$_3$ to remove trifluoroacetic acid. Evaporation of solvent afforded the bi-functional linker TU633-010 as a clear oil. MS (ESI$^+$) calced. 603.3. found 603.3 (MH$^+$).

Example 37-5

Synthesis of m-PEG-AAP 29k (TU633-084)

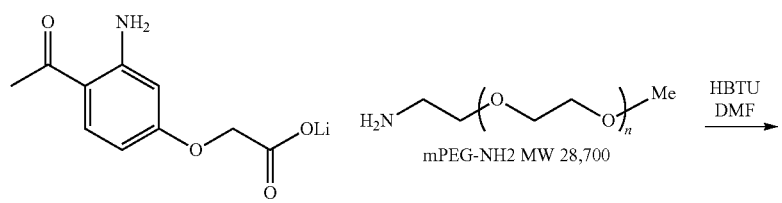

TU633-084 m-PEG-AAP-29 k

Lithium 2-(4-acetyl-3-aminophenoxy)acetate (187 mg) and HBTU (330 mg) were put in a 20 mL glass vial and 10 mL dry DMF was added. The resulting slurry was stirred at ambient temperature. Within 20 minutes, the reaction turned into a yellow solution and after 80 minutes a 9.5 mL aliquot of the reaction mixture was added to mPEG-NH$_2$ (Laysan Bio, MW28,700) dissolved in 40 mL dry DMF in a 100 mL round bottom flask. The reaction was shaken at ambient temperature for 19 hours. The reaction mixture was then applied to 24 pieces of PD-10 columns (GE Helthtech) and the desired product was eluted with water according to the supplier's instruction. The pooled eluents were frozen and lyophilized, affording a white solid. The solid was dissolved in doubly deionized water, and dialyzed exhaustively against doubly deionized water using a dialysis membrane of MWCO 3500. The dialyzed solution was frozen and lyophilized, affording TU633-084 as white fluffy solid. (Note; the chacterization of high MW PEG reagents was obtained only after they were conjugated to the PCL containing proteins.)

Example 37-6

Synthesis of mPEG-AAP-30k (TU633-120)

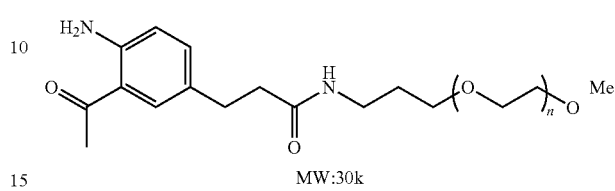

MW:30k

Lithium 3-(3-acetyl-4-aminophenyl)propanoate (139 mg) and HBTU (247 mg) were put in a 20 mL glass vial, and 13 mL dry DMF was added. The resulting slurry was stirred at ambient temperature for 30 minutes and the resulting solution was used for preparation of TU633-120, TU633-122, TU633-124 and TU633-126. In a 45 mL glass vial was put mPEGamine (NOF Corp., SUNBRIGHT MEPA-30T MW 30,298, 3.0 g), and 20 mL dry DMF was added, followed by gentle heating to dissolve mPEGamine in DMF. To the resulting mPEGamine solution was added a 2.2 mL aliquot of the activated ester solution, and the vial was shaken at ambient temperature for 18 hours and then at 37° C. for 24 hours. The reaction mixtures was transferred to dialysis membrane tubing (Fisher Scientific, cat #21-152-9, MWCO 3500) and dialyzed exhaustively against doubly deionized water over 2 days. The dialyzed solution was frozen and lyophilized, affording TU633-120 as white cotton-like solid. (Note; the chacterization of high MW PEG reagents was obtained only after they were conjugated to the PCL containing proteins.)

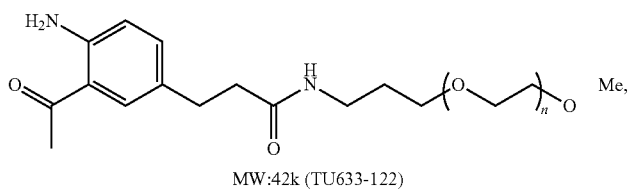

MW:42k (TU633-122)

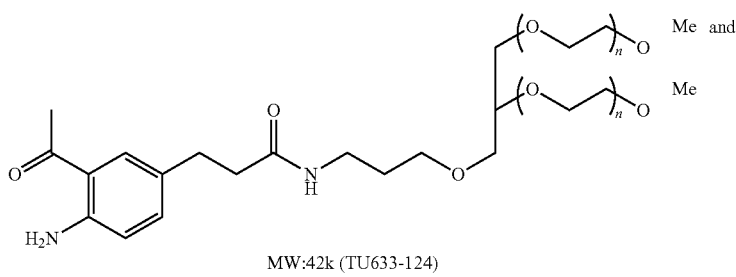

MW:42k (TU633-124)

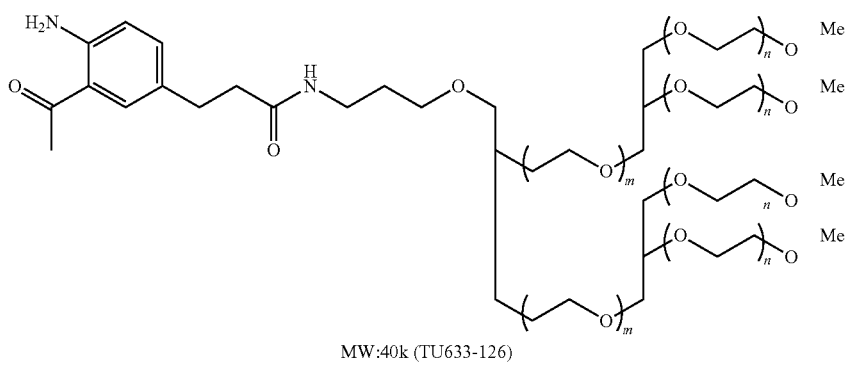

MW:40k (TU633-126)

were prepared in a similar way except for using the corresponding activated PEGs from NOF Corp., SUNBRIGHT-MEPA-40T (MW 42036), SUNBRIGHT GL2-400PA (MW 42348), SUNBRIGHT GL4-400PA, respectively, instead of SUNBRIGHT MEPA-30T. (Note; the chacterization of high MW PEG reagents was obtained only after they were conjugated to the PCL containing proteins.)

Example 37-7

Synthesis of mPEG-ABA-30kD (TU3627-024)

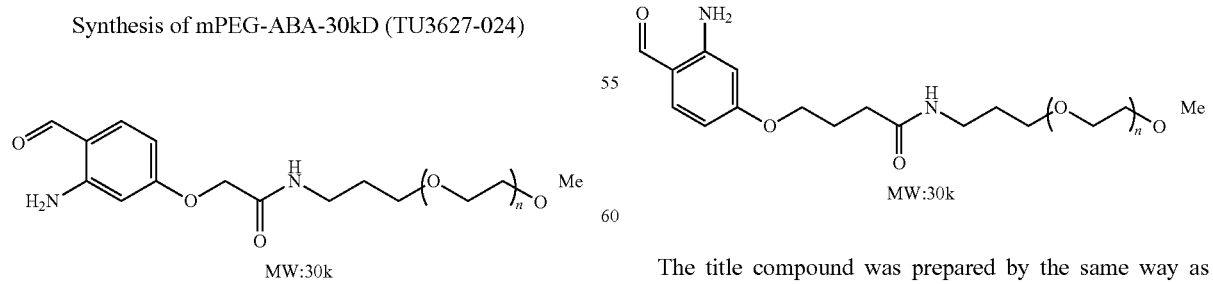

MW:30k

The title compound was prepared by the same way as TU633-120 except for using lithium 2-(3-amino-4-formylphenoxy)acetate instead of lithium 3-(3-acetyl-4-aminophenyl)propanoate. (Note; the chacterization of high MW PEG reagents was obtained only after they were conjugated to the PCL containing proteins.)

Example 37-8

Synthesis of mPEG-ABA-30k (TU3627-084)

MW:30k

The title compound was prepared by the same way as TU633-120 except for using lithium 4-(3-amino-4-formylphenoxy)butanoate instead of lithium 3-(3-acetyl-4-aminophenyl)propanoate. The H NMR analysis revealed no unmodified starting PEG in the product. Terminal activity: >95% by H-NMR.

Example 37-9

Synthesis of mPEG-ABA-40k (TU3627-086)

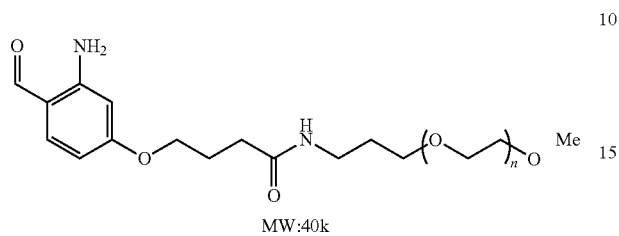

MW:40k

The title compound was prepared by the same way as TU3627-084 except for using SUNBRIGHTMEPA-40T instead of SUNBRIGHTMEPA-30T. The H NMR analysis revealed no unmodified starting PEG in the product. Terminal activity: >95% by H-NMR.

Example 37-10

Synthesis of $N^1$-(18-(3-Amino-4-formylphenoxy)-15-oxo-4,7,10-trioxa-14-azaoctadecyl)-$N^{19}$-(18-(3-amino-4-formylphenoxy)-15-oxo-4,7,10-trioxa-9,14-diazaoctadecyl)-4,7,10,13,16-pentaoxanonadecane-1,19-diamide (X3678-40)

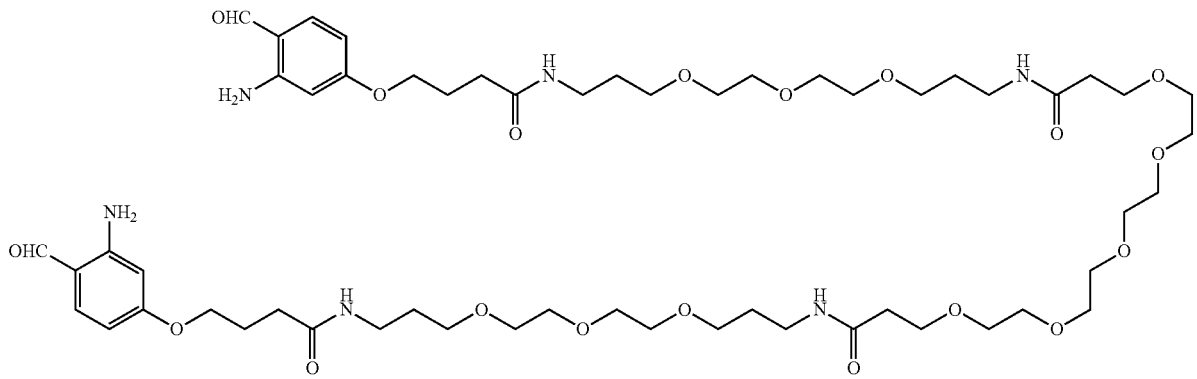 [SMILES: Nc1cc(OCCCC(=O)NCCCOCCOCCOCCCNC(=O)CCOCCOCCOCCOCCOCCC(=O)NCCCOCCOCCOCCCNC(=O)CCCOc2ccc(C=O)c(N)c2)ccc1C=O]

Lithium 4-(3-amino-4-formylphenoxy)butanoate (94.5 mg) was activated with HBTU (151.7 mg) in 4 mL DMF. Diamido-dPEG™₁₁-diamine (QuantaBiodesign, Cat #10361, 74.3 mg) was added to the reaction mixture and stirred at room temperature overnight. DIEA (17.5 μL, 0.1 mmol) was added and the mixture was heated at 40° C. for several hours. The title compound was isolated by preparative RP-HPLC and TFA was removed by passing though a PL- HCO₃ MP SPE cartridge (Varian Inc.). MS (ESI+) m/z 1153.60 (MH+).
Example 38
Synthesis of Reagent for Coupling of Immune Modulators to Proteins
Example 38-1
Synthesis of N-(1-(3-Amino-4-formylphenoxy)-2-oxo-7,10,13-trioxa-3-azahexadecan-16-yl)-4-((4-(2-(5-amino-8-methylbenzo[f][1,7]naphthyridin-2-yl)ethyl)-3-methylphenoxy)methyl)benzamide (TU3627-042)
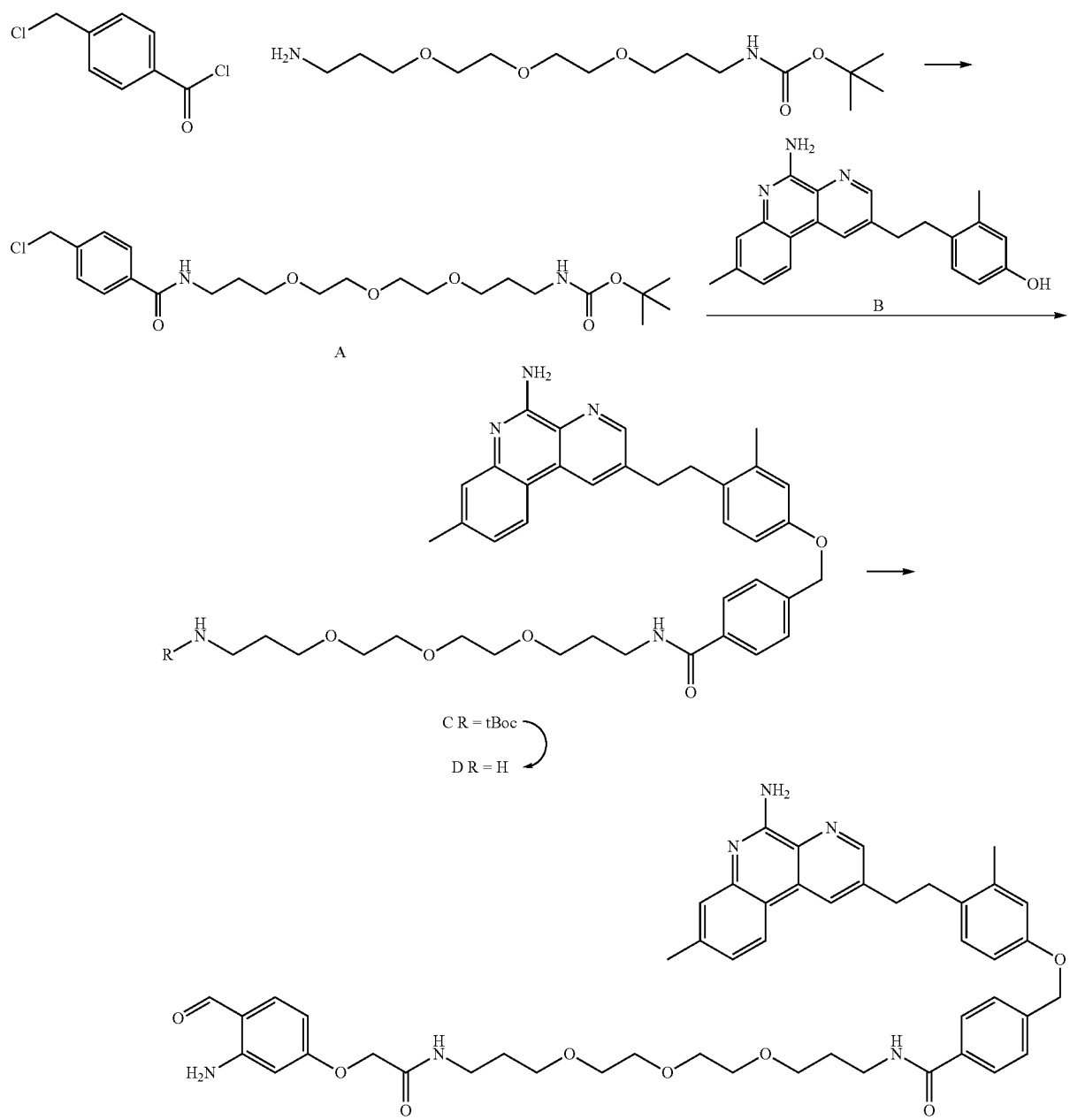

To t-butyl 3-(2-(2-(3-aminopropoxy)ethoxy)ethoxy)propylcarbamate (QuantaBiodesign, cat #10225, 500 mg) and DIEA (348 µL) in 10 mL DCM was added 4-chloromethylbenzoyl chloride in 2 mL DCM with cooling in an ice bath. The reaction was stirred at the same temperature for 1 hour. The reaction mixture was diluted with EtOAc, washed successively with H$_2$O, dilute aqueous citric acid, aqueous NaHCO$_3$ and sat. aqueous NaCl, dried over Na$_2$SO$_4$, filtered and concentrated under reduced pressure, affording the product (A) as a clear viscous oil. MS (ESI+): calcd. 473.2. found 473.3 (MH+). H-NMR (400 MHz, CDCl$_3$): 1.405 (9H, s), 1.685 (2H, m), 1.879 (2H, m), 3.173 (2H, m), 3.438 (4H, m), 3.567 (4H, m), 3.633 (6H, m), 4.584 (2H, s), 4.933 (1H, br.s), 7.246 (1H, br.s), 7.411 (2H, d, J=8.4 Hz), 7.789 (2H, d, J=8.4 Hz). C-NMR (100 MHz, CDCl$_3$): 28.385, 28.673, 29.553, 38.430, 39.087, 45.447, 69.474, 70.042, 70.216, 70.379, 70.516, 70.798, 78.882, 127.430, 128.496, 134.745, 140.341, 155.966, 166.550.

The product, A, from above (303 mg), compound B (200 mg), cesium carbonate (208 mg) and anhydrous DMSO were combined and the reaction was stirred at ambient temperature. After 18 hours, an additional 60 mg of compound A dissolved in 8 mL DMSO and an additional 30 mg of cesium carbonate were added to the reaction and the reaction was stirred for 40 hours at ambient temperature, by which time only trace amount of compound B remained, indicated by the LCMS analysis. The reaction mixture was diluted with EtOAc, washed successively with H$_2$O, sat. aqueous NaCl, dryed over Na$_2$SO$_4$, filtered and concentrated under reduced pressure. The residue was purified by a silica gel flash chromatography using a linear gradient of 1 to 5% solvent B in A (A: DMC; B: 2% NH3 in MeOH), affording the partially purified desired compound. After recrystallized from MTBE, the product as a slightly yellow crystals was obtained. MS (ESI+): calcd. 780.43. found 780.50 (MH+). H-NMR (400 MHz, DMSO-d6): 1.357 (9H, s), 1.578 (2H, quint, J=6.8 Hz), 1.751 (2H, quint, J=6.8 Hz), 2.264 (3H, s), 2.439 (3H, s), 2.94 (4H, m), 3.08 (2H, m), 3.34 (4H, m), 3.45 (4H, m), 3.50 (6H, m), 5.105 (2H, s), 6.757 (1H, dd, J=2.4, 8.4 Hz), 6.77 (1H, br.s), 6.836 (1H, d, J=2.8 Hz), 7.060 (2H, br.s), 7.091 (1H, d, J=8.4 Hz), 7.138 (1H, dd, J=2.4, 8.4 Hz), 7.349 (1H, s), 7.495 (2H, d, J=8.4 Hz), 7.837 (2H, d, J=8.4 Hz), 8.330 (1H, d, J=8.4 Hz), 8.439 (1H, t, J=5.6 Hz), 8.701 (1H, d, J=2.0 Hz), 8.827 (1H, d, J=1.6 Hz). C-NMR (100 MHz, DMSO-d6): 19.153, 21.206, 28.178, 29.297, 29.638, 33.166, 33.336, 36.584, 37.085, 67.989, 68.200, 68.455, 69.495, 69.678, 69.703, 77.307, 111.863, 116.456, 117.005, 122.743, 123.321, 125.292, 127.047, 127.178, 127.764, 129.725, 129.823, 131.414, 132.600, 133.883, 137.040, 138.775, 139.426, 140.303, 144.984, 149.405, 155.471, 155.663, 156.341, 165.783.

The Boc group of compound C was removed by treatment with 3M methanolic HCl at ambient temperature. The concentration of the reaction mixture under reduced pressure afforded compound D as dihydrochloride salt. MS (ESI+): calcd. 680.4. found 680.4 (MH+). H-NMR (400 MHz, DMSO-d6): 1.77 (4H, m), 2.289 (3H, s), 2.504 (overlapping with DMSO-d6 signal), 2.85 (2H, m), 2.98 (2H, m), 3.14 (2H, m), 3.31 (2H, m), 3.5 (12H, m), 5.109 (2H, s), 6.768 (1H, dd, J=2.4, 8.4 Hz), 6.852 (1H, d, J=2.4 Hz), 7.107 (1H, d, J=2.4 Hz), 7.427 (1H, d, J=8.4 Hz0, 7.496 (2H, d, 8.4 Hz), 7.532 (1H, s), 7.858 (2H, d, J=8.0 Hz), 7.89 (3H, br.s), 8.53 (2 h, m), 8.872 (1H, s), 9.01 (1H, br.s), 9.03 (1H, s), 9.731 (1H, s). C-NMR (100 MHz, DMSO-d6): 19.183, 21.127, 27.076, 29.325, 32.793, 33.290, 36.601, 67.251, 68.198, 68.423, 69.389, 69.480, 69.587, 69.693, 111.903, 115.654, 116.491, 117.597, 124.065, 126.488, 127.058, 127.227, 129.646, 129.818, 130.877, 131.129, 131.841, 132.733, 133.850, 137.112, 140.296, 141.702, 143.879, 151.265, 153.598, 156.424, 165.789.

Lithium 2-(3-amino-4-formylphenoxy)acetate (20 mg) and HBTU (38 mg) were put in a 20 mL glass vial, and 2 mL dry DMF was added. The resulting slurry was stirred at ambient temperature for 30 min, and then compound D (38 mg) and DIEA (52 µh) were added. The reaction was stirred at ambient temperature for 17 hours. The LCMS analysis revealed no starting materials remained but formation of bis-acylated byproduct together with the desired product. The reaction mixture was diluted with EtOAc, washed successively with H$_2$O and sat aqueous NaCl, dried over Na$_2$SO$_4$, filtered and concentrated under reduced pressure. The residue was taken up in 5 mL THF, and treated with a 1 mL aliquot of 1M aqueous LiOH at ambient temperature for 2 hours, by which time the LC-MS analysis showed a hydrolysis of the bis-acylated product to the desired product. The reaction mixture was partitioned between EtOAc and water, and the organic layer was separated, washed with sat aqueous NaCl, dried over Na$_2$SO$_4$, filtered and concentrated under reduced pressure. The crude material was applied to a preparative RP-HPLC for purification. The HPLC eluent containing the desired product was diluted with EtOA, and washed with sat aqueous NaHCO$_3$ and sat aqueous NaCl to remove trifluoroacetic acid, dried over Na$_2$SO$_4$, filtered and concentrated under reduced pressure, affording the title compound N-(1-(3-Amino-4-formylphenoxy)-2-oxo-7,10,13-trioxa-3-azahexadecan-16-yl)-4-((4-(2-(5-amino-8-methylbenzo[f][1,7]naphthyridin-2-yl)ethyl)-3-methylphenoxy)methyl)benzamide (TU3627-042). MS (ESI+): m/z 857.40 (MH+). H-NMR (400 MHz, DMSO-d6): 1.651 (2H, quint, J=6.6 Hz), 1.747 (2H, quint, J=6.6 Hz), 2.264 (3H, s), 2.443 (3H, s), 2.96 (2H, m), 3.08 (2H, m), 3.16 (3H, m) 3.27-3.29 (m overlapping with H$_2$O signal), 3.45 (4H, m), 3.50 (7H, m), 4.451 (2H, s), 5.102 (2H, s), 6.198 (1H, d, J=2.0 Hz), 6.268 (1H, dd, J=2.0, 8.8 Hz), 6.755 (1H, 2.4, 8.4 Hz), 6.836 (1H, d, J=2.4 Hz), 7.095 (1H, d, J=8.4 Hz), 7.158 (1H, d, J=8.0 Hz), 7.208 (2H, br.s), 7.362 (1H, s), 7.435 91H, d, J=8.8 Hz), 7.493 (2H, d, J=8.4 Hz), 7.834 (2H, d, J=8.0 Hz) 8.070 (1H, t, J=5.6 Hz), 8.349 (1H, d, J=8.4 Hz), 8.440 (t, J=5.6 Hz), 8.711 (1H, d, J=1.6 Hz), 8.840 (1H, d, J=1.6 Hz), 9.636 (1H, s).

Synthesis of 4-(2-(5-amino-8-methylbenzo[f][1,7]naphthyridin-2-yl)ethyl)-3-methylphenol (Compound B)

To a round bottom flask capped with septa was added 1-ethynyl-4-methoxy-2-methylbenzene (commercially available) (1.1 eq), 3,5-dichloropicolinonitrile (1 eq.), triethylamine (5 eq.), and anhydrous DMF (0.2 M). Vacuumed and nitrogen flushed for three times. CuI (0.05 eq.) and bis(triphenylphosphine)dichloro-palladium(II) (0.05 eq) were added. The septum was replaced with a refluxing condenser and the flask was heated at 60° C. overnight under nitrogen atmosphere. Upon completion of the reaction as monitored by TLC, the content of the flask was loaded onto a large silica gel column pretreated with hexanes. Flash chromatography (silica gel, hexanes:EtOAc (1:4%)) afforded the product 3-Chloro-5-((4-methoxy-2-methylphenyl)ethynyl)picolinonitrile.

To a round bottom flask with refluxing condenser were added 3-Chloro-5-((4-methoxy-2-methylphenyl)ethynyl)picolinonitrile (from the previous step) (1 eq.), tert-butyl 2-(4,4,5,5-tetramethyl-1,3,2-dioxaborolan-2-yl)phenylcarbamate (1.25 eq.), K$_3$PO$_4$ (2 eq.), tris(dibenzylideneacetone)dipalladium(0) (0.05 eq.), and 2-dicyclohexylphosphino-2',6'- dimethoxybiphenyl (0.1 eq.). n-Butanol and water (5:2, 0.2 M) were added, and the content were degassed (vacuum followed by nitrogen flush) for three times. The reaction mixture was stirred vigorously under nitrogen at 100° C. overnight in an oil bath. The contents were cooled down and were taken up in 200 mL of water followed by extraction with methylene chloride. Combined organic layers were dried ($Na_2SO_4$) and concentrated. Flash chromatography (silica gel, 0-50% EtOAc in $CH_2Cl_2$) afforded the product 2-((4-methoxy-2-methylphenyl)ethynyl)-8-methylbenzo[f][1,7]naphthyridin-5-amine.

To a round bottom flask was added 2-((4-methoxy-2-methylphenyl)ethynyl)-8-methylbenzo[f][1,7]naphthyridin-5-amine (from the previous step) (1 eq.) with a stirring bar. Ethanol and methylene chloride (1:2, 0.2 M) were added, followed by palladium in carbon (activated powder, wet, 10% on carbon, 0.1 eq.). The content were vacuumed followed by hydrogen flush for three times. The reaction mixture was stirred vigorously under hydrogen balloon at room temperature overnight. Afterwards the reaction mixture was filtered through a celite pad, and the celite pad was washed subsequently with methylene chloride and EtOAc until the filtrate had no UV absorption. Combined organic washes were concentrated. Flash chromatography (silica gel, 0-50% EtOAc in $CH_2Cl_2$) afforded the product 2-(4-Methoxy-2-methylphenethyl)-8-methylbenzo[f][1,7]naphthyridin-5-amine.hylphenethyl)-8-methylbenzo[f][1,7]naphthyridin-5-amine. $^1$H NMR ($CDCl_3$): δ 8.53 (d, 1H), 8.29 (d, 1H), 8.01 (d, 1H), 7.44 (s, 1H), 7.12 (dd, 1H), 6.93 (d, 1H), 6.67 (d, 1H), 6.60 (dd, 1H), 5.93 (bs, 2H), 3.70 (s, 3H), 3.05-3.00 (dd, 2H), 2.93-2.88 (dd, 2H), 2.44 (s, 3H), 2.19 (s, 3H). LRMS [M+H]=358.2

To a stirred solution of 2-(4-methoxy-2-methylphenethyl)-8-methylbenzo[f][1,7]naphthyridin-5-amine in methylene chloride (0.2 M) in an ice-water bath was added 1 N solution of $BBr_3$ (2 eq) in $CH_2Cl_2$ in a drop-wise fashion. In 30 minutes the reaction was quenched with methanol and was concentrated en vaccuo to obtain a crude residue. The crude material was purified by flash chromatography on a COMBI-FLASH® system (ISCO) using 0-20% methanol in dichloromethane to give 4-(2-(5-amino-8-methylbenzo[f][1,7]naphthyridin-2-yl)ethyl)-3-methylphenol as a white solid. $^1$H NMR (DMSO-$d_6$): δ 8.99 (s, 1H), 8.75 (d, 1H), 8.60 (d, 1H), 8.27 (d, 1H), 7.28 (s, 1H), 7.09 (dd, 1H), 6.99 (bs, 2H), 6.88 (d, 1H), 6.49 (d, 1H), 6.42 (dd, 1H), 3.02-2.96 (dd, 2H), 2.86-2.81 (dd, 2H), 2.38 (s, 3H), 2.13 (s, 3H). LRMS [M+H]=344.2

Example 38-2

Synthesis of 4-((4-(2-(5-Amino-8-methylbenzo[f][1,7]naphthyridin-2-yl)ethyl)-3-methylphenoxy)methyl)-N-(1-(aminooxy)-2-oxo-7,10,13-trioxa-3-azahexadecan-16-yl)benzamide hydrochloride (TU3627-044)

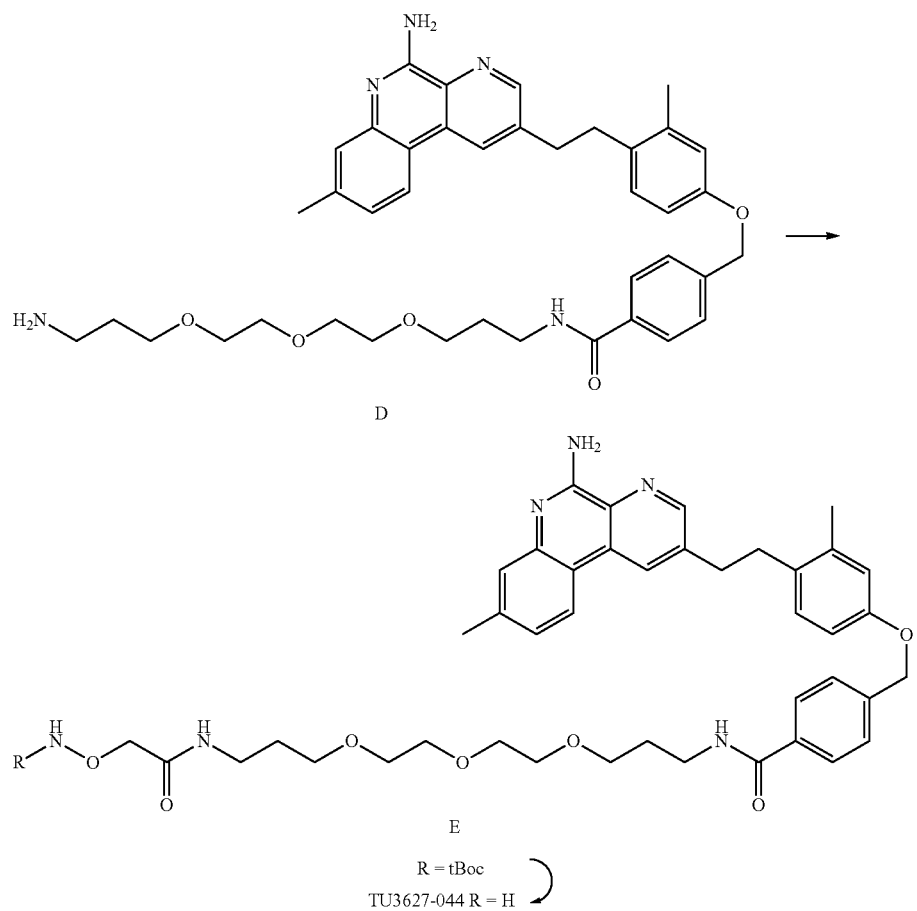

HBTU (38 mg), 2-(tert-Butoxycarbonylaminooxy)acetic acid (Fluka, 25 mg), DIEA (44 µL) and 5 mL DMF were combined in a 20 mL glass vial. The reaction was stirred at ambient temperature for 30 minutes, and then compound D (38 mg) was added. The reaction was stirred at ambient temperature for 17 hours. The LC-MS analysis revealed no starting materials remained but formation of several overacylated byproducts together with the desired product. The reaction mixture was diluted with EtOAc, washed successively with H$_2$O and sat aqueous NaCl, dried over Na$_2$SO$_4$, filtered and concentrated under reduced pressure. The residue was taken up in 5 mL THF, and treated with a 1 mL aliquot of 1M aqueous LiOH at ambient temperature for 2 hours, by which time the LC-MS analysis showed hydrolysis of the overacylated products to the desired product. The reaction mixture was partitioned between EtOAc and water, and the organic layer was separated, washed with sat aqueous NaCl, dried over Na2SO4, filtered and concentrated under reduced pressure. The crude material was purified by a silica gel flash chromatography using 5% solvent B in A (A: DMC; B: 2% NH$_3$ in MeOH), affording the desired compound, E. MS (ESI+): calcd. 853.44. found 853.50 (MH+). H-NMR (400 MHz, DMSO-d6): 1.401 (9H, s), 1.643 (2H, quint. J=6.8 Hz), 1.750 (2H, quint. J=6.8 Hz), 2.269 (3H, s), 2.453 (3H, s), 2.96 (2H, m), 3.09 (2H, m), 3.162 (2H, q, J=6.0 Hz), 3.298 (overlapping with H$_2$O signal), 3.393 (2H, t, J=5.6 Hz), 3.45 (4H, m), 3.51 (6H, m), 4.219 (2H, s), 5.106 (2H, s), 6.758 (1H, dd, J=2.4, 8.4 Hz), 6.840 (1H, d, J=2.8 Hz), 7.094 (1H, d, J=8.4 Hz), 7.102 (1H, br.d, J=8.0 Hz), 7.394 (1H, s), 7.495 (2H, d, J=8.4 Hz), 7.837 (2H, d, J=8.4 Hz), 7.994 91H, br.t, 5.2 Hz), 8.379 (1H, d, 8.4 Hz), 8.441 (1H, t, 5.4 Hz), 8.737 (1H, s), 8.869 (1H, s), 10.307 (1H, br.s).

Compound E (28 mg) was treated with 3M methanolic HCl at ambient temperature for 30 minutes, and concentrated under reduced pressure. This operation was repeated. The title compound 4-((4-(2-(5-Amino-8-methylbenzo[f][1,7]naphthyridin-2-yl)ethyl)-3-methylphenoxy)methyl)-N-(1-(aminooxy)-2-oxo-7,10,13-trioxa-3-azahexadecan-16-yl) benzamide hydrochloride (TU3627-044) was obtained as a yellow solid. MS (ESI+): m/z 753.40 (MH+). H-NMR (400 MHz, DMSO-d6): 1.651 (2H, quint, J=6.6 Hz), 1.752 (2H, quint, J=6.6 Hz), 2.290 (3H, s), 2.5 (one methyl peak overlapping with DMSO signal), 2.98 (2H, m), 3.15 (4H, m), 3.155 (2H, q, J=7.2 Hz), 3.47 (12H, m), 4.463 (2H, s), 5.109 (2H, s), 6.767 (1H, dd, J=2.8, 8.4 Hz), 6.854 (1H, d, J=2.8 Hz), 7.108 (1H, d, 8.4 Hz), 7.431 (1H, d, J=8.4 Hz), 7.498 (2H, d, J=8.4 Hz), 7.545 (1H, s), 7.848 (2H, d, J=8.4 Hz), 8.240 (1H, t, 5.6 Hz), 8.467 (1H, t, J=5.6 Hz), 8.542 (1H, d, J=8.4 Hz0, 8.875 (1H, 2d, J=2.0 Hz), 8.993 (1H, br.s), 9.027 (1H, d, J=2.0 Hz), 9.729 (1H, br.s). C-NMR (100 MHz, DMSO-d6): 19.177, 21.141, 29.034, 29.322, 32.851, 33.345, 35.615, 36.581, 67.843, 68.199, 68.426, 69.470, 69.503, 69.685, 69.713, 71.237, 111.909, 115.691, 116.495, 117.691, 124.022, 126.495, 127.069, 127.212, 129.652, 129.824, 130.850, 131.127, 131.872, 132.820, 133.883, 137.116, 140.285, 141.689, 143.895, 151.303, 153.491, 156.438, 165.784, 166.659.

Example 38-3

Synthesis of N-(58-(3-amino-4-formylphenoxy)-15, 55-dioxo-4,7,10,18,21,24,27,30,33,36,39,42,45,48, 51-pentadecaoxa-14,54-diazaoctapentacontyl)-4-((4-(2-(5-amino-8-methylbenzo[f][1,7]naphthyridin-2-yl)ethyl)-3-methylphenoxy)methyl)benzamide (X3678-114)

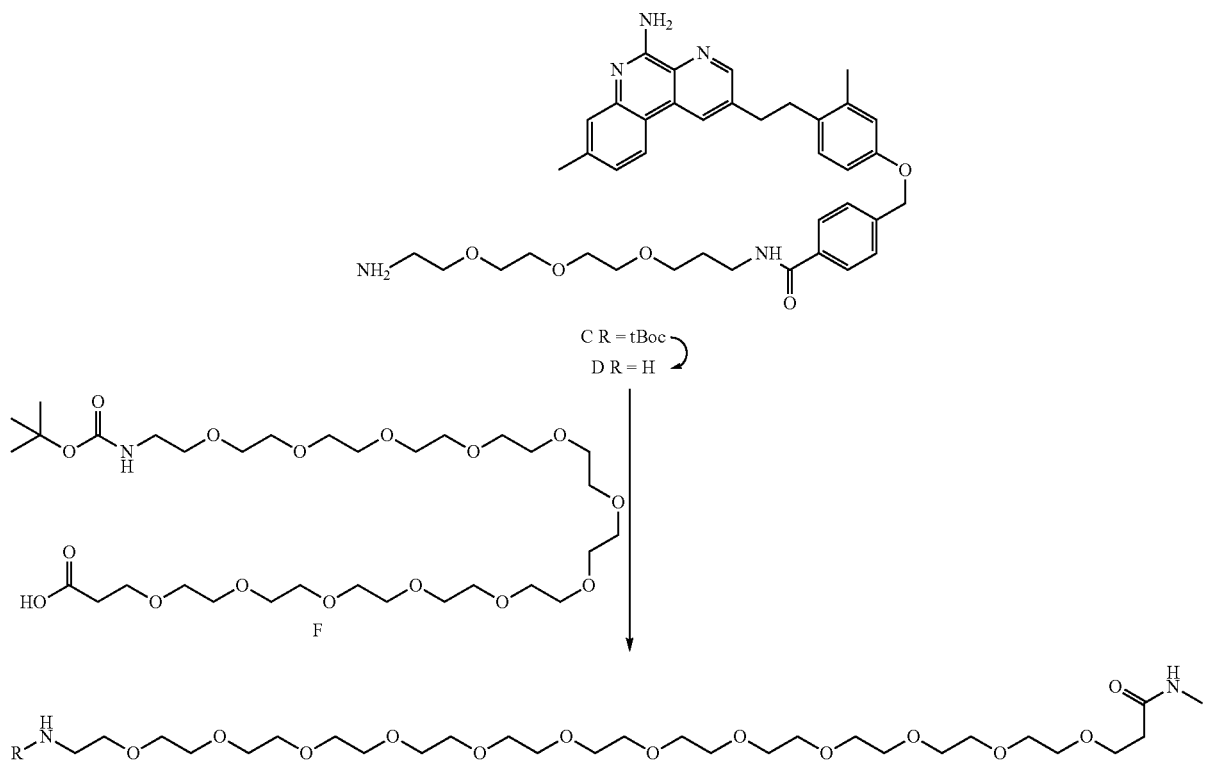

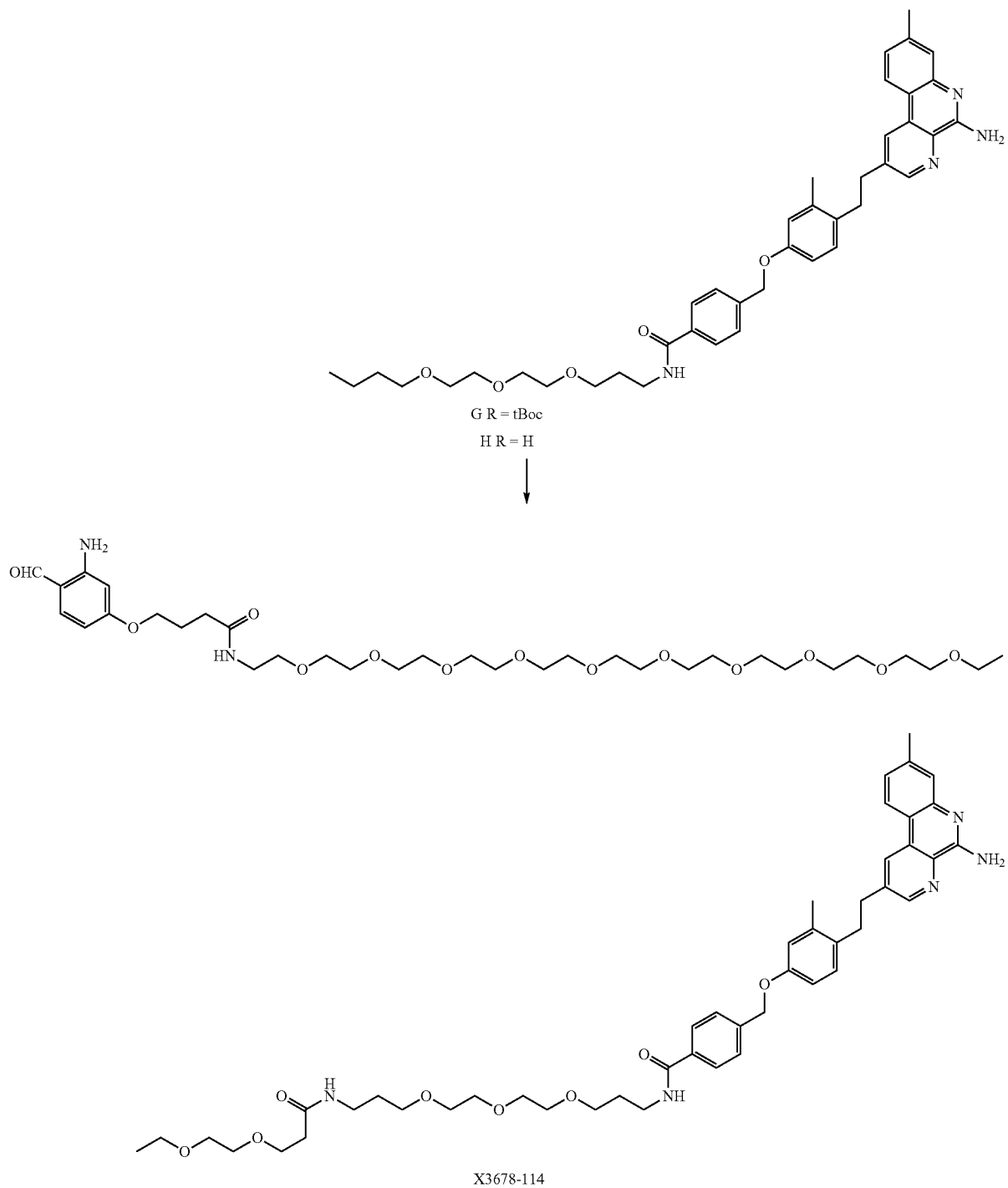

A mixture of dPEG-acid F (100 mg), HATU (52.8 mg) and DIEA (97 μL) in 2.0 mL DMF was stirred at room temperature for 30 minutes. Amine D (prepared from 109 mg of compound C) was added and the reaction was stirred at room temperature until completion as monitored by HPLC. The product was isolated by preparative RP-HPLC. The Boc group of product G (138 mg) from the previous step was removed by treatment of 3 N HCl in methanol, followed by concentration to dryness. A mixture of lithium 4-(3-amino-4-formylphenoxy)butanoate (25.2 mg), HATU (38.0 mg) and DIEA (69.7 μL) in 2.0 mL DMF was stirred at room temperature for 30 minutes. Amine H was added and the reaction was stirred at room temperature until completion monitored by HPLC. The product (X3678-114) was isolated by preparative HPLC. MS (ESI+): m/z 743.00 ($MH_2^{2+}/2$).

Example 38-4

Synthesis of 2-(4-Acetyl-3-aminophenoxy)-N-(3-nitrobenzyl)acetamide (TU633-068)

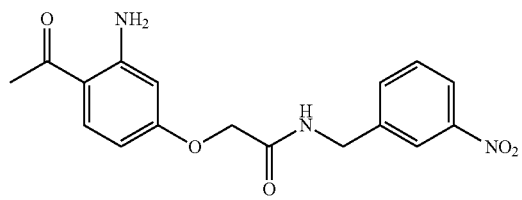 [SMILES: CC(=O)c1ccc(OCC(=O)NCc2cccc([N+](=O)[O-])c2)cc1N]

Lithium 2-(4-acetyl-3-aminophenoxy)acetate (215 mg), HBTU (379 mg), and 10 mL DMF were combined in a 20 mL glass vial and the resulting slurry was stirred at ambient temperature for 1 hour at which time the reaction mixture became almost homogeneous. To the vial, then, were added 3'-nitrobenzylamine HCl (192 mg) and DIEA (191 µL), and the reaction was stirred at ambient temperature for 30 minutes. The reaction mixture was diluted with EtOAc, washed successively with water, sat aq. NaCl, dried over Na$_2$SO$_4$, filtered and concentrated under reduced pressure. The crude material was purified by silica gel flash chromatography (hexanes/EtOAc), affording the title compound as a yellow solid. MS (ESI+): m/z 344.10 (MH+). H-NMR (400 MHz, CDCl3): 2.526 (3H, 3), 4.587 (2H, s), 4.641 (2H, d, J=6.4 Hz), 6.091 (1H, d, J=2.8 Hz), 6.239 (1H, dd, J=2.8 Hz, 8.8 Hz), 6.969 (1H, br.s), 7.511 (1H, t, J=7.6 Hz), 7.624 (1H, d, J=7.6 Hz), 7.678 (1H, d, J=8.8 Hz), 7.849 (1H, m), 8.131 (1H, s), 8.141 (1H, d, J=7.6 hz).

Example 38-5

Synthesis of 2-(3-Amino-4-formylphenoxy)-N-(4-nitrobenzyl)acetamide (TU3627-020)

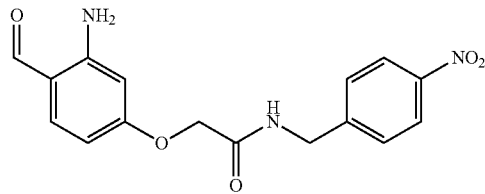 [SMILES: Nc1cc(OCC(=O)NCc2ccc([N+](=O)[O-])cc2)ccc1C=O]

Lithium 2-(3-amino-4-formylphenoxy)acetate (44.2 mg) and HBTU (79.6 mg) were put in a 20 mL glass vial and dry DMF (5 mL) was added. The resulting slurry was stirred at ambient temperature, which turned homogeneous within 10 minutes. After 15 min DIEA (50 µL) and 4'-nitrobenzylamine HCl (37.7 mg) were added to the reaction mixture, and the reaction was stirred at ambient temperature. After 30 minutes LC-MS analysis revealed a complete reaction. The reaction mixture was partitioned between EtOAc and water. The organic layer was separated, washed successively with dil. aq. citric acid, sat. aq. NaHCO$_3$, and sat. aq. NaCl, dried over Na$_2$SO$_4$, filtered and concentrated under reduced pressure, affording the title compound as a tan solid. MS (ESI+): m/z 330.10 (MH+). H-NMR (400 MHz, DMSO-d6): 4.463 (2H, d, J=6.0 Hz), 4.597 (2H, s), 6.246 (1H, d, J=2.4 hz), 6.308 (1H, dd, J=2.4 Hz, 8.8 Hz), 7.235 (1H, br.s), 7.465 (1H, d, J=8.8 Hz), 7.518 (2H, d, J=8.8 Hz), 8.173 (2H, d, J=8.8 Hz), 8.821 (1H, t, J=6.2 Hz), 9.657 (1H, s). C-NMR (400 MHz, DMSO-d6): 41.415, 66.627, 98.724, 104.297, 113.217, 123.267, 128.056, 137.581, 146.303, 147.287, 152.698, 162.872, 167.526, 191.685.

Example 38-6

Synthesis of 2-(3-Amino-4-formylphenoxy)-N-(2-(2,4-dinitrophenylamino)ethyl)acetamide (TU3627-022)

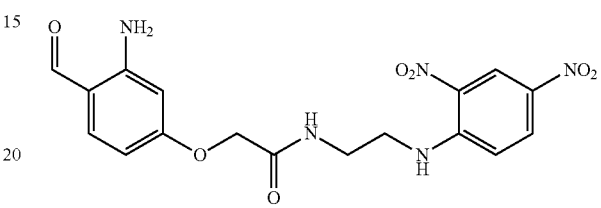

The title compound was prepared in the same way as TU3627-020 except that N$^1$-(2,4-dinitrophenyl)ethane-1,2-diamine (Oakwood, cat #015083, 45.2 mg) was used instead of 4'-nitrobenzylamine HCl in the absence of DIEA. TU3627-022 was obtained as a yellow solid. Rf. 0.15 (SiO2, 5% MeOH in DCM). MS (ESI+): m/z 404.10 (MH+). H-NMR (400 MHz, DMSO-d6): 3.420 (2H, m), 3.593 (2H, m), 4.467 (2H, s), 6.181 (1H, d, 2.0 Hz), 9.248 (1H, dd, J=2.4, 8.8 Hz), 7.173 (2H, br.s), 7.302 (1H, d, J=9.6 Hz), 7.406 (1H, d, J=8.4 hz), 8.230 (1H, dd, J=2.4, 9.6 Hz), 8.370 (1H, t, J=6.0 Hz), 8.841 (1H, d, J=2.8 Hz), 8.924 (1H, t, J=5.6 Hz), 9.618 (1H, s).

Example 38-7

Synthesis of 4-(3-Amino-4-formylphenoxy)-N-(2-(2,4-dinitrophenylamino)ethyl)butanamide (TU3627-088)

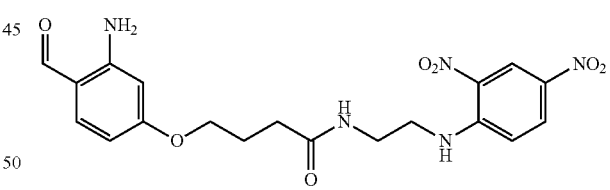

Lithium 4-(3-amino-4-formylphenoxy)butanoate (50 mg), HBTU (80 mg) and DMF (2 mL) were combined in a 20 mL glass vial and stirred at ambient temperature. After 30 minutes, N$^1$-(2,4-dinitrophenyl)ethane-1,2-diamine (Oakwood, 45 mg) was added in one portion and the reaction was stirred at ambient temperature overnight. The reaction mixture was diluted with EtOAc, washed successively with dilute aq. citric acid, water, sat. aq.NaHCO$_3$, water, and sat. aq.NaCl, dried over Na$_2$SO$_4$, filtered and concentrated under reduced pressure, affording the title compound as a yellow solid. Rf: 0.18 (SiO2, EtOAc). MS (ESI+): m/z 432.20 (MH+). H-NMR (400 MHz, DMSO-d6): 1.914 (2H, quint, J=7.0 Hz), 2.224 (2H, t, J=7.0 Hz), 3.349 (2H, q, J=6.0 Hz), 3.538 (2H, q, J=6.0 Hz), 3.928 (2H, t, J=6.4 Hz), 6.165 (1H, s), 6.176 (1H, dd, J=2.4, 10.0 Hz), 7.133 (1H, br.s), 7.268 (1H, d, J=10.0 Hz), 7.371 (1H, d, J=8.4 Hz), 8.167 (1H, t, J=5.8 Hz), 8.250 (1H, dd, J=2.8, 8.8 Hz), 8.835 (1H, d, J=2.8 Hz), 8.913 (1H, t, J=5.6 Hz), 9.599 (1H, s). C-NMR (100 MHz, DMSO-d6): 24.489, 31.436, 37.331, 42.745, 66.782, 98.040, 104.339, 112.751, 115.130, 123.472, 123.564, 129.725, 134.731, 137.484, 148.305, 152.824, 163.873, 172.251, 191.400.

Example 38-8

Synthesis of 4-(3-Amino-4-formylphenoxy)-N-(4-nitrobenzyl)butanamide (3793-001)

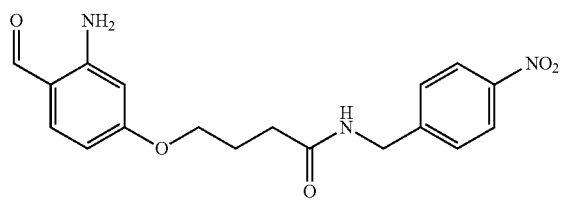 [SMILES: Nc1cc(OCCCC(=O)NCc2ccc([N+](=O)[O-])cc2)ccc1C=O]

HATU (114.1 mg) was added to a 1 mL DMF solution of lithium 4-(3-amino-4-formylphenoxy)-butanoate (68.7 mg), and the reaction was shaken at room temperature for 1 hour. The resulting solution was then added to a 1 mL DMF solution of 4-nitrobenzylamine HCl salt (56.6 mg) and triethylamine (84 µL), with another 1 mL DMF to help transfer. The reaction was stirred at room temperature for 2 hours. Upon completion, the reaction mixture was partitioned between 4 mL of 10% NaCl$_{(aq)}$ and 8 mL of EtOAc. The phases were separated and the aqueous layer was extracted again with 8 mL EtOAc. The combined organic layers were dried over Na$_2$SO$_4$, filtered and concentrated under reduced pressure, affording a crude orange oil. The crude oil was purified by silica gel flash column chromatography with gradient elution of 0-10% MeOH/DCM to give the desired product as a light yellow solid. MS (ESI+): m/z 358.2. $^1$H NMR (400 MHz, CDCl$_3$): 9.70 (s, 1H), 8.14 (d, J=8.8 Hz, 2H), 7.40 (d, J=8.8 Hz, 2H), 7.35 (d, J=8.4 Hz, 1H), 6.26 (dd, J=2.2 Hz, 8.8 Hz, 1H), 6.20 (br, 2H), 6.03 (d with br, J=2.0 Hz, 2H), 4.54 (d, J=6.0 Hz, 2H), 4.02 (t, J=5.8 Hz, 2H), 2.47 (t, J=7.0 Hz, 2H), 2.17 (quintet, J=6.5 Hz, 2H). $^{13}$C NMR (100 MHz, CDCl$_3$): 192.0, 172.2, 164.4, 152.2, 147.2, 145.8, 137.8, 128.2, 123.9, 113.9, 105.3, 98.9, 66.7, 42.8, 32.5, 24.8.

Example 38-9

Synthesis of 3-(4-acetyl-3-aminophenyl)-2-(4-nitrobenzamido)propanoic acid (X3471-116)

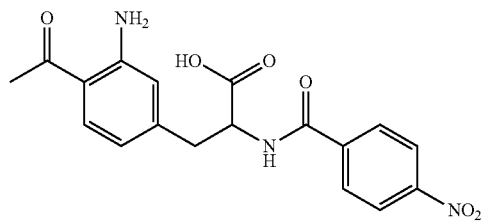 [SMILES: CC(=O)c1ccc(CC(NC(=O)c2ccc([N+](=O)[O-])cc2)C(=O)O)cc1N]

To 4-nitrobenzoic acid (50.1 mg), HATU (114 mg) and DIEA (105 µL) was added 1 mL DMF and the mixture was stirred for 30 minutes. Then the resulting solution was added to 3-(4-acetyl-3-aminophenyl)-2-aminopropanoic acid (66.7 mg, 1.0 equiv) in 1.0 mL DMF, and the reaction was stirred at room temperature, monitored by LC-MS. The title product was then isolated by preparative HPLC. $^1$H NMR (400 MHz, MeOD): δ 8.28 (d, J=8.8 Hz, 2H), 7.93 (d, J=8.8 Hz, 2H), 7.72 (d, J=8.4 Hz, 1H), 6.69 (d, J=1.6 Hz, 1H), 6.61 (dd, J'=8.4 Hz, J''=1.6 Hz, 1H), 3.28 (dd, J'=13.8 Hz, J''=10.0 Hz, 1H), 3.02 (dd, J'=13.8 Hz, J''=10.0 Hz, 1H), 2.51 (s, 3H); ESI-MS (m/z) 372.34 (MH$^+$).

Example 38-10

Synthesis of 4-(3-Amino-4-formylphenoxy)butanoyl-AlaGlySerArgSerGly(D-Ala)LysChaValAlaAlaTrpThrLeuLysAla(D-Ala)Gly-OH (3647-104)

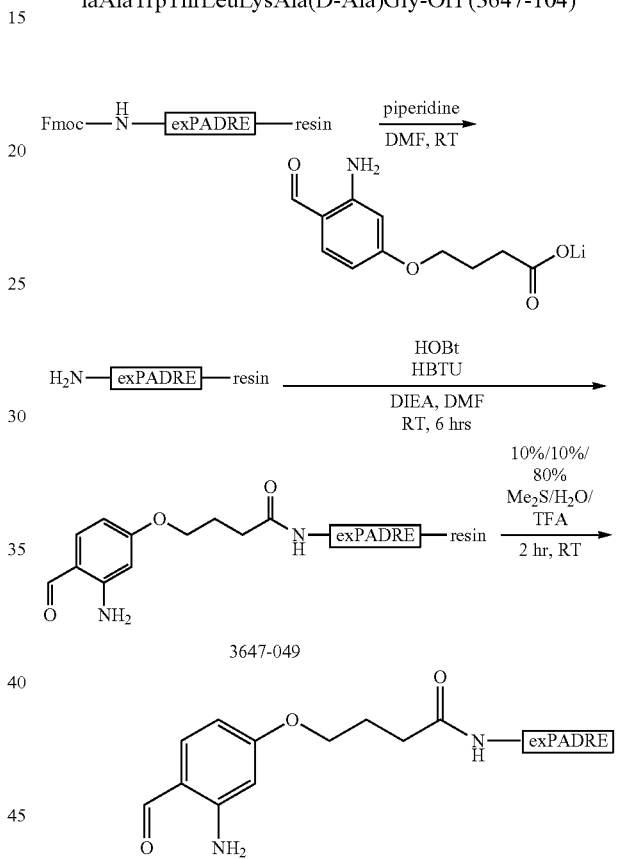

exPADRE = AlaIGlySerArgSerGly(DAla)LysChaValAlaAlaTrpThrLeuLysAla(D-Ala)Gly-OH

The Fmoc group of Fmoc-exPADRE CLEAR resin (549.3 mg, 0.1 mmol, purchased from Peptide International Inc.) was removed by 20% piperidine/DMF (8 mL×3). The resin was washed by DMF (1.5 mL×5). Then the resin was treated with a 3 mL DMF solution of lithium 4-(3-amino-4-formylphenoxy)-butanoate (34.4 mg), HBTU (45.5 mg), HOBt (16.2 mg), and DIEA (52 µL) for 6 hours at room temperature. The resin was washed with DMF and the peptide was cleaved from the resin using H$_2$O/Me$_2$S/TFA (10/10/80 v/v %, 10 mL) for 2 hours at room temperature. The cleavage slurry was filtered through glass wool, and most of the TFA was removed from the filtrate by evaporation. The residue was neutralized with 1 N NaOH$_{(aq)}$ and diluted with acetonitrile, followed by dialysis using SpectraPro™ dialysis membrane (MWCO of 1000) in 50% MeCN$_{(aq)}$ (4 L×10). The solution remained in the dialysis membrane was lyophilized, affording the desired product as white solid. ESI-MS calculated for $C_{94}H_{150}N_{26}O_{26}$ $[M+2H]^{2+}/2$: 1030.6, $[M+3H]^{3+}/3$: 687.4; observed: 1030.7, 687.6.

Example 38-11

Synthesis of 3-(4-Acetyl-3-aminophenyl)propanoyl-Gly(D-Ala)LysChaValAlaAlaTrpThrLeuLysAla(D-Ala)Gly-OH (3465-143)

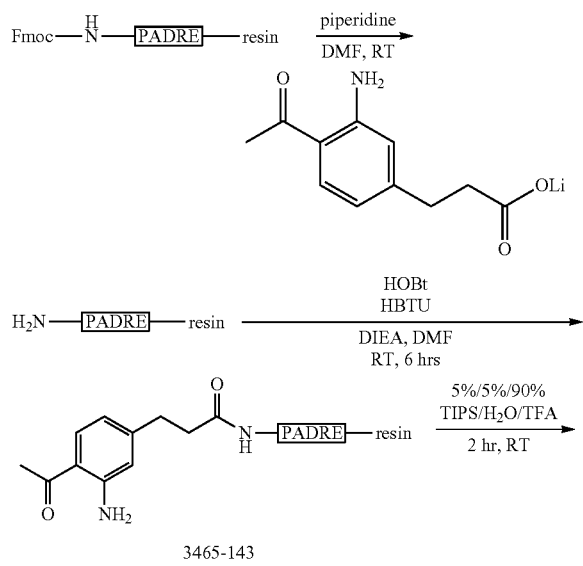

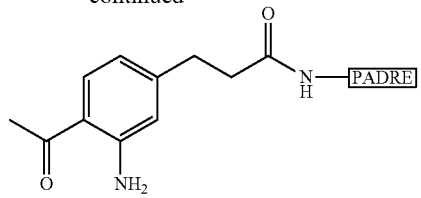

3465-143

PADRE = Gly(DAla)LysChaValAlaAlaTrpThrLeuLysAla(D-Ala)Gly-OH

The Fmoc group of Fmoc-PADRE CLEAR resin (105.3 mg, 0.02 mmol, purchased from Peptide International Inc.) was removed by 20% piperidine/DMF (8 mL×3). The resin was washed by DMF (1.5 mL×5). Then the resin was coupled with a 0.5 mL DMF solution of lithium 3-(4-acetyl-3-aminophenyl)propanoate (5.1 mg), HBTU (9.1 mg), and HOBt (3.3 mgl) for 7 hours at room temperature. The resin was washed with DMF and the peptide was cleaved from the resin by TIPS/H₂O/TFA (5/55/90 v/v %, 3 mL) for 2 hours. The cleavage slurry was filtered through glass wool and most TFA was removed from the filtrate by evaporation. The residue was washed by hexanes (3 mL×3), and dissolved in 50% $MeCN_{(aq)}$. After lyophilization, the crude product was obtained which was then purified by preparative HPLC, affording the desired product as a light yellow powder. ESI-MS calculated for $C_{77}H_{120}N_{18}O_{18}$ $[M+2H]^{2+}$: 793.5, $[M+3H]^{3+}/3$: 529.3; observed: 793.6, 529.4.

Example 38-12

Synthesis of 6-(4-(3-Amino-4-formylphenoxy)butanamido)hexyl-5'-\*T\*C\*C\*A\*T\*G\*A\*C\*G\*T\*T\*C\*C\*T\*G\*A\*C\*G\*T\*T-3' (\*: phosphothioate) (3647-057)

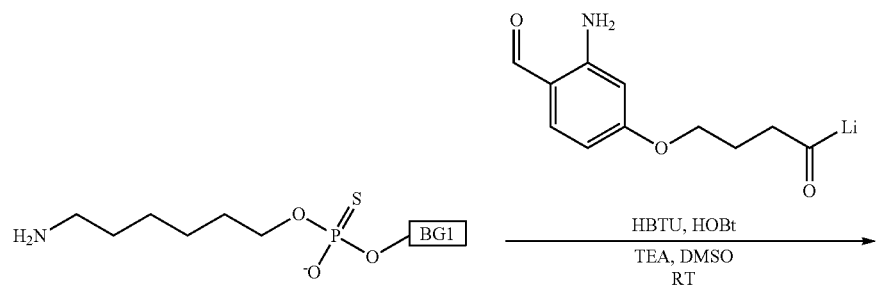

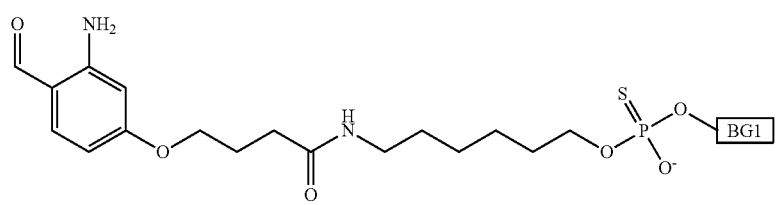

3647-057

BG1 = 5'\*T\*C\*C\*A\*T\*G\*A\*C\*G\*T\*T\*C\*C\*T\*G\*A\*C\*G\*T\*T-3' (\*: phosphothioate)

HBTU (6.1 mg), HOBt (2.2 mg), and triethylamine (7 µL) were added to a 1 mL DMSO solution of lithium 4-(3-amino-4-formylphenoxy)-butanoate (4.6 mg), and the reaction was shaken at room temperature for 1 hour. A 276 µL aliquot of the resulting solution was then added to a 1.2 mL DMSO solution of amino-modified BG1 oligo (12.1 mg, 1.8 µmol, purchased from Integrated DNA Technologies, Inc.) and triethylamine (15 µL), and the reaction was shaken at room temperature for 2 days. The reaction mixture was diluted with water and dialyzed against water (4 L×10) using Slide-A-Lyzer™ (MWCO of 3500). The dialyzed solution was lyophilized, affording the desired product as a white solid ESI-Q-TOF calculated for $C_{211}H_{273}N_{69}O_{108}P_{20}S_{20}$: 6759.7; observed: 6759.1.

Example 38-13

Synthesis of 6-(3-(4-acetyl-3-aminophenyl)propanamido)hexyl-5'-*T*C*G*T*C*G*T*T*T*T* C*G*G*C*G*C*G*C*G*C*C*G-3' (*:phosphothioate) (3597-033)

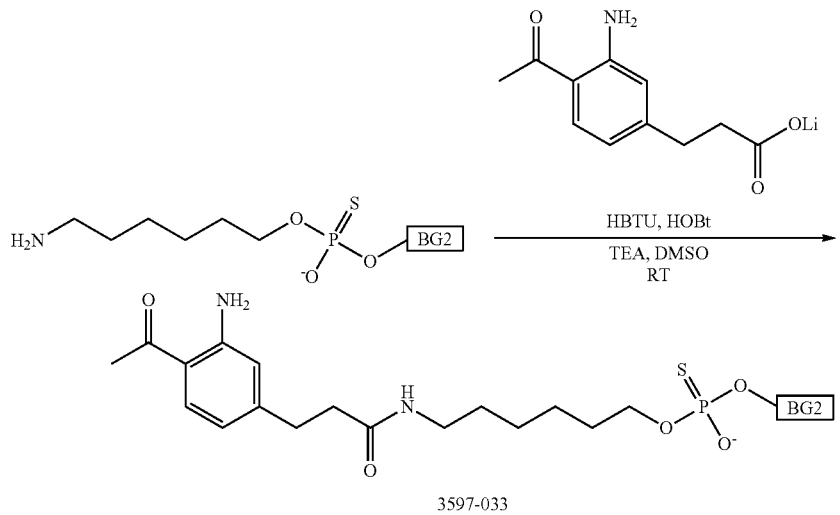

BG2 = 5'*T*C*G*T*C*G*T*T*T*T*C*G*G*C*G*C*G*C*G*C*C*G-3' (*: phosphothioate)

HBTU (5.9 mg) and HOBt (2.1 mg) was added into a 1 mL DMSO solution of lithium 3-(4-acetyl-3-aminophenyl)propanoate (3.3 mg), and the reaction was shaken at room temperature for 1 hour. A 20 µL aliquot of the resulting solution was then added to a 0.2 mL DMSO solution of amino-modified BG2 oligo (1.88 mg, 0.26 µmol, purchased from Integrated DNA Technologies, Inc.) and triethylamine (2 µL), and the reaction was shaken at room temperature for 20 hours. The reaction mixture was applied to a NAP-25™ column equilibrated with $H_2O$ and eluted with $H_2O$. Every 1 mL fraction was monitored by LC-MS and the fractions containing the desired product were combined and lyophilized, affording the desired product as a white solid. MS (ESI+): m/z 1858.8 ($[M+4H]^{4+}/4$).

Example 38-14

Synthesis of 6-(4-(3-amino-4-formylphenoxy)butanamido)hexyl-5'-*T*C*G*T*C*G*T*T*T*T*C*G*G*C*G*C*G*C*G*C*C*G-3' (*:phosphothioate) (3597-167)

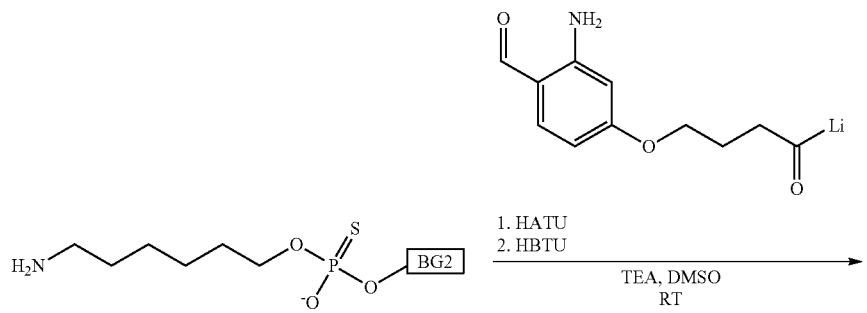

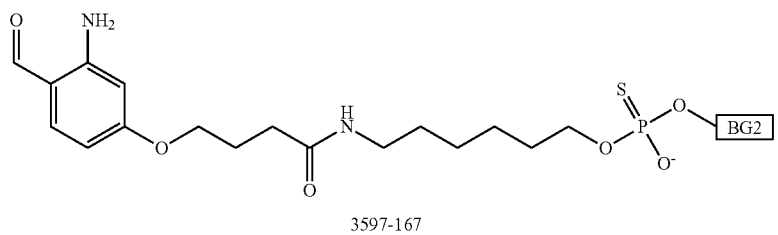

3597-167

HATU (7.4 mg) was added to a 1 mL DMSO solution of lithium 4-(3-amino-4-formylphenoxy)-butanoate (5.5 mg), and the reaction was shaken at room temperature for 1 hour. A 60 µL aliquot of the resulting solution was then added to a 0.6 mL DMSO solution of amino-modified BG2 oligo (6.9 mg, 1.0 µmol) and triethylamine (7.5 µL), and the reaction was shaken at room temperature for 20 hours. Then another 60 µL aliquot of the activated ester solution that was freshly prepared in the same way except for using HBTU instead of HATU was added to the reaction mixture, and the reaction was shaken for an additional 2 days. The reaction mixture was separated into 3 portions. Each portion was applied to a NAP-25™ column equilibrated with $H_2O$ and eluted with $H_2O$. Every 1 mL fraction was monitored by LC-MS and the fractions containing the desired product were combined and lyophilized, affording the desired product as a white solid. ESI-Q-TOF calculated for $C_{229}H_{296}N_{78}O_{120}P_{22}S_{22}$: 7442.8; observed: 7442.7.

Example 39

Synthesis of Spin-Label-ABA Reagents

Example 39-1

Synthesis of N-(3-Amino-4-formylphenyl)-1-hydroxy-2,2,5,5-tetramethyl-3-pyrrolin-1-oxyl-3-carboxamide (X3626-112b)

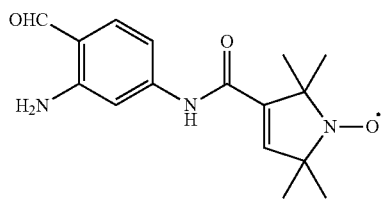

To 2,2,5,5-tetramethyl-3-pyrrolin-1-oxyl-3-carboxylic acid (55.3 mg), HBTU (102 mg) and DIEA (105 μL) were added 2.0 mL DMF. After stirred at room temperature for 30 minutes, 2,4-diaminobenzaldehyde (40.8 mg) was added. The mixture was stirred at room temperature until the reaction was complete, monitored by HPLC. The title product was isolated by preparative HPLC. MS (ESI+): m/z 303.15 (MH+).

Example 40

Synthesis of Biotin-ABA Reagents

Example 40-1

Synthesis of N-(3-amino-4-formylphenyl)-1-(biotinamido)-3,6,9,12-tetraoxapentadecan-15-amide (X3626-140)

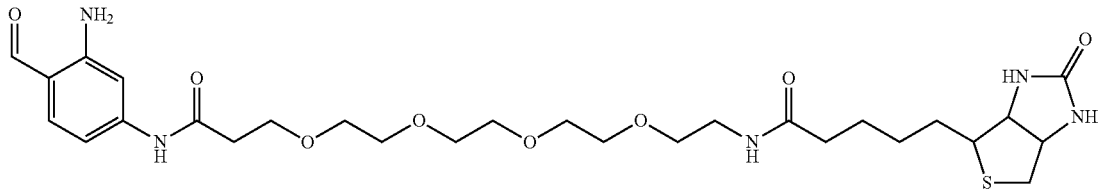 [SMILES: Nc1cc(NC(=O)CCOCCOCCOCCOCCNC(=O)CCCCC2SCC3NC(=O)NC32)ccc1C=O]

To 2,4-diaminobenzaldehyde (11.5 mg), NHS-dPEG™4 biotin (QuantaBiodesign, cat #10200, 50 mg) and DMAP (10.4 mg) was added 1.0 mL DMF. The reaction mixture was stirred at room temperature until the reaction was complete, monitored by HPLC. The product was isolated by silica gel flash chromatography. MS (ESI+): 610.28 (MH+).

Example 40-2

Synthesis of N-(1-(3-Amino-4-formylphenoxy)-2-oxo-7,10,13-trioxa-3-azahexadecan-16-yl)-biotinamide (X3626-142)

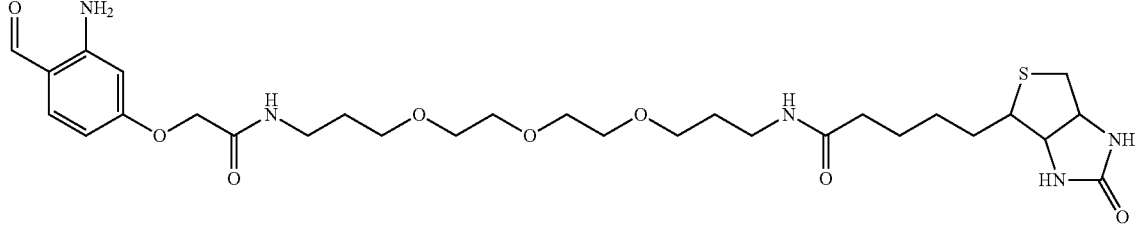 [SMILES: Nc1cc(OCC(=O)NCCCOCCOCCOCCCNC(=O)CCCCC2SCC3NC(=O)NC32)ccc1C=O]

To lithium 2-(3-amino-4-formylphenoxy)acetate (45.3 mg), HBTU (77.8 mg) and DIEA (31 μL) was added 1 mL DMF, and the mixture was stirred for 30 minutes. The resulting solution was added to biotin-dPEG™$_3$-NH$_3$$^+$TFA (QuantaBiodesign, cat #10193, 100 mg), DIEA (47 μL) in 1.0 mL DMF, and the reaction was stirred at room temperature, monitored by LCMS. The product was isolated by preparative HPLC. MS (ESI+): 624.30 (MH+).

Example 41

Synthesis of Fluorescent-PEG-ABA Reagents

Example 41-1

Synthesis of Fluorescein-PEG-ABA (X3757-48)

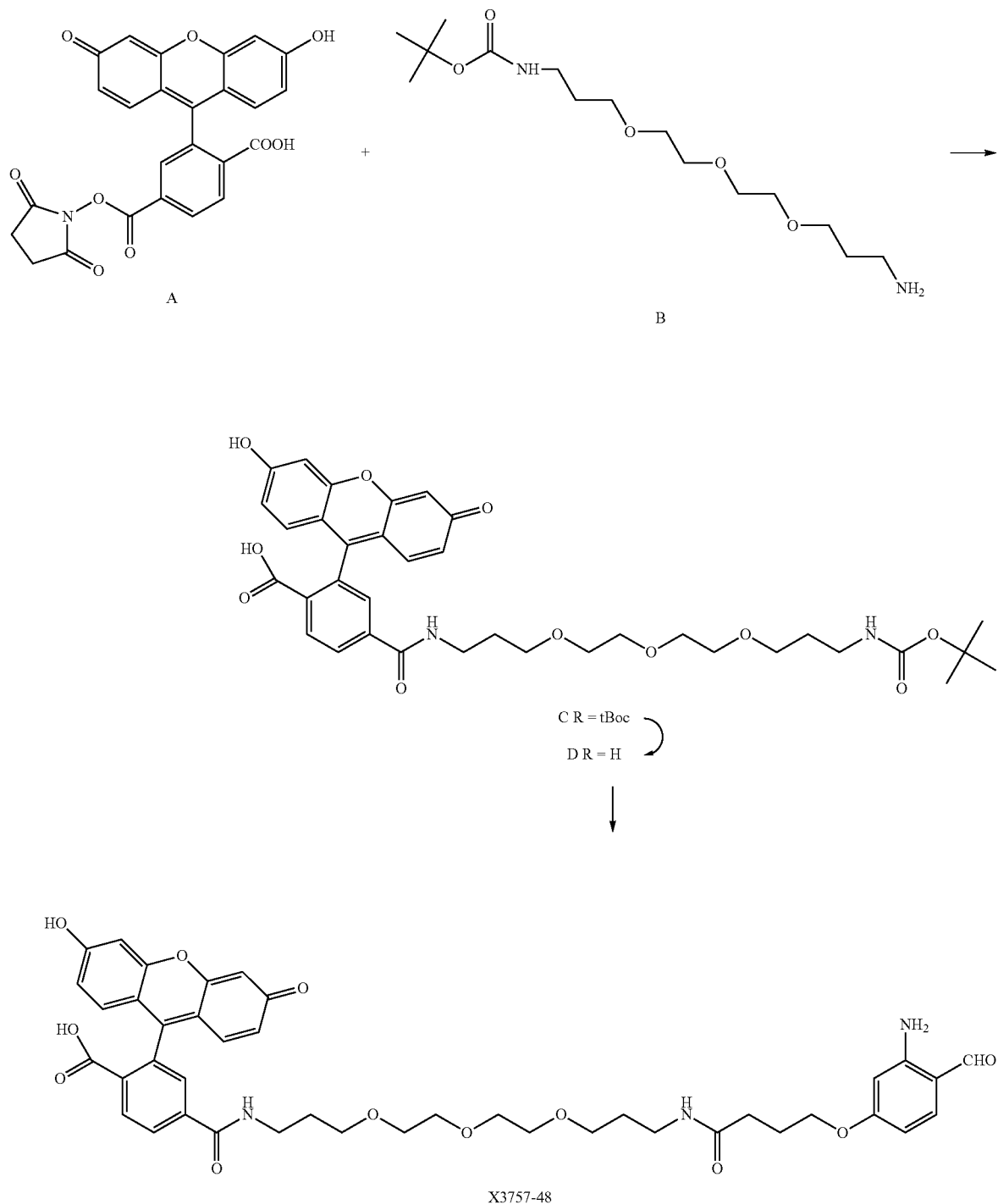

DMF (2.0 mL) was added to NHS-Fluorescein A (23.6 mg), amine B (17.6 mg) and DIEA (8.7 μL). The mixture was stirred at room temperature until A was consumed, monitored by HPLC. The product C was isolated by preparative HPLC. ESI-MS (m/z) 679.72 (MH$^+$). The product (C, 7.4 mg) from then dissolved in 3 M HCl (1.0 mL), and methanol was removed by evaporation after stirring 5 minutes at room temperature. This operation was repeated, resulting in removal of the Boc group giving amine D. To amine D were added lithium 4-(3-amino-4-formylphenoxy)butanoate (2.3 mg), HBTU (3.8 mg), DIEA (7.0 µL) and DMF (2 mL) at room temperature. The title product was then isolated by preparative HPLC. MS (ESI+): 784.30 (MH+).

Example 42

Synthesis of Oligosaccharide-ABA Reagents

Example 42-1

Synthesis of Gal-Glu-1-amide of 3-amino-4-formylphenoxybutyrate (3793-050)

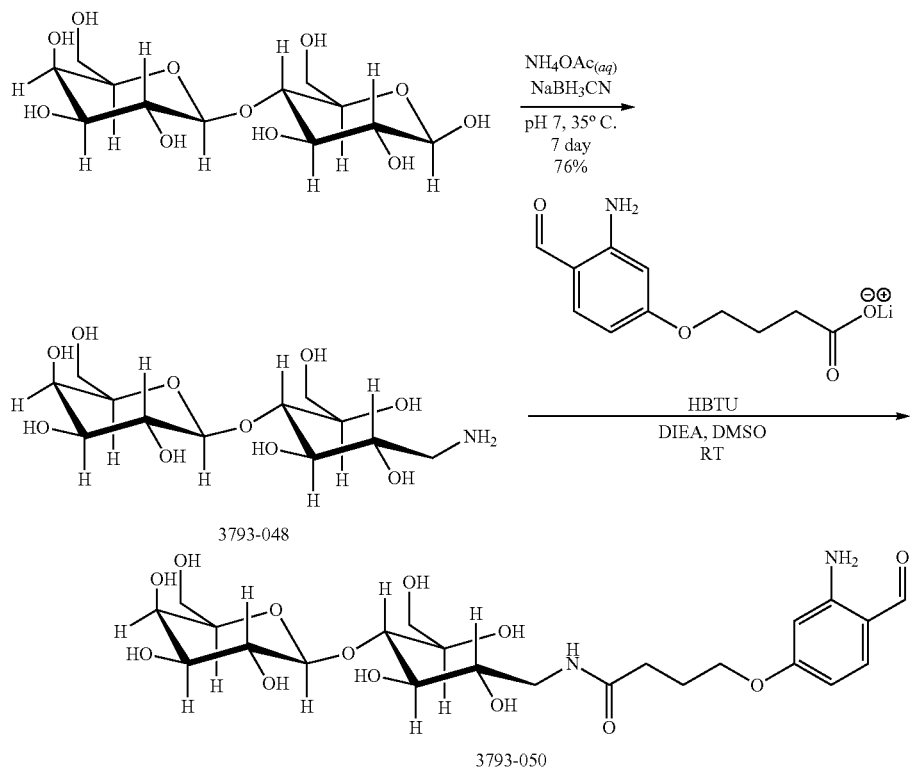

NaBH$_3$CN (94.3 mg) was added to a H$_2$O (10 mL) solution of NH$_4$OAc (771 mg) and lactose (180 mg) at pH 7 and the reaction was stirred at 35° C. for 7 days. The reaction mixture was lyophilized, and the residue was dissolved in H$_2$O, followed by a passage through Dowex 1X8-400 anion exchange resin (OH– form, 45 g) to remove excess BH$_3$CN$^-$, its byproducts and acetate. The eluent was lyophilized, affording the crude product, which was purified by cation exchange chromatography using Dowex 50WX8-400 resin (H+ form, 30 g), affording the desired product (3793-048) as light yellow powder. ESI-MS calculated for C$_{12}$H$_{25}$NO$_{10}$ [MH]$^+$: 344.1; observed: 344.2.

Lithium 3-amino-4-formylphenoxybutyrate (6.0 mg) was treated with HBTU (9.9 mg) and DIEA (7.7 µL) in anhydrous DMSO (200 µL) for 1 hour. A DMSO (250 µL) solution of Gal-Glu-1-amine (3793-048) (7.7 mg) from above was then added to the reaction mixture at room temperature, followed by agitation for 1 day. The reaction mixture was lyophilized and purified by prep HPLC-MS with NH₄OAc elution, affording the desired product (3793-050) as a yellow powder. ESI-MS calculated for $C_{23}H_{36}N_2O_{13}$ [MH]⁺: 549.2; observed: 549.3

Example 43

Synthesis of Phospholipid-ABA Reagents

Example 43-1

Synthesis of DOPE-ABA (TU3627-092)

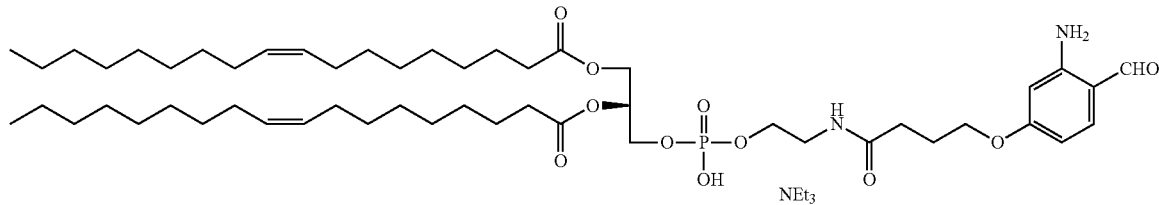 [SMILES: CCCCCCCC/C=C\CCCCCCCC(=O)OC[C@H](COP(=O)(O)OCCNC(=O)CCCOc1ccc(C=O)c(N)c1)OC(=O)CCCCCCC/C=C\CCCCCCCC ; "NEt3"]

Lithium 4-(3-amino-4-formylphenoxy)butanoate (34 mg) and HBTU (57 mg) were put in a 20 mL glass vial, and 2 mL DMF was added. The reaction was stirred at ambient temperature for 30 min for activation. In a separate 20 mL vial was put DOPE (76 mg, 1,2,-dioleoyl-sn-glycero-phosphoethanolamine, NOF Corp.), followed by DIEA (35 µL) and 3 mL DCM. The yellow solution of the activated ester in the first vial was transferred to the second vial, and the reaction was stirred at ambient temperature. After 24 hours, the whole reaction mixture was applied to a 12 g pre-packed SiO₂ column equilibrated with solvent A (solvent A: 5% NEt₃ in DMC, solvent B: 5% NEt₃ in MeOH), and the column was eluted with a linear gradient of 0 to 15% B in A over 15 minutes, affording partially purified product as a light yellow very viscous oil. This product was purified again by flash chromatography using a 12 g SiO₂ column (solvent A: 5% NEt₃ in DMC, solvent B: 5% NEt₃ in MeOH), and eluted with a linear gradient of 2 to 10% B in A over 15 minutes. The fraction containing the pure product was concentrated under reduced pressure, affording the triethylammonium salt of the title compound. Rf: 0.43 (SiO2, 10% MeOH in DCM). MS (ESI+): m/z 949.60 (MH+). H-NMR (400 MHz, CDCl3): 0.875 (6H, t, J=6.8 Hz), 1.28 (40H, broad multiple peaks), 1.318 (9H, t, J=7.4 Hz), 1.582 (4H, m), 2.00 (m, 8H), 2.124 (2H, quint, J=6.8 Hz), 2.28 (4H, m), 2.373 (2H, t, J=7.0 Hz), 3.042 (6H, q, J=7.2 Hz), 3.476 (2H, m), 4.00 (6H, m), 4.154 (1H, dd, J=6.8, 12.0 Hz), 4.373 (1H, dd, J=3.2, 12.0 Hz), 5.233 (1H, m), 5.337 (4H, m), 6.217 (1H, d, J=2.0 Hz), 6.255 (1H, dd, J=2.0, 8.4 Hz), 6.56 (2H, very broad peak), 7.313 (1H, d, J=8.8 Hz), 7.432 (1H, br.t, J=8.4 Hz), 9.674 (1H, s), 11.97 (1H, br.s)

Example 44

Reduction of PCL Coupling Linkage

Figure 54:
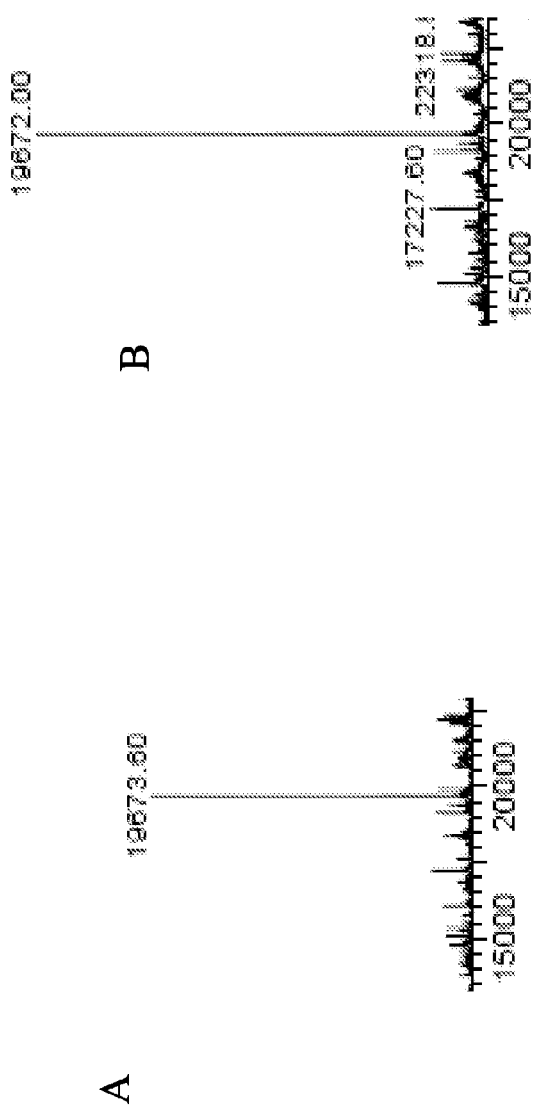
FIG. 54.

Reduction of the PCL coupling linkage was found to prevent the dissociation of PCL-based protein conjugates. FIG. 54A shows the ESI mass spectrometric analysis of hFGF21-Lys150PCL coupled to 2-ABA and then reduced with 20 mM NaCNBH₃ for 1 hour. FIG. 54B shows the ESI mass spectrometric analysis of the reduced hFGF21-Lys150PCL 2-ABA conjugate after being dialyzed into 10 mM phosphate buffer (pH 7.5) and incubated at 50° C. for 1 day.

Figure 55:
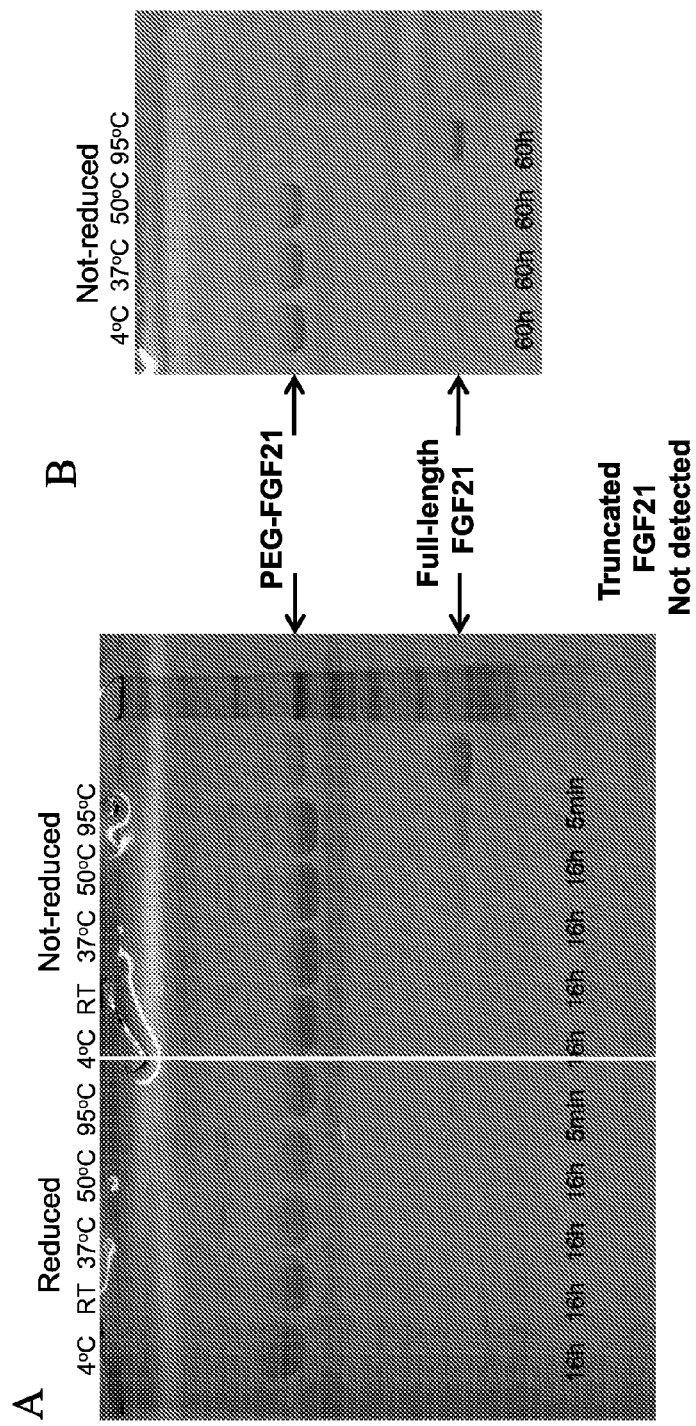
FIG. 55.

FIG. 55 demonstrates the stability of the PCL linkage for PEGylated FGF21 with and without reduction using NaCNBH₃. FGF21 mutant Arg154PCL was reacted with 30.3 kDa-2-ABA-PEG (see TU3627-024; Example 37-7) and purified. The purified FGF21Arg154PCL-30.3 kDa-2-ABA-PEG was reduced with 20 mM NaBH₃CN for 16 hrs (room temperature, pH 7.5, 100 mM protein). Samples were incubated for 16 hours at 4° C., room temperature, 37° C. and 50° C., and at 95° C. for 5 minutes. An SDS-PAGE gel of reduced samples and non-reduced samples are shown in FIG. 55A. In addition, FIG. 55B shows an SDS-PAGE gel for non-reduced samples incubated at for 60 hours at 4° C., room temperature, 37° C. and 50° C., and 95° C.

Example 45

NMR studies of PCL-A (Lys-P5C) and PCL-B (Lys-P2C) Covalently Modified by 2-ABA

The reaction of PCL-A (see 3647-125, Example 36-1) and PCL-B (see 3793-011, Example 36-2) with 2-aminobenzyaldehyde (2-ABA) and the structure of the resulting PCL-ABA adduct were studied by standard 1D and 2D nuclear magnetic resonance (NMR) spectroscopy.

For the PCL-A and PCL-B reaction with 2-ABA and subsequent characterization of the products, NMR data was acquired at 300 K on a Bruker Avance 400 MHz NMR instrument (Bruker Biospin, Billerica, Mass.) equipped with a ¹H/¹³C/¹⁹F/³¹P-QNP-cryoprobe. ¹H 1D spectra were typically recorded with 16 scans, relaxation delay of 5 s, 16384 complex data points with a sweep width of 12 ppm. ¹H-¹H COSY spectra were typically recorded with 4 scans, 256 t₁ experiments and ¹H-¹H ROESY spectra with 8 scans, 512 t₁ experiments. ¹H-¹³C HMBC spectra were typically recorded with 32 scans, 256 t₁ experiments and ¹H—¹³C HMQC spectra were typically recorded with 4 scans, 128 t₁ experiments using a spectral width of 222 ppm in the carbon dimension and 12 ppm or 7.5 ppm in the proton dimension.

For the characterization of the reduced adduct, all spectra were recorded at 300 K on a Bruker Avance 600 MHz instrument equipped with a ¹H/¹³C/¹⁵N-TXI-cryoprobe. ¹H spectra were typically recorded with 64 scans, relaxation delay of 2 s, 16384 complex data points with a sweep width of 14 ppm with excitation sculpting for water suppression. ¹H—¹H COSY spectra were typically recorded with 16 scans, 1024 t₁ experiments using a spectral width of 10 ppm. ¹H-¹³C HMQC spectra were typically recorded with 8 scans, 256 t₁ experiments using a spectral width of 160 ppm in the carbon dimension and 10 ppm in the proton dimension. ¹H-¹³C HMBC spectra were typically recorded with 88 scans, 256 t₁ experiments at 300K using a spectral width of 180 ppm in the carbon dimension and 10 ppm in the proton dimension.

The reaction of PCL-A with 2-ABA was monitored as follows: 1.0 mg of PCL-A synthesized as described in Example 36-1 was disolved in 0.5 mL of 1X PBS in $D_2O$. 10 μL of 10 mM 3-(trimethylsilyl)propionic acid (TSP) in $D_2O$ were added as internal standard and for concentration determination by NMR. 3.7 mg of 2-aminobenzaldehyde (2-ABA; purchased from Sigma) was dissolved in 0.5 mL of 1×PBS in $D_2O$ and 10 μL of 10 mM TSP. The concentration of both samples was determined by NMR. NMR signals of starting materials (Table 7) were assigned using standard NMR methods including $^1H$ 1D, $^1H$-$^1H$ COSY, $^1H$-$^1H$ ROESY, $^1H$-$^{13}C$ HMBC and $^1H$-$^{13}C$ HMQC experiments.

TABLE 7

NMR Signal Assignments of unreacted PCL-A and 2-ABA

| Atom Number | Shift (pp2m) | H's | Type | J (Hz) |
|---|---|---|---|---|
| 19 | 1.31 | 2 | m | — |
| 18 | 1.47 | 2 | quin | 7.34 |
| 4 | 1.68 | 1 | m | — |
| 20 | 1.74 | 1 | m | — |
| 4 | 2.16 | 1 | m | — |
| 3 | 2.57 | 1 | m | — |
| 17 | 3.14 | 1 | t | 6.97 |
| 21 | 3.59 | 1 | t | 6.24 |
| 5 | 4.51 | 1 | m | — |
| 12, 10 | 6.76 | 1 | m | — |
| 11 | 7.34 | 1 | ddd | 8.50, 7.03, 1.59 |
| 13 | 7.53 | 1 | dd | 8.19, 1.59 |
| 2 | 7.76 | 1 | m | — |
| 7 | 9.68 | 1 | s | — |

Figure 56:
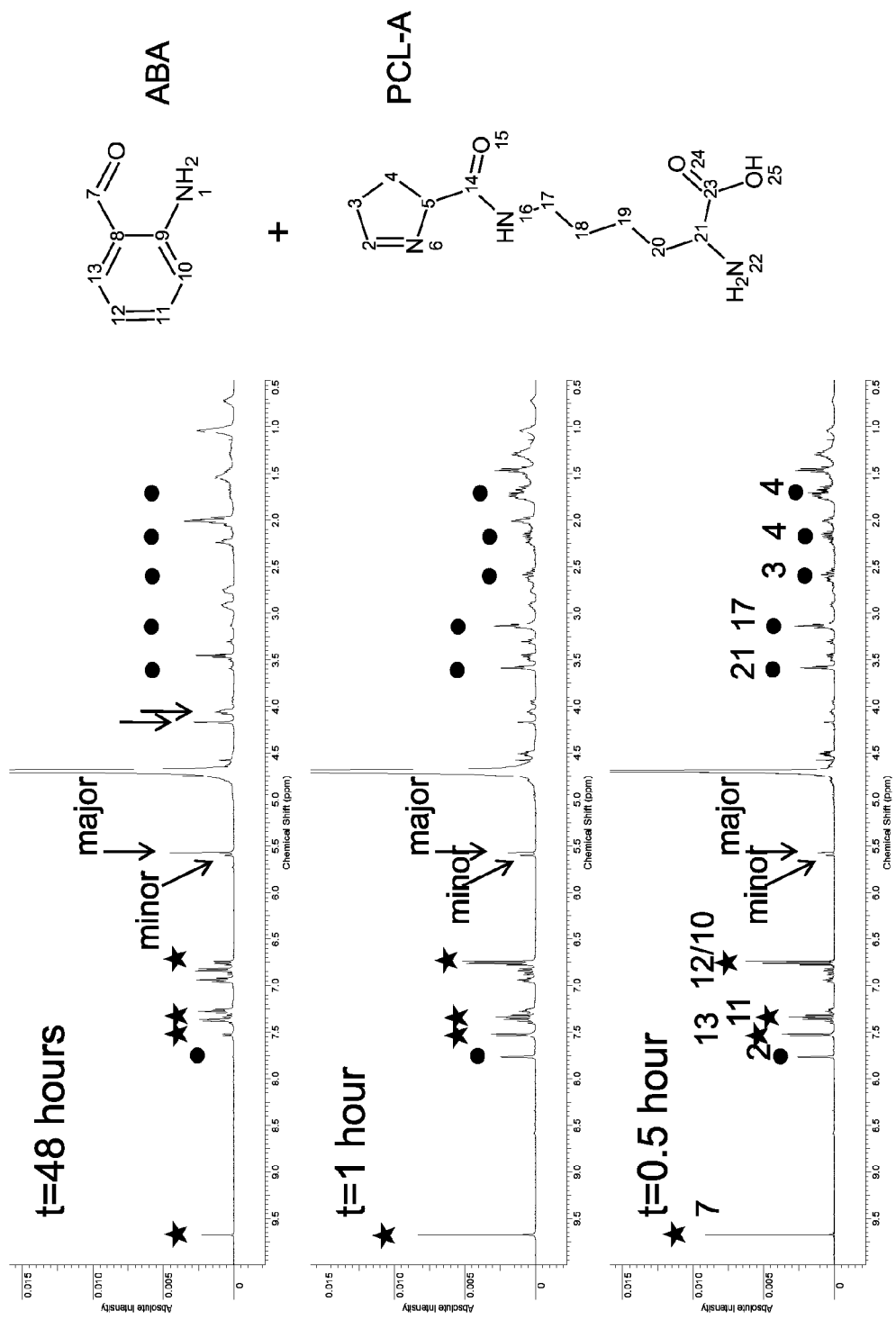
FIG. 56. NMR analysis of PCL-A reaction with 2-ABA

To initiate the reaction, 325 μL of PCL-A solution were mixed with 175 μL of the 2-ABA solution. The resulting reaction mixture was transferred to an NMR tube and contained PCL-A and 2-ABA at an approximate 1:1 molar ratio. The reaction was allowed to proceed at room temperature and NMR spectra were periodically acquired at the indicated times (FIG. 56). During the reaction signals for starting PCL-A material (dots) and for the 2-ABA reactant (stars) quickly disappeared and the reaction proceeded to completion with all PCL-A being converted (There was a slight excess of 2-ABA in the sample). In the first time point acquired 0.5 hrs after mixing, two new species were detected at a ratio of approximately 2:1 (representative resonances are marked by arrows). The minor species over the course of several days completely converted to the major species.

The final reaction product of PCL-A with 2-ABA was characterized by standard 1D $^1H$ and $^{13}C$, 2D $^1H$-$^1H$ COSY, $^1H$-$^1H$ ROESY, $^1H$-$^{13}C$ HMBC and $^1H$-$^{13}C$ HMQC NMR spectroscopy with samples prepared in $D_2O$ and d6-DMSO. The sample in d6-DMSO was purified by HPLC. Signal assignments for proton and carbon resonances and the observed correlations in $^1H$-$^{13}C$ HMBC spectra in d6-DMSO are summarized in Table 8.

TABLE 8

$^1H$—$^{13}C$ HMBC correlations observed for the major form of the PCL-A/2-ABA adduct (in d6-DMSO)

| | Correlations between | | $^1H$ | $^{13}C$ |
|---|---|---|---|---|
| No. | F2 Atom | F1 Atom | F2 (ppm) | F1 (ppm) |
| 1 | 1 | 2 | 5.77 | 72.69 |
| 2 | 4 | 2 | 2.00 | 72.73 |
| 3 | 4 | 2 | 1.84 | 72.83 |
| 4 | 5 | 2 | 3.78 | 72.59 |
| 5 | 7 | 2 | 5.42 | 72.72 |
| 6 | 1 | 3 | 5.76 | 32.36 |
| 7 | 2 | 3 | 4.06 | 32.20 |
| 8 | 4 | 3 | 1.82 | 26.41 |
| 9 | 4 | 3 | 1.82 | 32.22 |
| 10 | 4 | 3 | 2.01 | 32.42 |
| 11 | 5 | 3 | 3.78 | 32.41 |
| 12 | 2 | 4 | 4.06 | 26.55 |
| 13 | 5 | 4 | 3.78 | 26.55 |
| 14 | 7 | 4 | 5.43 | 26.38 |
| 15 | 2 | 5 | 4.06 | 64.16 |
| 16 | 4 | 5 | 1.85 | 63.96 |
| 17 | 4 | 5 | 2.01 | 64.04 |
| 18 | 10 | 7 | 6.66 | 71.92 |
| 19 | 13 | 7 | 7.21 | 71.95 |
| 20 | 17 | 7 | 2.87 | 71.90 |
| 21 | 17 | 7 | 2.38 | 71.99 |
| 22 | 1 | 8 | 5.76 | 120.55 |
| 23 | 7 | 8 | 5.42 | 120.43 |
| 24 | 10 | 8 | 6.67 | 120.29 |
| 25 | 11 | 8 | 7.09 | 120.35 |
| 26 | 12 | 8 | 6.70 | 120.32 |
| 27 | 1 | 9 | 5.77 | 148.47 |
| 28 | 2 | 9 | 4.06 | 148.42 |
| 29 | 7 | 9 | 5.42 | 148.50 |
| 30 | 11 | 9 | 7.09 | 148.43 |
| 31 | 12 | 9 | 6.70 | 148.55 |
| 32 | 13 | 9 | 7.21 | 148.39 |
| 33 | 1 | 10 | 5.77 | 115.57 |
| 34 | 7 | 10 | 5.43 | 115.78 |
| 35 | 11 | 10 | 7.09 | 115.53 |
| 36 | 12 | 10 | 6.70 | 115.47 |
| 37 | 13 | 10 | 7.21 | 115.50 |
| 38 | 13 | 11 | 7.21 | 129.27 |
| 39 | 10 | 12 | 6.66 | 118.14 |
| 40 | 1 | 13 | 5.77 | 128.39 |
| 41 | 7 | 13 | 5.43 | 128.48 |
| 42 | 11 | 13 | 7.09 | 128.49 |
| 43 | 12 | 13 | 6.70 | 128.11 |
| 44 | 4 | 14 | 2.00 | 173.00 |
| 45 | 4 | 14 | 1.88 | 173.08 |
| 46 | 4 | 14 | 1.83 | 173.09 |
| 47 | 5 | 14 | 3.78 | 173.11 |
| 48 | 17 | 14 | 2.87 | 173.28 |
| 49 | 17 | 14 | 2.37 | 173.29 |
| 50 | 18 | 17 | 1.04 | 39.08 |
| 51 | 18 | 17 | 0.73 | 39.40 |
| 52 | 19 | 17 | 1.04 | 39.08 |
| 53 | 17 | 18 | 2.37 | 26.26 |
| 54 | 17 | 18 | 2.86 | 26.47 |
| 55 | 19 | 18 | 1.03 | 26.58 |
| 56 | 20 | 18 | 1.48 | 26.36 |
| 57 | 20 | 18 | 1.34 | 26.48 |
| 58 | 17 | 19 | 2.86 | 22.49 |
| 59 | 17 | 19 | 2.37 | 22.95 |
| 60 | 18 | 19 | 0.72 | 22.37 |
| 61 | 18 | 19 | 1.07 | 22.53 |
| 62 | 20 | 19 | 1.49 | 22.52 |
| 63 | 20 | 19 | 1.34 | 22.55 |
| 64 | 21 | 19 | 2.93 | 22.55 |
| 65 | 18 | 20 | 1.02 | 30.46 |
| 66 | 18 | 20 | 0.73 | 30.63 |
| 67 | 19 | 20 | 1.02 | 30.46 |
| 68 | 20 | 20 | 1.50 | 30.66 |
| 69 | 21 | 20 | 2.93 | 30.83 |
| 70 | 19 | 21 | 1.02 | 54.23 |
| 71 | 20 | 21 | 1.34 | 53.98 |
| 72 | 20 | 21 | 1.48 | 54.02 |
| 73 | 20 | 23 | 1.35 | 169.78 |
| 74 | 20 | 23 | 1.49 | 169.78 |
| 75 | 21 | 23 | 2.94 | 169.73 |

Figure 57:
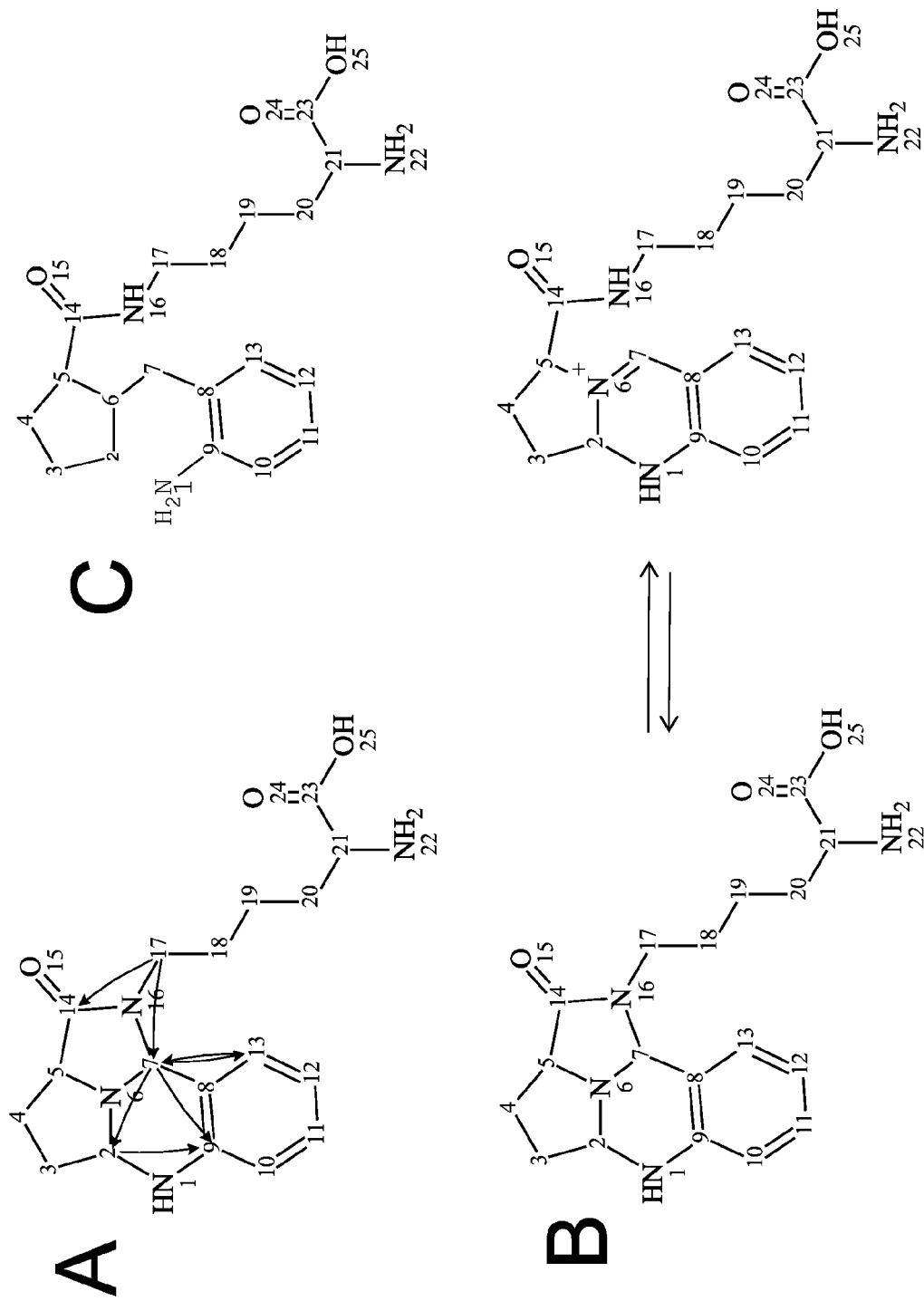
FIG. 57.

The numbering of the atoms and selected through bond correlations in the HMBC are shown in FIG. 57A. In contrast to the observations in the PCL-A starting material, the two methylene protons on carbon 17 are observed at two different chemical shift values. These protons also show a heteronuclear through bond correlation in the HMBC spectra to carbon 7 suggesting the formation of a covalent bond between nitrogen 16 and carbon 7. The proton on carbon 7 resonates at 5.6 ppm (proton 7 is the signal of the PCL-A/2-ABA adduct highlighted in FIG. 201) and shows correlations to carbon 2, 8, 9, 5 and 13. Similarly the proton on carbon 2 exhibits a HMBC correlation to carbon 9. These observations and all other NMR observations for the two samples characterized in $D_2O$ and in D6-DMSO are consistent with the structure in FIG. 57A drawn for the major product of the PCL-A/2-ABA adduct. Thus, overall, the NMR evidence points to the following structure for the product of the reaction between PCL-A and 2-ABA:

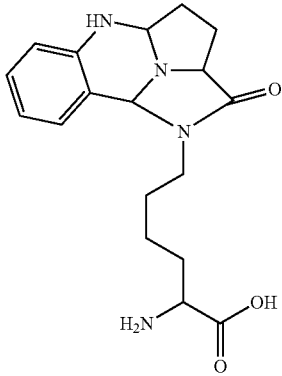 [SMILES: NC(CCCCN1C(=O)C2CCC3Nc4ccccc4C1N32)C(=O)O]

A structural characterization of the minor form observed in the reaction mixture (FIG. 56) has also been attempted. The analysis is complicated by the low concentration of the minor form and the fact that it slowly converts to the major form. The analysis is inconclusive. Both minor and major forms have one proton on carbon 7 and the chemical shifts of both are very similar (arrows at 5.6 ppm in FIG. 56). Through-space ROESY contacts are similar in both forms as well. The two methylene protons on carbon 17 are degenerated, meaning they exhibit the same chemical shift, for the minor form of the PCL-A/2-ABA adduct as well as for unreacted PCL-A. These protons however have distinct chemical shifts in the major form. These protons also show a HMBC correlation to carbon 7 in both minor and major forms suggesting a covalent bond between carbon 7 and nitrogen 16. The observation of degenerate chemical shifts of the methylene protons on carbon 17 in the minor form may imply that the covalent bond between carbon 7 and nitrogen 16 could be semi-stable, and that the NMR observations for the minor form are the result of chemical exchange between two or more species. It is conceivable that the minor form is an alternative semi-stable stereo-isomer of the major form in chemical exchange with the protonated form of the PCL-A/2-ABA adduct (FIG. 57B).

In addition, solutions of synthetic PCL-A and 2-ABA in $D_2O$ were mixed as described above and the reaction was allowed to proceed to completion as monitored by NMR. Addition of aliquots of a sodium cyanoborohydride (NaCNBH$_3$) solution in $D_2O$ to the NMR tube resulted in reduction of the PCL-A/2-ABA adduct to a new species. Additional NaCNBH$_3$ aliquots were added until the resonance at 5.6 ppm that is characteristic for the PCL-A/2-ABA adduct (FIG. 56, arrows) completely disappeared. The NMR sample of the completely reduced PCL-A/2-ABA adduct was then repeatedly lyophilized and redisolved in dry $D_2O$ in order to reconcentrate the sample and to remove water. The final sample was reconstituted in 0.5 mL of dry $D_2O$. The reduced form was characterized by standard 2D $^1H$-$^1H$ COSY, $^1H$-$^{13}C$ HMBC and $^1H$-$^{13}C$ HMQC NMR spectroscopy. Signal assignments of protons and carbon resonances and heteronuclear through bond correlations from the $^1H$-$^{13}C$ HMBC spectra are summarized in Table 9.

TABLE 9

$^1H$—$^{13}C$ HMBC correlations observed for the reduced form of the PCL-A/2-ABA adduct (in D2O)

| No. | Correlations between | | $^1H$ | $^{13}C$ |
|---|---|---|---|---|
| | F2 Atom | F1 Atom | F2 (ppm) | F1 (ppm) |
| 1 | 3 | 2 | 1.85 | 54.62 |
| 2 | 7 | 2 | 3.58 | 54.79 |
| 3 | 7 | 2 | 3.89 | 54.86 |
| 4 | 2 | 3 | 2.60 | 23.39 |
| 5 | 4 | 3 | 1.76 | 23.31 |
| 6 | 4 | 3 | 2.29 | 23.38 |
| 7 | 2 | 4 | 3.27 | 30.38 |
| 8 | 5 | 4 | 3.21 | 30.39 |
| 9 | 2 | 5 | 3.27 | 67.08 |
| 10 | 4 | 5 | 2.29 | 67.06 |
| 11 | 4 | 5 | 1.77 | 67.09 |
| 12 | 7 | 5 | 3.89 | 66.98 |
| 13 | 7 | 5 | 3.58 | 67.05 |
| 14 | 2 | 7 | 2.61 | 56.85 |
| 15 | 5 | 7 | 3.21 | 56.79 |
| 16 | 13 | 7 | 7.22 | 56.83 |
| 17 | 7 | 8 | 3.89 | 123.94 |
| 18 | 7 | 8 | 3.58 | 124.02 |
| 19 | 10 | 8 | 6.90 | 124.03 |
| 20 | 12 | 8 | 6.87 | 124.06 |
| 21 | 7 | 9 | 3.89 | 145.27 |
| 22 | 7 | 9 | 3.58 | 145.30 |
| 23 | 11 | 9 | 7.24 | 145.30 |
| 24 | 13 | 9 | 7.21 | 145.25 |
| 25 | 12 | 10 | 6.87 | 116.70 |
| 26 | 13 | 11 | 7.22 | 129.05 |
| 27 | 10 | 12 | 6.90 | 119.25 |
| 28 | 7 | 13 | 3.58 | 130.66 |
| 29 | 7 | 13 | 3.89 | 130.71 |
| 30 | 11 | 13 | 7.24 | 130.59 |
| 31 | 4 | 14 | 1.76 | 177.53 |
| 32 | 4 | 14 | 2.29 | 177.58 |
| 33 | 5 | 14 | 3.21 | 177.50 |
| 34 | 17 | 14 | 2.97 | 177.56 |
| 35 | 18 | 17 | 1.37 | 38.49 |
| 36 | 18 | 17 | 1.42 | 38.56 |
| 37 | 18 | 17 | 1.34 | 38.59 |
| 38 | 19 | 17 | 1.37 | 38.49 |
| 39 | 19 | 17 | 1.34 | 38.59 |
| 40 | 17 | 18 | 2.97 | 27.90 |
| 41 | 19 | 18 | 1.30 | 27.87 |
| 42 | 17 | 19 | 2.97 | 21.71 |
| 43 | 18 | 19 | 1.35 | 21.70 |
| 44 | 18 | 19 | 1.42 | 21.72 |
| 45 | 20 | 19 | 1.86 | 21.71 |
| 46 | 21 | 19 | 3.72 | 21.70 |
| 47 | 18 | 20 | 1.31 | 29.99 |
| 48 | 18 | 20 | 1.42 | 30.15 |
| 49 | 18 | 20 | 1.36 | 30.26 |
| 50 | 19 | 20 | 1.31 | 29.99 |
| 51 | 19 | 20 | 1.36 | 30.26 |
| 52 | 21 | 20 | 3.72 | 30.16 |
| 53 | 19 | 21 | 1.30 | 54.62 |
| 54 | 20 | 21 | 1.85 | 54.62 |
| 55 | 20 | 23 | 1.87 | 175.22 |
| 56 | 21 | 23 | 3.72 | 175.17 |

The numbering of the atoms is shown in FIG. 57C. Key differences to the observed correlations in the major form of the PCL-A/2-ABA adduct are the lack of a heteronuclear through bond correlation between the methylene protons on carbon 17 and carbon 7 and the absence of a through bond correlation between the protons on carbon 2 and carbon 9. These and all other NMR observations are consistent with the following structure (also in FIG. 57C) for the reduced PCL-A/2-ABA adduct:

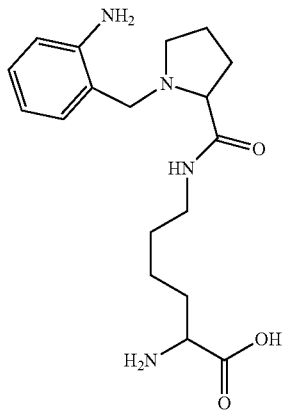 [SMILES: Nc1ccccc1CN1CCCC1C(=O)NCCCCC(N)C(=O)O]

The reaction of PCL-B with 2-ABA was also studied under identical conditions as those for the reaction of PCL-A with 2-ABA. PCL-B synthesized as described in Example 36-2 was dissolved in $D_2O$ (as above), and a reaction mixture with PCL-B and 2-ABA at an approximate molar ratio of 1:1 was transferred into an NMR tube. The signal assignments of the starting materials are listed in Table 10.

TABLE 10

NMR Signal Assignments of unreacted PCL-B and 2-ABA

| Atom Number | Shift (ppm) | H's | Type | J (Hz) |
|---|---|---|---|---|
| 19 | 1.33 | 1 | m | — |
| 18 | 1.50 | 1 | q | 7.02 |
| 20 | 1.77 | 1 | m | — |
| 3 | 1.88 | 1 | m | — |
| 4 | 2.69 | 1 | m | — |
| 17 | 3.21 | 1 | t | 6.94 |
| 21 | 3.61 | 1 | m | — |
| 2 | 3.85 | 1 | m | — |
| 12, 10 | 6.76 | 2 | m | — |
| 11 | 7.34 | 1 | ddd | 8.44, 7.05, 1.61 |
| 13 | 7.53 | 1 | dd | 8.18, 1.61 |
| 7 | 9.67 | 1 | s | — |

Figure 58:
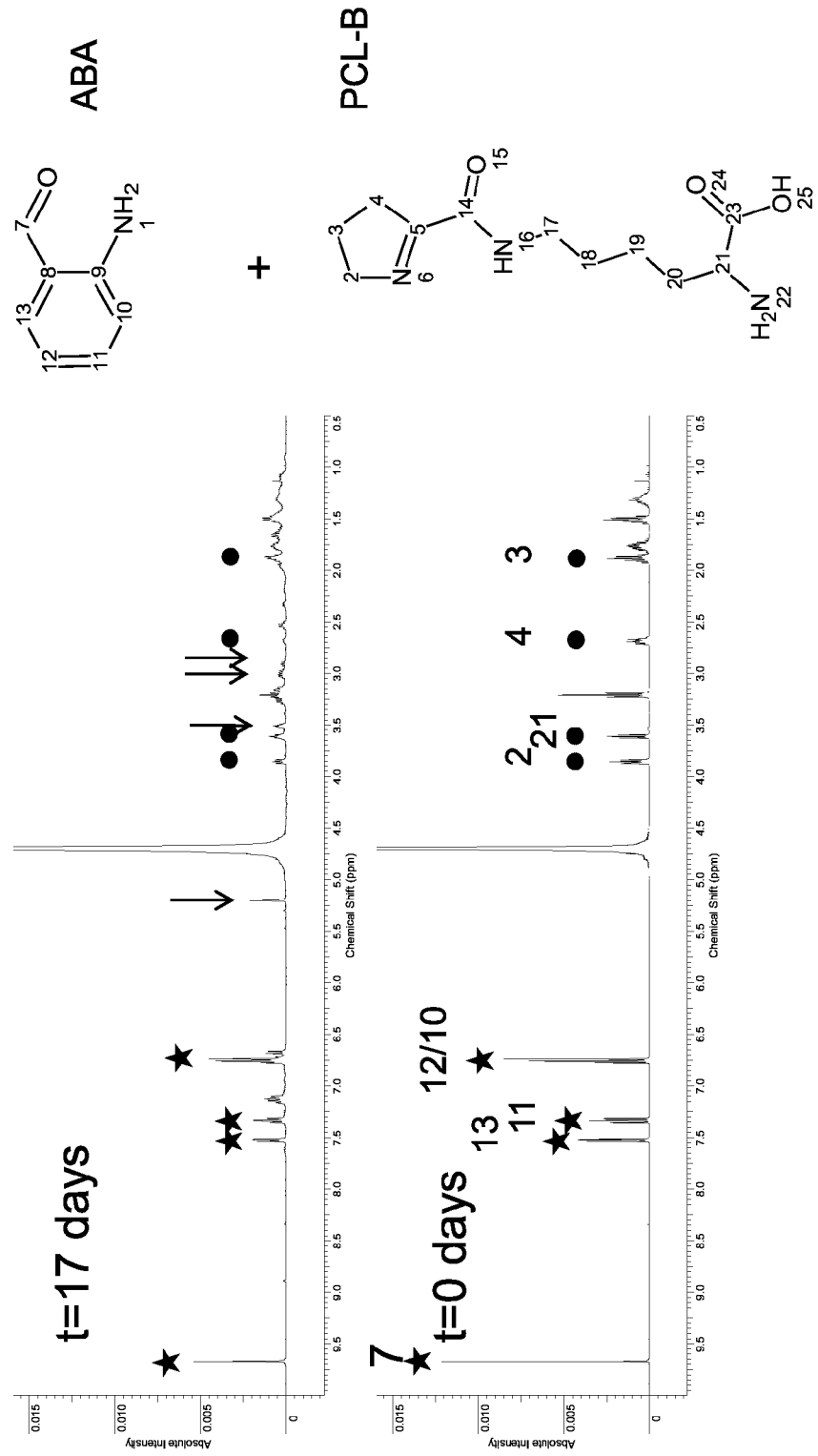
FIG. 58. NMR analysis of PCL-B reaction with 2-ABA.

The reaction was allowed to proceed at room temperature and NMR spectra were periodically acquired at the indicated times (FIG. 58). In contrast to the PCL-A sample, PCL-B did not react readily with 2-ABA. Even after 17 days much of the starting material (stars for 2-ABA; dots for PCL-B) is still present although a small amount is converted into a new species (arrows). This species could not be characterized further. However, the NMR analysis of the two reactions clearly indicates that the reactivity of PCL-A with 2-ABA is much higher than that of PCL-B.

Example 46

Derivatization of Pyrrolysine (Pyl) and PCL Incorporated into mEGF

The incorporation of pyrrolysine (Pyl) and PCL into mEGF was accomplished as described in Example 14, except that *E. coli* BL21(DE3) cells were co-transformed with pAra-pylSTBCD and the mutant mEGF Tyr10TAG gene on a pET22b vector. The resulting mEGF mutant is hereafter referred to as mEGF-Tyr10PCL/Pyl. ESI-MS analysis revealed that both PCL and PYL were incorporated at position 10 of mEGF (FIG. 59A; expected mass of mEGF Tyr10PCL=7296 Da; expected mass of mEGF Tyr10Pyl=7310 Da). Thus a mixture of mEGF protein was obtained with either PCL or PYL incorporated. In this particular sample, the predominant species was mEGF with PCL incorporated therein.

Figure 59:
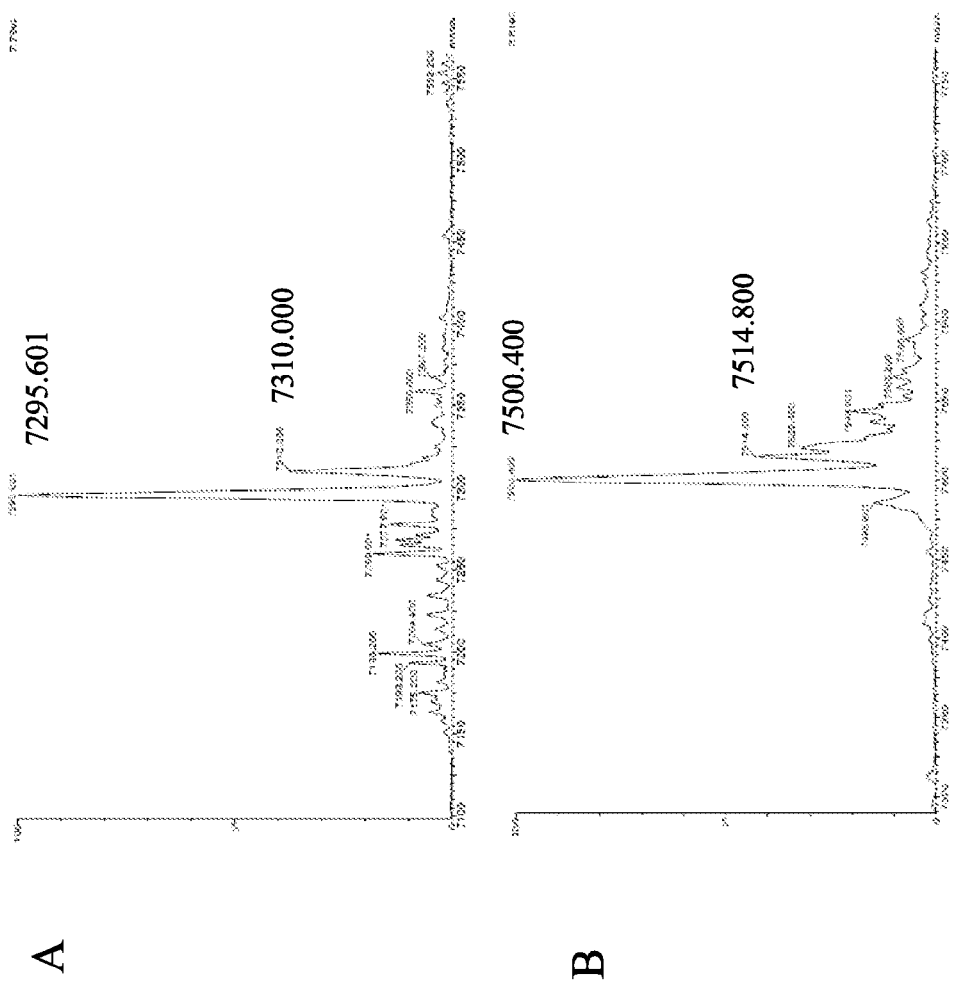
FIG. 59. Derivatization of Pyrrolysine (Pyl) and PCL incorporated into mEGF.

To demonstrate derivatization of this mixture and to demonstrate that PYL is modified using the methods provided herein, coupling of the ABA reagent TU3627-014 (see Example 34-2) to mEGF Tyr10PCL/PYL was carried out in 10×PBS (pH 7.0) and 1% (v/v) DMSO at 25° C. for 16 hours. The conjugation reaction was initiated by the addition of 10 µM mEGF Tyr10PCL/PYL and 1 mM TU3627-014. Formation of the protein conjugates was confirmed by electrospray ionization-mass spectrometry (ESI-MS) (FIG. 59B). The ratio between the PCL and PYL adduct resembles the ratio of PCL and PYL in the unreacted protein (FIG. 58A), thereby indicating similar reactivity for PCL and Pyl.

It is understood that the examples and embodiments described herein are for illustrative purposes only and that various modifications or changes in light thereof will be suggested to persons skilled in the art and are to be included within the spirit and purview of this application and scope of the appended claims.

We claim:

1. A compound having the structure of Formula (II):

$$R_1\text{-(BB)}_n\text{-}R_2 \qquad (II)$$

wherein:

$R_1$ is H or an amino terminus modification group;

$R_2$ is OH or a carboxy terminus modification group;

n is an integer from 1 to 5000;

each BB is independently selected from an amino acid residue, a pyrrolysine analogue amino acid residue having the structure of Formula (D-1), and a pyrrolysine analogue amino acid residue having the structure of Formula (F 1):

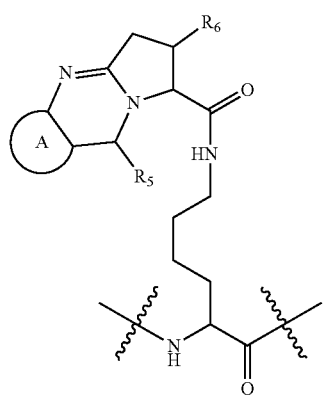

(D-1)

wherein:

$R_5$ is selected from H, —OH, —NO$_2$, halo, $C_{1-8}$alkyl, halo-substituted-$C_{1-8}$alkyl, hydroxy-substituted-$C_{1-8}$alkyl, aryl, heteroaryl, heterocycloalkly or cycloalkyl and -LX$^1$;

$R_6$ is H or $C_1$alkyl;

A is a phenyl optionally substituted with 1 to 3 substituents independently selected from —OH, —NO$_2$, halo, $C_{1-8}$alkyl, halo-substituted-$C_{1-8}$ alkyl, hydroxy-substituted-$C_{1-8}$alkyl, aryl, heteroaryl, heterocycloalkly, or cycloalkyl and -LX$^1$;

L is selected from a bond, $C_{1-8}$alkylene, halo-substituted-$C_{1-8}$alkylene, hydroxy-substituted-$C_{1-8}$alkylene, $C_{2-8}$alkenylene, halo-substituted-$C_{2-8}$alkenylene, hydroxy-substituted-$C_{2-8}$alkenylene,

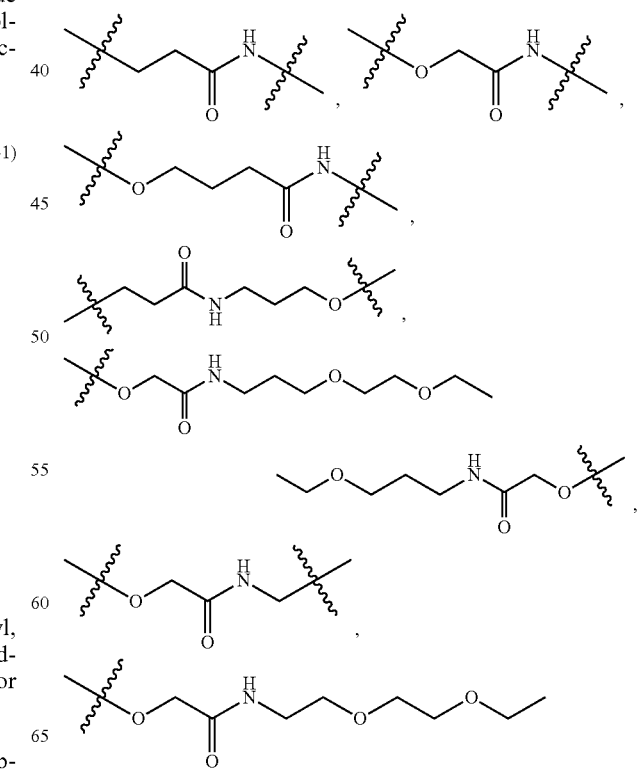

275
-continued
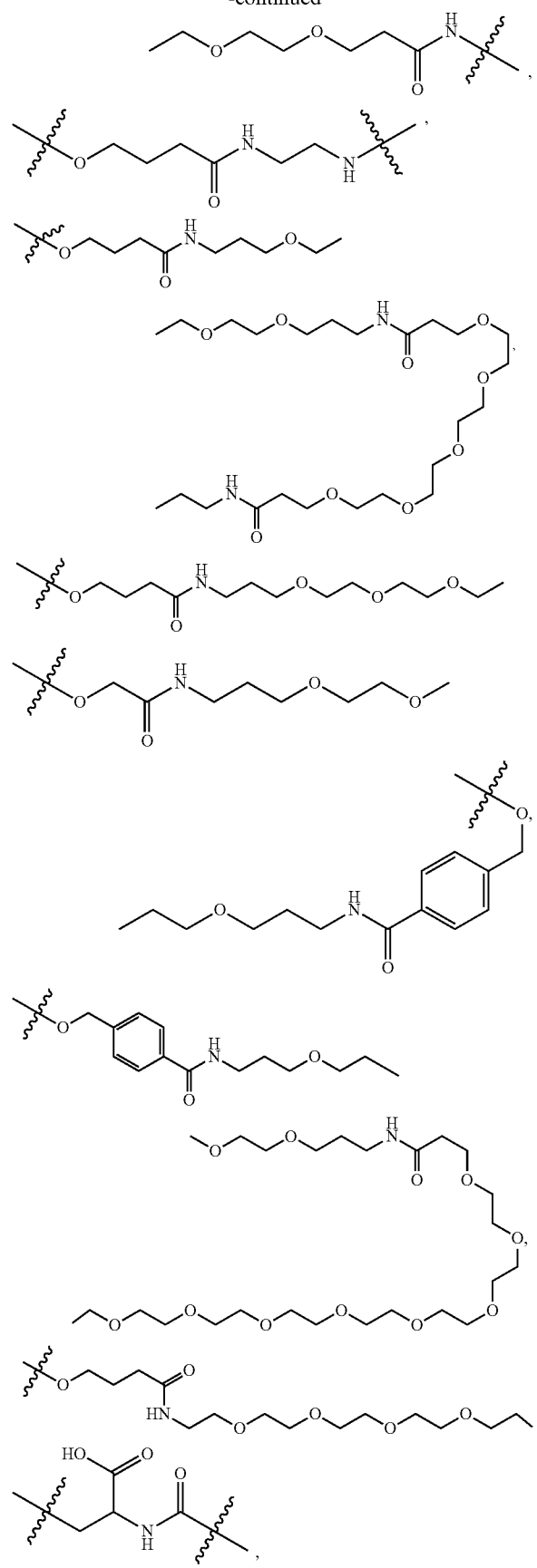
276
-continued
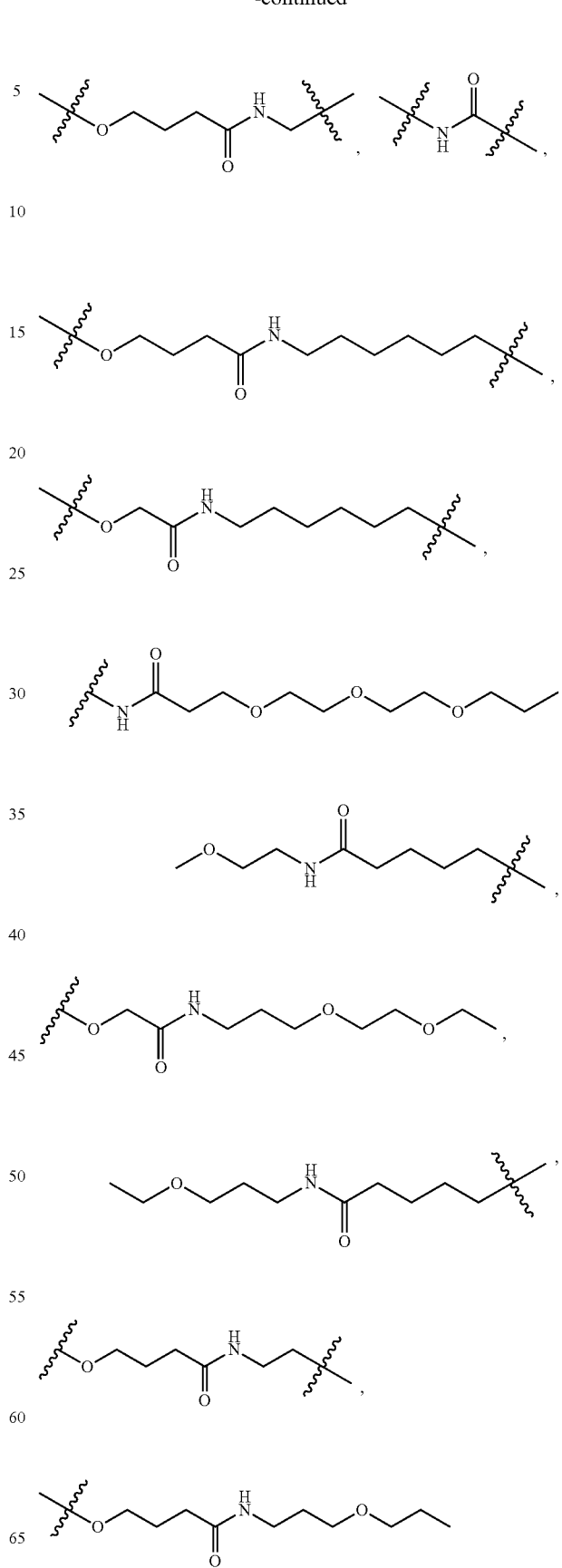

-continued

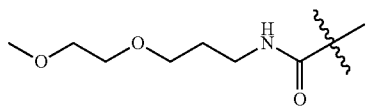

—O(CR$^{11}$R$^{12}$)$_k$—, —S(CR$^{11}$R$^{12}$)$_k$, —S(O)$_k$(CR$^{11}$R$^{12}$)$_k$—, —O(CR$^{11}$R$^{12}$)$_k$—NR$^{11}$C(O)—, —O(CR$^{11}$R$^{12}$)$_k$C(O)NR$^{11}$—, —C(O)—, —C(O)(CR$^{11}$R$^{12}$)$_k$—, —C(S)—, —C(S)(CR$^{11}$R$^{12}$)$_k$—, —C(O)NR$^{11}$—, —NR$^{11}$C(O)—, —NR$^{11}$(CR$^{11}$R$^{12}$)$_k$—, —CONR$^{11}$(CR$^{11}$R$^{12}$)$_k$—, —N(R$^{11}$)CO(CR$^{11}$R$^{12}$)$_k$—, —C(O)NR$^{11}$(CR$^{11}$R$^{12}$)$_k$—, —NR$^{11}$C(O)CR$^{11}$R$^{12}$)$_k$—, where each R$^{11}$ and R$^{12}$ are independently H, C$_{1-8}$alkyl, halo-substituted-C$_{1-8}$alkyl, or hydroxy-substituted-C$_{1-8}$alkyl, and k is an integer from 1 to 12, and X$^1$ is selected from a water-soluble polymer, a polyalkylene glycol, a poly(ethylene glycol), a derivative of poly(ethylene glycol), a sugar, a lipid, a cytotoxic compound, an affinity label, a peptide, a protein, an antibody or antibody fragment, a carbohydrate, a DNA, a RNA, phosphorothioate-modified DNA, a saccharide, a disaccharide, an oligosaccharide, a polysaccharide, a spin label, a fluorophore, a radioactive moiety a photocaged moiety, biotin, a biotin analogue, a TLR2 agonist, a TLR4 agonist, a TLR7 agonist, a TLR9 agonist, a TLR8 agonist, a T-cell epitope, a phospho-lipid, a LPS-like molecule, an immunogenic hapten, an immune response potentiator, a solid support, —CH$_2$CH$_2$—(OCH$_2$CH$_2$O)$_p$—OX$^2$, —O—(CH$_2$CH$_2$O)$_p$CH$_2$CH$_2$—X$^2$, and any combination thereof, wherein p is 1 to 10,000 and X$^2$ is H, a C$_{1-8}$alkyl, a protecting group or a terminal functional group, and wherein:
at least one BB in the compound of Formula (II) is a pyrrolysine analogue amino acid residue having the structure of Formula (D-1).
2. The compound of claim 1, wherein ring A is a phenyl substituted with -LX$^1$.
3. The compound of claim 1, wherein each BB is independently selected from an amino acid residue, a pyrrolysine analogue amino acid residue having the structure of Formula (D-2);

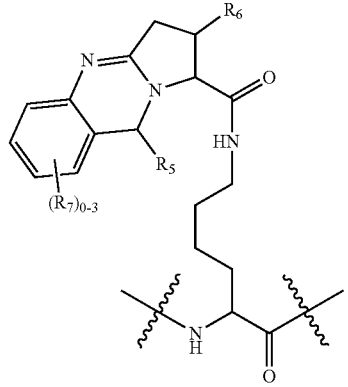

(D-2)

wherein,
R$_5$ is selected from H, —OH, —NO$_2$, halo, C$_{1-8}$alkyl, halo-substituted-C$_{1-8}$alkyl, hydroxy-substituted-C$_{1-8}$alkyl, aryl, heteroaryl, heterocycloalkly or cycloalkyl and -LX$^1$;
R$_6$ is H or C$_1$alkyl;
when present each R$_7$ is independently selected from —OH, —NO$_2$, halo, C$_{1-8}$alkyl, halo-substituted-C$_{1-8}$alkyl, hydroxy-substituted-C$_{1-8}$alkyl, aryl, heteroaryl, heterocycloalkly, or cycloalkyl and -LX$^1$;
L is selected from a bond, C$_{1-8}$alkylene, halo-substituted-C$_{1-8}$alkylene, hydroxy-substituted-C$_{1-8}$alkylene, C$_{2-8}$alkenylene, halo-substituted-C$_{2-8}$alkenylene, hydroxy-substituted-C$_{2-8}$alkenylene,

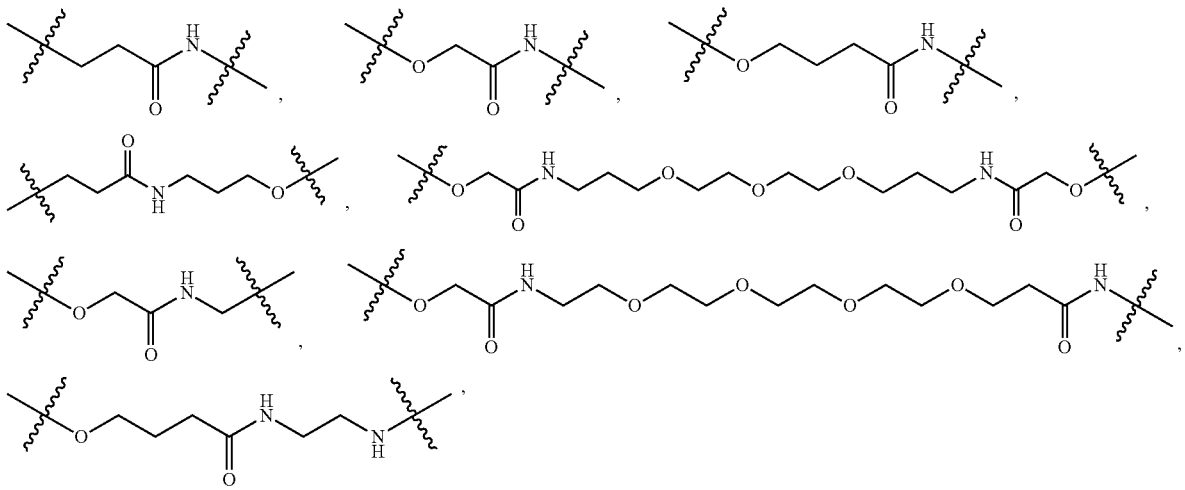

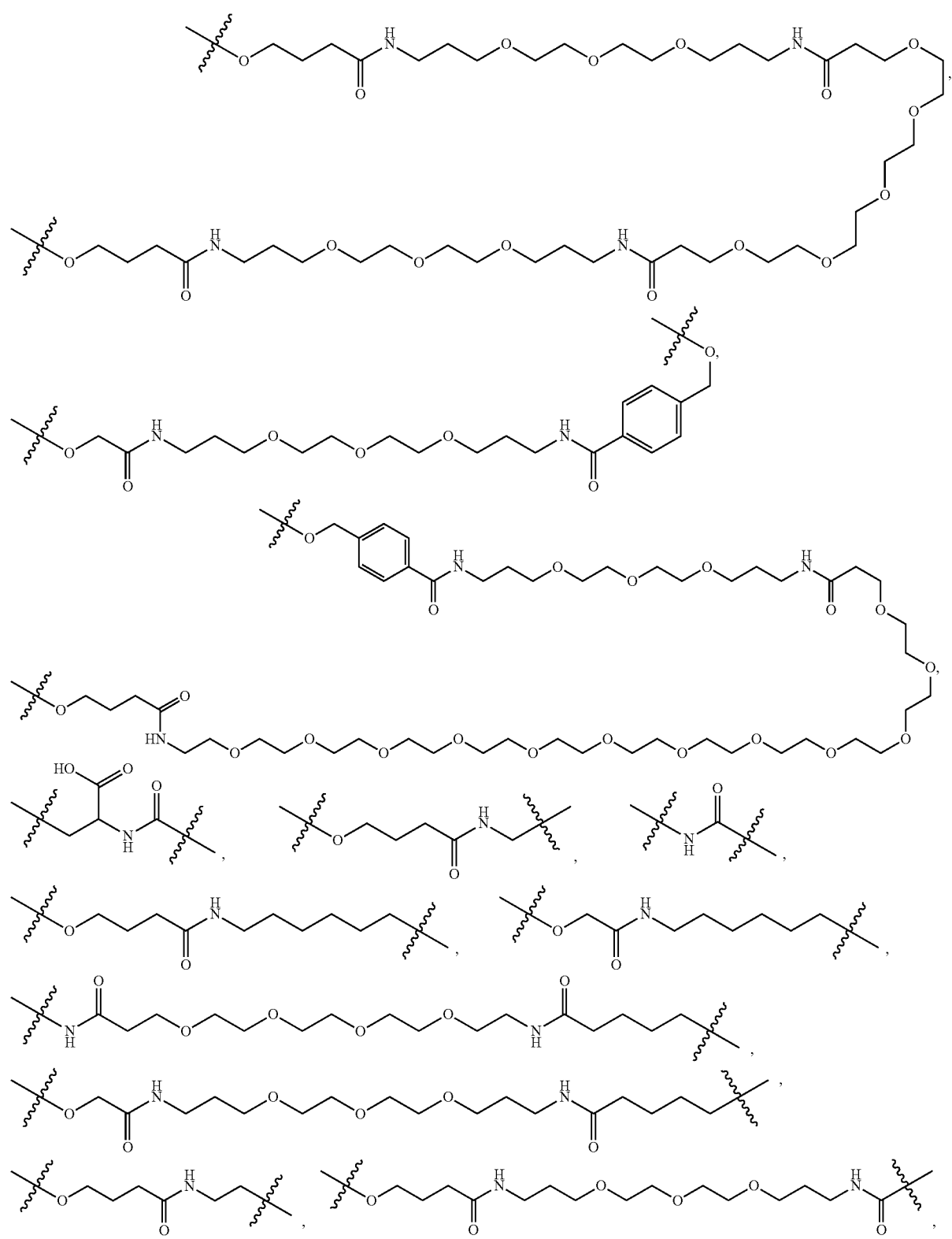
—O(CR$^{11}$R$^{12}$)$_k$—, —S(CR$^{11}$R$^{12}$)$_k$, —S(O)$_k$(CR$^{11}$R$^{12}$)$_k$—, —O(CR$^{11}$R$^{12}$)$_k$—NR$^{11}$C(O)—, —O(CR$^{11}$R$^{12}$)$_k$C(O)NR$^{11}$—, —C(O)—, —C(O)(CR$^{11}$R$^{12}$)$_k$—, —C(S)—, —C(S)(CR$^{11}$R$^{12}$)$_k$—, —C(O)NR$^{11}$—, —NR$^{11}$C(O)—, —NR$^{11}$(CR$^{11}$R$^{12}$)$_k$—, —CONR$^{11}$(CR$^{11}$R$^{12}$)$_k$—, —N(R$^{11}$)CO(CR$^{11}$R$^{12}$)$_k$—, —C(O)NR$^{11}$(CR$^{11}$R$^{12}$)$_k$—, —NR$^{11}$C(O)CR$^{11}$R$^{12}$)$_k$—, where each R$^{11}$ and R$^{12}$ are independently H, $C_{1-8}$alkyl, halo-substituted-$C_{1-8}$alkyl, or hydroxy-substituted-$C_{1-8}$alkyl, and k is an integer from 1 to 12, and $X^1$ is selected from a water-soluble polymer, a polyalkylene glycol, a poly(ethylene glycol), a derivative of poly(ethylene glycol), a sugar, a lipid, a cytotoxic compound, an affinity label, a peptide, a protein, an antibody or antibody fragment, a carbohydrate, a DNA, a RNA, phosphorothioate-modified DNA, a saccharide, a disaccharide, an oligosaccharide, a polysaccharide, a spin label, a fluorophore, a radioactive moiety, a photocaged moiety, biotin, a biotin analogue, a TLR2 agonist, a TLR4 agonist, a TLR7 agonist, a TLR9 agonist, a TLR8 agonist, a T-cell epitope, a phospho-lipid, a LPS-like molecule, an immunogenic hapten, an immune response potentiator, a solid support, —$CH_2CH_2$—$(OCH_2CH_2O)_p$—$OX^2$, —O— $(CH_2CH_2O)_pCH_2CH_2$—$X^2$, and any combination thereof, wherein p is 1 to 10,000 and $X^2$ is H, a $C_{1-8}$alkyl, a protecting group or a terminal functional group.

4. The compound of claim 3, wherein $R_7$ is -$LX^1$.

5. The compound of claim 1, wherein $X^1$ is a sugar, a polyethylene glycol, a fluorophore, an immunomodulator, a ribonucleic acid (RNA), a deoxyribonucleic acid (DNA), a protein, a peptide, a biotin, a phospholipid, a TLR7 agonist, an immunogenic hapten, a T-cell epitope, a lipid, a carbohydrate, phosphorothioate-modified DNA, a saccharide, a disaccharide, an oligosaccharide, a polysaccharide, a spin label, an immune response potentiator, a cytotoxic compound or a solid support.

6. The compound of claim 5, wherein L is a poly(alkyleneglycol), a poly(ethyleneglycol), $C_{1-8}$alkylene, halo-substituted-$C_{1-8}$alkylene, hydroxy-substituted-$C_{1-8}$alkylene,

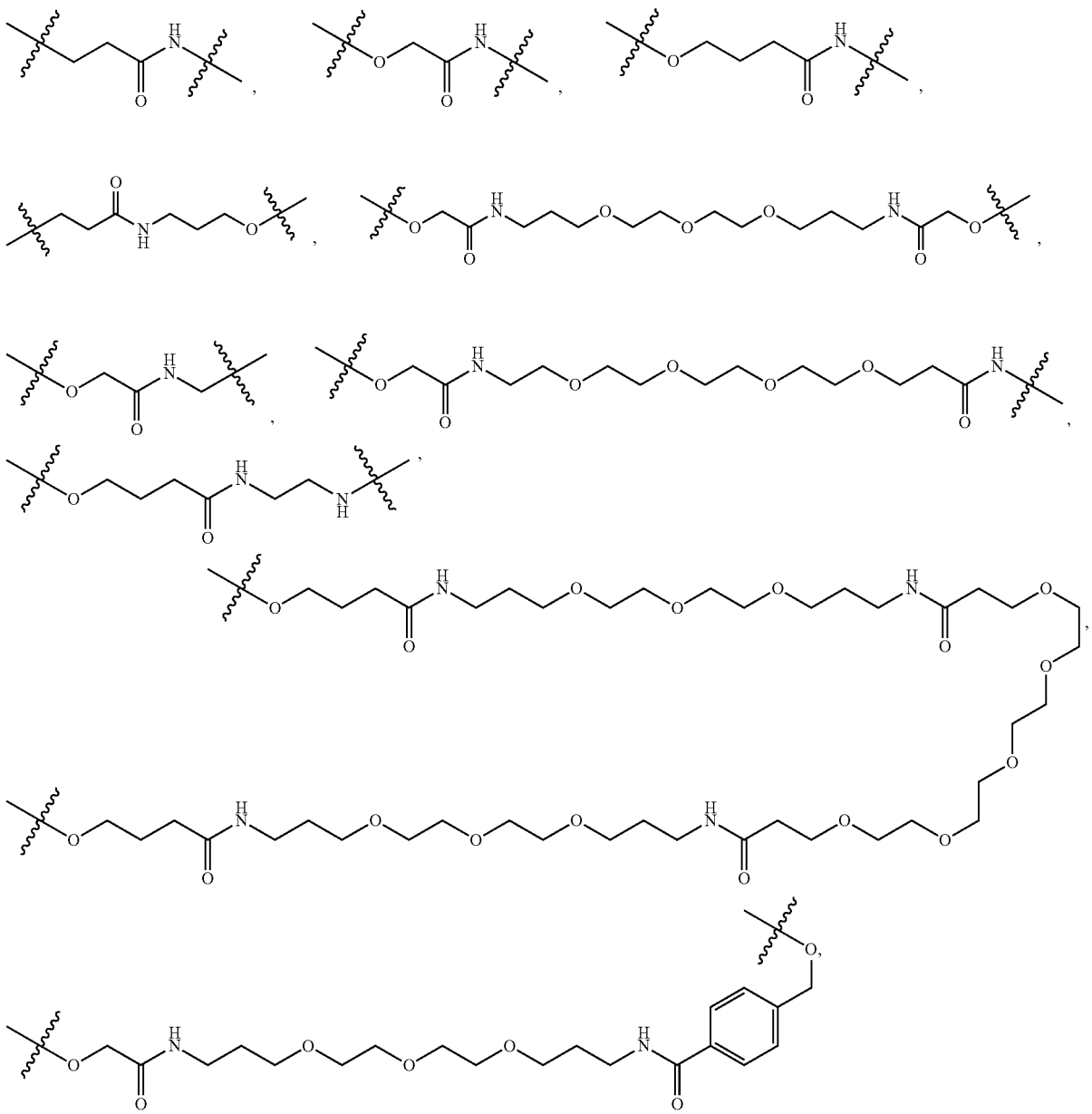

-continued
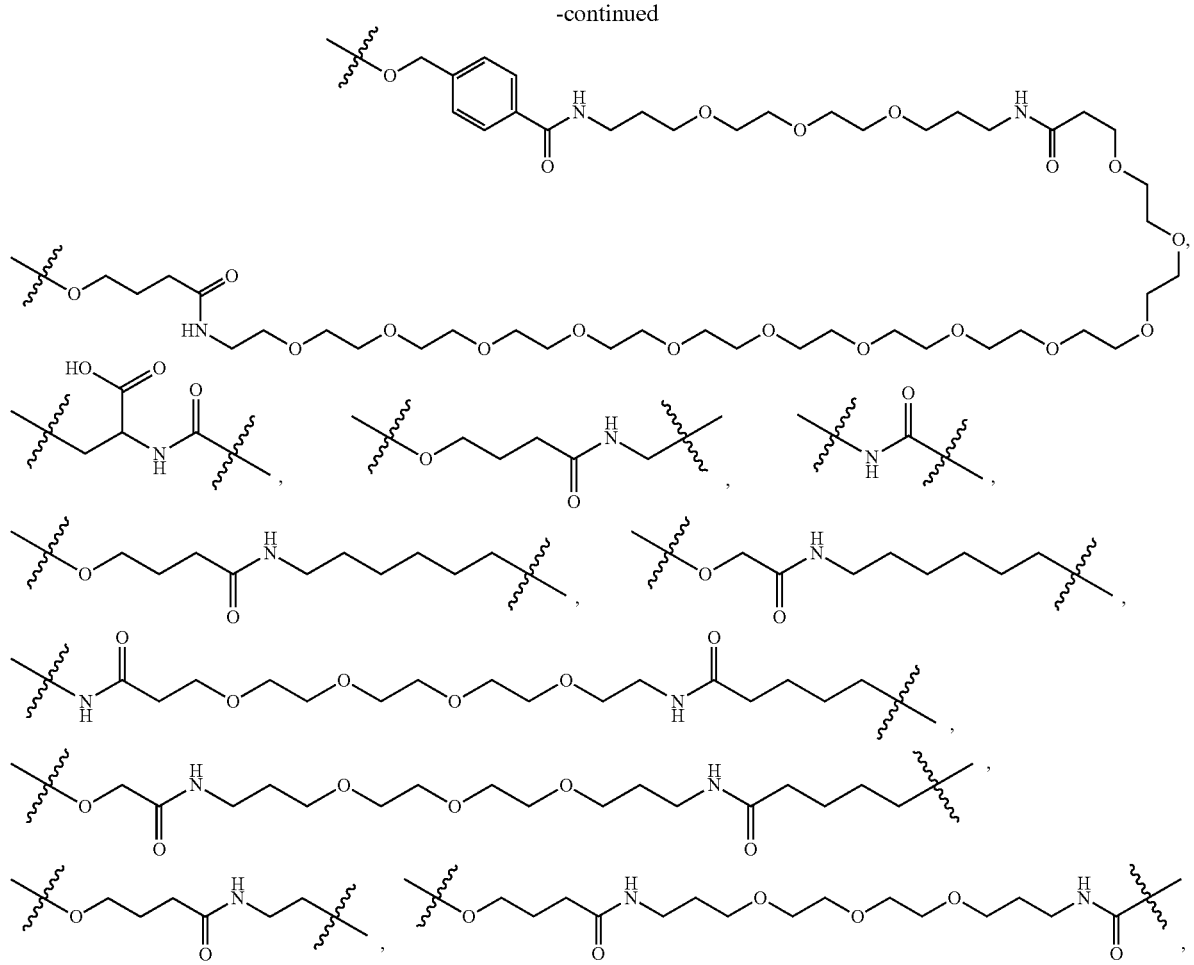
7. The compound of claim 6, wherein $R_6$ is H.
* * * * *